US010647715B2

(12) United States Patent
Marx et al.

(10) Patent No.: US 10,647,715 B2
(45) Date of Patent: *May 12, 2020

(54) KRAS G12C INHIBITORS

(71) Applicants: Mirati Therapeutics, Inc., San Diego, CA (US); Array BioPharma Inc., Boulder, CO (US)

(72) Inventors: Matthew Arnold Marx, San Diego, CA (US); Thomas P. Bobinski, San Diego, CA (US); Aaron Craig Burns, San Diego, CA (US); John Gaudino, Boulder, CO (US); Julia Haas, Boulder, CO (US); John Michael Ketcham, San Diego, CA (US); John David Lawson, Carlsbad, CA (US); Brad Newhouse, Boulder, CO (US); Spencer Pajk, Boulder, CO (US); Christopher Ronald Smith, San Diego, CA (US); Tony P. Tang, Boulder, CO (US)

(73) Assignees: MIRATI THERAPEUTICS, INC., San Diego, CA (US); ARRAY BIOPHARMA INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,091

(22) Filed: May 14, 2019

(65) Prior Publication Data
US 2019/0270743 A1    Sep. 5, 2019

Related U.S. Application Data

(63) Continuation-in-part of application No. 16/191,190, filed on Nov. 14, 2018.

(60) Provisional application No. 62/586,775, filed on Nov. 15, 2017.

(51) Int. Cl.
C07D 471/04    (2006.01)
A61P 35/00    (2006.01)
C07D 519/00    (2006.01)

(52) U.S. Cl.
CPC ............ *C07D 471/04* (2013.01); *A61P 35/00* (2018.01); *C07D 519/00* (2013.01)

(58) Field of Classification Search
CPC ...... C07D 519/00; C07D 471/04; A61P 35/00
USPC .................................................. 514/210.21
See application file for complete search history.

(56) References Cited

U.S. PATENT DOCUMENTS

| 8,163,763 | B2 | 4/2012 | Bergeron et al. |
| 9,562,019 | B2 | 2/2017 | Djaballah et al. |
| 9,840,516 | B2 | 12/2017 | Li et al. |
| 10,125,134 | B2 | 11/2018 | Blake et al. |
| 2003/0191143 | A1 | 10/2003 | Pitts et al. |
| 2009/0253693 | A1 | 10/2009 | Koltun et al. |
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2018/0015087 | A1 | 1/2018 | Liu et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |
| 2018/0282308 | A1 | 10/2018 | Li et al. |
| 2018/0289683 | A1 | 10/2018 | McCormick et al. |
| 2019/0284275 | A1 | 9/2019 | Zhou et al. |
| 2019/0292182 | A1 | 9/2019 | Kuramoto et al. |

FOREIGN PATENT DOCUMENTS

| WO | 02/053558 A1 | 7/2002 |
| WO | 02/087513 A2 | 11/2002 |
| WO | 2007/146122 A2 | 12/2007 |

(Continued)

OTHER PUBLICATIONS

Sung, Y. et al. "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436 , Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

(Continued)

Primary Examiner — Kahsay Habte
(74) Attorney, Agent, or Firm — Wood, Phillips, Katz, Clark & Mortimer

(57) ABSTRACT

The present invention relates to compounds that inhibit KRas G12C. In particular, the present invention relates to compounds that irreversibly inhibit the activity of KRas G12C, pharmaceutical compositions comprising the compounds and methods of use therefor.

9 Claims, No Drawings

(56) References Cited

FOREIGN PATENT DOCUMENTS

| | | |
|---|---|---|
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 2019/110751 A1 | 6/2019 |
| WO | 2019/150305 A1 | 8/2019 |
| WO | 2019/155399 A1 | 8/2019 |

OTHER PUBLICATIONS

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specitic Inhibitor", Cell 172, 578-589, Jan. 25, 2018.

Singh et al., "A Gene Expression Signature Associated with K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290-CD-13/0646; Cancer Discovery Published OnlineFirst Jan. 20, 2014.

Simanshu et al., "RAS Proteins and Their Regulators in Human Disease", Cell 170, p. 17, Jun. 29, 2017.

Pacold et al., "Crystal Structure and Functional Analysis of Ras Binding to Its Effector Phosphoinositide 3-Kinase gamma", Cell, vol. 103, p. 931-943, Dec. 8, 2000.

Lech-Gustav et al., "The Renaissance of Ras", ACS Chem. Biol., 2014, 9, 2447-2458.

Karachaliou et al., "KRAS Mutations in Lung Cancer", Clinical Lung Cancer, vol. 14, No. 3, p. 2015-2014, 2013.

Schwartz et al., "Covalent EGFR inhibitor analysis reveals importance of reversible interactions to potency and mechanisms of drug resistance", PNAS, vol. 111, No. 1, p. 173-178, Jan. 7, 2014.

Sun et al., "A method for the second-site screening of K-Ras in the presence of a covalently attached first-site ligand", J. Biomol. NMR (2014) vol. 60 p. 11-14.

Kyriakis, J., "Thinking Outside the Box about Ras", J. Biol. Chem. 2009, 284:10993-10994, published online Dec. 17, 2008.

Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.

Serafimova et al., "Reversible targeting of noncatalytic cysteines with chemically tuned electrophiles", Nat Chem Biol.; 8(5):471-476. doi:10.1038/nchembio.925.

Walker et al., "Structural insights into phosphoinositide 3-kinase catalysis and signalling", Nature vol. 402, p. 18 Nov. 1999; www.nature.com.

Barbie et al., "Systematic RNA interference reveals that oncogenic KRAS-driven cancers require TBK1", Nature, vol. 462, p. 108, Nov. 5, 2009; doi:10.1038/nature08460.

Zimmermann et al., "Small molecule inhibition of the KRAS-PDEdelta interaction impairs oncogenic KRAS signalling", Nature, vol. 497, p. 638, May 30, 2013.

Karnoub et al., "Ras oncogenes: split personalities", Nature Reviews, molecular Cell Biology, vol. 9, Jul. 2008 p. 517.

Nassar et al., "Ras/Rap effector specificity determined by charge reversal", Nature Structural Biology, vol. 3, No. 8, Aug. 1996.

De Rooij et al., "Minimal Ras-binding domain of Raf1 can be used as an activation-specific probe for Ras", Oncogene (1997) 14, 623-625, 1997 Stockton Press.

Cox et al., "The dark side of RAs: regulation of apoptosis", Oncogene (2003) 22, 8999-9006, 2003 Nature Publishing Group.

Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.

Grant et al., "Novel Allosteric Sites on Ras for Lead Generation", PLOS ONE, vol. 6, Issue 10, Oct. 2011.

Maegley et al., "Ras-catalyzed hydrolysis of GTP: A new perspective from model studies", Proc. Natl. Acad. Sci. USA, vol. 93, pp. 8160-8166, Aug. 1996.

Ahmadian et al., "Guanosine triphosphatase stimulation of oncogenic Ras mutants", Proc. Natl. Acad. Sci. USA, vol. 96, pp. 7065-7070, Jun. 1999.

Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.

Kotting et al., "The GAP arginine finger movement into the catalytic site of Ras increases the activation entropy", PNAS, vol. 105, No. 17, p. 6260-6265, Apr. 29, 2008.

Shaw et al., "Selective killing of K-ras mutant cancer cells by small molecule inducers of oxidative stress", PNAS, vol. 108, No. 21, p. 8773-8778, May 24, 2011.

(56) References Cited

OTHER PUBLICATIONS

Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 dated Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
International Search Report and Written Opinion for PCT Application No. PCT/US2017/33099 dated Aug. 24, 2017.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi:10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS ONE | DOI:10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonsmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer the End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed Superimposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 12, 2013; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.

(56) References Cited

OTHER PUBLICATIONS

Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15/1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Rudoni, S. et al., "Role of guanine nucleotides in the regulation of the Ras/cAMP pathway in *Saccharomyces cerevisiae*", Biochimica et Biophysica Acta 1538 (2001)181189.
Samatar, A. et al., "Targeting RAS—ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.

Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K Inhibition, Downloaded from clincancerres.aacrjournals.org on Oct. 22, 2018. © 2018 American Association for Cancer Research.
Nabet, B. et al., "It Takes Two to Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancer-res.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter, DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/541598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Jarvis, "Notorious KRAS: Taking down cancer researchers' biggest foe", Oncology, vol. 97, Issue 37, Sep. 23, 2019.
Kessler et al., "Drugging and undruggable pocket on KRAS", PNAS, p. 1-7, www.pnas.org/cgi/doi/10.1073/pnas.1904529116.
Rajitha et al., "Synthesis and pharmacological evaluations of novel 2H-benzo[b](1,4)oxazin3(4H)-one derivatives as a new class of anti-cncer agents", European Journal of Medicinal Chemistry, 2011, vol. 46, pp. 4887-4896, Table 1.

KRAS G12C INHIBITORS

CROSS REFERENCE

This application claims benefit of priority under 35 U.S.C. § 120 from U.S. application Ser. No. 16/191,190, filed Nov. 14, 2018, which claims priority under 35 U.S.C. § 119 (e) to U.S. Provisional Application No. 62/586,775, filed Nov. 15, 2017, and the entire content of each of these applications is hereby incorporated by reference in their entirety.

FIELD OF THE INVENTION

The present invention relates to compounds that inhibit KRas G12C. In particular, the present invention relates to compounds that irreversibly inhibit the activity of KRas G12C, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRAs in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

Thus, there is a need to develop new KRas G12C inhibitors that demonstrate sufficient efficacy, stability and/or safety for treating KRas G12C-mediated cancer.

SUMMARY OF THE INVENTION

In one aspect of the invention, compounds are provided that inhibit KRas G12C activity. In certain embodiments, the compounds are represented by Formula (II):

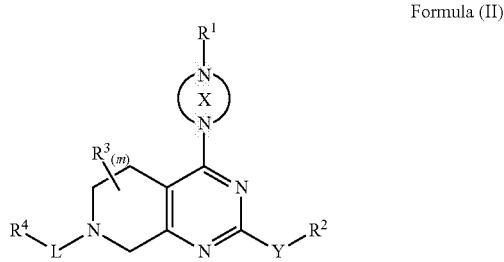

Formula (II)

or a pharmaceutically acceptable salt thereof:
wherein:
X is a 4-12 membered saturated or partially saturated monocyclic, bridged or spirocyclic ring, wherein the saturated or partially saturated monocyclic ring is optionally substituted with one or more $R^8$;
Y is a bond, O, S or $NR^5$;
$R^1$ is $-C(O)C(R^A)$═$C(R^B)_p$ or $-SO_2C(R^A)$═$C(R^B)_p$;
$R^2$ is hydrogen, alkyl, haloalkyl, hydroxyalkyl, dihydroxyalkyl, alkylaminylalkyl, dialkylaminylalkyl, $-Z-NR^5R^{10}$, heterocyclyl, cycloalkyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;
each Z is C1-C4 alkylene;
each $R^3$ is independently C1-C3 alkyl, oxo, haloalkyl, hydroxyl or halogen;
L is a bond, $-C(O)-$, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;
each $R^5$ is independently hydrogen or C1-C3 alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;
$R^8$ is oxo, C1-C3 alkyl, C2-C4 alkynyl, heteroalkyl, cyano, $-C(O)OR^5$, $-C(O)N(R^5)_2$, $-N(R^5)_2$, wherein the C1-C3 alkyl may be optionally substituted with cyano, halogen, $-OR^5$, $-N(R^5)_2$, or heteroaryl;
each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, amino, dialkylaminyl, dialkylamidoalkyl, dialkylaminylalkyl or oxo, wherein the C1-C6 alkyl may be optionally substituted with cycloalkyl or cyano;
each $R^{10}$ is independently hydrogen, acyl, C1-C3 alkyl, haloalkyl, heteroalkyl or hydroxyalkyl;
$R^{11}$ is haloalkyl;
$R^A$ is absent, hydrogen, deuterium, cyano, halogen, C1-C-3 alkyl, haloalkyl, heteroalkyl, $-C(O)N(R^5)_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —$ZNR^5R^{11}$, —$C(O)N(R^5)_2$, —NHC(O) C1-C3 alkyl, —$CH_2NHC(O)$C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

or when ═══ is a double bond and p is two, one $R^B$ is hydrogen and $R^A$ and one $R^B$ and the carbon atoms to which they are attached form a 5-8 membered partially saturated cycloalkyl substituted with oxo;

m is zero or an integer between 1 and 2;

p is one or two; and wherein, when ═══ is a triple bond then $R^A$ is absent, p equals one and $R^B$ is hydroxyalkyl, or when ═══ is a double bond then $R^A$ is present, $R^B$ is present and p equals two, wherein when $R^A$ is hydrogen or C1-C3 alkyl at least one $R^B$ is deuterium, cyano, halogen, haloalkyl, hydroxyalkyl, heteroalkyl, heteroaryl, heteroarylalkyl, —$ZNR^5R^{11}$, —$C(O)N(R^5)_2$, —NHC(O)C1-C3 alkyl, —$CH_2NHC(O)$C1-C3 alkyl or heterocyclylalkyl, wherein the heterocyclyl portion is substituted with one or more substituents independently selected from halogen, hydroxyl, alkoxy or C1-C3 alkyl; or when each $R^B$ is hydrogen, then $R^A$ is deuterium, cyano, halogen, haloalkyl, —$C(O)N(R^5)_2$, hydroxyalkyl or heteroalkyl.

Also included are compounds of Formula (II) having the Formula II-A:

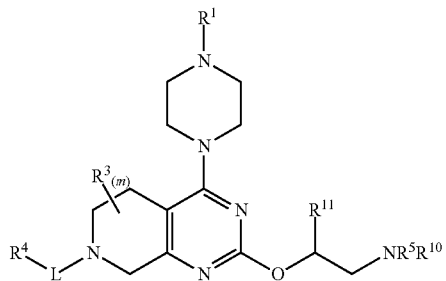

Formula II-A wherein $R^1$, $R^3$, $R^4$, $R^5$, $R^{10}$, L and m are as defined for Formula II, $R^{11}$ is hydrogen, C1-C3 alkyl or hydroxyalkyl, and the piperazinyl ring is optionally substituted with $R^8$ wherein $R^8$ is as defined for Formula II.

Also included are compounds of Formula (II) having the Formula II-B:

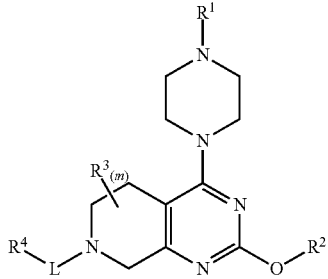

Formula II-B where $R^1$, $R^3$, $R^4$, $R^8$, L and m are as defined for Formula II, $R^2$ is heterocyclylalkyl optionally substituted with one or more $R^9$, and the piperazinyl ring is optionally substituted with $R^8$, where $R^8$ is as defined for Formula II.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12C activity in a in a cell, comprising contacting the cell with a compound of Formula (II), Formula II-A or Formula II-B. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (Ii), Formula II-A, or Formula II-B, or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12C-associated disease or disorder in a patient in need of such treatment, the method comprising administering to the patient a therapeutically effective amount of a compound of Formula (II), Formula II-A, or Formula II-B, or a pharmaceutically acceptable salt or solvate thereof, or a pharmaceutical composition thereof as defined herein.

Also provided herein is a compound of Formula (II), Formula II-A, or Formula II-B, or a pharmaceutically acceptable salt or solvate thereof, or a pharmaceutical composition thereof as defined herein for use in therapy.

Also provided herein is a compound of Formula (II), Formula II-A, or Formula II-B, or a pharmaceutically acceptable salt or solvate thereof or a pharmaceutical composition thereof as defined herein for use in the treatment of cancer.

Also provided herein is a compound of Formula (II), Formula II-A, or Formula II-B, or a pharmaceutically acceptable salt or solvate thereof for use in the inhibition of KRas G12C.

Also provided herein is a compound of Formula (II), Formula II-A, or Formula II-B, or a pharmaceutically acceptable salt or solvate thereof or a pharmaceutical composition thereof as defined herein, for use in the treatment of a KRas G12C-associated disease or disorder.

Also provided herein is the use of a compound of Formula (II), Formula II-A, or Formula II-B, or a pharmaceutically acceptable salt or solvate thereof, as defined herein in the manufacture of a medicament for the treatment of cancer.

Also provided herein is a use of a compound of Formula (II), Formula II-A, or Formula II-B, or a pharmaceutically acceptable salt or solvate thereof, as defined herein in the manufacture of a medicament for the inhibition of activity of KRas G12C.

Also provided herein is the use of a compound of Formula (II), Formula II-A, or Formula II-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that the cancer is associated with a KRas G12C mutation (i.e., a KRas G12C-associated cancer); and (b) administering to the patient a therapeutically effective amount of a compound of Formula (II), Formula II-A, or Formula II-B, or a pharmaceutically acceptable salt thereof, or a pharmaceutical composition thereof.

Also provided herein is a process for preparing a compound of Formula (II), Formula II-A, or Formula II-B, or a pharmaceutically acceptable salt or solvate thereof.

Also provided herein is a compound of Formula (II), Formula II-A, or Formula II-B, or a pharmaceutically acceptable salt thereof obtained by a process of preparing the compound as defined herein.

DETAILED DESCRIPTION OF THE INVENTION

The present invention relates to inhibitors of KRas G12C. In particular, the present invention relates to compounds that irreversibly inhibit the activity of KRas G12C, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by Formula (II), Formula II-A, or Formula II-B as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

In some embodiments of any of the methods or uses described herein, an assay is used to determine whether the patient has KRas G12C mutation using a sample (e.g., a biological sample or a biopsy sample (e.g., a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to —NH$_2$;

The term "acyl" refers to —C(O)CH$_3$.

The term "alkyl" as employed herein refers to straight and branched chain aliphatic groups having from 1 to 12 carbon atoms, 1-8 carbon atoms 1-6 carbon atoms, or 1-3 carbon atoms which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain in which one or more hydrogen has been replaced by a halogen. Examples of haloalkyls are trifluoromethyl, difluoromethyl and fluoromethyl.

The term "haloalkyloxy" refers to —O-haloalkyl.

An "alkylene," group is an alkyl group, as defined hereinabove, that is positioned between and serves to connect two other chemical groups. Exemplary alkylene groups include, without limitation, methylene, ethylene, propylene, and butylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

The term "heteroalkyl" refers to an alkyl group, as defined hereinabove, wherein one or more carbon atoms in the chain are replaced by a heteroatom selected from the group consisting of O, S, and N.

As used herein, the term "hydroxyalkyl" refers to -alkyl-OH.

The term "dihydroxyalkyl" refers to an alkyl group as defined herein wherein two carbon atoms are each substituted with a hydroxyl group.

The term "alkylaminyl" refers to —$NR^x$-alkyl, wherein $R^x$ is hydrogen. In one embodiment, $R^x$ is hydrogen.

The term "dialkylaminyl" refers to —$N(R^y)_2$, wherein each $R^y$ is C1-C3 alkyl.

The term "alkylaminylalkyl" refers to -alkyl-$NR^x$-alkyl, wherein $R^x$ is hydrogen. In one embodiment, $R^x$ is hydrogen.

The term "dialkylaminylalkyl" refers to -alkyl-$N(R^y)_2$, wherein each $R^y$ is C1-C4 alkyl, wherein the alkyl of the-alkyl-$N(R^y)_2$ may be optionally substituted with hydroxy or hydroxyalkyl.

An "aryl" group is a $C_6$-$C_{14}$ aromatic moiety comprising one to three aromatic rings, which is optionally substituted. As one embodiment, the aryl group is a $C_6$-$C_{10}$ aryl group. Examples of aryl groups include, without limitation, phenyl, naphthyl, anthracenyl, fluorenyl, and dihydrobenzofuranyl.

An "aralkyl" or "arylalkyl" group comprises an aryl group covalently linked to an alkyl group, either of which may independently be optionally substituted or unsubstituted. An example of an aralkyl group is $(C_1$-$C_6)$alkyl$(C_6$-$C_{10})$aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with $R^7$ on ring carbon or ring nitrogen at one or more positions, wherein $R^7$ is as defined for Formula II. The heterocyclic group is also independently optionally substituted on a ring nitrogen atom with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanes, azabicycloheptanes, azabicyclooctanes, azabicyclononanes (e.g., octahydroindolizinyl), azaspiroheptanes, dihydro-1H,3H,5H-oxazolo[3,4-c]oxazolyl, tetrahydro-1'H, 3'H-spiro[cyclopropane-1,2'-pyrrolizine], hexahydro-1H-pyrrolo[2,1-c][1,4]oxazine, octahydroindolizinyl, oxaazaspirononanes, diazaspirononanes, and oxa azabicycloheptanes. Specifically excluded from the scope of this term are compounds having adjacent annular 0 and/or S atoms The term "heterocyclylalkyl" refers to a heterocyclyl group as defined herein linked to the remaining portion of the molecule via an alkyl group as defined herein, wherein the alkyl portion of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group as defined herein, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein, "an effective amount" of a compound is an amount that is sufficient to negatively modulate or inhibit the activity of KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by Formula (II):

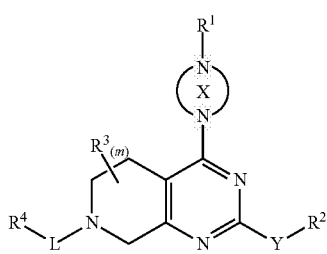

Formula (II)

or a pharmaceutically acceptable salt thereof:
wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is $-C(O)C(R^A)\!=\!\!=\!\!=\!C(R^B)_p$ or $-SO_2C(R^A)\!=\!\!=\!\!=\!C(R^B)_p$;

$R^2$ is hydrogen, alkyl, haloalkyl, hydroxyalkyl, dihydroxyalkyl, alkylaminylalkyl, dialkylaminylalkyl, $-Z-NR^5R^{10}$, heterocyclyl, cycloalkyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

each Z is C1-C4 alkylene;

each $R^3$ is independently C1-C3 alkyl, oxo, haloalkyl, hydroxyl or halogen;

L is a bond, $-C(O)-$, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, $-C(O)OR^5$, $-C(O)N(R^5)_2$, $-N(R^5)_2$, wherein the C1-C3 alkyl may be optionally substituted with cyano, halogen, $-OR^5$, $-N(R^5)_2$, or heteroaryl;

each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl or cyano;

each $R^{10}$ is independently hydrogen, acyl, C1-C3 alkyl, haloalkyl, heteroalkyl or hydroxyalkyl;

$R^{11}$ is haloalkyl;

$R^A$ is absent, hydrogen, deuterium, cyano, halogen, C1-C3 alkyl, haloalkyl, heteroalkyl, $-C(O)N(R^5)_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, $-ZNR^5R^{11}$, $-C(O)N(R^5)_2$, $-NHC(O)$ C1-C3 alkyl, $-CH_2NHC(O)$C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

or when $=\!\!=\!\!=$ is a double bond and p is two, one $R^B$ is hydrogen and $R^A$ and one $R^B$ and the carbon atoms to which they are attached form a 4-8 membered partially saturated cycloalkyl substituted with oxo;

m is zero or an integer between 1 and 2;

p is one or two; and wherein, when $=\!\!=\!\!=$ is a triple bond then $R^A$ is absent, p equals one and $R^B$ is hydroxyalkyl, or when $=\!\!=\!\!=$ is a double bond then $R^A$ is present, $R^B$ is present and p equals two, wherein when $R^A$ is hydrogen or C1-C3 alkyl, at least one $R^B$ is deuterium, cyano, halogen, haloalkyl, hydroxyalkyl, heteroalkyl, heteroaryl, heteroarylalkyl, $-ZNR^5R^{11}$, $-C(O)N(R^5)_2$, $-NHC(O)$C1-C3 alkyl, $-CH_2NHC(O)$C1-C3 alkyl or heterocyclylalkyl, wherein the heterocyclyl portion is substituted with one or more substituents independently selected from halogen, hydroxyl, alkoxy and C1-C3 alkyl; or when each $R^B$ is hydrogen, then $R^A$ is deuterium, cyano, halogen, haloalkyl, $-C(O)N(R^5)_2$, hydroxyalkyl or heteroalkyl.

In certain embodiments, $R^1$—X is:

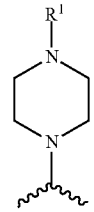

wherein $R^1$ is are defined for Formula (II) and the piperazinyl ring is optionally substituted with $R^8$, where $R^8$ is as defined for Formula (II). In certain embodiments, $R^8$ is C1-C3 alkyl wherein the alkyl is optionally substituted with cyano or $OR^5$, or $-C(O)N(R^5)_2$, wherein each $R^5$ is independently hydrogen or C1-C3 alkyl.

In particular embodiments, $R^1$ is $-C(O)C(R^A)\!=\!\!=\!\!=\!C(R^B)_p$ where $R^A$, $R^B$ and p are as defined for Formula (II). In one embodiment, $R^1$ is $-C(O)C(R^A)\!=\!\!=\!\!=\!C(R^B)_p$, wherein $=\!\!=\!\!=$ is a triple bond and $R^A$ is absent, p is one and $R^B$ is hydroxyalkyl.

In one embodiment, $R^1$ is $-C(O)C(R^A)\!=\!\!=\!\!=\!C(R^B)_p$, wherein $=\!\!=\!\!=$ is a double bond and $R^A$ is hydrogen or C1-C3 alkyl, p is two and at least one $R^B$ is deuterium, cyano, C1-C3 alkyl, hydroxyalkyl, heteroalkyl, C1-C3 alkoxy, halogen, haloalkyl, $-ZNR^5R^{11}$, $-C(O)N(R^5)_2$, $-NHC(O)$C1-C3 alkyl, $-CH_2NHC(O)$C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$. In one embodiment, when $=\!\!=\!\!=$ is a double bond, the double bond is in the E configuration. In one embodiment, the double bond is in the Z configuration.

In certain embodiments, one $R^B$ is heterocyclylalkyl substituted with one or more substituents independently selected from halogen, hydroxyl, alkoxy or C1-C3 alkyl and the other $R^B$ is hydrogen. In one embodiment, the heterocyclyl portion of the heterocyclylalkyl is azetidinyl substituted with a halogen. In certain embodiments, the halogen is fluorine. In one embodiment, the heterocyclyl portion of the heterocyclylalkyl is pyrrolidinyl substituted with one or more halogen. In certain embodiments, the halogen-substituted pyrrolidinyl is fluoropyrrolidinyl or difluorpyrrolidinyl.

In certain embodiments, one $R^B$ is halogen and the other $R^B$ is hydrogen. In one embodiment, the halogen is chlorine.

In certain embodiments, one $R^B$ is haloalkyl and the other $R^B$ is hydrogen. In one embodiment, the haloalkyl is chloromethyl, fluoromethyl, difluoromethyl or trifluoromethyl.

In certain embodiments, one $R^B$ is heteroalkyl and the other $R^B$ is hydrogen. In one embodiment, the heteroalkyl is methoxymethyl.

In certain embodiments, one $R^B$ is —$ZNR^5R^{11}$, wherein Z is methylene, $R^5$ is methyl and $R^{11}$ is trifluoromethyl or 2,2,2-trifluoroethyl, and the other $R^B$ is hydrogen.

In certain embodiments, one $R^B$ is hydroxyalkyl and the other $R^B$ is hydrogen.

In certain embodiments, one $R^B$ is heteroaryl optionally substituted with one or more $R^7$ and the other $R^B$ is hydrogen. In one embodiment, the heteroaryl is pyrrolyl, imidazolyl, pyrazolyl, triazolyl, pyridyl, pyridazinyl, pyrimidinyl, pyrazinyl or triazinyl, each substituted with one or more $R^7$.

In certain embodiments, one $R^B$ is heteroarylalkyl optionally substituted with one or more $R^7$, and the other $R^B$ is hydrogen. In one embodiment, the heteroaryl portion of the heteroarylalkyl is pyrrolyl, imidazolyl, pyrazolyl, triazolyl, pyridyl, pyridazinyl, pyrimidinyl, pyrazinyl or triazinyl, each optionally substituted with one or more $R^7$. In one embodiment, the one or more $R^7$ is C1-C3 alkyl.

In certain embodiments, one $R^B$ is —$C(O)N(R^5)_2$ and the other $R^B$ is hydrogen. In one embodiment, each $R^5$ is hydrogen. In one embodiment, each $R^5$ is C1-C3 alkyl.

In certain embodiments, one $R^B$ is —NHC(O)C1-C3 alkyl or —$CH_2$NHC(O)C1-C3 alkyl and the other $R^B$ is hydrogen. In one embodiment, the C1-C3 alkyl is methyl.

In one embodiment, $R^1$ is —$C(O)C(R^A)\!\!=\!\!C(R^B)_p$, wherein $R^A$ is deuterium, cyano, halogen, C1-C-3 alkyl, haloalkyl, heteroalkyl, —$C(O)N(R^5)_2$, or hydroxyalkyl, p is two, each $R^B$ is hydrogen. In one embodiment, $R^A$ is halogen. In one embodiment, the halogen is fluorine or chlorine. In one embodiment, $R^A$ is haloalkyl. In one embodiment, the haloalkyl is trifluoromethyl. In one embodiment, $R^A$ is cyano. In one embodiment, $R^A$ is heteroalkyl. In one embodiment, the heteroalkyl is methoxy. In one embodiment, $R^A$ is hydroxyalkyl.

In one embodiment, $R^1$ is —$C(O)C(R^A)\!\!=\!\!C(R^B)_p$, wherein $=\!\!=$ is a double bond and $R^A$ is deuterium, p is two and at least one $R^B$ is deuterium.

In one embodiment, $R^1$ is —$C(O)C(R^A)\!\!=\!\!(R^B)_p$, wherein $=\!\!=$ is a double bond and p is two, one $R^B$ is hydrogen and $R^A$ and one $R^B$ and the carbon atoms to which they are attached form a 5-8 membered partially saturated cycloalkyl substituted with oxo.

In one embodiment, $R^1$ is —$C(O)C(R^A)\!\!=\!\!C(R^B)_p$, wherein $=\!\!=$ is a double bond and p is two, one $R^B$ is hydrogen, the second $R^B$ is dialkylaminylalkyl, and $R^A$ is halogen In one embodiment, Y is O or $NR^5$ and $R^2$ is heterocyclyl or heterocyclylalkyl optionally substituted with one or more $R^9$. Nonlimiting examples of one or more $R^9$ when $R^2$ is heterocyclyl or heterocyclylalkyl include C1-C3 alkyl, acyl, oxo, cyano, alkoxy, cycloalkyl, cycloalkylmethyl, halogen, and hydroxyl. Nonlimiting examples of $R^2$ heterocyclyls optionally substituted with one or more $R^9$ include azetidinyl, C1-C3 alkyl-substituted azetidinyl (e.g., methylazetidinyl), halo-substituted azetidinyl (e.g., difluoroazetidinyl), tetrahydropyran, pyrrolidinyl, C1-C3 alkyl-substituted pyrrolidinyl (e.g., methylpyrrolidinyl, dimethylpyrrolidinyl, and isopropylpyrrolidinyl), cycloalkylalkylpyrrolidinyl, hydroxypyrrolindinyl, halo-substituted pyrrolidinyl (e.g., fluoropyrrolidinyl and difluoropyrrolidinyl), halo-substituted N-methylpyrrolidinyl (e.g., N-methylfluoropyrrolidinyl and N-methyldifluoropyrrolidinyl), methoxyethylpyrrolidinyl, alkoxy-substituted N-methylpyrrolidinyl (e.g., (N-methyl)methoxypyrrolidinyl), piperazinyl, dimethylaminylpyrrolidinyl, morpholinyl, methylmorpholinyl, 1,4-oxazepanyl, piperidinyl, C1-C3 alkyl-substituted piperidinyl (e.g., methylpiperidinyl), acylpiperidinyl, cyanopiperidinyl, cycloalkylpiperidinyl, halopiperidinyl (e.g., fluoropiperidinyl), dihalopiperidinyl (e.g., difluoropiperidinyl), alkoxypiperidinyl, pyrrolidonyl, piperidonyl, thiomorpholinyl-1,1-dioxide, 3-azabicyclo[3.1.0]hexanyl, oxa-5-azabicyclo[2.2.1]heptan-5-yl, and azabicyclo[2.2.1]heptan-2-yl.

In one embodiment, the heterocyclyl portion of the heterocyclylalkyl is N-methylpyrrolidinyl. In one embodiment, the heterocyclyl portion of the heterocyclylalkyl is 3,3-difluoro-1-methylpyrrolidinyl.

In certain other embodiments, $R^4$ is aryl. In one embodiment, $R^4$ is selected from the group consisting of phenyl and naphthyl and is optionally substituted with one or more $R^6$ or $R^7$. Examples of $R^7$ substituents include halogen, hydroxyl, C1-C6 alkyl (e.g., C1-C3 alkyl), cycloalkyl, haloalkyl, Q-haloalkyl, amino, cyano, hydroxyalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, hydroxyl, fluoro, and chloro. In one embodiment, the aryl is phenyl substituted with one to three $R^7$ groups independently selected from methyl, hydroxyl, trifluoromethyl, fluorine and chlorine. In one embodiment, the aryl is phenyl substituted with hydroxyl and C1-C3 alkyl or two C1-C3 alkyl. In one embodiment, the aryl is phenyl substituted with trifluoromethyl and C1-C3 alkyl or two C1-C3 alkyl.

In one embodiment, $R^4$ is aryl wherein aryl is naphthyl optionally substituted with one or more $R^7$. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more R⁷ substituents independently selected from hydroxyl, halogen, C1-C3 alkyl, amino, and haloalkyl. In one embodiment, R⁴ is naphthyl optionally substituted with one to three R⁷ substituents independently selected from difluoromethyl, methyl, hydroxyl, amino, fluoro, and chloro. In one embodiment, the substituted naphthyl is 8-chloronaphthyl or 8-methylnaphthyl.

In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl.

In one embodiment, R⁴ is heteroaryl optionally substituted with one or more R⁶, R⁷ or R⁸. In one embodiment, R⁴ is heteroaryl optionally substituted with one or more R⁷ or R⁸ independently selected from halogen, hydroxyl, C3 alkyl, haloalkyl, Q-haloalkyl, alkoxy and amino. In one embodiment, R⁴ is indoyl, indazolyl, quinolinyl, isoquinolinyl, pyridinyl or benzo[d]thiazolyl optionally substituted with one or more R⁶, R⁷ or R⁸. In one embodiment, R⁴ is indoyl, indazolyl, quinolinyl, isoquinolinyl, pyridinyl or benzo[d]thiazolyl optionally substituted with one or more R⁷ or R⁸ independently selected from oxo, halogen, hydroxyl, C1-C3 alkyl, haloalkyl, Q-haloalkyl, alkoxy and amino.

In yet other embodiments, R⁴ is heteroaryl, optionally an indoyl or an indazolyl, each of which may be substituted with one or more R⁶, R⁷ or R⁸. In one embodiment, R⁴ is heteroaryl optionally substituted with one or more R⁷ or R⁸ substituents independently selected from the group consisting of halogen, hydroxyl, C3 alkyl, haloalkyl, Q-haloalkyl and alkoxy. In one embodiment, the R⁴ heteroaryl is indazolyl optionally substituted with one or two R⁷ or R⁸ independently selected from oxo, trifluoromethyl, alkoxy, haloalkyl, and C1-C6 alkyl. In other embodiments, the R⁴ heteroaryl is a quinolinyl or isoquinolinyl, each optionally substituted with one or more R⁷. In one embodiment, the R⁴ heteroaryl is a quinolinyl or isoquinolinyl, each optionally substituted with one or more R⁷ independently selected from amino, hydroxyl, C1-C3 alkyl, and hydroxyl. In one embodiment, the R⁴ heteroaryl is a quinolinyl or isoquinolinyl, each optionally substituted with R⁷ selected from hydroxyl and amino. In one embodiment, the R⁴ heteroaryl is a pyridinyl optionally substituted with one or more R⁶, R⁷ or R⁸. In one embodiment, the R⁴ heteroaryl is pyridinyl optionally substituted with one or more R⁷ independently selected from C1-C3 alkyl, halogen and haloalkyl. In one embodiment, the R⁴ heteroaryl is indolyl optionally substituted with one or more R⁶, R⁷ or R⁸. In one embodiment, the R⁴ heteroaryl is indolyl optionally substituted with one or two R⁷ independently selected from hydroxyl, trifluoromethyl and C1-C3alkyl.

In one embodiment, Lisa bond.

In one embodiment, m is zero.

In one embodiment, R⁸ is heteroalkyl, C2-C4 alkynyl or C1-C3 alkyl optionally substituted with —OR⁵, cyano or heteroaryl. In one embodiment, R⁸ is methyl, cyanomethyl, methoxymethyl, hydroxymethyl. In one embodiment, R⁸ is methyl. In one embodiment, R⁸ is cyanomethyl. In one embodiment, R⁸ is hydroxymethyl.

In one embodiment, Formula (II) includes compounds having the Formula II-A:

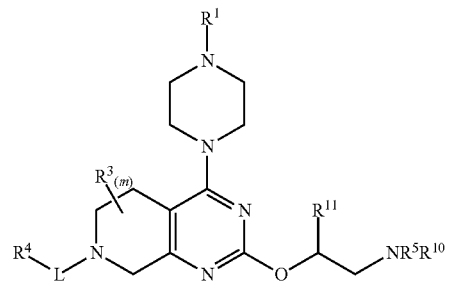

Formula II-A wherein R¹, R³, R⁴, R⁵, R¹⁰, L and m are as defined for Formula (II), R¹¹ is hydrogen, methyl or hydroxyalkyl, and the piperazinyl ring is optionally substituted with R⁸ wherein R⁸ is as defined for Formula (II).

In particular embodiments, R¹ is —C(O)C(R$^A$)═══C(R$^B$)$_p$ where R$^A$, R$^B$ and p are as defined for Formula (II). In one embodiment, R¹ is —C(O)C(R$^A$)═══C(R$^B$)$_p$, wherein ═══ is a triple bond and R$^A$ is absent, p is one and R$^B$ is hydroxyalkyl.

In one embodiment, R¹ is —C(O)C(R$^A$)═══C(R$^B$)$_p$, wherein ═══ is a double bond and R$^A$ is hydrogen or C1-C3 alkyl, p is two and at least one R$^B$ is deuterium, cyano, C1-C3 alkyl, hydroxyalkyl, heteroalkyl, C1-C3 alkoxy, halogen, haloalkyl, —ZNR⁵R¹¹, —C(O)N(R⁵)₂, —NHC(O)C1-C3 alkyl, —CH₂NHC(O)C1-C3 alkyl, heteroaryl, heteroarylalkyl, or heterocyclylalkyl wherein the heterocyclyl portion is substituted with one or more substituents independently selected from halogen, hydroxyl, alkoxy and C1-C3 alkyl, wherein the heteroaryl or the heteroarylalkyl portion of the heteroarylalkyl is optionally substituted with one or more R⁷.

In one embodiment, R¹ is —C(O)C(R$^A$)═C(R$^B$)$_p$, wherein R$^A$ is deuterium, cyano, halogen, haloalkyl, heteroalkyl, —C(O)N(R⁵)₂, or hydroxyalkyl, p is two, and each R$^B$ is hydrogen. In one embodiment, R$^A$ is halogen. In one embodiment, the halogen is fluorine or chlorine. In one embodiment, R$^A$ is haloalkyl. In one embodiment, the haloalkyl is trifluoromethyl. In one embodiment, R$^A$ is cyano. In one embodiment, R$^A$ is heteroalkyl. In one embodiment, the heteroalkyl is methoxymethyl. In one embodiment, R$^A$ is hydroxyalkyl.

In one embodiment, R¹ is —C(O)C(R$^A$)═══C(R$^B$)$_p$, wherein ═══ is a double bond and R$^A$ is deuterium, p is two and at least one R$^B$ is deuterium.

In one embodiment, R¹ is —C(O)C(R$^A$)═══C(R$^B$)$_p$, wherein ═══ is a double bond and p is two, one R$^B$ is hydrogen and R$^A$ and one R$^B$ and the carbon atoms to which they are attached form a 5-8 membered partially saturated cycloalkyl substituted with oxo.

In one embodiment, R¹ is —C(O)C(R$^A$)═══C(R$^B$)$_p$, wherein ═══ is a double bond and p is two, one R$^B$ is hydrogen, the second R$^B$ is dialkylaminylalkyl, and R$^A$ is halogen.

In one embodiment, L is a bond. In one embodiment, R⁴ is aryl or heteroaryl, each of which is optionally substituted with one or more R⁶, R⁷ or R⁸. In one embodiment, R⁴ is aryl or heteroaryl, each of which is optionally substituted with one or more IC. In one embodiment, each R⁷ or R⁸ is independently selected from oxo, hydroxyl, amino, halogen, C1-C3 alkyl, haloalkyl, Q-haloalkyl, cycloalkyl and alkoxy. In one embodiment, $R^5$ and $R^{10}$ are each C1-C3 alkyl. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ or $R^8$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl. In one embodiment, $R^4$ is heteroaryl, wherein the heteroaryl is indazolyl optionally substituted with one or two $R^7$ or $R^8$ independently selected from oxo, alkoxy, haloalkyl, and C1-C6 alkyl. In one embodiment, $R^4$ is heteroaryl, wherein the heteroaryl is quinolinyl or isoquinolinyl, each optionally substituted with one or more $R^7$. In one embodiment, $R^4$ is heteroaryl, wherein the heteroaryl is quinolinyl or isoquinolinyl, each optionally substituted with one or more $R^7$ independently selected from amino, hydroxyl, C1-C3alkyl, and hydroxyl. In one embodiment, the $R^4$ heteroaryl is a pyridinyl optionally substituted with one or more $R^6$, $R^7$ or $R^8$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is indolyl optionally substituted with one or more $R^7$. In one embodiment, the $R^4$ heteroaryl is indolyl optionally substituted with one or two $R^7$ independently selected from hydroxyl and C1-C3alkyl. In one embodiment, $R^{11}$ is methyl. In one embodiment, the piperazinyl ring is unsubstituted. In one embodiment, the piperazinyl ring is substituted with $R^8$. In one embodiment, $R^8$ is C1-C3 alkyl optionally substituted with cyano or hydroxyl. In one embodiment, $R^8$ is methyl, cyanomethyl or hydroxymethyl. In one embodiment, $R^8$ is methyl. In one embodiment, $R^8$ is cyanomethyl. In one embodiment, $R^8$ is hydroxymethyl. In another embodiment, $R^5$ and $R^{10}$ are each C1-C3 alkyl, $R^{11}$ is methyl, $R^8$ is methyl, cyanomethyl or hydroxymethyl, L is a bond, and $R^4$ is aryl or heteroaryl, each optionally substituted with one or more $R^6$ or $R^7$.

In one embodiment, Formula (II) includes compounds having the Formula II-B:

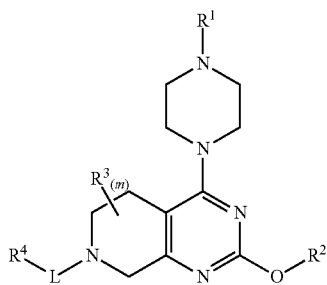

Formula II-B where $R^1$, $R^3$, $R^4$, L and m are as defined for Formula (II), $R^2$ is heterocyclylalkyl optionally substituted with one or more $R^9$ wherein $R^9$ is as defined for Formula (II), and the piperazinyl ring is optionally substituted with $R^8$, where $R^8$ is as defined for Formula (II).

In particular embodiments, $R^1$ is —C(O)C($R^A$)═C($R^B$)$_p$ where $R^A$, $R^B$ and p are as defined for Formula (II). In one embodiment, $R^1$ is —C(O)C($R^A$)═C($R^B$)$_p$, wherein ═ is a triple bond and $R^A$ is absent, p is one and $R^B$ is hydroxyalkyl.

In one embodiment, $R^1$ is —C(O)C($R^A$)═C($R^B$)$_p$, wherein ═ is a double bond and $R^A$ is hydrogen or C1-C3 alkyl, p is two and at least one $R^B$ is deuterium, cyano, C1-C3 alkyl, hydroxyalkyl, heteroalkyl, C1-C3 alkoxy, halogen, haloalkyl, —ZN$R^5R^{11}$, —C(O)N($R^5$)$_2$, —NHC(O)C1-C3 alkyl, —CH$_2$NHC(O)C1-C3 alkyl, heteroaryl, heteroarylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$.

In one embodiment, $R^1$ is —C(O)C($R^A$)═C($R^B$)$_p$, wherein $R^A$ is deuterium, cyano, halogen, haloalkyl, heteroalkyl, —C(O)N($R^5$)$_2$, or hydroxyalkyl, p is two, and each $R^B$ is hydrogen. In one embodiment, $R^A$ is halogen. In one embodiment, the halogen is fluorine or chlorine. In one embodiment, $R^A$ is haloalkyl. In one embodiment, the haloalkyl is trifluoromethyl. In one embodiment, $R^A$ is cyano. In one embodiment, $R^A$ is heteroalkyl. In one embodiment, the heteroalkyl is methoxymethyl. In one embodiment, $R^A$ is hydroxyalkyl.

In one embodiment, $R^1$ is —C(O)C($R^A$)═C($R^B$)$_p$, wherein ═ is a double bond and $R^A$ is deuterium, p is two and at least one $R^B$ is deuterium.

In one embodiment, $R^1$ is —C(O)C($R^A$)═C($R^B$)$_p$, wherein ═ is a double bond and p is two, one $R^B$ is hydrogen and $R^A$ and one $R^B$ and the carbon atoms to which they are attached form a 5-8 membered partially saturated cycloalkyl substituted with oxo.

In one embodiment, $R^1$ is —C(O)C($R^A$)═C($R^B$)$_p$, wherein ═ is a double bond and p is two, one $R^B$ is hydrogen, the second $R^B$ is dialkylaminylalkyl, and $R^A$ is halogen.

In one embodiment, the heterocyclyl portion of the $R^2$ heterocyclylalkyl is a monocyclic, bicyclic, or bridged ring system having one or two ring heteroatoms independently selected from N and O. In one embodiment, $R^2$ heterocyclyl is azetidinyl, methylazetidinyl, difluoroazetidinyl, tetrahydropyran, pyrrolidinyl, methylpyrrolidinyl, diemethylpyrrolidinyl, isopropylpyrrolidinyl, cycloalkylalkylpyrrolidinyl, hydroxypyrrolindinyl, fluoropyrrolidinyl, difluoropyrrolidinyl, (N-methyl)fluoropyrrolidinyl, (N-methyl)difluoropyrrolidinyl, methoxyethylpyrrolidinyl, alkoxy-substituted N-methylpyrrolidinyl (e.g., (N-methyl)methoxypyrrolidinyl), piperazinyl, dimethylaminylpyrrolidinyl, morpholinyl, methylmorpholinyl, 1,4-oxazepanyl, piperidinyl, methylpiperidinyl acylpiperidinyl, cyanopiperidinyl, cycloalkylpiperidinyl, halopiperidinyl, dihalopiperidinyl, fluoropiperidinyl, difluoropiperidinyl, alkoxypiperidinyl, pyrrolidonyl, piperidinonyl, thiomorpholinyl-1,1-dioxide, 3-azabicyclo[3.1.0]hexanyl, oxa-5-azabicyclo[2.2.1]heptan-5-yl, or azabicyclo[2.2.1]heptan-2-yl, optionally substituted with one or more $R^9$. In one embodiment, each $R^9$ is selected from acyl, oxo, halogen, cyano, C1-C3 alkyl, alkoxy, hydroxyalkyl, heteroalkyl, cycloalkyl, heterocyclyl, aralkyl and dialkylamidoalkyl. In one embodiment, L is a bond. In one embodiment, the heterocyclyl portion of the $R^2$ heterocyclylalkyl is (N-methyl)difluoropyrrolidinyl, including 3,3-difluoro-1-methylpyrrolidinyl. In one embodiment, the heterocyclyl portion of the $R^2$ heterocyclylalkyl is N-methylpyrrolidinyl.

In one embodiment of Formula II-B, $R^2$ is a bicyclic heterocyclyl optionally substituted with one or more $R^9$ substituents. In one embodiment of Formula II-B, $R^2$ is a bicyclic heterocyclyl having a bridgehead nitrogen atom and optionally substituted with one or more $R^9$ substituents. In one embodiment, $R^2$ is a bicyclic heterocyclyl having a bridgehead nitrogen atom and optionally substituted with one or more $R^9$ substituents independently selected from halogen, C1-C6 alkyl, haloalkyl, heteroalkyl, hydroxyalkyl and oxo. In one embodiment of Formula II-B, $R^2$ is a bicyclic heterocyclyl selected from hexahydro-1H-pyrrolizinyl and octahydroindolizinyl, each of which is optionally substituted with one or more $R^9$ substituents independently selected from halogen, C1-C6 alkyl, haloalkyl, heteroalkyl, hydroxyalkyl and oxo.

In one embodiment of Formula II-B, $R^1$ is —C(O)C($R^A$)=C($R^B$)$_p$, wherein $R^A$ is halogen, one $R^B$ is hydrogen, and the other $R^B$ is hydrogen, haloalkyl or heteroalkyl; the piperazinyl ring is substituted with one $R^8$ wherein $R^8$ is C1-C3 alkyl substituted with cyano; L is a bond; $R^4$ is aryl optionally substituted with one or more $R^9$ substituents independently selected from halogen, C1-C6 alkyl and haloalkyl; $R^2$ is a bicyclic heterocyclyl having a bridgehead nitrogen atom and optionally substituted with one or more $R^9$ substituents independently selected from halogen, C1-C6 alkyl, haloalkyl, heteroalkyl, hydroxyalkyl and oxo; and m is 0.

In one embodiment, $R^4$ is aryl or heteroaryl, each of which is optionally substituted with one or more $R^6$, $R^7$ or $R^8$. In one embodiment, $R^4$ is aryl or heteroaryl, each of which is optionally substituted with one or more $R^7$. In one embodiment, each $R^7$ is independently selected from hydroxyl, amino, halogen, C1-C3 alkyl, haloalkyl, Q-haloalkyl, cycloalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, amino, and haloalkyl. In one embodiment, $R^4$ is naphthyl optionally substituted with one to three $R^7$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3alkyl. In one embodiment, the aryl is naphthyl substituted with hydroxyl. In one embodiment, $R^4$ is heteroaryl, wherein the heteroaryl is indazolyl optionally substituted with one or two $R^7$ independently selected from alkoxy, haloalkyl, and C1-C6 alkyl.

In one embodiment, $R^4$ is heteroaryl, wherein the heteroaryl is quinolinyl or isoquinolinyl, each optionally substituted with one or more $R^6$, $R^7$ or $R^8$. In one embodiment, $R^4$ is heteroaryl, wherein the heteroaryl is quinolinyl or isoquinolinyl, each optionally substituted with one or more $R^6$, $R^7$ or $R^8$ independently selected from oxo, amino, hydroxyl, C1-C3 alkyl, and hydroxyl. In one embodiment, the $R^4$ heteroaryl is a pyridinyl optionally substituted with one or more $R^6$, $R^7$ or $R^8$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is indolyl optionally substituted with one or more $R^6$, $R^7$ or $R^8$. In one embodiment, the $R^4$ heteroaryl is indolyl optionally substituted with one or two $R^7$ independently selected from hydroxyl and C1-C3 alkyl. In one embodiment, $R^{11}$ is methyl. In one embodiment, the piperazinyl ring is unsubstituted. In one embodiment, the piperazinyl ring of Formula II-B is substituted with $R^8$. In one embodiment, $R^8$ is C1-C3 alkyl optionally substituted with cyano, hydroxyl or methoxy. In one embodiment, $R^8$ is methyl, cyanomethyl, hydroxymethyl or methoxymethyl.

Nonlimiting examples of compounds of Formula (II), Formula II-A and Formula II-B are selected from the group consisting of:

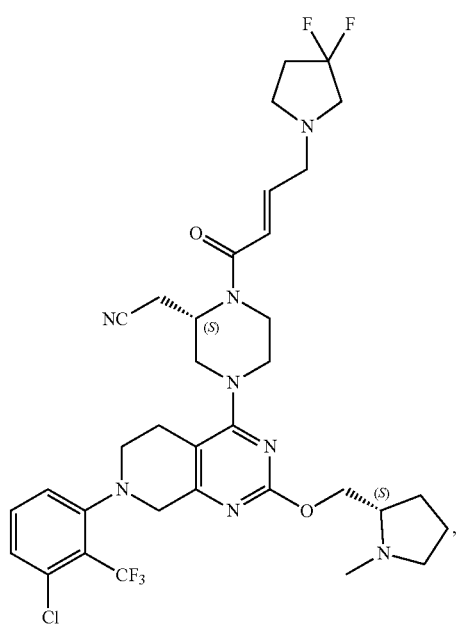
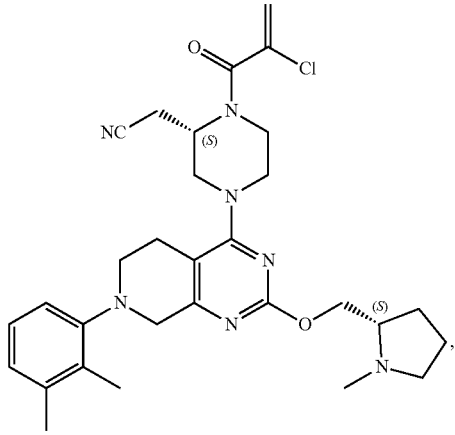
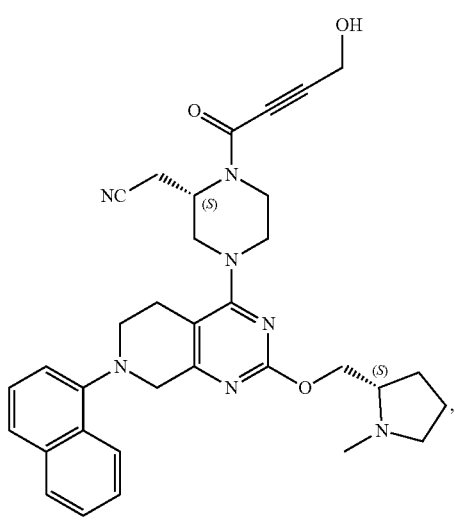
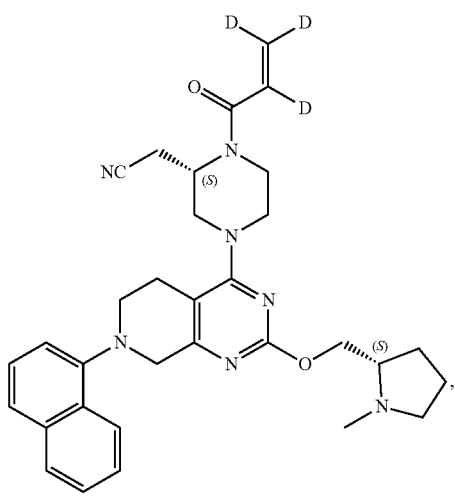

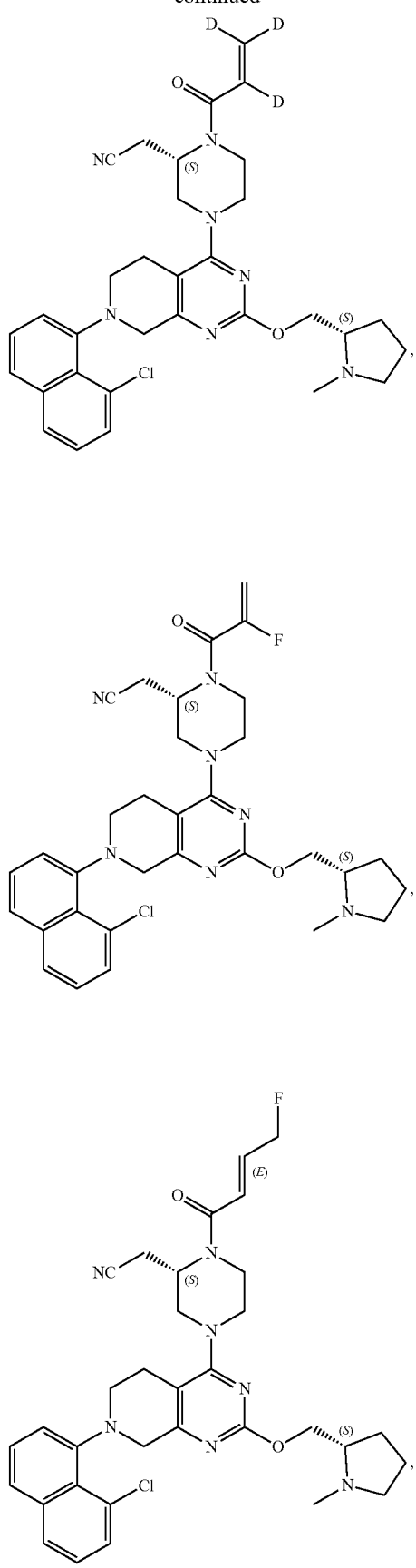
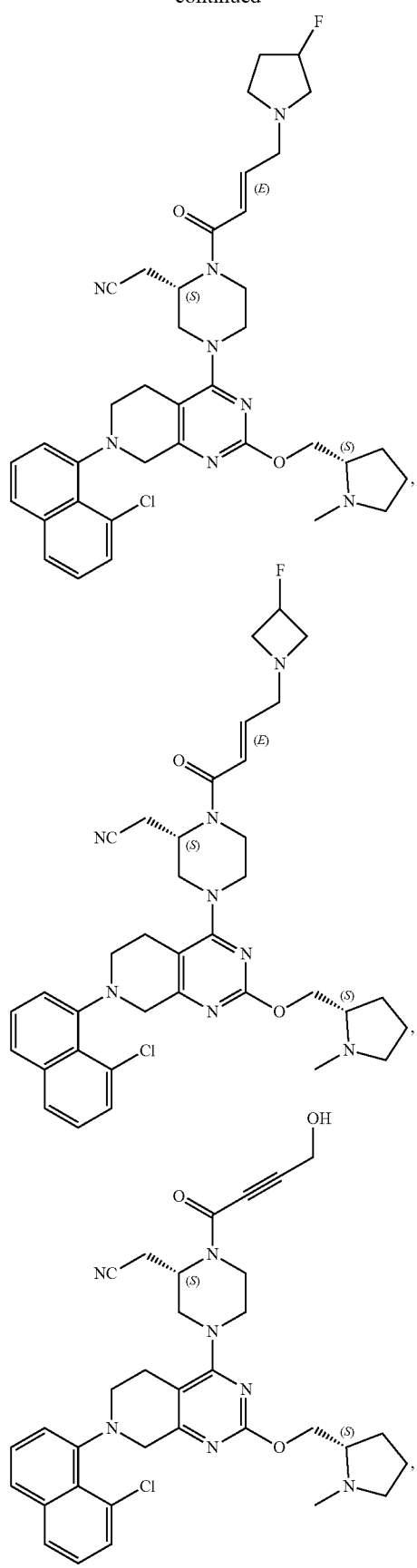

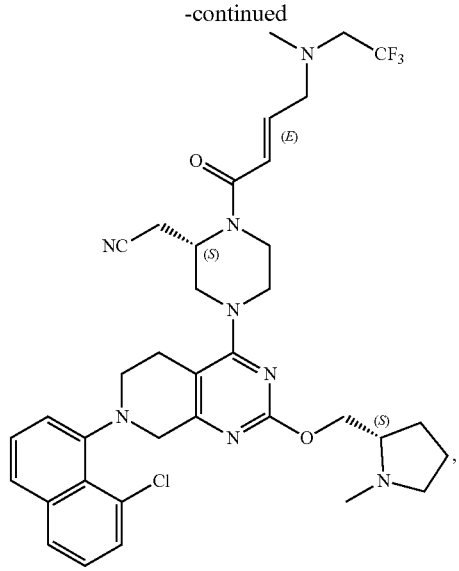
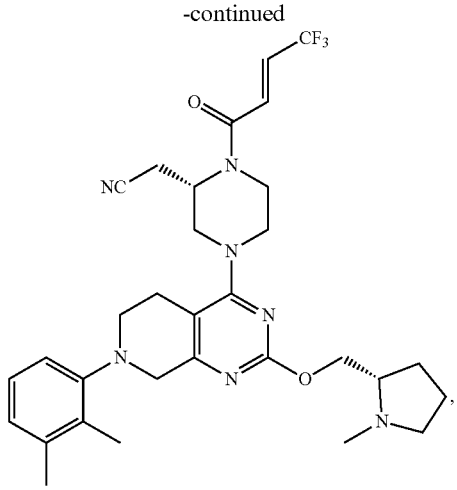
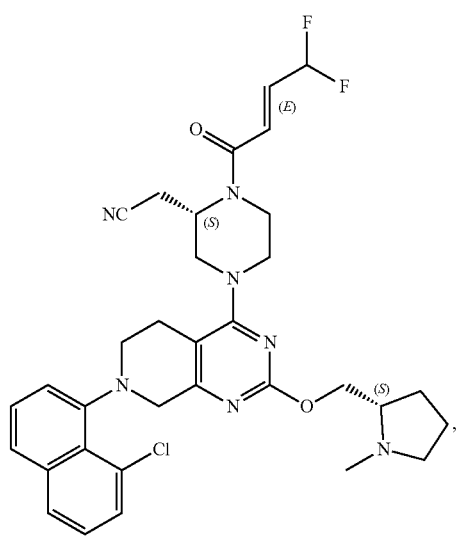
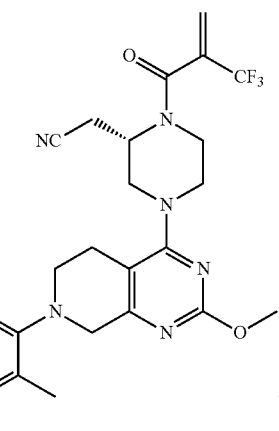
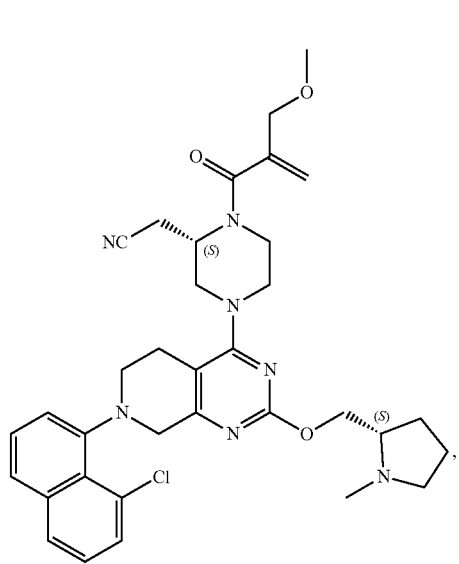
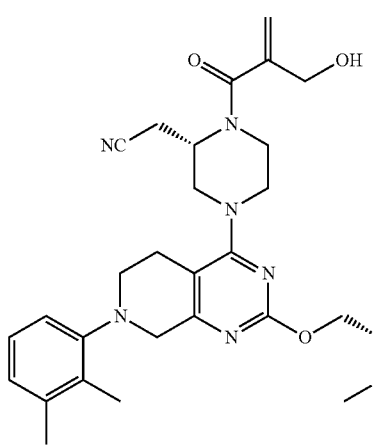

25
-continued
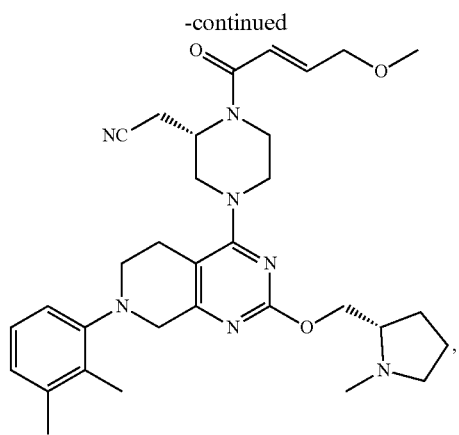
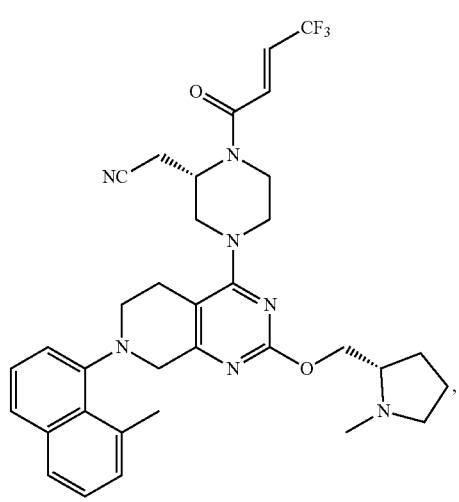
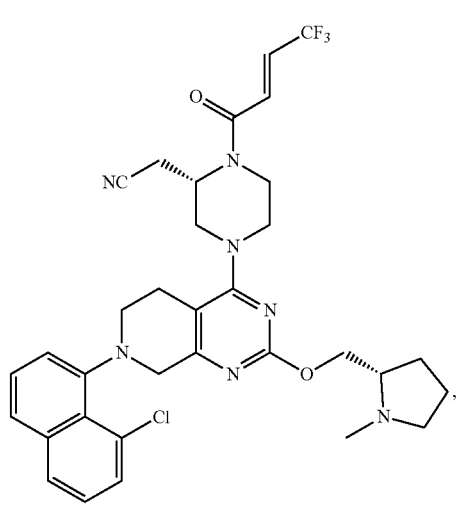
26
-continued
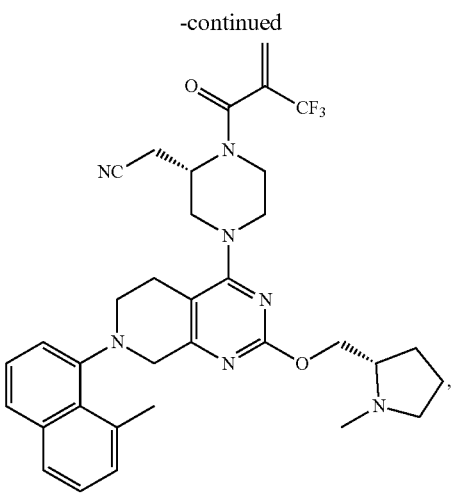
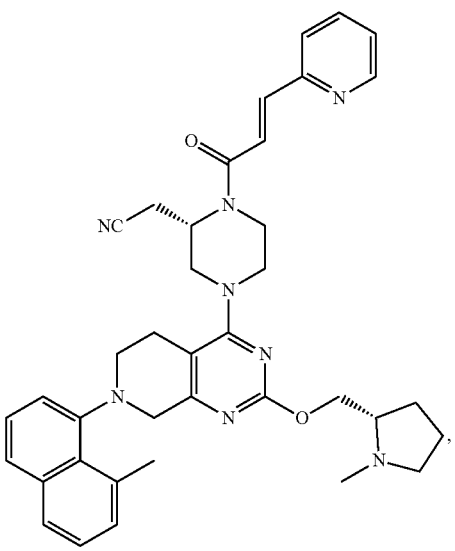
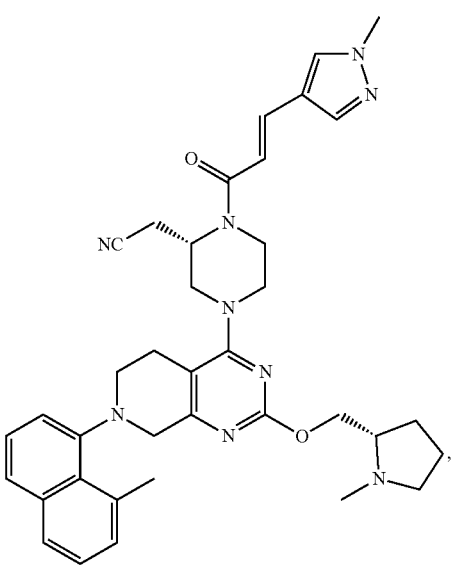

-continued
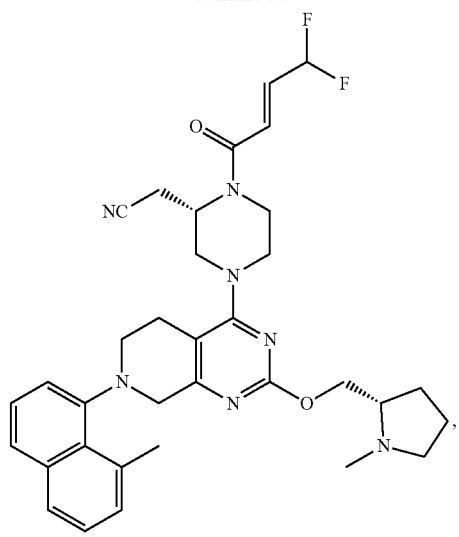
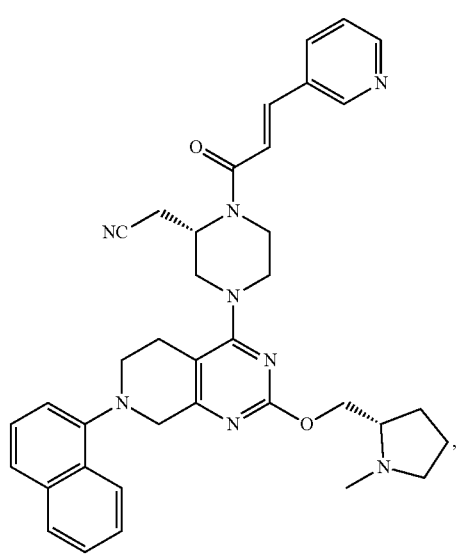
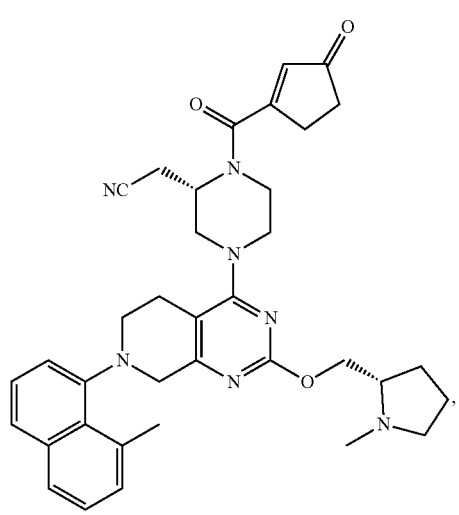
-continued
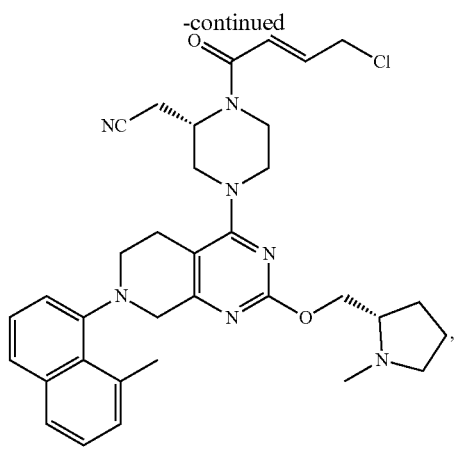
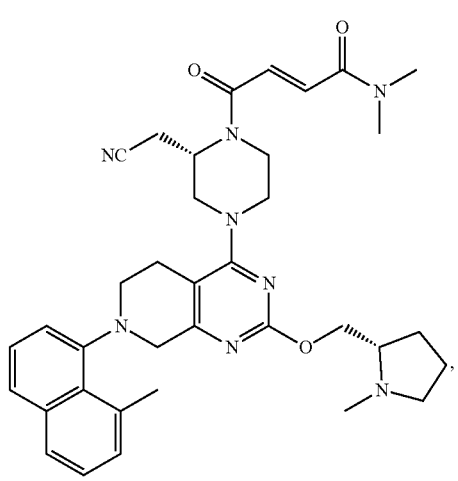
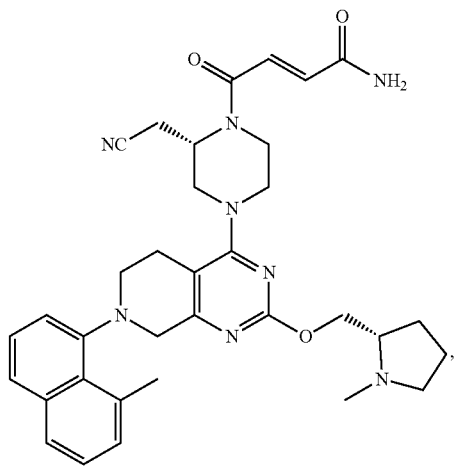

29
-continued
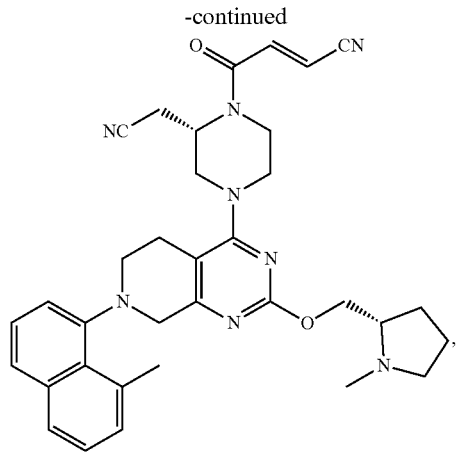
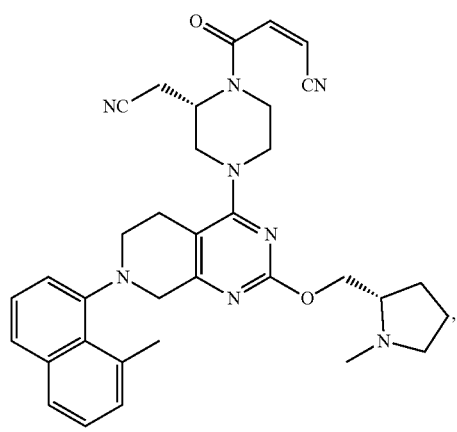
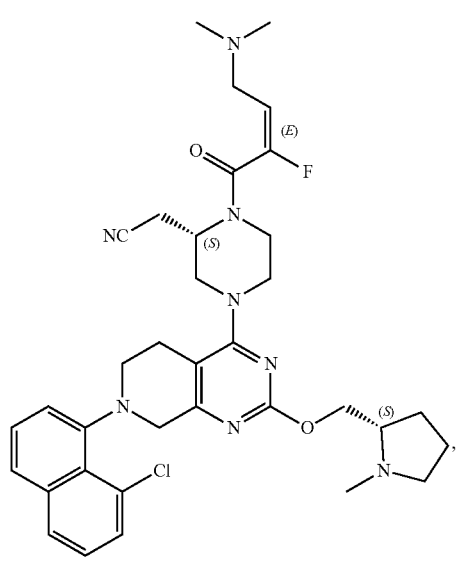
30
-continued
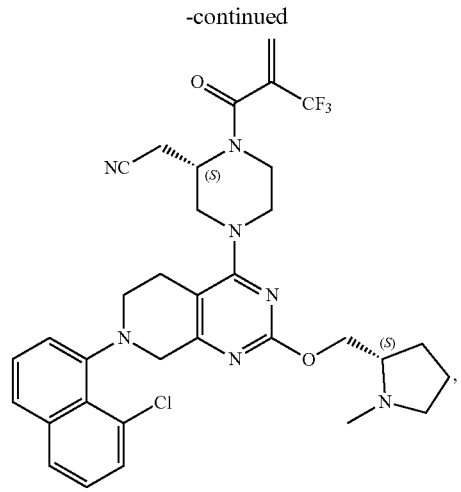
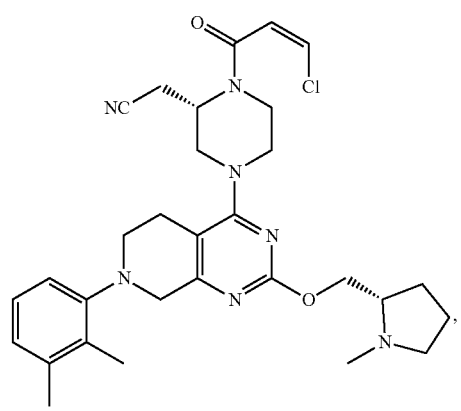
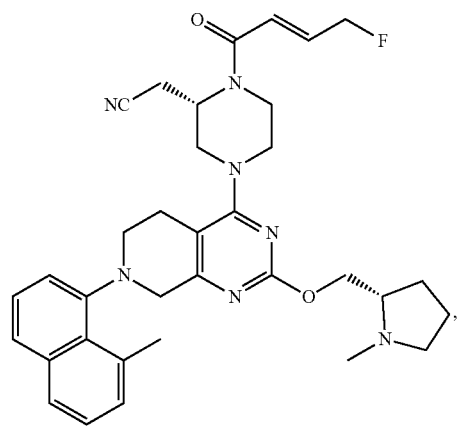

31
-continued
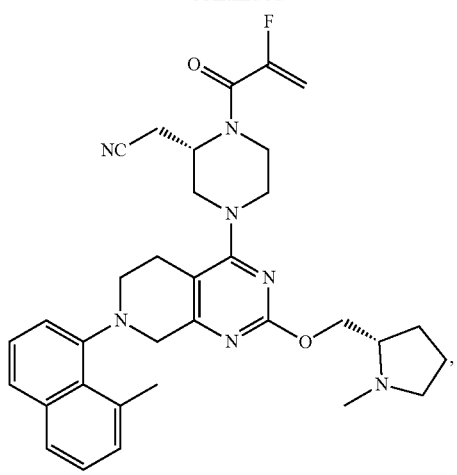
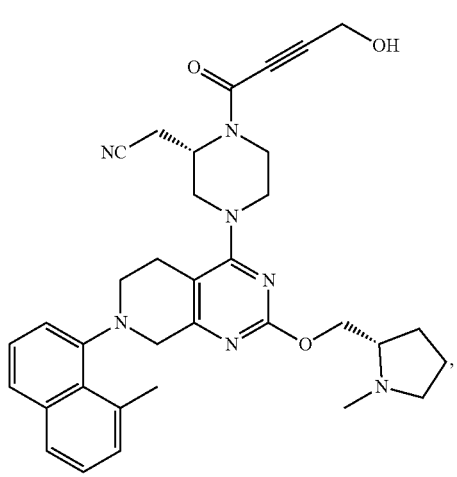
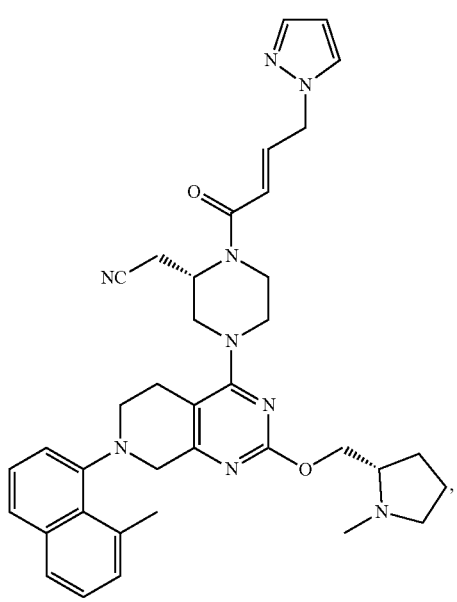
32
-continued
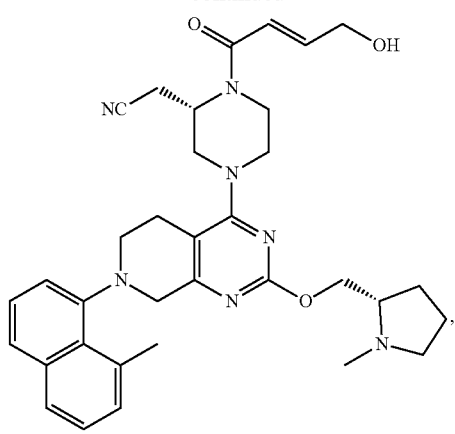
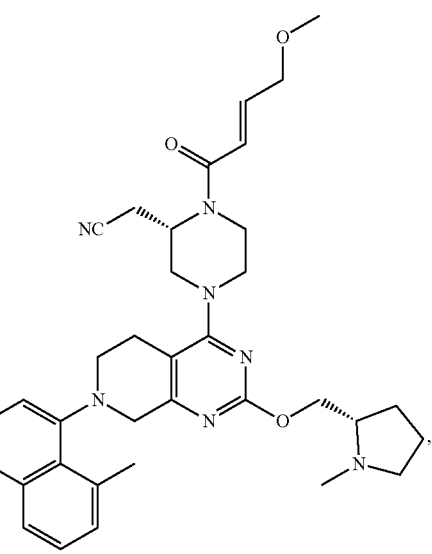
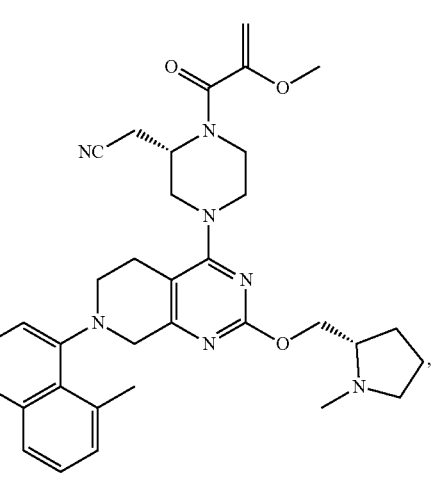

33
-continued
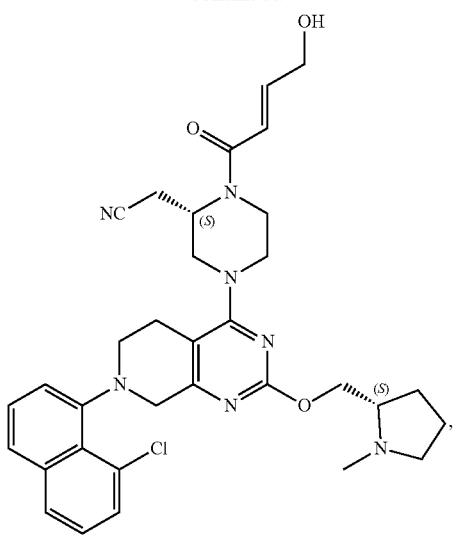
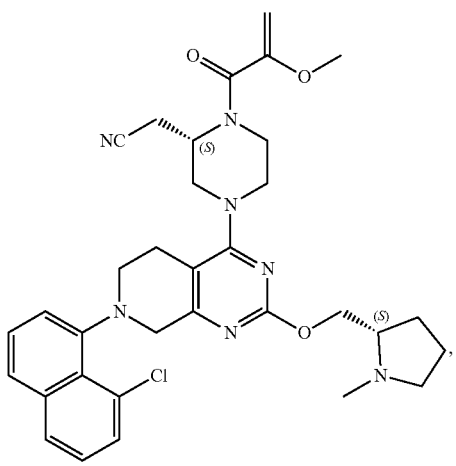
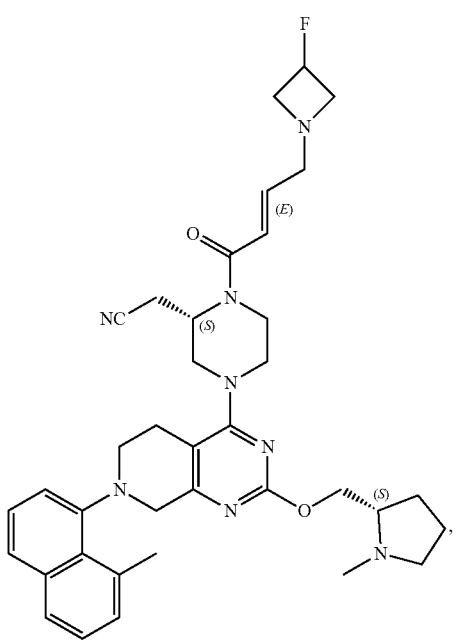
34
-continued
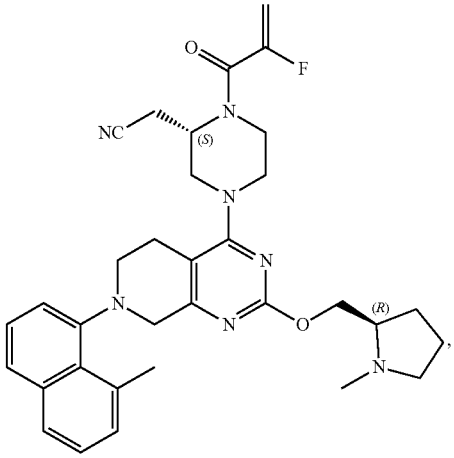
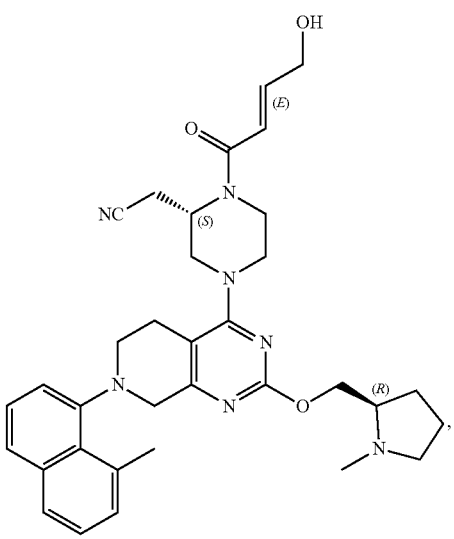
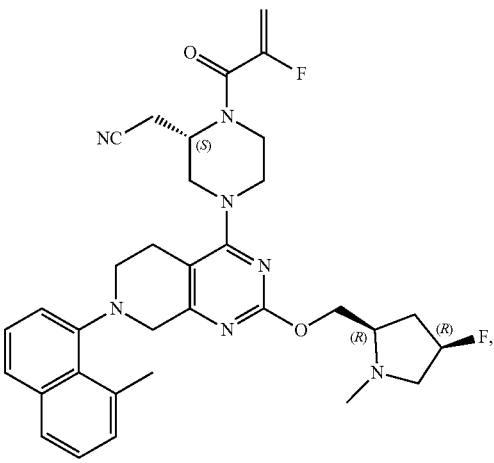

35
-continued
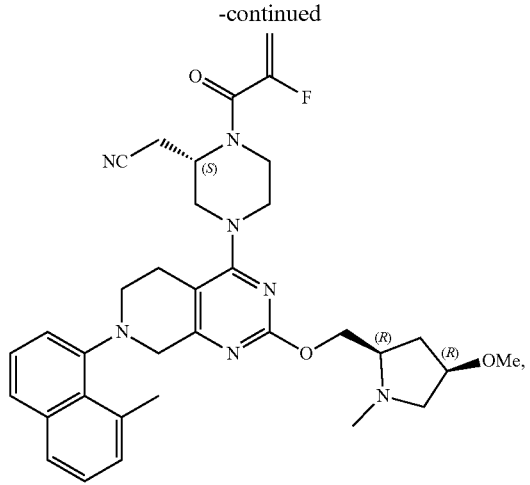
36
-continued
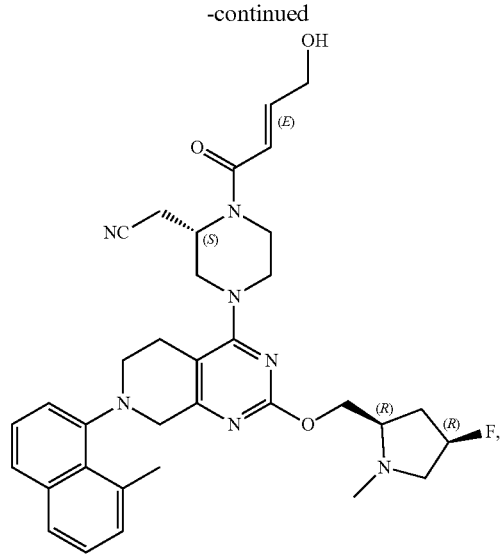
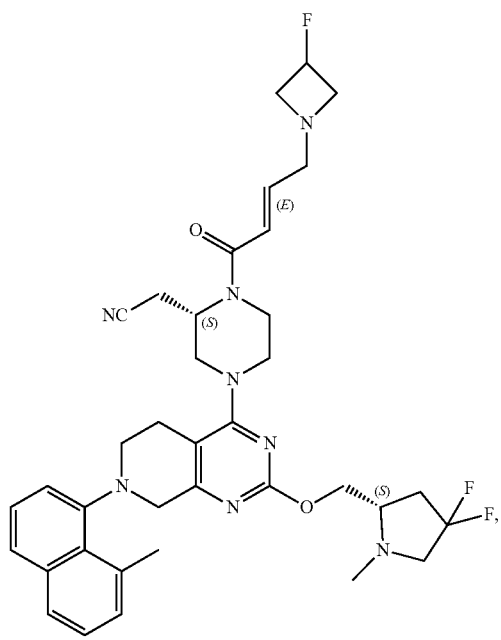
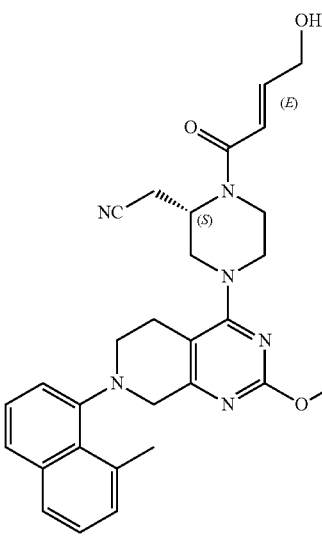
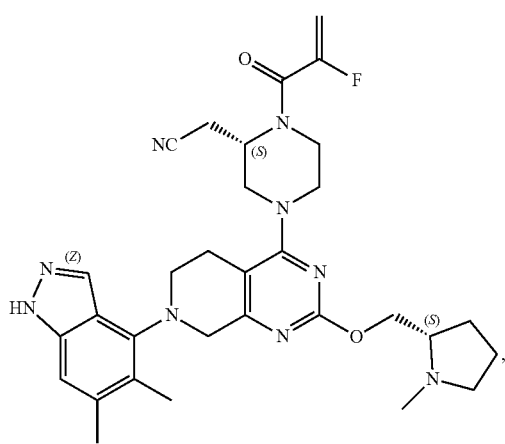
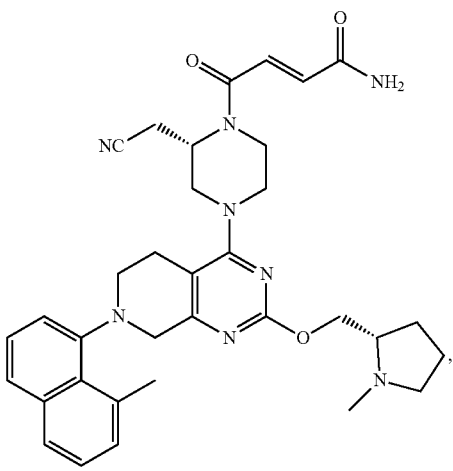

37
-continued
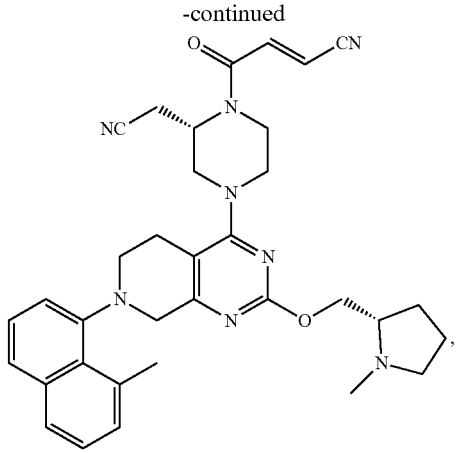
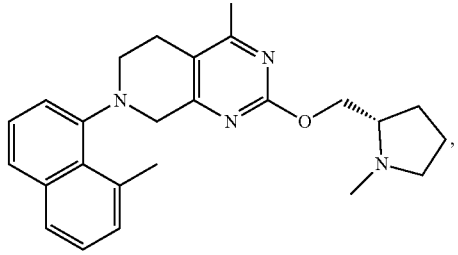
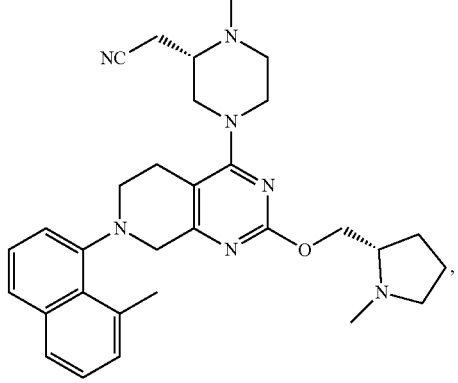
38
-continued
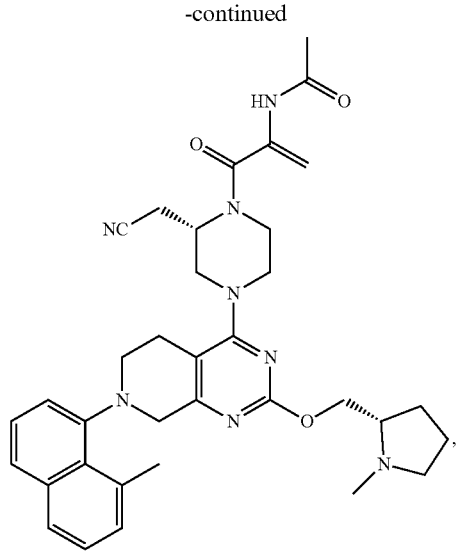
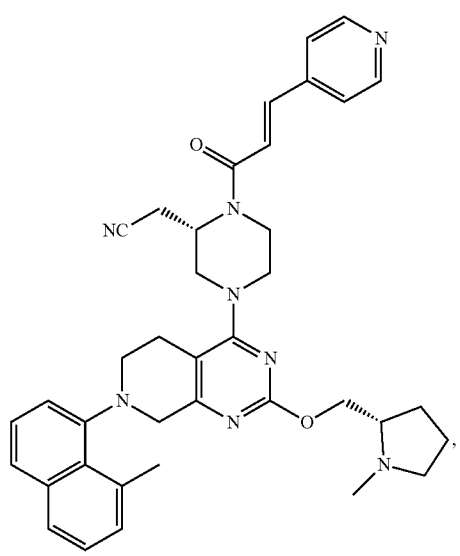
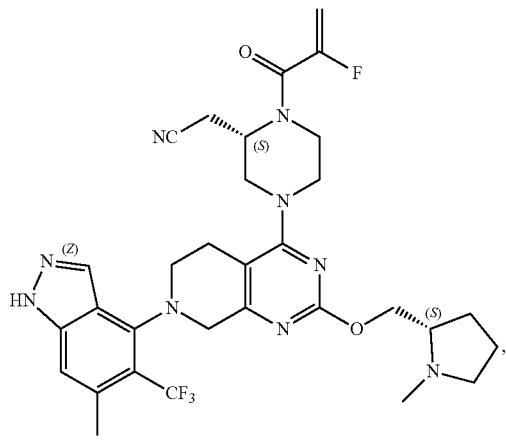

39
-continued
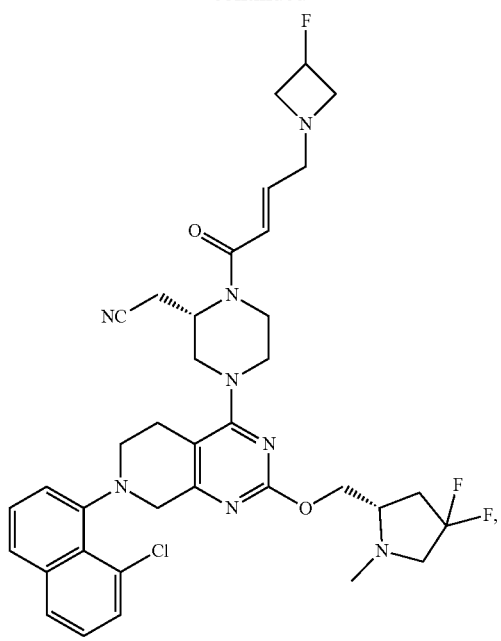
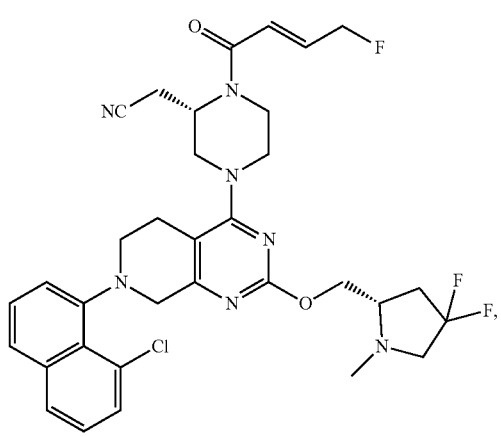
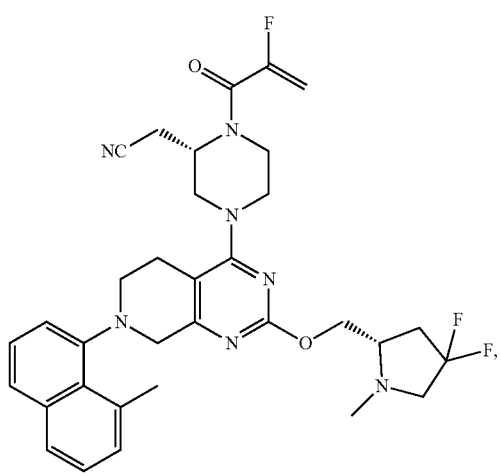
40
-continued
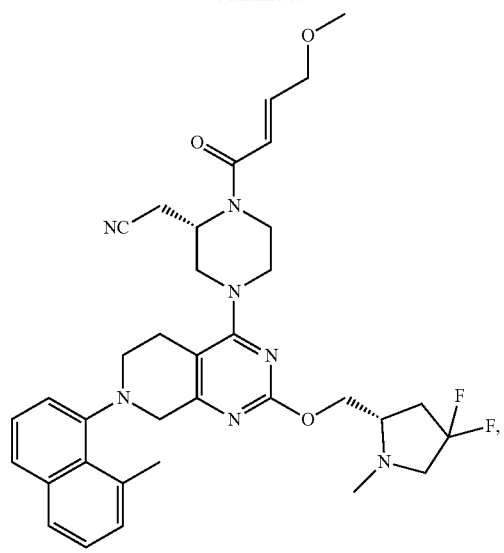
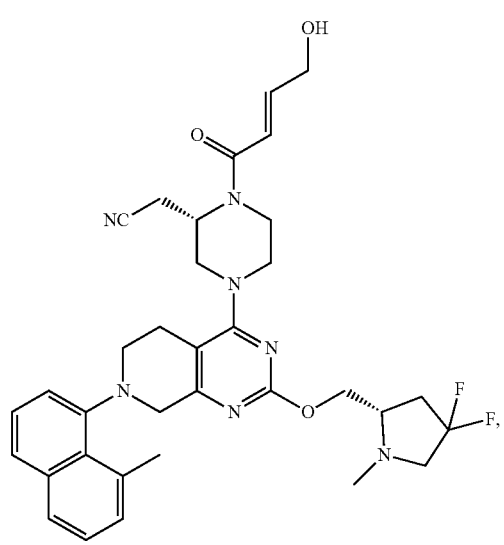
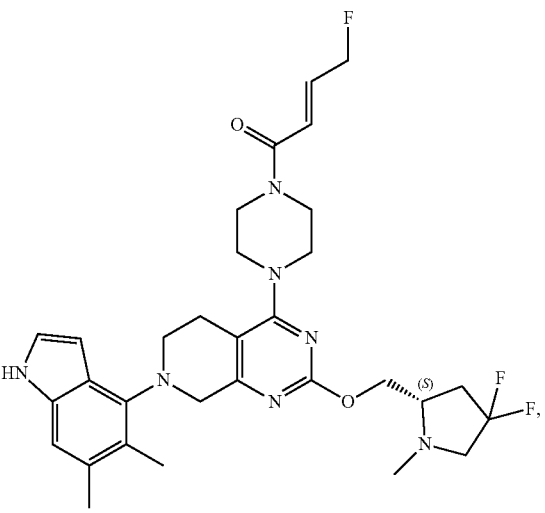

41
-continued
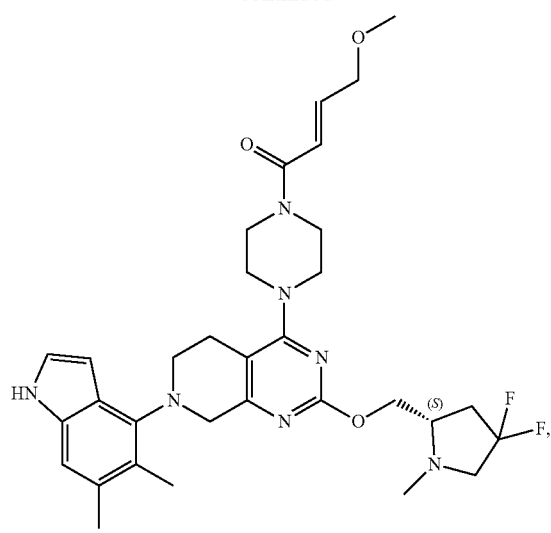
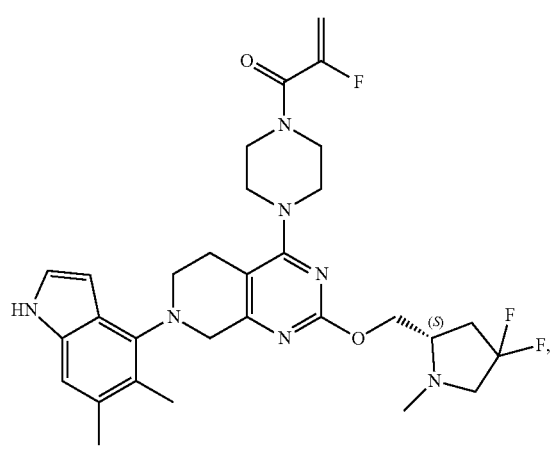
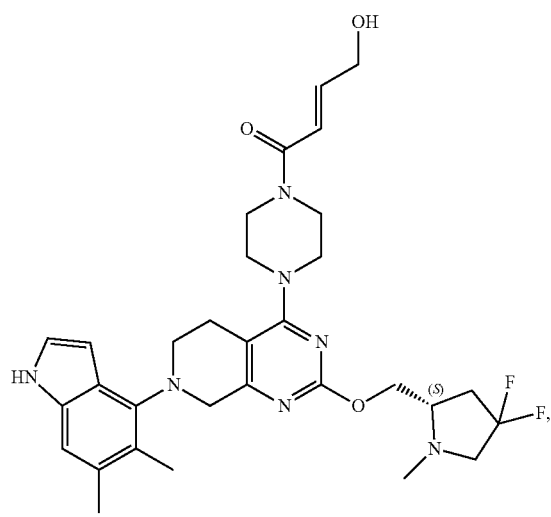
42
-continued
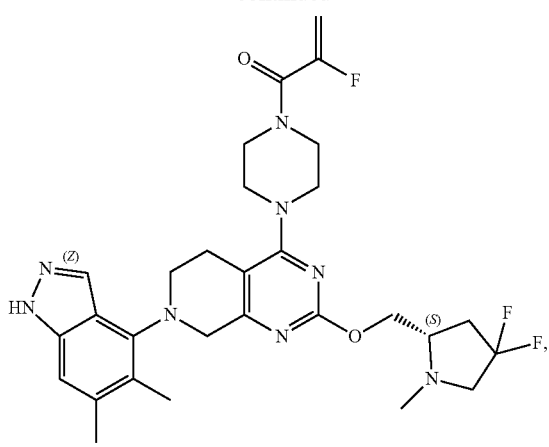
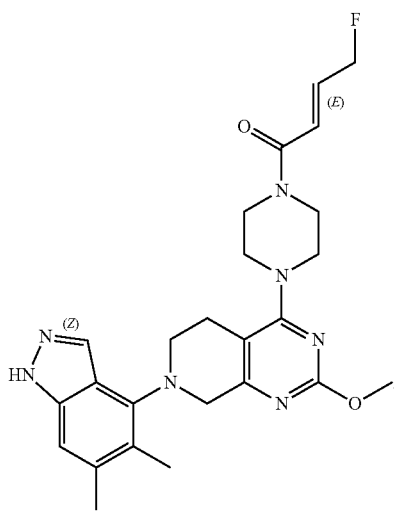
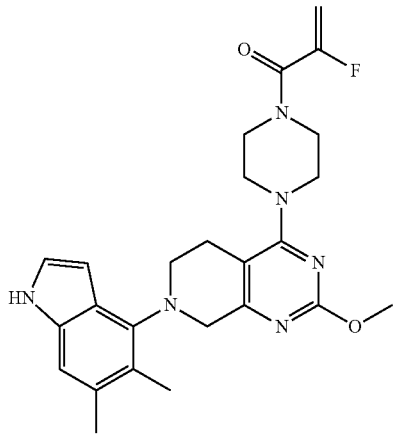

43
-continued
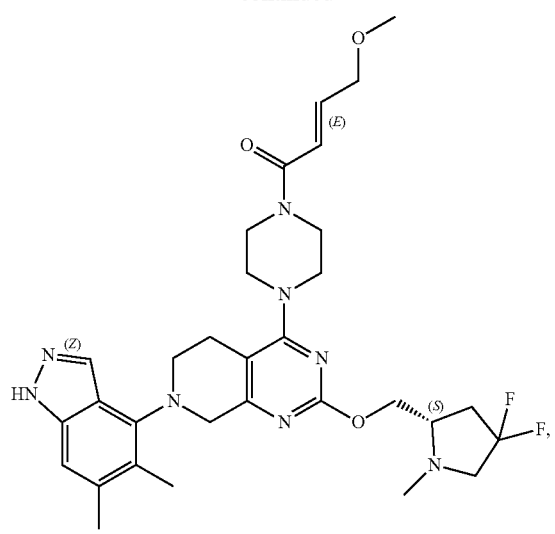
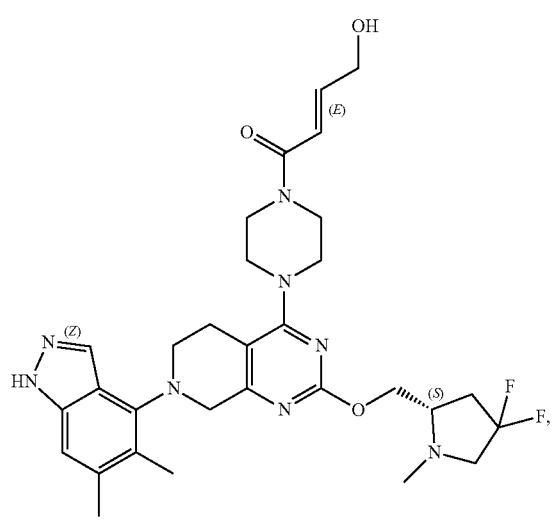
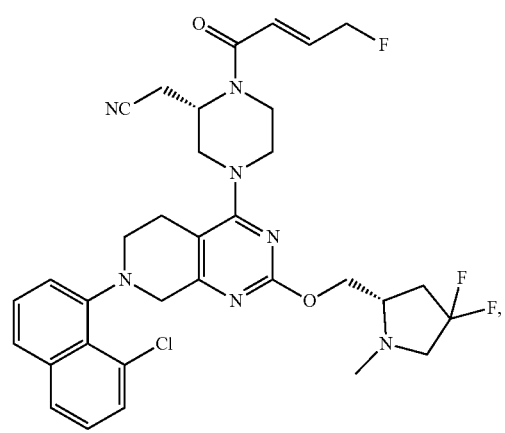
44
-continued
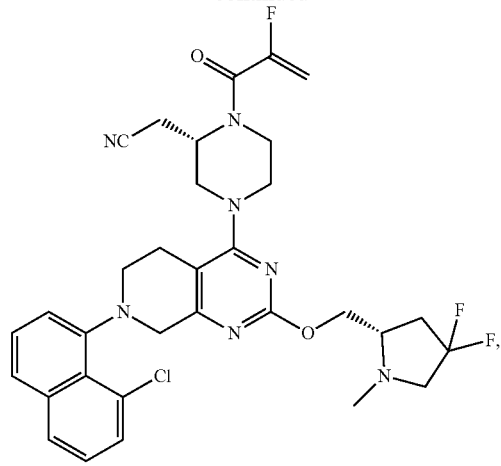
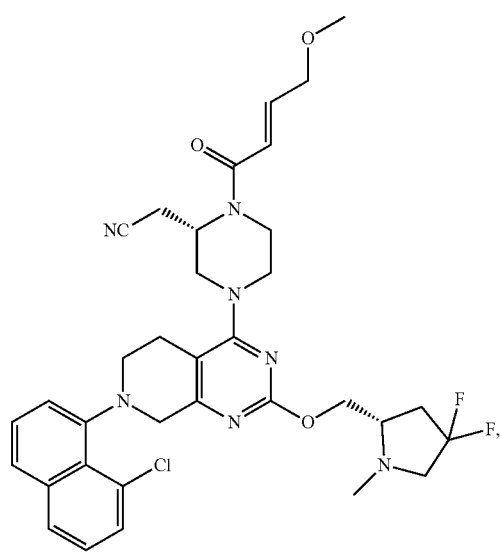
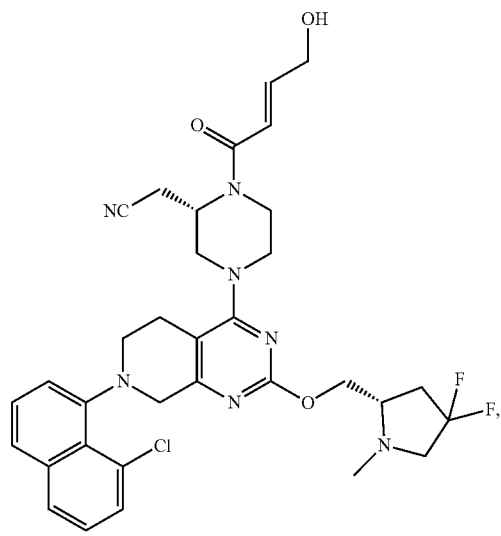

-continued
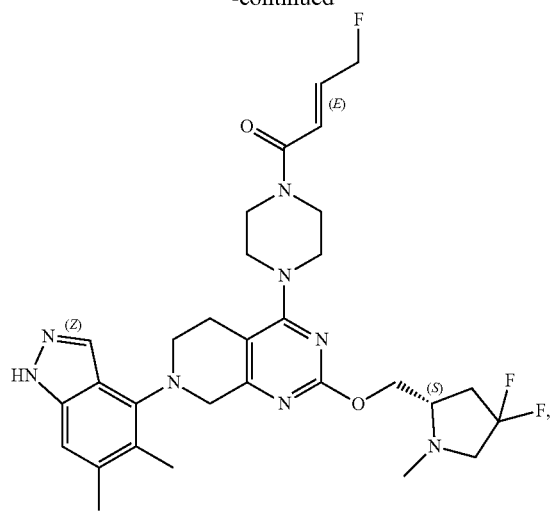
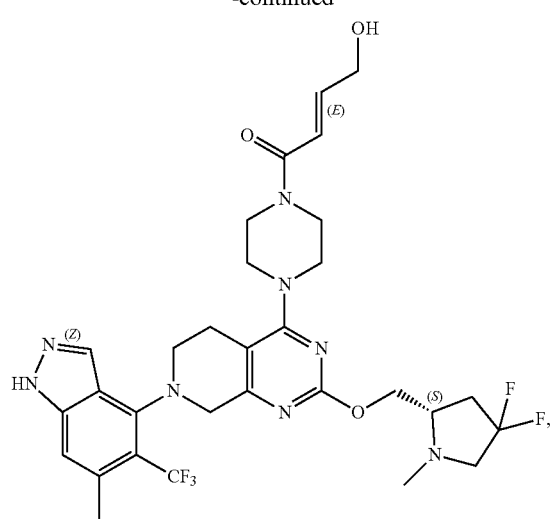
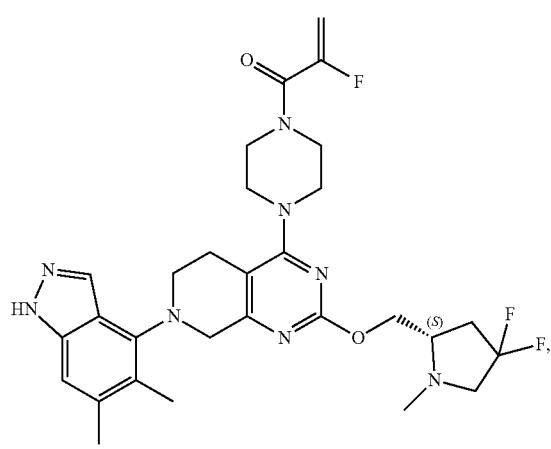
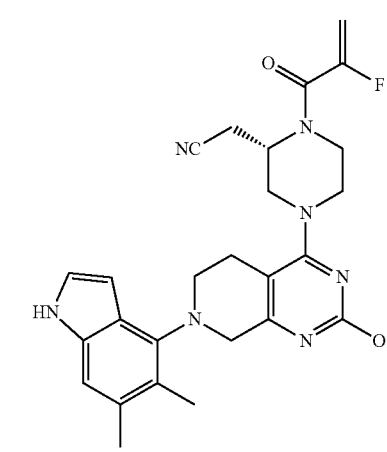
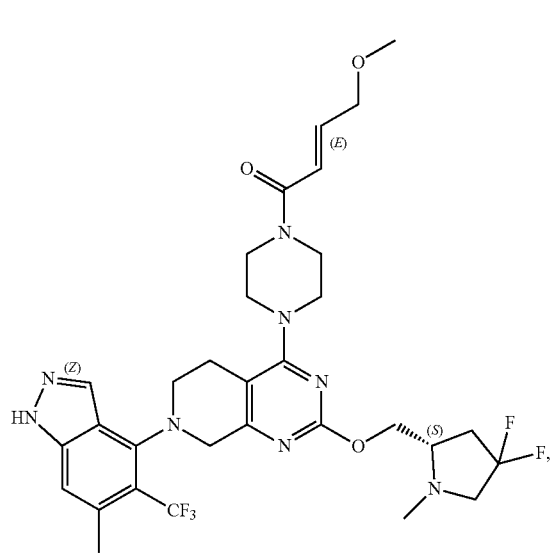
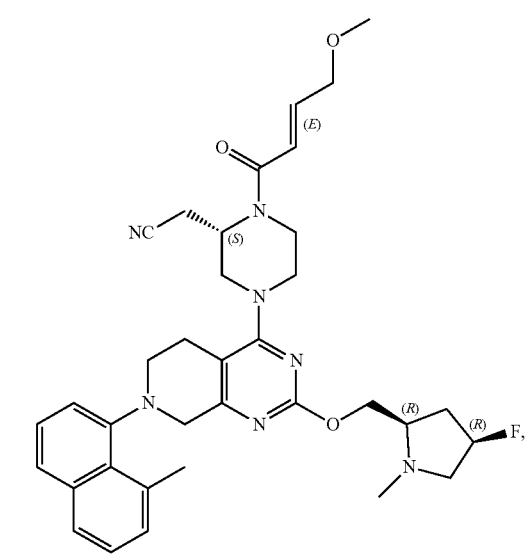

-continued
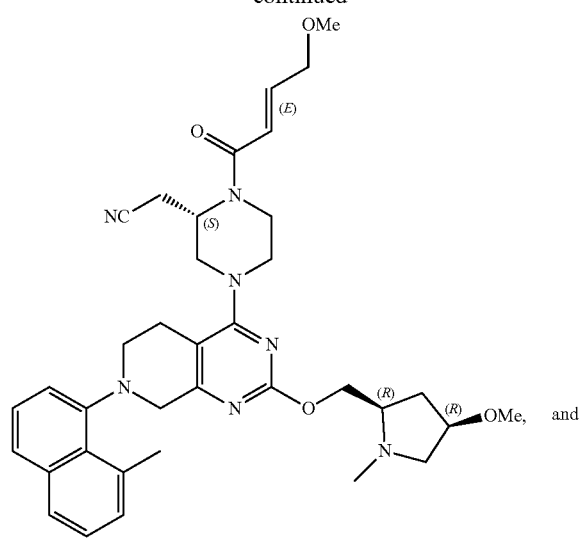
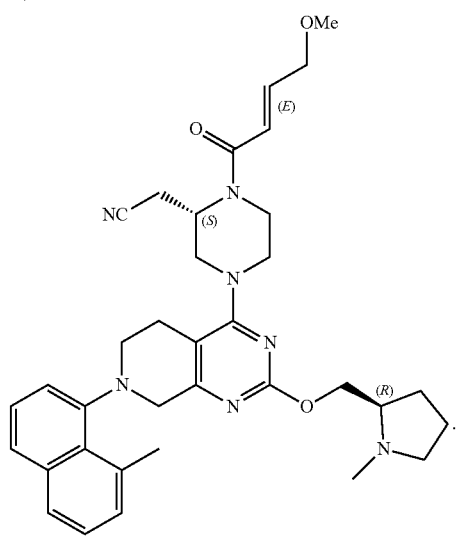
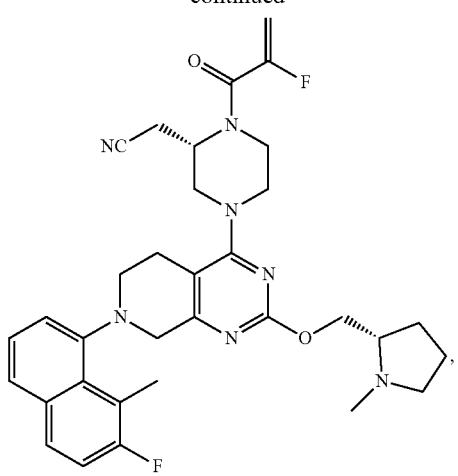
and
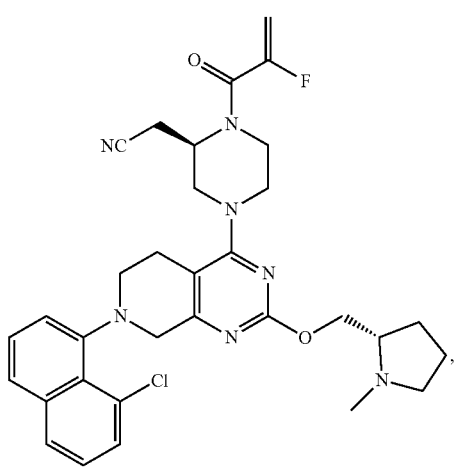
Additional nonlimiting examples of compounds of Formula (II), Formula II-A and Formula II-B are selected from the group consisting of:
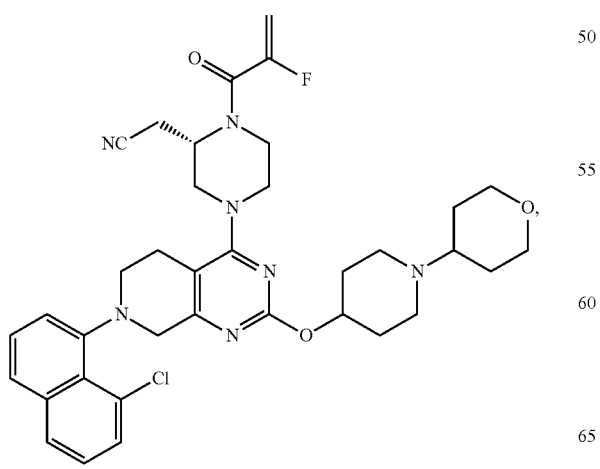
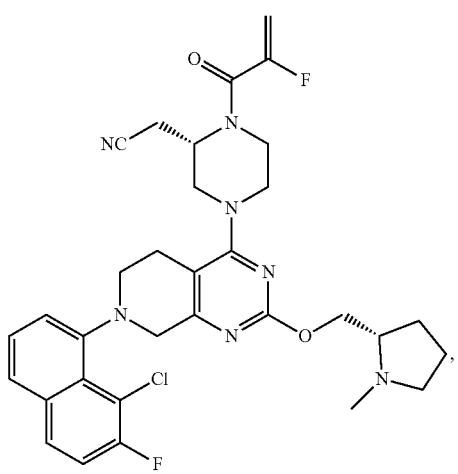

-continued
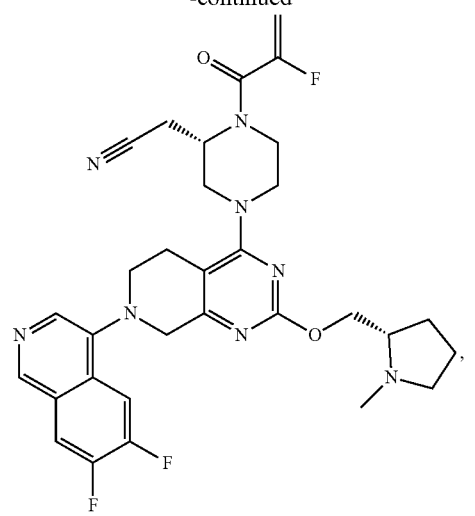
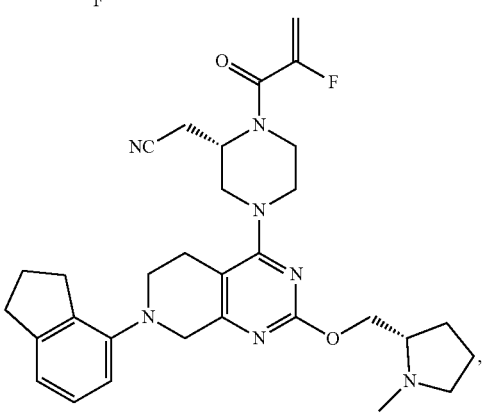
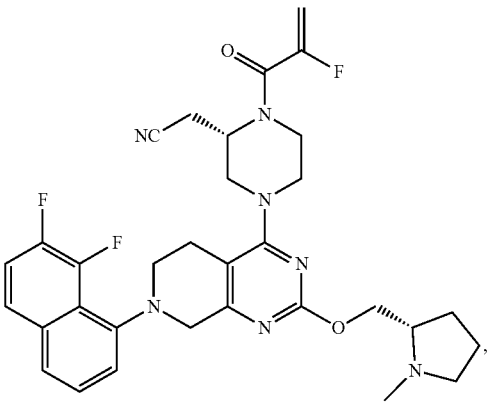
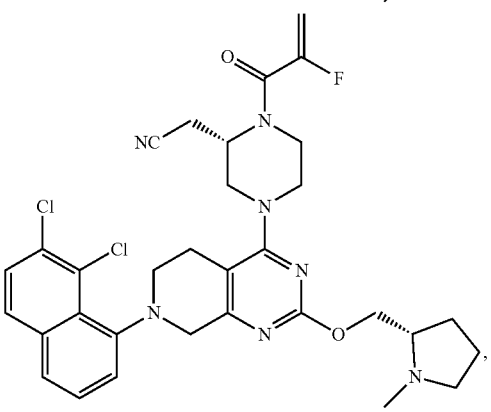
-continued
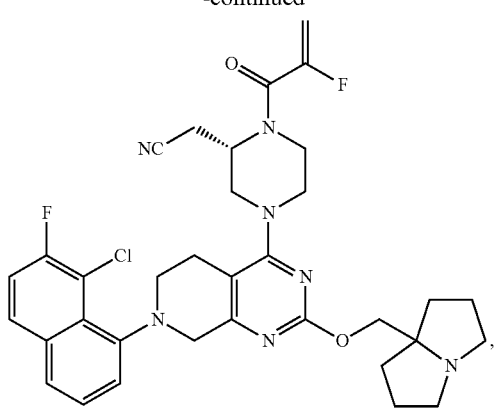
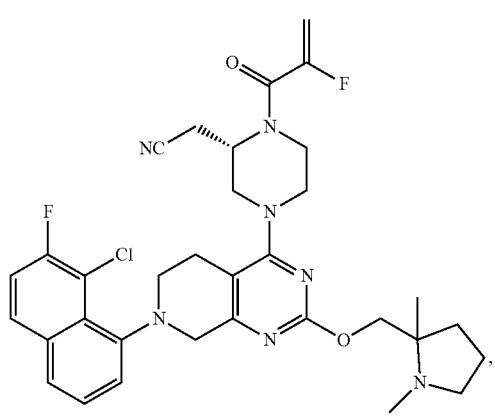
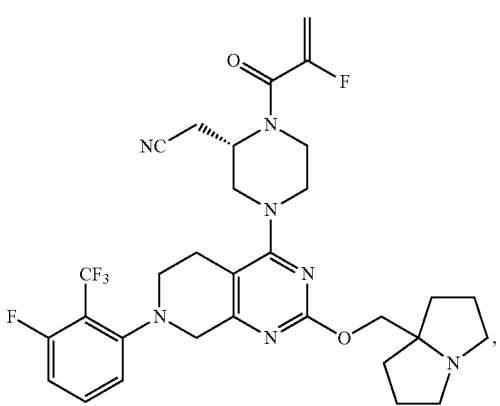
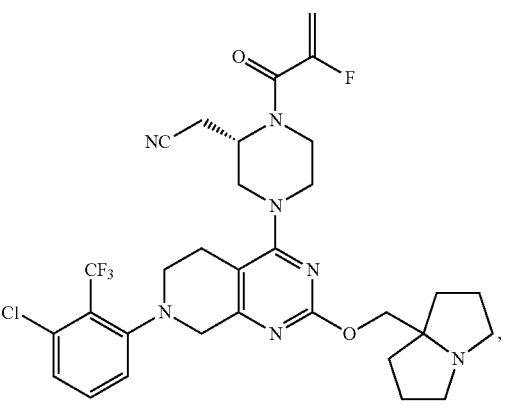

51
-continued
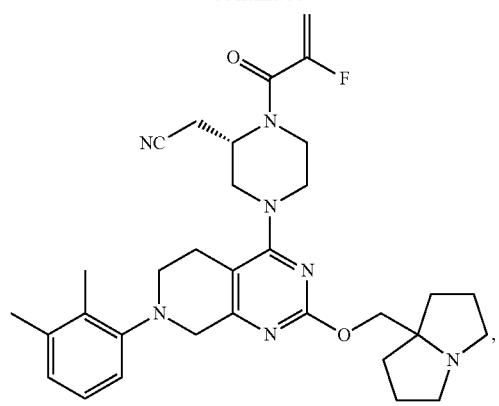
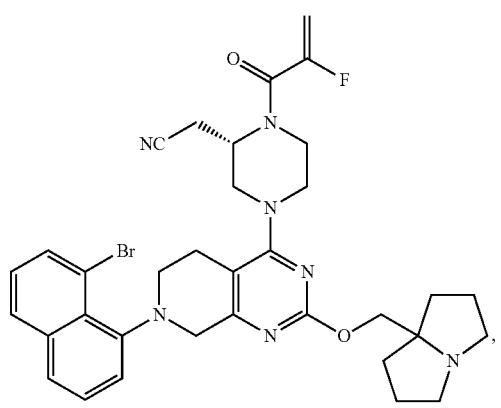
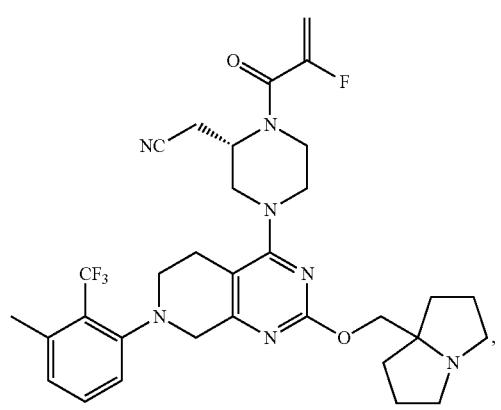
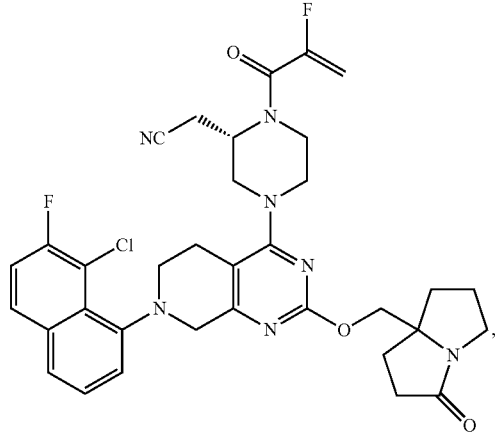
52
-continued
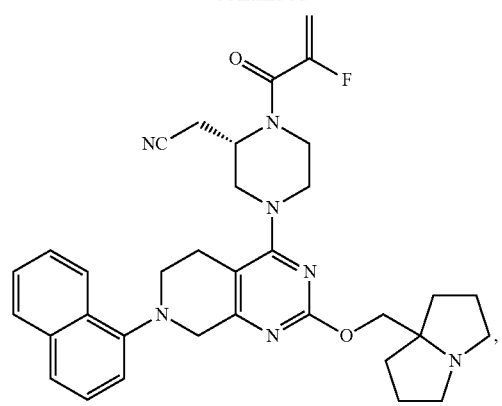
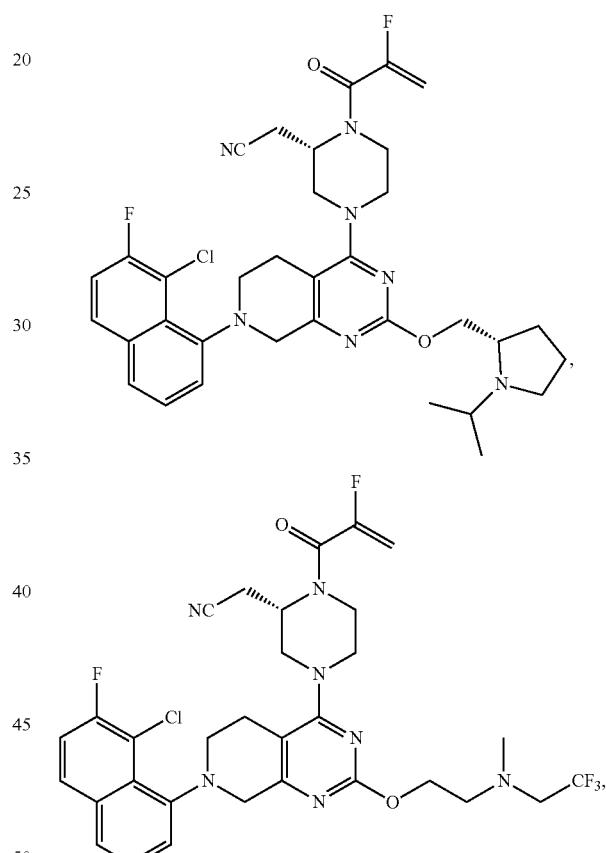
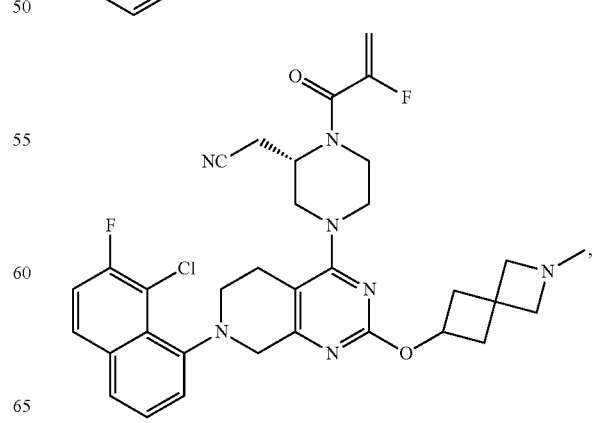

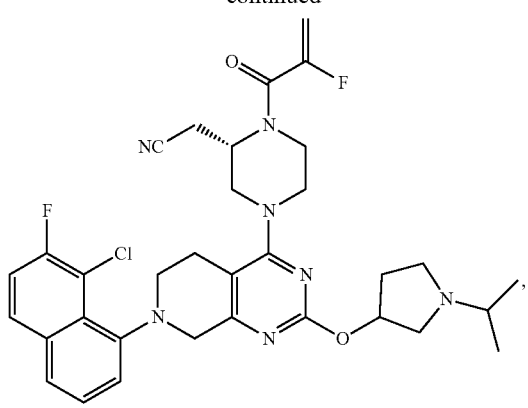
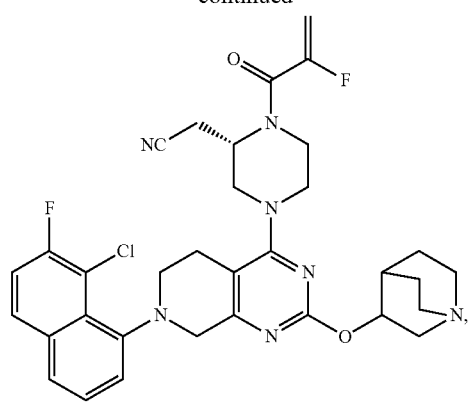
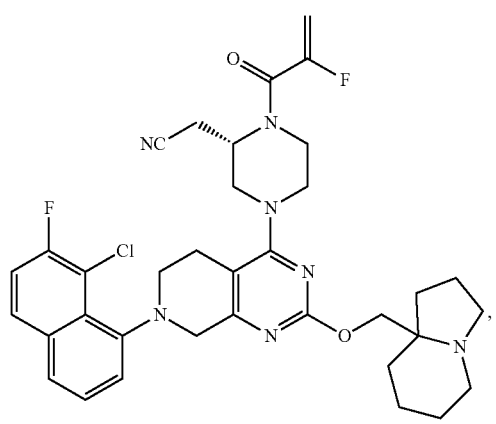
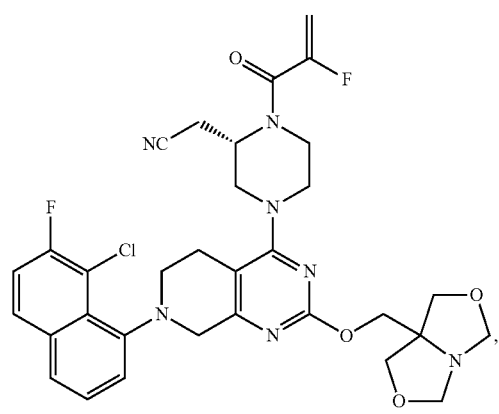
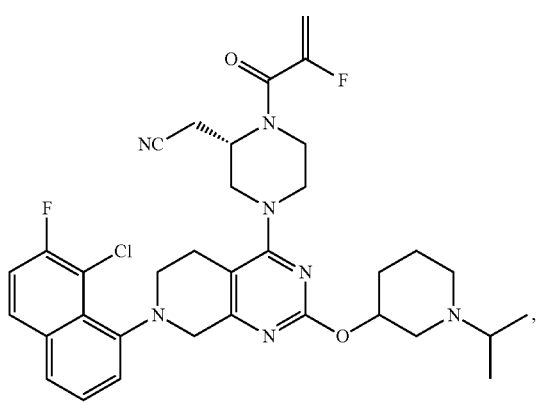
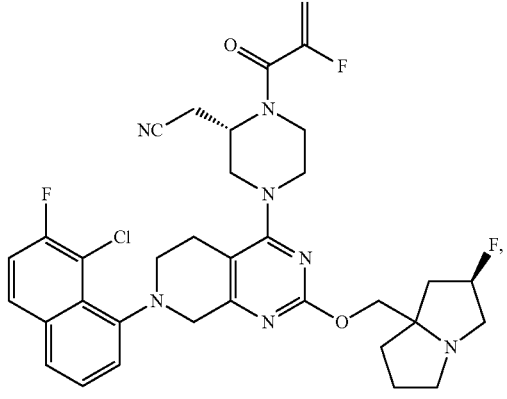
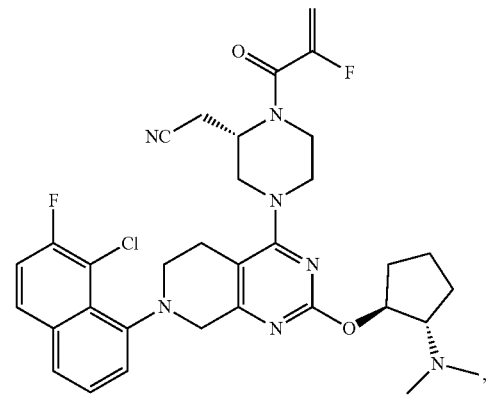
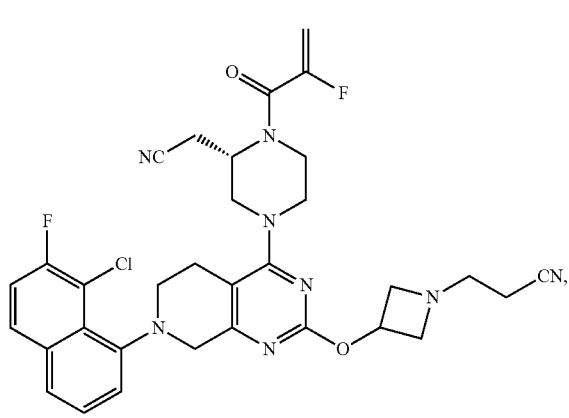

55
-continued
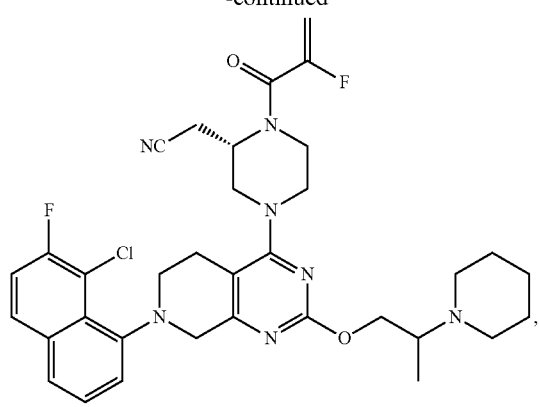
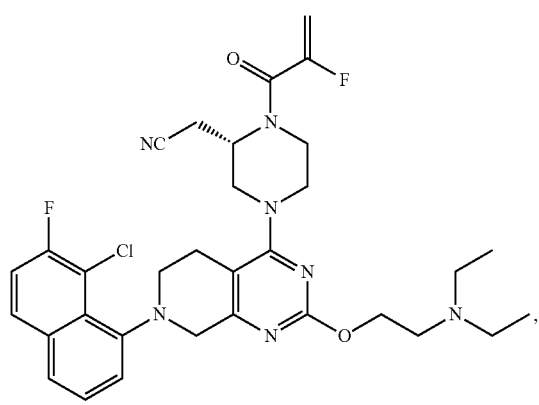
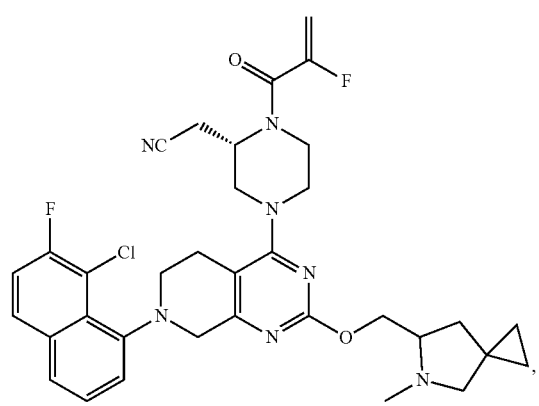
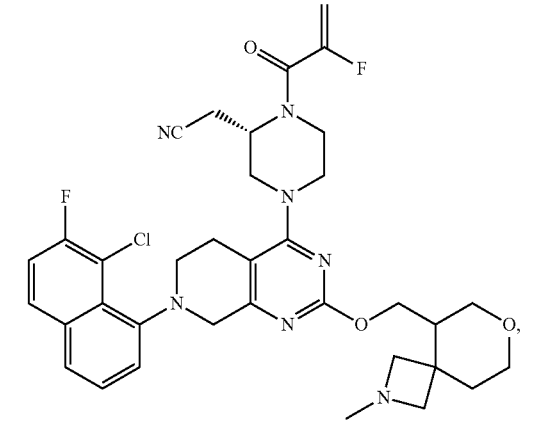
56
-continued
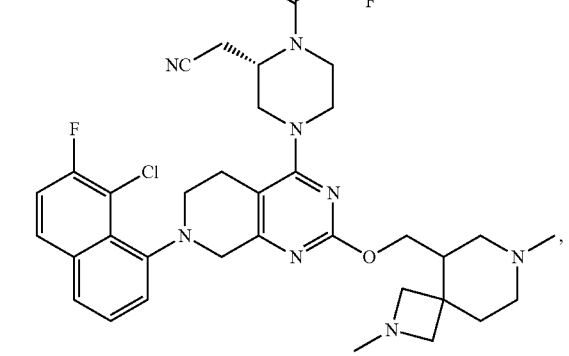
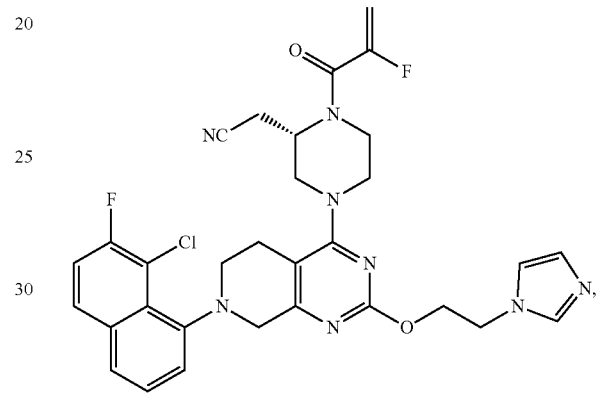
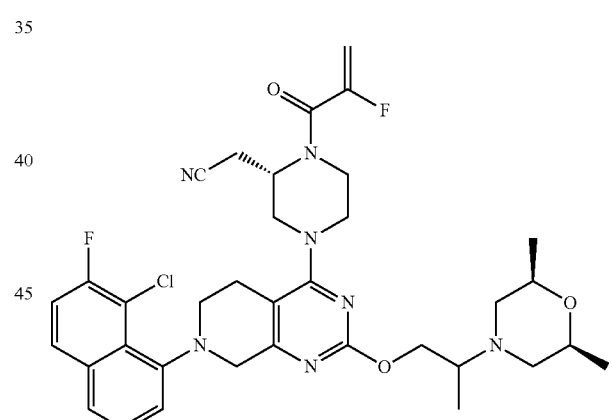
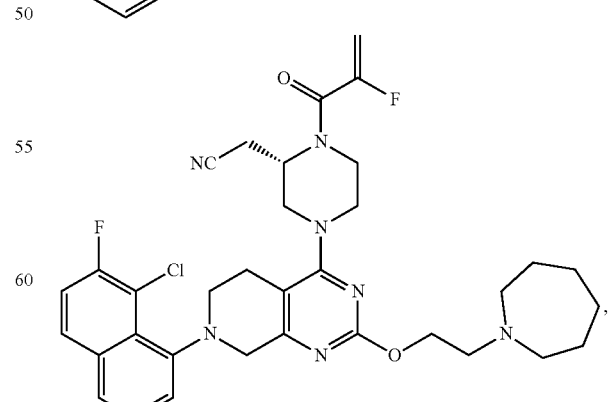

57
-continued
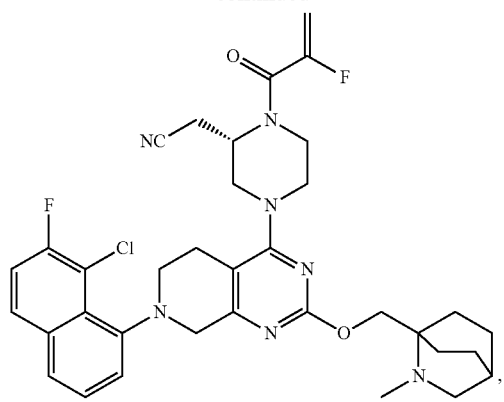
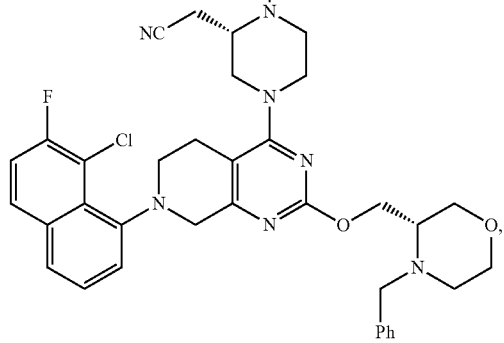
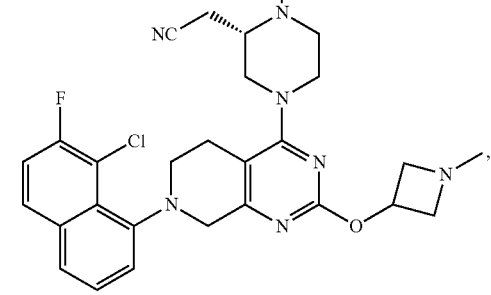
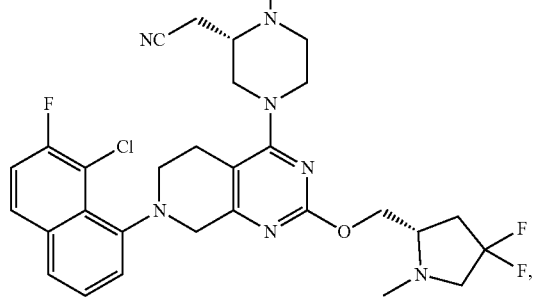
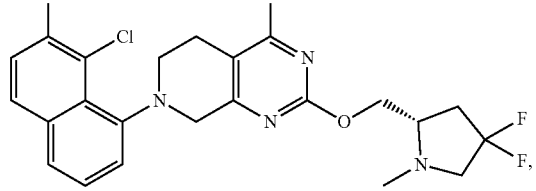
58
-continued
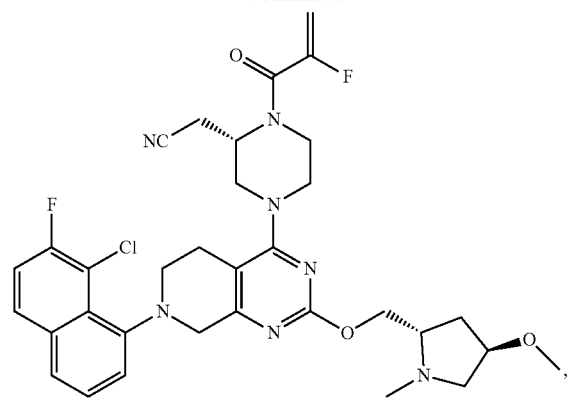
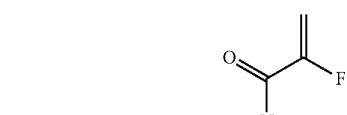
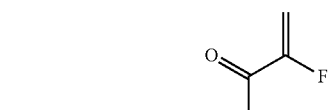
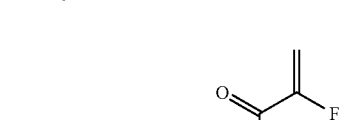
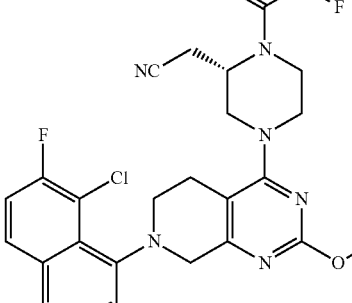

59
-continued
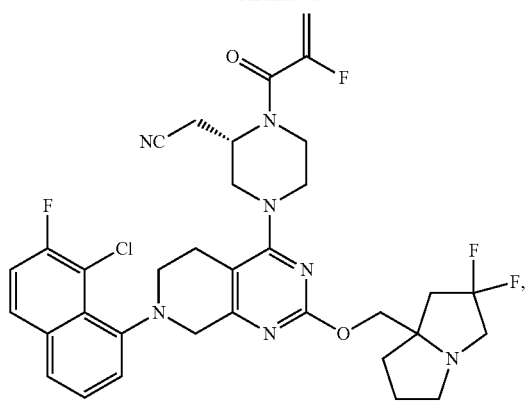
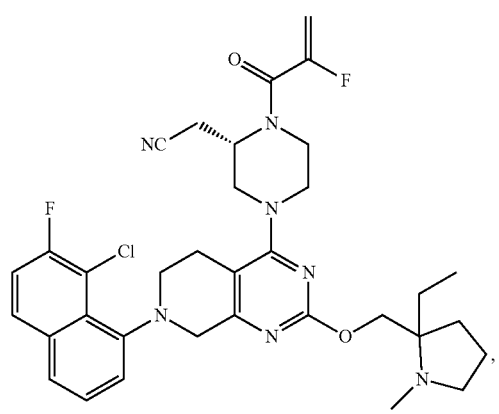
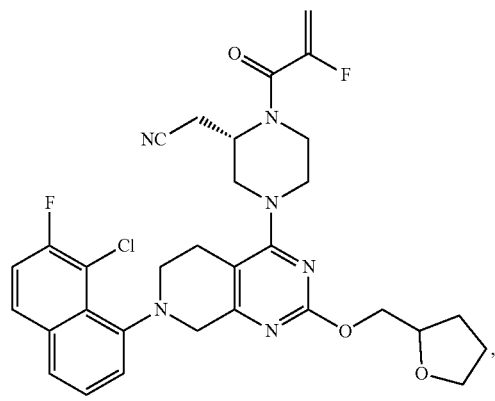
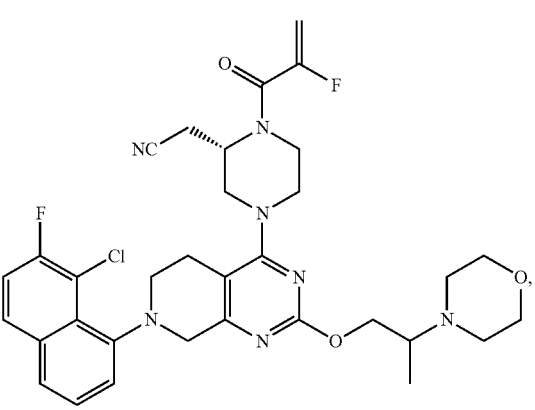
60
-continued
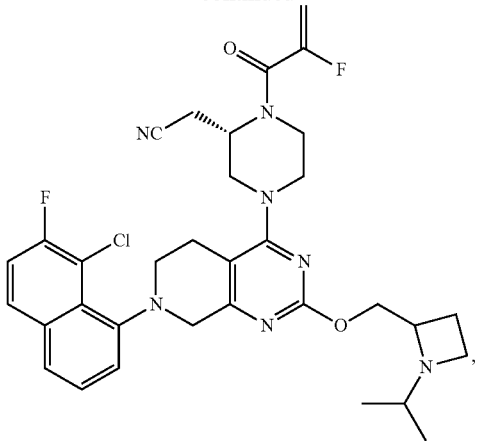
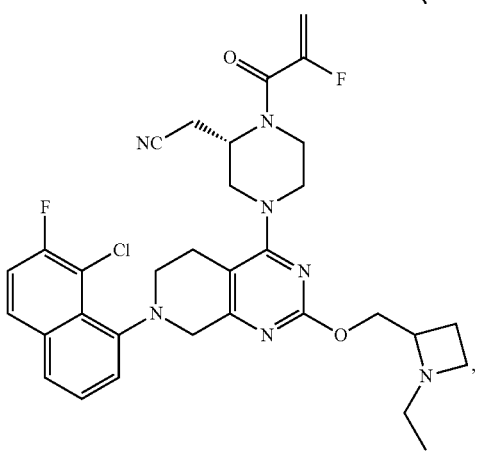
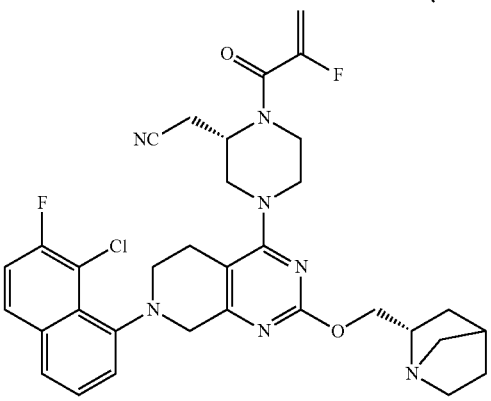
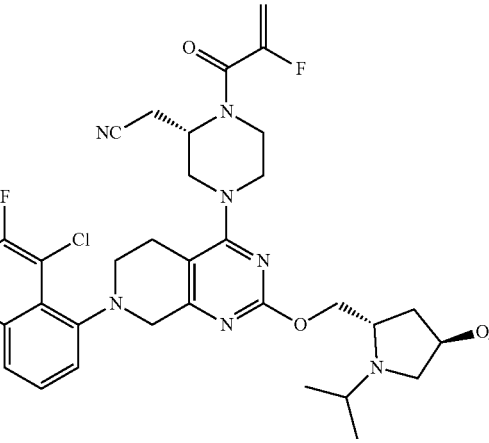

61
-continued
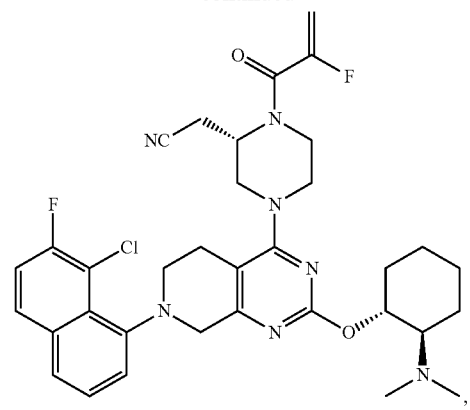
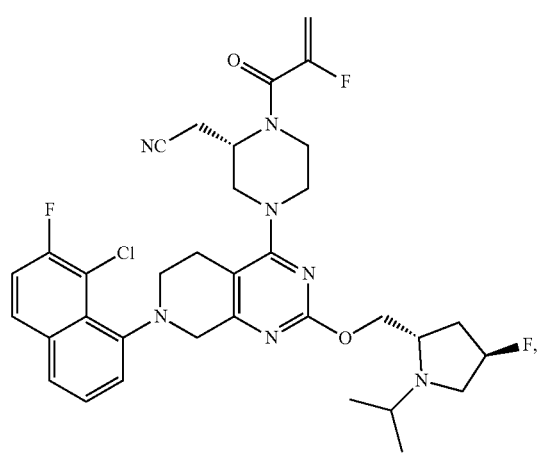
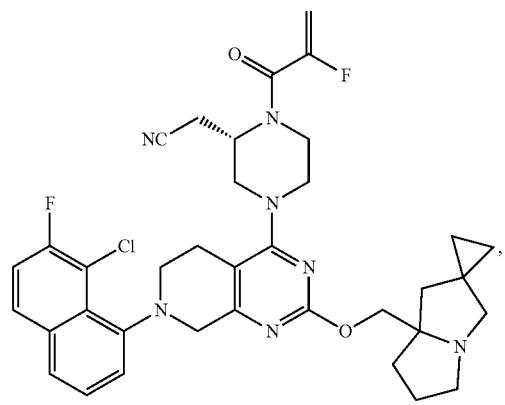
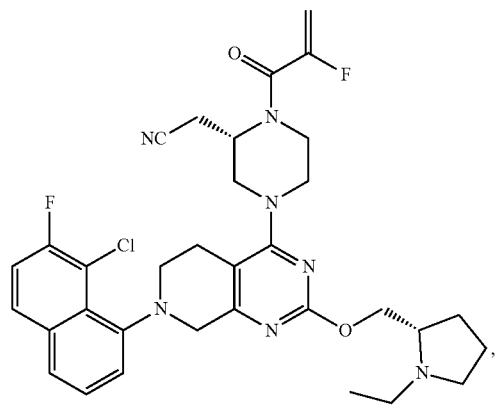
62
-continued
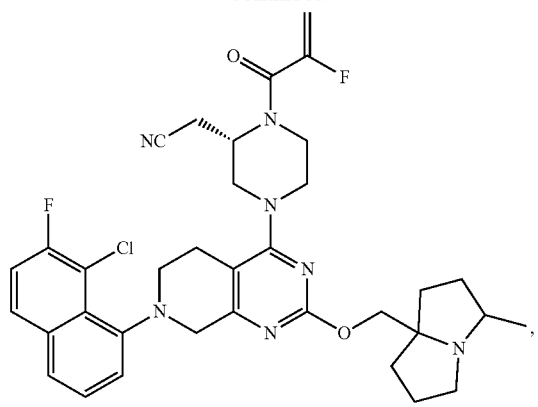
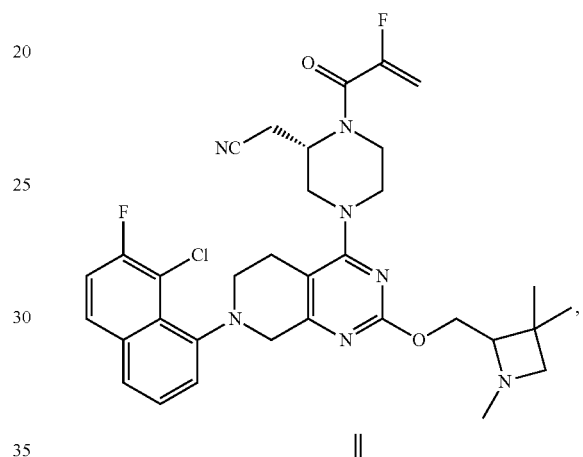
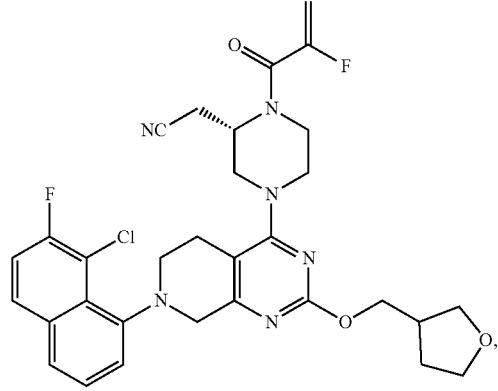

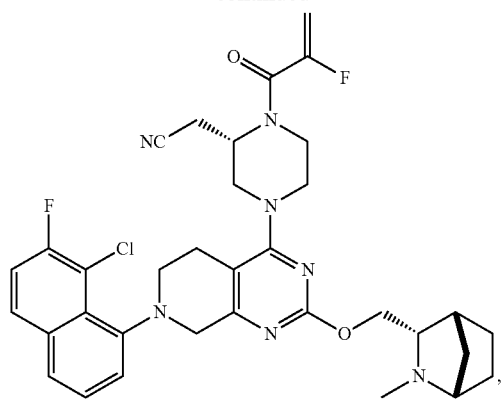
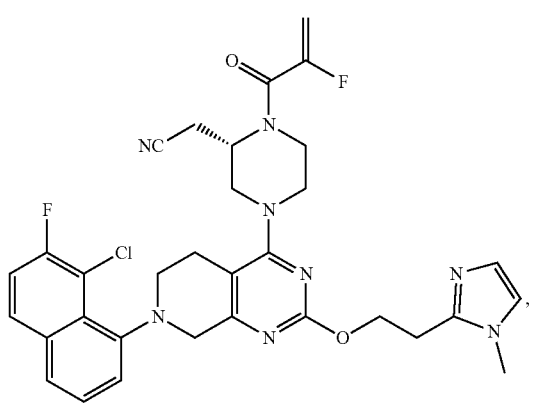
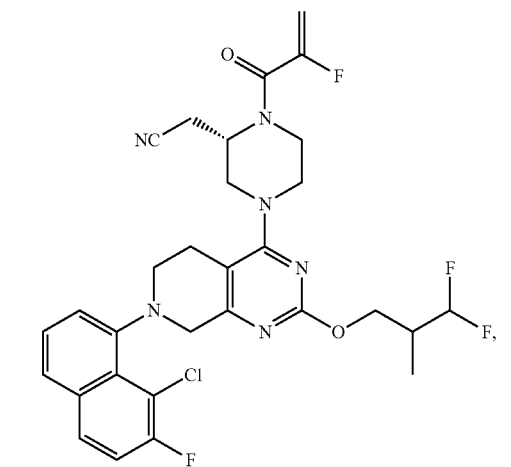
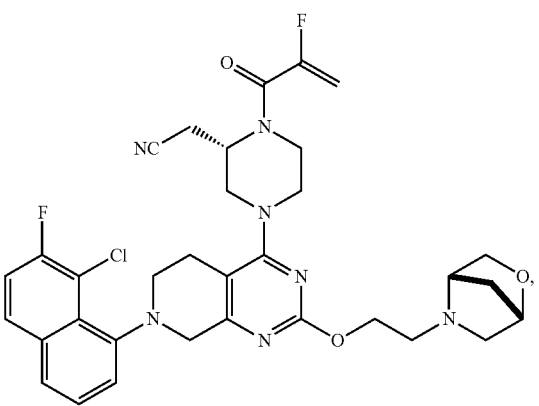
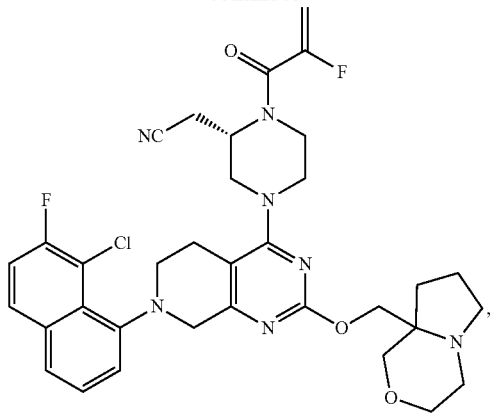
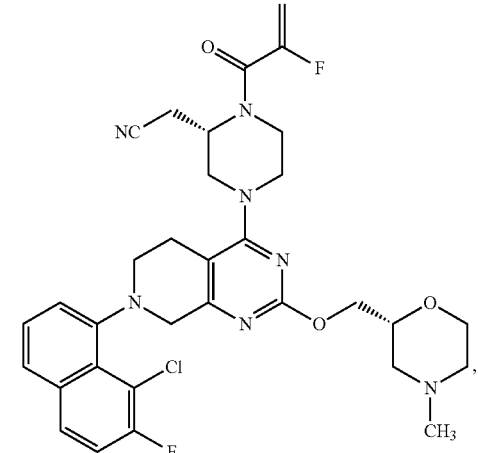
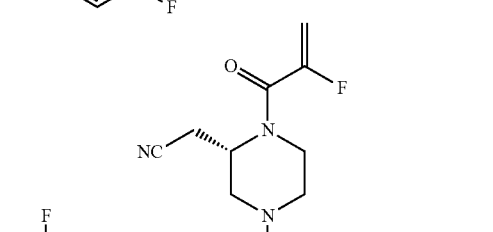
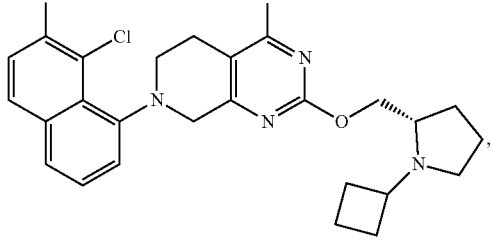

65
-continued
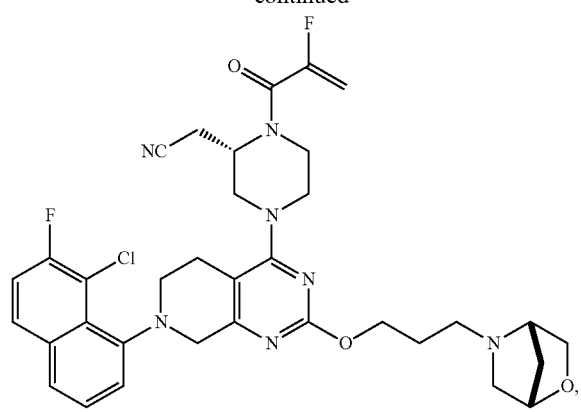
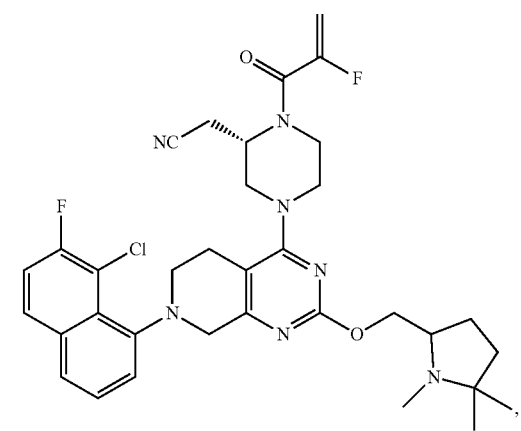
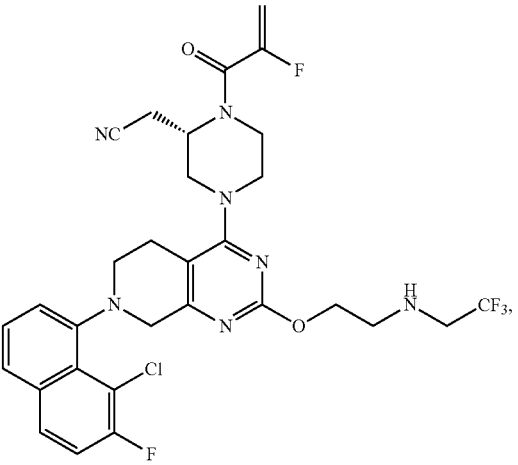
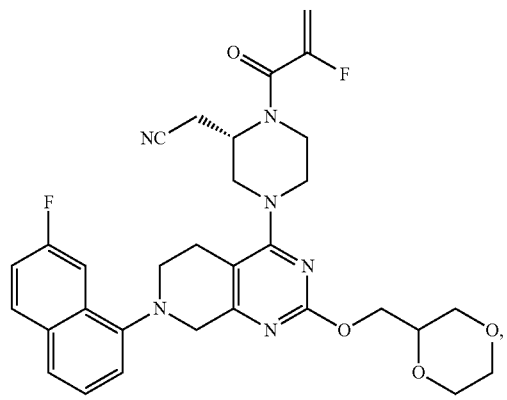
66
-continued
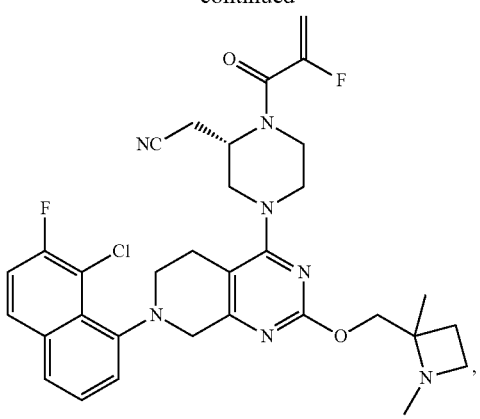
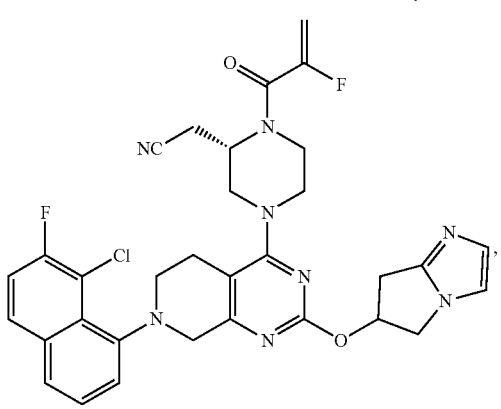
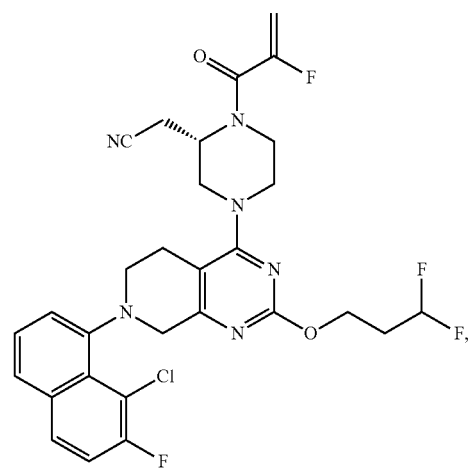
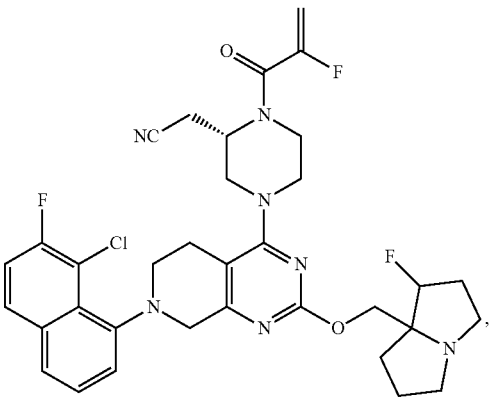

-continued
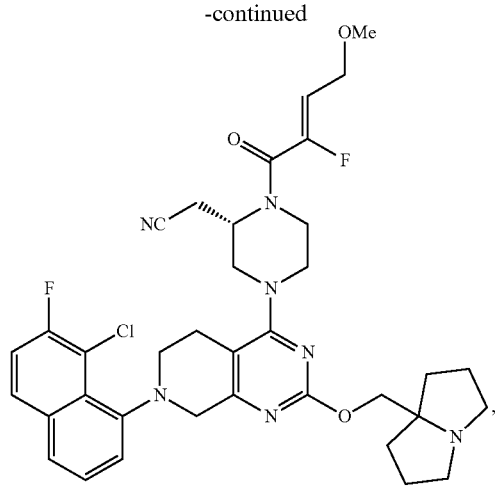
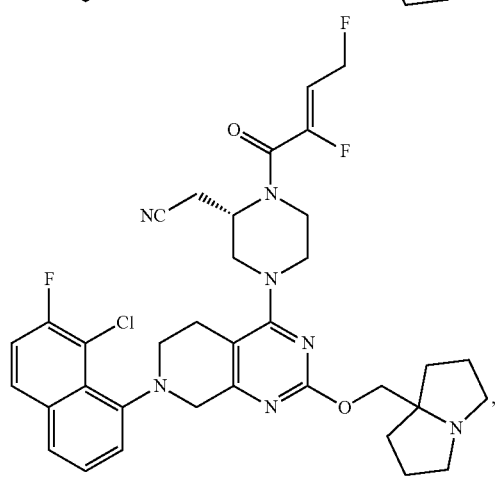
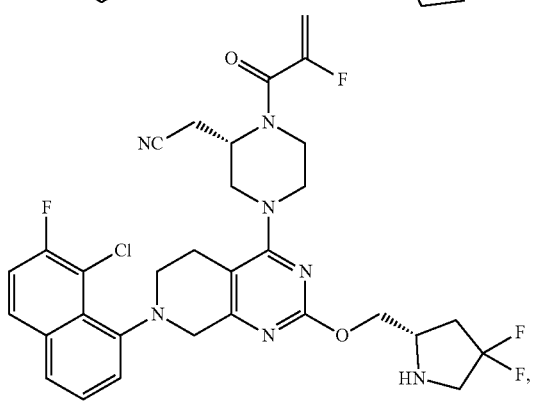
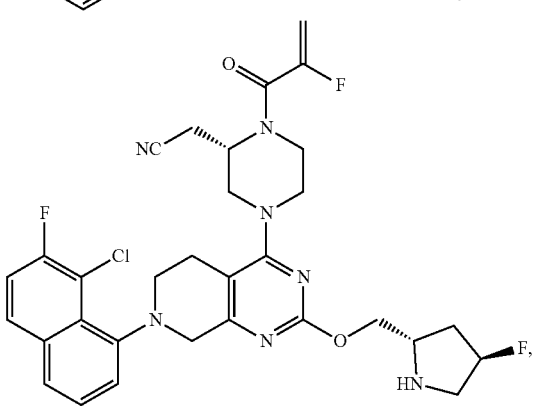
-continued
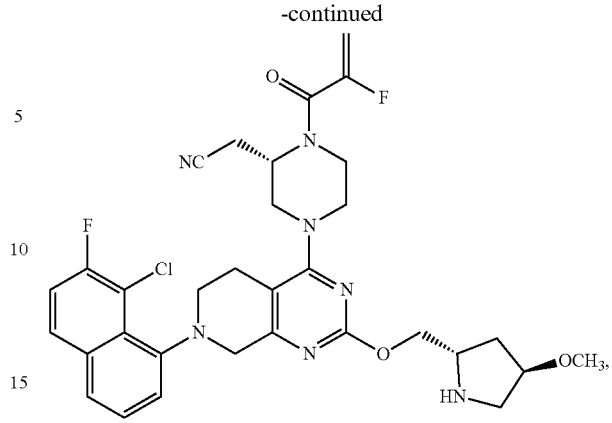
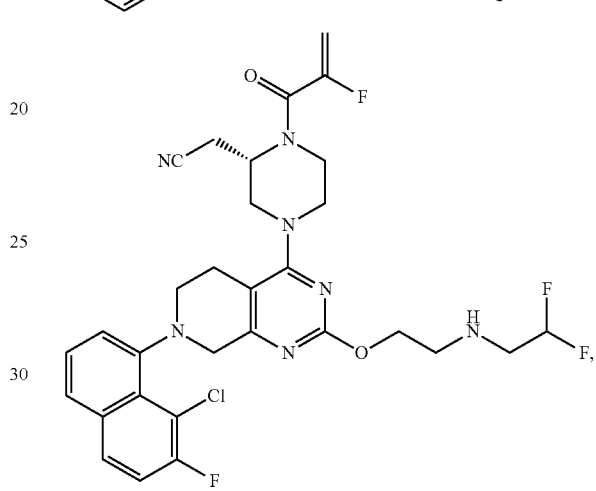
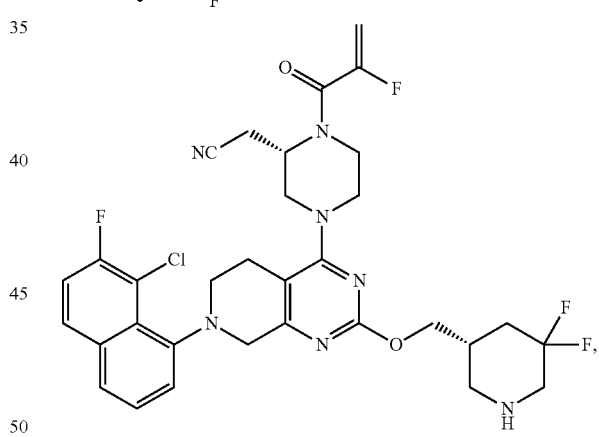
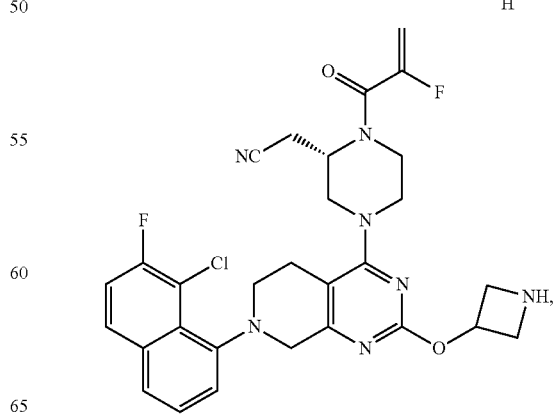

-continued
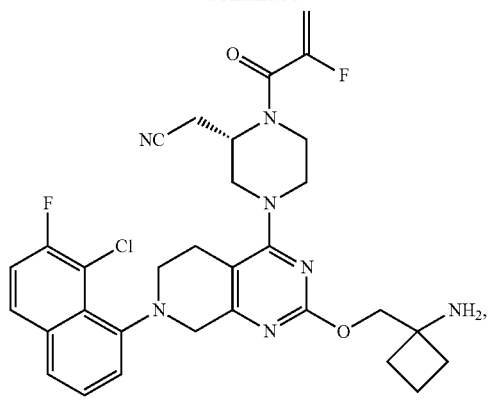
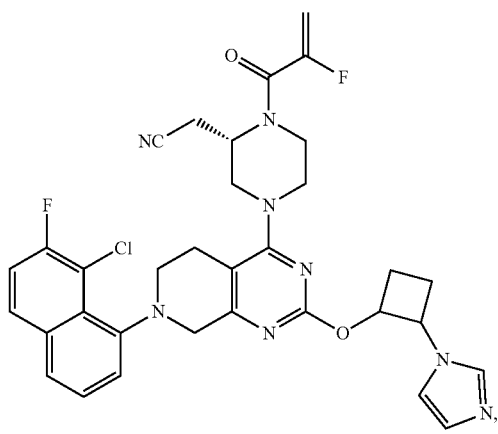
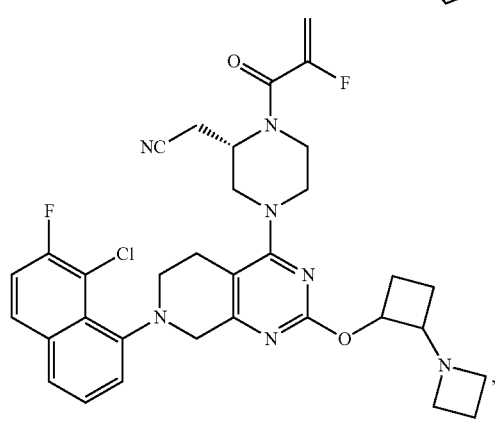
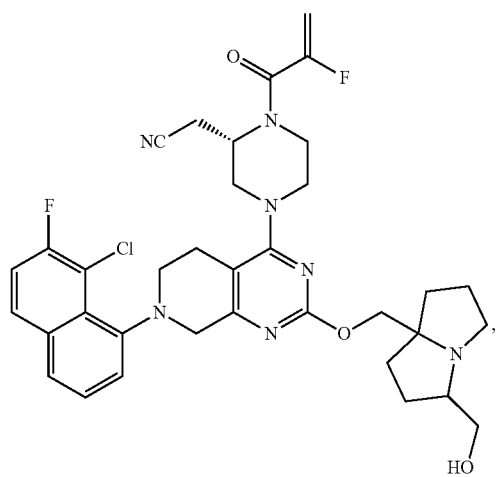
-continued
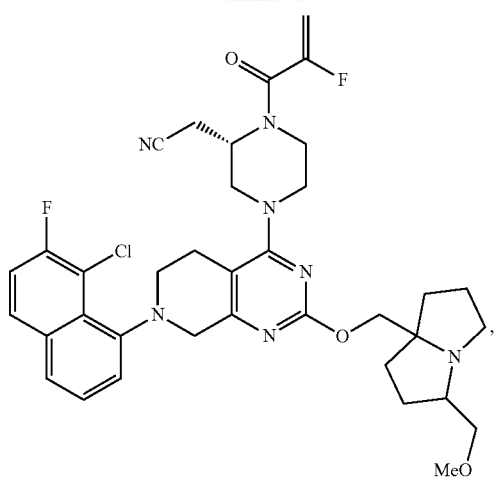
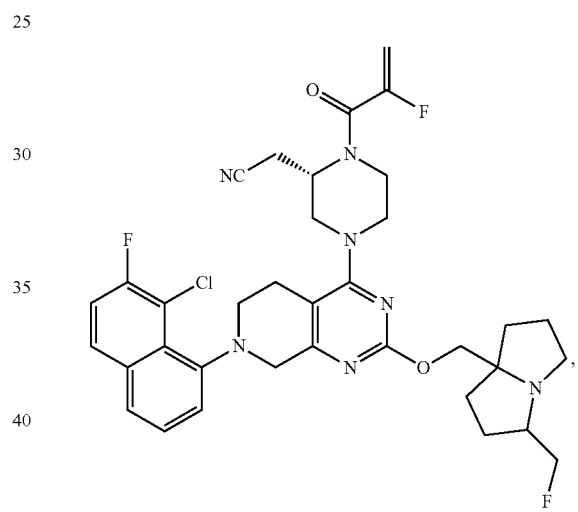
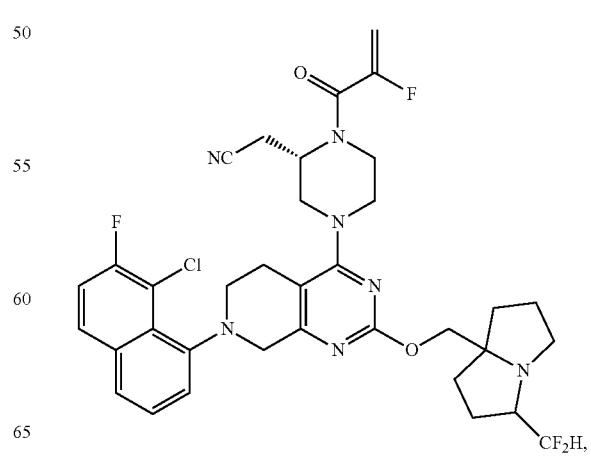

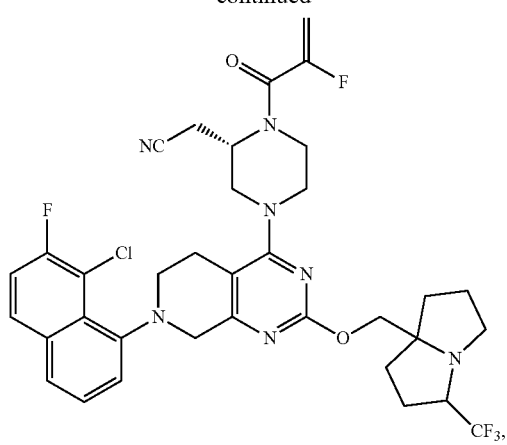
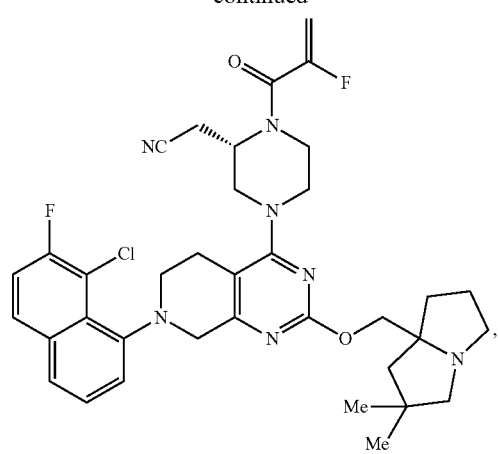
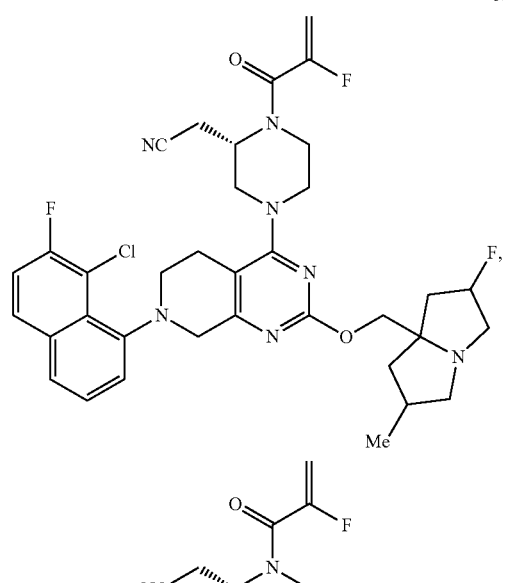
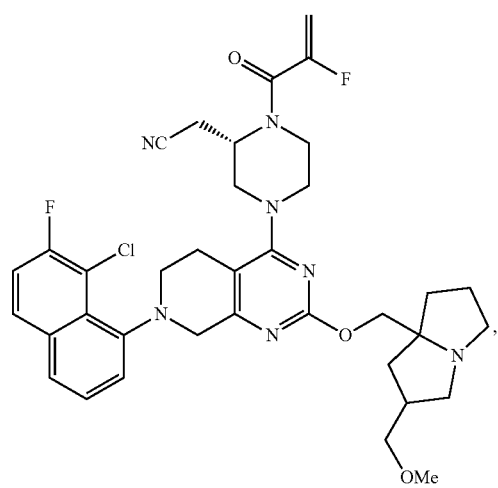
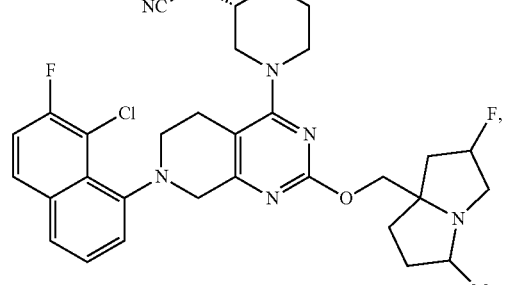
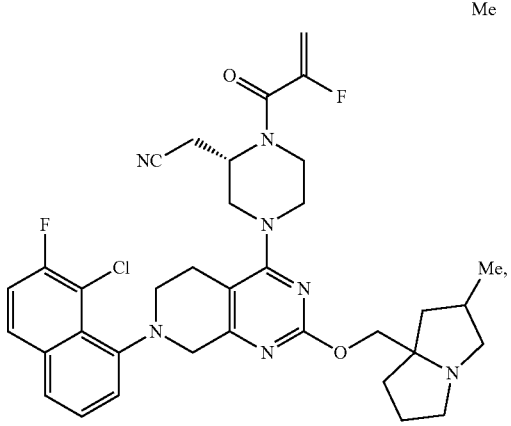

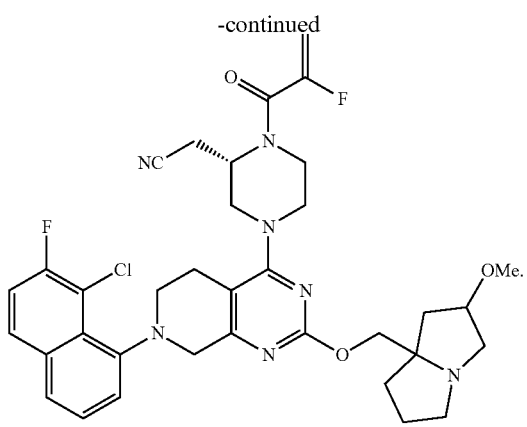

In one embodiment, the compounds of Formula (II) include trifluoroacetic acid salts of the above compounds. The compounds of Formula (II), Formula II-A, and Formula II-B, may be formulated into pharmaceutical compositions.

Pharmaceutical Compositions

In another aspect, the invention provides pharmaceutical compositions comprising a KRas G12C inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12C activity in a cell, comprising contacting the cell in which inhibition of KRas G12C activity is desired with an effective amount of a compound of Formula (II), Formula II-A, or Formula II-B, pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12C with a compound provided herein includes the administration of a compound provided herein to an individual or patient, such as a human, having KRas G12C, as well as, for example, introducing a compound provided herein into a sample containing a cellular or purified preparation containing the KRas G12C.

In one embodiment, a cell in which inhibition of KRas G12C activity is desired is contacted with an effective amount of a compound of Formula (II), Formula II-A, or Formula II-B, to negatively modulate the activity of KRas G12C. In other embodiments, a therapeutically effective amount of pharmaceutically acceptable salt or pharmaceutical compositions containing the compound of Formula (II), Formula II-A, or Formula II-B, may be used.

By negatively modulating the activity of KRas G12C, the methods described herein are designed to inhibit undesired cellular proliferation resulting from enhanced KRas G12C activity within the cell. The cells may be contacted in a single dose or multiple doses in accordance with a particular treatment regimen to effect the desired negative modulation of KRas G12C. The degree of covalent modification of KRas G12C may be monitored in vitro using well known methods, including those described in Example A below. In addition, the inhibitory activity of exemplary compounds in cells may be monitored, for example, by measuring the inhibition of KRas G12C activity of the amount of phosphylated ERK, including those described in Example B below, to assess the effectiveness of treatment and dosages may be adjusted accordingly by the attending medical practitioner.

In another aspect, methods of treating cancer in a patient in need thereof, comprising administering to said patient a therapeutically effective amount of a compound of Formula (II), Formula II-A, or Formula II-B, pharmaceutically acceptable salts thereof or pharmaceutical compositions comprising the compound or pharmaceutically acceptable salts thereof are provided.

The compositions and methods provided herein may be used for the treatment of a KRas G12C-associated cancer in a patient in need thereof, comprising administering to said patient a therapeutically effective amount of a compound of Formula (II), Formula II-A, or Formula II-B, pharmaceutically acceptable salts thereof or pharmaceutical compositions comprising the compound or pharmaceutically acceptable salts thereof are provided. In one embodiment, the KRas G12C-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively.

Also provided herein is a compound of Formula (II), Formula II-A or Formula II-B, or a pharmaceutically acceptable salt or solvate thereof, or a pharmaceutical composition thereof as defined herein for use in therapy.

Also provided herein is a compound of Formula (II), Formula II-A or Formula II-B, or a pharmaceutically acceptable salt or solvate thereof or a pharmaceutical composition thereof as defined herein for use in the treatment of cancer.

Also provided herein is a compound of Formula (II), Formula II-A or Formula II-B, or a pharmaceutically acceptable salt or solvate thereof for use in the inhibition of KRas G12C.

Also provided herein is a compound of Formula (II), Formula II-A, Formula II-B, or a pharmaceutically acceptable salt or solvate thereof or a pharmaceutical composition thereof as defined herein, for use in the treatment of a KRas G12C-associated disease or disorder.

Also provided herein is the use of a compound of Formula (II), Formula II-A or Formula II-B, or a pharmaceutically acceptable salt or solvate thereof, as defined herein in the manufacture of a medicament for the treatment of cancer.

Also provided herein is a use of a compound of Formula (II), Formula II-A or Formula II-B, or a pharmaceutically acceptable salt or solvate thereof, as defined herein in the manufacture of a medicament for the inhibition of activity of KRas G12C.

Also provided herein is the use of a compound of Formula (II), Formula II-A or Formula II-B, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a compound of Formula (II), Formula II-A or Formula II-B, or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Reaction Schemes and Examples

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I and II.

General Reaction Schemes

SCHEME I

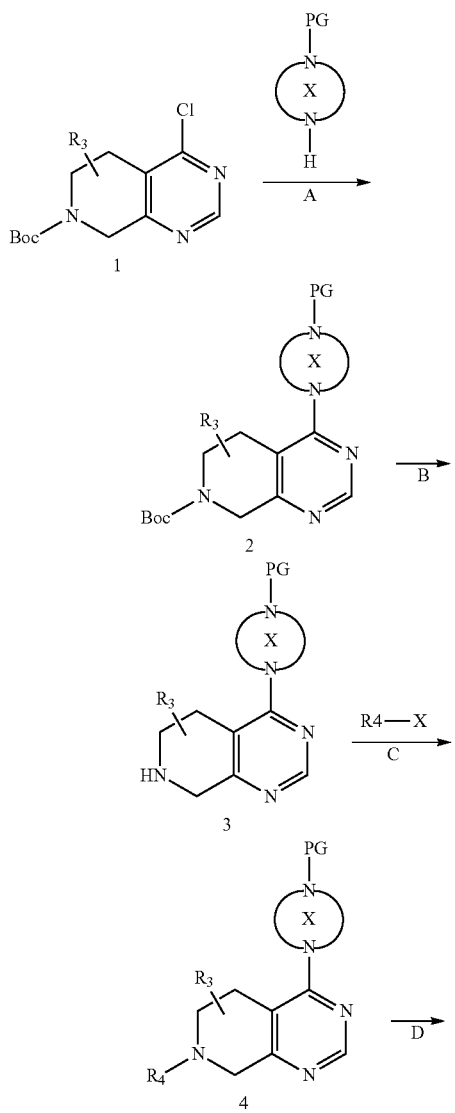

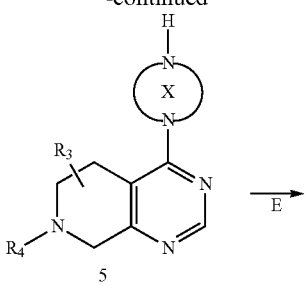

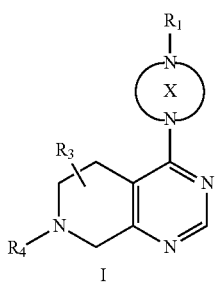

Compounds of Formula (II) wherein L and Y are bonds, $R^2$ is hydrogen and $R^4$ is aryl or heteroaryl can be prepared according to Scheme I. In step A, an appropriately functionalized tetrahydropyridopyrimidine (1) is coupled to a heterocycle containing one nucleophilic amine species, with the other bound to a protecting group to provide compound (2). This coupling proceeds in a solvent such as dichloromethane in the presence of a base such as triethylamine or Hunig's base. In step B, the Boc group of compound (2) is removed using conditions known in the art, for example with trifluoroacetic acid in a solvent such as dichloromethane, to provide compound (3). In step C, the substituent $R^4$ is introduced with a palladium coupling, using a suitable functionalized aryl or heteroaryl system, for example an aryl triflate, in the presence of a palladium catalyst such as $Pd_2DBA_3$/Xantphos in a solvent such as toluene with a base such as sodium tert-butoxide to provide compound (4). In step D, the protecting group of ring X compound (4) is removed, for example hydrogenolysis by Pd/C in the presence of $H_2$ in a polar solvent such as EtOH/THF to provide compound (5). In the final step, E, $R^1$ is introduced to provide a compound of Formula (II), for example by treating with an acid chloride having the formula Cl-C(O)C($R^A$)═══C($R^B$)$_p$ or Cl-SO$_2$C($R^A$)═══C($R^B$)$_p$, or an anhydride having the formula C($R^B$)$_p$═══C($R^A$)C(O)OC(O)C($R^A$)═══C($R^B$)$_p$, where $R^A$, $R^B$ and p are as defined for Formula (II). For example, in the case where $R^1$ is an acryloyl group, this reaction proceeds, for example, in a solvent such as methylene chloride in the presence of acryloyl chloride or an acryloyl anhydride and a base such as Hunig's base. In some cases, the species $R^4$ will also contain a protecting group, which can be removed at a subsequent step in the synthetic sequence.

Compounds (1), (2), (3), (4) and (5) as shown and described above for Scheme 1 are useful as intermediates for preparing compounds of Formula (II) and are provided as further aspects of the invention.

SCHEME II

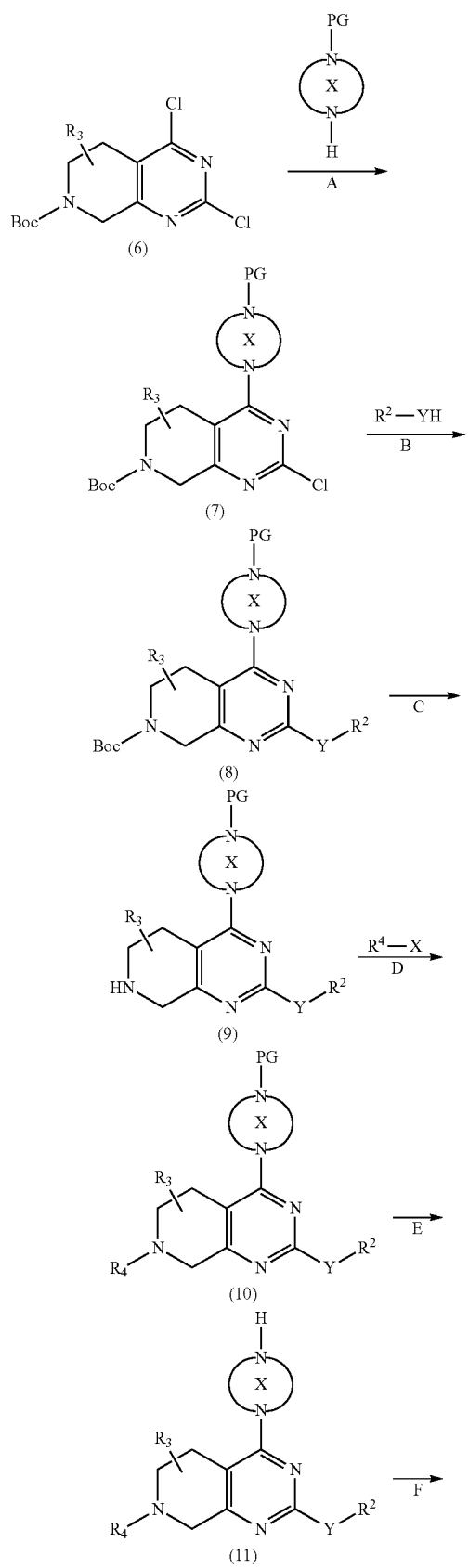

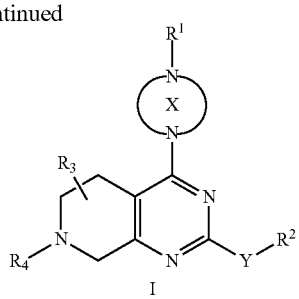

Compounds of Formula (II) wherein L is a bond, —Y—R² is other than hydrogen and R⁴ is aryl or heteroaryl can be prepared according to Scheme II. In step A, an appropriately functionalized tetrahydropyridopyrimidine (6) is coupled to a heterocycle containing one nucleophilic amine species, with the other bound to a protecting group to provide compound (7). This coupling proceeds in a solvent such as dichloromethane in the presence of a base such as triethylamine or Hunig's base. In step B, the substituent —Y—R² is introduced by substitution of the chlorine by a nucleophile, for example (S)-1-(dimethylamino-propan-2-ol in a polar solvent such as dioxane to provide compound (8). In step C, the Boc group is removed using conditions known in the art, for example with trifluoroacetic acid in a solvent such as dichloromethane to provide compound (9). In step D, the substituent R⁴ is introduced with a palladium coupling, using a suitable functionalized aryl or heteroaryl system, for example an aryl triflate, in the presence of a palladium catalyst such as Pd₂DBA₃/BINAP in a solvent such as toluene with a base such as sodium tert-butoxide to provide compound (10). In step E, the protecting group of ring X is removed, for example hydrogenolysis by Pd/C in the presence of H₂ in a polar solvent such as EtOH/THF to provide compound (11). In step F, R¹ is introduced to provide a compound of Formula (II), for example by treating with an acid chloride having the formula Cl—C(O)C(R$^A$)====C(R$^B$)$_p$ or Cl—SO₂C(R$^A$)====C(R$^B$)$_p$, or an anhydride having the formula C(R$^B$)$_p$====C(R$^A$)C(O)OC(O)C(R$^A$)====C(R$^B$)$_p$, where R$^A$, R$^B$ and p are as defined for Formula (II). For example, in the case where R¹ is an acryloyl group, this reaction proceeds, for example, in a solvent such as methylene chloride in the presence of acryloyl chloride acryloyl anhydride and a base such as Hunig's base. In some cases, the species R⁴ and R² may also contain protecting groups, which can be removed at a subsequent step in the synthetic sequence.

Compounds (6), (7), (8), (9), (10) and (11) as shown and described above for Scheme 2 are useful as intermediates for preparing compounds of Formula (II), Formula II-A or Formula II-B and are provided as further aspects of the invention.

Accordingly, also provide is a process for preparing a compound of Formula (II), comprising:

(a) for a compound of Formula (II) where Y is a bond and R² is hydrogen, reacting a compound of formula 5

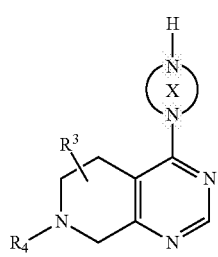

where X, R³ and R⁴ are as defined for Formula (II), with an acid chloride having the formula Cl—C(O)C(R$^A$)═C(R$^B$)$_p$ or Cl—SO$_2$C(R$^A$)═C(R$^B$)$_p$ or an anhydride having the formula C(R$^B$)$_p$═C(R$^A$)C(O)OC(O)C(R$^A$)═C(R$^B$)$_p$, where R$^A$, R$^B$ and p are as defined for Formula (II), in the presence of a base; or (b) for a compound of Formula (II) wherein L is a bond and —Y—R² is other than hydrogen, reacting a compound of formula (11)

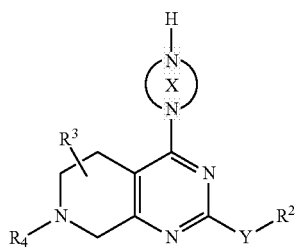

(11)

wherein L is a bond, —Y—R² is other than hydrogen, and X, R³ and R⁴ are as defined for Formula (II), with an acid chloride having the formula Cl—C(O)C(R$^A$)═C(R$^B$)$_p$ or Cl—SO$_2$C(R$^A$)═C(R$^B$)$_p$, or an anhydride having the formula C(R$^B$)$_p$═C(R$^A$)C(O)OC(O)C(R$^A$)═C(R$^B$)$_p$, where R$^A$, R$^B$ and p are as defined for Formula (II), in the presence of a base; and optionally forming a salt thereof.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The following Intermediates are intended to illustrate further certain embodiments of the invention and are not intended to limit the scope of the invention.

Intermediate 1

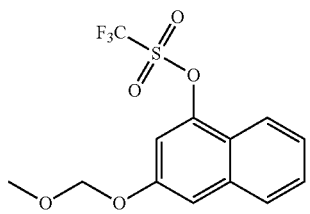 [SMILES: COCOc1cc(OS(=O)(=O)C(F)(F)F)c2ccccc2c1]

3-(methoxymethoxy)naphthalen-1-yl Trifluoromethanesulfonate

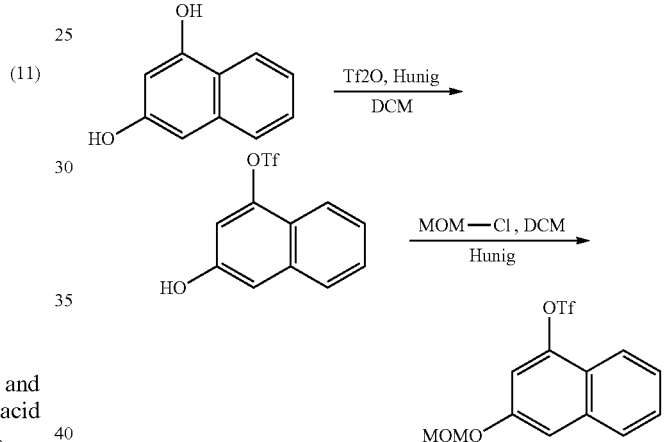

3-Hydroxynaphthalen-1-yl trifluoromethanesulfonate (13.101 g, 44.831 mmol) was dissolved in dichloromethane (100 mL) and stirred at 0° C. To this solution was added chloro(methoxy)methane (3.7456 ml, 49.315 mmol) and Hunig's base (11.745 mL, 67.247 mmol). The reaction was stirred at 0° C. for 4 hrs. The reaction was partitioned with 1M HCl and washed with saturated sodium bicarbonate. The combined organic layers were dried over magnesium sulfate and concentrated under vacuum. The concentrated material was loaded onto a 120 g RediSep® gold silica gel column with dichloromethane and purified by normal phase chromatography (CombiFlash®, 0%-20% ethyl acetate/hexanes as the eluent) to give 3-(methoxymethoxy)naphthalen-1-yl trifluoromethanesulfonate (11.785 g, 35.045 mmol, 78.171% yield).

Intermediate 2

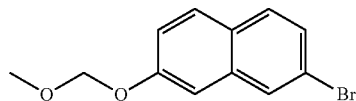

2-bromo-7-(methoxymethoxy)naphthalene

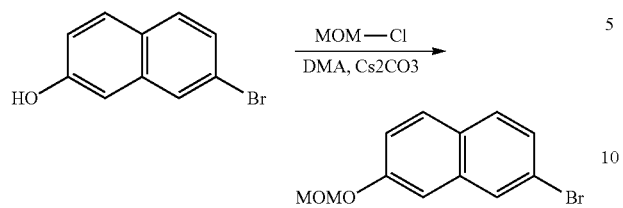

To a solution of 7-bromonaphthalen-2-ol (2.0 g, 9.0 mmol) in dimethyl acetamide (40 mL) was added chloro(methoxy)methane (1.4 g, 18 mmol) and cesium carbonate (5.8 g, 18 mmol) and the reaction mixture was stirred overnight at room temperature. The reaction was diluted with water and the aqueous layer washed with ethyl acetate. The combined organic layers were washed with water and brine, dried over magnesium sulfate and concentrated under vacuum. The crude material was purified by normal phase chromatography using 5-50% ethyl acetate/hexanes as the eluent to give 2-bromo-7-(methoxymethoxy)naphthalene (1.0 g, 3.7 mmol, 42% yield).

Intermediate 3

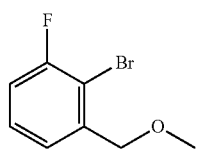

2-bromo-1-fluoro-3-(methoxymethyl)benzene

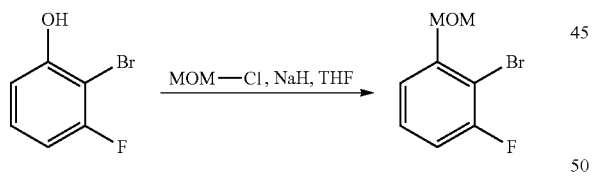

To a stirred solution of 2-bromo-3-fluorophenol (1422 mg, 7.445 mmol) in 22 mL tetrahydrofuran at room temperature under nitrogen was added NaH (327.6 mg, 8.190 mmol) neat as a solid portion wise. After 15 minutes, a solution had formed. Chloro(methoxy)methane (678.6 μL, 8.934 mmol) was added by syringe. After stirring for 2 hours, the reaction was quenched with saturated ammonium chloride solution and then partitioned between ethyl acetate (30 mL) and water (30 mL). The combined organic layers were isolated, washed with brine, dried over MgSO$_4$, filtered and concentrated. The crude product was loaded in a minimum of dichloromethane onto a 40 gram RediSep® column pre-wet with hexanes and eluted with an ethyl acetate/hexanes gradient (0% to 20% ethyl acetate). Fractions containing the product were combined and concentrated to provide the product as a clear oil (1.45 g, 83%).

Intermediate 4

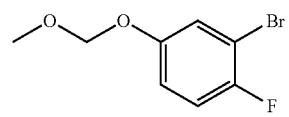

2-bromo-1-fluoro-4-(methoxymethoxy)benzene

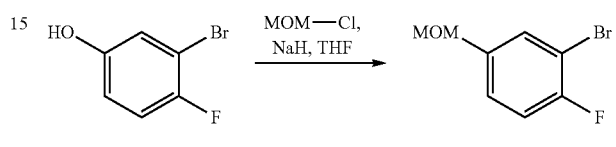

To a stirred solution of 3-bromo-4-fluorophenol (327 mg, 1.71 mmol) in 5.1 mL tetrahydrofuran at room temperature under nitrogen was added NaH (75.3 mg, 1.88 mmol) neat as a solid portion wise. After 15 minutes, a solution had formed. Chloro(methoxy)methane (156 μL, 2.05 mmol) was added by syringe. After stirring for 2 hours, the reaction was quenched with saturated ammonium chloride solution and partitioned between ethyl acetate and water. The combined organic layers were washed with brine, dried over MgSO$_4$, filtered and concentrated. The crude product was loaded in a minimum of dichloromethane onto a 24 gram RediSep® column pre-wet with hexanes and eluted with an ethyl acetate/hexanes gradient (0% to 20% ethyl acetate). Fractions containing the product were combined and concentrated to provide the product as a clear oil (120 mg, 29.8%)

Intermediate 5

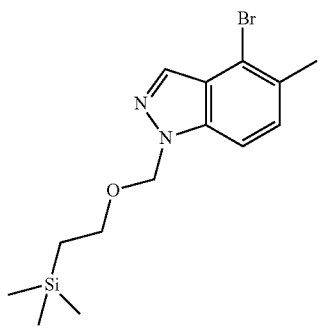

4-bromo-5-methyl-1-((2-(trimethylsilyl)ethoxy)methyl)-1H-indazole

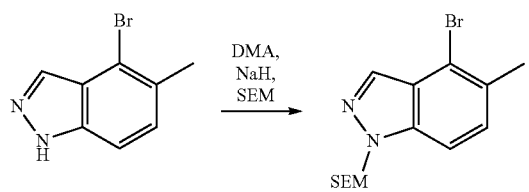 [SMILES: Cc1ccc2[nH]ncc2c1Br ; Cc1ccc2c(cnn2COCC[Si](C)(C)C)c1Br]

To a solution of 4-bromo-5-methyl-1H-indazole (0.7 g, 3.3 mmol) in dimethyl acetamide (30 mL) cooled to 0° C. was added NaH (0.19 g, 4.6 mmol) in portions and the reaction mixture was purged with nitrogen. The reaction was stirred for 20 minutes, and then (2-(chloromethoxy)ethyl) trimethylsilane (0.83 g, 5.0 mmol) was added and the reaction was stirred for 2 hours while warming to room temperature. The reaction was quenched by pouring into water and the aqueous layer was extracted into ethyl acetate. The combined organic layers were washed with water and brine, dried over MgSO₄ and concentrated under vacuum. The crude material was purified by chromatography using 10-50% ethyl acetate/hexanes as the eluent to give 4-bromo-5-methyl-1-((2-(trimethylsilyl)ethoxy)methyl)-1H-indazole (0.87 g, 79%).

Intermediate 6

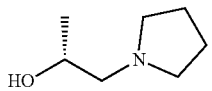

(R)-1-(pyrrolidin-1-yl)propan-2-ol

In a sealed tube, R-(+)-Propylene oxide (3.69 mL, 52.7 mmol) was cooled to −78° C. and then sparged with anhydrous dimethyl amine for a few minutes. The reaction mixture was heated to 70° C. for 16 hours. The reaction was cooled and concentrated in vacuo for 20 minutes to provide (R)-1-(pyrrolidin-1-yl)propan-2-ol (5.35 g, 41.4 mmol, 98.2% yield).

Intermediate 7

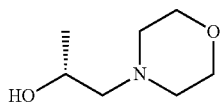

(R)-1-morpholinopropan-2-ol

In a sealed tube, R-(+)-Propylene oxide (2.111 mL, 30.13 mmol) and morpholine (1.490 mL, 17.22 mmol) were heated to 70° C. for 20 hours. The reaction was cooled and concentrated in vacuo to provide (R)-1-morpholinopropan-2-ol (2.47 g, 17.01 mmol, 98.80% yield).

Intermediate 8

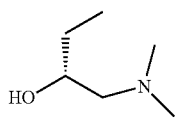

(R)-1-(dimethylamino)butan-2-ol

In a sealed tube, R-(+)-Propylene oxide (4.00 g, 55.5 mmol) and dimethylamine (1.00 g, 22.2 mmol), were heated to 65° C. for 18 hours. The reaction was cooled and concentrated in vacuo. The resulting residue was purified by silica gel (0-12% MeOH in DCM) to provide (R)-1-(dimethylamino)butan-2-ol (1.38 g, 11.8 mmol, 53.1% yield).

Intermediate 9

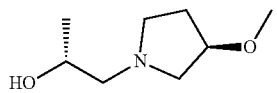

(R)-1-((R)-3-methoxypyrrolidin-1-yl)propan-2-ol

In a sealed tube, (R)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((R)-3-methoxypyrrolidin-1-yl)propan-2-ol (775 mg, 4.87 mmol, 67.0% yield).

Intermediate 10

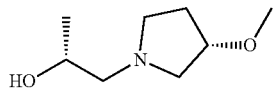

(R)-1-((S)-3-methoxypyrrolidin-1-yl)propan-2-ol

In a sealed tube, (S)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((S)-3-methoxypyrrolidin-1-yl)propan-2-ol (781 mg, 4.90 mmol, 67.5% yield)

Intermediate 11

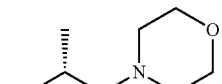

(R)-1-((S)-3-((tert-butyldimethylsilyl)oxy)pyrrolidin-1-yl)propan-2-ol

In a sealed tube, R-(+)-Propylene oxide (0.609 mL, 8.69 mmol) and (S)-3-((tert-butyldimethylsilyl)oxy)pyrrolidine (1.00 g, 4.97 mmol) were heated to 70° C. for 20 hours. The reaction was cooled and concentrated in vacuo to provide (R)-1-((S)-3-((tert-butyldimethylsilyl)oxy)pyrrolidin-1-yl)propan-2-ol (1.29 g, 4.20 mmol, 84.6% yield).

Intermediate 12

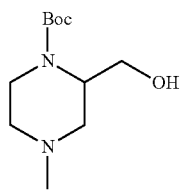

tert-butyl 2-(hydroxymethyl)-4-methylpiperazine-1-carboxylate

To a suspension of lithium chloride (246 mg, 5.81 mmol) and Lithium Borohydride (126 mg, 5.81 mmol) in ethanol (9 mL), at 0° C. under nitrogen, a solution of 1-(tert-butyl) 2-methyl 4-methylpiperazine-1,2-dicarboxylate (750 mg, 2.90 mmol) in dry THF (6 mL) was added dropwise. The reaction was stirred overnight forming a white precipitate. The precipitate was filtered and washed with ethanol. The combined filtrate and organic extracts were concentrated to provide a white residue which was extracted with ethyl acetate. The combined organic layers were washed with saturated sodium chloride solution, dried over sodium sulfate and concentrated in vacuo. The residue was purified by chromatography with isocratic 10% MeOH in DCM with 0.2% NH$_4$OH to provide tert-butyl 2-(hydroxymethyl)-4-methylpiperazine-1-carboxylate (104 mg, 0.452 mmol, 15.6% yield).

Intermediate 13

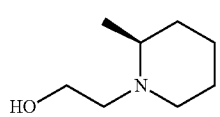

(S)-2-(2-methylpiperidin-1-yl)ethan-1-ol

A mixture of (S)-2-methylpiperidine (100 mg, 1.01 mmol), 2-bromoethanol (78 µL, 139 mg, 1.11 mmol, 1.1 eq.), sodium iodide (151 mg, 1 eq.), potassium carbonate (418 mg, 3 eq.) and acetonitrile (1 mL) in a 4-mL vial was purged with nitrogen, sealed and stirred at room temperature for 2 days. The reaction mixture was partitioned between diethyl ether (15 mL) and water (2 mL). The ether layer was washed with brine (2 mL), acidified with TFA and dried under high vacuum for 2 days. The residue was washed with ether (3 mL), diluted with water (0.5 mL) and basified with 10M NaOH (0.2 mL). The layers were separated and the upper layer was carefully dried over NaOH. The ether solution was evaporated under nitrogen to yield crude (S)-2-(2-methylpiperidin-1-yl)ethan-1-ol (100 mg, 0.698 mmol, 69.24% yield) as colorless oil.

Intermediate 14

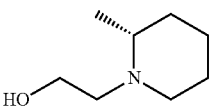

(R)-2-(2-methylpiperidin-1-yl)ethan-1-ol

Synthesized according to the method of Intermediate 13, using (R)-2-methylpiperidine (99 mg, 1 mmol) in place of (S)-2-methylpiperidine.

Intermediate 15

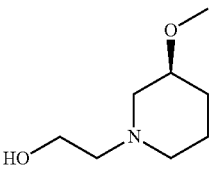

(S)-2-(3-methoxypiperidin-1-yl)ethan-1-ol

Synthesized according to the method of Intermediate 13, using (S)-3-methoxypiperidine (173 mg, 1.50 mmol) in place of (S)-2-methylpiperidine.

Intermediate 16

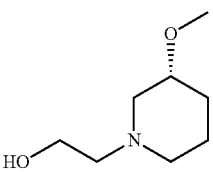

(R)-2-(3-methoxypiperidin-1-yl)ethan-1-ol

Synthesized according to the method of Intermediate 13, using R-3-methoxypiperidine (173 mg, 1.50 mmol) in place of (S)-2-methylpiperidine.

Intermediate 17

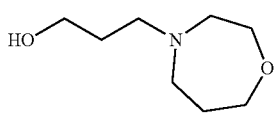

3-(1,4-oxazepan-4-yl)propan-1-ol

To a vial was added homomorpholine (0.250 g, 2.472 mmol), Acetonitrile (4.943 mL, 2.472 mmol) and 3-Bromo- 1-propanol (0.2459 mL, 2.719 mmol). Potassium carbonate (0.6832 g, 4.943 mmol) was added and the mixture was warmed to 50° C. and stirred for 6 hours. The mixture was cooled to ambient temperature, diluted with DCM, filtered and the collected solids were washed with DCM. The filtrate was concentrated in vacuo and the crude oil was purified via column chromatography (Biotage Isolera, 12 g Isco RediSep Gold, 10-20% MeOH/DCM with 0.2% NH$_4$OH) to afford 3-(1,4-oxazepan-4-yl)propan-1-ol (0.272 g, 1.708 mmol) as a colorless oil.

Intermediate 18

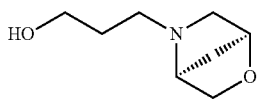

3-((1S,4S)-2-oxa-5-azabicyclo[2.2.1]heptan-5-yl) propan-1-ol

Synthesized according to the method of Intermediate 17, using (1S,4S)-2-Oxa-5-azabicyclo[2.2.1]heptane (0.250 g, 2.522 mmol) in place of homomorpholine.

Intermediate 19

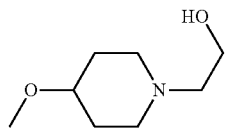

2-(4-methoxypiperidin-1-yl)ethan-1-ol

Synthesized according to the method of Intermediate 13, using 4-methoxypiperidine (173 mg, 1.50 mmol) in place of (S)-2-methylpiperidine.

Intermediate 20

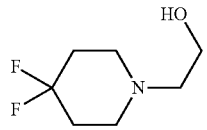

2-(4,4-difluoropiperidin-1-yl)ethan-1-ol

Synthesized according to the method of Intermediate 13, using 4,4-difluoropiperidine hydrochloride (173 mg, 1.50 mmol) in place of (S)-2-methylpiperidine.

Intermediate 21

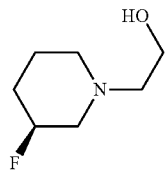

(S)-2-(3-fluoropiperidin-1-yl)ethan-1-ol

Synthesized according to the method of Intermediate 13, using S-3-fluoropiperidine hydrochloride (209 mg, 1.50 mmol) in place of (S)-2-methylpiperidine.

Intermediate 22

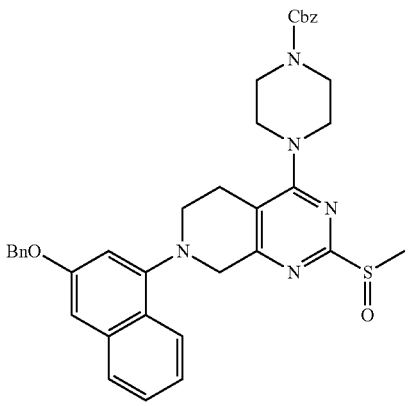

Benzyl 4-(7-(3-(benzyloxy)naphthalen-1-yl)-2-(methylsulfinyl)-5,6,7,8-tetrahydropyrido[3,4-d] pyrimidin-4-yl)piperazine-1-carboxylate Step A: Tert-Butyl 4-hydroxy-2-(methylthio)-5,8-dihydropyrido[3,4-d]pyrimidine-7(6H)-carboxylate To a stirred solution of 1-tert-butyl 4-ethyl 3-oxopiperidine-1,4-dicarboxylate (50.0 g, 184 mmol, 1.00 eq) in MeOH (1.00 L) at 25° C. under nitrogen was added NaOMe (49.8 g, 921 mmol, 5.00 eq), followed by 2-methylisothiourea (62.4 g, 331 mmol, 1.80 eq, H$_2$SO$_4$) as a solid. The reaction mixture was stirred at 25° C. for 16 hours. The reaction mixture was adjusted to pH 5 with HCl (2 M), and the mixture was concentrated under reduced pressure to removed MeOH. The residue was suspended in 300 mL of ethyl acetate and 300 mL of water and stirred rapidly. The suspension was filtered and the white solid was collected. The filtrate was separated and the organic layer was washed with water (1×300 mL) and brine (1×200 mL). The combined organic layers were isolated, dried over Na$_2$SO$_4$, filtered and concentrated to provide tert-butyl 4-hydroxy-2-methylsulfanyl-6,8-dihydro-5H-pyrido[3,4-d]pyrimidine-7-carboxylate (51.0 g, 138 mmol, 75.4% yield, 81.0% purity) as a white solid which as used directly in the next step without further purification. ESI MS m/z 298.2 [M+H]$^+$.

Step B: Tert-Butyl 2-methylsulfanyl-4-(trifluoromethylsulfonyloxy)-6,8-dihydro-5H-pyrido[3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (51.0 g, 171 mmol, 1.00 eq) in DCM (500 mL) at 0° C. was added DIEA (44.3 g, 343 mmol, 59.9 mL, 2.00 eq), followed by trifluoromethanesulfonic anhydride (72.6 g, 257 mmol, 42.4 mL, 1.50 eq) under nitrogen. Immediately a brown solution formed. After stirring at 25° C. for 16 hours, the reaction was concentrated to give a brown oil. The brown oil was purified by column chromatography (SiO$_2$, Petroleum ether/Ethyl acetate=1:0 to 10:1) to provide tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62.4% yield) as a yellow solid ESI MS m/z 430.2 [M+H]$^+$.

Step C: Tert-Butyl 4-(4-benzyloxycarbonylpiperazin-1-yl)-2-methylsulfanyl-6,8-dihydro-5H-pyrido[3,4-d]pyrimidine-7-carboxylate To a stirred solution of tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 1.00 eq) in DMF (500 mL) was added DIEA (27.7 g, 214 mmol, 37.4 mL, 2.00 eq) followed by benzyl piperazine-1-carboxylate (25.9 g, 117 mmol, 22.7 mL, 1.10 eq). The reaction was heated to 100° C. for 1 hour under a nitrogen atmosphere. The reaction mixture was poured into ethyl acetate (300 mL), washed with H$_2$O (300 mL×3) and brine (200 mL), dried over anhydrous Na$_2$SO$_4$, filtered and concentrated under vacuum. The residue was purified by column chromatography (SiO$_2$, Petroleum ether/Ethyl acetate=1:0 to 5:1) to give tert-butyl 4-(4-benzyloxycarbonylpiperazin-1-yl)-2-methylsulfanyl-6,8-dihydro-5H-pyrido[3,4-d]pyrimidine-7-carboxylate (51.0 g, 96.9 mmol, 90.5% yield, 92.0% purity) as a white solid ESI MS m/z 500.3 [M+H]$^+$.

Step D: Benzyl 4-(2-methylsulfanyl-5,6,7,8-tetrahydropyrido[3,4-d]pyrimidin-4-yl) piperazine-1-carboxylate To a solution of tert-butyl 4-(4-benzyloxycarbonylpiperazin-1-yl)-2-methylsulfanyl-6,8-dihydro-5H-pyrido[3,4-d]pyrimidine-7-carboxylate (25.0 g, 50.0 mmol, 1.00 eq) in DCM (50.0 mL) was added TFA (85.6 g, 750 mmol, 55.6 mL, 15.0 eq). After stirring at 25° C. for 1 hour, the reaction mixture was concentrated under reduced pressure. The residue was dissolved in 300 mL of ethyl acetate and 300 mL of water and stirred rapidly. The mixture was adjusted to pH 8 with Na$_2$CO$_3$. The organic layer was washed with water (1×300 mL) and brine (1×200 mL), dried over Na$_2$SO$_4$, filtered and concentrated under reduced pressure to provide benzyl 4-(2-methylsulfanyl-5,6,7,8-tetrahydropyrido[3,4-d]pyrimidin-4-yl) piperazine-1-carboxylate (19.0 g, 46.6 mmol, 93.2% yield, 98.0% purity) as a yellow oil. ESI MS m/z 400.2 [M+H]$^+$.

Step E: Benzyl 4-[7-(3-benzyloxy-1-naphthyl)-2-methylsulfanyl-6,8-dihydro-5H-pyrido[3,4-d]pyrimidin-4-yl]piperazine-1-carboxylate A mixture of 3-benzyloxy-1-bromo-naphthalene (16.3 g, 52.1 mmol, 1.30 eq), benzyl 4-(2-methylsulfanyl-5,6,7,8-tetrahydropyrido[3,4-d]pyrimidin-4-yl)piperazine-1-carboxylate (16.0 g, 40.1 mmol, 1.00 eq), Cs$_2$CO$_3$ (32.6 g, 100 mmol, 2.50 eq), Pd$_2$(dba)$_3$ (5.50 g, 6.01 mmol, 0.15 eq) and 2-dicyclohexylphosphino-2',6'-diisopropoxybiphenyl (RuPhos) (3.74 g, 8.01 mmol, 0.20 eq) in dioxane (300 mL) was degassed and purged with nitrogen 3 times. The mixture was stirred at 85° C. for 5 hours under a nitrogen atmosphere. The reaction mixture was quenched by adding water (200 mL) at 0° C., and extracted with ethyl acetate (3×200 mL). The combined organic layers were washed with brine (3×150 mL), dried over Na$_2$SO$_4$, filtered and concentrated under reduced pressure. The residue was purified by column chromatography (SiO$_2$, DCM/MeOH=10/1 to 5/1) to provide benzyl 4-[7-(3-benzyloxy-1-naphthyl)-2-methylsulfanyl-6,8-dihydro-5H-pyrido[3,4-d]pyrimidin-4-yl]piperazine-1-carboxylate (16.0 g, 22.8 mmol, 56.9% yield, 90.0% purity) as a yellow solid. ESI MS m/z 632.5 [M+H]$^+$.

Step F: Benzyl 4-[7-(3-benzyloxy-1-naphthyl)-2-methylsulfinyl-6,8-dihydro-5H-pyrido [3,4-d]pyrimidin-4-yl]piperazine-1-carboxylate To a stirred solution of benzyl 4-[7-(3-benzyloxy-1-naphthyl)-2-methylsulfanyl-6,8-dihydro-5H-pyrido[3,4-d]pyrimidin-4-yl]piperazine-1-carboxylate (8.00 g, 12.7 mmol, 1.00 eq) in DCM (200 mL) was added m-CPBA (2.73 g, 12.7 mmol, 80.0% purity, 1.00 eq) at 0° C. under nitrogen. After stirring at 0° C. for 2 hours under a nitrogen atmosphere, the reaction mixture was quenched by adding Na$_2$S$_2$O$_3$ (10.0 mL) at 0° C., diluted with water (100 mL) and extracted with DCM (200 mL). The combined organic layers were washed with brine (200 mL), dried over Na$_2$SO$_4$, filtered and concentrated under reduced pressure to give a residue. The residue was purified by column chromatography (SiO$_2$, DCM/MeOH=1/0 to 10/1) to provide benzyl 4-[7-(3-benzyloxy-1-naphthyl)-2-methylsulfinyl-6,8-dihydro-5H-pyrido[3,4-d]pyrimidin-4-yl]piperazine-1-carboxylate (3.50 g, 4.92 mmol, 38.8% yield, 91.0% purity) as a yellow solid. ESI MS m/z 648.5 [M+H]$^+$.

Intermediate 23

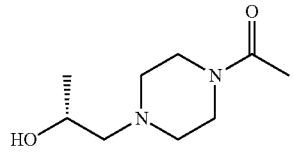

(R)-1-(4-(2-hydroxypropyl)piperazin-1-yl)ethan-1-one

Step A: 1-[4-[(2R)-2-hydroxypropyl]piperazin-1-yl]ethanone (2R)-2-methyloxirane (1.00 g, 17.2 mmol, 1.20 mL, 1.00 eq) and 1-piperazin-1-ylethanone (8.00 g, 62.4 mmol, 3.62 eq) were taken up into a microwave tube. The sealed tube was heated at 150° C. for 1 hour under microwave. The mixture was dissolved in DCM (80.0 mL), added (Boc)$_2$O (3.62 eq, 13.6 g) and stirred at 20° C. for 1 hour. The residue was purified by column chromatography (DCM/MeOH 100/1 to 10/1) to give 1-[4-[(2R)-2-hydroxypropyl]piperazin-1-yl]ethanone (3.80 g, 13.5 mmol, 78.2% yield, 66.0% purity) as a yellow oil.

Intermediate 24

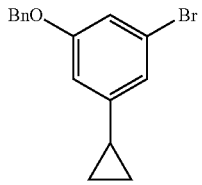

1-(benzyloxy)-3-bromo-5-cyclopropylbenzene

Step A: 1-benzyloxy-3,5-dibromo-benzene

To a mixture of 3,5-dibromophenol (1.50 g, 5.95 mmol, 1.00 eq) and K₂CO₃ (2.47 g, 17.9 mmol, 3.00 eq) in MeCN (30.0 mL) was added benzyl bromide (1.07 g, 6.25 mmol, 742 µL, 1.05 eq), the reaction mixture was stirred at 80° C. for 2 hours. The reaction mixture was filtered and concentrated. The residue was purified by column chromatography (SiO₂, Petroleum ether/Ethyl acetate=1:1 to give 1-benzyloxy-3,5-dibromobenzene (1.60 g, 4.68 mmol, 78.6% yield) as colorless oil.

Step B: 1-benzyloxy-3-bromo-5-cyclopropylbenzene

To a mixture of 1-benzyloxy-3,5-dibromobenzene (1.20 g, 3.51 mmol, 1.00 eq) and cyclopropylboronic acid (392 mg, 4.56 mmol, 1.30 eq) in H₂O (4.00 mL) and dioxane (20.0 mL) was added Pd(dppf)Cl₂ (513 mg, 702 µmol, 0.20 eq) and Cs₂CO₃ (2.29 g, 7.02 mmol, 2.00 eq). The reaction mixture was stirred at 90° C. for 12 hours under N₂. The reaction mixture was added to water (20 mL) and extracted with ethyl acetate (2×15 mL). The combined organic layers were dried over Na₂SO₄, filtered and concentrated. The residue was purified by column chromatography (SiO₂, Petroleum ether/Ethyl acetate=1:1 to give 1-benzyloxy-3-bromo-5-cyclopropyl-benzene (270 mg, 890 µmol, 25.4% yield) as colorless oil.

Intermediate 25

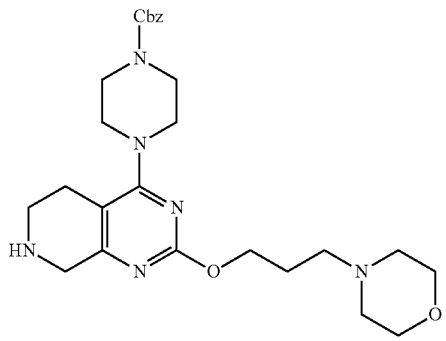 [SMILES: O=C(OCc1ccccc1)N1CCN(c2nc(OCCCN3CCOCC3)nc3c2CCNC3)CC1]

Benzyl 4-(2-(3-morpholinopropoxy)-5,6,7,8-tetrahydropyrido[3,4-d]pyrimidin-4-yl)piperazine-1-carboxylate

Step A: Tert-Butyl 4-(4-benzyloxycarbonylpiperazin-1-yl)-2-(3-morpholinopropoxy)-6,8-dihydro-5H-pyrido[3,4-d]pyrimidine-7-carboxylate To a mixture of 3-morpholinopropan-1-ol (5.46 g, 37.6 mmol, 2.00 eq) in THF (100 mL) was added NaH (2.26 g, 56.4 mmol, 60.0% purity, 3.00 eq) in portions at 0° C. After the mixture was stirred at 0° C. for 0.5 hour, a solution of tert-butyl 4-(4-benzyloxycarbonylpiperazin-1-yl)-2-methyl sulfonyl-6,8-dihydro-5H-pyrido[3,4-d]pyrimidine-7-carboxylate (10.0 g, 18.8 mmol, 1.00 eq) in THF (100 mL) was added, and the reaction mixture was stirred at 0° C. for 1.5 hours under N₂. The mixture was poured into NH₄Cl aqueous (300 mL), and extracted with DCM (2×200 mL). The combined organic layers were dried over Na₂SO₄, filtered and concentrated. The residue was purified by column chromatography (SiO₂, Petroleum ether/Ethyl acetate=50:1 to 10:1) to give tert-butyl 4-(4-benzyloxycarbonylpiperazin-1-yl)-2-(3-morpholinopropoxy)-6,8-dihydro-5H-pyrido[3,4-d]pyrimidine-7-carboxylate (7.70 g, 12.8 mmol, 67.8% yield, 98.8% purity) as a yellow oil. ESI MS m/z 597.4 [M+H]⁺.

Step B: Benzyl 4-[2-(3-morpholinopropoxy)-5,6,7,8-tetrahydropyrido[3,4-d]pyrimidin-4-yl]piperazine-1-carboxylate To a mixture of tert-butyl 4-(4-benzyloxycarbonylpiperazin-1-yl)-2-(3-morpholinopropoxy)-6,8-dihydro-5H-pyrido[3,4-d]pyrimidine-7-carboxylate (7.70 g, 12.9 mmol, 1.00 eq) in DCM (80.0 mL) was added TFA (119 g, 1.04 mol, 76.9 mL, 80.6 eq), and the reaction mixture was stirred at 15° C. for 1 hour. The reaction mixture was concentrated, then diluted with DCM (100 mL) and adjusted to pH 8 with aqueous NaOH. The organic layer was separated, dried over Na₂SO₄, filtered and concentrated to give benzyl 4-[2-(3-morpholinopropoxy)-5,6,7,8-tetrahydropyrido[3,4-d]pyrimidin-4-yl]piperazine-1-carboxylate (6.00 g, 11.2 mmol, 86.9% yield, 92.8% purity) as yellow oil. ESI MS m/z 497.4 [M+H]⁺.

Intermediate 26

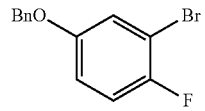

4-(benzyloxy)-2-bromo-1-fluorobenzene

To a solution of 3-bromo-4-fluorophenol (4.00 g, 20.9 mmol, 1.00 eq) and K₂CO₃ (8.68 g, 62.8 mmol, 3.00 eq) in ACN (80.0 mL) was added benzyl bromide (3.65 g, 21.4 mmol, 2.54 mL, 1.02 eq) and the reaction mixture was stirred at 60° C. for 2 hrs. The reaction mixture was filtered and concentrated in vacuum. The residue was purified by silica gel chromatography (petroleum ether:ethyl acetate; gradient from 1:0 to 10:1) to give 4-benzyloxy-2-bromo-1- fluoro-benzene (5.02 g, 17.0 mmol, 81.0% yield, 95% purity) was obtained as white solid.

Intermediate 27

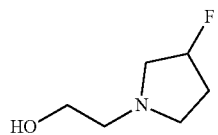

2-(3-fluoropyrrolidin-1-yl)ethan-1-ol

Step A: Tert-Butyl 3-fluoropyrrolidine-1-carboxylate

To a solution of tert-butyl 3-hydroxypyrrolidine-1-carboxylate (10.0 g, 53.4 mmol, 1.00 eq) in DCM (150.00 mL) was added diethylaminosulfur trifluoride (DAST) (12.9 g, 80.1 mmol, 10.6 mL, 1.50 eq) at −40° C. under a nitrogen atmosphere. After stirring at −40° C. for 2 hours, the mixture was warmed to 20° C. and stirred for 16 hours. The mixture was poured into 5% aqueous sodium bicarbonate (200 mL) and extracted with dichloromethane (2×100 mL). The organic layer was dried over sodium sulfate, filtered and concentrated under vacuum. The residue was purified by column chromatography over silica gel (petroleum ether/ethyl acetate 100:1 to 5:1). The desired fractions were collected and concentrated under vacuum to give tert-butyl 3-fluoropyrrolidine-1-carboxylate (4.30 g, 22.7 mmol, 42.6% yield) as a colorless oil. $^1$H NMR (400 MHz, Chloroform-d) δ=5.27 (t, J=3.6 Hz, 0.5H), 5.13 (t, J=3.6 Hz, 0.5H), 3.77-3.38 (m, 4H), 2.26-2.15 (m, 1H), 2.08-1.85 (m, 1H), 1.46 (s, 9H).

Step B: 3-fluoropyrrolidine

To a solution of tert-butyl 3-fluoropyrrolidine-1-carboxylate (4.30 g, 22.7 mmol, 1.00 eq) in DCM (50.00 mL) was added HCl/dioxane (4 M, 35.0 mL, 6.16 eq) dropwise at 0° C. The mixture was warmed to 20° C. and stirred for 1 hour. The mixture was concentrated under vacuum. The residue was triturated with diisopropyl ether (20 mL) and the precipitate was filtered and dried under vacuum to provide 3-fluoropyrrolidine (2.70 g, 21.5 mmol, 94.6% yield, HCl) as a white solid. $^1$H NMR (400 MHz, Methanol-$d_4$) δ=5.51 (t, J=3.6 Hz, 0.5H), 5.38 (t, J=3.6 Hz, 1H), 3.66-3.27 (m, 5H), 2.45-2.12 (m, 2H).

Step C: Methyl 2-(3-fluoropyrrolidin-1-yl)acetate

A suspension of 3-fluoropyrrolidine (2.70 g, 21.5 mmol, 1.00 eq, HCl) in DCM (27.00 mL) was cooled to 0° C. Triethylamine (5.44 g, 53.8 mmol, 7.45 mL, 2.50 eq) and methyl 2-bromoacetate (3.62 g, 23.7 mmol, 2.23 mL, 1.10 eq) were added and the reaction mixture was stirred at 20° C. for 16 h. The reaction mixture was diluted with CH2C12 (100 mL) and water (50 mL). The organic layer was washed with 5% aqueous citric acid solution (1×50 mL). The water layer was basified by saturated aqueous sodium carbonate solution (20 mL) and extracted with ethyl acetate (3×100 mL). The combined organic layers were dried over sodium sulfate and concentrated in vacuo to give methyl 2-(3-fluoropyrrolidin-1-yl)acetate (2.20 g, 13.7 mmol, 63.5% yield). $^1$H NMR (400 MHz, Chloroform-d) δ=5.22-5.02 (m, 1H), 3.66 (s, 3H), 3.35 (s, 2H), 3.07-2.93 (m, 1H), 2.91-2.77 (m, 2H), 2.67 (dt, J=5.2, 8.4 Hz, 1H), 2.21-1.93 (m, 2H).

Step D: 2-(3-fluoropyrrolidin-1-yl)ethanol

To a solution of LiAlH$_4$ (706 mg, 18.6 mmol, 1.50 eq) in THF (20 mL) was added a solution of methyl 2-(3-fluoropyrrolidin-1-yl)acetate (2.00 g, 12.4 mmol, 1.00 eq) in THF (10 mL) dropwise at 0° C. The mixture was warmed up to 20° C. and stirred for 3 hours. The mixture was quenched with saturated aqueous sodium sulfate solution (1 mL). The mixture was filtered and the filtrate was concentrated under vacuum. The product was purified by silica gel chromatography using 5% MeOH in DMC. The desired fractions were collected and concentrated under vacuum to give 2-(3-fluoropyrrolidin-1-yl)ethanol (1.20 g, 9.01 mmol, 72.6% yield) as a colorless oil. $^1$H NMR (400 MHz, Chloroform-d) δ=5.28-5.05 (m, 1H), 3.68-3.61 (m, 2H), 2.99-2.73 (m, 4H), 2.72-2.67 (m, 2H), 2.58-2.45 (m, 1H), 2.28-1.97 (m, 2H).

Intermediate 28

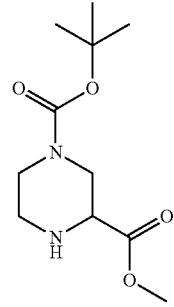

1-(tert-butyl) 3-methyl piperazine-1,3-dicarboxylate

Step A: Methyl piperazine-2-carboxylate

To a mixture of 1-tert-butyl 2-methyl piperazine-1,2-dicarboxylate (5.0 g, 22.6 mmol, 1.00 eq) in MeOH (50.0 mL) was added HCl/dioxane (4.0 M, 134 mL). The reaction mixture was degassed and purged with nitrogen 3 times, and the mixture was stirred at 25° C. for 12 hours under a nitrogen atmosphere. The reaction mixture was concentrated under reduced pressure to dryness to give methyl piperazine-2-carboxylate (4.89 g, 2HCl, crude) as a white solid, which was used directly in the next step without further purification.

Step B: 1-(tert-butyl) 3-methyl piperazine-1,3-dicarboxylate

To a solution of methyl piperazine-2-carboxylate (4.30 g, crude) and TEA (8.02 g, 79.2 mmol, 11.0 mL) in MeOH (50.0 mL) was added di-tert-butyl dicarbonate (4.32 g, 19.8 mmol, 4.55 mL). After stirring at 25° C. for 12 hours, the reaction mixture was filtered and concentrated under reduced pressure to dryness. The residue was purified by column chromatography (SiO$_2$, DCM/MeOH=1:0 to 20:1) to give 1-(tert-butyl) 3-methyl piperazine-1,3-dicarboxylate (4.80 g, 19.7 mmol, two steps, 99.0% yield) as a colorless oil. $^1$H NMR (400 MHz, chloroform-d) δ=4.10-3.85 (m, 1H), 3.73 (s, 3H), 3.71-3.65 (m, 1H), 3.47-3.38 (m, 1H), 3.10-2.98 (m, 2H), 2.78-2.66 (m, 1H), 2.17 (s, 1H), 1.46 (s, 9H).

Intermediate 29

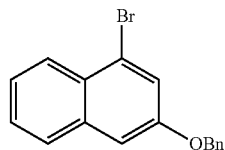 [SMILES: Brc1cc(OCc2ccccc2)cc2ccccc12]

4-bromonaphthalen-2-ol

Step A: 2,4-dibromonaphthalen-1-amine

To a solution of $Br_2$ (246 g, 1.54 mol, 79.3 mL, 2.18 eq) in AcOH (750 mL) was added a solution of naphthalen-1-amine (101 g, 705 mmol, 99.0 mL, 1.00 eq) in AcOH (500 mL) at ambient temperature, and the reaction was stirred at 70° C. for 1 hour. The reaction mixture was cooled at room temperature and filtered. The filter cake was washed with AcOH (300 mL), then added to 20% aqueous of NaOH (1.2 L). The mixture was stirred for 20 min and filtered. The isolated solid was washed with water (1 L) and dried under vacuum to provide 2,4-dibromonaphthalen-1-amine (200 g, 664 mmol, 94.2% yield) as gray solid. ESI MS m/z 301. 9 [M+H]$^+$.

Step B: 4-bromo-1-diazonio-naphthalen-2-olate

To a solution of 2,4-dibromonaphthalen-1-amine (60.0 g, 199 mmol, 1.00 eq) in AcOH (900 mL) and propionic acid (150 mL) was added $NaNO_2$ (16.5 g, 239 mmol, 13.0 mL, 1.20 eq) portionwise at 5-8° C. over 30 min, and then the reaction mixture was stirred at 5-8° C. for 30 min. The reaction mixture was poured into ice-water (4000 mL), and the resulting solid was collected and washed with water (2×50 mL) to provide 4-bromo-1-diazonio-naphthalen-2-olate (150 g, wet crude) as gray solid which was used directly in the next step. $^1$H NMR (400 MHz, CDCl$_3$) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

Step C: 4-bromonaphthalen-2-ol

To a solution of 4-bromo-1-diazonio-naphthalen-2-olate (100 g, 402 mmol, 1.00 eq) in EtOH (2.00 L) was added portionwise NaBH$_4$ (30.4 g, 803 mmol, 2.00 eq) at 13-15° C. over 1 h, and the reaction mixture was stirred at 15-18° C. for 3 hrs. The reaction was filtered and concentrated to dryness. The residue was dissolved in DCM (1000 mL) and washed with water (500 mL×2). The organic phase was dried over Na$_2$SO$_4$ and concentrated to dryness. The residue was purified by silica gel column chromatograph, eluting with diethyl ether/ethyl acetate (60:1 to 10:1). The isolated product was further purified by reversed phase HPLC to provide 4-bromonaphthalen-2-ol (40.0 g, 139 mmol, 17.3% yield, 77.4% purity) as a gray solid. $^1$H NMR (400 MHz, CDCl$_3$) δ 8.07-8.05 (d, J=8.0 Hz, 1H), 7.60-7.58 (d, J=7.6 Hz, 1H), 7.41-7.36 (m, 3H), 7.07 (s, 1H).

Step D: 3-benzyloxy-1-bromo-naphthalene

A mixture of 4-bromonaphthalen-2-ol (30.0 g, 134 mmol, 1.00 eq), benzyl bromide (25.3 g, 148 mmol, 17.6 mL, 1.10 eq) and K$_2$CO$_3$ (55.7 g, 403 mmol, 3.00 eq) in MeCN (500 mL) was heated at 80° C. for 1 hr. The reaction mixture was filtered and concentrated to dryness. The residue was purified by silica gel column chromatography, eluting with diethyl ether/ethyl acetate (100:1 to 60:1) to provide 3-benzyloxy-1-bromo-naphthalene (40.0 g, 128 mmol, 95% yield) as yellow oil. $^1$H NMR (400 MHz, CDCl$_3$) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 30

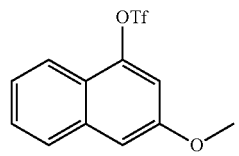 [SMILES: COc1cc(OS(=O)(=O)C(F)(F)F)c2ccccc2c1]

3-methoxynaphthalen-1-yl trifluoromethanesulfonate

Step A: 3-methoxynaphthalen-1-ol

To a solution of naphthalene-1,3-diol (3.00 g, 18.7 mmol, 1.00 eq) in MeOH (60.0 mL) was added HCl/MeOH (4 M, 60.0 mL, 12.8 eq) at 0° C. The mixture was stirred at 25° C. for 60 hours. The solvent was removed under vacuum. The residue was purified by silica gel chromatography (diethyl ether:ethyl acetate=10:1 to 5:1) to give 3-methoxynaphthalen-1-ol (2.10 g, 12.1 mmol, 64.4% yield) as a brown solid. $^1$H NMR (400 MHz, CDCl$_3$-d$_6$) δ=8.10-8.08 (d, J=8.4 Hz, 1H). 7.73-7.71 (d, J=8.4 Hz, 1H), 7.47-7.45 (m, 1H), 7.38-7.35 (m, 1H), 6.80-6.79 (d, J=2.0 Hz, 1H), 6.56-6.55 (d, J=2.4 Hz, 1H), 3.92 (s, 3H).

Step B: (3-methoxy-1-naphthyl) trifluoromethanesulfonate

To a solution of 3-methoxynaphthalen-1-ol (2.10 g, 12.0 mmol, 1.00 eq) in DCM (40.0 mL) was added DIEA (7.79 g, 60.3 mmol, 10.5 mL, 5.00 eq) and trifluoromethanesulfonic anhydride (5.10 g, 18.1 mmol, 2.98 mL, 1.50 eq) at 0° C. The mixture was stirred at 25° C. for 1 hour. The mixture was diluted with DCM (30 mL) and water (10 mL) and extracted with DCM (20 mL). The combined organic layers were washed with brine (5 mL), dried over Na$_2$SO$_4$ and concentrated under vacuum. The residue was purified by silica gel chromatography (diethyl ether:ethyl acetate=20:1 to 10:1) to give (3-methoxy-1-naphthyl) trifluoromethanesulfonate (3.00 g, 8.52 mmol, 70.7% yield, 87.0% purity) as a brown oil. ESI MS m/z 307.1 [M+H]$^+$.

Intermediate 31

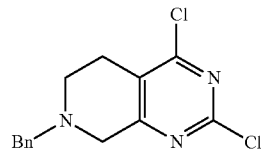

7-benzyl-2,4-dichloro-6,8-dihydro-5H-pyrido[3,4-d]pyrimidine

Step A: 7-benzyl-6,8-dihydro-5H-pyrido[3,4-d]pyrimidine-2,4-diol

To EtOH (600 mL) was added Na (5.56 g, 241 mmol, 5.73 mL, 2.40 eq) in portions. The reaction mixture was stirred for 1 hour. To the mixture was added ethyl 1-benzyl-3-oxo-piperidine-4-carboxylate (30.0 g, 100 mmol, 1.00 eq, HCl) and urea (14.5 g, 242 mmol, 13.0 mL, 2.40 eq). The reaction mixture was stirred at 75° C. for 36 hours, and then the solvent was removed under vacuum. The residue was dissolved in water (50 mL) and acidified with HCl (120 mL, 2M). A white solid precipitated from the solution and was collected by filtration. The filter cake was dried under vacuum to provide 7-benzyl-6,8-dihydro-5H-pyrido[3,4-d]pyrimidine-2,4-diol (22.0 g, 83.8 mmol, 83.2% yield, 98% purity) as a white solid. $^1$HNMR (400 MHz, DMSO-$d_6$) δ=10.97 (br s, 1H), 10.66 (br s, 1H), 7.55-6.95 (m, 5H), 3.81-3.50 (m, 2H), 3.26-2.91 (m, 2H), 2.77-2.58 (m, 2H), 2.34-2.09 (m, 2H).

Step B: 7-benzyl-2,4-dichloro-6,8-dihydro-5H-pyrido[3,4-d]pyrimidine

To a solution of DIEA (30.1 g, 233 mmol, 40.7 mL, 3.00 eq) in POCl$_3$ (330 g, 2.15 mol, 200 mL) was added 7-benzyl-6,8-dihydro-5H-pyrido[3,4-d]pyrimidine-2,4-diol (20.0 g, 77.7 mmol, 1.00 eq). The reaction mixture was stirred at 110° C. for 5 hours. The reaction mixture was concentrated under vacuum. The residue was dissolved in DCM (400 mL) and poured into saturated NaHCO$_3$ (200 mL). The mixture was extracted with DCM (2×400 mL). The combined organic layers were washed with brine (100 mL), dried over Na$_2$SO$_4$ and concentrated under vacuum. The residue was purified by silica gel chromatography (diethyl ether: DCM=10:1 to 0:1) to give 7-benzyl-2,4-dichloro-6,8-dihydro-5H-pyrido[3,4-d]pyrimidine (7.70 g, 26.2 mmol, 33.7% yield) as a brown oil. $^1$HNMR (300 MHz, chloroform-d) δ=7.43-7.28 (m, 5H), 3.73 (s, 2H), 3.66 (br s, 2H), 2.84 (br s, 4H)

Intermediate 32

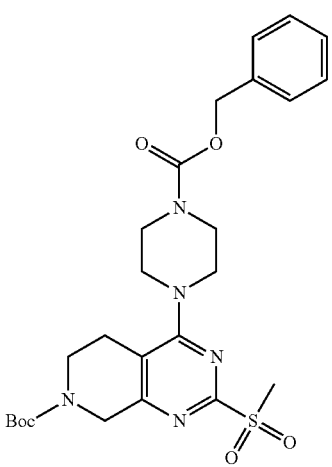 [SMILES: CC(C)(C)OC(=O)N1CCc2c(nc(S(C)(=O)=O)nc2N2CCN(C(=O)OCc3ccccc3)CC2)C1]

tert-butyl4-(4-((benzyloxy)carbonyl)piperazin-1-yl)-2-(methylsulfonyl)-5,6-dihydropyrido[3,4-d]pyrimidine-7(8H)-carboxylate

Step A: Tert-butyl4-hydroxy-2-methylsulfanyl-6,8-dihydro-5H-pyrido[3,4-d]pyrimidine-7-carboxylate To a stirred solution of 1-tert-butyl 4-ethyl-3-oxopiperidine-1,4-dicarboxylate (44.0 g, 162 mmol, 1.00 eq) in MeOH (1.00 mL) at 25° C. under nitrogen was added a solution of NaOMe (35.0 g, 649 mmol, 4.00 eq) in MeOH (600 mL) by syringe followed by 2-methylisothiourea (61.1 g, 324 mmol, 2.00 eq, H$_2$SO$_4$). After stirring at 25° C. for 16 hours, the reaction mixture was concentrated under reduced pressure to removed MeOH. The residue was suspended in 500 mL of ethyl acetate and 500 mL of water and stirred rapidly. The reaction mixture was adjusted to pH 5 with HCl (2 M). The precipitate was filtered and the white solid was washed with ethyl acetate and dried under vacuum to give tert-butyl4-hydroxy-2-methylsulfanyl-6,8-dihydro-5H-pyrido[3,4-d]pyrimidine-7-carboxylate (33.0 g, 103 mmol, 63.8% yield, 93.2% purity) as a white solid, which was used directly in the next step without further purification. $^1$H NMR (400 MHz, DMSO-$d_6$) δ=4.19 (s, 2H), 3.49 (br s, 2H), 2.46 (s, 3H), 2.35 (br t, J=5.2 Hz, 2H), 1.42 (s, 9H).

Step B: Give Tert-Butyl 2-methylsulfanyl-4-(trifluoromethylsulfonyloxy)-6,8-dihydro-5H-pyrido [3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (15.0 g, 50.4 mmol, 1.00 eq) in DCM (200 mL) was added DIEA (26.1 g, 202 mmol, 35.2 mL, 4.00 eq) at 0° C. under nitrogen and followed by trifluoromethanesulfonic anhydride (28.5 g, 101 mmol, 16.6 mL, 2.00 eq) by syringe. Immediately a brown solution formed. The reaction mixture was stirred at 25° C. for 12 hours. The reaction mixture was purified by column chromatography (SiO$_2$, Petroleum ether/Ethyl acetate=1:0 to 10:1) to give tert-butyl 2-methylsulfanyl-4-(trifluoromethylsulfonyloxy)-6,8-dihydro-5H-pyrido[3,4-d]pyrimidine-7-carboxylate (16.7 g, 35.7 mmol, 70.9% yield, 91.9% purity) as a white solid. ESI MS m/z 374.0 [M+H]$^+$.

Step C: Tert-Butyl 4-(4-benzyloxycarbonylpiperazin-1-yl)-2-methylsulfanyl-6,8-dihydro-5H-pyrido[3,4-d]pyrimidine-7-carboxylate To a stirred solution of tert-butyl2-methylsulfanyl-4-(trifluoromethylsulfonyloxy)-6,8-dihydro-5H-pyrido[3,4-d]pyrimidine-7-carboxylate (16.7 g, 38.9 mmol, 1.00 eq) in DMF (100 mL) was added DIEA (10.0 g, 77.9 mmol, 2.00 eq) and benzyl piperazine-1-carboxylate (9.41 g, 42.8 mmol, 1.10 eq). The reaction was heated to 100° C. and stirred for 1 hour under a nitrogen atmosphere. The reaction mixture was diluted with water (150 mL) and the reaction mixture was adjusted to pH 5 with HCl (2 M) and extracted with DCM (3×200 mL). The combined organic layers were washed with saturated NaHCO$_3$ (3×150 mL), brine (3×150 mL) and H$_2$O (3×150 mL), dried over Na$_2$SO$_4$, filtered and concentrated under reduced pressure to give tert-butyl 4-(4-benzyloxycarbonylpiperazin-1-yl)-2-methylsulfanyl-6,8-dihydro-5H-pyrido[3,4-d]pyrimidine-7-carboxylate (18.1 g, 36.2 mmol, 93.0% yield, 94.1% purity) as a yellow solid, which was used directly in the next step without further purification. ESI MS m/z 500.1 [M+H]$^+$.

Step D: Tert-Butyl 4-(4-benzyloxycarbonylpiperazin-1-yl)-2-methylsulfonyl-6,8-dihydro-5H-pyrido[3,4-d]pyrimidine-7-carboxylate To a stirred solution of tert-butyl4-(4-benzyloxycarbonylpiperazin-1-yl)-2-methylsulfanyl-6,8-dihydro-5H-pyrido[3,4-d]pyrimidine-7-carboxylate (14.4 g, 28.9 mmol, 1.00 eq) in DCM (150 mL) at 0° C. under nitrogen was added meta-chloroperoxybenzoic acid (17.4 g, 101 mmol, 3.50 eq) as a solid. After stirring at 0° C. for 2 hours under a nitrogen atmosphere, the reaction mixture was diluted with water (300 mL) and the reaction mixture was adjusted to pH 8 with saturated aqueous NaHCO$_3$ and extracted with DCM (3×200 mL). The combined organic layers were washed with brine (3×200 mL), dried over Na$_2$SO$_4$, filtered and concentrated under reduced pressure to dryness. The residue was purified by column chromatography (SiO$_2$, Petroleum ether/Ethyl acetate=10:1 to 1:2) to give tert-butyl 4-(4-benzyloxycarbonylpiperazin-1-yl)-2-methyl sulfonyl-6,8-dihydro-5H-pyrido[3,4-d]pyrimidine-7-carboxylate (11.0 g, 19.7 mmol, 68.6% yield, 95.4% purity) as a white solid. ESI MS m/z 532.1 [M+H]$^+$.

Intermediate 33

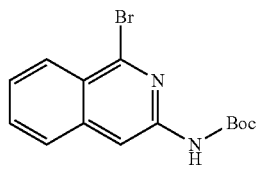 [SMILES: CC(C)(C)OC(=O)Nc1cc2ccccc2c(Br)n1]

Tert-Butyl (1-bromoisoquinolin-3-yl)carbamate

Step A

A mixture of 1-bromoisoquinolin-3-amine (400 mg, 1.79 mmol, 1.00 eq) and tert-butoxycarbonyl tert-butyl carbonate (3.91 g, 17.9 mmol, 4.12 mL, 10.0 eq) was stirred at 70° C. for 16 hours. The residue was purified by column chromatography (SiO$_2$, diethyl ether/ethyl acetate=5:1) to give tert-butyl N-(1-bromo-3-isoquinolyl) carbamate (400 mg, 1.24 mmol, 69.2% yield) as a yellow solid. ESI MS m/z 322.1, 324.1 [M+H]$^+$.

Intermediate 34

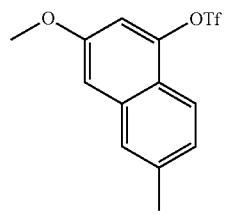 [SMILES: COc1cc(OS(=O)(=O)C(F)(F)F)c2ccc(C)cc2c1]

3-methoxy-6-methylnaphthalen-1-yl trifluoromethanesulfonate

Step A: 3-methoxynaphthalen-1-ol

To a solution of naphthalene-1,3-diol (40.0 g, 250 mmol, 1.00 eq) in MeOH (800 mL) was added HCl (4 M, 750 mL, 12.0 eq, 4 M in MeOH) at 0° C. The mixture was warmed up to 18° C. and stirred for 30 hours. The mixture was concentrated under vacuum. The residue was purified by column chromatography over silica gel (petroleum ether/ethyl acetate 100/1 to 1/1). The desired fractions were collected and concentrated under vacuum to give 3-methoxynaphthalen-1-ol (17.7 g, 96.5 mmol, 38.6% yield, 95% purity) as a red oil. $^1$H NMR (400 MHz, Chloroform-d) δ=8.17 (d, J=8.4 Hz, 1H), 7.74 (d, J=8.0 Hz, 1H), 7.50 (ddd, J=1.2, 6.8, 8.0 Hz, 1H), 7.38 (ddd, J=1.2, 6.8, 8.0 Hz, 1H), 6.81 (d, J=2.0 Hz, 1H), 6.76 (br s, 1H), 6.62 (d, J=2.4 Hz, 1H), 3.91 (s, 3H).

Step B: Tert-butyl-[(3-methoxy-1-naphthyl)oxy]-dimethyl-silane

To a solution of 3-methoxynaphthalen-1-ol (20.0 g, 115 mmol, 1.00 eq) and imidazole (23.5 g, 344 mmol, 3.00 eq) in THF (400 mL) was added TBSCl (26.0 g, 172 mmol, 21.1 mL, 1.50 eq) dropwise at 0° C. The mixture was warmed up to 25° C. and stirred for 16 hours. The mixture was diluted with petroleum ether (600 mL) and ethyl acetate (200 mL), and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). tert-butyl-[(3-methoxy-1-naphthyl)oxy]-dimethyl-silane (28.0 g, 97.1 mmol, 84.6% yield) was obtained as a colorless oil. $^1$H NMR (400 MHz, Chloroform-d) δ=8.01 (d, J=8.4 Hz, 1H), 7.61 (d, J=8.0 Hz, 1H), 7.35 (dt, J=1.2, 7.6 Hz, 1H), 7.24 (dt, J=1.2, 7.6 Hz, 1H), 6.71 (d, J=2.0 Hz, 1H), 6.48 (d, J=2.4 Hz, 1H), 3.82 (s, 3H), 1.02 (s, 9H), 0.23 (s, 6H).

Step C: Tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilane A mixture of tert-butyl-[(3-methoxy-1-naphthyl) oxy]-dimethyl-silane (26.0 g, 90.1 mmol, 1.00 eq), 4,4,5,5-tetramethyl-2-(4,4,5,5-tetramethyl-1,3,2-dioxaborolan-2-yl)-1,3,2-dioxaborolane (45.8 g, 180 mmol, 2.00 eq), (1Z,5Z)-cycloocta-1,5-diene; 2,4-dimethyl-BLAHbicyclo[1.1.0]butane (2.39 g, 3.61 mmol, 0.04 eq) and 4-tert-butyl-2-(4-tert-butyl-2-pyridyl)pyridine (1.45 g, 5.41 mmol, 0.06 eq) in hexane (500 mL) was stirred at 100° C. under nitrogen atmosphere for 16 hours. The mixture was diluted with water (500 mL) and ethyl acetate (1000 mL). The separated organic layer was washed with brine (1×500 mL), dried over sodium sulfate, filtered and concentrated under vacuum. The residue was purified by column chromatography over silica gel (petroleum ether/ethyl acetate 100/1 to 10/1). The desired fractions were collected and concentrated under vacuum to give a mixture of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)

dimethylsilane (38.0 g, 85.3 mmol, 94.6% yield, 93% purity) as a light yellow oil. ESI MS m/z 415.5 [M+H]$^+$ Step D: 8-[tert-butyl(dimethyl)silyl]oxy-6-methoxy-naphthalen-2-ol To a solution of mixture (36.0 g, 86.9 mmol, 1.00 eq) of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilanein in acetone (400 mL) was added a solution of Oxone (58.7 g, 95.6 mmol, 1.10 eq) in H$_2$O (400 mL) at 0° C. The mixture was stirred at 0° C. for 1 hour. The mixture was quenched with 5% aqueous sodium thiosulfate solution (50 mL) and extracted with ethyl acetate (2×300 mL). The extracts were combined and washed with water (1×200 mL), brine (1×200 mL), dried over magnesium sulfate, filtered and the filtrate was concentrated under vacuum. The residue was purified by column chromatography over silica gel (petroleum ether/ethyl acetate 200/1 to 20/1). The desired fractions were collected and concentrated under vacuum to give 8-[tert-butyl(dimethyl)silyl]oxy-6-methoxy-naphthalen-2-ol (9.00 g, 28.4 mmol, 32.7% yield, 96% purity) as a colorless oil and 5-[tert-butyl(dimethyl)silyl]oxy-7-methoxy-naphthalen-2-ol (9.00 g, 29.0 mmol, 33.4% yield, 98% purity) as a white solid. ESI MS m/z 305.2 [M+H]$^+$ Step E: [5[tert-butyl(dimethyl)silyl]oxy-7-methoxy-2-naphthyl]trifluoromethanesulfonate To a solution of 5-[tert-butyl(dimethyl)silyl]oxy-7-methoxy-naphthalen-2-ol (11.0 g, 36.1 mmol, 1.00 eq) and DIEA (14.0 g, 108 mmol, 18.9 mL, 3.00 eq) in DCM (150 mL) was added Tf$_2$O (12.2 g, 43.4 mmol, 7.15 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). The desired fractions were collected and concentrated under vacuum to give [5-[tert-butyl(dimethyl)silyl]oxy-7-methoxy-2-naphthyl] trifluoromethanesulfonate (13.0 g, 29.8 mmol, 82.4% yield, 100% purity) as a white solid. ESI MS m/z 436.9 [M+H]$^+$ Step F: tert-butyl-[(3-methoxy-6-methyl-1-naphthyl) oxy]-dimethyl-silane To a solution of [5[tert-butyl(dimethyl)silyl]oxy-7-methoxy-2-naphthyl]trifluoromethanesulfonate (12.5 g, 28.6 mmol, 1.00 eq) and K$_2$CO$_3$ (11.9 g, 85.9 mmol, 3.00 eq) in dioxane (160 mL) was added Pd(PPh$_3$)$_4$ (3.31 g, 2.86 mmol, 0.10 eq) and trimethylboroxine (14.4 g, 57.3 mmol, 16.0 mL, 2.00 eq) under nitrogen atmosphere. The reaction was heated to 100° C. for 16 hours. The mixture was diluted with ethyl acetate (200 mL) and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 5/1). The desired fractions were collected and concentrated under vacuum to give tert-butyl-[(3-methoxy-6-methyl-1-naphthyl)oxy]-dimethyl-silane (8.00 g, 24.6 mmol, 85.9% yield, 93% purity) as a colorless oil as red solid. ESI MS m/z 303.2 [M+H]$^+$ Step G: 3-methoxy-6-methyl-naphthalen-1-ol To a solution of tert-butyl-[(3-methoxy-6-methyl-1-naphthyl) oxy]-dimethyl-silane (8.00 g, 26.5 mmol, 1.00 eq) in THF (100 mL) was added TBAF (10.4 g, 39.7 mmol, 1.50 eq) at 0° C. The mixture was stirred at 0° C. for 3 hours. The mixture was diluted with water (100 mL) and ethyl acetate (200 mL). The separated organic layer was washed with brine (1×100 mL), dried over sodium sulfate, filtered and concentrated under vacuum. The residue was purified by column chromatography over silica gel (petroleum ether/ethyl acetate 50/1 to 5/1). The desired fractions were collected and concentrated under vacuum to give 3-methoxy-6-methyl-naphthalen-1-ol (4.70 g, 25.0 mmol, 94.4% yield) as a red solid. ESI MS m/z 188.4 [M+H]$^+$ Step H: 3-methoxy-6-methyl-1-naphthyl trifluoromethanesulfonate To a solution of 3-methoxy-6-methyl-naphthalen-1-ol (4.70 g, 25.0 mmol, 1.00 eq) and DIEA (9.68 g, 74.9 mmol, 13.1 mL, 3.00 eq) in DCM (3.00 mL) was added Tf$_2$O (8.45 g, 30.0 mmol, 4.94 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). 3-methoxy-6-methyl-1-naphthyl trifluoromethanesulfonate (7.70 g, 24.0 mmol, 96.2% yield, 99.9% purity) was obtained as a colorless oil. ESI MS m/z 320.7 [M+H]$^+$.

The following intermediates were prepared according to the preparation for Intermediate 3, substituting the appropriate phenol for 2-bromo-3-fluorophenol.

| Intermediate No. | Structure | Name |
|---|---|---|
| Intermediate 35 | ![structure] | 2-bromo-4-(methoxymethoxy)-1-(trifluoromethoxy)benzene |

-continued

| Intermediate No. | Structure | Name |
|---|---|---|
| Intermediate 36 | 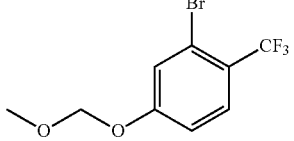 | 2-bromo-4-(methoxymethoxy)-1-(trifluoromethyl)benzene |
| Intermediate 37 | 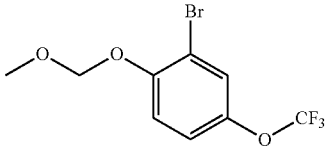 [SMILES: COCOc1ccc(OC(F)(F)F)cc1Br] | 2-bromo-1-(methoxymethoxy)-4-(trifluoromethoxy)benzene |
| Intermediate 38 | 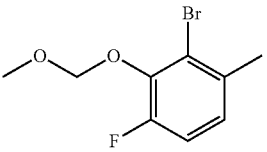 | 2-bromo-4-fluoro-3-(methoxymethoxy)-1-methylbenzene |
| Intermediate 39 | 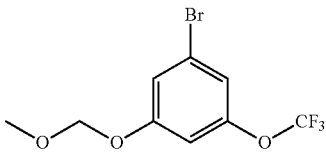 [SMILES: COCOc1cc(Br)cc(OC(F)(F)F)c1] | 1-bromo-3-(methoxymethoxy)-5-(trifluoromethoxy)benzene |
| Intermediate 40 | 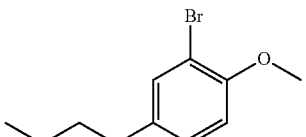 | 2-bromo-1-methoxy-4-(methoxymethoxy)benzene |
| Intermediate 41 | 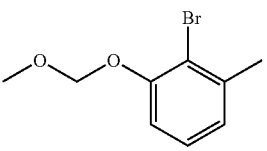 | 2-bromo-1-(methoxymethoxy)-3-methylbenzene |
| Intermediate 42 | 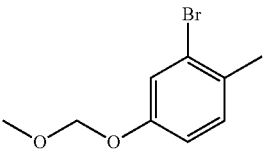 | 2-bromo-4-(methoxymethoxy)-1-methylbenzene |
| Intermediate 43 | 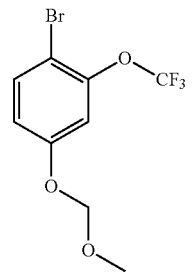 [SMILES: COCOc1ccc(Br)c(OC(F)(F)F)c1] | 1-bromo-4-(methoxymethoxy)-2-(trifluoromethoxy)benzene |

Intermediate 44

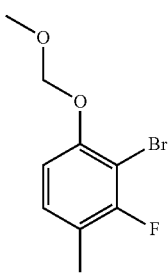

2-bromo-3-fluoro-1-(methoxymethoxy)-4-methyl-benzene

Step 1

3-fluoro-4-methylphenol (1.016 g, 8.055 mmol) was placed in $Cs_2$ (3.9 mL, 64.44 mmol) and was cooled to 0° C. $Br_2$ (0.4150 mL, 8.055 mmol) was added and the mixture was stirred at room temperature for 2 hrs. 10% $Na_2S_2O_2$ was added and the mixture was extracted with DCM. The organic layers were combined, dried and filtered to provide 2-bromo-3-fluoro-4-methylphenol (1.389 g, 6.775 mmol, 84.10% yield) which was used directly in the next step.

Step 2

2-bromo-3-fluoro-1-(methoxymethoxy)-4-methylbenzene was prepared according to the procedure for Intermediate 8 using 2-bromo-3-fluoro-4-methylphenol in place of 2-bromo-3-fluorophenol.

Intermediate 45

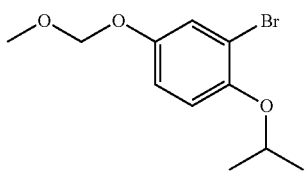

2-bromo-1-isopropoxy-4-(methoxymethoxy)benzene

Step 1

4-isopropoxyphenol (1.00 g, 6.57 mmol) and TEA (1.83 mL, 13.1 mmol) were placed in DCM (25 mL). Acetyl chloride (7.56 mL, 7.56 mmol) was added dropwise and the reaction was stirred at room temperature for 2 hr. Water was added and the mixture was extracted with DCM. The organic layer was dried, filtered and concentrated to provide 4-isopropoxyphenyl acetate (1.24 g, 6.38 mmol, 97.2% yield) which was directly in the next step.

Step 2

4-Isopropoxyphenyl acetate (1.24 g, 6.585 mmol) was placed in ACN (20 mL) and N-bromosuccinimide (1.173 g, 6.590 mmol) was added. The mixture was stirred for 18 hr. Water was added and the mixture was extracted with ether. The organic layers were combined, dried, and concentrated to provide 3-bromo-4-isopropoxyphenyl acetate (1.584 g, 5.800 mmol, 88.00% yield) which was directly in the next step.

Step 3

3-Bromo-4-isopropoxyphenyl acetate (500 mg, 1.83 mmol) was placed in MeOH (7 mL). A solution of KOH (111 mg, 1.98 mmol) in water (2 mL) was added to mixture and was stirred for 1 hr at room temperature. The reaction mixture was adjusted to pH 3 by the addition of 1N HCl. The mixture was extracted with DCM. The extracts were combined, dried, filtered and concentrated to provide crude 3-bromo-4-isopropoxyphenol which was used directly the next reaction.

Step 4

2-Bromo-1-isopropoxy-4-(methoxymethoxy)benzene was prepared according to the procedure for Intermediate 8 using 3-bromo-4-isopropoxyphenol in place of 2-bromo-3-fluorophenol

Intermediate 46

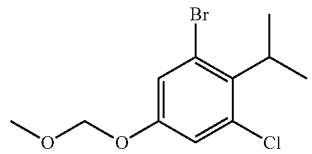

1-bromo-3-chloro-2-isopropyl-5-(methoxymethoxy)benzene

Step 1

1-bromo-3-chloro-2-isopropyl-5-methoxybenzene (952 mg, 3.61 mmol) was placed in DCM (3 mL) and was cooled to 0° C. BBr3 (9030 µL, 9.03 mmol) was added and the reaction was stirred at 0° C. for 2 hr. Water was added and the mixture was extracted with DCM. The extracts were combined and concentrated. The resulting residue was purified by silica gel (0-20% EtOAc in hexane) to provide 3-bromo-5-chloro-4-isopropylphenol (575 mg, 2.30 mmol, 63.8% yield)

Step 2: 1-bromo-3-chloro-2-isopropyl-5-(methoxymethoxy)benzene was prepared according to the procedure for Intermediate 8 using 3-bromo-5-chloro-4-isopropylphenol in place of 2

Intermediate 47

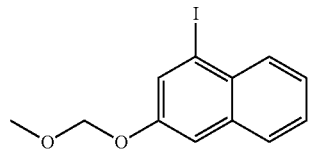

1-iodo-3-(methoxymethoxy)naphthalene

To a solution of 4-iodonaphthalen-2-ol (0.80 g, 3.0 mmol) in DCM (20 mL) was added N-ethyl-N-isopropylpropan-2-amine (1.1 mL, 5.9 mmol) and chloro(methoxy)methane (0.29 g, 3.6 mmol) and the reaction stirred at room temperature for 4 hours, with additional chloro(methoxy)methane (0.15 g) being added after 2 hours. The reaction was washed with brine and concentrated in vacuo. The material was purified by chromatography using a gradient of 0 to 10% EtOAc/hexanes as the eluent to give 1-iodo-3-(methoxymethoxy)naphthalene (0.80 g, 2.5 mmol, 86% yield).

Intermediate 48

3-benzyloxy-1-bromo-naphthalene

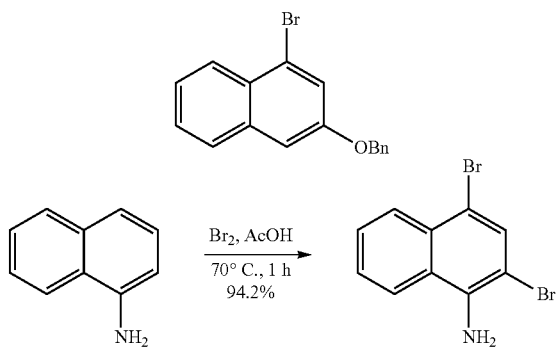

Step A: 2,4-dibromonaphthalen-1-amine

To a solution of Br$_2$ (246 g, 1.54 mol, 79.3 mL) in AcOH (750 mL) was added a solution of naphthalen-1-amine (101 g, 705 mmol, 99.0 mL) in AcOH (500 mL) at room temperature and the reaction stirred at 70° C. for 1 hour. The reaction mixture was cooled to room temperature and filtered. The filter cake was washed with AcOH (300 mL). The solid was next suspended in 20% aqueous of NaOH (1.2 L). The mixture was stirred for 20 minutes and filtered. The solid was washed with water (1 L) and dried under vacuum to give 2,4-dibromonaphthalen-1-amine (200 g, 664 mmol, 94.2% yield) as gray solid. ES+APCI MS m/z 301.9 [M+H]$^+$.

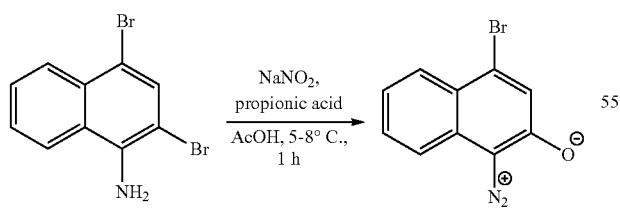

Step B: 4-bromo-1-diazonio-naphthalen-2-olate

To a solution of 2,4-dibromonaphthalen-1-amine (60.0 g, 199 mmol) in AcOH (900 mL) and propionic acid (150 mL) was added NaNO$_2$ (16.5 g, 239 mmol, 13.0 mL) portionwise at 5-8° C. over 30 minutes and the reaction mixture stirred at 5-8° C. for 30 minutes. The reaction mixture was poured into ice-water (4000 mL), the slurry filtered and the solid washed with water (2×50 mL) to give 4-bromo-1-diazonio-naphthalen-2-olate (150 g, wet crude) which was used crude in the next step immediately. $^1$H NMR (400 MHz, CDCl$_3$) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

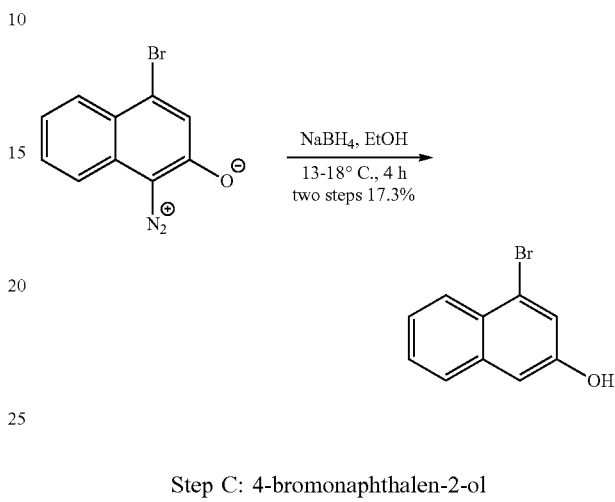

Step C: 4-bromonaphthalen-2-ol

To a solution of 4-bromo-1-diazonio-naphthalen-2-olate (100 g, 402 mmol) in EtOH (2.00 L) was added portion-wise NaBH$_4$ (30.4 g, 803 mmol) at 13-15° C. over 1 hour and the reaction stirred at 15-18° C. for 3 hours. The reaction was filtered and concentrated to dryness. The residue was dissolved in DCM (1000 mL) and washed with water (500 mL×2). The organics were dried over Na$_2$SO$_4$ and concentrated to dryness. The residue was purified by chromtography eluting with petroleum ether/EtOAc (60/1→10/1) and material re-purified by reversed phase HPLC to give 4-bromonaphthalen-2-ol (40.0 g, 139 mmol, 17.3% yield, 77.4% purity) as a gray solid. $^1$H NMR (400 MHz, CDCl$_3$) δ 8.07-8.05 (d, J=8.0 Hz, 1H), 7.60-7.58 (d, J=7.6 Hz, 1H), 7.41-7.36 (m, 3H), 7.07 (s, 1H).

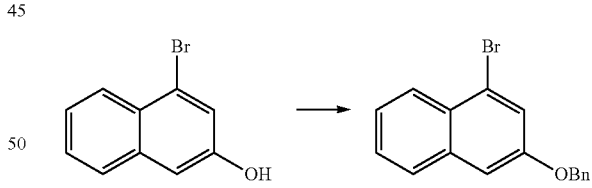

Step D: 3-benzyloxy-1-bromo-naphthalene

A mixture of 4-bromonaphthalen-2-ol (30.0 g, 134 mmol), BnBr (25.3 g, 148 mmol, 17.6 mL) and K$_2$CO$_3$ (55.7 g, 403 mmol) in MeCN (500 mL) was heated at 80° C. for 1 hr. The reaction mixture was filtered and concentrated to dryness. The residue was purified by silica gel column eluting with PE/EA (100/1 to 60/1) to give 3-benzyloxy-1-bromo-naphthalene (40.0 g, 128 mmol, 95% yield). $^1$H NMR (400 MHz, CDCl$_3$) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 49

Benzyl 4-(7-(3-(benzyloxy)naphthalen-1-yl)-2-(methylsulfinyl)-5,6,7,8-tetrahydropyrido[3,4-d]pyrimidin-4-yl)piperazine-1-carboxylate

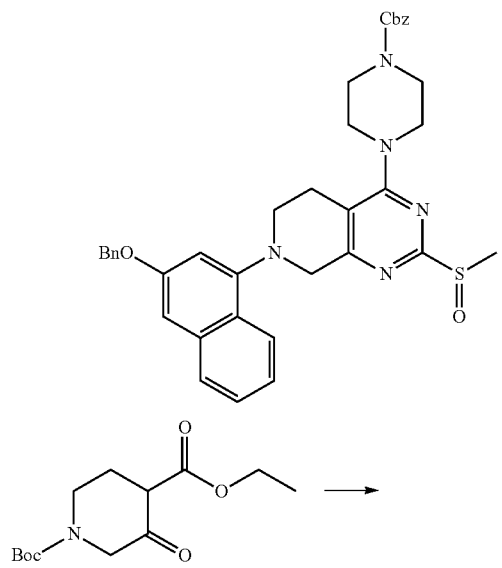

Step A: Tert-Butyl 4-hydroxy-2-methylsulfanyl-6,8-dihydro-5H-pyrido[3,4-d]pyrimidine-7-carboxylate To a solution of 1-tert-butyl 4-ethyl 3-oxopiperidine-1,4-dicarboxylate (50.0 g, 184 mmol) in MeOH (1.00 L) under nitrogen was added NaOMe (49.8 g, 921 mmol) and 2-methylisothiourea (62.4 g, 331 mmol, $H_2SO_4$). The reaction mixture was stirred at 25° C. for 16 hours. HCl (2 M) was added to the reaction mixture until pH-5 and then the mixture was concentrated under reduced pressure. The residue was suspended in 300 mL of ethyl acetate and 300 mL of water. The suspension was filtered. The organic phase was washed with water (1×300 mL), brine (1×200 mL), dried over $Na_2SO_4$, filtered and concentrated to give tert-butyl 4-hydroxy-2-methylsulfanyl-6,8-dihydro-5H-pyrido[3,4-d]pyrimidine-7-carboxylate (51.0 g, 138 mmol, 75.4% yield, 81.0% purity) which was used directly in the next reaction. ES+APCI MS m/z 298.2 [M+H]+.

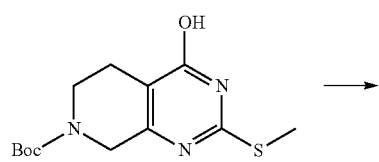

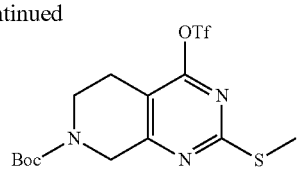

Step B: Tert-Butyl 2-methylsulfanyl-4-(trifluoromethylsulfonyloxy)-6,8-dihydro-5H-pyrido[3,4-d]pyrimidine-7-carboxylate To a solution of tert-butyl 4-hydroxy-2-methylsulfanyl-6,8-dihydro-5H-pyrido[3,4-d]pyrimidine-7-carboxylate (51.0 g, 171 mmol) in DCM (500 mL) was added DIEA (44.3 g, 343 mmol, 59.9 mL) and $Tf_2O$ (72.6 g, 257 mmol, 42.4 mL) sequentially at 0° C. under nitrogen. The reaction mixture was warmed up to 25° C. and stirred for 16 hours. The reaction mixture was concentrated and the residue purified by column chromatography eluting with EtOAc/Petroleum 0→10% to give tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62.4% yield). ES+APCI MS m/z 430.2 [M+H]+.

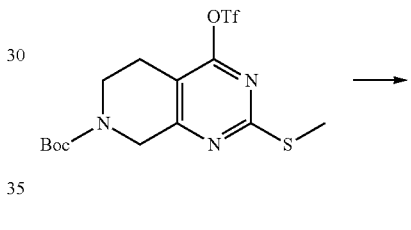

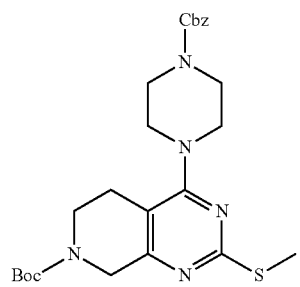

Step C: Tert-Butyl 4-(4-benzyloxycarbonylpiperazin-1-yl)-2-methylsulfanyl-6,8-dihydro-5H-pyrido[3,4-d]pyrimidine-7-carboxylate To a solution of tert-butyl 2-methylsulfanyl-4-(trifluoromethylsulfonyloxy)-6,8-dihydro-5H-pyrido[3,4-d]pyrimidine-7-carboxylate (46.0 g, 107 mmol in DMF (500 mL) was added DIEA (27.7 g, 214 mmol, 37.4 mL) and benzyl piperazine-1-carboxylate (25.9 g, 117 mmol, 22.7 mL). The reaction was heated to 100° C. for one hour under $N_2$ atmosphere. The reaction mixture was poured into ethyl acetate (300 mL). The mixture was washed with $H_2O$ (300 mL×3). The organic phase was washed with brine (200 mL), dried over anhydrous $Na_2SO_4$, concentrated in vacuo. The residue was purified by column chromatography using 0→20% EtOAc/Petroleum as eluent to give tert-butyl 4-(4-benzyloxycarbonylpiperazin-1-yl)-2-methylsulfanyl-6,8-dihydro-5H-pyrido[3,4-d]pyrimidine-7-carboxylate (51.0 g, 96.9 mmol, 90.5% yield, 92.0% purity) ES+APCI MS m/z 500.3 [M+H]+.

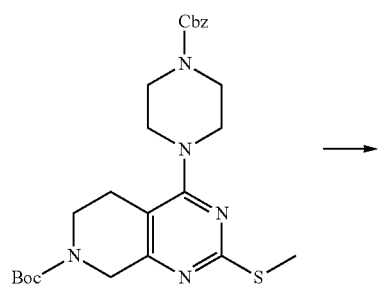

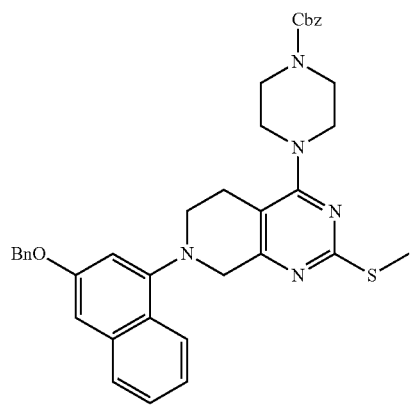

Step E: Benzyl 4-[7-(3-benzyloxy-1-naphthyl)-2-methylsulfanyl-6,8-dihydro-5H-pyrido[3,4-d]pyrimidin-4-yl]piperazine-1-carboxylate A mixture of 3-benzyloxy-1-bromo-naphthalene (16.3 g, 52.1 mmol), benzyl 4-(2-methylsulfanyl-5,6,7,8-tetrahydropyrido[3,4-d]pyrimidin-4-yl)piperazine-1-carboxylate (16.0 g, 40.1 mmol), Cs₂CO₃ (32.6 g, 100 mmol), Pd₂(dba)₃ (5.50 g, 6.01 mmol) and RuPhos (3.74 g, 8.01 mmol) in dioxane (300 mL) was degassed with N₂ 3 times and the mixture stirred at 85° C. for 5 hour under N₂ atmosphere. The reaction mixture was quenched by addition water (200 mL) at 0° C., and extracted with EtOAc (3×200 mL). The combined organic layers were washed with brine (3×150 mL), dried over Na₂SO₄, filtered and concentrated under reduced pressure. The residue was purified by column chromatography eluting with 10420% MeOH/DCM to give benzyl 4-[7-(3-benzyloxy-1-naphthyl)-2-methylsulfanyl-6,8-dihydro-5H-pyrido[3,4-d]pyrimidin-4-yl]piperazine-1-carboxylate (16.0 g, 22.8 mmol, 56.9% yield, 90.0% purity ES+APCI MS m/z 632.5 [M+H]⁺.

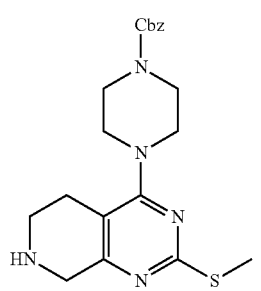

Step D: Benzyl 4-(2-methylsulfanyl-5,6,7,8-tetrahydropyrido[3,4-d]pyrimidin-4-yl)piperazine-1-carboxylate To a solution of tert-butyl 4-(4-benzyloxycarbonylpiperazin-1-yl)-2-methylsulfanyl-6,8-dihydro-5H-pyrido[3,4-d]pyrimidine-7-carboxylate (25.0 g, 50 mmol) in DCM (50 mL) was added TFA (85.6 g, 750 mmol, 55.6 mL). The mixture was stirred at 25° C. for 1 hour. The reaction mixture was concentrated under reduced pressure and the residue was dissolved in 300 mL of ethyl acetate and 300 mL of water and Na₂CO₃ added until pH-8. The organic layer was washed with water (1×300 mL), brine (1×200 mL) and dried over Na₂SO₄, filtered and concentrated under reduced pressure to give benzyl 4-(2-methylsulfanyl-5,6,7,8-tetrahydropyrido[3,4-d]pyrimidin-4-yl)piperazine-1-carboxylate. The product was used directly to the next step without further purification. ES+APCI MS m/z 400.2 [M+H]⁺.

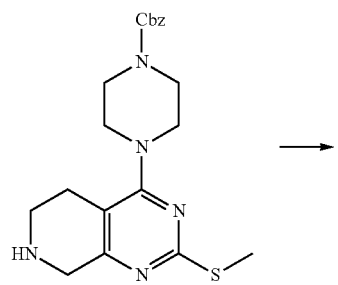

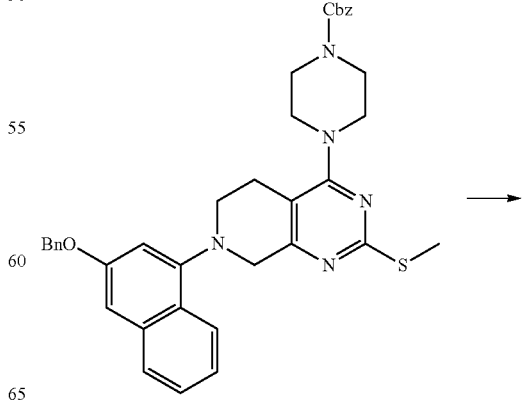

115

-continued

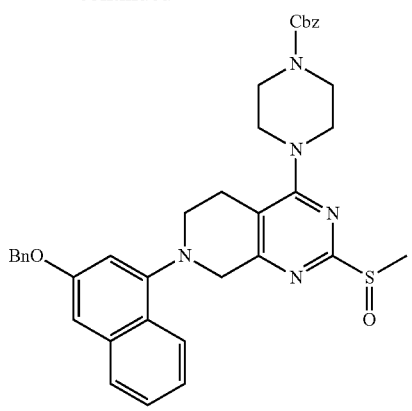

Step F: Benzyl 4-[7-(3-benzyloxy-1-naphthyl)-2-methylsulfinyl-6,8-dihydro-5H-pyrido[3,4-d]pyrimidin-4-yl]piperazine-1-carboxylate To a solution of benzyl 4-[7-(3-benzyloxy-1-naphthyl)-2-methylsulfanyl-6,8-dihydro-5H-pyrido[3,4-d]pyrimidin-4-yl]piperazine-1-carboxylate (8.00 g, 12.7 mmol) in DCM (200 mL) was added m-CPBA (2.73 g, 12.7 mmol, 80.0% purity) at 0° C. under nitrogen atmosphere. The reaction mixture was stirred for two hours under 0° C. The reaction mixture was quenched by addition $Na_2S_2O_3$ (10 mL) at 0° C., and then diluted with water (100 mL) and extracted with DCM (200 mL). The combined organic layers were washed with brine (200 mL), dried over $Na_2SO_4$, filtered and concentrated under reduced pressure. The residue was purified by column chromatography eluting with 0→10% MeOH/DCM to benzyl 4-[7-(3-benzyloxy-1-naphthyl)-2-methylsulfinyl-6,8-dihydro-5H-pyrido[3,4-d]pyrimidin-4-yl]piperazine-1-carboxylate (3.50 g, 4.92 mmol, 38.8% yield, 91.0% purity) ES+APCI MS m/z 648.5 [M+H]+.

Intermediate 50 tert-butyl 4-(4-benzyloxycarbonylpiperazin-1-yl)-2-methylsulfonyl-6,8-dihydro-5H-pyrido[3,4-d]pyrimidine-7-carboxylate

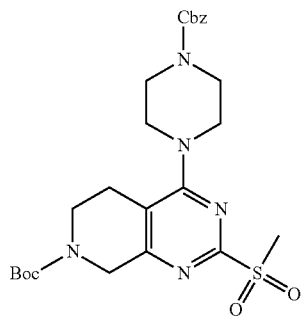

116

-continued

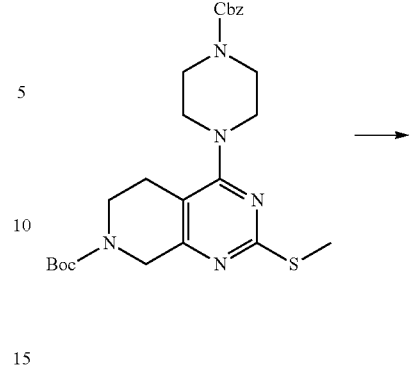

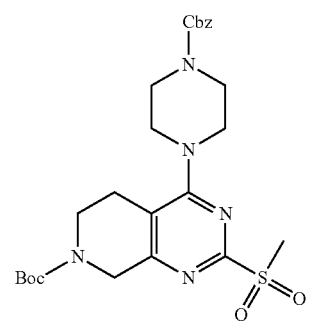

Step A: Tert-Butyl 4-(4-benzyloxycarbonylpiperazin-1-yl)-2-methylsulfonyl-6,8-dihydro-5H-pyrido[3,4-d]pyrimidine-7-carboxylate To a stirred solution of tert-butyl4-(4-benzyloxycarbonylpiperazin-1-yl)-2-methylsulfanyl-6,8-dihydro-5H-pyrido[3,4-d]pyrimidine-7-carboxylate (14.4 g, 28.9 mmol) in DCM (150 mL) was added m-CPBA solid (17.4 g, 101 mmol) at 0° C. under nitrogen. After stirring at 0° C. for 2 hours, the reaction mixture was diluted with water (300 mL) and basified with saturated $NaHCO_3$ aqueous solution to pH~8 and then extracted with DCM (3×200 mL). The combined organic layers were washed with brine (3×200 mL), dried over $Na_2SO_4$, filtered and concentrated under reduced pressure. The residue was purified by column chromatography ($SiO_2$, Petroleum ether/Ethyl acetate 10/1 to 1/2) to give tert-butyl 4-(4-benzyloxycarbonylpiperazin-1-yl)-2-methylsulfonyl-6,8-dihydro-5H-pyrido[3,4-d]pyrimidine-7-carboxylate (11.0 g, 19.7 mmol, 68.6% yield, 95.4% purity). ES+APCI MS m/z 532.1 [M+H]+.

Intermediate 51

4-bromo-5-methyl-1-tetrahydropyran-2-yl-indazole

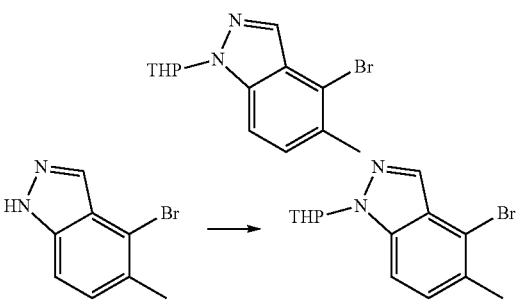

Step A:
4-bromo-5-methyl-1-tetrahydropyran-2-yl-indazole

To a mixture of 4-bromo-5-methyl-1H-indazole (3 g, 14.2 mmol) and 3,4-dihydro-2H-pyran (2.39 g, 28.4 mmol, 2.60 mL) in DCM (30 mL) was added TsOH*H₂O (270 mg, 1.42 mmol) and the mixture stirred at 15° C. for 2 hours. After completion, the reaction mixture was concentrated under vacuum and the residue purified by column chromatography using 5→20& EtOAc/Petroleum Ether as eluent to give 4-bromo-5-methyl-1-tetrahydropyran-2-yl-indazole (4 g, 13.6 mmol, 95.3% yield) as white solid. ¹H NMR (400 MHz, chloroform-d) δ 8.01 (s, 1H), 7.47 (d, J=8.4 Hz, 1H), 7.25 (d, J=8.4 Hz, 1H), 5.70 (dd, J=2.8, 9.2 Hz, 1H), 4.05-3.96 (m, 1H), 3.79-3.70 (m, 1H), 2.66-2.44 (m, 4H), 2.25-2.04 (m, 2H), 1.84-1.56 (m, 3H).

Intermediate 52

4-bromo-5-methoxy-1-(tetrahydro-2H-pyran-2-yl)-1H-indazole

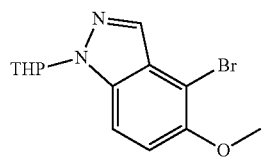

4-bromo-5-methoxy-1-(tetrahydro-2H-pyran-2-yl)-1H-indazole was prepared following Intermediate 51 substituting 4-bromo-5-methoxy-1H-indazole for 4-bromo-5-methyl-1H-indazole in Step A. ¹H NMR (400 MHz, chloroform-d) δ 8.00 (s, 1H), 7.53 (d, J=9.2 Hz, 1H), 7.16 (d, J=9.2 Hz, 1H), 5.70 (dd, J=2.8, 9.2 Hz, 1H), 4.04-3.98 (m, 1H), 3.96 (s, 3H), 2.55-2.49 (m, 1H), 2.23-2.05 (m, 2H), 1.83-1.69 (m, 3H).

Intermediate 53

3-(benzyloxy)-1-bromo-2-methylnaphthalene

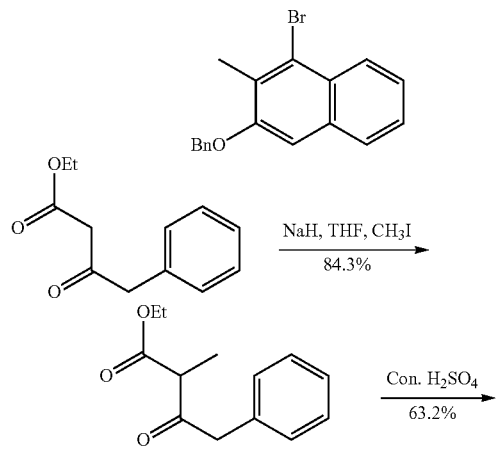

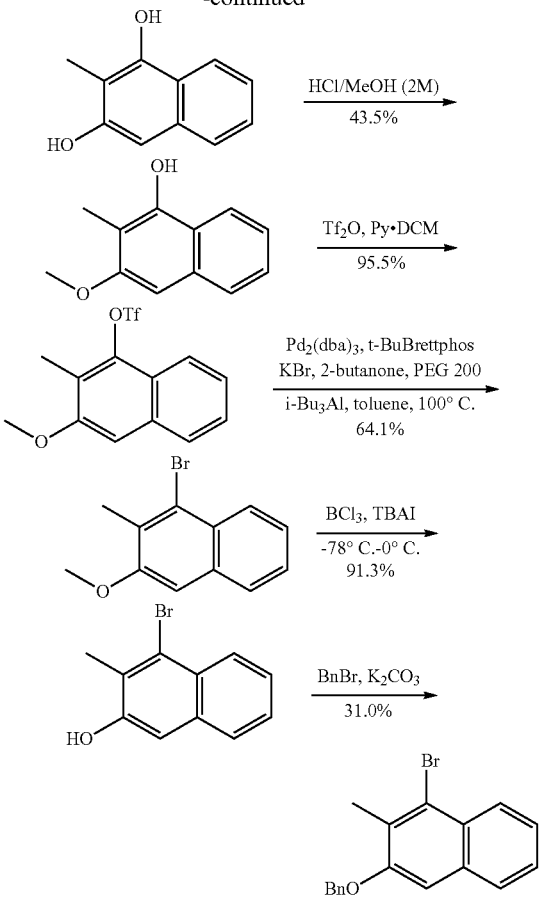

Step A: Ethyl 2-methyl-3-oxo-4-phenyl-butanoate

To a dried 250 ml three-necked flask was added ethyl 3-oxo-4-phenyl-butanoate (4.00 g, 19.4 mmol.), THF (50.0 mL), sodium hydride (931 mg, 23.3 mmol) and the reaction stirred for 0.5 hours at 0° C. A solution of methyl iodide (3.03 g, 21.3) was next added drop-wise. After addition was completed, the reaction mixture was warmed to 20° C. and stirred for two hours at 20° C. The reaction mixture was quenched by addition of water (10.0 mL) at 20° C. and then diluted with ethyl acetate (20.0 mL) and the layers separated. The aqueous layer was next extracted with ethyl acetate (20.0 mL×3). The combined organic layers were washed with brine (30.0 mL), dried over anhydrous sodium sulfate, filtered and concentrated under reduced pressure to give a residue. The residue was purified by column chromatography (SiO₂, Petroleum ether:Ethyl acetate 20:1 to 10:1) to give ethyl 2-methyl-3-oxo-4-phenyl-butanoate (3.60 g, 16.3 mmol, 84.3% yield) as a colorless oil. ¹H NMR (400 MHz, CDCl₃) δ=7.38-7.28 (m, 3H), 7.25-7.19 (m, 2H), 4.22-4.15 (m, 2H), 3.87 (d, J=2.0 Hz, 2H), 3.65 (q, J=7.2 Hz, 1H), 1.34 (d, J=7.2 Hz, 3H), 1.30-1.26 (m, 3H).

Step B: 2-methylnaphthalene-1,3-diol

A solution of ethyl 2-methyl-3-oxo-4-phenyl-butanoate (3.60 g, 16.3 mmol) in concentrated sulfuric acid (19.9 g, 203 mmol) was stirred at 15° C. for 12 hours. The reaction mixture was poured into ice-water (30.0 mL) and the resulting solid collected by filtration and dried under vacuum to afford 2-methylnaphthalene-1,3-diol (1.80 g, 10.3 mmol, 63.2% yield) as a red solid. $^1$H NMR (400 MHz, CDCl$_3$) δ=8.02 (d, J=8.0 Hz, 1H), 7.65-7.54 (m, 1H), 7.41 (t, J=7.2 Hz, 1H), 7.36-7.31 (m, 1H), 6.80 (s, 1H), 4.29-4.20 (s, 2H), 2.41-2.24 (s, 3H).

Step C: 3-methoxy-2-methyl-naphthalen-1-ol 2-methylnaphthalene-1,3-diol (1.70 g, 9.76 mmol) was added to HCl/MeOH (2 M, 35.0 mL) and the result mixture was stirred at 30° C. for 3 days. The reaction was concentrated in vacuo and the residue purified by Prep-TLC (Petroleum ether:Ethyl acetate 1:1) to give 3-methoxy-2-methyl-naphthalen-1-ol (800 mg, 4.25 mmol, 43.5% yield) as a white solid. $^1$H NMR (400 MHz, CDCl$_3$) δ=8.02 (d, J=8.4 Hz, 1H), 7.69 (d, J=8.4 Hz, 1H), 7.44-7.38 (m, 1H), 7.37-7.31 (m, 1H), 6.79 (s, 1H), 5.14 (s, 1H), 3.94 (s, 3H), 2.29 (s, 3H).

Step D: (3-methoxy-2-methyl-1-naphthyl)trifluoromethanesulfonate

To a mixture of 3-methoxy-2-methyl-naphthalen-1-ol (800 mg, 4.25 mmol.) and pyridine (504 mg, 6.38 mmol) in DCM (10.0 mL) was added trifluoroacetic anhydride (1.44 g, 5.10 mmol) dropwise at 0° C. under N$_2$ atmosphere. The mixture was warmed to 20° C. and stirred for an additional 5 hours. The solvent was removed under vacuum and the residue purified by Prep-TLC (Petroleum ether:Ethyl acetate 1:1) to give (3-methoxy-2-methyl-1-naphthyl)trifluoromethanesulfonate (1.30 g, 4.06 mmol, 95.5% yield) as a white solid. $^1$H NMR (400 MHz, CDCl$_3$) δ=7.97 (d, J=7.6 Hz, 1H), 7.79-7.74 (m, 1H), 7.52-7.43 (m, 2H), 7.14 (s, 1H), 3.99 (s, 3H), 2.42 (s, 3H)

Step E: 1-bromo-3-methoxy-2-methyl-naphthalene

In a sealed tube was added (3-methoxy-2-methyl-1-naphthyl)trifluoromethanesulfonate (466 mg, 1.45 mmol), t-Bu-Brettphos (154 mg, 290 umol), potassium bromide (259 mg, 2.17 mmol), PEG-200 (175 mg), 2-butanone (157 mg, 2.17 mmol) and Pd$_2$(dba)$_3$ (133 mg, 145 umol) in toluene (10.0 mL) and the mixture de-gassed with N$_2$ for 5 minutes. Next, triisobutylaluminum (431 mg, 2.17 mmol) was added dropwise at 20° C. The mixture was heated to 100° C. for 24 hrs. The reaction mixture was poured into water (30.0 mL) and the aqueous layer extracted with ethyl acetate (20.0 mL×3). The combined organics were washed with brine (30.0 mL), dried over anhydrous sodium sulfate and concentrated in vacuo to give a residue which was pre-purified by column chromatography (Petroleum ether:Ethyl acetate 10:1) and then by Prep-TLC (Petroleum ether:Ethyl acetate 10:1) to give 1-bromo-3-methoxy-2-methyl-naphthalene (700 mg, 2.79 mmol, 64.1% yield) as a white solid. $^1$H NMR (400 MHz, CDCl$_3$) δ=8.26-8.17 (m, 1H), 7.73-7.69 (m, 1H), 7.47-7.40 (m, 2H), 7.09 (s, 1H), 3.98-3.95 (m, 3H), 2.56 (s, 3H).

Step F: 4-bromo-3-methyl-naphthalen-2-ol

To a solution of 1-bromo-3-methoxy-2-methyl-naphthalene (580 mg, 2.31 mmol) and tetrabutylammonium iodide (2.13 g, 5.78 mmol) in DCM (11.0 mL) cooled to −78° C. was added a solution of BCl$_3$ (1 M, 5.78 mL) dropwise over a period of 10 minutes while under N$_2$. The reaction mixture was warmed to 0° C. and stirred for 2 hours at room temperature. Next the solvent was removed under vacuum and the residue was purified by Prep-TLC (Petroleum ether:Ethyl acetate 5:1) to give 4-bromo-3-methyl-naphthalen-2-ol (500 mg, 2.11 mmol, 91.3% yield) as a white solid. $^1$H NMR (400 MHz, CDCl$_3$) δ=8.26-8.15 (m, 1H), 7.63 (dd, J=3.6, 6.0 Hz, 1H), 7.45-7.38 (m, 2H), 7.11 (s, 1H), 5.09 (s, 1H), 2.60 (s, 3H), 1.56 (s, 3H).

Step G: 3-benzyloxy-1-bromo-2-methyl-naphthalene

To a mixture of 4-bromo-3-methyl-naphthalen-2-ol (265 mg, 1.12 mmol) and benzyl bromide (201 mg, 1.18 mmol) in acetonitrile (3.00 mL) was added potassium carbonate (310 mg, 2.24 mmol) in one portion at 20° C. under N$_2$. The mixture was next stirred at 60° C. for two hours. The solvent was removed under vacuum and the residue purified by Prep-TLC (Petroleum ether:Ethyl acetate 5:1) to give the 3-benzyloxy-1-bromo-2-methyl-naphthalene (250 mg, 695 umol, 31.0% yield, 91.0% purity) as a white solid. ES+APCI MS m/z 327.0, 329.0 [M+H]$^+$.

Intermediate 54 tert-butyl-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate

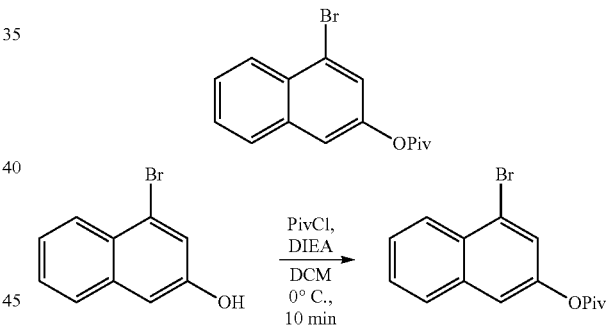

Step A: (4-bromo-2-naphthyl) 2,2-dimethylpropanoate

To a solution of 4-bromonaphthalen-2-ol (10 g, 44.8 mmol) and TEA (9.07 g, 89.7 mmol) in DCM (200 mL) was added 2,2-dimethylpropanoyl chloride (8.11 g, 67.2 mmol) at 0° C. The reaction mixture was stirred at 0° C. for 10 min. T reaction mixture was quenched by addition of water (50 mL) and the layers separated. The organic layer was washed with brine (30 mL), dried over Na$_2$SO$_4$ filtered and concentrated under vacuum. The residue was purified by silica gel chromatography (PE:EA=1:0 to 100:1) to give (4-bromo-2-naphthyl) 2,2-dimethylpropanoate (9 g, 29.3 mmol, 65.4% yield) as a red oil. $^1$H NMR (400 MHz, CHLOROFORM-d) δ=8.22 (d, J=8.0 Hz, 1H), 7.83-7.77 (m, 1H), 7.63-7.49 (m, 4H), 1.41 (s, 9H).

Intermediate 55 tert-butyl 4-(2-(3-morpholinopropoxy)-5,6,7,8-tetra-hydropyrido[3,4-d]pyrimidin-4-yl) piperazine-1-carboxylate

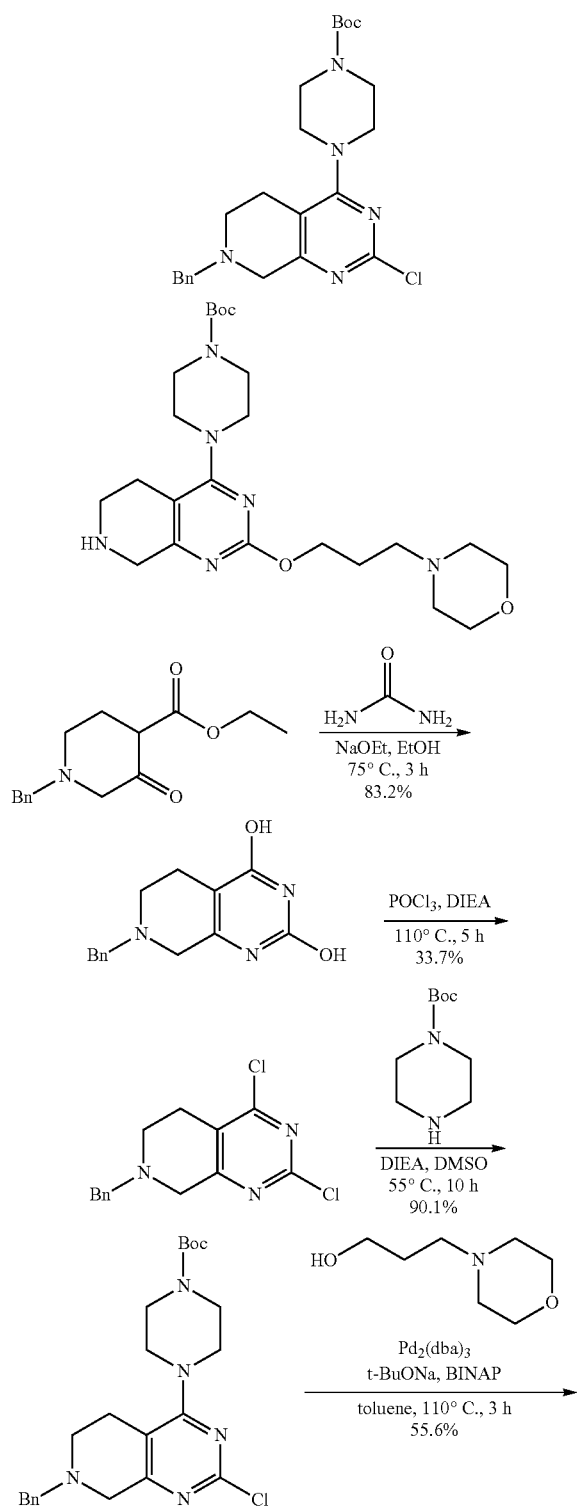

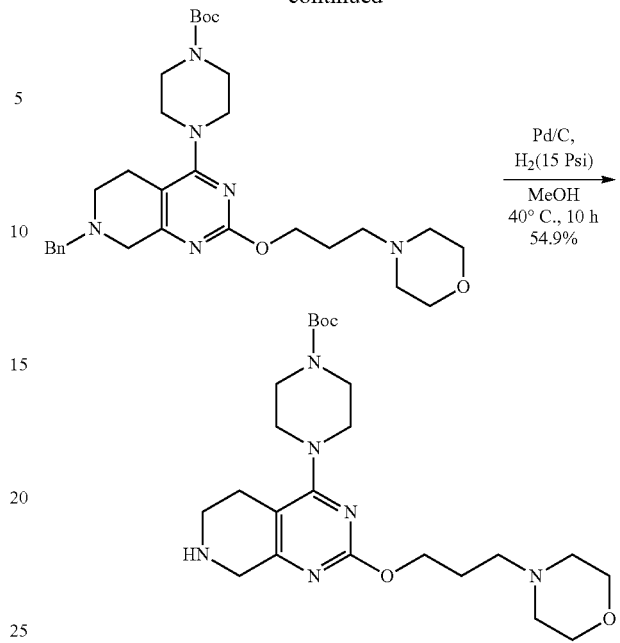

Step A: 7-benzyl-6,8-dihydro-5H-pyrido[3,4-d]pyrimidine-2,4-diol

To EtOH (600 mL) was added Na (5.56 g, 241 mmol) in portions and the mixture stirred for 1 hour. To this solution was added ethyl 1-benzyl-3-oxo-piperidine-4-carboxylate (30.0 g, 100 mmol) and urea (14.5 g, 242 mmol) and the reaction mixture stirred at 75° C. for 36 hours. The solvent was removed under vacuum and the residue dissolved in water (50 mL) and acidified by addition of HCl (120 mL, 2M) at which point a solid precipitated. The solid was filtered and the filter cake dried under vacuum to give 7-benzyl-6,8-dihydro-5H-pyrido[3,4-d]pyrimidine-2,4-diol (22.0 g, 83.8 mmol). $^1$HNMR (400 MHz, DMSO-$d_6$) δ=10.97 (br s, 1H), 10.66 (br s, 1H), 7.55-6.95 (m, 5H), 3.81-3.50 (m, 2H), 3.26-2.91 (m, 2H), 2.77-2.58 (m, 2H), 2.34-2.09 (m, 2H).

Step B: 7-benzyl-2,4-dichloro-6,8-dihydro-5H-pyrido[3,4-d]pyrimidine

To a solution of DIEA (30.1 g, 233 mmol) in POCl$_3$ (330 g, 2.15 mol) was added 7-benzyl-6,8-dihydro-5H-pyrido[3,4-d]pyrimidine-2,4-diol (20.0 g, 77.7 mmol) and the reaction mixture stirred at 110° C. for 5 hours. Upon completion, the reaction mixture was concentrated under vacuum. The residue was dissolved in DCM (400 mL) and poured into sat. NaHCO$_3$ (200 mL) and the layers separated. The aqueous layer was extracted with DCM (2×400 mL). The combined organics were washed with brine (100 mL), dried over Na$_2$SO$_4$ and concentrated under vacuum. The residue was purified by silica gel chromatography (PE/DCM=10/1 to 0/1) to give 7-benzyl-2,4-dichloro-6,8-dihydro-5H-pyrido[3,4-d]pyrimidine (7.70 g, 26.2 mmol). $^1$HNMR (300 MHz, chloroform-d) δ=7.43-7.28 (m, 5H), 3.73 (s, 2H), 3.66 (br s, 2H), 2.84 (br s, 4H).

Step C: Tert-Butyl 4-(7-benzyl-2-chloro-6,8-dihydro-5H-pyrido[3,4-d]pyrimidin-4-yl) piperazine-1-carboxylate To a solution of 7-benzyl-2,4-dichloro-6,8-dihydro-5H-pyrido[3,4-d]pyrimidine (17.3 g, 58.8 mmol) in DMSO (200 mL) was added DIEA (19.0 g, 147 mmol) and tert-butyl piperazine-1-carboxylate (11.5 g, 61.7 mmol) and the mixture stirred at 55° C. for 10 hours. The reaction mixture was poured into ethyl acetate (200 mL) and washed with water (3×200 mL). The combined organics were washed with brine (200 mL), dried over anhydrous Na$_2$SO$_4$ and concentrated under vacuum to give a residue. The residue was purified by trituration from MTBE (200 mL) to give tert-butyl 4-(7-benzyl-2-chloro-6,8-dihydro-5H-pyrido[3,4-d]pyrimidin-4-yl) piperazine-1-carboxylate (24 g, 52.9 mmol). ES+APCI MS m/z 444.2 [M+H]$^+$.

Step D: Tert-Butyl 4-[7-benzyl-2-(3-morpholinopropoxy)-6,8-dihydro-5H-pyrido[3,4-d]pyrimidin-4-yl] piperazine-1-carboxylate A mixture of 3-morpholinopropan-1-ol (11.8 g, 81.1 mmol), tert-butyl 4-(7-benzyl-2-chloro-6,8-dihydro-5H-pyrido[3,4-d]pyrimidin-4-yl)piperazine-1-carboxylate (18 g, 40.5 mmol), BINAP (5.05 g, 8.11 mmol), t-BuONa (9.74 g, 101 mmol) and Pd$_2$(dba)$_3$ (3.71 g, 4.05 mmol) in toluene (300 mL) was degassed and purged with N$_2$ 3 times, and the mixture stirred at 110° C. for 3 hours under N$_2$ atmosphere. The reaction mixture was poured into H$_2$O (200 mL) and the aqueous layer extracted with ethyl acetate (3×300 mL). The combined organics were washed with brine (200 mL), dried over anhydrous Na$_2$SO$_4$ and concentrated under vacuum to give a residue. The residue was purified by column chromatography (SiO$_2$, Petroleum ether/Ethyl acetate=100/1 to 5/1) to give tert-Butyl 4-[7-benzyl-2-(3-morpholinopropoxy)-6,8-dihydro-5H-pyrido[3,4-d]pyrimidin-4-yl] piperazine-1-carboxylate (14 g, 22.5 mmol). ES+APCI MS m/z 553.4 [M+H]$^+$.

Step E: Tert-Butyl 4-[2-(3-morpholinopropoxy)-5,6,7,8-tetrahydropyrido[3,4-d]pyrimidin-4-yl] piperazine-1-carboxylate To a solution of tert-butyl 4-[7-benzyl-2-(3-morpholinopropoxy)-6,8-dihydro-5H-pyrido[3,4-d]pyrimidin-4-yl]piperazine-1-carboxylate (14 g, 25.3 mmol) in MeOH (1 L) was added dry Pd/C (3 g, 10% purity) under N$_2$. The suspension was degassed under vacuum and purged with H$_2$ several times. The mixture was stirred under H$_2$ (15 psi) at 40° C. for 10 hours. The mixture was filtered and the filtrate concentrated in vacuo to give a residue. The residue was purified by reversed phase flash [water (0.1 TFA)/acetonitrile] to give tert-butyl 4-[2-(3-morpholinopropoxy)-5,6,7,8-tetrahydropyrido[3,4-d]pyrimidin-4-yl] piperazine-1-carboxylate (6.5 g, 13.9 mmol). ES+APCI MS m/z 463.4 [M+H]$^+$.

Intermediate 56

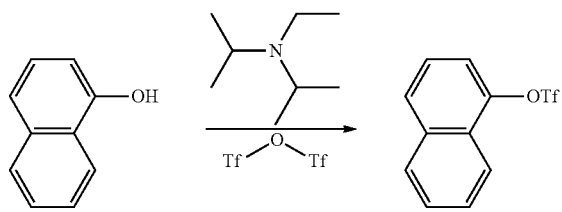

Naphthalen-1-yl Trifluoromethanesulfonate alpha-Naphthol (4 g, 27.74 mmol) was dissolved in DCM (200 mL) in a 3 neck flask. The reaction was cooled to 10° C. in a water bath. N-ethyl-N-isopropylpropan-2-amine (4.846 ml, 27.74 mmol) and trifluoromethanesulfonic anhydride (4.668 ml, 27.74 mmol) were added to the solution dropwise. The reaction was stirred at 10° C. for 2 hours. TLC (25% EtOAc, UV vis) showed reaction complete. The organics were with water (2×) and brine (2×). The organics were dried over MgSO$_4$ and concentrated in vacuo. The concentrate was purified using normal phase chromatography on the CombiFlash (0%-12% EtOAc:Hexanes). All fractions containing clean product were combined and concentrated in vacuo to give naphthalen-1-yl trifluoromethanesulfonate (6.77 g, 24.51 mmol, 88.34% yield).

Intermediate 57

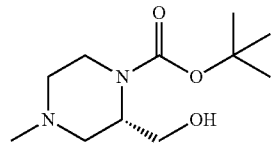 [SMILES: CN1CCN(C(=O)OC(C)(C)C)[C@H](CO)C1]

Tert-butyl (S)-2-(hydroxymethyl)-4-methylpiperazine-1-carboxylate

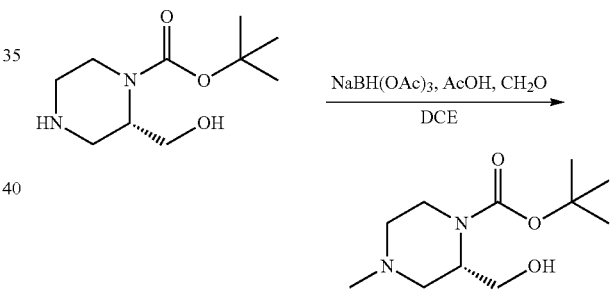

To a solution of (S)-1-Boc-2-hydroxymethylpiperazine (1.0 g, 4.62 mmol) in DCE (92.47 ml, 4.624 mmol) was added formaldehyde (3.474 ml, 46.24 mmol) (37% in water) followed by sodium triacetoxyborohydride (4.9 g, 23.12 mmol). The mixture was stirred vigorously at room temperature for 2.5 hours. The mixture was treated with saturated sodium bicarbonate (30 mL), stirred for 10 min then extracted with DCM (3×10 mL). The combined organic phases were dried over sodium sulfate, filtered and concentrated. ES+APCI MS m/z 231.1 [M+H]$^+$.

Intermediate 58

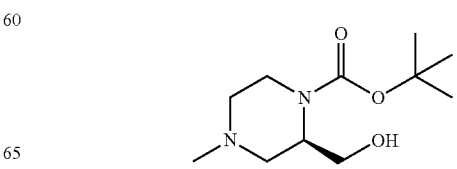

125

Tert-Butyl (R)-2-(hydroxymethyl)-4-methylpiperazine-1-carboxylate

Title compound was prepared as in Intermediate 57, substituting tert-butyl (R)-2-(hydroxymethyl)piperazine-1-carboxylate for (S)-1-Boc-2-hydroxymethylpiperazine. ES+APCI MS m/z 231.1 [M+H]+

Intermediate 59

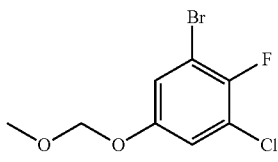

1-bromo-3-chloro-2-fluoro-5-(methoxymethoxy)benzene

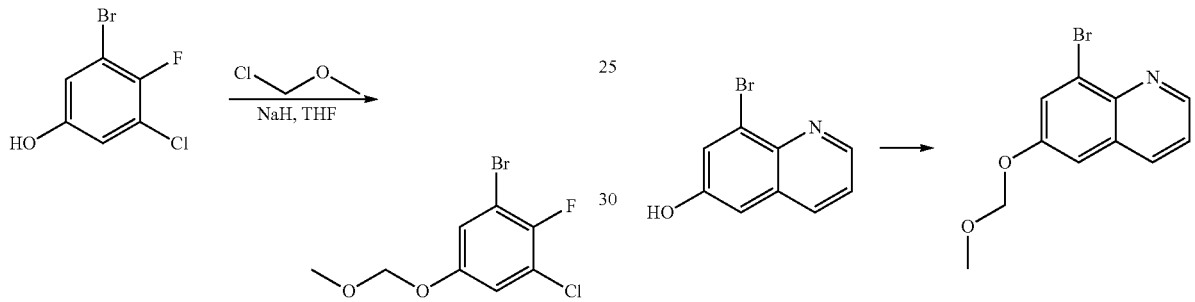

To a round bottom flask was added THF (8.87 ml, 4.44 mmol) followed by sodium hydride, 60% dispersion in mineral oil (0.213 g, 5.32 mmol). The mixture was cooled to 0° C. then 3-bromo-5-chloro-4-fluorophenol (1.0 g, 4.44 mmol) was added portionwise. Once the bubbling had ceased the resulting dark mixture was stirred at 0° C. for 30 min. Then chloromethyl methyl ether (0.421 ml, 5.54 mmol) was added and the mixture was warmed to ambient temperature where it was stirred for 2 hr. A saturated aqueous ammonium chloride solution was added and the mixture was extracted with DCM. The organic layer was dried over sodium sulfate, filtered and concentrated. Crude material was chromatographed (0-15% EtOAc in hexanes) to provide product as clear oil.

Intermediate 60

4-bromo-1-tetrahydropyran-2-yl-5-(trifluoromethyl)indazole

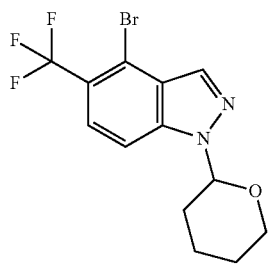 [SMILES: FC(F)(F)c1ccc2c(cnn2C2CCCCO2)c1Br]

126

Step A: 4-bromo-1-tetrahydropyran-2-yl-5-(trifluoromethyl)indazole

To a solution of 4-bromo-5-(trifluoromethyl)-1H-indazole (500 mg, 1.89 mmol, 1 eq) in DCM (10 mL) was added 3,4-dihydro-2H-pyran (476 mg, 5.66 mmol, 517 μL, 3 eq) and TsOH.H2O (35.9 mg, 188 umol, 0.1 eq). The mixture was stirred at 15° C. for 1 hour. The mixture was concentrated. The residue was purified by column chromatography (SiO2, PE:EA=10:1 to 1:1) to give 4-bromo-1-tetrahydropyran-2-yl-5-(trifluoromethyl)indazole (480 mg, 1.37 mmol, 72.9% yield) as yellow oil. ¹H NMR (400 MHz, chloroform-d) δ 8.20 (s, 1H), 7.69-7.63 (m, 2H), 5.70 (dd, J=2.8, 8.8 Hz, 1H), 4.05-3.96 (m, 1H), 3.79-3.70 (m, 1H), 2.56-2.50 (m, 1H), 2.27-2.04 (m, 2H), 1.80-1.74 (m, 2H), 1.60-1.54 (m, 1H).

Intermediate 61

8-bromo-6-(methoxymethoxy)quinoline

A stirred suspension of 8-bromoquinolin-6-ol (1.00 g, 4.46 mmol) in DCM (20 mL) was cooled to 0° C. and diisopropylethylamine (1.2 mL, 6.7 mmol, 1.5 eq.) was added followed by chloro(methoxy)methane (0.41 mL, 5.4 mmol, 1.2 eq.) dropwise and the reaction mixture was warmed to room temperature overnight. Concentrated aqueous ammonia (0.5 mL, ~5 mmol) was next added and the resulted mixture was stirred for 1 hour at room temperature. The mixture was evaporated in vacuo and chromatographed on silica gel, Redisep 40 g, using 20% EtOAc/hexane as eluent to give a colorless powder (0.52 g, 44%). ES+APCI MS m/z 268.0, [M+H]+.

Intermediate 62

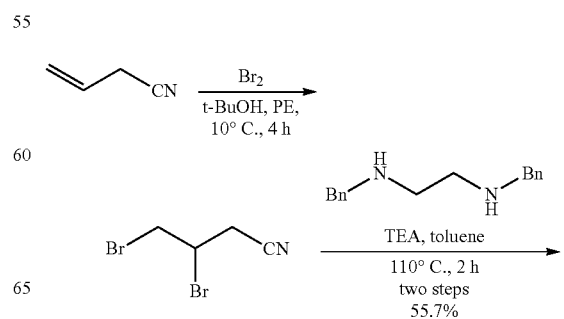

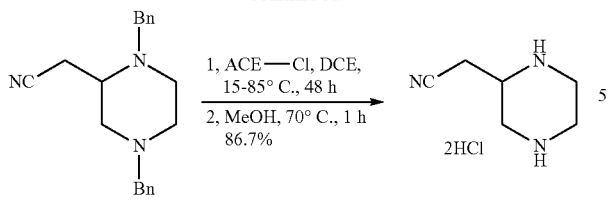

To a solution of but-3-enenitrile (80.0 g, 1.19 mol, 96.4 mL, 1.00 eq) in tert-butanol (130 mL) and petroleum ether (480 mL) was added a solution of Br₂ (191 g, 1.19 mol, 61.5 mL, 1.00 eq) in tert-butanol (130 mL). The mixture was stirred at 10° C. for 4 hours. The mixture was used into next step without any workup.

To the above mixture (274 mL) was added a solution of N,N-dibenzylethane-1,2-diamine (160 g, 445 mmol, 157 mL, 2 HOAc) and Et₃N (178 g, 1.76 mol, 245 mL) in toluene (300 mL). After was stirred at 110° C. for 2 hours, the mixture was filtered and the filtrate was concentrated under vacuum. The residue was purified by column chromatography (SiO₂, petroleum ether/ethyl acetate=3/1) to give 2-(1,4-dibenzylpiperazin-2-yl)acetonitrile (75.0 g, 246 mmol, two steps 55.7% yield) as a yellow solid. LCMS [ESI, M+1]: 306.

¹H NMR (400 MHz, chloroform-d) δ=7.37-7.23 (m, 10H), 3.80 (d, J=13.2 Hz, 1H), 3.60-3.42 (m, 3H), 3.06-2.96 (m, 1H), 2.95-2.83 (m, 1H), 2.69-2.53 (m, 4H), 2.52-2.35 (m, 3H).

To a solution of 2-(1,4-dibenzylpiperazin-2-yl)acetonitrile (160 g, 524 mmol, 1.00 eq) in dichloroethane (1.50 L) was added 1-chloroethyl carbonochloridate (300 g, 2.10 mol, 4.00 eq) at 15° C. After stirred at 85° C. for 48 h, the mixture was concentrated under vacuum. The residue was then taken up into methanol (1.50 L) and heated to reflux for 1 hour. The mixture was concentrated. The solid was treated with methyl tert-butyl ether (1.00 L), 2-piperazin-2-ylacetonitrile (Intermediate 62, 90.0 g, 454 mmol, 86.7% yield, 2HCl) was obtained as a white solid and used for next step without further purification.

¹H NMR (400 MHz, DMSO-d6) δ=10.19 (br s, 2H), 4.01-3.73 (m, 1H), 3.69-3.41 (m, 4H), 3.32 (dt, J=2.8, 13.2 Hz, 1H), 3.27-3.10 (m, 3H).

Intermediate 63

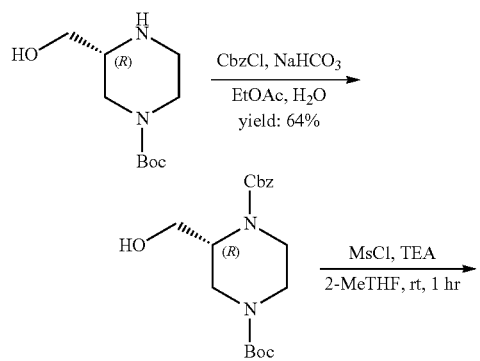

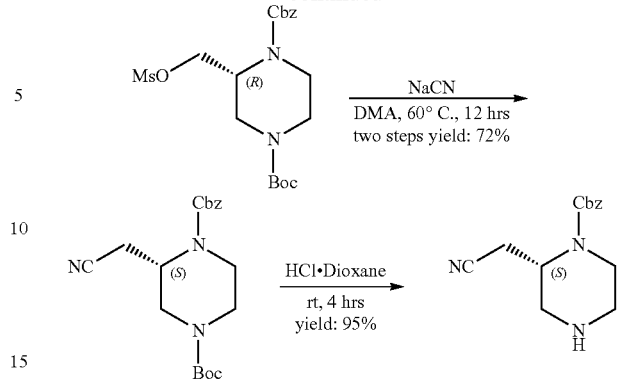

To a solution of tert-butyl (3R)-3-(hydroxymethyl)piperazine-1-carboxylate (80.0 g, 370 mmol, 1.0 eq) in Ethyl acetate (1400 mL) was added NaHCO₃ (93.2 g, 1.11 mol, 43.2 mL, 3.0 eq), H₂O (700 mL) and benzyl carbonochloridate (82.0 g, 481 mmol, 68.4 mL, 1.30 eq). The mixture was stirred at 25° C. for 12 hour. After completion, the organic phase was separated, washed with water (500 mL×2) dried over Na₂SO₄ and filtered. The solvent was removed under vacuum to give a residue. The residue was purified by column chromatography (SiO₂, Petroleum ether/ Ethyl acetate=40/1 to 1/1). The product 1-benzyl 4-tert-butyl (2R)-2-(hydroxymethyl)piperazine-1,4-dicarboxylate (85.0 g, 235 mmol, 64% yield, 96% purity) was obtained as a yellow oil. LCMS [ESI, M−99]: 251.

To a solution of 1-benzyl 4-tert-butyl (2R)-2-(hydroxymethyl)piperazine-1,4-dicarboxylate (20.0 g, 57.1 mmol, 1.0 eq) in 2-Methyltetrahydrofuran (240 mL) was added TEA (17.3 g, 171.23 mmol, 23.8 mL, 3.0 eq) and methanesulfonyl chloride (7.74 g, 67.6 mmol, 5.23 mL, 1.18 eq). The mixture was stirred at 20° C. for 1 hour. The reaction mixture was quenched by addition H₂O 150 mL at 20° C. The reaction mixture was extracted with Ethyl acetate (300 mL×2). The organic layers were washed with H₂O (100 mL), dried over Na₂SO₄, and filtered. The solvent was removed under vacuum. 1-benzyl 4-tert-butyl (2R)-2-(methylsulfonyloxymethyl)piperazine-1,4-dicarboxylate (22.0 g, crude) was obtained as a yellow oil. The crude product was used directly to the next step without further purification.

To a solution of 1-benzyl 4-tert-butyl (2R)-2-(methylsulfonyloxymethyl)piperazine-1,4-dicarboxylate (22.0 g, 51.3 mmol) in DMA (150 mL) was added NaCN (10.4 g, 211 mmol). The mixture was stirred at 60° C. for 12 hour. The solvent was removed under vacuum to give a oil residue. The residue was diluted with H₂O (40.0 mL) and extracted with Ethyl acetate (50.0 mL×3). The combined organic layers were washed with saturated brine (80.0 mL), dried over Na₂SO₄, filtered and concentrated under reduced pressure to give a residue. The residue was purified by column chromatography (Sift, Petroleum ether/Ethyl acetate=40/1 to 5:1) The product 1-benzyl 4-tert-butyl (2S)-2-(cyanomethyl)piperazine-1,4-dicarboxylate (18.5 g, 46.4 mmol, two steps yield 72%) was obtained as a yellow oil. LCMS [ESI, M+1]: 360.

To a solution of 1-benzyl 4-tert-butyl (2S)-2-(cyanomethyl)piperazine-1,4-dicarboxylate (18.5 g, 43.3 mmol, 1.00 eq) in dioxane (40.0 mL) was added HCl.dioxane (4 M, 54.1 mL, 5.0 eq). The mixture was stirred at 20° C. for 1 hour. Then the reaction mixture was added NaHCO₃ to pH>7, and concentrated under reduced pressure to remove dioxane. The residue was diluted with H₂O (50.0 mL) and extracted with Ethyl acetate (50.0 mL×3). The combined organic layers were washed with H₂O (20.0 mL), dried over Na₂SO₄, filtered and concentrated under reduced pressure to give a residue. The product benzyl (2S)-2-(cyanomethyl) piperazine-1-carboxylate (Intermediate 63, 11.5 g, 91.8% purity, 95% yield) was obtained as a yellow oil. LCMS [ESI, M+1]: 260.

¹H NMR (400 MHz, CHLOROFORM-d) δ=7.37-7.31 (m, 5H), 5.14 (s, 2H), 4.49 (br, s, 1H), 3.93 (br, s, 1H), 3.07-2.81 (m, 5H), 2.78-2.54 (m, 2H).

Intermediate 64

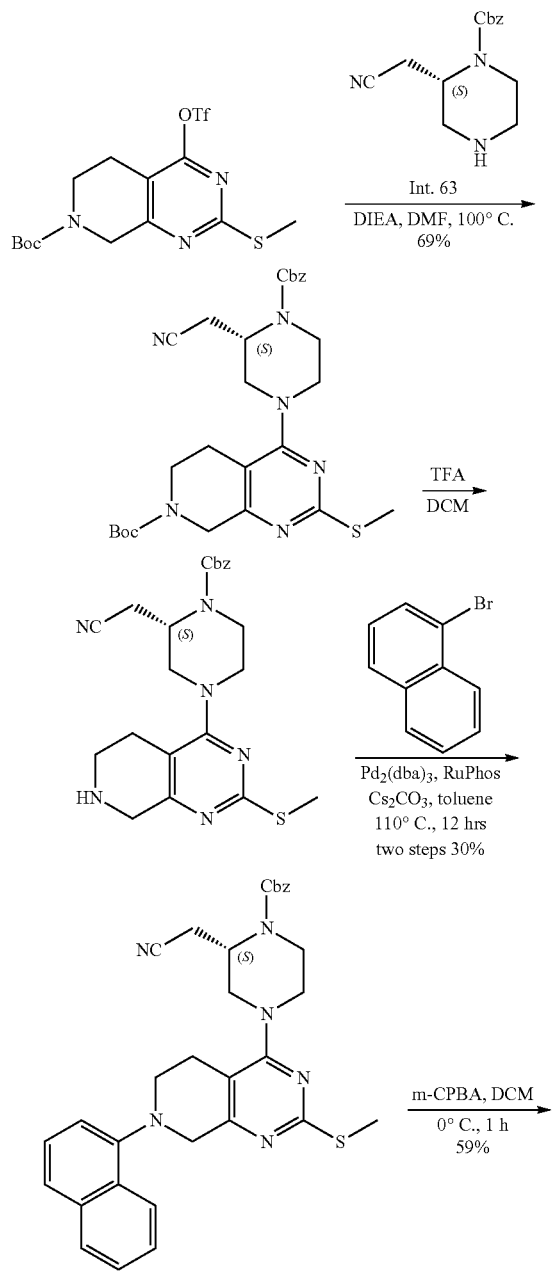

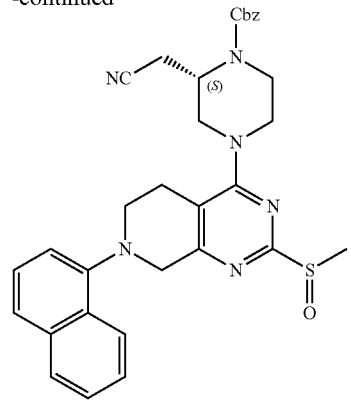

A mixture of tert-butyl 2-methylsulfanyl-4-(trifluoromethylsulfonyloxy)-6,8-dihydro-5H-pyrido[3,4-d]pyrimidine-7-carboxylate (3.81 g, 8.87 mmol, 1.0 eq), benzyl(2S)-2-(cyanomethyl)piperazine-1-carboxylate (Intermediate 63, 2.30 g, 8.87 mmol, 1.0 eq), DIEA (3.44 g, 26.6 mmol, 4.63 mL, 3.0 eq) in DMF (20.0 mL) was degassed and purged with N₂ for 3 times, and then the mixture was stirred at 100° C. for 1 hour under N₂ atmosphere. After completion, the solvent was removed under vacuum. The residue was purified by column chromatography (SiO₂, Petroleum ether/Ethyl acetate=3/1 to 1:1) to give tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (3.6 g, 6.16 mmol, 69% yield, 92.2% purity) as a yellow solid. LCMS [ESI, M+1]: 539.

A mixture of tert-butyl 4-[(3S)-4-benzyloxycarbonyl-3-(cyanomethyl)piperazin-1-yl]-2-methylsulfanyl-6,8-dihydro-5Hpyrido[3,4-d]pyrimidine-7-carboxylate (6.0 g, 11.1 mmol, 1.0 eq), TFA (30.8 g, 270 mmol, 20.0 mL, 24.3 eq) in DCM (20.0 mL) was degassed and purged with N₂ for 3 times, and then the mixture was stirred at 20° C. for 1 hour under N₂ atmosphere. After completion, the reaction mixture was quenched with saturated NaHCO₃ solution (500 mL). The mixture was extracted with ethyl acetate (3×300 mL) and the organic layer was dried over Na₂SO₄ and filtered. The solvent was removed under vacuum to give benzyl (2S)-2-(cyanomethyl)-4-(2-methylsulfanyl-5,6,7,8-tetrahydropyrido[3,4-d]pyrimidin-4-yl)piperazine-1-carboxylate (4.8 g, crude) as a yellow solid which was used for the next step without further purification.

A mixture of benzyl (2S)-2-(cyanomethyl)-4-(2-methylsulfanyl-5,6,7,8-tetrahydropyrido[3,4-d]pyrimidin-4-yl)piperazine-1-carboxylate (4.8 g), 1-bromonaphthalene (3.8 g, 18.35 mmol, 2.55 mL), Pd₂(dba)₃ (1.0 g, 1.09 mmol), RuPhos (1.02 g, 2.19 mmol) and Cs₂CO₃ (12.0 g, 36.8 mmol) in toluene (30.0 mL) was degassed and purged with N₂ for 3 times, and then the mixture was stirred at 100° C. for 12 hours under N₂ atmosphere. After completion, the reaction mixture was filtered. The organic solvent was removed under vacuum to give an oil residue. The residue was purified by column chromatography (SiO₂, Petroleum ether/Ethyl acetate=5/1 to 3:1) to give benzyl (2S)-2-(cyanomethyl)-4-[2-methylsulfanyl-7-(1-naphthyl)-6,8-dihydro-5H-pyrido[3,4-d]pyrimidin-4-yl]piperazine-1-carboxylate (2.2 g, 3.31 mmol, 85.3% purity, two steps yield 30%) was obtained as a yellow solid. LCMS [ESI, M+1]: 565.

A mixture of benzyl (2S)-2-(cyanomethyl)-4-[2-methylsulfanyl-7-(1-naphthyl)-6,8-dihydro-5H-pyrido[3,4-d]pyrimidin-4-yl]piperazine-1-carboxylate (2.8 g, 3.97 mmol, 1.0 eq), m-CPBA (1.05 g, 5.16 mmol, 1.3 eq) in DCM (4.0 mL) was degassed and purged with N₂ for 3 times, and then the mixture was stirred at 0° C. for 1 hour under N₂ atmosphere. After completion, the reaction is quenched by adding saturated Na₂SO₃ solution (50 mL). The mixture was extracted with ethyl acetate (3×10 mL). The combined organic layer was dried with Na₂SO₄ and filtered. The solvent was removed to give a oil residue. The residue was purified by column chromatography (SiO₂, Metheanol/Ethyl acetate=1/20 to 1:10) to give benzyl (2S)-2-(cyanomethyl)-4-[2-methylsulfinyl-7-(1-naphthyl)-6,8-dihydro-5H-pyrido[3,4-d]pyrimidin-4-yl]piperazine-1-carboxylate (Intermediate 64, 1.5 g, 2.35 mmol, 59% yield, 90.8% purity) as a yellow solid. LCMS [ESI, M+1]: 581.

Intermediate 65

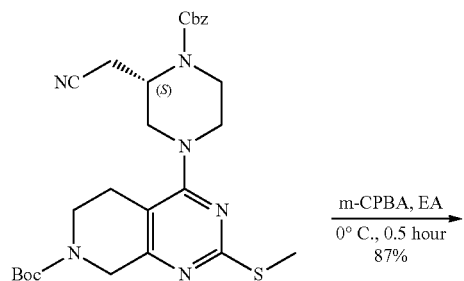

m-CPBA, EA
0° C., 0.5 hour
87%

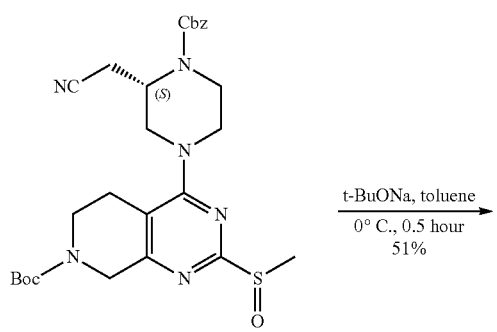

t-BuONa, toluene
0° C., 0.5 hour
51%

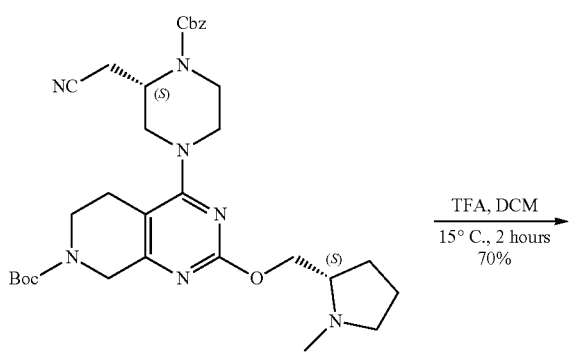

TFA, DCM
15° C., 2 hours
70%

-continued

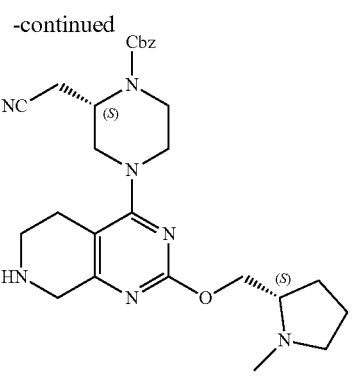

To a solution of tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (24.3 g, 45.0 mmol, 1.0 eq) in Ethyl acetate (480 mL) was added m-CPBA (8.69 g, 42.8 mmol, 85% purity, 0.95 eq) portionwise at 0° C. The mixture was stirred at 0° C. for 0.5 hour. Upon completion, the mixture was diluted with water (50.0 mL) and extracted with ethyl acetate (2×300 mL). The organic layers were dried over Na₂SO₄ and concentrated under vacuum. The residue was purified by reversed-phase flash [water (0.1% FA)/acetonitrile]. The mixture was neutralized with saturated sodium bicarbonate solution, concentrated under vacuum to remove MeCN and extracted with ethyl acetate (3×1000 mL). The organic layers were dried over Na₂SO₄ and concentrated under vacuum to give tert-butyl 4-[(3S)-4-benzyloxycarbonyl-3-(cyanomethyl)piperazin-1-yl]-2-methylsulfinyl-6,8-dihydro-5H-pyrido[3,4-d]pyrimidine-7-carboxylate (22.8 g, 39.3 mmol, 87% yield, 95.8% purity) as a yellow solid.

¹H NMR (400 MHz, chloroform-d) δ 7.37-7.23 (m, 5H), 5.12 (s, 2H), 4.75-4.41 (m, 3H), 4.17-4.05 (m, 2H), 3.86 (d, J=11.6 Hz, 1H), 3.81-3.62 (m, 1H), 3.46-3.18 (m, 3H), 3.10 (d, J=3.6, 12.0 Hz, 1H), 2.81 (d, J=3.2 Hz, 3H), 2.77-2.56 (m, 4H), 1.42 (s, 9H).

To a solution of tert-butyl 4-[(3S)-4-benzyloxycarbonyl-3-(cyanomethyl)piperazin-1-yl]-2-methylsulfinyl-6,8-dihydro-5H-pyrido[3,4-d]pyrimidine-7-carboxylate (5.0 g, 9.01 mmol, 1.0 eq) and [(2S)-1-methylpyrrolidin-2-yl] methanol (1.82 g, 15.8 mmol, 1.88 mL, 1.75 eq) in toluene (50.0 mL) was added t-BuONa (1.73 g, 18.0 mmol, 2.0 eq). The mixture was stirred at 0° C. for 0.5 hour. After completion, the mixture was added cold water (50.0 mL) and extracted with ethyl acetate (5×50.0 mL). The combined organic layer was dried over Na₂SO₄, filtered and concentrated. The obtained product was purified by column chromatography (SiO₂, PE:EA=10:1-EA:MeOH=5:1) to give tert-butyl 4-[(3S)-4-benzyloxycarbonyl-3-(cyanomethyl) piperazin-1-yl]-2-[[(2S)-1-methylpyrrolidin-2-yl]methoxy]-6,8-dihydro-5H-pyrido[3,4-d]pyrimidine-7-carboxylate (2.80 g, 4.62 mmol, 51.0% yield) as yellow solid.

¹H NMR (400 MHz, chloroform-d) δ 7.44-7.35 (m, 5H), 5.21 (s, 2H), 4.73-4.54 (m, 2H), 4.44-4.33 (m, 2H), 4.22-4.10 (m, 2H), 3.41-3.93 (m, 1H), 3.82 (br d, J=11.6 Hz, 2H), 3.39-3.22 (m, 3H), 3.11 (br t, J=7.8 Hz, 1H), 2.99 (d, J=3.6, 12.8 Hz, 1H), 2.90-2.56 (m, 5H), 2.49 (s, 3H), 2.35-2.25 (m, 1H), 2.07-2.02 (m, 1H), 1.91-1.76 (m, 3H), 1.50 (s, 9H).

To a solution of tert-butyl 4-[(3S)-4-benzyloxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (2.40 g, 3.96 mmol, 1.0 eq) in DCM (8.0 mL) was added TFA (13.9 g, 122 mmol, 9.0 mL, 30.7 eq).

The mixture was stirred at 15° C. for 2 hours. After completion, the mixture was concentrated. The residue was added saturated NaHCO₃ aqueous (20.0 mL) and extracted with DCM (5×10.0 mL). The organic layer was dried over Na₂SO₄, filtered and concentrated. The product benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1.40 g, 2.77 mmol, 70% yield) was obtained as yellow solid. LCMS [ESI, M+1]: 506.

Intermediate 66

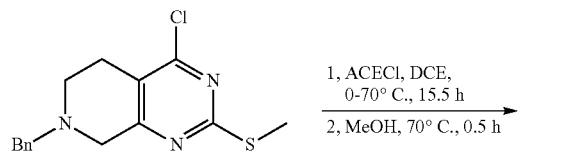

1, ACECl, DCE, 0-70° C., 15.5 h
2, MeOH, 70° C., 0.5 h

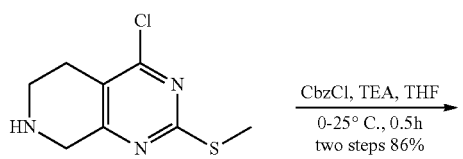

CbzCl, TEA, THF
0-25° C., 0.5h
two steps 86%

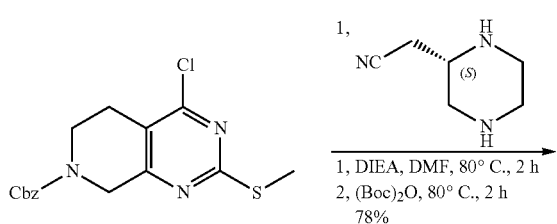

1, <small>NC-CH₂ piperazine (S)</small>
1, DIEA, DMF, 80° C., 2 h
2, (Boc)₂O, 80° C., 2 h
78%

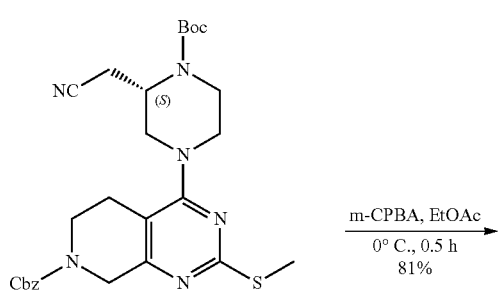

m-CPBA, EtOAc
0° C., 0.5 h
81%

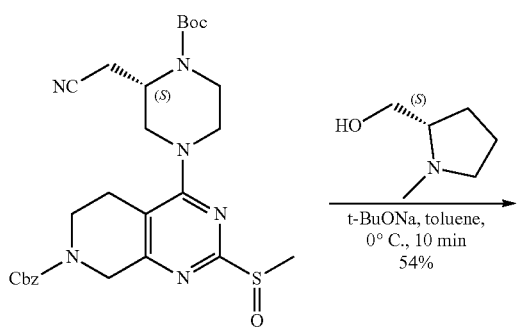

HO-CH₂-(S)-N-methylpyrrolidine
t-BuONa, toluene,
0° C., 10 min
54%

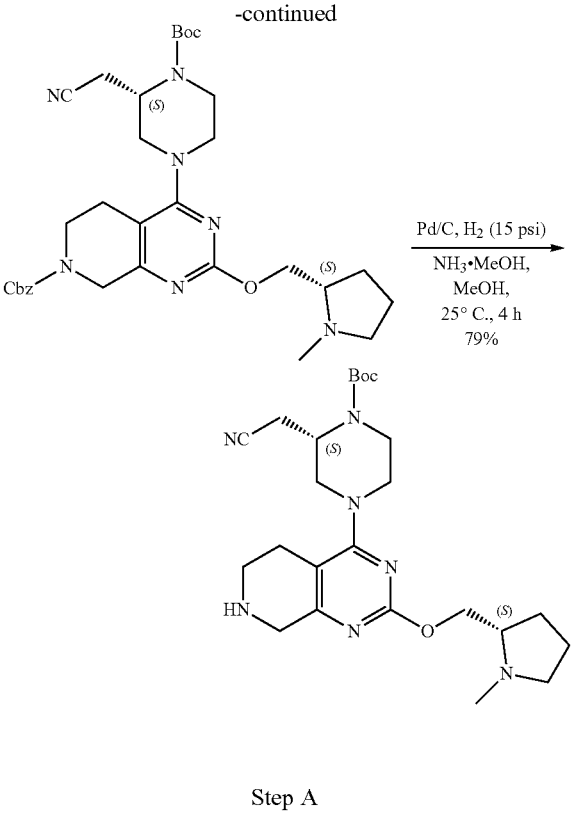

Pd/C, H₂ (15 psi)
NH₃·MeOH,
MeOH,
25° C., 4 h
79%

Step A

To a solution of 7-benzyl-4-chloro-2-methylsulfanyl-6,8-dihydro-5H-pyrido[3,4-d]pyrimidine (20.0 g, 65.4 mmol, 1 eq) in DCE (200 mL) was added 1-chloroethyl carbonochloridate (28.1 g, 196 mmol, 3 eq) at 0° C. The mixture was stirred at 0° C. for 30 minutes and 70° C. for 15 hours. The mixture was concentrated under vacuum. The residue was dissolved in MeOH (200 mL) and stirred at 70° C. for 0.5 hours. Upon completion, the mixture was concentrated under vacuum. The residue was triturated with methyl tert-butyl ether (60 mL). The precipitate was collected by filtration, washed with methyl tert-butyl ether (20 mL) and dried under vacuum to give 4-chloro-2-methylsulfanyl-5,6,7,8-tetrahydropyrido[3,4-d]pyrimidine (17.2 g, crude, HCl) as a yellow solid which was used directly in the next step without further purification.

¹H NMR (400 MHz, methanol-d₄) δ=4.35 (s, 2H), 3.60 (t, J=6.4 Hz, 2H), 3.05 (t, J=6.4 Hz, 2H), 2.55 (s, 3H).

Step B

To a solution of 4-chloro-2-methylsulfanyl-5,6,7,8-tetrahydropyrido[3,4-d]pyrimidine (16.5 g, crude, HCl) and TEA (20.0 g, 196 mmol, 27.3 mL) in THF (400 mL) was added benzyl carbonochloridate (16.7 g, 98.1 mmol, 13.9 mL) dropwise at 0° C. The mixture was stirred at 25° C. for 0.5 hour. Upon completion, the mixture was diluted with water (80 mL) and the organic layer was separated. The aqueous phase was extracted with EtOAc (200 mL). The combined organic layers were dried over MgSO₄, filtered and concentrated under vacuum. The residue was purified by silica gel chromatography (PE/EtOAc 80/1 to 5/1) to give benzyl 4-chloro-2-methylsulfanyl-6,8-dihydro-5H-pyrido[3,4-d]pyrimidine-7-carboxylate (19.6 g, 50.4 mmol, two steps 86% yield, 90% purity) as a yellow oil.

¹H NMR (300 MHz, chloroform-d) δ=7.37 (s, 5H), 5.18 (s, 2H), 4.63 (s, 2H), 3.877 (d, J=8.0, 2H), 2.80 (br s, 2H), 2.54 (s, 3H).

Step C

To a solution of benzyl 4-chloro-2-methylsulfanyl-6,8-dihydro-5H-pyrido[3,4-d]pyrimidine-7-carboxylate (21.5 g, 55.3 mmol, 1.00 eq) in DMF (400 mL) was added DIEA (35.7 g, 277 mmol, 48.2 mL, 5.00 eq) and 2-[(2S)-piperazin-2-yl]acetonitrile (6.92 g, 55.3 mmol, 1.00 eq). After stirred at 80° C. for 2 hours, (Boc)₂O (60.4 g, 277 mmol, 63.5 mL, 5.00 eq) was added into above mixture and stirred at 80° C. for another 2 hours. Upon completion, the mixture was diluted with water (800 mL) and extracted with EtOAc (2×400 mL). The organic layers were washed with brine (300 mL), dried over Na₂SO₄ and concentrated under vacuum. The residue was purified by silica gel chromatography (PE/EtOAc 10/1 to 1/1) to give benzyl 4-[(3S)-4-tert-butoxycarbonyl-3-(cyanomethyl) piperazin-1-yl]-2-methylsulfanyl-6,8-dihydro-5H-pyrido[3,4-d]pyrimidine-7-carboxylate (24.3 g, 43.0 mmol, 78% yield, 95% purity) as a yellow solid.

¹H NMR (400 MHz, chloroform-d) δ=7.43-7.29 (m, 5H), 5.18 (s, 2H), 4.76-4.54 (m, 2H), 4.46 (br d, J=18.4 Hz, 1H), 4.08-3.69 (m, 4H), 3.53-3.35 (m, 1H), 3.34-3.03 (m, 2H), 3.03-2.89 (m, 1H), 2.81-2.55 (m, 4H), 2.50 (s, 3H), 1.51 (s, 9H).

Step D

To a solution of benzyl 4-[(3S)-4-tert-butoxycarbonyl-3-(cyanomethyl) piperazin-1-yl]-2-methylsulfanyl-6,8-dihydro-5H-pyrido[3,4-d]pyrimidine-7-carboxylate (24.3 g, 45.1 mmol, 1 eq) in EtOAc (480 mL) was added m-CPBA (8.70 g, 42.9 mmol, 85% purity, 0.95 eq) portionwise at 0° C. The mixture was stirred at 0° C. for 0.5 hour. Upon completion, the mixture was diluted with water (800 mL). The pH was adjusted to 8 with NaHCO₃ and the organic layer was separated. The aqueous phase was extracted with EtOAc (2×400 mL). The organic layers were dried over Na₂SO₄ and concentrated under vacuum. The residue was purified by silica gel chromatography (EtOAc/MeOH 100/1 to 10/1) to give benzyl 4-[(3S)-4-tert-butoxycarbonyl-3-(cyanomethyl)piperazin-1-yl]-2-methyl sulfinyl-6,8-dihydro-5H-pyrido[3,4-d]pyrimidine-7-carboxylate (20.9 g, 36.4 mmol, 81% yield, 96% purity) as a white solid. LCMS [ESI, M+1]: 555.

Step E

To a solution of benzyl 4-[(3S)-4-tert-butoxycarbonyl-3-(cyanomethyl) piperazin-1-yl]-2-methylsulfinyl-6,8-dihydro-5H-pyrido[3,4-d]pyrimidine-7-carboxylate (20.9 g, 37.6 mmol, 1 eq) and [(2S)-1-methylpyrrolidin-2-yl]methanol (8.67 g, 75.3 mmol, 8.94 mL, 2 eq) in toluene (400 mL) was added t-BuONa (7.23 g, 75.3 mmol, 2 eq) at 0° C. After stirred at 0° C. for 10 minutes, the mixture was concentrated under vacuum. The residue was diluted with water (200 mL) and extracted with EtOAc (2×400 mL). The organic layers were dried over Na₂SO₄ and concentrated under vacuum. The residue was purified by reversed-phase flash [water (0.1% FA)/acetonitrile]. The mixture was neutralized with saturated sodium bicarbonate solution, concentrated under vacuum to remove MeCN and extracted with EtOAc (2×1000 mL). The organic layers were dried over Na₂SO₄ and concentrated under vacuum to give benzyl 4-[(3S)-4-tert-butoxycarbonyl-3-(cyanomethyl)piperazin-1-yl]-2-[[(2S)-1-methylpyrrolidin-2-yl]methoxy]-6,8-dihydro-5H-pyrido[3,4-d]pyrimidine-7-carboxylate (13.5 g, 20.5 mmol, 54% yield, 92% purity) as a yellow solid. LCMS [ESI, M+1]: 606.

Step F

To a solution of benzyl 4-[(3S)-4-tert-butoxycarbonyl-3-(cyanomethyl) piperazin-1-yl]-2-[[(2S)-1-methylpyrrolidin-2-yl]methoxy]-6,8-dihydro-5H-pyrido[3,4-d]pyrimidine-7-carboxylate (3.50 g, 5.78 mmol, 1 eq) in MeOH (60.0 mL) was added NH₃/MeOH (60.0 mL), Pd/C (1.00 g, 10% purity) under N₂. The suspension was degassed under vacuum and purged with H₂ several times. The mixture was stirred under H₂ (15 psi) at 25° C. for 4 hours. Upon completion, the catalyst was filtered off and the filtrate was concentrated under vacuum to give tert-butyl (2S)-2-(cyanomethyl)-4-[2-[[(2S)-1-methylpyrrolidin-2-yl] methoxy]-5,6,7,8-tetrahydropyrido[3,4-d]pyrimidine-4-yl]piperazine-1-carboxylate (Intermediate 66, 2.33 g, 4.55 mmol, 79% yield, 92% purity) as a yellow solid which was used directly in the next step without further purification.

¹H NMR (400 MHz, chloroform-d) δ=4.58 (br s, 1H), 4.34 (dd, J=5.2, 10.8 Hz, 1H), 4.11 (dd, J=6.8, 10.8 Hz, 1H), 4.08-3.88 (m, 4H), 3.84 (br d, J=12.8 Hz, 1H), 3.25-3.03 (m, 4H), 3.01-2.88 (m, 2H), 2.82-2.51 (m, 5H), 2.47 (s, 3H), 2.27 (dt, J=7.2, 9.2 Hz, 1H), 2.11-1.97 (m, 1H), 1.92-1.75 (m, 3H), 1.50 (s, 9H).

Intermediate 67

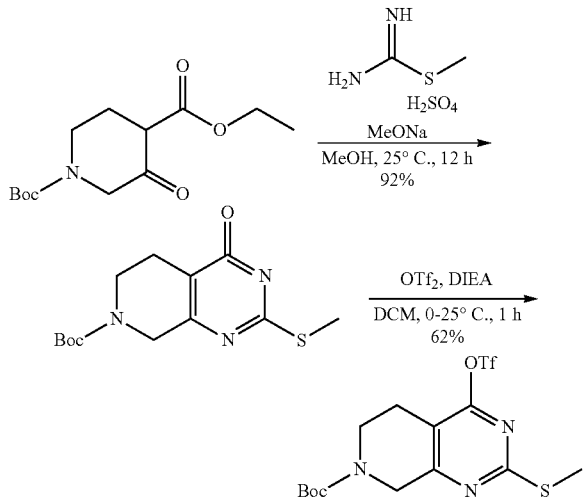

Tert-Butyl 2-methylsulfanyl-4-(trifluoromethylsulfonyloxy)-6,8-dihydro-5H-pyrido[3,4-d]pyrimidine-7-carboxylate Step A: Tert-Butyl 4-hydroxy-2-methylsulfanyl-6,8-dihydro-5H-pyrido[3,4-d]pyrimidine-7-carboxylate To a stirred solution of 1-tert-butyl 4-ethyl 3-oxopiperidine-1,4-dicarboxylate (50.0 g, 184 mmol, 1.00 eq) in MeOH (1.00 L) at 25° C. under nitrogen was added NaOMe (49.8 g, 921 mmol, 5.00 eq), followed by 2-methylisothiourea (62.4 g, 331 mmol, 1.80 eq, H₂SO₄) as a solid. The reaction mixture was stirred at 25° C. for 16 hours. The reaction mixture was acidified with HCl (2 M) until pH~5, and then the mixture was concentrated under reduced pressure to removed MeOH. The residue was suspended in 300 mL of ethyl acetate and 300 mL of water and stirred rapidly. The suspension was filtered and the white solid was collected. The filtrate was separated and the organics washed with water (1×300 mL) and brine (1×200 mL). The organics were isolated, dried over Na₂SO₄, filtered and concentrated to a white solid. tert-butyl 4-hydroxy-2-methylsulfanyl-6,8-dihydro-5H-pyrido[3,4-d]pyrimidine-7-carboxylate (51.0 g, 138 mmol, 75.4% yield, 81% purity) was obtained as a white solid and used directly for next step without further purification. LCMS [M+1]: 298.

$^1$H NMR (400 MHz, chloroform-d) δ=4.33 (s, 2H), 3.61 (t, J=5.6 Hz, 2H), 2.68-2.49 (m, 5H), 1.50 (s, 9H).

Step B: Tert-Butyl 2-methylsulfanyl-4-(trifluoromethylsulfonyloxy)-6,8-dihydro-5H-pyrido[3,4-d]pyrimidine-7-carboxylate To a stirred suspension of tert-butyl 4-hydroxy-2-methylsulfanyl-6,8-dihydro-5H-pyrido[3,4-d]pyrimidine-7-carboxylate (51.0 g, 171 mmol, 1.00 eq) in DCM (500 mL) at 0° C. was added DIEA (44.3 g, 343 mmol, 59.9 mL, 2.00 eq), followed by Tf₂O (72.6 g, 257 mmol, 42.4 mL, 1.50 eq) under nitrogen. Immediately a brown solution formed. After stirring at 25° C. for 16 hours, the reaction was concentrated to give a brown oil. The brown oil was purified by column chromatography (SiO₂, Petroleum ether/Ethyl acetate=I/O to 10/1). Title compound tert-butyl 2-methylsulfanyl-4-(trifluoromethylsulfonyloxy)-6,8-dihydro-5H-pyrido[3,4-d]pyrimidine-7-carboxylate (46.0 g, 107 mmol, 62% yield) was obtained as a yellow solid. LCMS [M+1]: 430.

Intermediate 68

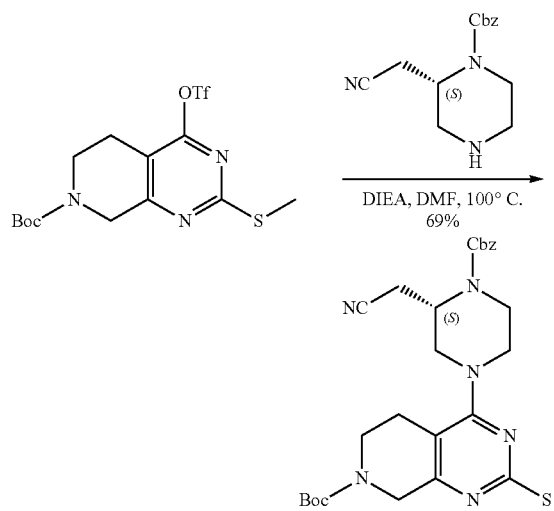

Tert-Butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate Step A: Tert-Butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate A mixture of tert-butyl 2-methylsulfanyl-4-(trifluoromethylsulfonyloxy)-6,8-dihydro-5H-pyrido[3,4-d]pyrimidine-7-carboxylate (3.81 g, 8.87 mmol, 1.0 eq), benzyl(2S)-2-(cyanomethyl)piperazine-1-carboxylate (Intermediate 63, 2.30 g, 8.87 mmol, 1.0 eq), DIEA (3.44 g, 26.6 mmol, 4.63 mL, 3.0 eq) in DMF (20.0 mL) was degassed and purged with N₂ for 3 times, and then the mixture was stirred at 100° C. for 1 hour under N₂ atmosphere. After completion, the solvent was removed under vacuum. The residue was purified by column chromatography (SiO₂, Petroleum ether/Ethyl acetate=3/1 to 1:1) to give title compound tert-butyl 4-[(3S)-4-benzyloxycarbonyl-3-(cyanomethyl)piperazin-1-yl]-2-methylsulfanyl-6,8-dihydro-5H-pyrido[3,4-d]pyrimidine-7-carboxylate (3.6 g, 6.16 mmol, 69% yield, 92.2% purity) as a yellow solid.

Intermediate 69

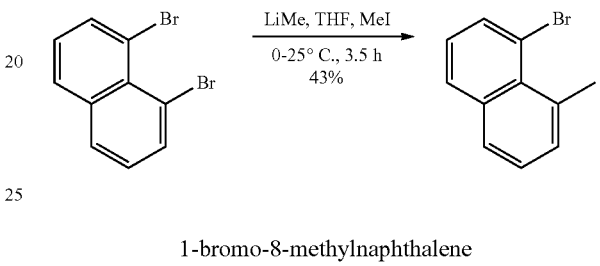

1-bromo-8-methylnaphthalene

Step A: 1-bromo-8-methyl-naphthalene

To a solution of 1,8-dibromonaphthalene (1 g, 3.50 mmol, 1 eq) in THF (20 mL) was added MeLi (1.6 M in diethyl ether, 2.62 mL, 1.2 eq) at 0° C. dropwise. After stirring for 30 minutes at 0° C., iodomethane (3.38 g, 23.8 mmol, 1.48 mL, 6.81 eq) was added dropwise. The mixture was warmed up to 25° C. and stirred for another 3 hours. The reaction mixture was quenched with water (20 mL) and extracted with ethyl acetate (20 mL×3). The combined organic layers were washed with brine (20 mL), dried over Na₂SO₄, filtered and concentrated under reduced pressure to give a residue. The residue was purified by prep-HPLC (column: Phenomenex Gemini C18 250*50 mm*10 um; mobile phase: [water (0.05% ammonia hydroxide v/v)—ACN]; B %: 45%-70%, 28 MIN; 40% min). Title compound 1-bromo-8-methyl-naphthalene (340 mg, 1.49 mmol, 43% yield, 97% purity) was obtained as a yellow solid after lyophilisation.

$^1$H NMR (400 MHz, chloroform-d) δ=7.75 (dd, J=0.8, 7.2 Hz, 1H), 7.69 (dd, J=0.8, 8.0 Hz, 1H), 7.66-7.59 (m, 1H), 7.30-7.22 (m, 2H), 7.13 (t, J=8.0 Hz, 1H), 3.05 (s, 3H).

Intermediate 70

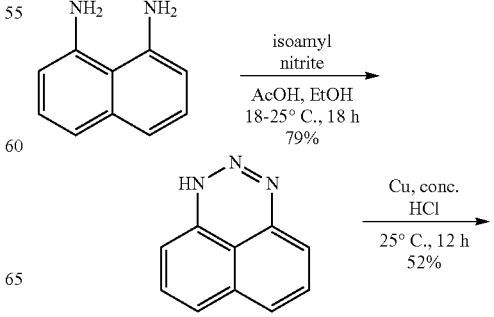

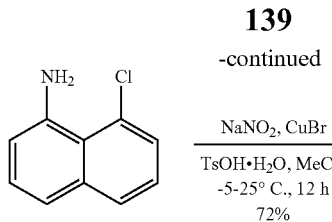

1-bromo-8-chloronaphthalene

Step A: 1H-naphtho[1,8-de][1,2,3]triazine

To a solution of naphthalene-1,8-diamine (100 g, 632 mmol, 1 eq) in AcOH (200 mL) and EtOH (1000 mL) was added isoamyl nitrite (72.6 g, 619 mmol, 83.4 mL, 0.98 eq) dropwise over a period of 2 h with temperature controlled between 18 and 21° C. under a cold-water bath. After the addition, the resulting red suspension was stirred at 25° C. for 16 hours. The solid was collected by filtration, washed with ethanol (2×500 mL) and dried under vacuum. Compound 1H-naphtho[1,8-de][1,2,3]triazine (84 g, 496 mmol, 79% yield) was obtained as a red crystalline solid and directly used next step without purification. LCMS [ESI, M+1]: 170.

Step B: 8-chloronaphthalen-1-amine

To a solution of 1H-naphtho[1,8-de][1,2,3]triazine (84 g, 496 mmol, 1 eq) in HCl (1.5 L) was added Cu (2.10 g, 33.1 mmol, 234 µL, 0.0665 eq). The mixture was stirred at 25° C. for 12 hours. The resulting mixture was diluted with water (500 mL) and heated at 85° C. for 30 mins. The resulting almost clear aqueous solution was filtered, cooled, basified with aqueous ammonia (until blue to litmus paper) and the solution was extracted with ether acetate (2×1000 mL). The combined extracts were dried over Na₂SO₄, filtered and concentrated under vacuum. The residue was purified by column chromatography (SiO₂, Petroleum ether/Ethyl acetate=200/1 to 5/1). Compound 8-chloronaphthalen-1-amine (57 g, 259 mmol, 52% yield, 81% purity) was obtained as a red solid. LCMS [ESI, M+1]: 178.

Step C: 1-bromo-8-chloro-naphthalene

To a solution of 8-chloronaphthalen-1-amine (57 g, 320 mmol, 1 eq) and TsOH·H₂O (219 g, 1.16 mol, 3.6 eq) in MeCN (1000 mL) was added a solution of NaNO₂ (39.8 g, 577 mmol, 1.8 eq) and CuBr (138 g, 963 mmol, 29.3 mL, 3 eq) in H₂O (120 mL) at −5° C., then the reaction mixture was stirred at 25° C. for 12 hours. The reaction mixture was added saturated Na₂SO₃ solution (100 mL) and stirred for 15 mins, then extracted with ethyl acetate (1000 mL×3). The combined organic layers were washed with brine (500 mL), dried over Na₂SO₄, filtered and concentrated under reduced pressure to give a residue. The residue was purified by column chromatography (SiO₂, Petroleum ether). Title compound 1-bromo-8-chloro-naphthalene (56 g, 229 mmol, 72% yield, 99% purity) was obtained as white solid.

¹H NMR (400 MHz, chloroform-d) δ=7.93 (dd, J=1.2, 7.6 Hz, 1H), 7.82 (dd, J=1.2, 8.4, 1H), 7.79 (dd, J=1.2, 8.4, 1H), 7.67 (dd, J=1.2, 7.6 Hz, 1H), 7.37 (t, J=8.0 Hz, 1H), 7.28 (t, J=8.0 Hz, 1H).

Intermediate 71

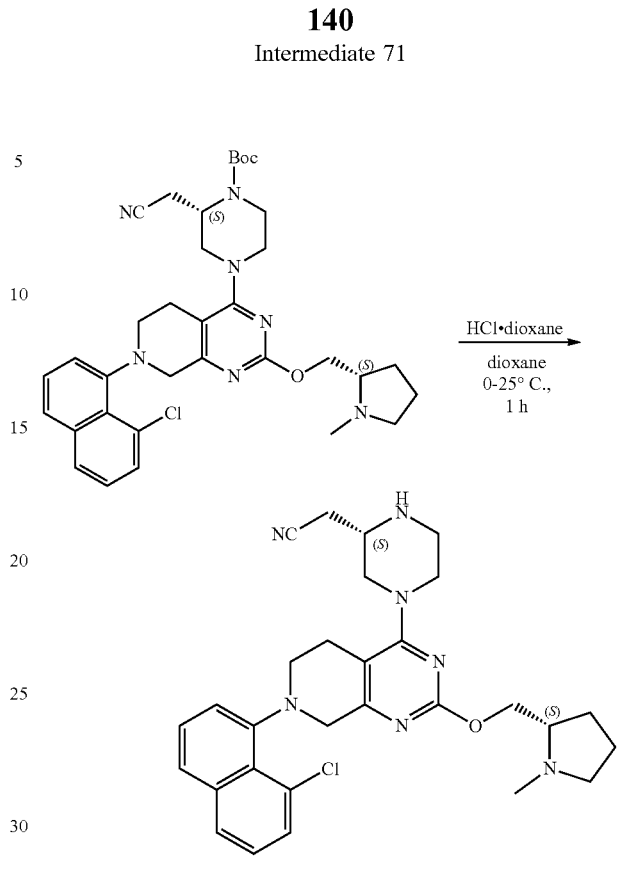

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (0.5 g, 791 umol, 1 eq) in dioxane (5 mL) was added HCl.dioxane (4 M, 5.00 mL, 25.3 eq) at 0° C. The mixture was stirred at 25° C. for 1 hour. Upon completion, the mixture was concentrated under vacuum to give an impure product (500 mg, crude, HCl) as a brown solid. 60 mg of the impure product was purified by prep-HPLC (column: Phenomenex Gemini 150*25 mm*10 um; mobile phase: [water (0.04% NH₃—H₂O+10 mM NH₄HCO₃)—ACN]; B %: 50%-80%, 10 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (19.3 mg, 36.1 umol, 34% purification yield, 99.2% purity) as a off-white solid. LCMS [ESI, M+1]:532.

¹H NMR (400 MHz, chloroform-d) δ=7.75 (d, J=8.4 Hz, 1H), 7.60 (dd, J=1.6, 8.0 Hz, 1H), 7.52 (dd, J=0.8, 7.2 Hz, 1H), 7.44 (dt, J=3.6, 7.6 Hz, 1H), 7.36-7.29 (m, 1H), 7.22 (t, J=6.8 Hz, 1H), 4.46-4.34 (m, 2H), 4.15 (td, J=6.4, 10.6 Hz, 1H), 4.04 (br d, J=12.4 Hz, 0.5H), 3.95-3.79 (m, 2H), 3.74

(br d, J=12.8 Hz, 0.5H), 3.63-3.48 (m, 1H), 3.40-2.99 (m, 7H), 2.98-2.80 (m, 2H), 2.73-2.61 (m, 1H), 2.60-2.49 (m, 3H), 2.47 (d, J=2.4 Hz, 3H), 2.32-2.23 (m, 1H), 2.10-1.99 (m, 1H), 1.82-1.68 (m, 3H).

Intermediate 72

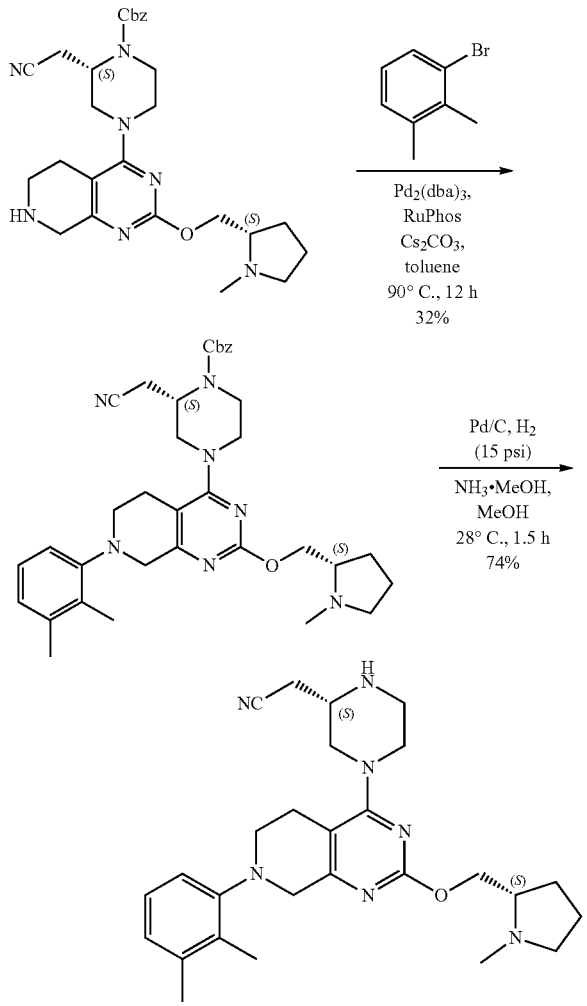

Int. 72

2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile Step A: (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (1.22 g, 1.98 mmol, 1.0 eq), 1-bromo-2,3-dimethyl-benzene (1.10 g, 5.93 mmol, 802 μL, 3.0 eq), $Cs_2CO_3$ (1.93 g, 5.93 mmol, 3 eq), RuPhos (185 mg, 396 umol, 0.2 eq) and $Pd_2(dba)_3$ (181 mg, 198 umol, 0.1 eq) in toluene (8 mL) was de-gassed and then heated to 90° C. for 12 hours under $N_2$. Upon completion, the mixture was concentrated under vacuum. The residue was diluted with water (20 mL) and extracted with EtOAc (3×30 mL). The organic layers were dried over $Na_2SO_4$, filtered and concentrated under vacuum. The residue was purified by reversed-phase flash [water (0.1% FA)/acetonitrile]. The collected desired fractions were neutralized with saturated aqueous sodium bicarbonate and concentrated under vacuum to remove MeCN, and then extracted with EtOAc (3×50 mL). The organic layers were dried over $Na_2SO_4$ and concentrated under vacuum to give (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (380 mg, 623 umol, 32% yield, 100% purity) as a yellow solid. LCMS [ESI, M+1]: 610.

Step B: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile $NH_3$ was bubbled into MeOH (20 mL) at −70° C. for 30 minutes. A solution of benzyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (380 mg, 623 umol, 1.0 eq) was added the above solution followed by Pd/C (200 mg, 10% purity) under $N_2$. The suspension was degassed under vacuum and purged with $H_2$ several times. The reaction was stirred under $H_2$ (15 psi) at 25° C. for 1 hour. Upon completion, the catalyst was filtered and the filtrate was concentrated to give title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (230 mg, 459 umol, 74% yield, 95% purity) as a yellow solid.

$^1$H NMR (400 MHz, chloroform-d) δ=7.11 (t, J=8.0 Hz, 1H), 6.96 (d, J=8.0 Hz, 2H), 4.39 (dd, J=4.8, 10.4 Hz, 1H), 4.14 (dd, J=7.2, 9.6 Hz, 1H), 4.02-3.95 (m, 3H), 3.84-3.78 (m, 1H), 3.31-3.19 (m, 1H), 3.17-3.04 (m, 5H), 3.04-2.95 (m, 1H), 2.89 (dd, J=9.2, 11.6 Hz, 1H), 2.76-2.62 (m, 3H), 2.58-2.50 (m, 2H), 2.48 (s, 3H), 2.30 (s, 3H), 2.29-2.23 (m, 4H), 2.12-2.00 (m, 1H), 1.89-1.76 (m, 3H).

Intermediate 73

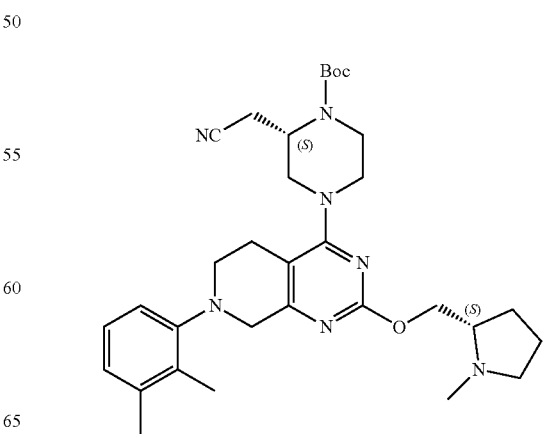

tert-butyl(2S)-2-(cyanomethyl)-4-[7-(2,3-dimethyl-phenyl)-2-[[(2S)-1-methylpyrrolidin-2-yl]methoxy]-6,8-dihydro-5H-pyrido[3,4-d]pyrimidin-4-yl]pipera-zine-1-carboxylate Step A: Tert-Butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate A mixture of tert-butyl (2S)-2-(cyanomethyl)-4-(2-methylsulfanyl-5,6,7,8-tetrahydropyrido[3,4-d]pyrimidin-4-yl)piperazine-1-carboxylate (1.60 g, 3.96 mmol, 1.0 eq), 1-bromo-2,3-dimethyl-benzene (1.61 g, 8.70 mmol, 1.18 mL, 2.20 eq), Pd$_2$(dba)$_3$ (362 mg, 395 umol, 0.10 eq), RuPhos (369 mg, 791 umol, 0.20 eq) and Cs$_2$CO$_3$ (3.87 g, 11.9 mmol, 3.0 eq) in toluene (8.0 mL) was degassed and purged with N$_2$ for 3 times, and then the mixture was stirred at 90° C. for 12 hrs under N$_2$ atmosphere. The organic solvent was washed with water (20.0 mL). The aqueous phase was extracted with ethyl acetate (3×30.0 mL). Combine extracts were washed with brine (80.0 mL), dried with Na$_2$SO$_4$ the solvent was then removed under vacuum. The residue was purified by column chromatography (SiO$_2$, Petroleum ether:Ethyl acetate=3:1 to Ethyl acetate:Methanol=10:1). Compound tert-butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate (900 mg, 1.59 mmol, 40% yield, 90% purity) was obtained as a yellow solid. LCMS [ESI, M+1]: 509.

$^1$H NMR (400 MHz, Chloroform-d) δ 7.11 (t, J=15.6 Hz, 1H), 6.95 (d, J=8.0 Hz, 2H), 4.63 (br s, 1H), 4.10-3.93 (m, 4H), 3.89 (br d, J=4.8 Hz, 1H), 3.27 (dd, J=3.6 Hz, J=13.6 Hz, 1H), 3.24-3.05 (m, 3H), 3.05-2.95 (m, 1H), 2.89-2.67 (m, 4H), 2.52 (s, 3H), 2.30 (s, 3H), 2.28 (s, 3H), 1.52 (s, 9H).

Step B: Tert-Butyl (2S)-2-(cyanomethyl)-4-[7-(2,3-dimethylphenyl)-2-methylsulfinyl-6,8-dihydro-5H-pyrido[3,4-d]pyrimidin-4-yl]piperazine-1-carboxylate A mixture of tert-butyl (2S)-2-(cyanomethyl)-4-[7-(2,3-dimethylphenyl)-2-methylsulfanyl-6,8-dihydro-5H-pyrido[3,4-d]pyrimidin-4-yl]piperazine-1-carboxylate (500 mg, 983 umol, 1.0 eq), 3-chlorobenzenecarboperoxoic acid (200 mg, 983 umol, 1.0 eq) in DCM (5.0 mL) was degassed and purged with N$_2$ for 3 times, and then the mixture was stirred at 0° C. for 30 min under N$_2$ atmosphere. The organic solvent was washed with water (10.0 mL). The aqueous phase was extracted with ethyl acetate (3×20.0 mL). Combine extracts were washed with brine (50.0 mL), dried with Na$_2$SO$_4$ the solvent was then removed under vacuum. The residue was purified by column chromatography (SiO$_2$, Petroleum ether:Ethyl acetate=3:1 to Ethyl acetate:Methanol=10:1). Compound tert-butyl (2S)-2-(cyanomethyl)-4-[7-(2,3-dimethylphenyl)-2-methylsulfinyl-6,8-dihydro-5H-pyrido[3,4-d]pyrimidin-4-yl]piperazine-1-carboxylate (450 mg, 793 umol, 81% yield, 93% purity) was obtained as a yellow solid. LCMS [ESI, M+1]:525.

Step C: Tert-Butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate A mixture of tert-butyl (2S)-2-(cyanomethyl)-4-[7-(2,3-dimethylphenyl)-2-methyl sulfinyl-6,8-dihydro-5H-pyrido[3,4-d]pyrimidin-4-yl]piperazine-1-carboxylate (800 mg, 1.52 mmol, 1.0 eq), [(2S)-1-methylpyrrolidin-2-yl]methanol (369 mg, 3.20 mmol, 380 µL, 2.10 eq), t-BuONa (293 mg, 3.05 mmol, 2.0 eq) in toluene (10.0 mL) was degassed and purged with N$_2$ for 3 times, and then the mixture was stirred at 0° C. for 30 min under N$_2$ atmosphere. The reaction was quenched with water (20.0 mL). The crude mixture was extracted with ethyl acetate (3×30.0 mL). Combine extracts were washed with brine (80.0 mL), dried with Na$_2$SO$_4$ the solvent was then removed under vacuum. The residue was purified by column chromatography (SiO$_2$, Petroleum ether: Ethyl acetate=5:1 to Dichloromethane:Methanol=10:1). Title compound tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (740 mg, 1.22 mmol, 80% yield, 95% purity) was obtained as a yellow solid. LCMS [ESI, M+1]: 576.

$^1$H NMR (400 MHz, Chloroform-d) δ 7.10 (t, J=15.2 Hz, 1H), 6.95 (d, J=8.0 Hz, 2H), 4.61 (br s, 1H), 4.39 (dd, J=4.8 Hz, J=9.6 Hz, 1H), 4.13-4.00 (m, 4H), 3.89 (br d, J=12.4 Hz 1H), 3.27-3.13 (m, 3H), 3.13-2.95 (m, 3H), 2.87-2.65 (m, 5H), 2.49 (s, 3H), 2.30 (s, 3H), 2.27 (s, 3H), 2.09-2.06 (m, 1H), 2.06-2.04 (m, 1H), 1.93-1.62 (m, 4H), 1.51 (s, 9H).

Intermediate 74

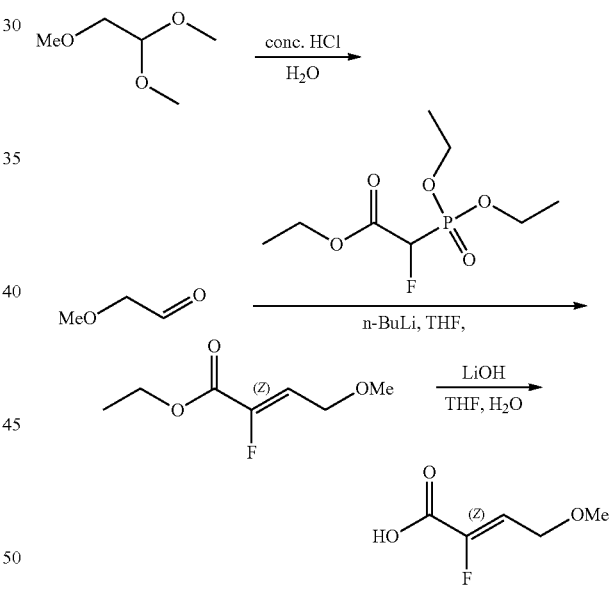

Step A

A mixture of 1,1,2-trimethoxyethane (30 g, 250 mmol, 32.2 mL, 1 eq) in HCl (12 M, 1 mL, 0.48 eq) and H$_2$O (100 mL) was stirred at 40° C. for 5 hours. After completion, the mixture was added NaCl (10 g), extracted with dichloromethane (2×50 mL). The mixture was distilled at 70° C. affording 2-methoxyacetaldehyde (6 g, 32%) as a colorless oil.

Step B

To a solution of ethyl 2-(diethoxyphosphoryl)-2-fluoroacetate (24.5 g, 101 mmol, 20.6 mL, 1.5 eq) in THF (50 mL)

was added n-BuLi (2.5 M, 32.4 mL, 1.2 eq) at −65° C. After stirring at −65° C. for 0.5 h, 2-methoxyacetaldehyde (5 g, 67.5 mmol, 1.09 mL, 1 eq) was added into the mixture. The mixture was stirred at −65° C. for 30 minutes, then the mixture was quenched with water (10 mL) at −78° C. The mixture was extracted with ethyl acetate (2×20 mL), the combined organic layers were washed brine (20 mL), dried over $Na_2SO_4$, filtered, and concentrated in vacuo. The residue was purified by column chromatography (3/1, petroleum ether/ethyl acetate) affording ethyl (Z)-2-fluoro-4-methoxybut-2-enoate (6 g, 55%) as a colorless oil. $R_f$=0.82 (3/1, petroleum ether/ethyl acetate).

$^1$H NMR (400 MHz, $CDCl_3$) δ=6.28-5.97 (m, 1H), 4.41 (dd, J=3.2, 6.0 Hz, 2H), 4.34-4.28 (m, 2H), 3.36 (s, 3H), 1.35 (t, J=7.2 Hz, 3H).

Step C

A mixture of ethyl (Z)-2-fluoro-4-methoxybut-2-enoate (1 g, 6.17 mmol, 1 eq) and LiOH (591 mg, 24.7 mmol, 4 eq) in THF (4 mL) and $H_2O$ (1 mL) was stirred at 15° C. for 3 hours. After completion, the pH was adjusted to 1 by addition of 1M HCl (in water). The mixture was extracted with ethyl acetate (2×10 mL), dried over $Na_2SO_4$, filtered, and concentrated in vacuo to provide (Z)-2-fluoro-4-methoxybut-2-enoic acid (600 mg, 73%) as a colorless oil.

$^1$H NMR (400 MHz, $CDCl_3$) δ=9.39 (br s, 1H), 6.16 (td, J=6.0, 19.2 Hz, 1H), 4.45 (dd, J=3.2, 6.0 Hz, 2H), 3.40 (s, 3H).

Intermediate 75

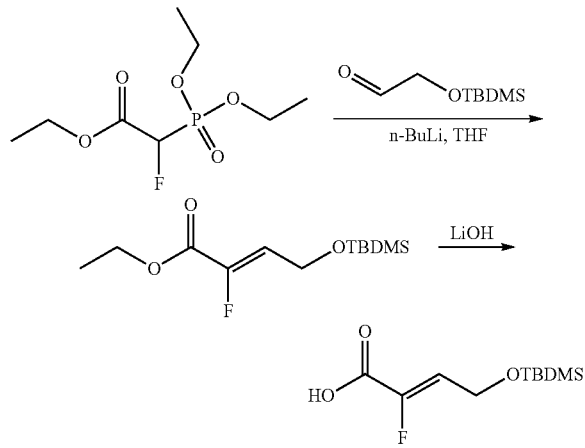

Step A

To a solution of ethyl 2-(diethoxyphosphoryl)-2-fluoroacetate (10.0 g, 41.3 mmol, 8.40 mL, 1.0 eq) in THF (60 mL) was added n-BuLi (2.5 M, 19.8 mL, 1.2 eq) dropwise under $N_2$ at −65° C., the mixture was stirred at −65° C. for 1 hour. Then to the mixture was added 2-[tert-butyl(dimethyl)silyl]oxyacetaldehyde (8.64 g, 49.5 mmol, 9.44 mL, 1.2 eq) at −65° C., the mixture was stirred at −65° C. for 1 hour. After completion, the reaction mixture was quenched by addition of saturated $NH_4Cl$ (aqueous solution, 2 mL) at −65° C., and then warmed to room temperature. The reaction mixture was concentrated under reduced pressure at 35° C. to remove THF, then diluted with water (20 mL) and extracted with ethyl acetate (3×20 mL). The combined organic layers were dried over anhydrous sodium sulfate and filtered. The filtrate was concentrated under reduced pressure and the resultant residue was purified by column chromatography ($SiO_2$, petroleum ether/ethyl acetate=1/0 to 10/1) to give ethyl (Z)-4-((tert-butyldimethylsilyl)oxy)-2-fluorobut-2-enoate (8.0 g, 74% yield) as a yellow oil. $R_f$=0.80 (petroleum ether/ethyl acetate=10/1).

$^1$H NMR (400 MHz, $CDCl_3$) δ 6.03 (td, J=5.6, 20.0 Hz, 1H), 4.75-4.57 (m, 2H), 4.31 (q, J=7.2 Hz, 2H), 1.36 (t, J=7.2 Hz, 3H), 0.91 (s, 9H), 0.15-0.05 (m, 6H).

Step B

To a solution of ethyl (Z)-4-((tert-butyldimethylsilyl)oxy)-2-fluorobut-2-enoate (500 mg, 1.91 mmol, 1.0 eq) in THF (3 mL) and $H_2O$ (3 mL) was added $LiOH \cdot H_2O$ (959 mg, 22.9 mmol, 12.0 eq) at 25° C., the mixture was stirred at 50° C. for 2 hours. After completion, the reaction mixture was concentrated under reduced pressure and the resultant residue was diluted with water (5 mL) and extracted with methyl tert-butyl ether (3×10 mL). The combined organic layers were dried over anhydrous sodium sulfate and filtered. The filtrate was concentrated under reduced pressure to provide ethyl (Z)-4-((tert-butyldimethylsilyl)oxy)-2-fluorobut-2-enoate (500 mg). as a yellow solid, which was used without further purification. $R_f$=0.10 (dichloromethane/methanol=10/1).

$^1$H NMR (400 MHz, $CDCl_3$) δ 5.78-5.62 (m, 1H), 4.63-4.50 (m, 2H), 0.89 (s, 9H), 0.07 (s, 6H); LCMS [M−1]: 233.2.

Intermediate 76

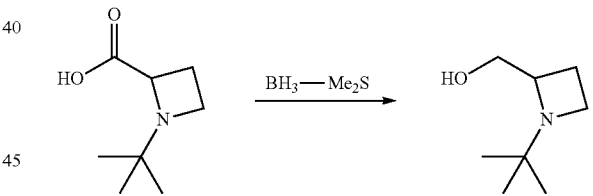

To a mixture of 1-tert-butylazetidine-2-carboxylic acid (2.50 g, 15.9 mmol, 1.0 eq) in THF (20.0 mL) was added $BH_3$-$Me_2S$ (9.54 mL, 6.00 eq) in portions at 0° C. under nitrogen. The mixture was stirred at 25° C. for 12 h. The reaction mixture was quenched by the addition methanol (25.0 mL) at 0° C. followed by adjusting the pH to 2 with aq HCl (2 M) and heating at 70° C. with stirring for 1 h. The pH of the mixture was adjusted to 12 with aq NaOH solution (40%), filtered and concentrated under reduced pressure to remove the majority of the methanol. The aqueous phase extracted with ethyl acetate (20.0 mL×3). The combined organic layer was dried over sodium sulfate, filtered and concentrated under reduced pressure to give a residue (1-tert-butylazetidin-2-yl)methanol (1.86 g, 13.0 mmol) as a colorless oil.

$^1$H NMR (400 MHz, $CDCl_3$): δ=3.66 (dt, J=3.6, 8.0 Hz, 1H), 3.48 (dd, J=3.6, 10.8 Hz, 1H), 3.29 (br d, J=10.8 Hz, 1H), 3.16 (dt, J=6.8, 8.4 Hz, 1H), 3.06-2.98 (m, 1H), 2.14-1.99 (m, 1H), 1.88-1.77 (m, 1H), 0.96 (s, 9H).

Intermediate 77

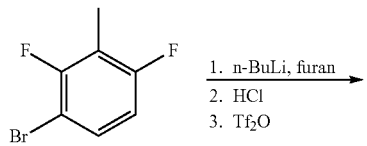

Step A

To a mixture of 1-bromo-2,4-difluoro-3-methyl-benzene (2.20 g, 10.6 mmol, 1.0 eq.) and furan (1.45 g, 21.2 mmol, 1.55 mL, 2.0 eq.) in toluene (30.0 mL) was added dropwise n-BuLi (2.5 M, 5.1 mL, 1.2 eq.) at −20° C. under nitrogen. The mixture was gradually warmed to room temperature over 14 h. The mixture was quenched with saturated aq NH$_4$Cl (200 mL) and then extracted with ethyl acetate (100 mL×3). The combined organic layer was concentrated at reduced pressure at 40° C. to dryness. The residue was purified by reversed-phase flash chromatography [water (0.1% formic acid)/acetonitrile] to afford 7-fluoro-5-methyl-11-oxatricycloundeca-1,3,5(7),6(8)-tetraene (448 mg, 2.54 mmol, 23.9% yield, 100% purity) as a yellow oil. LCMS [M+1]: 177.

$^1$H NMR (400 MHz, CDCl$_3$) δ=7.08-6.97 (m, 3H), 6.60 (dd, J=7.6, 10.4 Hz, 1H), 5.78 (s, 1H), 5.69 (d, J=0.8 Hz, 1H), 2.25 (d, J=1.6 Hz, 3H).

Step B

To a solution of 7-fluoro-5-methyl-11-oxatricycloundeca-1,3,5(7),6(8)-tetraene (550 mg, 3.12 mmol, 1.0 eq.) in ethanol (6.50 mL) was added conc. HCl (12.0 M, 3.50 mL, 13.4 eq.) at 25° C. The mixture was stirred at 78° C. for 1 h and subsequently the mixture was concentrated at reduced pressure at 45° C. The crude product was purified by reversed-phase flash chromatography [water (0.1% formic acid)/acetonitrile] to afford 7-fluoro-8-methyl-naphthalen-1-ol (500 mg, 2.84 mmol, 90.9% yield) as a brown solid.

$^1$H NMR (400 MHz, CDCl$_3$) δ=7.65 (dd, J=5.6, 8.8 Hz, 1H), 7.44 (d, J=8.0 Hz, 1H), 7.30-7.21 (m, 2H), 6.80 (d, J=7.6 Hz, 1H), 5.26 (s, 1H), 2.90 (d, J=2.8 Hz, 3H).

Step C

A mixture of 7-fluoro-8-methyl-naphthalen-1-ol (500 mg, 2.8 mmol, 1.0 eq.), DIEA (1.1 g, 8.5 mmol, 1.48 mL, 3.0 eq.) and 4 Å molecular sieves (100 mg) in dichloromethane (10.0 mL) was stirred at −40° C. under an atmosphere of nitrogen for 20 min. To this solution was added dropwise Tf$_2$O (801 mg, 2.84 mmol, 468 μL, 1.0 eq.) at −40° C. and the mixture was stirred at this temperature for 40 min. The mixture was concentrated under reduced pressure at 40° C. and the resultant residue was purified by column chromatography (SiO$_2$, petroleum ether/ethyl acetate=1:0 to 100:1) to give (7-fluoro-8-methyl-1-naphthyl)trifluoromethanesulfonate (900 mg, crude) as a white solid.

$^1$H NMR (400 MHz, CDCl$_3$) δ=7.84 (dd, J=0.8, 8.0 Hz, 1H), 7.75 (dd, J=5.6, 9.2 Hz, 1H), 7.53 (d, J=7.6 Hz, 1H), 7.47-7.40 (m, 1H), 7.34 (t, J=9.2 Hz, 1H), 2.78 (d, J=2.8 Hz, 3H).

Intermediate 78

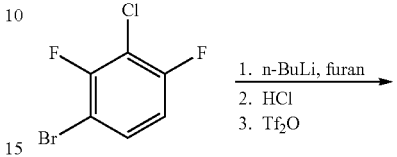

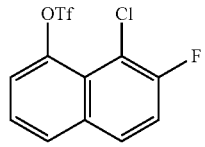

Step A

To a solution 1-bromo-3-chloro-2,4-difluoro-benzene (20 g, 87.9 mmol, 1 eq.) and furan (12.0 g, 176 mmol, 12.8 mL, 2 eq.) in toluene (400 mL) was added n-BuLi (2.5 M, 42.2 mL, 1.2 eq.) in hexane dropwise over 0.5 hour at −15° C. The reaction mixture gradually warmed to room temperature over 12 h. The reaction mixture was quenched by water (100 mL) and filtered. The aqueous layer was separated and extracted with ethyl acetate (3×100 mL). The combined organic layers were dried over Na$_2$SO$_4$, filtered and concentrated at reduced pressure. The residue was purified by reversed-phase flash [water (0.1% formic acid)/acetonitrile] to afford 7-chloro-5-fluoro-10-oxatricycloundeca-,2,4(6),5(7)-tetraene (7 g, 34.2 mmol, 39% yield, 96% purity) was obtained as a yellow oil.

$^1$H NMR (400 MHz, CDCl$_3$) δ=7.11-7.07 (m, 2H), 7.05 (dd, J=4.0, 8.0 Hz, 1H), 6.74 (dd, J=7.8, 9.2 Hz, 1H), 5.89 (s, 1H), 5.75 (s, 1H).

Step B

A reaction mixture of 7-chloro-5-fluoro-10-oxatricycloundeca-,2,4(6),5(7)-tetraene (7 g, 35.6 mmol, 1.0 eq.) in concentrated HCl (51.0 g, 503 mmol, 50 mL, 36% purity, 14.1 eq) and EtOH (80 mL) was heated to 78° C. for 2 h. Subsequently, the reaction mixture was concentrated under reduced pressure to provide the crude residue. The residue was purified by silica gel chromatography (petroleum ether: ethyl acetate=1:0 to 50:1) to give 7 g of the crude product. The product was triturated with petroleum ether (20 mL) and filtered. The filter cake was dried under vacuum to afford 8-chloro-7-fluoro-naphthalen-1-ol (5.3 g, 26.6 mmol, 75% yield, 98.8% purity) was obtained as a white solid.

$^1$H NMR (400 MHz, CDCl$_3$) δ=7.81 (s, 1H), 7.65 (dd, J=5.6, 9.2 Hz, 1H), 7.34-7.27 (m, 2H), 7.23-7.17 (m, 1H), 7.03-6.97 (m, 1H).

Step C

A reaction mixture of 8-chloro-7-fluoro-naphthalen-1-ol (1 g, 5.09 mmol, 1 eq.) and DIEA (3.29 g, 25.4 mmol, 4.43 mL, 5.0 eq.), 4 Å molecular sieves (1 g) in DCM (20 mL) was stirred for 10 min at 20° C. To this mixture was added Tf$_2$O (1.87 g, 6.61 mmol, 1.09 mL, 1.3 eq.) at −40° C. The reaction mixture was allowed to stir at this temperature for 10 min. The reaction was subsequently quenched with water (1 mL) and the layers were separated. The aqueous layer was extracted with ethyl acetate (2×3 mL). The combined organic layers were dried over Na₂SO₄ and concentrated under vacuum. The residue was purified by silica gel chromatography (petroleum ether:ethyl acetate=1:0 to 100:1) to afford (8-chloro-7-fluoro-1-naphthyl) trifluoromethanesulfonate (1.3 g, 3.96 mmol, 78% yield) was obtained as a colorless oil.

Intermediate 79

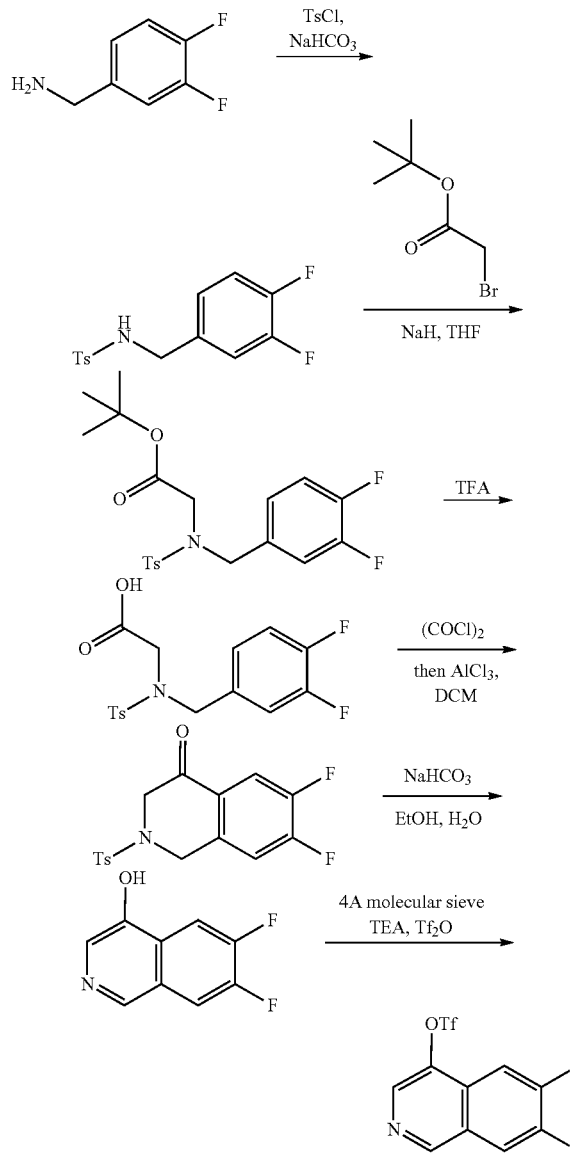

Step A

To a solution of (3,4-difluorophenyl)methanamine (5 g, 34.9 mmol, 4.13 mL, 1 eq) and NaHCO₃ (5.87 g, 69.9 mmol, 2.72 mL, 2 eq) in ethyl acetate (100 mL) was added 4-toluenesulfonyl chloride (7.99 g, 42.0 mmol, 1.2 eq) at 5-10° C., The reaction mixture was stirred at this temperature for 1 hour, then at 20-25° C. for 16 hours. The mixture was washed with water (100 mL). The aqueous phase was extracted with ethyl acetate (50 mL), the combined organic phase was dried over Na₂SO₄ and concentrated to dryness. The residue was purified by column chromatography (SiO₂, Petroleum ether/ethyl acetate=30/1 to 3/1) to give N-(3,4-difluorobenzyl)-4-methylbenzenesulfonamide (7.1 g, 23.9 mmol, 68% yield, 100% purity) as a yellow solid. LCMS [M+1]: 298.

Step B

To a solution of N-(3,4-difluorobenzyl)-4-methylbenzenesulfonamide (7.1 g, 23.9 mmol, 1 eq) in THF (106 mL) was added NaH (1.24 g, 31.0 mmol, 60% purity, 1.3 eq) at −5° C., after 30 min, tert-butyl 2-bromoacetate (6.99 g, 35.82 mmol, 5.29 mL, 1.5 eq) was added at −5° C. The reaction mixture was stirred at −5° C. for 2 hours. The mixture was quenched by saturated NH₄Cl aqueous (150 mL), then extracted with ethyl acetate (100 mL×2). The combined organic layers was dried over Na₂SO₄ and concentrated to dryness. The residue was purified by column chromatography (SiO₂, Petroleum ether/ethyl acetate=50/1 to 5/1) to give tert-butyl N-(3,4-difluorobenzyl)-N-tosylglycinate (9.09 g, 22.1 mmol, 93% yield, 100% purity) as an off-white solid. LCMS [M−55]: 356.
¹H NMR (400 MHz, CDCl₃) δ=7.75 (d, J=8.4 Hz, 2H), 7.32 (d, J=8.0 Hz, 2H), 7.16-7.06 (m, 2H), 7.00 (ddd, J=2.0, 4.0, 6.4 Hz, 1H), 4.45 (s, 2H), 3.81 (s, 2H), 2.44 (s, 3H), 1.34 (s, 9H).

Step C

A solution of tert-butyl N-(3,4-difluorobenzyl)-N-tosylglycinate (10.3 g, 25.0 mmol, 1 eq) in TFA (50 mL) was stirred at 25° C. for 1 hour. The mixture was concentrated in vacuo, and the crude product was triturated with MTBE (10 mL) at 25° C. for 20 min to give N-(3,4-difluorobenzyl)-N-tosylglycine (8.6 g, 24.1 mmol, 96% yield, 99.7% purity) as a yellow solid. LCMS [M+1]: 356.

Step D

A solution of N-(3,4-difluorobenzyl)-N-tosylglycine (4.5 g, 12.7 mmol, 1 eq) in (COCl)₂ (32.6 g, 257 mmol, 22.5 mL, 20.3 eq) was stirred at 55° C. for 2 hours. Then the mixture was monitored by TLC. After completion, the mixture was concentrated in vacuo and the residue was dissolved in DCM (45 mL). To the mixture was added AlCl₃ (8.44 g, 63.3 mmol, 3.46 mL, 5.0 eq) at 0° C. and stirred at 25° C. for 1.5 hours. The reaction mixture was quenched by addition HCl (1 M, 25 mL) at 0° C., then diluted with water (150 mL) and extracted with ethyl acetate (2×200 mL). The combined organic layers were dried over sodium sulfate, filtered, and concentrated under reduced pressure to give a residue. The residue was purified by column chromatography (SiO₂, petroleum ether/ethyl acetate=50/1 to 2:1) to give 6,7-difluoro-2-tosyl-2,3-dihydroisoquinolin-4(1H)-one (3.2 g, 8.42 mmol, 67% yield, 88.8% purity) as a white solid. LCMS [M+1]: 338.
¹H NMR (400 MHz, CDCl₃) δ=7.67 (dd, J=8.0, 10.0 Hz, 1H), 7.62 (d, J=8.4 Hz, 2H), 7.27 (s, 2H), 7.08 (dd, J=7.2, 9.6 Hz, 1H), 4.49 (s, 2H), 4.02 (s, 2H), 2.40 (s, 3H).

Step E

To a solution of 6,7-difluoro-2-tosyl-2,3-dihydroisoquinolin-4(1H)-one (5.08 g, 15.1 mmol, 1 eq) in EtOH (450 mL) was added a solution of NaHCO₃ (21.0 g, 250 mmol, 9.72 mL, 16.6 eq) in H₂O (250 mL), and the mixture was stirred at 100° C. for 16 hours. The mixture was then concentrated in vacuo and to the resultant residue was added water (150 mL). The aqueous layer was extracted with ethyl acetate (500 mL), and the organic layers were dried over Na₂SO₄, filtered, and concentrated in vacuo pressure to give 6,7-difluoroisoquinolin-4-ol (3.11 g) as a yellow solid. The crude product was used without further purification. LCMS [M+1]: 182. ¹H NMR (400 MHz, CD₃OD) δ=8.68 (s, 1H), 8.00-7.87 (m, 3H). Step F: To a mixture of 6,7-difluoroisoquinolin-4-ol (1.50 g, 8.28 mmol, 1 eq), Et₃N (5.03 g, 49.7 mmol, 6.92 mL, 6 eq) and 4 Å molecular sieves (1.5 g) in DCM (75 mL) was stirred at 25° C. for 10 min. The mixture was then cooled to −40° C. and was dropwise added a solution of trifluoromethanesulfonic anhydride (3.50 g, 12.4 mmol, 2.05 mL, 1.5 eq) in DCM (10 mL). The mixture was stirred at −40° C. for 0.5 hour. The reaction mixture was quenched with water (50 mL) and the organic layer was separated, then washed with brine (90 mL), dried over sodium sulfate, filtered, and concentrated under reduced pressure to give a residue. The residue was purified by column chromatography (SiO₂, petroleum ether/ethyl acetate=50/1 to 10/1) to give 6,7-difluoroisoquinolin-4-yl trifluoromethanesulfonate (668 mg, 1.94 mmol, 23% yield, 90.8% purity) as a yellow solid. LCMS [M+1]: 314.

Intermediate 80

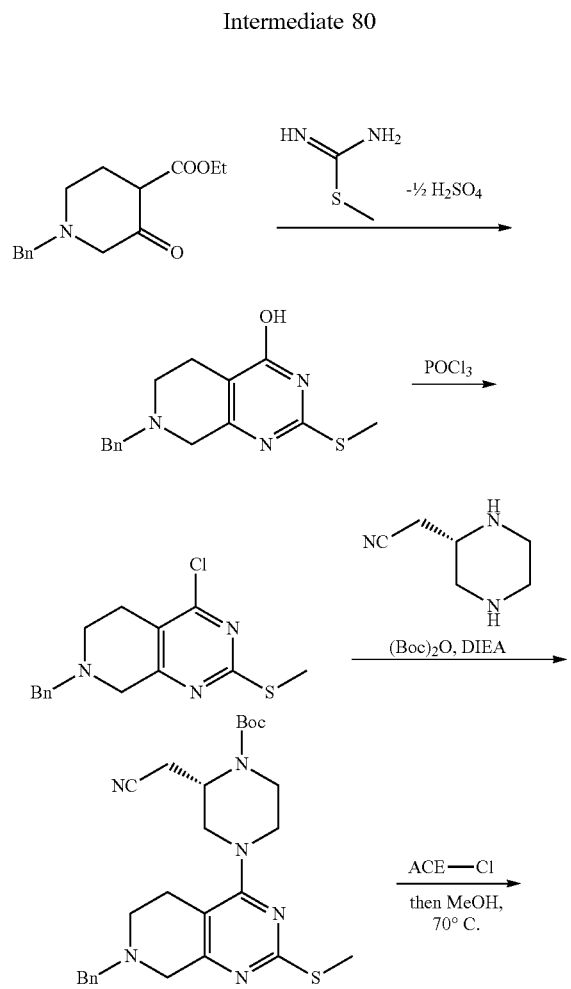

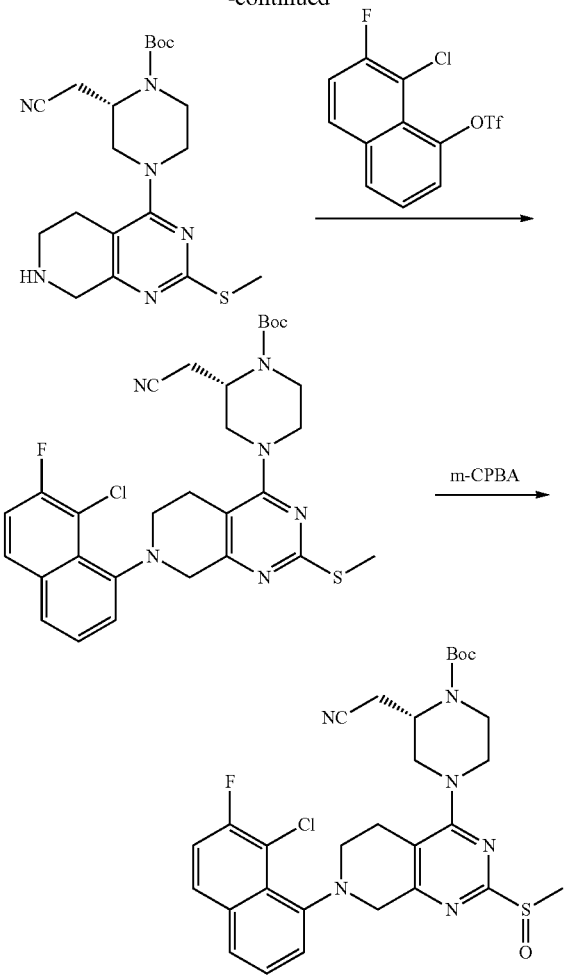

Step A

To a mixture of ethyl 1-benzyl-3-oxo-piperidine-4-carboxylate (50 g, 168 mmol, 1.0 eq, HCl) and NaOMe (36.3 g, 672 mmol, 4.0 eq) in MeOH (1000 mL) was added 2-methylisothiourea hemisulfate salt (35.1 g, 252 mmol, 1.5 eq) and stirred at 20° C. for 12 hours. Upon completion, the mixture was acidified by aq HCl (1 M, 200 mL) to pH=6. The mixture was filtered and the filter cake was washed with water (2×50 mL) and dried in vacuo to provide 7-benzyl-2-(methylthio)-5,6,7,8-tetrahydropyrido[3,4-d]pyrimidin-4-ol (40 g, 111 mmol, 66% yield, 80% purity) as a white solid.

Step B

To a solution of 7-benzyl-2-(methylthio)-5,6,7,8-tetrahydropyrido[3,4-d]pyrimidin-4-ol (40 g, 139 mmol, 1.0 eq) in CHCl₃ (500 mL) was added POCl₃ (128 g, 835 mmol, 77.6 mL, 6.0 eq). The reaction mixture was stirred at 80° C. for 12 hours. Upon completion, the reaction mixture was concentrated in vacuo. The residue was dissolved in ethyl acetate (500 mL) and poured into saturated aqueous NaHCO₃ (1 L). The resulting mixture was separated, and the aqueous layer was extracted with ethyl acetate (2×500 mL). The combined organic layers were washed with brine (300 mL), dried over anhydrous sodium sulfate, filtered, and concentrated in vacuo to provide the crude material. The crude product was purified by silica gel chromatography (5:1, petroleum ether/ethyl acetate) affording 7-benzyl-4-chloro-2-(methylthio)-5,6,7,8-tetrahydropyrido[3,4-d]pyrimidine (28 g, 90.6 mmol, 65% yield, 99% purity) as a yellow solid. LCMS [M+1]: 306.

$^1$H NMR (400 MHz, CDCl$_3$) δ 7.38-7.27 (m, 5H), 3.71 (s, 2H), 3.60 (s, 2H), 2.80 (s, 4H), 2.53 (s, 3H).

Step C

To a solution of 7-benzyl-4-chloro-2-(methylthio)-5,6,7,8-tetrahydropyrido[3,4-d]pyrimidine (23 g, 75.2 mmol, 1.0 eq) and DIEA (29.2 g, 226 mmol, 39.3 mL, 3.0 eq) in DMAc (230 mL) was added (S)-2-(piperazin-2-yl)acetonitrile (11.3 g, 90.3 mmol, 1.2 eq). The reaction mixture was stirred at 80° C. for 3 hrs. After this time, was added (Boc)$_2$O (49.2 g, 226 mmol, 51.8 mL, 3.0 eq) and the mixture was stirred at 80° C. for 1 h. The reaction mixture was then poured into ice water (800 mL) and extracted with ethyl acetate (3×300 mL). The combined organic layers were dried over anhydrous sodium sulfate, filtered, and concentrated in vacuo to provide the crude material, which was purified by silica gel chromatography (3:1, petroleum ether:ethyl acetate) to give tert-butyl (S)-4-(7-benzyl-2-(methylthio)-5,6,7,8-tetrahydropyrido[3,4-d]pyrimidin-4-yl)-2-(cyanomethyl)piperazine-1-carboxylate (32.8 g, 65.7 mmol, 87% yield, 99% purity) as a yellow oil. LCMS [M+1]: 495.

Step D

To a solution of (S)-4-(7-benzyl-2-(methylthio)-5,6,7,8-tetrahydropyrido[3,4-d]pyrimidin-4-yl)-2-(cyanomethyl) piperazine-1-carboxylate (35 g, 70.8 mmol, 1.0 eq) and DIEA (27.4 g, 212 mmol, 37.0 mL, 3.0 eq) in DCE (700 mL) was added 1-chloroethyl carbonochloridate (25.3 g, 177 mmol, 2.5 eq) at 0° C. After stirring at 0-10° C. for 1 hour, the mixture was concentrated in vacuo. The residue was dissolve in MeOH (700 mL) and stirred at 70° C. for 1 hour. Upon completion, the reaction mixture was concentrated in vacuo to remove most of the MeOH. The residual MeOH layer was washed with petroleum ether (5×30 mL). The layer was concentrated in vacuo and diluted with ethyl acetate (50 mL) and water (20 mL). The mixture was basified by NaHCO$_3$ (saturated aqueous solution) to pH>7 and extracted with ethyl acetate (2×100 mL). The combined organic layers were dried over anhydrous sodium sulfate and concentrated under vacuum to provide crude material. The crude material was purified by column chromatography (SiO$_2$, 5:1, ethyl acetate/MeOH) to provide tert-butyl (S)-2-(cyanomethyl)-4-(2-(methylthio)-5,6,7,8-tetrahydropyrido[3,4-d]pyrimidin-4-yl)piperazine-1-carboxylate (24 g, 57.0 mmol, 80% yield, 96% purity) as a brown solid. LCMS [M+1]: 405.

$^1$H NMR (400 MHz, CDCl$_3$) δ 4.52 (br s, 1H), 4.32-4.20 (m, 1H), 4.05-3.84 (m, 4H), 3.75 (br d, J=12.4 Hz, 1H), 3.30-3.01 (m, 4H), 2.99-2.88 (m, 1H), 2.86-2.57 (m, 4H), 2.43 (s, 3H), 1.43 (s, 9H).

Step E

To a reaction mixture of tert-butyl (S)-2-(cyanomethyl)-4-(2-(methylthio)-5,6,7,8-tetrahydropyrido[3,4-d]pyrimidin-4-yl)piperazine-1-carboxylate (2 g, 4.94 mmol, 1.0 eq), 4 Å MS (5 g, 4.94 mmol, 1.0 eq), and Cs$_2$CO$_3$ (4.03 g, 12.4 mmol, 2.5 eq) in toluene (40 mL) was added 8-chloro-7-fluoronaphthalen-1-yl trifluoromethanesulfonate (2.44 g, 7.42 mmol, 1.5 eq), XantPhos Pd G3 (469 mg, 494 μmol, 0.1 eq) and Xantphos (572 mg, 989 μmol, 0.2 eq). The reaction mixture was stirred at 110° C. for 24 h under a nitrogen atmosphere. Upon completion, the reaction mixture was filtered and the filtered cake was washed with ethyl acetate (2×20 mL). The filtrate was concentrated in vacuo to provide crude material, which was purified by silica gel chromatography (4:1, petroleum/ethyl acetate), followed by reversed-phase column chromatography [water (0.1% formic acid)/acetonitrile] to yield tert-butyl (S)-4-(7-(8-chloro-7-fluoronaphthalen-1-yl)-2-(methylthio)-5,6,7,8-tetrahydropyrido[3,4-d]pyrimidin-4-yl)-2-(cyanomethyl) piperazine-1-carboxylate (1.8 g, 3.07 mmol, 62% yield, 99.6% purity) as a yellow solid. LCMS [M+1]: 583.

$^1$H NMR (400 MHz, CDCl$_3$) δ 7.77-7.73 (m, 1H), 7.65-7.56 (m, 1H), 7.46-7.38 (m, 1H), 7.35-7.27 (m, 2H), 4.63 (br s, 1H), 4.41 (dd, J=14.0, 17.6 Hz, 1H), 4.10-3.79 (m, 4H), 3.61-3.52 (m, 1H), 3.41-2.54 (m, 8H), 2.52 (d, J=2.0 Hz, 3H), 1.52 (s, 9H).

Step F

To a solution of tert-butyl (S)-4-(7-(8-chloro-7-fluoronaphthalen-1-yl)-2-(methylthio)-5,6,7,8-tetrahydropyrido[3,4-d]pyrimidin-4-yl)-2-(cyanomethyl)piperazine-1-carboxylate (3.6 g, 6.17 mmol, 1.0 eq) in DCM (80 mL) was added m-CPBA (1.73 g, 8.03 mmol, 80% purity, 1.3 eq) at 0° C. The reaction mixture was stirred at 0° C. for 30 min. Upon completion, the reaction mixture was washed with NaHCO$_3$ (saturated aqueous solution, 3×50 mL), dried over anhydrous sodium sulfate, filtered, and concentrated under vacuum to provide tert-butyl (2S)-4-(7-(8-chloro-7-fluoronaphthalen-1-yl)-2-(methylsulfinyl)-5,6,7,8-tetrahydropyrido[3,4-d]pyrimidin-4-yl)-2-(cyanomethyl)piperazine-1-carboxylate (3.7 g, 5.56 mmol, 90% yield, 90% purity) as a brown solid. LCMS [M+1]: 599.

Intermediate 81

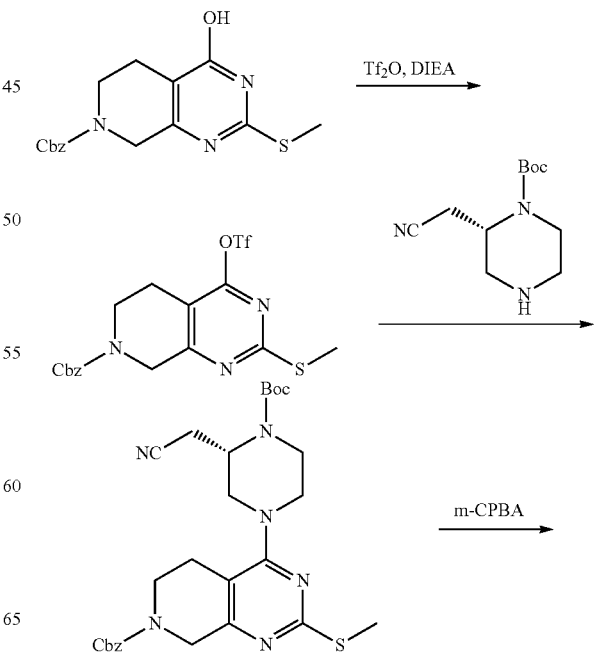

-continued

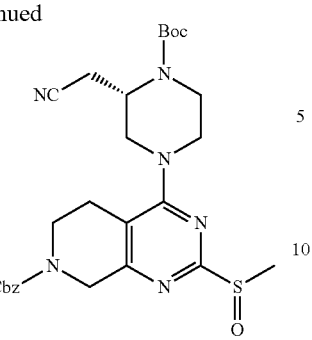

Step A

To a mixture of benzyl 4-hydroxy-2-methylsulfanyl-6,8-dihydro-5H-pyrido[3,4-d]pyrimidine-7-carboxylate (3.00 g, 9.05 mmol, 1.0 eq) in dichloromethane (45 mL) was added DIEA (4.68 g, 36.2 mmol, 6.31 mL, 4.0 eq) and Tf$_2$O (5.11 g, 18.1 mmol, 2.99 mL, 2.0 eq) at −40° C. The mixture was stirred at −40° C. for 1 hour. After completion, the mixture was diluted with water (40 mL) and extracted with dichloromethane (2×30 mL). The combined organic layers were washed with saturated brine (30 mL), dried over Na$_2$SO$_4$, filtered and concentrated under vacuum. The residue was purified by column chromatography (SiO$_2$, petroleum ether/ethyl acetate=10/1) to give benzyl 2-(methylthio)-4-(((trifluoromethyl)sulfonyl)oxy)-5,8-dihydropyrido[3,4-d]pyrimidine-7(6H)-carboxylate (3.84 g, 7.36 mmol, 81% yield, 88.8% purity) as a brown oil. LCMS [M+1]: 464.

Step B

To a mixture of benzyl 2-(methylthio)-4-(((trifluoromethyl)sulfonyl)oxy)-5,8-dihydropyrido[3,4-d]pyrimidine-7(6H)-carboxylate (3.84 g, 8.29 mmol, 1.0 eq) in DMAc (60 mL) was added DIEA (2.14 g, 16.6 mmol, 2.89 mL, 2.0 eq) and tert-butyl (S)-2-(cyanomethyl)piperazine-1-carboxylate (1.68 g, 7.46 mmol, 0.9 eq). The mixture was stirred at 15° C. for 30 minutes. After this time, the mixture was diluted with ethyl acetate (70 mL), washed with water (300 mL) and separated. The aqueous phase was extracted with ethyl acetate (1×70 mL) and the organic layer was washed with saturated brine (2×50 mL), dried over Na$_2$SO$_4$, filtered, and concentrated in vacuo. The residue was purified by column chromatography (SiO$_2$, petroleum ether/ethyl acetate=3/1) to give benzyl (S)-4-(4-(tert-butoxycarbonyl)-3-(cyanomethyl)piperazin-1-yl)-2-(methylthio)-5,8-dihydropyrido[3,4-d]pyrimidine-7(6H)-carboxylate (3.93 g, 6.86 mmol, 83% yield, 94.0% purity) as a yellow oil. LCMS [M+1]: 539.

$^1$H NMR (400 MHz, CDCl$_3$) δ=7.41-7.31 (m, 5H), 5.19 (s, 2H), 4.74-4.56 (m, 2H), 4.46 (d, J=18.8 Hz, 1H), 4.08-3.90 (m, 3H), 3.84-3.71 (m, 1H), 3.52-3.11 (m, 3H), 3.05-2.91 (m, 2H), 2.81-2.59 (m, 4H), 2.50 (s, 3H), 1.51 (s, 9H).

Step C

To a mixture of benzyl (S)-4-(4-(tert-butoxycarbonyl)-3-(cyanomethyl)piperazin-1-yl)-2-(methylthio)-5,8-dihydropyrido[3,4-d]pyrimidine-7(6H)-carboxylate (3.90 g, 7.24 mmol, 1.0 eq) in dichloromethane (40 mL) was added m-CPBA (1.56 g, 7.24 mmol, 80% purity, 1.0 eq) at 0° C. The mixture was stirred at 0° C. for 1 hour. The mixture was then washed with saturated Na$_2$CO$_3$ (in water, 2×40 mL) and brine (1×30 mL), then dried over Na$_2$SO$_4$, filtered, and concentrated in vacuo to give benzyl 4-((S)-4-(tert-butoxycarbonyl)-3-(cyanomethyl)piperazin-1-yl)-2-(methylsulfinyl)-5,8-dihydropyrido[3,4-d]pyrimidine-7(6H)-carboxylate (3.58 g) as a white solid which was used without further purification. LCMS [M+1]: 555.

The following Examples are intended to illustrate further certain embodiments of the invention and are not intended to limit the scope of the invention.

Example 1

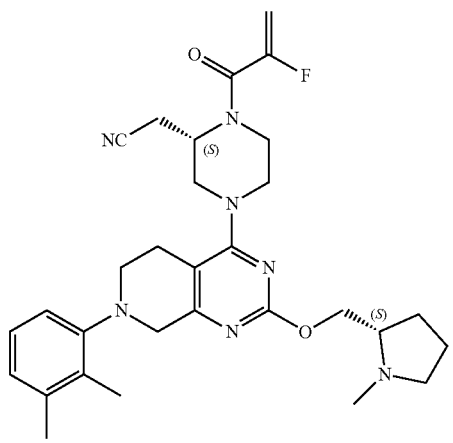

2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

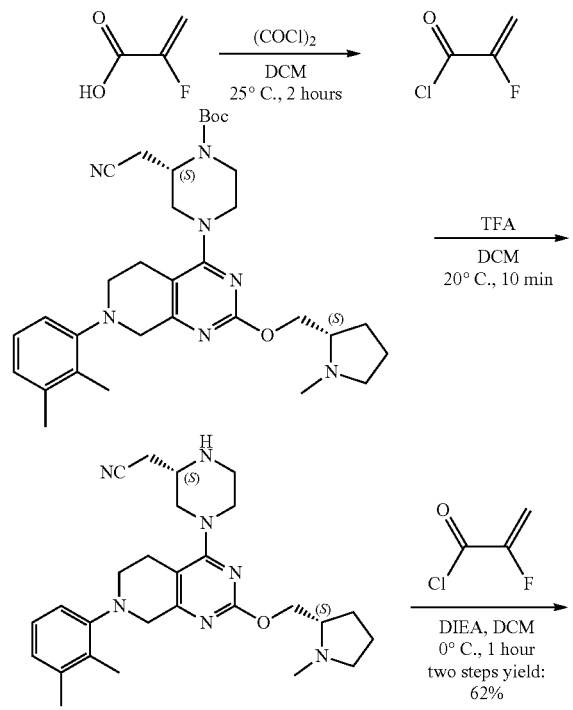

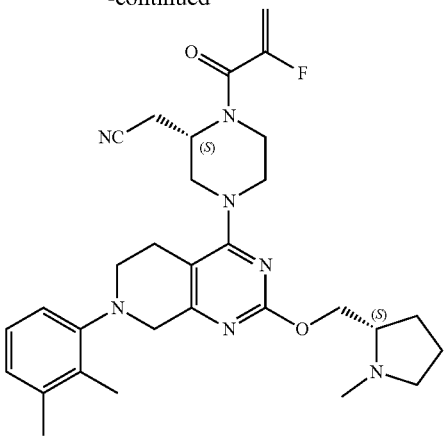

2-chloroprop-2-enoyl chloride

To a solution of 2-fluoroprop-2-enoic acid (400 mg, 4.44 mmol, 1.0 eq) in DCM (1.50 mL) was added (COCl)$_2$ (846 mg, 6.66 mmol, 583 µL, 1.50 eq) and DMF (32.5 mg, 444 umol, 34.2 µL, 0.10 eq). The mixture was stirred at 25° C. for 2 hours. 2-chloroprop-2-enoyl chloride (400 mg, crude) was used for the next step directly.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (200 mg, 347 umol, 1.0 eq) in DCM (2.0 mL) was added TFA (3.08 g, 27.0 mmol, 2.0 mL, 77.8 eq). The mixture was stirred at 20° C. for 10 min. The reaction mixture was concentrated under reduced pressure to give a residue. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude, TFA) was obtained as a yellow solid and used into the next step without further purification.

Step B: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 339 umol, 1.0 eq, TFA) in DCM (2.0 mL) was added DIEA (1.11 g, 8.61 mmol, 1.50 mL, 25.4 eq) and 2-fluoroprop-2-enoyl chloride (200 mg, 1.84 mmol, 5.43 eq) in DCM (2.0 mL). The mixture was stirred at 0° C. for 1 hour. The reaction mixture was concentrated under reduced pressure to give a residue. The residue was purified by prep-HPLC (column: Phenomenex Gemini 150*25 mm*10 um; mobile phase: [water (0.05% ammonia hydroxide v/v)-ACN]; B %: 55%-83%, 12 min). Title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 1, 120 mg, 217 umol, two steps 62% yield, 98.9% purity) was obtained as a yellow solid. LCMS [ESI, M+1]: 548.

$^1$H NMR (400 MHz, CHLOROFORM-d) δ=7.11 (t, J=7.8 Hz, 1H), 7.01-6.91 (m, 2H), 5.52-5.32 (m, 1H), 5.26 (dd, J=3.2, 16.8 Hz, 1H), 5.08-4.70 (br s, 1H), 4.39 (dd, J=5.2, 10.4 Hz, 1H), 4.25-4.02 (m, 5H), 3.97 (d, J=12.8 Hz, 1H), 3.43-3.73 (br s, 1H) 3.32 (d, J=13.2 Hz, 1H), 3.25-3.16 (m, 1H), 3.15-3.02 (m, 3H), 3.01-2.91 (m, 1H), 2.90-2.80 (m, 2H) 2.79-2.60 (m, 2H), 2.49 (s, 3H), 2.31-2.28 (m, 7H), 2.13-1.97 (m, 1H), 1.90-1.70 (m, 3H).

Example 2

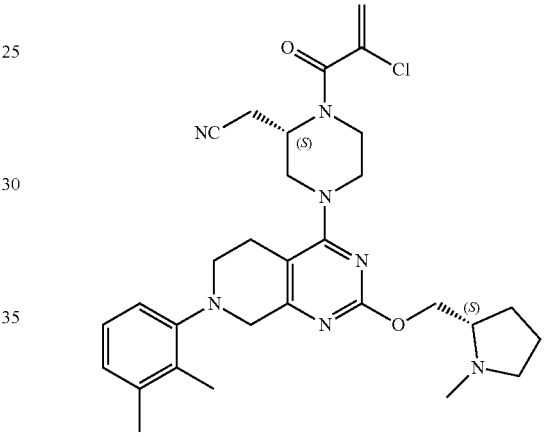

2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile

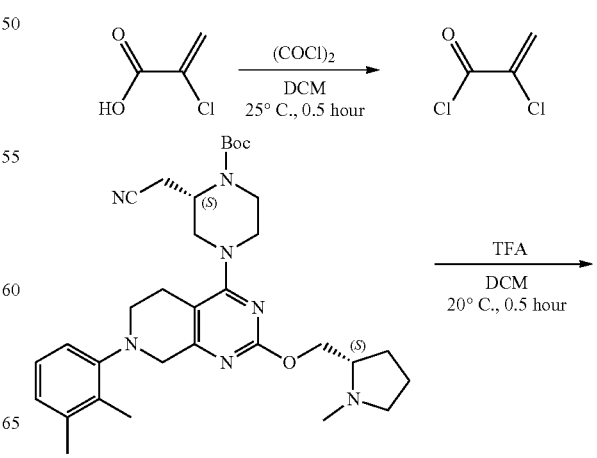

159

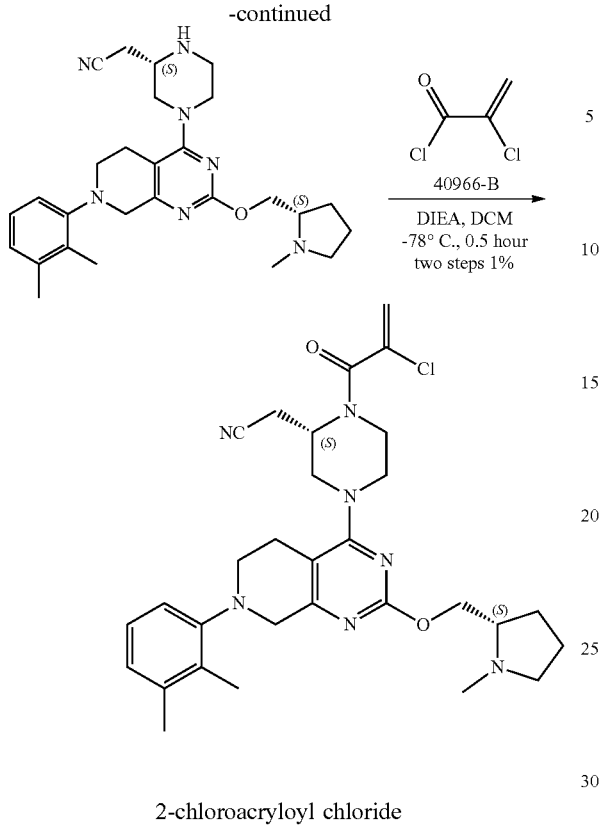

2-chloroacryloyl chloride

A solution of 2-chloroprop-2-enoic acid (400 mg, 3.76 mmol, 1.0 eq) and (COCl)$_2$ (715 mg, 5.63 mmol, 493 μL, 1.50 eq) in DCM (1.0 mL) was stirred at 25° C. for 0.5 hour. After completion, the reaction mixture was not work-up, and used for the next step directly.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (Intermediate 73, 400 mg, 695 umol, 1.0 eq) in DCM (0.50 mL) was added TFA (3.08 g, 27.0 mmol, 2.0 mL, 38.9 eq). The mixture was stirred at 20° C. for 0.5 hour. After completion, the mixture was concentrated and adjusts with saturated NaHCO$_3$ aqueous to pH-7, then extracted with DCM (5.0 mL×3). The organic layer was dried over Na$_2$SO$_4$, filtered and concentrated. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (400 mg, crude) was obtained as yellow oil and used to the next step without further purification.

Step B: 2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile

160

(300 mg, 631 umol, 1.0 eq) and DIEA (245 mg, 1.89 mmol, 330 μL, 3.0 eq) in DCM (1.0 mL) was added 2-chloroprop-2-enoyl chloride (236 mg, 1.89 mmol, 3.0 eq) at −78° C. The mixture was stirred at −78° C. for 0.5 hour. After completion, the mixture was added saturated NaHCO$_3$ aqueous (2.0 mL) and extracted with EA (10.0 mL×3). The obtained product was purified by prep-HPLC (column: Gemini 150*25 5 u; mobile phase: [water (0.05% ammonia hydroxide v/v)-ACN]; B %: 53%-83%,12 min) to give title compound 2-[(2S)-1-(2-chloroprop-2-enoyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 2, 4.72 mg, 8.35 umol, two steps 1% yield, 99.8% purity) as white solid. LCMS [ESI, M+1]: 564.

$^1$H NMR (400 MHz, Chloroform-d) δ 7.11 (t, J=7.8 Hz, 1H), 6.98-6.94 (m, 2H), 5.86-5.78 (m, 1H), 5.77-5.72 (m, 1H), 5.15-4.78 (m, 1H), 4.45-4.30 (m, 1H), 4.21-4.12 (m, 1H), 4.10-4.03 (m, 3H), 3.96 (br d, J=12.4 Hz, 2H), 3.30 (br dd, J=3.2, 13.6 Hz, 1H), 3.23-3.04 (m, 4H), 3.04-2.54 (m, 6H), 2.50 (br s, 3H), 2.34-2.23 (m, 7H), 2.12-2.02 (m, 1H), 1.91-1.66 (m, 3H).

Example 3

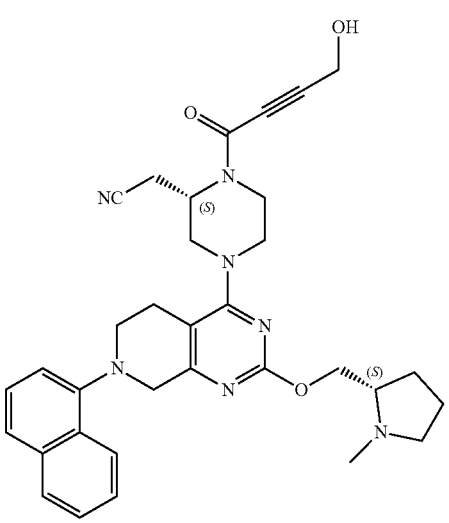

2-((S)-1-(4-hydroxybut-2-ynoyl)-4-(2-(((S)-1-methylpyrrolidin-2-yl)methoxy)-7-(naphthalen-1-yl)-5,6,7,8-tetrahydropyrido[3,4-d]pyrimidin-4-yl)piperazin-2-yl)acetonitrile

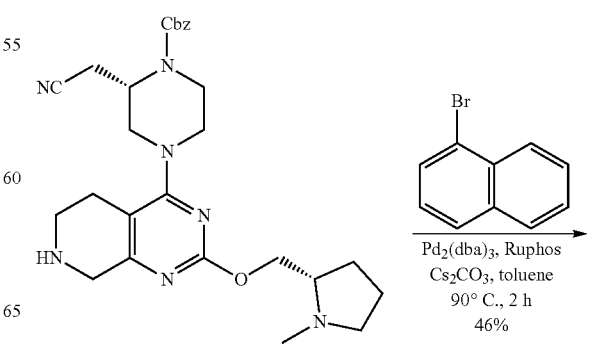

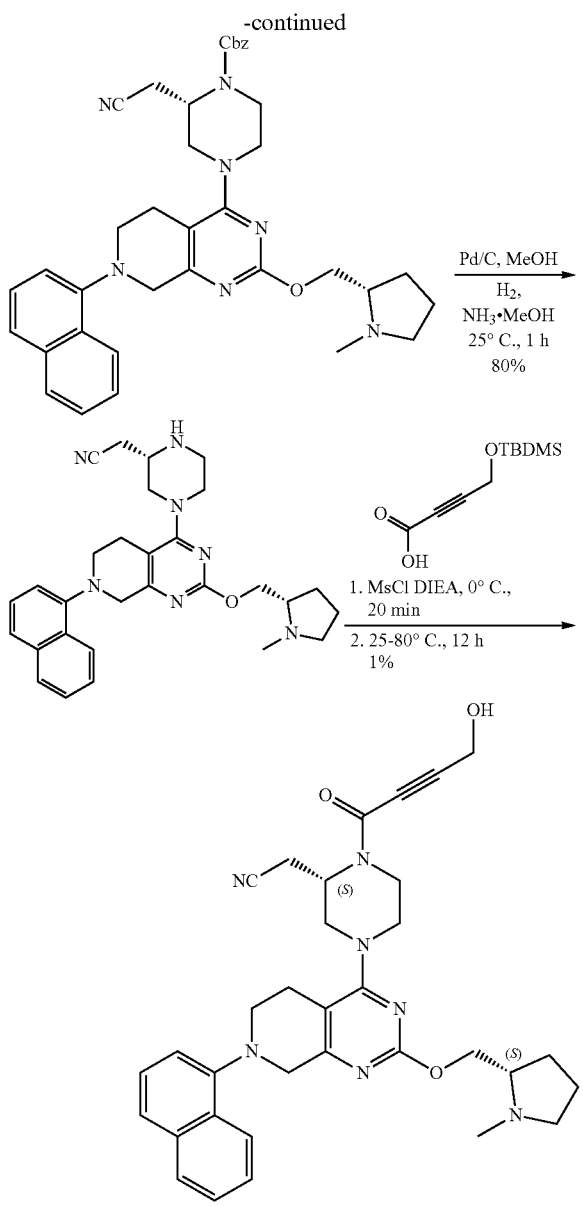

Step A: Benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate To a mixture of benzyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (Intermediate 65, 1 g, 1.58 mmol, 1 eq) and 1-bromonaphthalene (655 mg, 3.16 mmol, 440 µL, 2 eq) in toluene (20 mL) was added Pd₂(dba)₃ (145 mg, 158 umol, 0.1 eq), RuPhos (148 mg, 316 umol, 0.2 eq), Cs₂CO₃ (1.55 g, 4.75 mmol, 3 eq) in one portion. The mixture was degassed and purged with N₂ for 3 times, then heated to 90° C. and stirred for 2 hours. The reaction mixture was diluted with water (15 mL) and extracted with ethyl acetate (50 mL×3). The combined organic layers were washed with water (50 mL×1), dried over Na₂SO₄, filtered and concentrated under reduced pressure to give a residue. The residue was purified by reversed phase flash [water (0.1% TFA)/acetonitrile]. The desired fractions were collected and neutralized with saturated NaHCO₃ solution (6 mL) and extracted with ethyl acetate (100 mL×2). The separated organic layers were dried over sodium sulfate, filtered and concentrated under vacuum. Compound benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (515 mg, 726 umol, 45.9% yield, 89.1% purity) was obtained as a yellow solid. LCMS [ESI, M+1]: 632.

Step B

2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile. To a solution of benzyl (2S)-2-(cyanomethyl)-4-[2-[[(2S)-1-methylpyrrolidin-2-yl]methoxy]-7-(1-naphthyl)-6,8-dihydro-5H-pyrido[3,4-d]pyrimidin-4-yl]piperazine-1-carboxylate (1 g, 1.58 mmol, 1 eq) in MeOH (60 mL) was added Pd/C (500 mg, 10% purity) and NH₃-MeOH (20%, 50 mL) under N₂. The suspension was degassed under vacuum and purged with H₂ three times. The mixture was stirred under H₂ (15 psi) at 25° C. for 1 hour. The reaction mixture was concentrated under reduced pressure. Compound 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (680 mg, 1.26 mmol, 80% yield, 92.3% purity) was obtained as a yellow solid which was used directly into the next step without further purification. LCMS [ESI, M+1]: 498.

¹H NMR (400 MHz, chloroform-d) δ=8.26-8.19 (m, 1H), 7.89-7.83 (m, 1H), 7.60 (d, J=8.4 Hz, 1H), 7.53-7.47 (m, 2H), 7.43 (t, J=7.6 Hz, 1H), 7.16-7.12 (m, 1H), 4.41 (dd, J=5.2, 10.8 Hz, 1H), 4.26 (s, 2H), 4.16 (dd, J=7.2, 10.8 Hz, 1H), 4.01 (br d, J=12.4 Hz, 1H), 3.95-3.82 (m, 1H), 3.44-3.21 (m, 3H), 3.18-2.97 (m, 4H), 2.95-2.76 (m, 3H), 2.74-2.63 (m, 1H), 2.55 (dd, J=1.2, 5.6 Hz, 2H), 2.51-2.46 (m, 3H), 2.33-2.22 (m, 1H), 2.12-1.99 (m, 1H), 1.88-1.80 (m, 3H).

Step C: 2-[(2S)-1-(4-hydroxybut-2-ynoyl)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile To a solution of 4-[tert-butyl(dimethyl)silyl]oxybut-2-ynoic acid (172 mg, 803 umol, 2 eq) and DIEA (155 mg, 1.21 mmol, 210 µL, 3 eq) in MeCN (5 mL) was added MsCl (92.1 mg, 803 umol, 62.2 µL, 2 eq) at 0° C. After stirring at 0° C. for 20 minutes, to the mixture was added 2-[(2S)-4-[2-[[(2S)-1-methylpyrrolidin-2-yl]methoxy]-7-(1-naphthyl)-6,8-dihydro-5H-pyrido[3,4-d]pyrimidin-4-yl]piperazin-2-yl]acetonitrile (200 mg, 402 umol, 1 eq) and the mixture was stirred at 25° C. for 2 hours. Then the reaction mixture was heated to 80° C. and stirred for 10 hours. The reaction mixture was diluted with water (20 mL) and extracted with ethyl acetate (20 mL×3). The combined organic layers were washed with brine (20 mL), dried over Na₂SO₄, filtered and concentrated under reduced pressure to give a residue. The residue was purified by prep-HPLC (column: Boston Green ODS 150*30 5 u; mobile phase: [water (0.225% FA)-ACN]; B %: 25%-45%, 10 min) and further purified by prep-HPLC (column: Phenomenex Gemini 150*25 mm*10 um; mobile phase: [water (0.05% ammonia hydroxide v/v)—ACN]; B %: 45%-75%, 12 min). Title compound 2-[(2S)-1-(4-hydroxybut-2-ynoyl)-4-[2-[[(2S)-1-methylpyrrolidin-2-yl]methoxy]-7-(1-naphthyl)-6, 8-dihydro-5H-pyrido[3,4-d]pyrimidin-4-yl]piperazin-2-yl] acetonitrile (EXAMPLE 3, 1.43 mg, 2.39 umol, 1% yield, 96.7% purity) was obtained as a white solid. LCMS [ESI, M+1]: 580.

$^1$H NMR (400 MHz, chloroform-d) δ=8.22 (d, J=6.8 Hz, 1H), 7.90-7.82 (m, 1H), 7.61 (d, J=8.4 Hz, 1H), 7.55-7.47 (m, 2H), 7.44 (t, J=7.6 Hz, 1H), 7.15 (d, J=7.2 Hz, 1H), 5.26-4.89 (m, 1H), 4.60-4.34 (m, 4H), 4.33-4.16 (m, 3H), 4.14-3.96 (m, 1H), 3.95-3.80 (m, 1H), 3.78-3.50 (m, 2H), 3.50-3.28 (m, 2H), 3.27-3.07 (m, 3H), 3.06-2.82 (m, 3H), 2.80-2.64 (m, 2H), 2.51 (d, J=12.4 Hz, 3H), 2.38-2.24 (m, 1H), 2.14-2.00 (m, 1H), 1.97-1.85 (m, 2H).

Example 4

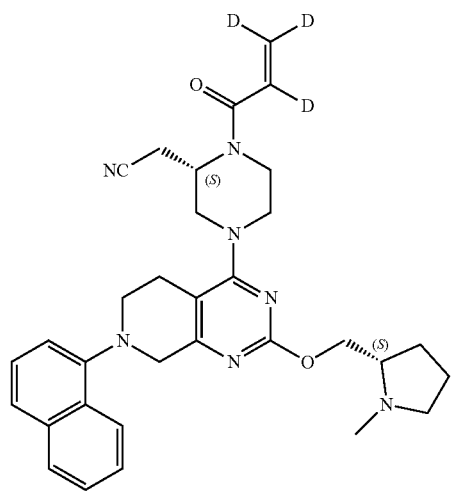

2-[(2S)-4-[2-[[(2S)-1-methylpyrrolidin-2-yl] methoxy]-7-(1-naphthyl)-6,8-dihydro-5H-pyrido[3, 4-d]pyrimidin-4-yl]-1-(2,3,3-trideuterioprop-2-enoyl)piperazin-2-yl]acetonitrile

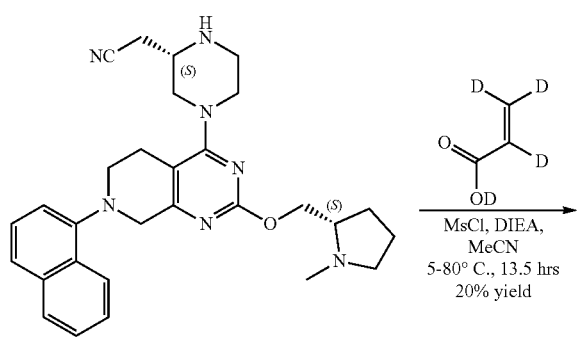

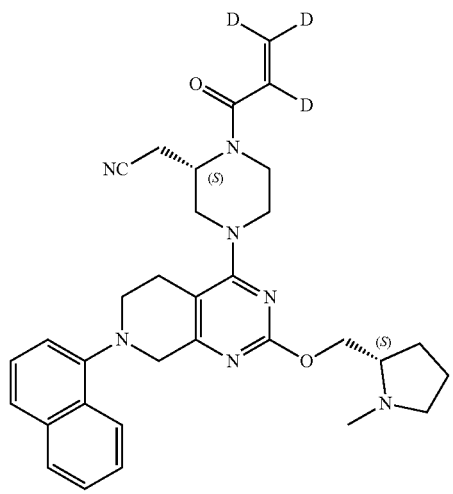

Step A: 2-[(2S)-4-[2-[[(2S)-1-methylpyrrolidin-2-yl] methoxy]-7-(1-naphthyl)-6,8-dihydro-5H-pyrido[3, 4-d]pyrimidin-4-yl]-1-(2,3,3-trideuterioprop-2-enoyl)piperazin-2-yl]acetonitrile To a solution of deuterio 2,3,3-trideuterioprop-2-enoate (68.8 mg, 904 umol, 3 eq) and DIEA (234 mg, 1.81 mmol, 315 μL, 6 eq) in MeCN (3 mL) was added MsCl (69.1 mg, 603 umol, 46.7 μL, 2 eq) at 5° C. for 0.5 hour. To the resulting reaction was added 2-[(2S)-4-[2-[[(2S)-1-methyl-pyrrolidin-2-yl]methoxy]-7-(1-naphthyl)-6,8-dihydro-5H-pyrido[3,4-d]pyrimidin-4-yl]piperazin-2-yl]acetonitrile (150 mg, 301 umol, 1 eq). The reaction mixture was stirred at 5° C. for 1 hour. Then the reaction mixture was heated to 80° C. for 12 hrs. Upon completion, the reaction mixture was quenched by water (0.5 mL). The residue mixture was purified by prep-HPLC (column: Phenomenex Gemini 150*25 mm*10 um; mobile phase: [water (0.05% ammonia hydroxide v/v)-ACN]; B %: 50%-80%,12 min) to give title compound 2-[(2S)-4-[2-[[(2S)-1-methylpyrrolidin-2-yl] methoxy]-7-(1-naphthyl)-6,8-dihydro-5H-pyrido[3,4-d]py-rimidin-4-yl]-1-(2,3,3-trideuterioprop-2-enoyl)piperazin-2-yl]acetonitrile (EXAMPLE 4, 34.2 mg, 60.2 umol, 20% yield, 97.7% purity) as a white solid. LCMS [ESI, M+1]: 555.

$^1$H NMR (400 MHz, CHLOROFORM-d) δ=8.28-8.16 (m, 1H), 7.91-7.83 (m, 1H), 7.63 (d, J=8.0 Hz, 1H), 7.56-7.48 (m, 2H), 7.45 (t, J=7.6 Hz, 1H), 7.16 (d, J=7.2 Hz, 1H), 5.28-4.94 (m, 1H), 4.41 (dd, J=5.2, 10.8 Hz, 1H), 4.36-4.24 (m, 2H), 4.23-4.11 (m, 2H), 4.04 (br d, J=11.6 Hz, 2H), 3.73-3.25 (m, 3H), 3.22-2.74 (m, 7H), 2.69 (td, J=6.4, 13.2 Hz, 1H), 2.50 (s, 3H), 2.36-2.24 (m, 1H), 2.15-2.02 (m, 1H), 1.83-1.77 (m, 3H).

Example 5

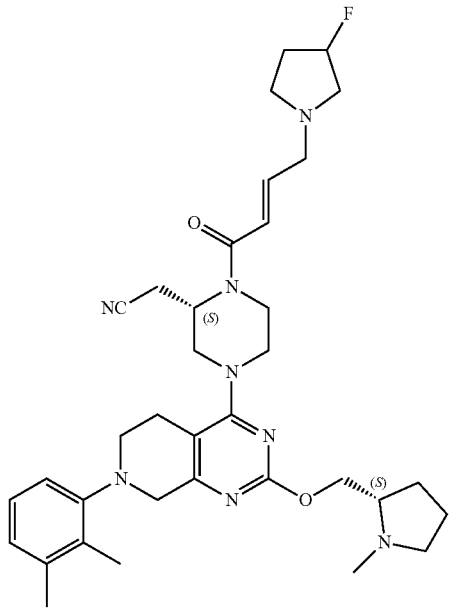

2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile

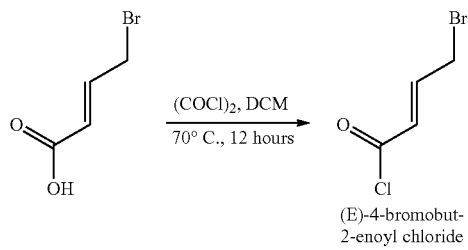

(E)-4-bromobut-2-enoyl chloride

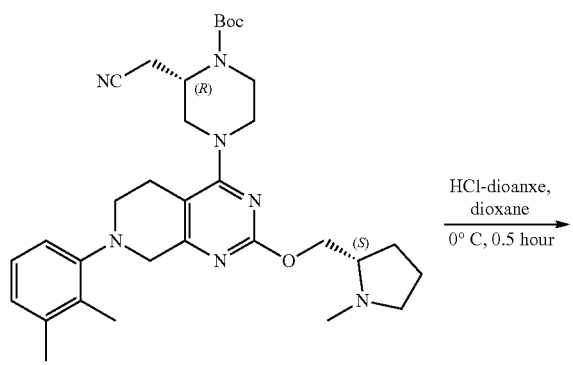

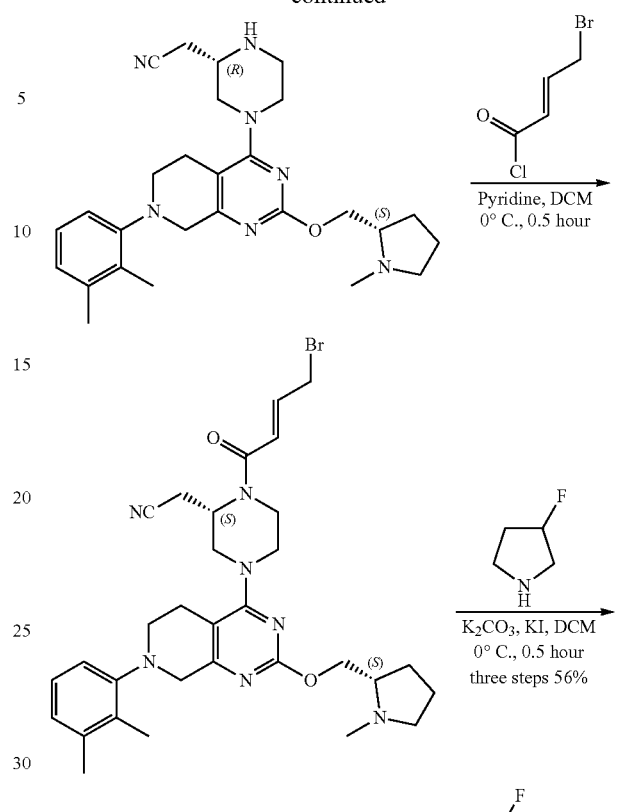

Insert: (E)-4-bromobut-2-enoyl Chloride

A solution of (E)-4-bromobut-2-enoic acid (1.0 g, 6.06 mmol, 1.0 eq) in (COCl)$_2$ (14.5 g, 114 mmol, 10.0 mL, 18.9 eq) and DCM (10.0 mL) was stirred at 70° C. for 2 hours. After completion, the mixture was concentrated under vacuum. The product (E)-4-bromobut-2-enoyl chloride (1.0 g, crude) was obtained as yellow oil. The crude compound was used directly to the next step without further purification.

Step A: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazine-1-carboxylate (Intermediate 73, 200 mg, 347 umol, 1.0 eq) in dioxane (2.0 mL) was added HCl.dioxane (4.0 M, 2.0 mL, 23.0 eq). The mixture was stirred at 25° C. for 0.5 hour. After completion, the reaction mixture was concentrated under reduced pressure to give a residue. The residue was adjusted pH=7 with saturated of NaHCO$_3$ aqueous solution and extracted with EA (5.0 mL×3). The combined organic layers were washed with brine (10.0 mL), dried over Na$_2$SO$_4$, filtered and concentrated under reduced pressure to give the residue. The product 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (160 mg, crude) was obtained as a yellow solid and used into the next step without further purification.

Step B: 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (160 mg, 336 umol, 1.0 eq) in DCM (6.0 mL) was added Py (532 mg, 6.73 mmol, 543 µL, 20.0 eq) and (E)-4-bromobut-2-enoyl chloride (246 mg, 1.35 mmol, 4.0 eq) in DCM (2.0 mL). The mixture was stirred at 0° C. for 1 hour. After completion, the reaction mixture was quenched by addition MeOH (5.0 mL) at 0° C., and then concentrated under reduced pressure to give a residue. The product 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude) was obtained as a yellow oil and used into the next step without further purification. LCMS [ESI, M+1]: 622.

Step C: 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile To a solution of 2-[(2S)-1-[(E)-4-bromobut-2-enoyl]-4-[7-(2,3-dimethylphenyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, 321 umol, 1.0 eq) in DCM (3.0 mL) was added K$_2$CO$_3$ (88.8 mg, 642 umol, 2.0 eq), KI (2.67 mg, 16.1 umol, 0.05 eq) and 3-fluoropyrrolidine (403 mg, 3.21 mmol, 10.0 eq, HCl salt). The mixture was stirred at 0° C. for 1 hour. After completion, the reaction mixture was concentrated under reduced pressure to give a residue. The residue was adjusted pH=7 with saturated of NaHCO$_3$ aqueous solution and extracted with EA (10.0 mL×3). The combined organic layers were washed with brine (20.0 mL), dried over Na$_2$SO$_4$, filtered and concentrated under reduced pressure to give the residue. The residue was purified by prep-HPLC (column: Gemini 150*25 5 u; mobile phase: [water (0.04% NH3H2O)-ACN]; B %: 60%-84%,10 min). The residue was concentrated under reduced pressure and then lyophilization to give title compound 2-[(2S)-4-[7-(2,3-dimethylphenyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile (EXAMPLE 5, 123 mg, 193 umol, 56% yield in three steps, 99.2% purity) was obtained as a yellow solid. LCMS [ESI, M+1]: 631.

$^1$H NMR (400 MHz, Chloroform-d) δ 7.16-7.07 (m, 1H), 7.02-6.92 (m, 3H), 6.59-6.41 (m, 1H), 5.31-5.10 (m, 1H), 5.09-4.46 (m, 1H), 4.38 (dd, J=4.8, 10.4 Hz, 1H), 4.26-3.83 (m, 6H), 3.80-3.45 (m, 1H), 3.42-3.24 (m, 3H), 3.23-3.15 (m, 1H), 3.14-3.03 (m, 3H), 3.02-2.83 (m, 4H), 2.82-2.62 (m, 4H), 2.54-2.49 (m, 1H), 2.47 (s, 3H), 2.32-2.26 (m, 6H), 2.25-2.17 (m, 1H), 2.16-2.09 (m, 1H), 2.08-2.02 (m, 1H), 1.92-1.78 (m, 4H).

Example 6

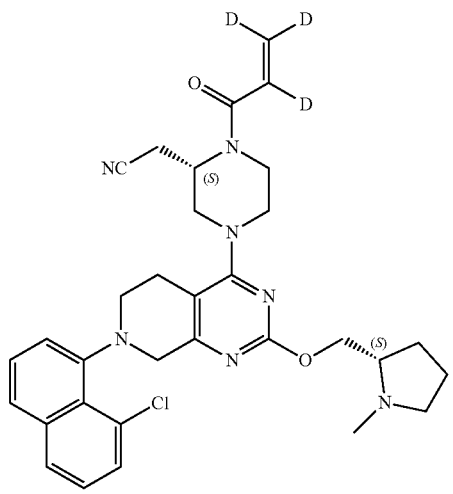

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2,3,3-trideuterioprop-2-enoyl)piperazin-2-yl]acetonitrile

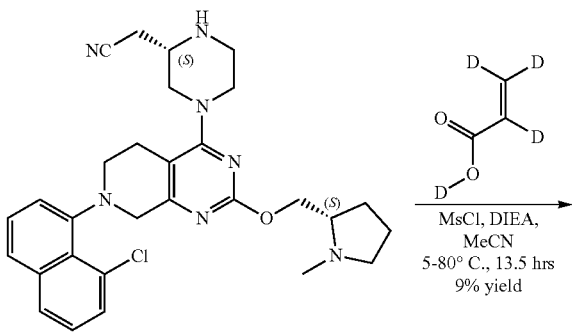

169
-continued

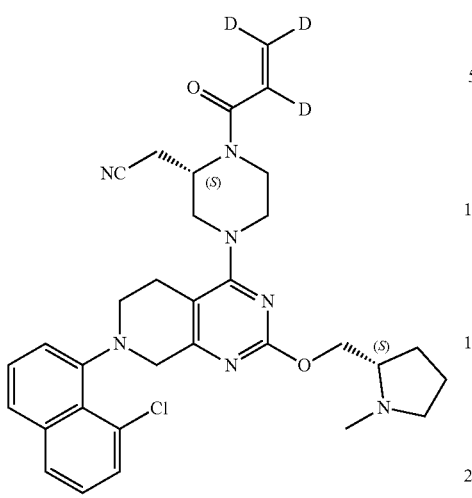

Step A

2-[(2S)-4-[7-(8-chloro-1-naphthyl)-2-[[(2S)-1-methyl-pyrrolidin-2-yl]methoxy]-6,8-dihydro-5H-pyrido[3,4-d]pyrimidin-4-yl]-1-(2,3,3-trideuterioprop-2-enoyl)piperazin-2-yl]acetonitrile. To the solution of deuterio 2,3,3-trideuterioprop-2-enoate (56.6 mg, 744 umol, 3 eq) and DIEA (481 mg, 3.72 mmol, 648 μL, 15 eq) in ACN (3 mL) was added MsCl (56.8 mg, 496 umol, 38.4 μL, 2 eq) at 5° C., the mixture was stirred at 5° C. for 0.5 hour. Then to the mixture was added 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 248 umol, 1 eq, 2 HCl), the resulting mixture was stirred at 5° C. for 1 hour. Then the mixture was heated to 80° C. and stirred at 80° C. for 12 hours. The mixture was quenched by Water (0.5 mL). The reaction mixture was purified by prep-HPLC (column: Phenomenex Gemini 150*25 mm*10 um; mobile phase: [water (0.05% ammonia hydroxide v/v)-ACN]; B %: 50%-80%,10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2,3,3-trideuterioprop-2-enoyl)piperazin-2-yl]acetonitrile (EXAMPLE 6, 13.0 mg, 21.6 umol, 9% yield, 98.2% purity) as a off-white solid. LCMS [ESI, M+1]: 589.

$^1$H NMR (400 MHz, chloroform-d) δ=7.76 (br d, J=8.4 Hz, 1H), 7.62 (t, J=7.6 Hz, 1H), 7.53 (d, J=7.2 Hz, 1H), 7.45 (td, J=8.0, 13.2 Hz, 1H), 7.34 (t, J=7.6 Hz, 1H), 7.26-7.18 (m, 1H), 5.10 (br s, 1H), 4.49-4.33 (m, 2H), 4.21-4.01 (m, 3H), 3.96-3.79 (m, 2H), 3.60 (br d, J=6.8 Hz, 1H), 3.44 (br d, J=13.6 Hz, 1H), 3.32-2.97 (m, 5H), 2.88-2.53 (m, 4H), 2.48 (d, J=2.8 Hz, 3H), 2.29 (br d, J=8.8 Hz, 1H), 2.11-2.00 (m, 1H), 1.87-1.71 (m, 3H).

Example 7

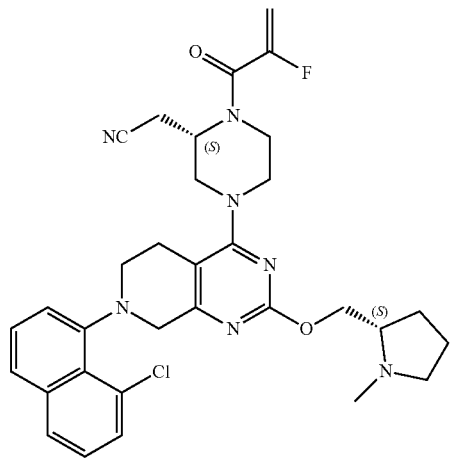

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

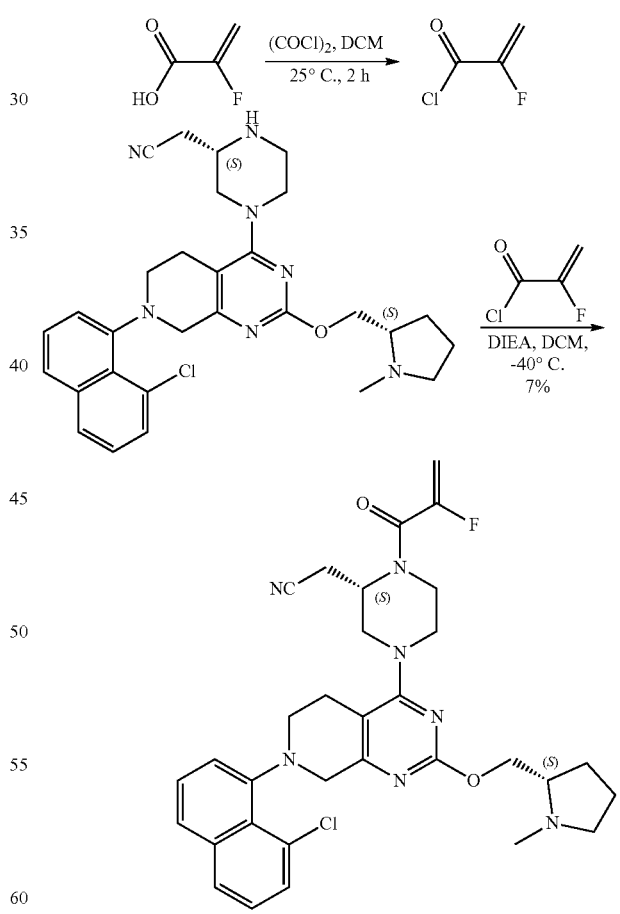

2-fluoroprop-2-enoyl chloride. To a solution of 2-fluoroprop-2-enoic acid (400 mg, 4.44 mmol, 1 eq) in DCM (4 mL) was added (COCl)$_2$ (846 mg, 6.66 mmol, 583 μL, 1.5 eq) and DMF (32.5 mg, 444 umol, 34.2 μL, 0.1 eq). The mixture was stirred at 25° C. for 2 hrs. The reaction mixture was concentrated under reduced pressure to remove a part of solvent and give a residue in DCM. Compound 2-fluoro-prop-2-enoyl chloride (400 mg, crude) was obtained as a yellow liquid and used into the next step without further purification.

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 528 umol, 1 eq, HCl) in DCM (5 mL) was added DIEA (1.73 g, 13.4 mmol, 2.33 mL, 25.4 eq) and 2-fluoroprop-2-enoyl chloride (286 mg, 2.64 mmol, 5 eq) in DCM (5 mL). The mixture was stirred at 0° C. for 1 hour. The reaction mixture was concentrated under reduced pressure to give a residue. The residue was purified by column chromatography (Al$_2$O$_3$, Dichloromethane/Methanol=10/1 to 10/1). The residue was purified by prep-HPLC (column: Gemini 150*25 5 u; mobile phase: [water (0.05% ammonia hydroxide v/v)—ACN]; B %: 55%-85%, 12 min). The residue was purified by prep-HPLC (column: Phenomenex Synergi C18 150*30 mm*4 um; mobile phase: [water (0.225% FA)—ACN]; B %: 20%-50%, 10.5 min). The residue was concentrated under reduced pressure to remove ACN, and then lyophlization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 7, 24.1 mg, 36.7 umol, 7% yield, 99.1% purity, FA) was obtained as a brown solid.

SFC condition: "AD-3S_b 3_5_40_3 ML Column: Chiralpak AD-3 100×4.6 mm I.D., 3 um Mobile phase: methanol (0.05% DEA) in CO$_2$ from 5% to 40% Flow rate: 3 mL/min Wavelength: 220 nm".

$^1$H NMR (400 MHz, Acetic) δ=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13 (m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

Example 8

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile

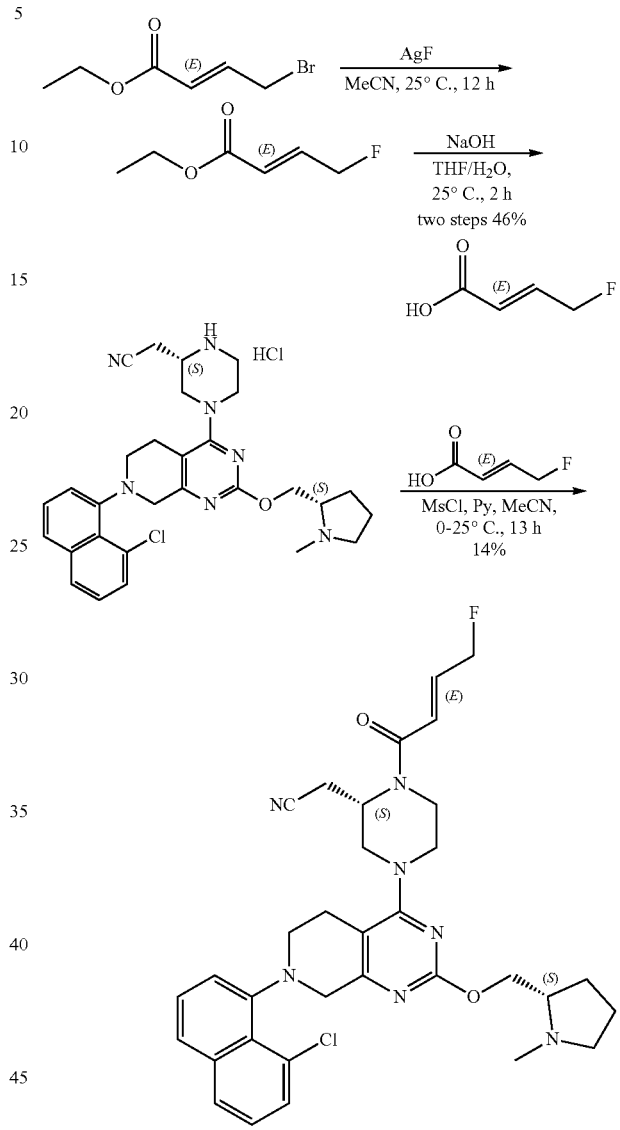

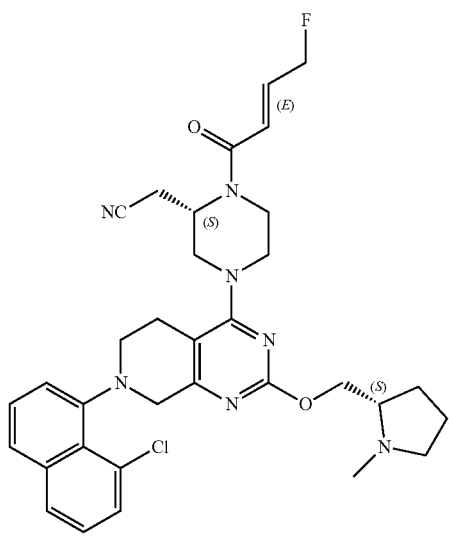

Step A: ethyl (E)-4-fluorobut-2-enoate

A mixture of ethyl (E)-4-bromobut-2-enoate (2.00 g, 10.4 mmol, 1.43 mL, 1.00 eq) and AgF (3.94 g, 31.1 mmol, 674 μL, 3.00 eq) in acetonitrile (20.0 mL) was stirred at 25° C. for 12 hours. The mixture was filtered and washed with THF (10.0 mL), then concentrated under vacuum to give ethyl (E)-4-fluorobut-2-enoate (2.50 g, crude) as a yellow oil and used into next step without further purification.

$^1$H NMR (400 MHz, chloroform-d) δ=7.04-6.89 (m, 1H), 6.12 (qd, J=2.0, 16.0 Hz, 1H), 5.14-4.94 (m, 2H), 4.22 (q, J=6.8 Hz, 2H), 1.30 (t, J=6.8 Hz, 3H).

Step B: (E)-4-fluorobut-2-enoic acid

A mixture of ethyl (E)-4-fluorobut-2-enoate (0.10 g, crude) and NaOH (121 mg, 3.03 mmol) in THF (1.00 mL) and H$_2$O (1.00 mL) was stirred at 25° C. for 2 hours. The pH value was adjusted to 1-3 by HCl (1N, 5.00 mL), extracted with ethyl acetate (3×10.0 mL), the organic layer was dried over Na₂SO₄, filtered and concentrated under vacuum to give (E)-4-fluorobut-2-enoic acid (0.02 g, 192 mmol, two steps 46%) as a yellow oil and used into next step without further purification.

¹H NMR (400 MHz, chloroform-d) δ=8.37-7.31 (m, 1H), 7.15-7.01 (m, 1H), 6.15 (dd, J=1.6, 16.0 Hz, 1H), 5.22-4.96 (m, 2H).

Step C: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile To a solution of (E)-4-fluorobut-2-enoic acid (7.32 mg, 70.4 umol, 2 eq) and Py (8.35 mg, 106 umol, 8.52 μL, 3.00 eq) in acetonitrile (1.00 mL) was added MsCl (8.06 mg, 70.4 umol, 5.45 μL, 2.00 eq) at 0° C. After stirred at 0° C. for 1 hour, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.02 g, 35.2 umol, 1.00 eq, HCl) was added into the mixture. The mixture was stirred at 25° C. for 12 h. The mixture was diluted with water (5.00 mL), extracted with ethyl acetate (3×5.00 mL), the organic layer was dried over Na₂SO₄, filtered and concentrated under vacuum. The residue was purified by prep-HPLC (column: Gemini 150*25 5 u; mobile phase: [water (0.05% ammonia hydroxide v/v)—ACN]; B %: 50%-80%, 12 min). The desired fraction was collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-fluorobut-2-enoyl]piperazin-2-yl]acetonitrile (EXAMPLE 8, 3.01 mg, 4.82 umol, 14% yield, 98.9% purity) as a brown solid. LCMS [ESI, M+1]: 618.

¹H NMR (400 MHz, CHLOROFORM-d) δ=7.76 (br d, J=8.0 Hz, 1H), 7.62 (t, J=7.2 Hz, 1H), 7.53 (d, J=7.2 Hz, 1H), 7.45 (td, J=7.6, 12.8 Hz, 1H), 7.34 (t, J=7.6 Hz, 1H), 7.26-7.17 (m, 1H), 7.09-6.91 (m, 1H), 6.59 (br d, J=15.6 Hz, 1H), 5.19-5.05 (m, 2H), 4.49-4.36 (m, 2H), 4.22-3.79 (m, 5H), 3.76-2.96 (m, 8H), 2.92-2.55 (m, 4H), 2.48 (d, J=2.4 Hz, 3H), 2.29 (br d, J=9.6 Hz, 1H), 2.06 (br d, J=10.0 Hz, 1H), 1.83-1.71 (m, 3H).

Example 9

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile

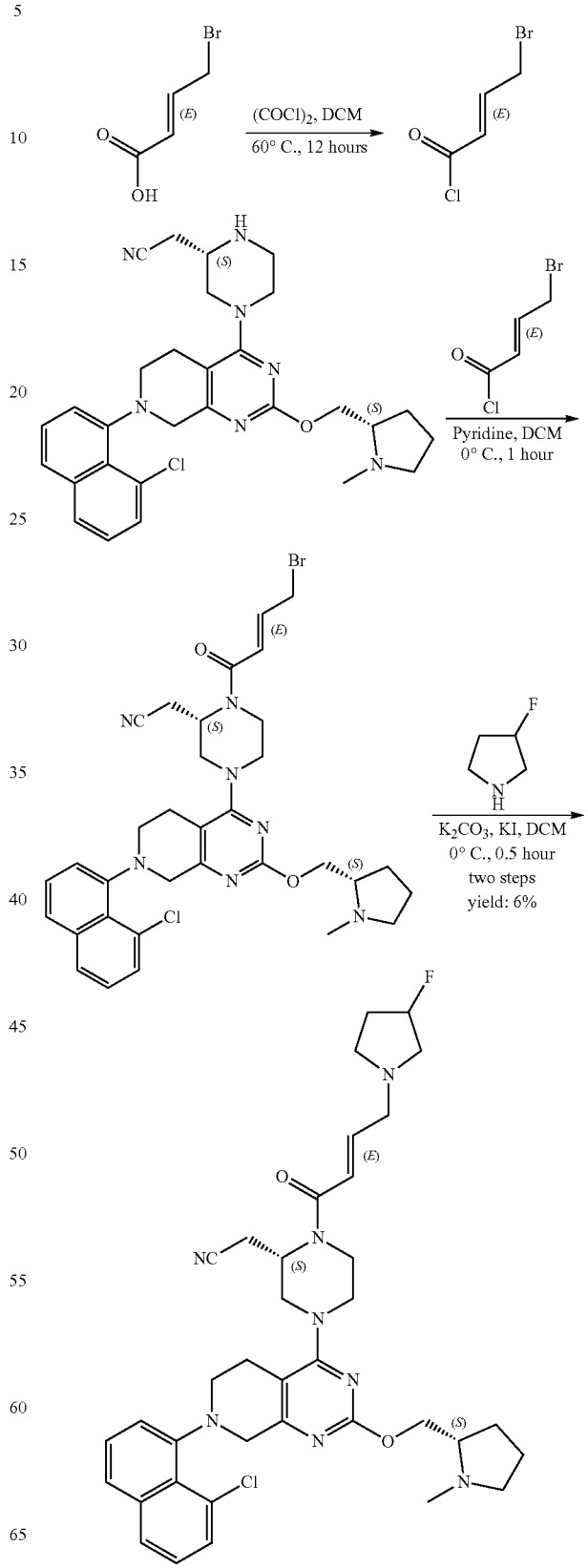

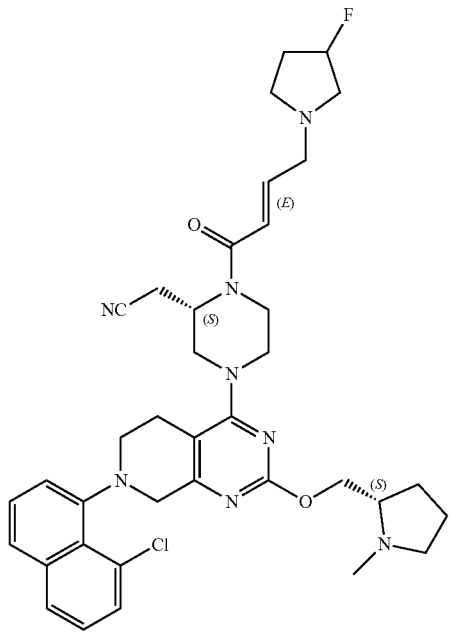

Insert: (E)-4-bromobut-2-enoyl Chloride

To a solution of (E)-4-bromobut-2-enoic acid (930 mg, 5.64 mmol, 1.0 eq) in DCM (2.0 mL) was added (COCl)$_2$ (2.90 g, 22.9 mmol, 2.0 mL, 4.05 eq). The mixture was stirred at 60° C. for 12 hours. After completion, the mixture was concentrated under vacuum. The product (E)-4-bromobut-2-enoyl chloride (650 mg, crude) was obtained as yellow oil and used directly to the next step without further purification.

Step A: 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 282 umol, 1.0 eq) in DCM (3.0 mL) was added Py (446 mg, 5.64 mmol, 455 µL, 20.0 eq) and (E)-4-bromobut-2-enoyl chloride (207 mg, 1.13 mmol, 4.0 eq) in DCM (1.0 mL). The mixture was stirred at 0° C. for 1 hour. After completion, the reaction mixture was concentrated under reduced pressure to give a residue. The product 2-[(2S)-1-[(E)-4-bromobut-2-enoyl]-4-[7-(8-chloro-1-naphthyl)-2-[[(2S)-1-methylpyrrolidin-2-yl] methoxy]-6,8-dihydro-5H-pyrido[3,4-d]pyrimidin-4-yl]piperazin-2-yl]acetonitrile (150 mg, crude) was obtained as brown oil and used into the next step without further purification. LCMS [ESI, M+1]: 680.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile To a solution of 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 221 umol, 1.0 eq) in DCM (10.0 mL) was added K$_2$CO$_3$ (366 mg, 2.65 mmol, 12.0 eq), KI (1.83 mg, 11.0 umol, 0.05 eq) and 3-fluoropyrrolidine (277 mg, 2.21 mmol, 10.0 eq, HCl). The mixture was stirred at 0° C. for 0.5 hour. After completion, the reaction mixture was concentrated under reduced pressure to give a residue. The residue was adjusted pH-7 with saturated NaHCO$_3$ aqueous solution and extracted with EA (3×10 mL). The combined organic layers were washed with brine (20 mL), dried over Na$_2$SO$_4$, filtered and concentrated under reduced pressure to give the residue. The residue was purified by prep-HPLC (column: Gemini 150*25 5 u; mobile phase: [water (0.04% NH$_3$—H$_2$O)-ACN]; B %: 60%-84%, 10 min). The residue was concentrated under reduced pressure and then lyophilization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoropyrrolidin-1-yl)but-2-enoyl]piperazin-2-yl]acetonitrile (EXAMPLE 9, 9.67 mg, 14.0 umol, 6% yield, 99.2% purity) was obtained as yellow solid. LCMS [ESI, M+1]: 687.

$^1$H NMR (400 MHz, Chloroform-d) δ 7.76 (br d, J=8.0 Hz, 1H), 7.62 (t, J=7.8 Hz, 1H), 7.26 (br d, J=7.2 Hz, 1H), 7.49-7.40 (m, 1H), 7.34 (t, J=7.8 Hz, 1H), 7.27-7.17 (m, 1H), 7.05-6.92 (m, 1H), 6.57-6.42 (m, 1H), 5.32-5.11 (m, 1H), 5.10-4.50 (m, 1H), 4.47-4.35 (m, 2H), 4.19-4.00 (m, 2H), 3.95-3.75 (m, 2H), 3.65-3.55 (m, 1H), 3.47-3.28 (m, 3H), 3.24-3.05 (m, 4H), 3.04-2.86 (m, 4H), 2.85-2.71 (m, 2H), 2.70-2.50 (m, 3H), 2.47-2.45 (m, 3H), 2.32-2.15 (m, 2H), 2.14-2.02 (m, 2H), 1.87-1.67 (m, 4H).

Example 10

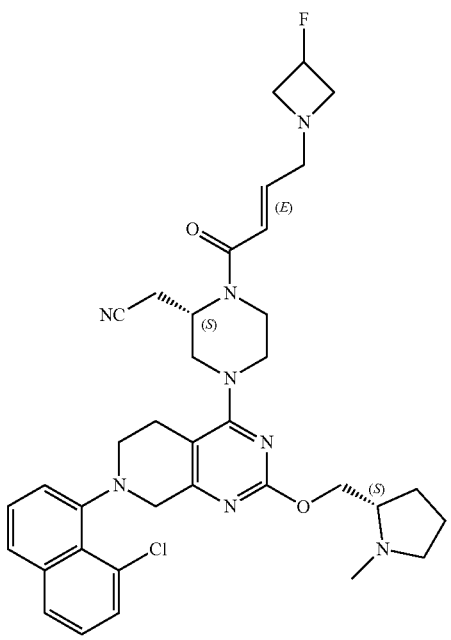

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile

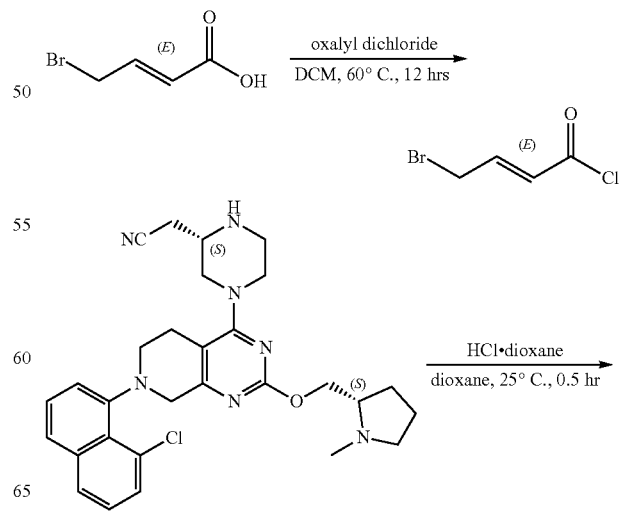

-continued

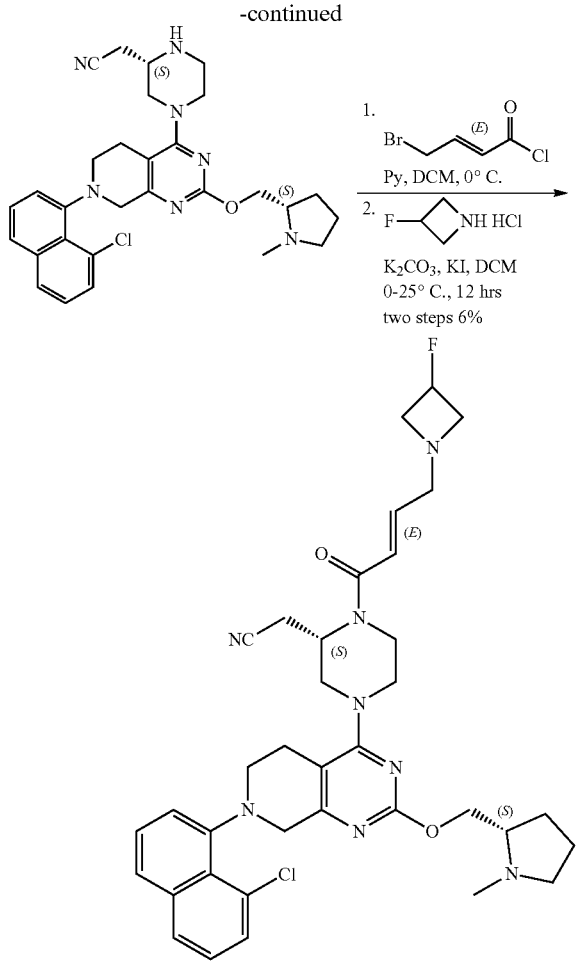

Insert: (E)-4-bromobut-2-enoyl Chloride

To a solution of (E)-4-bromobut-2-enoic acid (1 g, 6.06 mmol, 1.0 eq) in DCM (5.0 mL) was added oxalyl dichloride (7.25 g, 57.1 mmol, 5.0 mL, 9.4 eq). The mixture was stirred at 60° C. for 12 hours. After completion, the reaction mixture was concentrated under reduced pressure to give (E)-4-bromobut-2-enoyl chloride (850 mg, crude) as yellow oil which was used for the next step without further purification.

Step A: Intermediate 71,2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazine-1-carboxylate (310 mg, 414 umol, 1.0 eq) in dioxane (4.0 mL) was added HCl/dioxane (4.0 M, 4.0 mL, 39.0 eq) at 25° C. The mixture was stirred at 25° C. for 0.5 hour. After completion, the reaction mixture was quenched by saturated NaHCO₃ aqueous solution (20.0 mL), and then extracted with EA (3×40.0 mL). The combined organic layers were washed with saturated NaCl aqueous solution (100.0 mL), dried over Na₂SO₄, filtered and concentrated to give a residue 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (250 mg, crude) as yellow solid. The crude product was used into the next step without further purification. LCMS [ESI, M+1]: 532.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 150 mg, 282 umol, 1.0 eq, crude) in DCM (6.0 mL) was added Py (446 mg, 5.6 mmol, 455 μL, 20.0 eq) and (E)-4-bromobut-2-enoyl chloride (207 mg, 1.2 mmol, 4.0 eq, crude) in DCM (1.0 mL). The mixture was stirred at 0° C. for 1 hour. Then K₂CO₃ (779 mg, 5.6 mmol, 20.0 eq), KI (4.6 mg, 28.2 umol, 0.1 eq) and 3-fluoroazetidine (472 mg, 4.2 mmol, 15.0 eq, HCl) was added at 0° C. Then the mixture was stirred at 25° C. for 12 hours. After completion, the mixture was filtered and concentrated under reduced pressure. The residue was purified by prep-HPLC (column: Phenomenex Gemini 150*25 mm*10 um; mobile phase: [water (10.0 mM NH₄HCO₃)-ACN]; B %: 55%-85%, 10 min.) and lyophilization to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(3-fluoroazetidin-1-yl)but-2-enoyl]piperazin-2-yl]acetonitrile (EXAMPLE 10, 10.8 mg, 15.7 umol, 6% yield, 98% purity) as yellow solid. LCMS [ESI, M+1]: 673.

SFC Conditions: 100%.e.e.

¹H NMR (400 MHz, Chloroform-d) δ 7.77 (d, J=8.0 Hz, 1H), 7.63 (t, J=7.8 Hz, 1H), 7.54 (d, J=7.2 Hz, 1H), 7.50-7.43 (m, 1H), 7.35 (t, J=7.8 Hz, 1H), 7.26-7.21 (m, 1H), 6.89 (d, J=15.2 Hz, 1H), 6.42 (d, J=14.8 Hz, 1H), 5.26-4.62 (m, 1H), 5.11 (t, J=5.2 Hz, 1H), 4.80-4.37 (m, 2H), 4.20-4.08 (m, 2H), 3.92 (br d, J=17.6 Hz, 1H), 3.86-3.71 (m, 3H), 3.60 (s, 1H), 3.52-3.47 (m, 1H), 3.45-3.33 (m, 1H), 3.28-3.21 (m, 3H), 3.16-3.11 (m, 3H), 3.03 (dd, J=8.4, 16.8 Hz, 1H), 2.82-2.60 (m, 4H), 2.49 (d, J=2.8 Hz, 3H), 2.37-2.25 (m, 1H), 2.09-2.03 (m, 1H), 1.86-1.83 (m, 1H), 1.78-1.76 (m, 3H).

Example 11

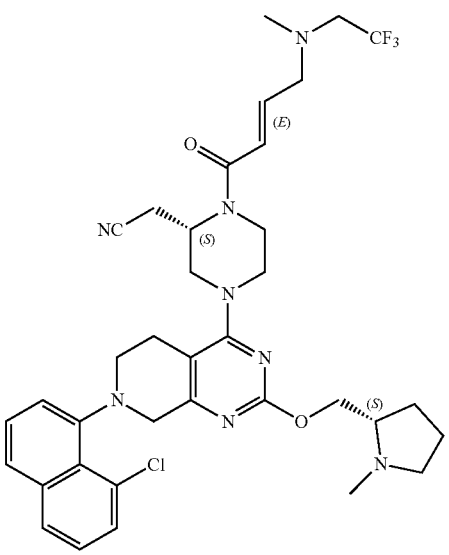

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile

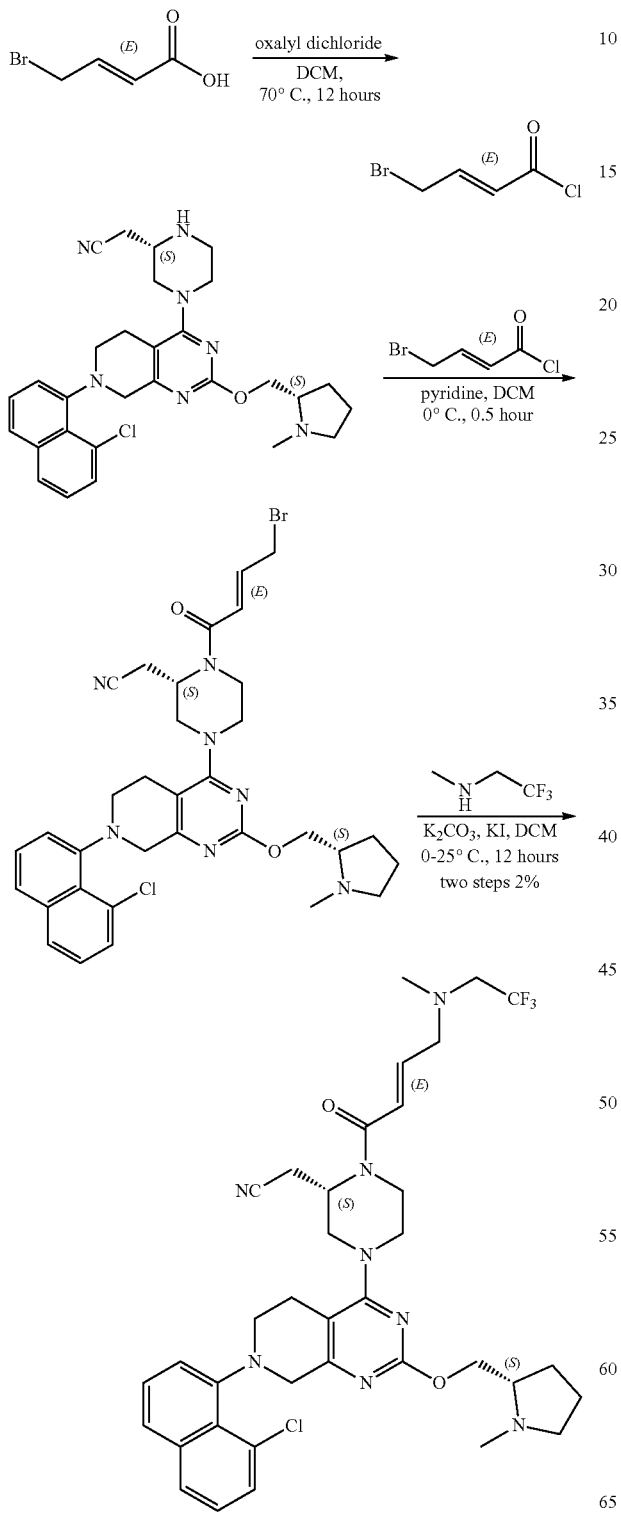

Insert: (E)-4-bromobut-2-enoyl Chloride

A solution of (E)-4-bromobut-2-enoic acid (600 mg, 3.64 mmol, 1.0 eq) in $(COCl)_2$ (10.2 g, 80.0 mmol, 7.0 mL, 22.0 eq) and DCM (7.0 mL) was stirred at 70° C. for 12 hours. After completion, the reaction mixture was concentrated to give (E)-4-bromobut-2-enoyl chloride (500 mg, crude) as yellow oil. The crude product was used for the next step without further purification.

Step A: 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (100 mg, 188 umol, 1.0 eq) and pyridine (119 mg, 1.50 mmol, 121 µL, 8.0 eq) in DCM (2.0 mL) was added (E)-4-bromobut-2-enoyl chloride (138 mg, 752 umol, 4.0 eq). The mixture was stirred at 0° C. for 0.5 hour. After completion, the reaction mixture was concentrated to give 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (130 mg, crude) as yellow oil. LCMS [ESI, M+1]: 678, 680.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile To a solution of 2-[(2S)-1-[(E)-4-bromobut-2-enoyl]-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (128 mg, 189 umol, 1.0 eq), $K_2CO_3$ (130 mg, 943 umol, 5.0 eq) and KI (9.39 mg, 56.6 umol, 0.30 eq) in DCM (3.0 mL) was added 2,2,2-trifluoro-N-methyl-ethanamine (213 mg, 1.88 mmol, 10.0 eq) in portions. The mixture was stirred at 0-25° C. for 12 hours. After completion, the mixture was concentrated under vacuum. The obtained product was purified by prep-HPLC (column: Gemini 150*25 5 u; mobile phase: [water (0.04% $NH_3$—$H_2O$)-ACN]; B %: 70%-100%, 10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-[methyl(2,2,2-trifluoroethyl)amino]but-2-enoyl]piperazin-2-yl]acetonitrile (EXAMPLE 11, 2.87 mg, 3.84 umol, 2% yield, 95% purity) as white solid. LCMS [ESI, M+1]: 711.

$^1$H NMR (400 MHz, Chloroform-d) δ 7.76 (br d, J=7.6 Hz, 1H), 7.62 (t, J=7.6 Hz, 1H), 7.53 (d, J=7.2 Hz, 1H), 7.49-7.40 (m, 1H), 7.34 (t, J=7.8 Hz, 1H), 7.27-7.18 (m, 1H), 6.95-6.79 (m, 1H), 6.54-6.38 (m, 1H), 5.12-4.50 (m, 1H), 4.48-4.35 (m, 2H), 4.24-3.99 (m, 3H), 3.96-3.78 (m, 2H), 3.77-3.64 (m, 1H), 3.61-3.53 (m, 1H), 3.52-3.34 (m, 3H), 3.33-2.97 (m, 7H), 2.92-2.76 (m, 1H), 2.75-2.65 (m, 1H), 2.63-2.55 (m, 1H), 2.51 (s, 3H), 2.49 (br d, J=3.2 Hz, 3H), 2.35-2.25 (m, 1H), 2.13-1.99 (m, 1H), 1.89-1.67 (m, 3H).

Example 12

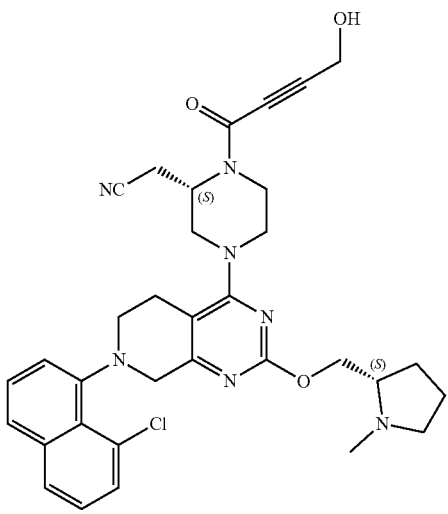

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl]acetonitrile

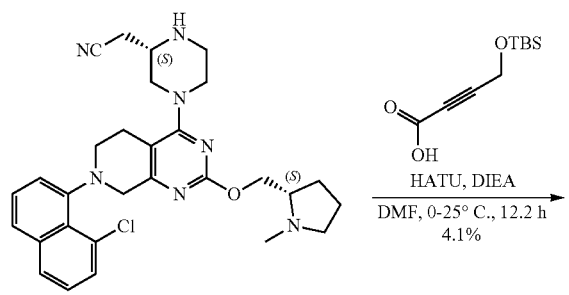

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl]acetonitrile To a solution of 4-[tert-butyl(dimethyl)silyl]oxybut-2-ynoic acid (129 mg, 564 umol, 1.50 eq) and DIEA (194 mg, 1.50 mmol, 262 µL, 4.00 eq) in DMF (2.00 mL) was added HATU (214 mg, 564 umol, 1.50 eq) at 0° C. After stirred at 0° C. for 10 mins, 2-[(2S)-4-[7-(8-chloro-1-naphthyl)-2-[[(2S)-1-methylpyrrolidin-2-yl] methoxy]-6,8-dihydro-5H-pyrido[3,4-d]pyrimidin-4-yl]piperazin-2-yl]acetonitrile (0.20 g, 376 umol, 1.00 eq) was added into the mixture. After stirred at 25° C. for 12 hours, the mixture was diluted with ethyl acetate (10.0 mL), washed with brine (3×10.0 mL), dried over Na$_2$SO$_4$, filtered and concentrated under vacuum. The residue was purified by reversed phase flash [water (FA, 0.10%)/acetonitrile]. The desired fractions were collected, neutralized with saturated sodium bicarbonate (5.00 mL) to pH>7 and extracted with ethyl acetate (3×20.0 mL). The organic layers were washed with brine (1×30.0 mL), dried over Na$_2$SO$_4$, filtered and concentrated under vacuum. The residue was purified by prep-HPLC column: Phenomenex Synergi C18 150*25*10 um; mobile phase: [water (0.225%, FA)-ACN]; B %: 10%-40%, 10 min. The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(4-hydroxybut-2-ynoyl)piperazin-2-yl]acetonitrile (EXAMPLE 12, 10.1 mg, 15.3 umol, 4.1% yield, 99.6% purity, FA) as a yellow solid. LCMS [ESI, M+1]: 614.

$^1$H NMR (400 MHz, Acetic acid-d4) δ=7.82 (d, J=8.4 Hz, 1H), 7.69 (d, J=8.4 Hz, 1H), 7.56 (d, J=7.6 Hz, 1H), 7.49 (t, J=7.6 Hz, 1H), 7.42-7.31 (m, 2H), 5.14-4.73 (m, 4H), 4.70-4.23 (m, 5H), 4.01-3.81 (m, 3H), 3.80-3.51 (m, 3H), 3.49-3.17 (m, 4H), 3.09 (m, 5H), 2.81-2.63 (m, 1H), 2.45-2.34 (m, 1H), 2.22-2.08 (m, 3H).

Example 13

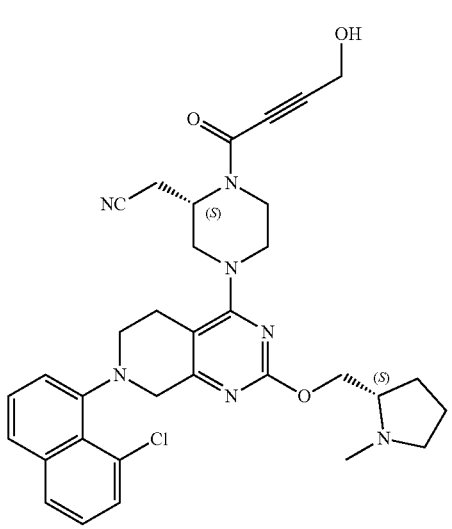

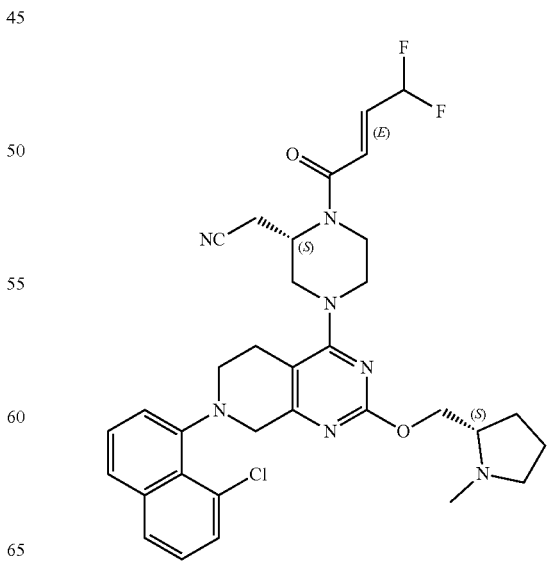

183

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile

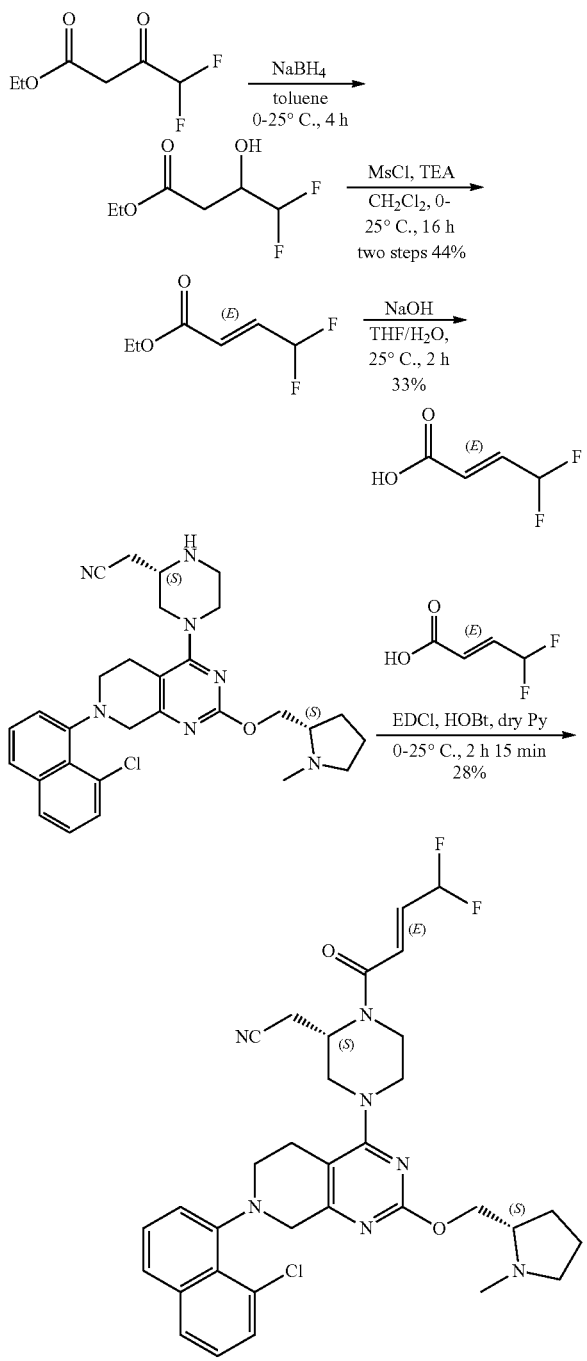

Step 1: 4,4-difluoro-3-hydroxy-butanoate

To a solution of ethyl 4,4-difluoro-3-oxo-butanoate (5.00 g, 30.1 mmol, 1.00 eq) in toluene (150 mL) was added NaBH₄ (1.20 g, 31.7 mmol, 1.05 eq) at 0° C. After stirred at 25° C. for 4 hours, the mixture was diluted with water (50.0 mL) at 0° C. and extracted with ethyl acetate (3×100 mL). The extracts were washed with brine (1×100 mL), dried over Na₂SO₄, filtered and concentrated under vacuum to give ethyl 4,4-difluoro-3-hydroxy-butanoate (4.30 g, crude) as a yellow oil and used into next step without further purification.

$^1$H NMR (400 MHz, DMSO-d6) δ=6.05-5.87 (m, 1H), 5.86-5.72 (m, 1H), 4.11-4.01 (m, 2H), 2.57 (dd, J=4.0, 15.6 Hz, 1H), 2.38 (dd, J=9.2, 15.6 Hz, 1H), 1.21-1.17 (m, 3H).

Step 2: Ethyl (E)-4,4-difluorobut-2-enoate

To a solution of ethyl 4,4-difluoro-3-hydroxy-butanoate (3.00 g, crude) in dichloromethane (20.0 mL) was added TEA (1.81 g, 17.8 mmol, 2.48 mL,) and MsCl (3.68 g, 32.1 mmol, 2.49 mL) at 0° C. After stirred for 4 hours, to the mixture was added TEA (3.61 g, 35.68 mmol, 4.97 mL, 2 eq) 0° C. After warmed up to 25° C. and stirred for 12 hours, the mixture was diluted with water (10.0 mL), washed with HCl (1N, 1×20.0 mL) and brine (1×20.0 mL), dried over Na₂SO₄, filtered and concentrated under vacuum to give ethyl (E)-4,4-difluorobut-2-enoate (1.40 g, 9.33 mmol, two steps 44% yield) as a colourless oil and used into next step with further purification.

$^1$H NMR (400 MHz, chloroform-d) δ=6.81 (m, 1H), 6.29 (dt, J=2.8, 1.6 Hz, 1H), 6.23 (dd, J=4.0, 55.2 Hz, 1H), 4.25 (q, J=7.2 Hz, 2H), 1.31 (t, J=7.2 Hz, 3H).

Step 3: (E)-4,4-difluorobut-2-enoic Acid

A mixture of ethyl (E)-4,4-difluorobut-2-enoate (1.30 g, 8.66 mmol, 1.00 eq) and NaOH (1.39 g, 34.6 mmol, 4.00 eq) in THF (5.00 mL) and H₂O (5.00 mL) was stirred at 25° C. for 2 hours. The mixture was acidified with HCl (2N, 20.0 mL) to pH=1~3 and extracted with ethyl acetate (3×20.0 mL). The organic layers were dried over Na₂SO₄, filtered and concentrated under vacuum to give (E)-4,4-difluorobut-2-enoic acid (0.35 g, 2.87 mmol, 33% yield) as a yellow solid and used into next step without further purification.

$^1$H NMR (400 MHz, chloroform-d) δ=6.92 (m, 1H), 6.32 (dtd, J=0.8, 2.8, 16.8 Hz, 1H), 6.27 (dtd, J=1.2, 54.8 Hz, 4.0, 1H).

Step A: 2-[(2s)-4-[7-(8-chloro-1-naphthyl)-2-[[(2s)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile A mixture of (E)-4,4-difluorobut-2-enoic acid (68.8 mg, 564 umol, 1.50 eq), EDCI (108 mg, 564 umol, 1.50 eq) and HOBt (50.8 mg, 376 umol, 1.00 eq) in Py (3 mL) was stirred at 0° C. for 15 min, then 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 0.20 g, 376 umol, 1.00 eq) was added into the mixture. After stirred at 0° C. for 1 hour and 25° C. for 1 hour, the mixture was diluted with water (10.0 mL), extracted with ethyl acetate (1×10.0 mL). The extracts were washed with brine (1×10.0 mL), dried over Na₂SO₄, filtered and concentrated under vacuum. The residue was purified by reversed phase flash [water (FA, 0.10%)/acetonitrile]. The desired fractions were collected and the mixture was neutralized with saturated sodium bicarbonate (5.00 mL), extracted with ethyl acetate (3×20.0 mL). The organic layers were washed with brine (1×30.0 mL), dried over Na₂SO₄, filtered and concentrated under vacuum. The residue was purified by prep-HPLC (column: Gemini 150*25 5 u; mobile phase: [water (0.05% ammonia hydroxide v/v)—

ACN]; B %: 55%-85%, 12 min). The desired fractions were collected and lyophilized to give title compound 2-[(2s)-4-[7-(8-chloro-1-naphthyl)-2-[[(2s)-1-methylpyrrolidin-2-yl]methoxy]-6,8-dihydro-5H-pyrido[3,4-d]pyrimidin-4-yl]-1-[(E)-4,4-difluorobut-2-enoyl]piperazin-2-yl]acetonitrile (EXAMPLE 13, 66.9 mg, 104 umol, 28% yield, 98.7% purity) as a yellow solid. LCMS [ESI, M+1]: 636.

¹H NMR (400 MHz, chloroform-d) δ=7.76 (d, J=8.0 Hz, 1H), 7.62 (t, J=7.2 Hz, 1H), 7.52 (d, J=7.2 Hz, 1H), 7.45 (td, J=7.6, 12.8 Hz, 1H), 7.37-7.31 (m, 1H), 7.27-7.18 (m, 1H), 6.88-6.71 (m, 2H), 6.45-6.12 (m, 1H), 5.17-4.59 (m, 1H), 4.55-4.41 (m, 1H), 4.40-4.33 (m, 1H), 4.21-3.69 (m, 5H), 3.64-3.32 (m, 2H), 3.31-2.97 (m, 5H), 2.96-2.52 (m, 4H), 2.47 (d, J=1.6 Hz, 3H), 2.33-2.23 (m, 1H), 2.11-2.00 (m, 1H), 1.90-1.77 (m, 3H).

Example 14

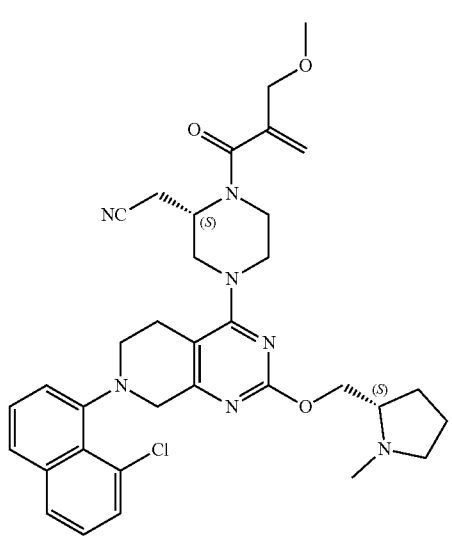

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile

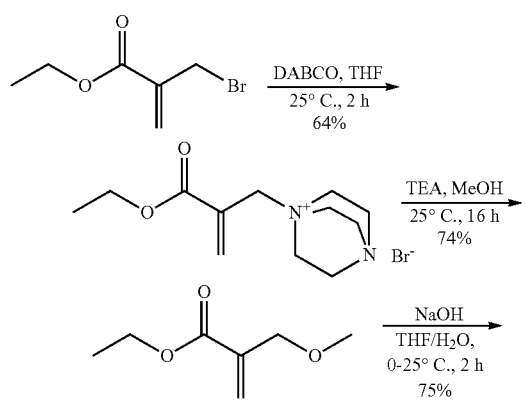

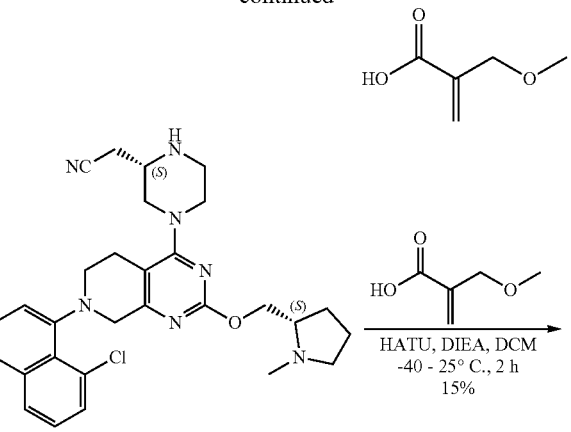

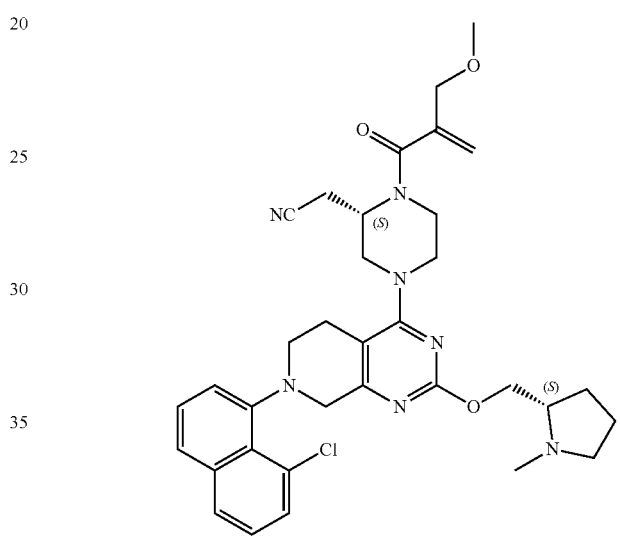

Step 1: 1-(2-(ethoxycarbonyl)allyl)-1,4-diazabicyclo[2.2.2]octan-1-ium Bromide.

To ethyl 2-(bromomethyl)prop-2-enoate (15 g, 77.7 mmol, 1 eq) in THF (5 mL) was added DABCO (10.5 g, 93.6 mmol, 10.3 mL, 1.20 eq) and the resulting mixture was stirred at 25° C. for 2 hours. The precipitate was formed and filtered under nitrogen atmosphere. The filter cake was collected to give 1-(2-(ethoxycarbonyl)allyl)-1,4-diazabicyclo[2.2.2]octan-1-ium bromide (15 g, 49.6 mmol, 64% yield) as a light yellow solid which was used directly in the next step without further purification.

Step 2: Ethyl 2-(methoxymethyl)prop-2-enoate

A mixture of 1-(2-(ethoxycarbonyl)allyl)-1,4-diazabicyclo[2.2.2] octan-1-ium bromide (15 g, 49.6 mmol, 1 eq) and TEA (10.5 g, 104 mmol, 14.5 mL, 2.09 eq) in MeOH (150 mL) was stirred at 25° C. for 16 hours. The solvent was evaporated under vacuum (25° C.). The residue was dissolved into DCM (40 ml) and then washed with 5% aqueous citric acid solution (1×40 mL) and saturated sodium bicarbonate aqueous solution (1×40 mL). The organic layer was dried over sodium sulfate, filtered and concentrated under vacuum at 25° C. to give ethyl 2-(methoxymethyl)prop-2- enoate (5.3 g, 36.8 mmol, 74% yield) as a yellow liquid which was used directly in the next step without further purification.

Step 3: 2-(methoxymethyl)prop-2-enoic Acid

To a solution of ethyl 2-(methoxymethyl)prop-2-enoate (5.1 g, 35.4 mmol, 1 eq) in THF (71 mL) was added a solution of NaOH (5.66 g, 142 mmol, 4 eq) in H₂O (71 mL) at 5° C. The mixture was stirred at 25° C. for 2 hours. Upon completion, the THF was evaporated under vacuum. The pH of the mixture was adjusted to 3 with 1 M HCl and extracted with EtOAc (3×70 mL). The organic layers were dried over Na₂SO₄ and concentrated under vacuum to give 2-(methoxymethyl)prop-2-enoic acid (3.4 g, 26.4 mmol, 75% yield, 90% purity) as a light yellow liquid which was used directly in the next step without further purification.

¹H NMR (400 MHz, chloroform-d) δ=6.45 (d, J=1.2 Hz, 1H), 5.98 (q, J=1.6 Hz, 1H), 4.16 (t, J=1.2 Hz, 2H), 3.42 (s, 3H).

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile To a solution of 2-(methoxymethyl)prop-2-enoic acid (175 mg, 1.50 mmol, 2 eq) and DIEA (389 mg, 3.01 mmol, 524 µL, 4 eq) in DCM (8 mL) was added HATU (429 mg, 1.13 mmol, 1.5 eq) at −40° C. After stirred at −40° C. for 10 minutes, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 400 mg, 752 umol, 1 eq) was added into the mixture. The mixture was stirred at −40° C. for 20 minutes, 0° C. for 0.5 hour and 25° C. for 1 hour. Upon completion, to the mixture was added water (10 mL) and extracted with DCM (2×20 mL). The combined organic layers were dried over Na₂SO₄, filtered and concentrated under vacuum. The residue was purified by chromatography (Al₂O₃, EtOAc/MeOH 100/1 to 40/1) and purified by prep-HPLC (column: Gemini 150*25 5 u; mobile phase: [water (0.05% ammonia hydroxide v/v)—ACN]; B %: 50%-80%, 12 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(methoxymethyl)prop-2-enoyl]piperazin-2-yl]acetonitrile (EXAMPLE 14, 73.0 mg, 116 umol, 15% yield, 98.9% purity) as a off-white solid. LCMS [ESI, M+1]:630.

SFC condition: Column: Chiralpak AS-3 100×4.6 mm I.D., 3 um Mobile phase: methanol (0.05% DEA) in CO₂ from 5% to 40% Flow rate: 3 mL/min Wavelength: 220 nm.

¹H NMR (400 MHz, chloroform-d) δ=7.76 (br d, J=8 Hz, 1H), 7.62 (t, J=7.6 Hz, 1H), 7.52 (d, J=7.6 Hz, 1H), 7.45 (td, J=7.6, 13.2 Hz, 1H), 7.37-7.30 (m, 1H), 7.26-7.17 (m, 1H), 5.51 (s, 1H), 5.32 (br s, 1H), 5.19-4.58 (m, 1H), 4.48-4.34 (m, 2H), 4.23-4.07 (m, 4H), 4.06-3.78 (m, 3H), 3.64-3.55 (m, 1H), 3.39 (s, 3H), 3.36-2.72 (m, 8H), 2.71-2.53 (m, 2H), 2.47 (s, 3H), 2.35-2.22 (m, 1H), 2.14-1.98 (m, 1H), 1.90-1.73 (m, 3H).

Example 15

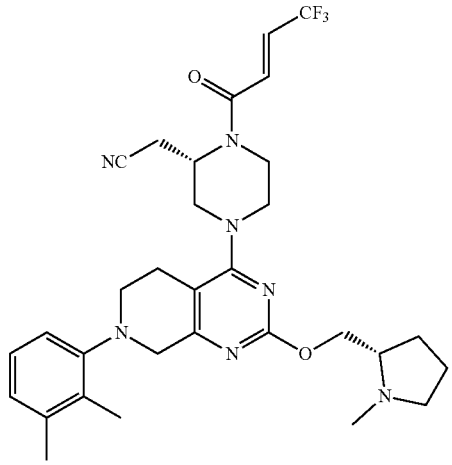 [SMILES: Cc1cccc(N2CCc3c(nc(OC[C@@H]4CCCN4C)nc3N3CCN(C(=O)/C=C/C(F)(F)F)[C@@H](CC#N)C3)C2)c1C]

2-((S)-4-(7-(2,3-dimethylphenyl)-2-(((S)-1-methyl-pyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile

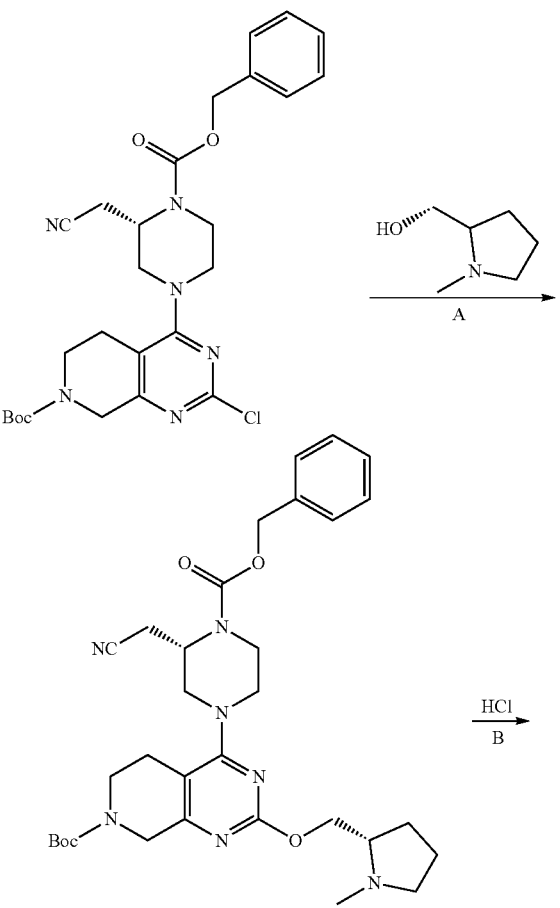

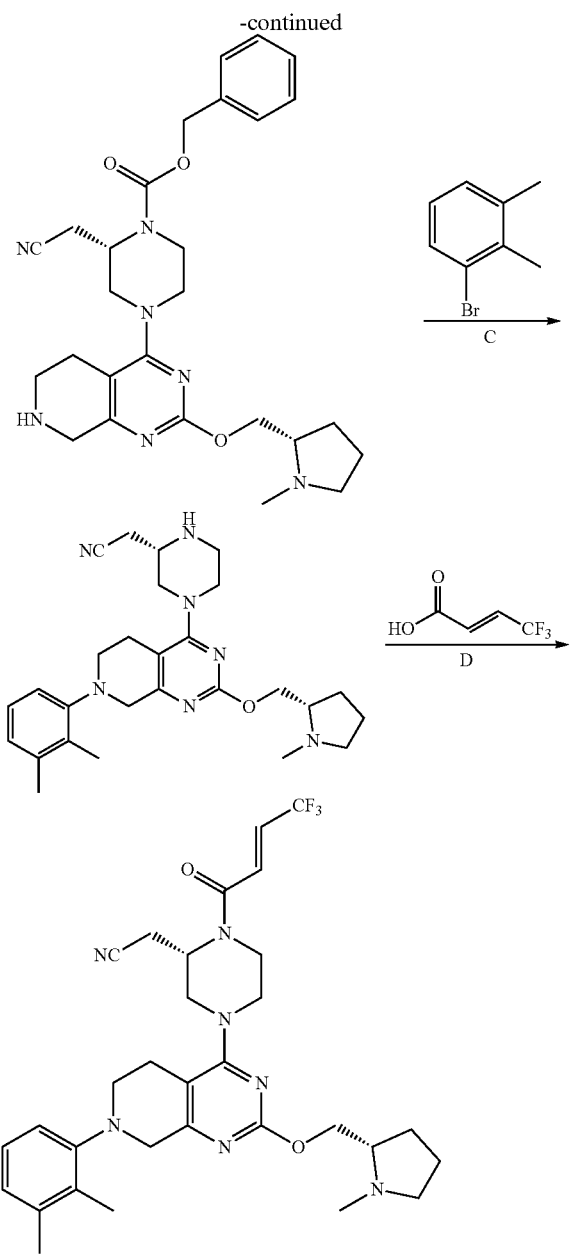

Step A: 2-tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate In a round bottom flask, a solution of tert-butyl (S)-4-(4-((benzyloxy)carbonyl)-3-(cyanomethyl)piperazin-1-yl)-2-chloro-5,8-dihydropyrido[3,4-d]pyrimidine-7(6H)-carboxylate (5 g, 9.487 mmol) in dioxane (94.87 ml, 9.487 mmol) was sparged with argon and (S)-(1-methylpyrrolidin-2-yl)methanol (3.278 g, 28.46 mmol), Cs$_2$CO$_3$ (9.273 g, 28.46 mmol), Methanesulfonato(2-dicyclohexylphosphino-2',6'-di-i-propoxy-1,1'-biphenyl)(2'-methylamino-1,1'-biphenyl-2-yl)palladium(II) (0.8078 g, 0.9487 mmol) were sequentially added under Argon and sparged for an additional 5 minutes. The reaction mixture was capped and heated at 100° C. overnight. The reaction was filtered through GF/F paper and concentrated in vacuo. The concentrate was purified on the Combi Flash (0-12% MeOH in DCM with 2% NH$_4$OH) to provide tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (5.425 g, 8.508 mmol, 89.68% yield). ESI+APCI MS m/z 606.4 [M+H]$^+$.

Step B: Benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate tert-butyl 4-((S)-4-((benzyloxy)carbonyl)-3-(cyanomethyl)piperazin-1-yl)-2-(((S)-1-methylpyrrolidin-2-yl)methoxy)-5,8-dihydropyrido[3,4-d]pyrimidine-7(6H)-carboxylate (5.4 g, 8.915 mmol) was dissolved in dichloromethane (89.15 ml, 8.915 mmol) and treated with Hydrochloric Acid (4.0M solution in 1,4-dioxane) (11.14 ml, 44.57 mmol). The reaction stirred at room temperature for 1 hour. The reaction was diluted with more DCM and 1M NaOH and the layers separated. The organics were next washed with brine, dried over Na$_2$SO$_4$ and concentrated in vacuo to give benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol, 96.82% yield). ESI+APCI MS m/z 506.3 [M+H]$^+$.

Step C: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile In a round bottom flask, a solution of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (4.364 g, 8.631 mmol) in dioxane (43.15 ml, 8.631 mmol) was sparged with Argon for 5 minutes. 1-Bromo-2,3-dimethylbenzene (5.851 ml, 43.15 mmol), Cs$_2$CO$_3$ (14.06 g, 43.15 mmol), and Methanesulfonato(2-dicyclohexylphosphino-2',6'-di-i-propoxy-1,1'-biphenyl)(2'-methylamino-1,1'-biphenyl-2-yl)palladium(II) (0.7348 g, 0.8631 mmol) were sequentially added under Argon and sparged for an additional 5 min. The reaction mixture was capped and heated at 100° C. ON. The reaction was cooled to room temperature. Ethyl acetate was added and the reaction filtered through GF/F paper and concentrated in vacuo. The concentrate was purified twice via normal phase chromatography on the CombiFlash using 0-15% MeOH in DCM with 2% NH$_4$OH as eluent. Fractions containing desired product were collected and concentrated in vacuo to give 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (0.411 g, 0.8641 mmol, 100.1% yield). ESI+APCI MS m/z 476.3 [M+H]$^+$.

Step D: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile To a solution of 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (200 mg, 0.420 mmol), 4,4,4-Trifluorocrotonic Acid (118 mg, 0.841 mmol), DIEA (367 μL, 2.10 mmol) in DCM (4205 μl, 0.420 mmol) was added HATU (240 mg, 0.631 mmol) and the resulting mixture was stirred at room temperature for 5 hours. The reaction mixture was washed with Brine and the aqueous layer extracted with DCM (2×). The combined organic layers were dried over Na₂SO₄, concentrated, diluted in 60:40 ACN:H₂O and purified on the Gilson (reverse prep HPLC), eluting with 5-->95% ACN/0.1% TFA in water/0.1% TFA. Fractions containing product were combined and free based with saturated bicarb and the organics extracted with DCM. The organics were dried over Na₂SO₄ and concentrated in vacuo to give title compound 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile (EXAMPLE 15, 28 mg, 0.0468 mmol, 11.1% yield). ESI+APCI MS m/z 598.3 [M+H]⁺.

Example 16

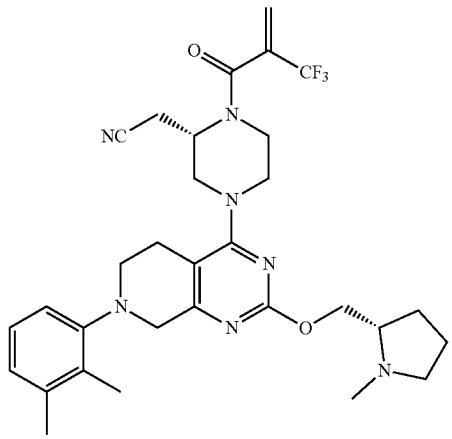 [SMILES: C=C(C(=O)N1CCN(c2nc(OC[C@@H]3CCCN3C)nc3c2CCN(c2cccc(C)c2C)C3)C[C@@H]1CC#N)C(F)(F)F]

2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile The title compound was prepared following Example 15 substituting 2-(Trifluoromethyl)propenoic acid for 4,4,4-Trifluorocrotonic Acid in Step D. ESI+APCI MS m/z 598.3 [M+H]⁺.

Example 17

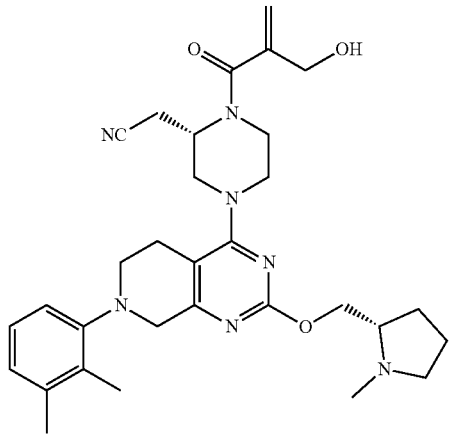 [SMILES: C=C(CO)C(=O)N1CCN(c2nc(OC[C@@H]3CCCN3C)nc3c2CCN(c2cccc(C)c2C)C3)C[C@@H]1CC#N]

2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-(2-(hydroxymethyl)acryloyl)piperazin-2-yl)acetonitrile 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-(2-(hydroxymethyl)acryloyl)piperazin-2-yl)acetonitrile The title compound was prepared following Example 15 substituting 2-(hydroxymethyl)prop-2-enoic acid for 4,4,4-Trifluorocrotonic Acid in Step D. ESI+APCI MS m/z 560.3 [M+H]⁺.

Example 18

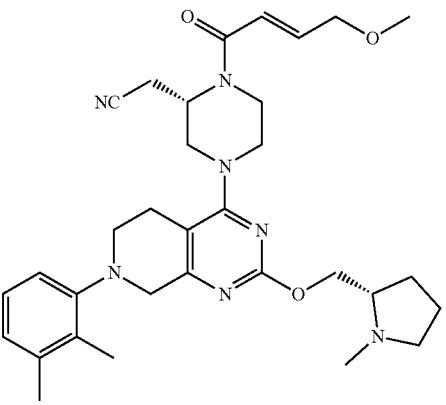 [SMILES: COC/C=C/C(=O)N1CCN(c2nc(OC[C@@H]3CCCN3C)nc3c2CCN(c2cccc(C)c2C)C3)C[C@@H]1CC#N]

2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile

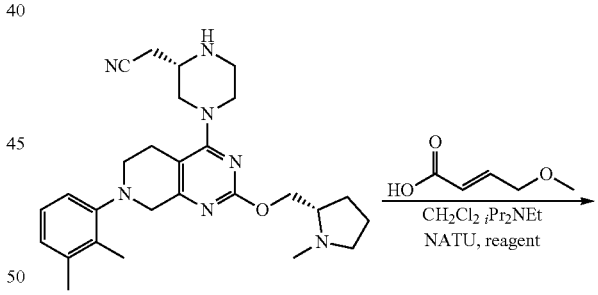

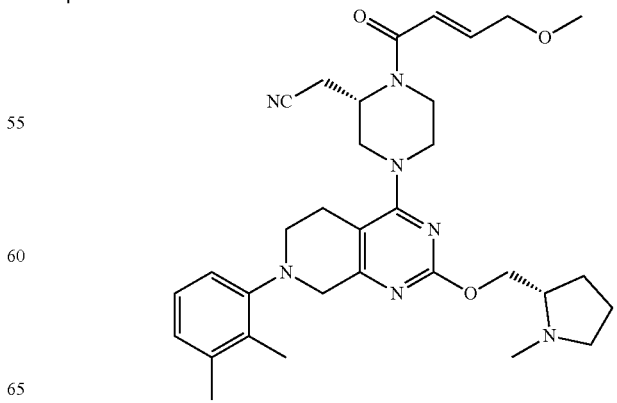

Step A: 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile To a solution of 2-((S)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile (50 mg, 0.1051 mmol) in DCM (1 mL) was added (E)-4-methoxybut-2-enoic acid (24.41 mg, 0.2102 mmol), N-ethyl-N-isopropylpropan-2-amine (0.03662 ml, 0.2102 mmol) and O-(7-azabenzotriazol-1-yl)-N,N,N',N'-tetramethyluronium $PF_6$ (59.96 mg, 0.1577 mmol) and the reaction mixture stirred at room temperature for 4 hours. Water (1 mL) was next added and the reaction mixture stirred for 5 minutes. The mixture was divided between EtOAc (10 mL) and 0.5M $NaHCO_3$ (5 mL) and the layers separated. The organics were washed with brine (3 mL), dried over $Na_2SO_4$ and evaporated in vacuo. The residue was chromatographed on silica gel using 3% MeOH+0.3% $NH_4OH$ to 4% MeOH+0.4% $NH_4OH$ as eluent to give title compound (EXAMPLE 18, 26 mg, 43%). ESI+APCI MS m/z 574.4 $[M+H]^+$.

Example 19

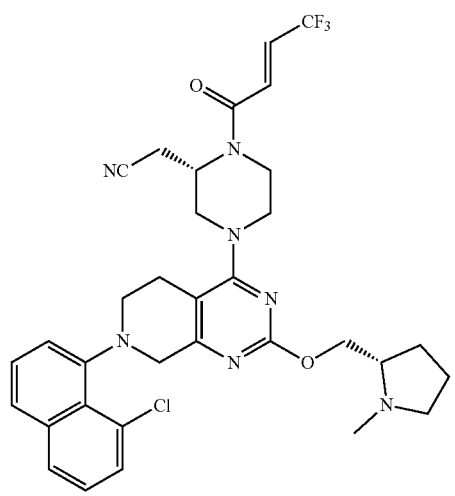 [SMILES: CN1CCC[C@H]1COc1nc2c(c(N3CCN(C(=O)/C=C/C(F)(F)F)[C@@H](CC#N)C3)n1)CCN(c1cccc3cccc(Cl)c13)C2]

2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile

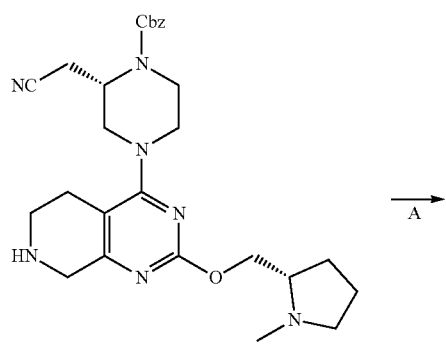

A

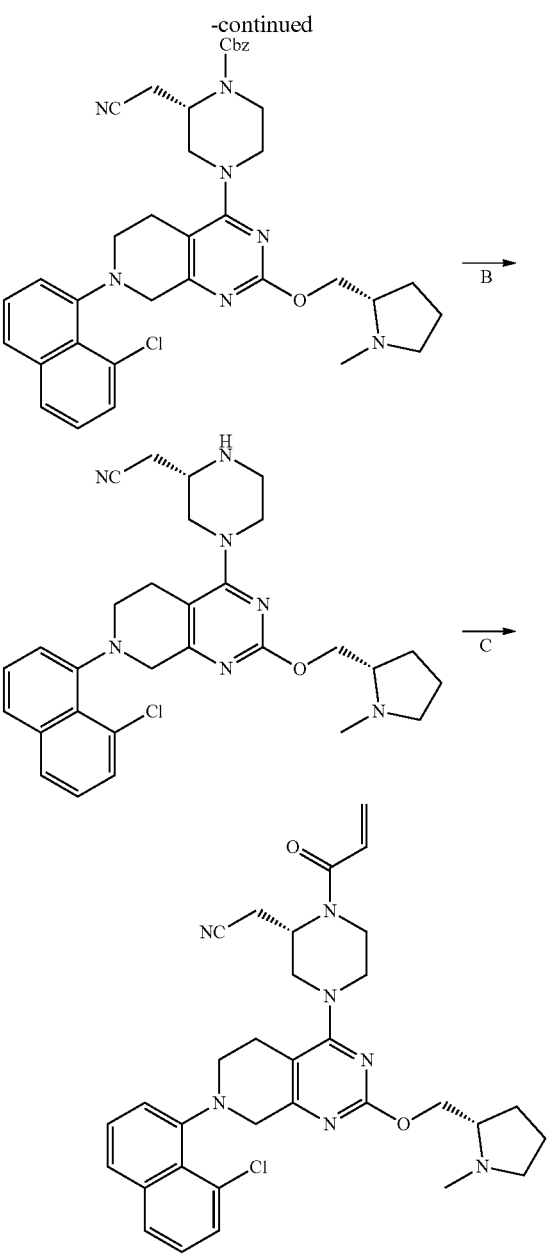

Step A: Benzyl (S)-4-(7-(8-chloronaphthalen-1-yl)-2-4(S)-1-methylpyrrolidin-2-yl)methoxy)-5,6,7,8-tetrahydropyrido[3,4-d]pyrimidin-4-yl)-2-(cyanomethyl)piperazine-1-carboxylate To a solution of benzyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (0.6 g, 1.2 mmol) in dioxanes (10 mL) was added 1-bromo-8-chloronaphthalene (0.37 g, 1.5 mmol) and the reaction degassed with Ar for 15 minutes followed by addition of $Cs_2CO_3$ (1.2 g, 3.6 mmol), $Pd_2(dba)_3$ (0.22 g, 0.24 mmol) and 2-Dicyclohexylphosphino-2',6'-di-i-propoxy-1,1'-biphenyl (0.11 g, 0.24 mmol) and the reaction heated to 100° C. for overnight. The reaction was next filtered through GFF paper and the filtrated concentrated in vacuo. The residue was next chromatographed using 1→10% (MeOH+2% $NH_4OH$)/DCM to give benzyl (S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (0.20 g, 0.30 mmol, 25% yield). ESI+APCI MS m/z 666.2 [M+H]$^+$.

Step B: 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A solution of benzyl (S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-2-(cyanomethyl)piperazine-1-carboxylate (0.17 g, 0.255 mmol) in THF (30 mL) was purged with N$_2$ followed by addition of Pd/C (0.0272 g, 0.255 mmol). The reaction was evacuated by vacuum and backfilled with H$_2$ 3× and the mixture was stirred for 3 days at room temperature. The reaction was again purged with N$_2$ followed by filtering through celite and the filtrate concentrated in vacuo. The material used crude in the next reaction. ESI+APCI MS m/z 532.2 [M+H]$^+$.

Step C: 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile To a solution of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (0.055 g, 0.10 mmol) in DCM (20 mL) was added N-ethyl-N-isopropylpropan-2-amine (0.040 g, 0.31 mmol), (E)-4,4,4-trifluorobut-2-enoic acid (0.017 g, 0.12 mmol) and 1-Propanephosphonic acid cyclic anhydride (0.033 g, 0.10 mmol) and the reaction stirred at room temperature for 30 minutes. Next additional TEP3 and acid (0.24 mmol) were added and and the reaction an addition 1 hour. The organics were next washed with 1 N NaOH, brine, dried over MgSO$_4$ and concentrated in vacuo. The material was chromatographed 2× on normal phase silica (1→10% (MeOH+2% NH$_4$OH)/DCM) followed by purification by gilson reverse prep HPLC using 5495% ACN/water with 0.1% TFA as additive. The PURE fractions were poured into basic water and extracted into EtOAc. The organics were washed with brine, dried over MgSO$_4$ and concentrated in vacuo to give title compound 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile (EXAMPLE 19, 0.0094 g, 0.014 mmol, 14% yield). ESI+APCI MS m/z 654.2 [M+H]$^+$.

Example 20

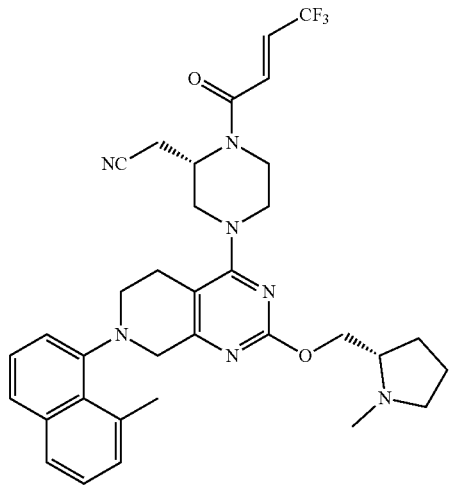 [SMILES: Cc1cccc2cccc(N3CCc4c(nc(OC[C@@H]5CCCN5C)nc4N4CCN(C(=O)/C=C/C(F)(F)F)[C@@H](CC#N)C4)C3)c12]

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile

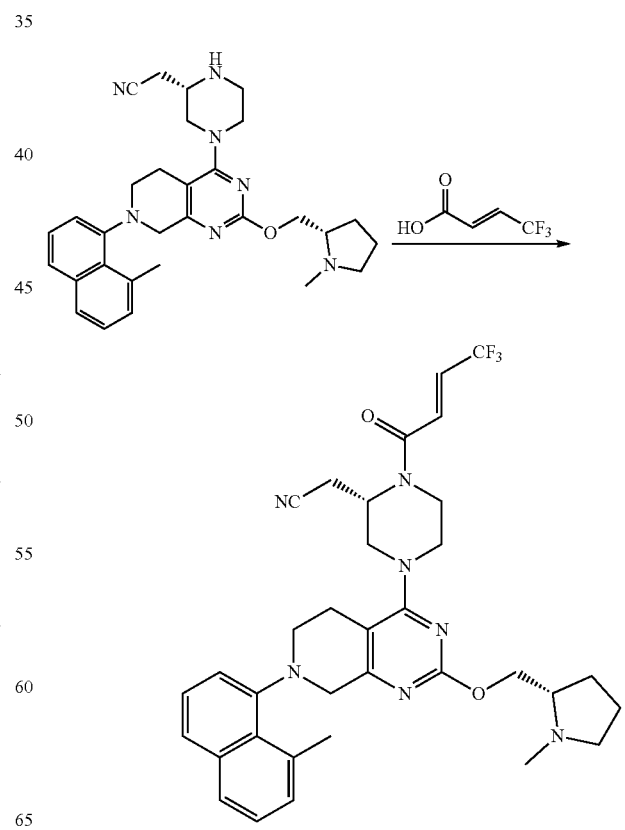

Step A: 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile At 0° C., to a 25 mL RBF containing N,N-dimethylformamide (2932 µl, 0.293 mmol) was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (150 mg, 0.293 mmol) and Hunig's base (102 µl, 0.586 mmol). The reaction mixture was vigorously stirred while (E)-4,4,4-trifluorobut-2-enoic acid (49.3 mg, 0.352 mmol) was added in one portion. Next, 1-Propanephosphonic acid cyclic anhydride (262 µl, 0.440 mmol) was added slowly to the stirring mixture. The reaction was stirred for 2 hours at 0° C. The reaction was treated with basic water and the aqueous layer extracted with EtOAc (3×). The combined organics were concentrated in vacuo and resuspended in a 60:40 mixture of ACN:H₂O and purified on the Gilson (reverse prep HPLC), eluting with 5-->95% ACN/0.1% TFA in water/0.1% TFA. Fractions containing product were combined and partitioned between saturated bicarb and DCM. The aqueous layer was extracted with DCM two more times. The organic layers were combined, dried over Na₂SO₄ and concentrated in vacuo to give title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-4,4,4-trifluorobut-2-enoyl)piperazin-2-yl)acetonitrile (EXAMPLE 20, 74.5 mg, 0.118 mmol, 40.1% yield). ESI+APCI MS m/z 634.3 [M+H]⁺.

Example 21

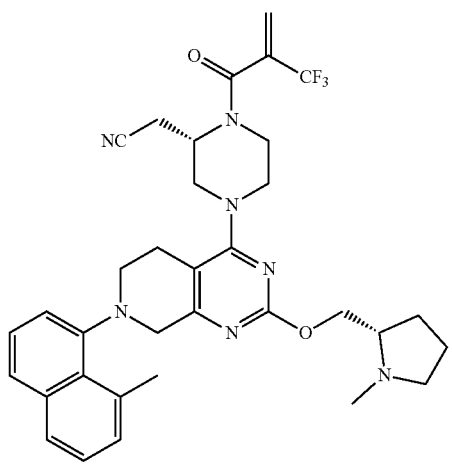 [SMILES: C=C(C(=O)N1CCN(c2nc(OC[C@@H]3CCCN3C)nc3c2CCN(c2cccc4cccc(C)c24)C3)C[C@@H]1CC#N)C(F)(F)F]

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(2-(trifluoromethyl)acryloyl)piperazin-2-yl)acetonitrile The title compound was prepared following Example 20 substituting 2-(trifluoromethyl)acrylic acid for (E)-4,4,4-trifluorobut-2-enoic acid in Step A. ESI+APCI MS m/z 634.2 [M+H]⁺.

Example 22

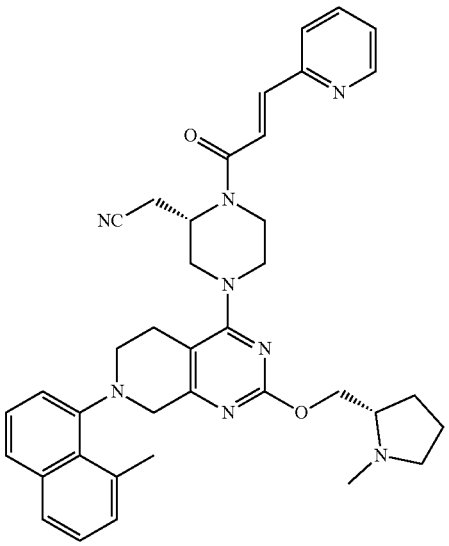 [SMILES: Cc1cccc2cccc(N3CCc4c(nc(OC[C@@H]5CCCN5C)nc4N4CCN(C(=O)/C=C/c5ccccn5)[C@@H](CC#N)C4)C3)c12]

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-2-yl)acryloyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-2-yl)acryloyl)piperazin-2-yl)acetonitrile The title compound was prepared following Example 20 substituting 3-(Pyridin-2-yl)acrylic acid for (E)-4,4,4-trifluorobut-2-enoic acid in Step A. ESI+APCI MS m/z 643.3 [M+H]⁺.

Example 23

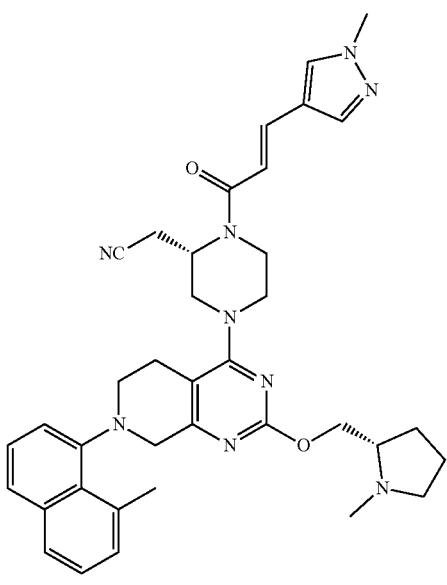 [SMILES: Cc1cccc2cccc(N3CCc4c(nc(OC[C@@H]5CCCN5C)nc4N4CCN(C(=O)/C=C/c5cnn(C)c5)[C@@H](CC#N)C4)C3)c12]

2-((S)-1-((E)-3-(1-methyl-1H-pyrazol-4-yl)acryloyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-((E)-3-(1-methyl-1H-pyrazol-4-yl)acryloyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile The title compound was prepared following Example 20 substituting (2E)-3-(1-Methyl-1H-pyrazol-4-yl)acrylic acid for (E)-4,4-trifluorobut-2-enoic acid in Step A. ESI+APCI MS m/z 646.4 [M+H]⁺.

Example 24

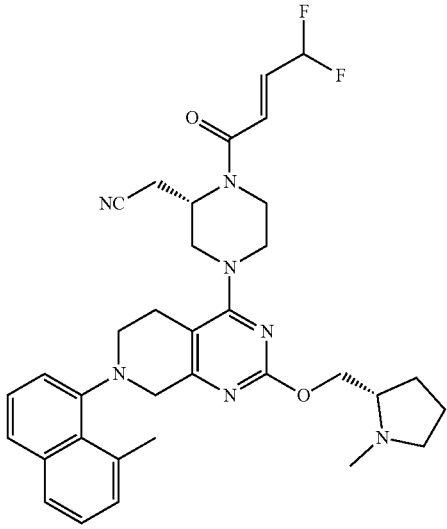 [SMILES: Cc1cccc2cccc(N3CCc4c(nc(OC[C@@H]5CCCN5C)nc4N4CCN(C(=O)/C=C/C(F)F)[C@@H](CC#N)C4)C3)c12]

2-((S)-1-((E)-4,4-difluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-((E)-4,4-difluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile The title compound was prepared following Example 20 substituting 4,4-Difluorobut-2-enoic acid for (E)-4,4-trifluorobut-2-enoic acid in Step A. ESI+APCI MS m/z 616.3 [M+H]⁺.

Example 25

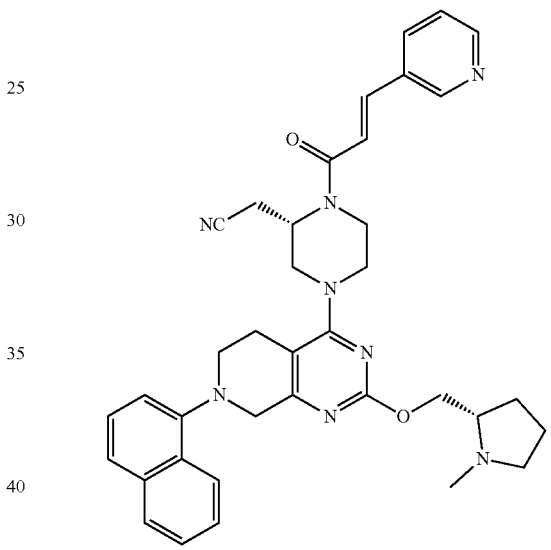

2-((S)-4-(2-(((S)-1-methylpiperidin-2-yl)methoxy)-7-(naphthalen-1-yl)-5,6,7,8-tetrahydropyrido[3,4-d]pyrimidin-4-yl)-1-((E)-3-(pyridin-3-yl)acryloyl)piperazin-2-yl)acetonitrile

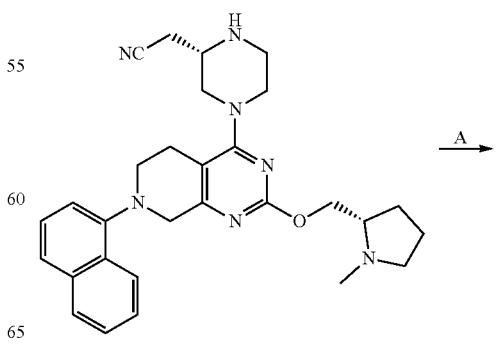
A→

-continued

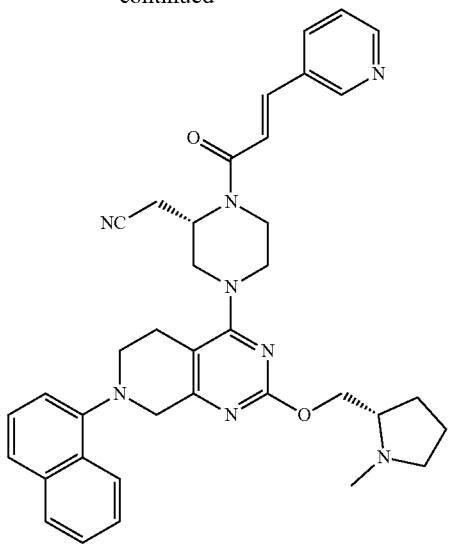

Step A

To a solution of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (0.12 g, 0.23 mmol) in DCM (10 mL)N-ethyl-N-isopropylpropan-2-amine (0.13 ml, 0.70 mmol), (E)-3-(pyridin-3-yl)acrylic acid (0.070 g, 0.47 mmol) and 2,4,6-tripropyl-1,3,5,2,4,6-trioxatriphosphinane 2,4,6-trioxide (0.30 g, 0.47 mmol) and the reaction stirred at room temperature for 3 hours. The reaction was next poured into 1N NaOH and the layers separated. The organics were next washed with brine, dried over MgSO₄ and concentrated in vacuo. The material was next purified by Gilson reverse prep HPLC eluting with 5→495 ACN/water with 0.1% TFA as modifier. Fractions containing product were poured into 1N NaOH and the aqueous layer extracted with EtOAc (3×). The combined organics were washed with brine, dried over MgSO₄ and concentrated in vacuo to give title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-3-yl)acryloyl)piperazin-2-yl)acetonitrile (EXAMPLE 25, 0.040 g, 0.062 mmol, 27% yield). ESI+APCI MS m/z 643.3 [M+H]⁺.

Example 26

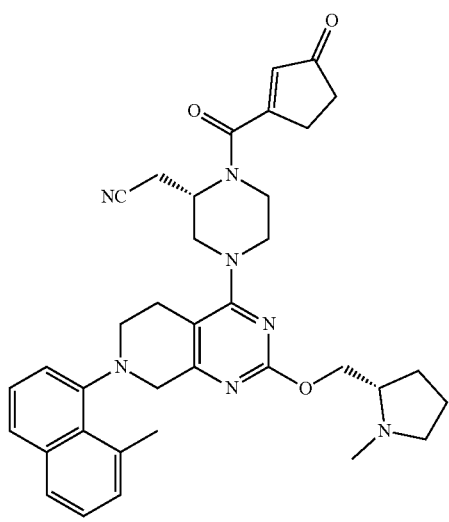 [SMILES: Cc1cccc2cccc(N3CCc4c(nc(OC[C@@H]5CCCN5C)nc4N4CCN(C(=O)C5=CC(=O)CC5)[C@@H](CC#N)C4)C3)c12]

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile

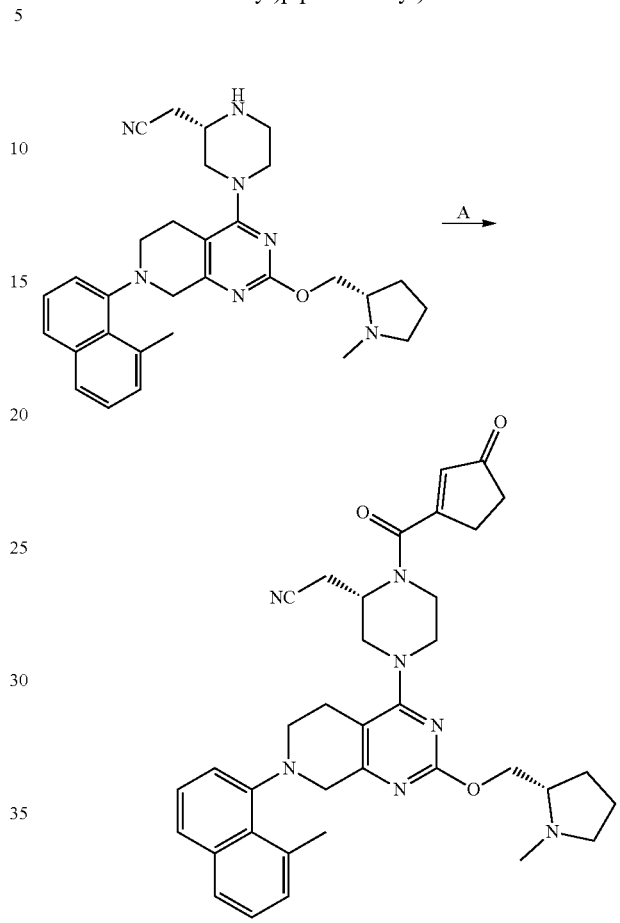

Step A: 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (30 mg, 0.05863 mmol) and 3-oxocyclopent-1-enecarboxylic acid (9.612 mg, 0.07622 mmol) were diluted with DMF (400 uL) followed by the addition of DIEA (20.48 µl, 0.1173 mmol) and 1-propanephosphonic acid cyclic anhydride (52.35 µl, 0.08795 mmol). After stirring for 12 hours, the reaction was diluted with ethyl acetate and saturated sodium bicarbonate. The layers were separated and the ethyl acetate was dried over MgSO₄, filtered and concentrated. The material was purified on silica gel eluting with 10% methanol/DCM (1% NH4OH) to afford title compound 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-(3-oxocyclopent-1-ene-1-carbonyl)piperazin-2-yl)acetonitrile (EXAMPLE 26, 2.3 mg, 0.003711 mmol, 6.329% yield). ESI+APCI MS m/z 620.3 [M+H]⁺.

Example 27

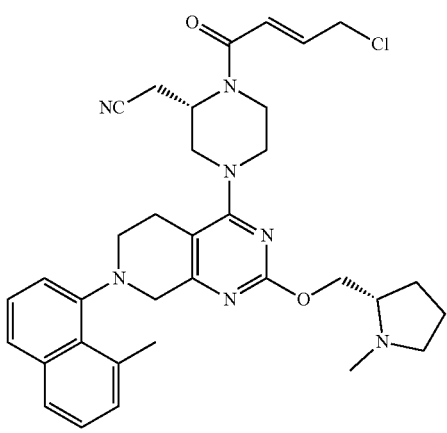

2-((S)-1-((E)-4-chlorobut-2-enoyl)-4-(7-(8-methyl-naphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

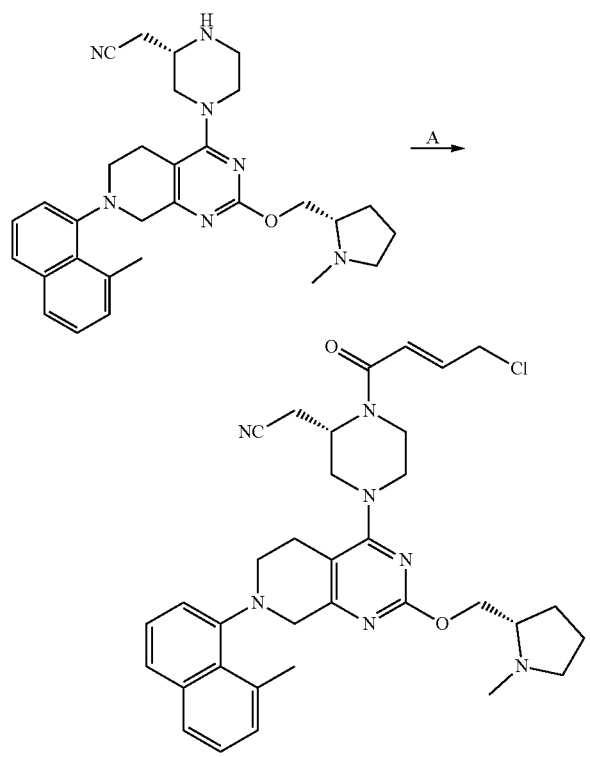

Step A: 2-((S)-1-((E)-4-chlorobut-2-enoyl)-4-(7-(8-methylnaphthalen-1-yl)-2-4(S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (30 mg, 0.05863 mmol) and gamma-chlorocrotonic acid (10.60 mg, 0.08795 mmol) were diluted with DMF (400 uL) followed by the addition of DIEA (20.48 µl, 0.1173 mmol) and 1-propane-phosphonic acid cyclic anhydride (55.84 µl, 0.09381 mmol). After stirring for 12 hours, the reaction was diluted with ethyl acetate and saturated sodium bicarbonate. The layers were separated and the ethyl acetate was dried over MgSO4, filtered and concentrated. The material was purified on silica gel eluting with 10% methanol/DCM (1% NH4OH) to afford title compound 2-((S)-1-((E)-4-chlorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 27, 4.5 mg, 0.007327 mmol, 12.50% yield). ESI+APCI MS m/z 614.3 [M+H]$^+$.

Example 28

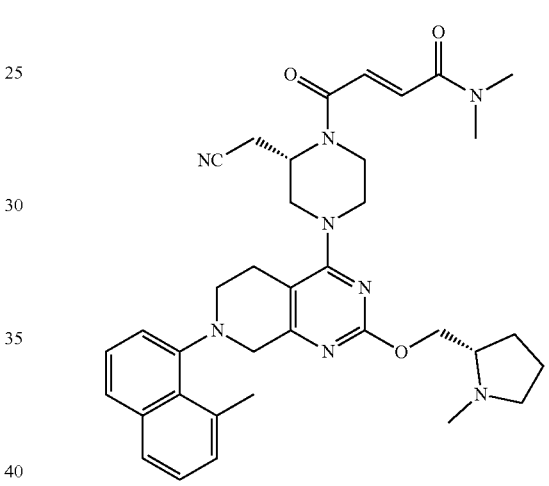

(E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-N,N-dimethyl-4-oxobut-2-enamide

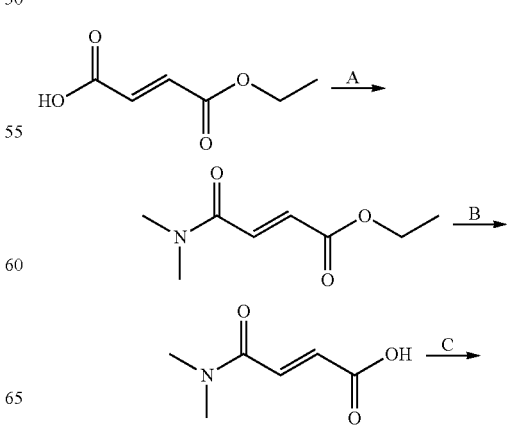

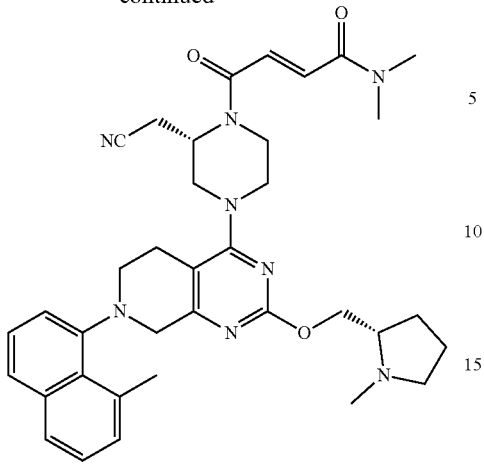

Step A: Ethyl (E)-4-(dimethylamino)-4-oxobut-2-enoate

Fumaric acid monoethyl ester (442 mg, 3.07 mmol) was diluted with DCM (5 mL) followed by the addition of oxalyl chloride (1533 μl, 3.07 mmol) and 1 drop of DMF. After stirring for 15 minutes, dimethylamine (4600 μl, 9.20 mmol) was added and the reaction was stirred for 3 hours. The reaction was diluted with ethyl acetate and water. The layers were separated and the ethyl acetate was dried over MgSO$_4$, filtered and concentrated. The material was purified on silica gel eluting with 10-70% ethyl acetate/hexanes to afford ethyl (E)-4-(dimethylamino)-4-oxobut-2-enoate (382 mg, 2.23 mmol, 72.8% yield). ESI+APCI MS m/z 172.1 [M+H]$^+$.

Step B: (e)-4-(dimethylamino)-4-oxobut-2-enoic Acid

Ethyl (E)-4-(dimethylamino)-4-oxobut-2-enoate (382 mg, 2.23 mmol) was diluted with methanol (8 mL) followed by the addition of NaOH (4463 μl, 8.93 mmol). After stirring for 4 hours, the reaction was diluted with 2N HCl (4.5 mL) and extracted with ethyl acetate. The ethyl acetate was dried over MgSO$_4$, filtered and concentrated to afford (E)-4-(dimethylamino)-4-oxobut-2-enoic acid.

Step C: (E)-4-((S)-2-(cyanomethyl)-4-(7-(8-methyl-naphthalen-1-yl)-2-(((S)-1-methylpyrrolidin-2-yl) methoxy)-5,6,7,8-tetrahydropyrido[3,4-d]pyrimidin-4-yl)piperazin-1-yl)-N,N-dimethyl-4-oxobut-2-enamide 2-((S)-4-(7-(8-methylnaphthalen-1-yl)-2-(((S)-1-methylpyrrolidin-2-yl)methoxy)-5,6,7,8-tetrahydropyrido[3,4-d] pyrimidin-4-yl)piperazin-2-yl)acetonitrile (30 mg, 0.05863 mmol) was diluted with DMF followed by the addition of (E)-4-(dimethylamino)-4-oxobut-2-enoic acid (10.07 mg, 0.07036 mmol), DIEA (20.48 μl, 0.1173 mmol) and 1-propanephosphonic acid cyclic anhydride (52.35 μl, 0.08795 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH4OH) to afford title compound (E)-4-((S)-2-(cyanomethyl)-4-(7-(8-methylnaphthalen-1-yl)-2-(((S)-1-methylpyrrolidin-2-yl) methoxy)-5,6,7,8-tetrahydropyrido[3,4-d]pyrimidin-4-yl) piperazin-1-yl)-N,N-dimethyl-4-oxobut-2-enamide (EXAMPLE 28, 3.7 mg, 0.005810 mmol, 9.910% yield). ESI+APCI MS m/z 637.3 [M+H]$^+$.

Example 29

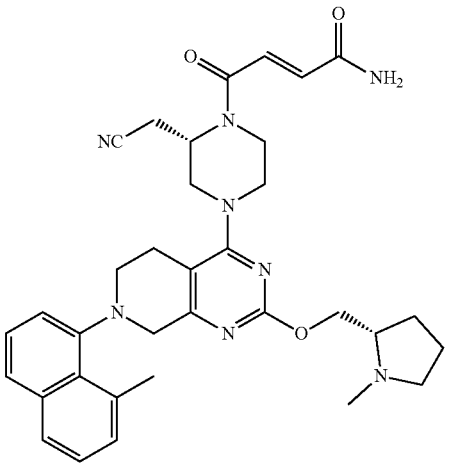 [SMILES: Cc1cccc2cccc(N3CCc4c(nc(OC[C@@H]5CCCN5C)nc4N4CCN(C(=O)/C=C/C(N)=O)[C@@H](CC#N)C4)C3)c12]

(E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enamide

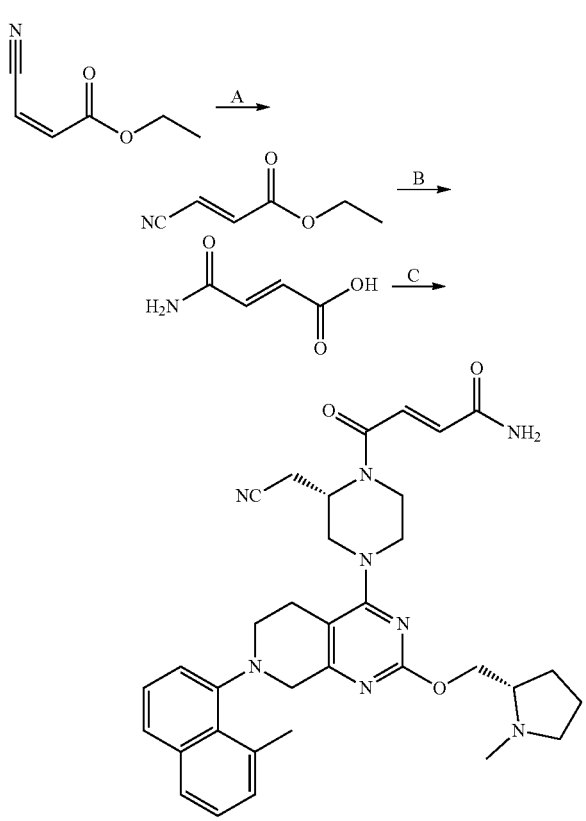

Step A: Ethyl (E)-3-cyanoacrylate

Ethyl cis-(beta-cyano)acrylate (1.0 g, 7.99 mmol) was diluted with ACN (30 mL), placed under nitrogen and heated to reflux for 3 days. The reaction was allowed to cool and then concentrated. The material was purified on silica gel eluting with hexanes to afford ethyl (E)-3-cyanoacrylate (300 mg, 2.40 mmol, 30.0% yield).

Step B: (E)-4-amino-4-oxobut-2-enoic Acid

Ethyl (E)-3-cyanoacrylate (300 mg, 2.40 mmol) was diluted with HCl (3996 μl, 24.0 mmol). The reaction was placed under nitrogen and heated to 100° C. for 4 hours. The reaction was allowed to cool and then concentrated to afford (E)-4-amino-4-oxobut-2-enoic acid (214 mg, 1.86 mmol, 77.6% yield).

Step C: (E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enamide 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (20 mg, 0.039 mmol), HATU (30 mg, 0.078 mmol) and (E)-4-amino-4-oxobut-2-enoic acid (9.0 mg, 0.078 mmol) were diluted with DMF (400 uL) followed by the addition of DIEA (14 μl, 0.078 mmol). After stirring for 12 hours, the reaction was diluted with ethyl acetate and saturated sodium bicarbonate. The layers were separated and the ethyl acetate was dried over MgSO₄, filtered and concentrated. The material was purified on silica gel eluting with 10% methanol/DCM (1% NH4OH) to afford title compound (E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enamide (EXAMPLE 29, 2.9 mg, 0.0048 mmol, 12% yield). ESI+ APCI MS m/z 609.3 [M+H]⁺.

Example 30

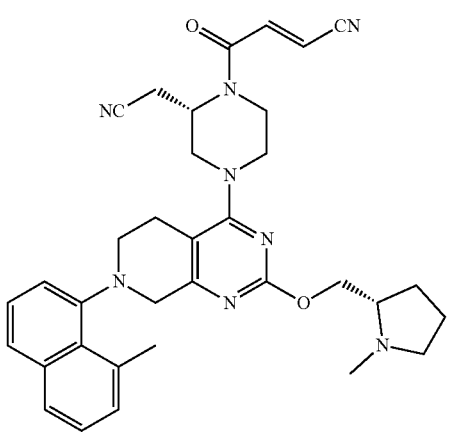 [SMILES: Cc1cccc2cccc(N3CCc4c(nc(OC[C@@H]5CCCN5C)nc4N4CCN(C(=O)/C=C/C#N)[C@@H](CC#N)C4)C3)c12]

(E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile

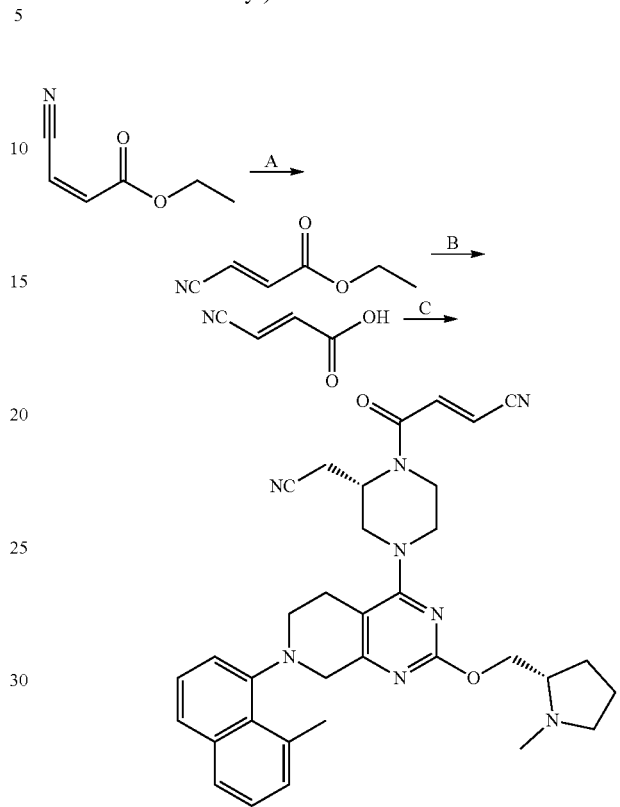

Step A: Ethyl (E)-3-cyanoacrylate

Ethyl cis-(beta-cyano)acrylate (1.0 g, 7.99 mmol) was diluted with ACN (30 mL), placed under nitrogen and heated to reflux for 3 days. The reaction was allowed to cool and then concentrated. The material was purified on silica gel eluting with hexanes to afford ethyl (E)-3-cyanoacrylate (300 mg, 2.40 mmol, 30.0% yield).

Step B: (E)-3-cyanoacrylic Acid

Ethyl (E)-3-cyanoacrylate (10 mg, 0.080 mmol) was diluted with HCl (133 μl, 0.80 mmol), placed under nitrogen and heated to 100° C. After stirring for 15 minutes the reaction was concentrated to afford (E)-3-cyanoacrylic acid (7.5 mg, 0.077 mmol, 97% yield).

Step C: (E)-4-((S)-2-(cyanomethyl)-4-(7-(8-methylnaphthalen-1-yl)-24(S)-1-methylpyrrolidin-2-yl)methoxy)-5,6,7,8-tetrahydropyrido[3,4-d]pyrimidin-4-yl)piperazin-1-yl)-4-oxobut-2-enenitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (20 mg, 0.03909 mmol) and (E)-3-cyanoacrylic acid (5.312 mg, 0.05472 mmol) were diluted with DMF (400 uL) followed by the addition of DIEA (13.65 μl, 0.07817 mmol) and 1-propanephosphonic acid cyclic anhydride (34.90 μl, 0.05863 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH4OH) to afford title compound (E)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile (EXAMPLE 30, 3.5 mg, 0.005925 mmol, 15.16% yield). ESI+APCI MS m/z 591.3 [M+H]$^+$.

Example 31

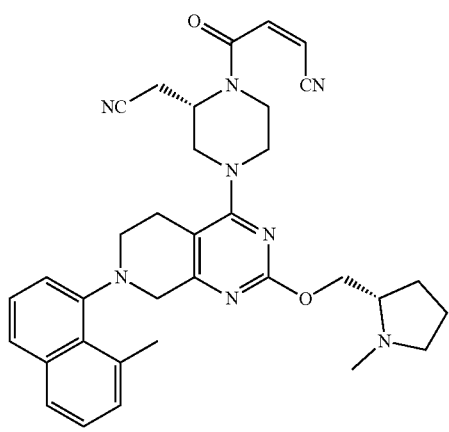 [SMILES: Cc1cccc2cccc(N3CCc4c(nc(OC[C@@H]5CCCN5C)nc4N4CCN(C(=O)/C=C\C#N)[C@@H](CC#N)C4)C3)c12]

(Z)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile

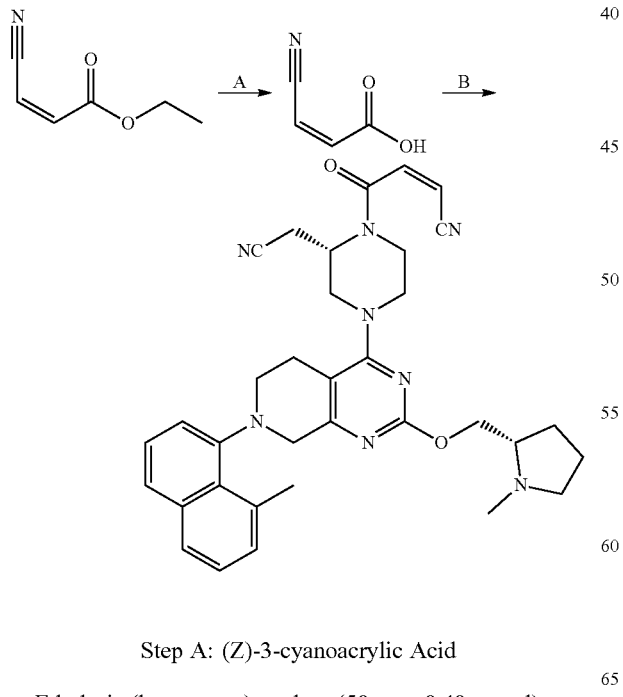

Step A: (Z)-3-cyanoacrylic Acid

Ethyl cis-(beta-cyano)acrylate (50 mg, 0.40 mmol) was diluted with HCl (200 µl, 1.2 mmol), placed under nitrogen and heated to 100° C. After stirring for 1 minute the reaction was cooled and concentrated to afford (Z)-3-cyanoacrylic acid (35 mg, 0.36 mmol, 90% yield).

Step B: (Z)-4-(S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (20 mg, 0.03909 mmol) and (Z)-3-cyanoacrylic acid (6.071 mg, 0.06254 mmol) were diluted with DMF (400 uL) followed by the addition of DIEA (13.65 µl, 0.07817 mmol) and 1-propanephosphonic acid cyclic anhydride (39.56 µl, 0.06645 mmol). After stirring for 12 hours, the reaction was diluted with ethyl acetate and saturated sodium bicarbonate. The layers were separated and the ethyl acetate was dried over MgSO$_4$, filtered and concentrated. The material was purified on silica gel eluting with 10% methanol/DCM (1% NH4OH) to afford title compound (Z)-4-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-4-oxobut-2-enenitrile (EXAMPLE 31, 2.1 mg, 0.003555 mmol, 9.095% yield). ESI+APCI MS m/z 591.3 [M+H]$^+$.

Example 32

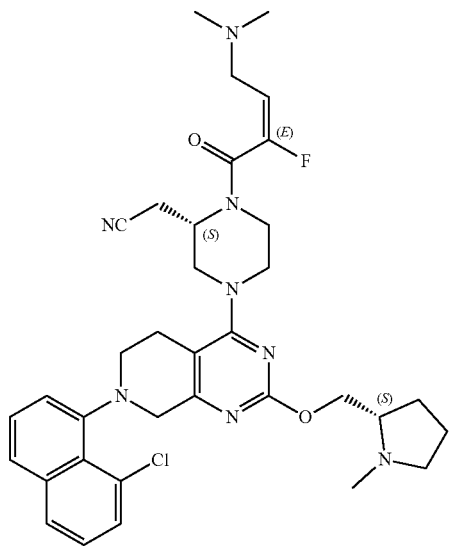

211

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile

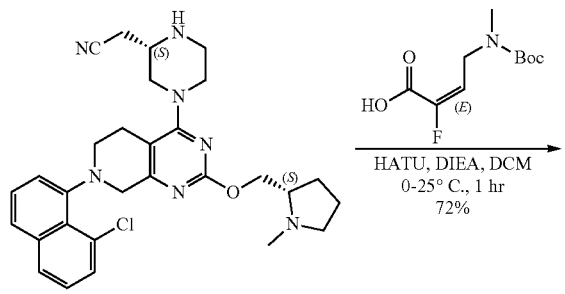

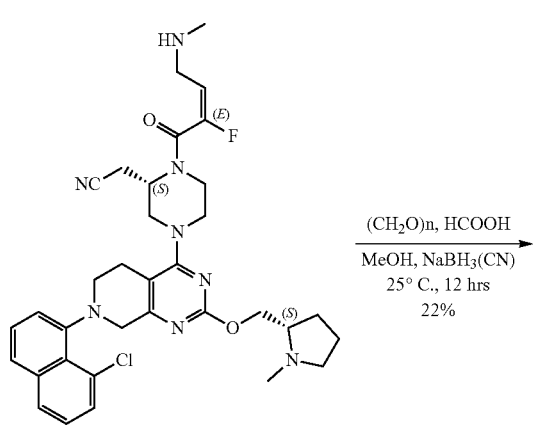

Step 1: (E)-4-[tert-butoxycarbonyl(methyl)amino]-2-fluoro-but-2-enoic Acid

To the solution of ethyl 2-diethoxyphosphoryl-2-fluoroacetate (2 g, 8.26 mmol, 1.68 mL, 1 eq) and tert-butyl N-methyl-N-(2-oxoethyl)carbamate (2.15 g, 12.4 mmol, 1.5 eq) in THF (40 mL) was added NaH (661 mg, 16.5 mmol, 60% purity, 2 eq). The mixture was stirred at 25° C. for 1.5 hour. Upon completion, the reaction mixture was quenched by saturated NH₄Cl (8 mL) and concentrated under vacuum. The residue was purified by prep-HPLC (column: Phenomenex Synergi Max-RP 250*50 mm*10 um; mobile phase: [water (0.225% FA)-ACN]; B %: 20ACN %-50ACN %,30 min; 50% min) to give (E)-4-[tert-butoxycarbonyl(methyl)amino]-2-fluoro-but-2-enoic acid (820 mg, 3.16 mmol, 38.3% yield, 90% purity) as a brown oil.

Step A: Tert-Butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 300 mg, 564 umol, 1 eq), (E)-4-[tert-butoxycarbonyl(methyl)amino]-2-fluoro-but-2-enoic acid (600 mg, 2.57 mmol, 4.56 eq) and DIEA (729 mg, 5.64 mmol, 982 μL, 10 eq) in DCM (10 mL) was added HATU (643 mg, 1.69 mmol, 3 eq) at 0° C. The reaction mixture was stirred at 25° C. for 1 hour. Upon completion, the reaction mixture was quenched by water (3 mL) and extracted with DCM (3×8 mL). The combined organic layers were dried over Na₂SO₄ and concentrated under vacuum. The residue was purified by reversed flash chromatography (FA condition: 60% MeCN in water (0.1% FA)) to give tert-butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate (330 mg, 404 umol, 72% yield, 91.5% purity) as a brown solid. LCMS [ESI, M+1]: 747.

Step B: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-2-fluoro-4-(methylamino)but-2-enoyl]piperazin-2-yl]acetonitrile To a solution of tert-butyl N-[(E)-4-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-2-(cyanomethyl)piperazin-1-yl]-3-fluoro-4-oxo-but-2-enyl]-N-methyl-carbamate (300 mg, 401 umol, 1 eq) in DCM (1 mL) was added TFA (915 mg, 8.03 mmol, 594 µL, 20 eq). The reaction mixture was stirred at 25° C. for 1 hour. Upon completion, the reaction mixture was diluted by DCM (10 mL) and basified by saturated NaHCO₃ (8 mL). The mixture was extracted with DCM (3×10 mL). The combined organic layer was dried over Na₂SO₄ and concentrated under vacuum to give 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-2-fluoro-4-(methylamino)but-2-enoyl]piperazin-2-yl]acetonitrile (240 mg, 356 umol, 89% yield, 95.9% purity) as a brown solid which was used for next step without further purification. LCMS [ESI, M+1]: 647.

Step C: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-2-fluoro-4-(methylamino)but-2-enoyl]piperazin-2-yl]acetonitrile (120 mg, 185 umol, 1 eq) and paraformaldehyde (83.5 mg, 927 umol, 5 eq), HCOOH (26.7 mg, 556 umol, 3 eq) in MeOH (5 mL) was added NaBH₃CN (35.0 mg, 556 umol, 3 eq). The reaction mixture was stirred at 25° C. for 12 hours. Upon completion, the reaction mixture was quenched by water (0.5 mL) and filtered. The residue was purified by silica gel chromatography (EA:MeOH:NH₃—H₂O=50:1:0 to 10:1:0.1), then prep-HPLC(column: Phenomenex Gemini 150*25 mm*10 um; mobile phase: [water (10 mM NH₄HCO₃)-ACN];B %:50%-100%,10 min) to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-(dimethylamino)-2-fluoro-but-2-enoyl]piperazin-2-yl]acetonitrile (EXAMPLE 32, 26.7 mg, 40.2 umol, 22% yield, 99.5% purity) as a yellow solid. LCMS [ESI, M+1]: 661.

¹H NMR (400 MHz, chloroform-d) δ=7.68 (d, J=8.0 Hz, 1H), 7.54 (t, J=7.2 Hz, 1H), 7.45 (d, J=7.2 Hz, 1H), 7.37 (td, J=7.6, 12.8 Hz, 1H), 7.26 (t, J=8.0 Hz, 1H), 7.19-7.08 (m, 1H), 5.81-5.60 (m, 1H), 5.04-4.41 (m, 1H), 4.40-4.25 (m, 2H), 4.16-3.91 (m, 3H), 3.88-3.71 (m, 2H), 3.66-3.46 (m, 2H), 3.36 (br d, J=10.8 Hz, 1H), 3.27-2.69 (m, 9H), 2.64-2.56 (m, 1H), 2.55-2.46 (m, 1H), 2.40 (d, J=2.4 Hz, 3H), 2.27-2.15 (m, 7H), 2.06-1.90 (m, 1H), 1.85-1.72 (m, 3H).

Example 33

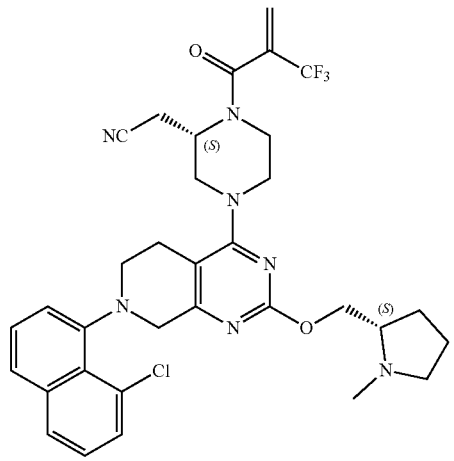

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile

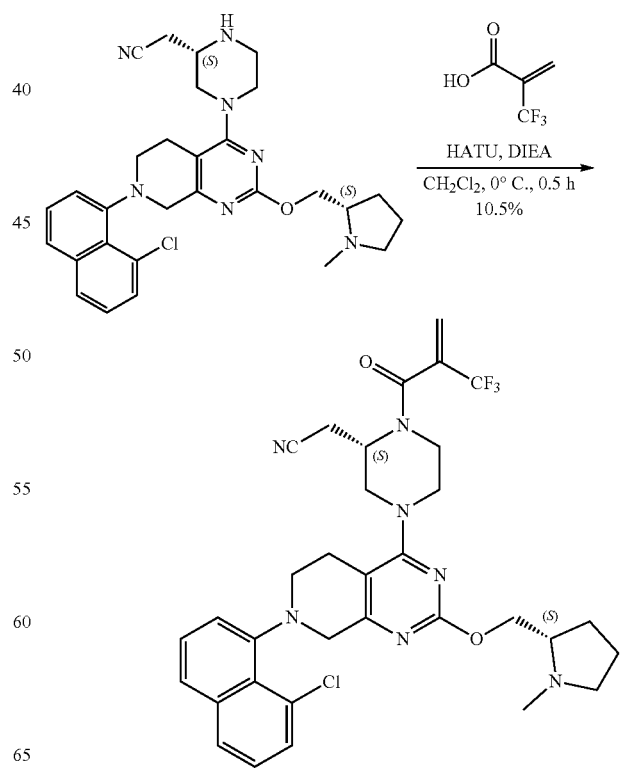

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile To a solution of 2-(trifluoromethyl)prop-2-enoic acid (39.5 mg, 282 umol, 1.50 eq), 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 0.10 g, 188 umol, 1.00 eq) and DIEA (48.6 mg, 376 umol, 65.5 µL, 2.00 eq) in dichloromethane (0.20 mL) was added HATU (107 mg, 282 umol, 1.50 eq) at 0° C. After stirred at 0° C. for 0.5 h, the mixture diluted with water and the layer was separated. The organic layer was dried over Na₂SO₄, filtered and concentrated under vacuum. The residue was purified by reverse phase flash [water (FA, 0.1%)/acetonitrile] and prep HPLC (column: Gemini 150*25 5 u; mobile phase: [water (0.05% ammonia hydroxide v/v)—ACN]; B %: 56%-86%, 12 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[2-(trifluoromethyl)prop-2-enoyl]piperazin-2-yl]acetonitrile (EXAMPLE 33, 13.1 mg, 19.6 umol, 10.5% yield, 97.9% purity) as a white solid. LCMS [ESI, M+1]: 654.

SFC condition: Column: Chiralcel OJ-3 50×4.6 mm I.D., 3 um, Mobile phase: methanol (0.05% DEA) in CO₂ from 5% to 40%, Flow rate: 3 mL/min, Wavelength: 220 nm.

¹H NMR (400 MHz, chloroform-d) δ=7.76 (d, J=8.4 Hz, 1H), 7.65-7.59 (m, 1H), 7.55-7.50 (m, 1H), 7.45 (td, J=7.6, 10.0 Hz, 1H), 7.34 (t, J=7.6 Hz, 1H), 7.26-7.18 (m, 1H), 6.18 (br s, 1H), 5.86 (br s, 1H), 5.11 (br s, 1H), 4.57-4.36 (m, 2H), 4.33-4.10 (m, 2H), 4.04 (br d, J=12.8 Hz, 1H), 3.97-3.79 (m, 2H), 3.66-3.54 (m, 1H), 3.50-3.33 (m, 1H), 3.29-3.07 (m, 4H), 3.04-2.72 (m, 4H), 2.63-2.50 (m, 4H), 2.45-2.32 (m, 1H), 2.15-2.04 (m, 1H), 1.90 (br s, 3H).

Example 34

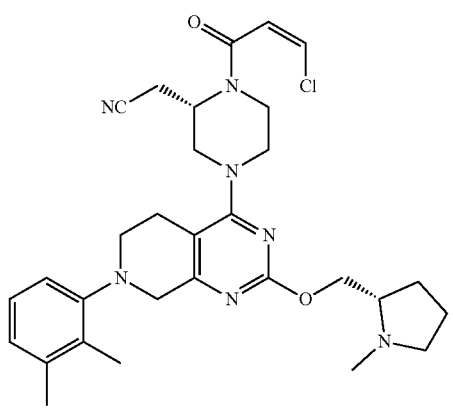 [SMILES: Cc1cccc(N2CCc3c(nc(OC[C@@H]4CCCN4C)nc3N3CCN(C(=O)/C=C\Cl)[C@@H](CC#N)C3)C2)c1C]

2-((S)-1-((Z)-3-chloroacryloyl)-4-(7-(2,3-dimethylphenyl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-((Z)-3-chloroacryloyl)-4-(7-(2,3-dimethylphenyl)-2-4(S)-1-methylpyrrolidin-2-yl)methoxy)-5,6,7,8-tetrahydropyrido[3,4-d]pyrimidin-4-yl)piperazin-2-yl)acetonitrile Was prepared following Example 18 Step A, substituting (Z)-3-chloroacrylic acid for (E)-4-methoxybut-2-enoic acid. ESI+APCI MS m/z 564.3 [M+H]⁺.

Example 35

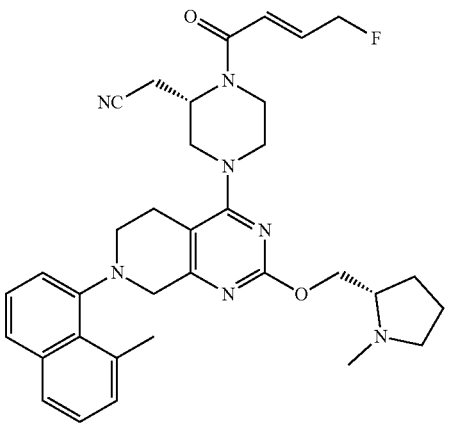 [SMILES: Cc1cccc2cccc(N3CCc4c(nc(OC[C@@H]5CCCN5C)nc4N4CCN(C(=O)/C=C/CF)[C@@H](CC#N)C4)C3)c12]

2-((S)-1-((E)-4-fluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

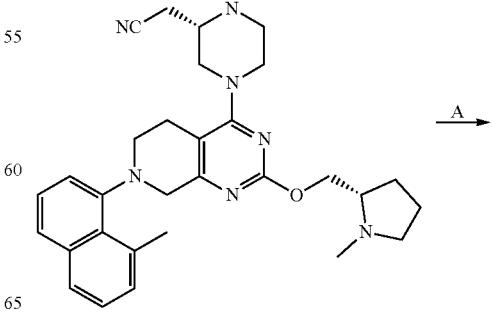

217

-continued

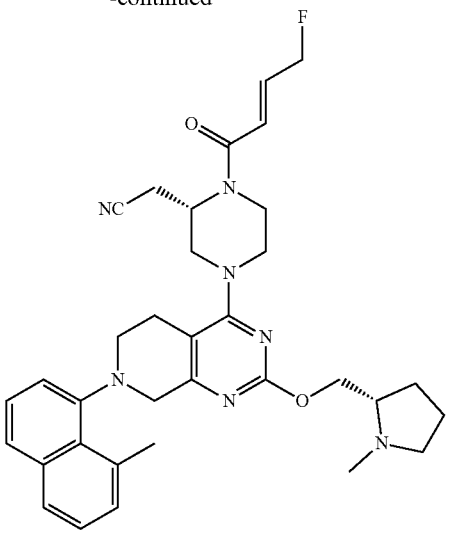

Step A: 2-((S)-1-((E)-4-fluorobut-2-enoyl)-4-(7-(8-methylnaphthalen-1-yl)-2-4(S)-1-methylpyrrolidin-2-yl)methoxy)-5,6,7,8-tetrahydropyrido[3,4-d]pyrimidin-4-yl)piperazin-2-yl)acetonitrile At 0° C., to a 25 mL RBF containing N,N-dimethylformamide (3909 µl, 0.39 mmol) was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (200 mg, 0.391 mmol) and triethylamine (136 µl, 0.98 mmol). The reaction mixture was vigorously stirred while (E)-4-fluorobut-2-enoic acid (61.0 mg, 0.59 mmol) was added in one portion. Next, 1-propanephosphonic acid cyclic anhydride (175 µl, 0.59 mmol) was added slowly to the stirring mixture. The reaction was stirred at room temperature for 18 hr. Water was added and the mixture was extracted with EtOAc (3×15 mL). The extracts were combined and washed with water (1×10 mL) and concentrated. The residue was purified by silica gel (5-18% MeOH in DCM with 0.25% NH$_4$OH) to provide title compound 2-((S)-1-((E)-4-fluorobut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 35, 89.3 mg, 0.15 mmol, 38% yield). ESI+APCI MS m/z 598.3 [M+H]$^+$.

Example 36

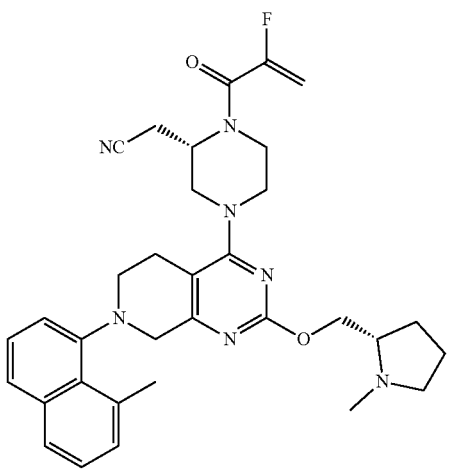 [SMILES: C=C(F)C(=O)N1CCN(c2nc(OC[C@@H]3CCCN3C)nc3c2CCN(c2cccc4cccc(C)c24)C3)C[C@@H]1CC#N]

218

2-((S)-1-(2-fluoroacryloyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile Step A: 2-((S)-1-(2-fluoroacryloyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (8 g, 15.63 mmol) was diluted with DMF (78.17 ml, 15.63 mmol), placed under nitrogen and cooled to 0° C. DIEA (6.827 ml, 39.09 mmol) was added followed by the addition of 2-Fluoroacrylic acid (2.112 g, 23.45 mmol) and the dropwise addition of 1-Propanephosphonic acid cyclic anhydride (9.307 ml, 15.63 mmol). The reaction was stirred at 0° C. for 6 hours and left to stir for an additional 10 hours warming to ambient temperature. The reaction was poured into a 5% sodium bicarbonate solution and extracted twice with ethyl acetate. The ethyl acetate was washed with water, brine, dried over MgSO$_4$, filtered and concentrated. The material was purified on silica gel eluting with 1-10% methanol/DCM (1% NH4OH as additive) to afford title compound 2-((S)-1-(2-fluoroacryloyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 36, 6.6 g, 11.31 mmol, 72.32% yield). ESI+APCI MS m/z 584.3 [M+H]$^+$.

Example 37

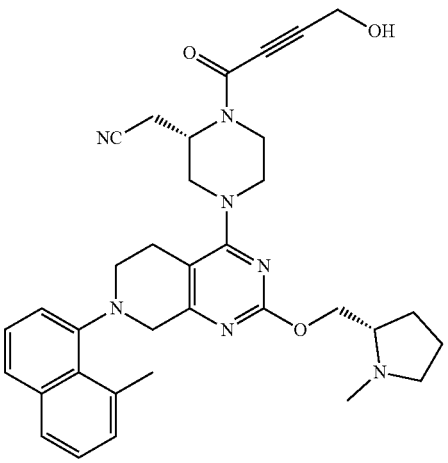 [SMILES: Cc1cccc2cccc(N3CCc4c(nc(OC[C@@H]5CCCN5C)nc4N4CCN(C(=O)C#CCO)[C@@H](CC#N)C4)C3)c12]

2-((S)-1-(4-hydroxybut-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile 2-((S)-1-(4-hydroxybut-2-ynoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile was prepared according to Example 36, Step A, substituting 4-((tert-butyldimethylsilyl)oxy)but-2-ynoic acid for 2-Fluoroacrylic acid. ESI+APCI MS m/z 594.3 [M+H]$^+$.

Example 38
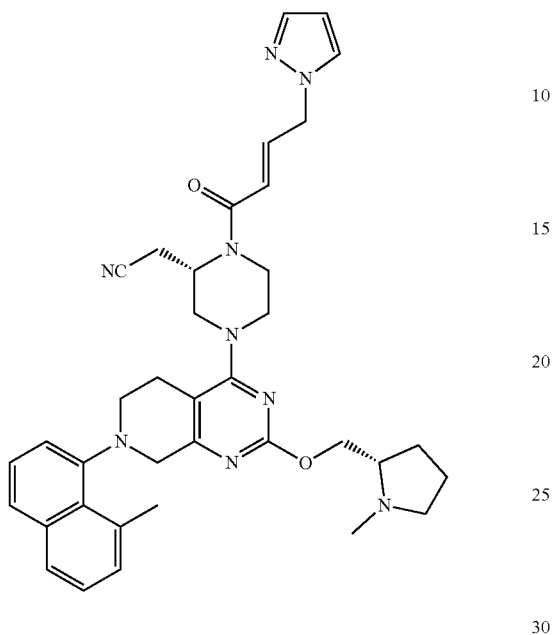
2-((S)-1-((E)-4-(1H-pyrazol-1-yl)but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile
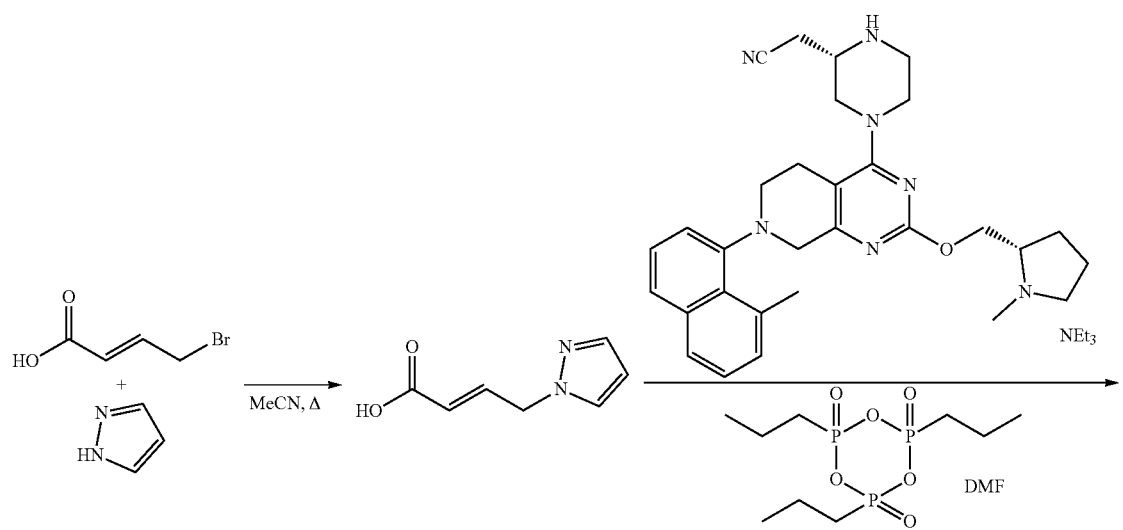

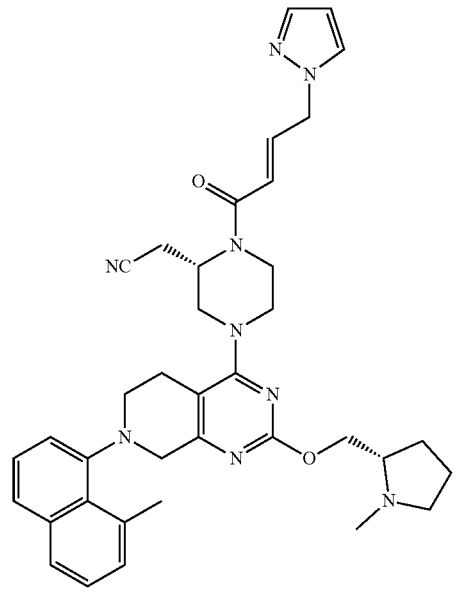 [SMILES: Cc1cccc2cccc(N3CCc4c(nc(OC[C@@H]5CCCN5C)nc4N4CCN(C(=O)/C=C/Cn5cccn5)[C@@H](CC#N)C4)C3)c12]

Step A: (E)-4-(1H-pyrazol-1-yl)but-2-enoic Acid

A solution of 4-bromocrotonic acid (100 mg, 0.606 mmol) and pyrazole (37.1 mg, 0.546 mmol) in acetonitrile (1 ml, 19.1 mmol) was heated in a closed vial for 48 h to 60° C. with stirring. The resulted light-green solution was divided between water (5 mL) and EtOAc (15 mL), the organics were separated, the organic layer was washed with brine, dried over $Na_2SO_4$ and evaporated in vacuo. The material was chromatographed on silica gel in 2 to 5% MeOH/DCM+ 0.2% TFA. The resulting solid was dissolved in minimal amount of 6M HCl and evaporated under slow $N_2$ flow. This material was used in the next step without further purification.

Step B: 2-((S)-1-((E)-4-(1H-pyrazol-1-yl)but-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (42.37 mg, 0.08281 mmol), (E)-4-(1H-pyrazol-1-yl)but-2-enoic acid (12.6 mg, 0.08281 mmol) and N,N-dimethylformamide (1 mL, 12.79 mmol) was cooled on ice-salt bath with stirring, and triethylamine (0.03463 mL, 0.2484 mmol) was added at once, followed by 2,4,6-tripropyl-1,3,5,2,4,6-trioxatriphosphinane 2,4,6-trioxide, 50% in EtOAc (0.07395 mL, 0.1242 mmol). The reaction mixture was allowed to warm up to r.t. over 5 min and was stirred at r.t. overnight. The reaction mixture was divided between 0.5M $Na_2CO_3$ (5 mL) and EtOAc (10 mL), the organics were separated, the organic layer was washed with water and brine (5 mL each), dried over $Na_2SO_4$ and evaporated in vacuo. The product was purified by silicia gel chromatography using 5% MeOH+0.5% $NH_4OH$ in DCM to give title compound as a colorless solid (EXAMPLE 38, 11.46 mg, 23%). ESI+APCI MS m/z 646.3 $[M+H]^+$.

Example 39

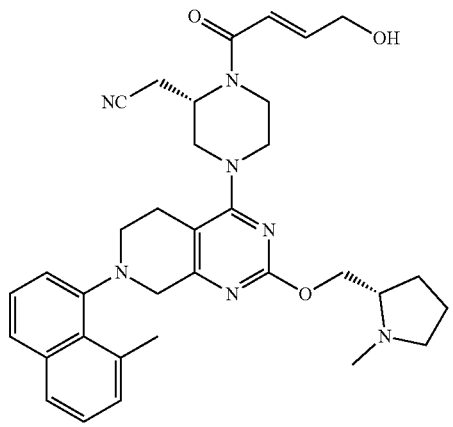 [SMILES: Cc1cccc2cccc(N3CCc4c(nc(OC[C@@H]5CCCN5C)nc4N4CCN(C(=O)/C=C/CO)[C@@H](CC#N)C4)C3)c12]

2-((S)-1-((E)-4-hydroxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

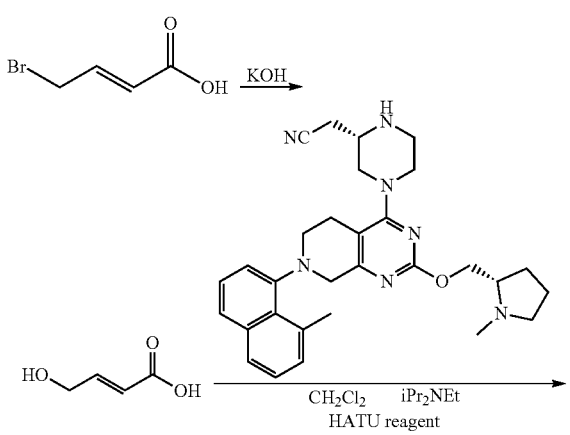

-continued

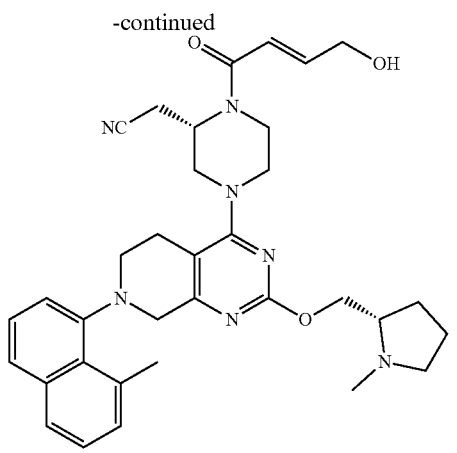

Step A: (E)-4-hydroxybut-2-enoic Acid

To a stirred suspension of 4-bromocrotonic acid (4824 mg, 29.24 mmol) in water (48 mL) a 2M solution of potassium hydroxide (4.921 g, 87.72 mmol) was added dropwise and the resulted solution was heated to reflux for 5 min. The reaction mixture was left under a $N_2$ stream to cool and concentrate. The residue was cooled on ice bath, acidified with 4M $H_2SO_4$ to pH 1-2, the resulted suspension was evaporated in vacuo by half and then extracted with EtOAc (3*60 mL). The combined extracts were dried over $Na_2SO_4$ and evaporated in vacuo. The material was purified by chromatography using 2 to 5% MeOH+0.2% TFA to afford the target acid as colorless crystals (2.165 g, 73%).

Step B: 2-((S)-1-((E)-4-hydroxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile To a stirred solution of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (100 mg, 0.1954 mmol), (2E)-4-hydroxybut-2-enoic acid (39.90 mg, 0.3909 mmol) and N-ethyl-N-isopropylpropan-2-amine (0.06809 ml, 0.3909 mmol) in DCM (5 mL), O-(7-Azabenzotriazol-1-yl)-N,N,N',N'-Tetramethyluronium hexafluorophosphate (111.5 mg, 0.2932 mmol) was added at once and the reaction mixture was stirred at r.t for 4 h. Water (1 mL) was added, the reaction mixture was stirred for 5 min and divided between EtOAc (10 mL) and sat. $NaHCO_3$ (5 mL). The organic layer was separated, washed with $NaHCO_3$, brine (5 mL each), dried over $K_2CO_3$ and evaporated in vacuo. The residue was chromatographed on silica gel with 5% MeOH+0.5% $NH_4OH$. Title compound as a colorless solid (EXAMPLE 39, 29 mg, 25%). ESI+APCI MS m/z 596.3 $[M+H]^+$.

Example 40

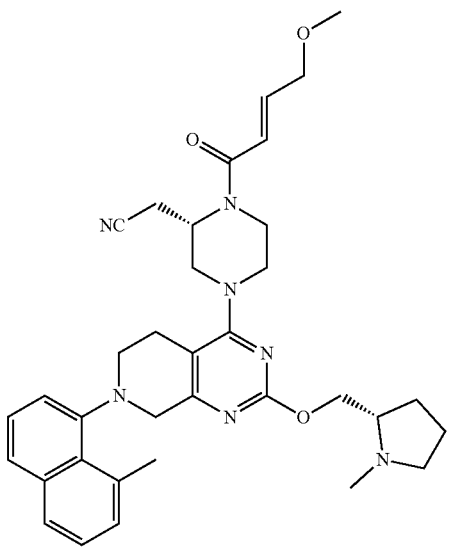

2-((S)-1-((E)-4-methoxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile

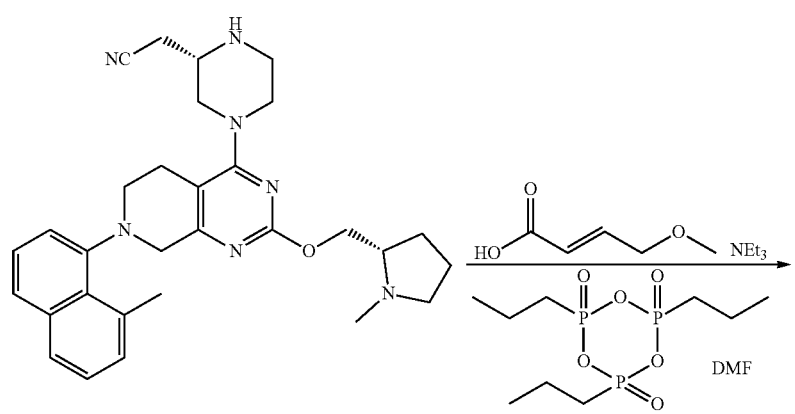

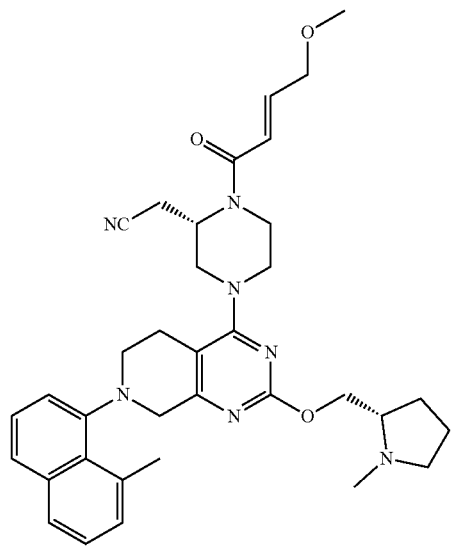 [SMILES: COC/C=C/C(=O)N1CCN(c2nc(OC[C@@H]3CCCN3C)nc3c2CCN(c2cccc4cccc(C)c24)C3)C[C@@H]1CC#N]

Step A: 2-((S)-1-((E)-4-methoxybut-2-enoyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile A stirred mixture of 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (250 mg, 0.4886 mmol), (E)-4-methoxybut-2-enoic acid (85.10 mg, 0.7329 mmol) and N,N-dimethylformamide (2 mL, 25.58 mmol) was cooled on an ice-salt bath and triethylamine (0.2043 mL, 1.466 mmol) was added at once, followed by 2,4,6-tripropyl-1,3,5,2,4,6-trioxatriphosphinane 2,4,6-trioxide, 50% in EtOAc (0.4363 mL, 0.7329 mmol). The reaction mixture was allowed to warm to r.t. over 5 min, and stirred at r.t. for 2 h. The resulted solution was divided between 0.5M Na$_2$CO$_3$ (10 mL) and EtOAc (30 mL), the organic layer was separated, washed with water and brine (10 mL each), dried over Na$_2$SO$_4$ and evaporated in vacuo. The material was purified by silica gel chromatography using 5% MeOH+0.5% NH$_4$OH in DCM. The material was further purified by the reverse phase chromatography, Gilson, 25 to 75% MeCN/H$_2$O+0.1% TFA. Target fractions were basified with excess of 2M Na$_2$CO$_3$ and extracted with DCM (3*50 mL). The combined organic extracts were washed with brine, dried over Na$_2$SO$_4$ and evaporated in vacuo. Title compound as a light-yellow solid (EXAMPLE 40, 123 mg, 41%). ESI+APCI MS m/z 610.3 [M+H]$^+$.

Example 41

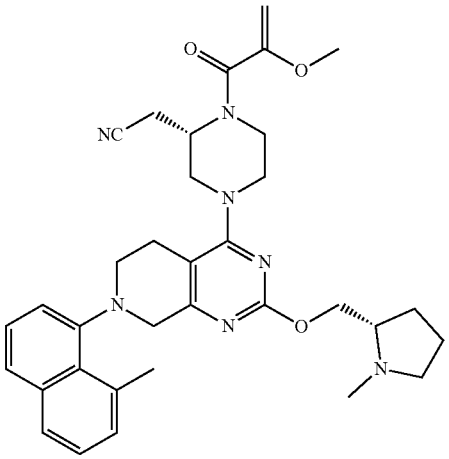 [SMILES: C=C(OC)C(=O)N1CCN(c2nc(OC[C@@H]3CCCN3C)nc3c2CCN(c2cccc4cccc(C)c24)C3)C[C@@H]1CC#N]

2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

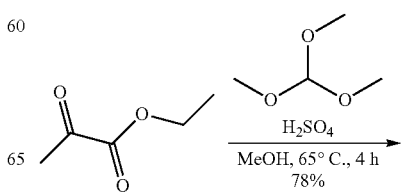

-continued

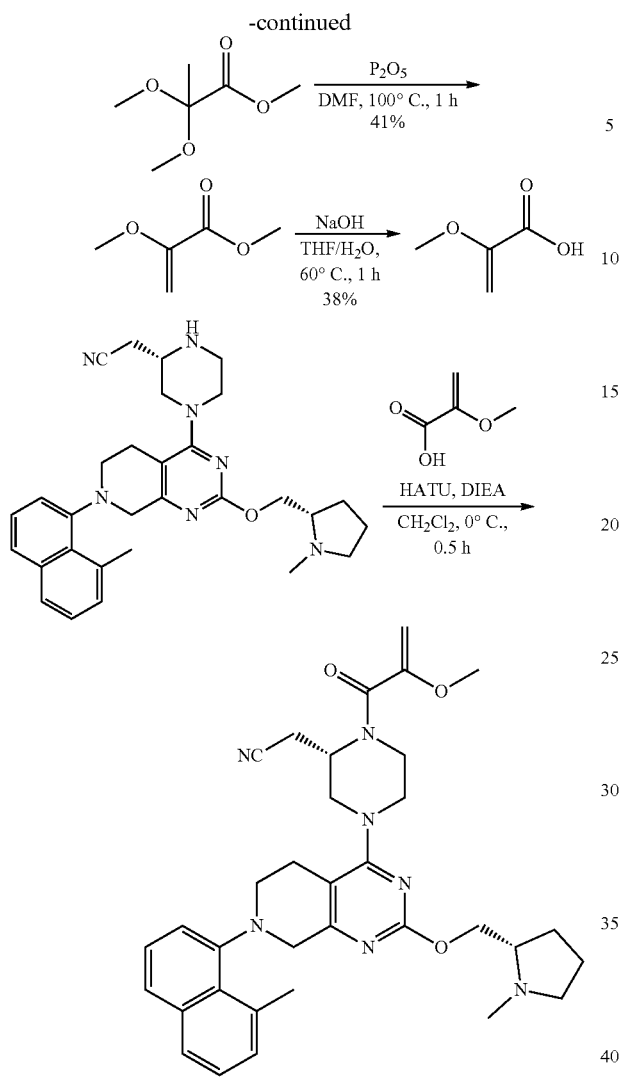

Step A: Methyl 2,2-dimethoxypropanoate

To a solution of ethyl 2-oxopropanoate (4.00 g, 34.5 mmol, 3.81 mL, 1.00 eq) and trimethoxymethane (4.75 g, 44.8 mmol, 4.91 mL, 1.30 eq) in methanol (10.0 mL) was added H$_2$SO$_4$ (33.8 mg, 344 umol, 18.4 μL, 0.01 eq). After stirred at 65° C. for 4 hours, the pH value was adjusted >7 by KOH (120 mg in 20.0 mL water) and extracted with ethyl acetate (3×20.0 mL). The organic layer was washed with brine (1×30.0 mL), dried over Na$_2$SO$_4$, filtered and concentrated under vacuum. The residue was distilled at 60° C. under oil pump to give methyl 2,2-dimethoxypropanoate (4.00 g, 27.0 mmol, 78% yield) as a colourless oil and used into next step without further purification.

$^1$H NMR (400 MHz, chloroform-d) δ=3.81 (s, 3H), 3.28 (s, 6H), 1.52 (s, 3H).

Step B: Methyl 2-methoxyprop-2-enoate

To a solution of methyl 2,2-dimethoxypropanoate (2.00 g, 13.5 mmol, 1.00 eq) in DMF (20.0 mL) was added P2O5 (1.05 g, 7.42 mmol, 458 μL, 0.55 eq) in portions. After heated to 100° C. for 1 hour, the mixture was diluted with saturated sodium bicarbonate (20.0 mL), extracted with isopropyl ether (3×30.0 mL), washed with brine (3×40.0 mL), dried over Na$_2$SO$_4$, filtered and concentrated under vacuum. The residue was distilled under oil pump to give methyl 2-methoxyprop-2-enoate (0.65 g, 5.60 mmol, 41% yield) as a colorless oil and used into next step without further purification.

Step C: 2-methoxyprop-2-enoic Acid

A mixture of methyl 2-methoxyprop-2-enoate (0.60 g, 5.17 mmol, 1.00 eq) and NaOH (827 mg, 20.7 mmol, 4.00 eq) in H$_2$O (5.00 mL) and THF (5.00 mL) was stirred at 60° C. for 1 hour. The mixture was adjusted to pH<3 by concentrated HCl (10.0 mL) and extracted with ethyl acetate (3×20.0 mL). The organic layer was dried over Na$_2$SO$_4$, filtered and concentrated under vacuum to give 2-methoxyprop-2-enoic acid (0.40 g, 1.96 mmol, 38% yield, 50% purity) as a pink oil and used into next step without further purification.

$^1$H NMR (400 MHz, chloroform-d) δ=8.63 (br s, 1H), 5.52 (d, J=2.8 Hz, 1H), 4.75 (d, J=2.8 Hz, 1H), 3.70 (s, 3H).

Step D: 2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.14 g, 274 umol, 1.00 eq), 2-methoxyprop-2-enoic acid (112 mg, 1.09 mmol, 4.00 eq) and DIEA (141 mg, 1.09 mmol, 191 μL, 4.00 eq) in dichloromethane (5.00 mL) was added HATU (208 mg, 547 umol, 2.00 eq) at 0° C. After stirred at 0° C. for 0.5 h, the mixture was diluted with water (3.00 mL). The organic layer was dried over Na$_2$SO$_4$, filtered and concentrated under vacuum. The residue was purified by reverse phase flash [water (FA, 0.10%)/acetonitrile] and prep-HPLC (column: Gemini 150*25 5 u; mobile phase: [water (0.05% ammonia hydroxide v/v)—ACN]; B %: 60%-90%, 12 min). The desired fraction was collected and lyophilized to give title compound 2-[(2S)-1-(2-methoxyprop-2-enoyl)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 41, 10.27 mg, 17.22 umol, 6.3% yield, 99.9% purity) as a off-white solid. LCMS [ESI, M+1]: 596.

SFC condition: "IC-3_S_3_40_3 ML Column: Chiralpak IC-3 100×4.6 mm I.D., 3 um, Mobile phase: 40% methanol (0.05% DEA) in CO$_2$, Flow rate: 3 mL/min, Wavelength: 220 nm".

$^1$H NMR (400 MHz, chloroform-d) δ=7.72-7.61 (m, 2H), 7.45-7.31 (m, 2H), 7.27-7.17 (m, 2H), 5.05-4.61 (m, 1H), 4.48 (br s, 1H), 4.37 (td, J=4.4, 10.0 Hz, 1H), 4.30-3.98 (m, 4H), 3.96-3.74 (m, 2H), 3.69 (br s, 3H), 3.59-3.28 (m, 2H), 3.27-2.93 (m, 6H), 2.92 (s, 3H), 2.88-2.51 (m, 4H), 2.47 (d, J=3.2 Hz, 3H), 2.33-2.23 (m, 1H), 2.11-1.98 (m, 1H), 1.89-1.74 (m, 3H).

Example 42

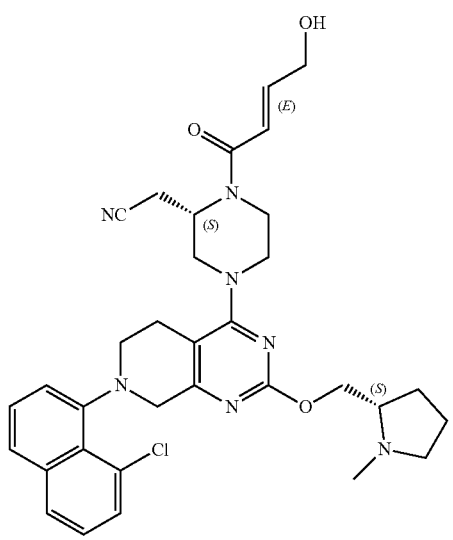

2-[(2S)-4-[7-(8-chloro-1-naphthyl)-2-[[(2S')-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile

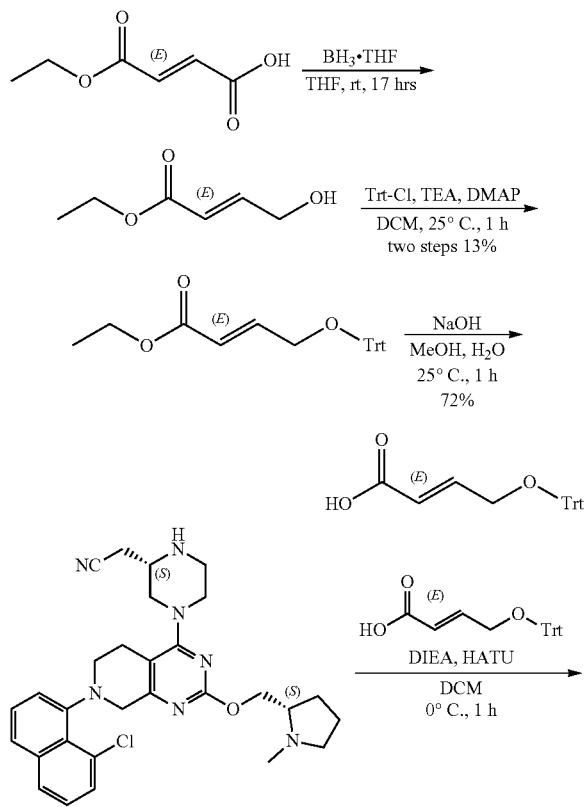

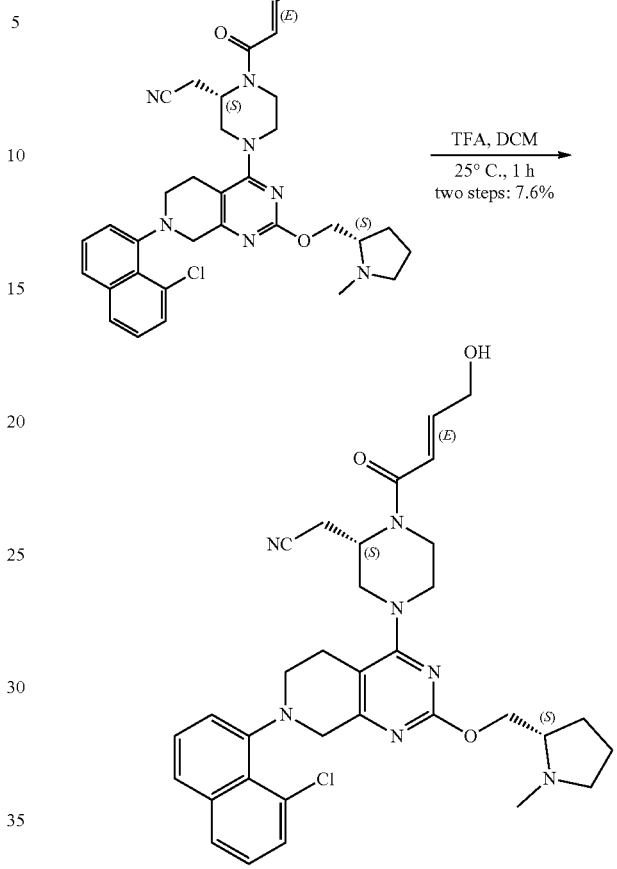

Step 1: Ethyl (E)-4-hydroxybut-2-enoate

To a solution of (E)-4-ethoxy-4-oxo-but-2-enoic acid (1.0 g, 7.29 mmol, 1.0 eq) in THF (6.0 mL) was added a solution of $BH_3\text{-}Me_2S$ (10.0 M, 692 µL, 0.95 eq) in THF (8.0 mL) dropwise over 1 hour at −10° C. The reaction mixture was gradually warmed to 25° C. and stirred for 17 hours. After completion, the reaction mixture was quenched by addition water (30.0 mL) and extracted with Ethyl acetate (30.0 mL×3). The combined organic layers were washed with brine (30.0 mL×2), dried over $Na_2SO_4$, filtered and concentrated under reduced pressure to give a residue. Compound ethyl (E)-4-hydroxybut-2-enoate (900 mg, crude) was obtained as colorless oil. The crude product was used directly in the next step without further purification.

Step 2: (E)-4-trityloxybut-2-enoate

A mixture of ethyl (E)-4-hydroxybut-2-enoate (900 mg, crude), [chloro(diphenyl)methyl]benzene (2.89 g, 10.4 mmol), DMAP (84.5 mg, 692 umol), TEA (1.4 g, 13.8 mmol, 1.9 mL) in DCM (5.0 mL) was degassed and purged with $N_2$ for 3 times, and then the mixture was stirred at 25° C. for 1 hour under $N_2$ atmosphere. After completion, the reaction mixture was quenched by addition $H_2O$ (10.0 mL) and extracted with Ethyl acetate (10.0 mL×3). The combined organic layers were dried over $Na_2SO_4$, filtered and concentrated under reduced pressure to give a residue. The residue was purified by column chromatography (SiO$_2$, Petroleum ether/Ethyl acetate=20:1 to 15:1). Compound ethyl (E)-4-trityloxybut-2-enoate (340 mg, 913 umol, 13% yield) was obtained as colorless oil.

$^1$H NMR (400 MHz, Chloroform-d) δ 7.38-7.35 (m, 6H), 7.26-7.22 (m, 6H), 7.18-7.15 (m, 3H), 6.88 (dt, J=15.6, 3.6 Hz, 1H), 6.29 (dt, J=15.6, 2.2 Hz, 1H), 4.16 (q, J=7.1 Hz, 2H), 3.72 (dd, J=2.4, 2.0 Hz, 2H), 1.25 (t, J=7.0 Hz, 3H).

Step 3: (E)-4-trityloxybut-2-enoic Acid

To a solution of ethyl (E)-4-trityloxybut-2-enoate (170 mg, 456 umol, 1.0 eq) in MeOH (1.0 mL) was added solution of NaOH (54.5 mg, 1.37 mmol, 3.0 eq) in H$_2$O (0.5 mL) and then the mixture was stirred at 40° C. for 1 hour under N$_2$ atmosphere. After completion, the reaction mixture was quenched by addition 1M HCl at 0° C. until pH=5, and then extracted with Ethyl acetate (8.0 mL×3). The combined organic layers were dried over Na$_2$SO$_4$, filtered and concentrated under reduced pressure to give a residue. The residue was purified by column chromatography (SiO$_2$, Petroleum ether/Ethyl acetate=3:1 to 1:1). Compound (E)-4-trityloxybut-2-enoic acid (113 mg, 328 umol, 72% yield) was obtained as a white solid.

$^1$H NMR (400 MHz, Chloroform-d) δ 7.38-7.36 (m, 6H), 7.26-7.24 (m, 5H), 7.20-7.16 (m, 4H), 7.0 (dt, J=15.6, 3.6 Hz, 1H), 6.32 (dt, J=15.6, 2.0 Hz, 1H), 3.76 (dd, J=3.2, 2.4 Hz, 2H).

Step A: 2-[(2)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (Intermediate 71, 60.0 mg, 113 umol, 1.0 eq), (E)-4-trityloxybut-2-enoic acid (77.8 mg, 226 umol, 2.0 eq) and DIEA (73.0 mg, 564 umol, 98 μL, 5.0 eq) in DCM (2.0 mL) was added HATU (64 mg, 169 umol, 1.5 eq) in one portion at 0° C. under N$_2$. The mixture was stirred at 25° C. for 1 hour. After completion, the reaction mixture was quenched by addition H$_2$O (8.0 mL) and then extracted with Ethyl acetate (10.0 mL×3). The combined organic layers were dried over Na$_2$SO$_4$, filtered and concentrated under reduced pressure to give a residue. Compound 2-[(2)-4-[7-(8-chloro-1-naphthyl)-2-[[(2)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (150 mg, crude) was obtained as a yellow solid, and the crude product was used directly in the next step without further purification. LCMS [ESI, M+1]: 858.

Step B: 2-[(2)-4-[7-(8-chloro-1-naphthyl)-2-[[(2)-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile To a solution of 2-[(2)-4-[7-(8-chloro-1-naphthyl)-2-[[(2)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (150 mg, crude) in DCM (1.0 mL) was added TFA (1.0 ml, 13.5 mmol). The mixture was stirred at 25° C. for 1 hour. After completion, the reaction mixture was quenched by addition NaHCO$_3$ aqueous solution at 0° C. until pH=8, and then extracted with Ethyl acetate (10.0 mL×3). The combined organic layers were dried over Na$_2$SO$_4$, filtered and concentrated under reduced pressure to give a residue. The residue was purified by prep-HPLC (column: Phenomenex Gemini 150*25 mm*10 um; mobile phase: [water (0.04% NH$_3$H$_2$O+10 mM NH$_4$HCO$_3$)-ACN]; B %: 48%-72%, 10 min.) and lyophilization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-[(E)-4-hydroxybut-2-enoyl]piperazin-2-yl]acetonitrile (EXAMPLE 42, 8.21 mg, 13.3 umol, 7.6% yield, 99.8% purity) was obtained as a white solid. LCMS [ESI, M+1]: 616.

SFC condition: 100% e.e.

$^1$H NMR (400 MHz, Chloroform-d) δ 7.68 (d, J=8.0 Hz, 1H), 7.70-7.33 (m, 1H), 7.49 (dd, J=6.8, 0.8 Hz, 1H), 7.37 (dt, J=11.98, 7.82 Hz, 1H), 7.26 (t, J=11.8 Hz, 1H), 7.19-7.11 (m, 1H), 6.99 (dt, J=14.8, 3.4 Hz, 1H), 6.56 (br s, 1H), 5.02-4.57 (m, 1H), 4.39-4.29 (m, 4H), 4.12-4.06 (m, 1H), 4.03-3.99 (m, 2H), 3.85-3.72 (m, 2H), 3.67-3.36 (m, 3H), 3.24-3.09 (m, 2H), 3.03-2.89 (m, 3H), 2.73 (br s, 1H), 2.63-2.61 (m, 1H), 2.50 (br s, 1H), 2.41 (s, 3H), 2.25-2.19 (m, 1H), 2.03-1.92 (m, 1H), 1.70-1.60 (m, 3H).

Example 43

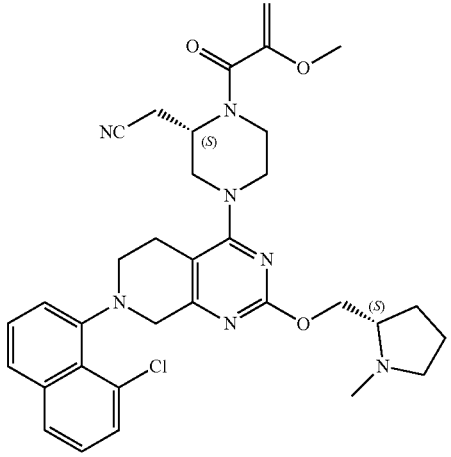

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-methoxyprop-2-enoyl)piperazin-2-yl]acetonitrile

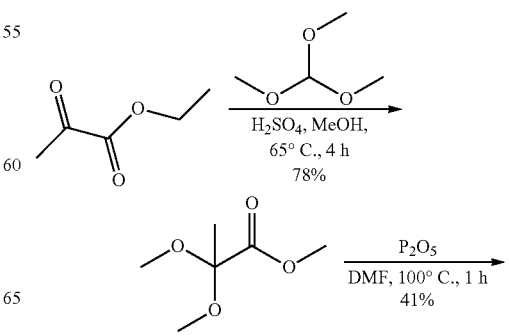

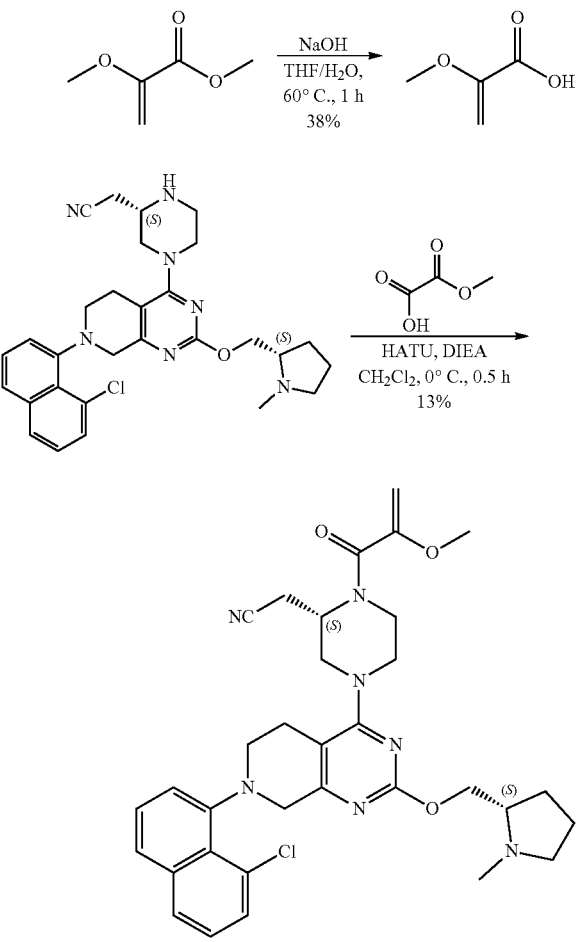

Step 1: Methyl 2,2-dimethoxypropanoate

To a solution of ethyl 2-oxopropanoate (4.00 g, 34.5 mmol, 3.81 mL, 1.00 eq) and trimethoxymethane (4.75 g, 44.8 mmol, 4.91 mL, 1.30 eq) in methanol (10.0 mL) was added $H_2SO_4$ (33.8 mg, 344 umol, 18.4 μL, 0.01 eq). After stirring at 65° C. for 4 hours, the reaction mixture was adjusted to pH value was adjusted >7 by KOH aqueous (120 mg in 20.0 mL water) and extracted with ethyl acetate (3×20.0 mL). The organic layers were washed with brine (1×30.0 mL), dried over $Na_2SO_4$, filtered and concentrated under vacuum. The residue was distilled at 60° C. under vacuum to give methyl 2,2-dimethoxypropanoate (4.00 g, 27.0 mmol, 78% yield) as a colorless oil.

$^1$H NMR (400 MHz, chloroform-d) δ=3.81 (s, 3H), 3.28 (s, 6H), 1.52 (s, 3H).

Step 2: Methyl 2-methoxyprop-2-enoate

To a solution of methyl 2,2-dimethoxypropanoate (2.00 g, 13.5 mmol, 1.00 eq) in DMF (20.0 mL) was added P2O5 (1.05 g, 7.42 mmol, 458 μL, 0.55 eq) in portions. After stirring at 100° C. for 1 hour, the mixture was diluted with saturated sodium bicarbonate (20.0 mL), extracted with isopropyl ether (3×30.0 mL). The extracts were washed with brine (3×40.0 mL), dried over $Na_2SO_4$, filtered and concentrated under vacuum. The residue was distilled under vacuum to give methyl 2-methoxyprop-2-enoate (0.65 g, 5.60 mmol, 41% yield) as a colorless oil which was used to next step without further purification.

$^1$H NMR (400 MHz, chloroform-d) δ=5.36 (d, J=2.8 Hz, 1H), 4.63 (d, J=2.8 Hz, 1H), 3.81 (s, 3H), 3.66 (s, 3H).

Step 3: 2-methoxyprop-2-enoic Acid

A mixture of methyl 2-methoxyprop-2-enoate (0.60 g, 5.17 mmol, 1.00 eq) and NaOH (827 mg, 20.7 mmol, 4.00 eq) in $H_2O$ (5.00 mL) and THF (5.00 mL) was stirred at 60° C. for 1 hour. The mixture was adjusted to pH<3 by concentrated HCl (10.0 mL) and extracted with ethyl acetate (3×20.0 mL). The organic layer was dried over $Na_2SO_4$, filtered and concentrated under vacuum to give 2-methoxyprop-2-enoic acid (0.40 g, 1.96 mmol, 38% yield, 50% purity) as a pink oil and used into next step without further purification.

$^1$H NMR (400 MHz, chloroform-d) δ=8.63 (br s, 1H), 5.52 (d, J=2.8 Hz, 1H), 4.75 (d, J=2.8 Hz, 1H), 3.70 (s, 3H).

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-methoxyprop-2-enoyl)piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (0.20 g, 376 umol, 1.00 eq), 2-methoxyprop-2-enoic acid (153 mg, 1.50 mmol, 4.00 eq) and DIEA (194 mg, 1.50 mmol, 262 μL, 4.00 eq) in dichloromethane (5.00 mL) was added HATU (286 mg, 752 umol, 2.00 eq) at 0° C. After stirred at 0° C. for 0.5 h, the reaction was purified by reversed phase flash [water (FA, 0.1%)/acetonitrile], prep-HPLC (column: Luna C18 150*25 5 u; mobile phase: [water (0.225% FA)—ACN]; B %: 25%-45%, 7.8 min) and further prep-HPLC (column: Waters Xbridge 150*25 5 u; mobile phase: [water (0.05% ammonia hydroxide v/v)—ACN]; B %: 55%-79%, 10 min). The desired fractions were collected and lyophilized to give title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-methoxyprop-2-enoyl)piperazin-2-yl]acetonitrile (EXAMPLE 43, 30.1 mg, 48.9 umol, 13% yield, 100% purity) as a yellow solid. LCMS [ESI, M+1]: 616.

SFC condition: "AS-3 MeOH (DEA)_5_40_3 mL-35T Column: Chiralpak AS-3 50×4.6 mm I.D., 3 um, Mobile phase: methanol (0.05% DEA) in $CO_2$ from 5% to 40%, Flow rate: 3 mL/min, Wavelength: 220 nm".

$^1$H NMR (400 MHz, chloroform-d) δ=7.76 (br d, J=8.0 Hz, 1H), 7.62 (t, J=7.6 Hz, 1H), 7.52 (d, J=7.2 Hz, 1H), 7.44 (td, J=7.6, 13.6 Hz, 1H), 7.34 (t, J=8.0 Hz, 1H), 7.27-7.18 (m, 1H), 5.07-4.63 (m, 1H), 4.57-4.29 (m, 4H), 4.21-3.96 (m, 3H), 3.95-3.77 (m, 2H), 3.69 (br s, 3H), 3.59 (br d, J=11.2 Hz, 1H), 3.51-3.32 (m, 1H), 3.30-3.02 (m, 5H), 2.89-2.50 (m, 4H), 2.47 (d, J=2.0 Hz, 3H), 2.32-2.23 (m, 1H), 2.11-2.00 (m, 1H), 1.89-1.72 (m, 3H).

Example 44

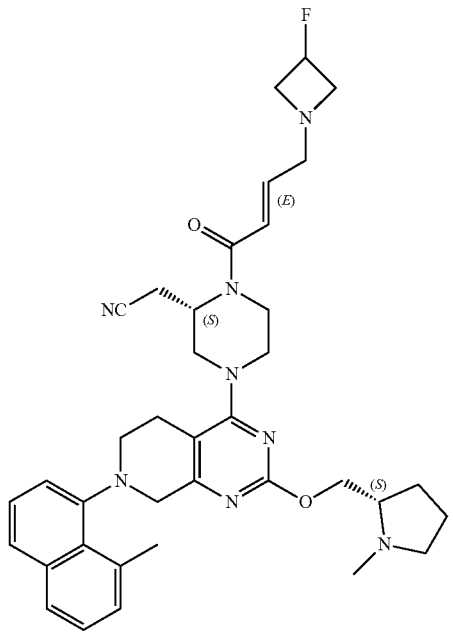

2-[(2S)-1-[(E)-4-(3-fluoroazetidin-1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile

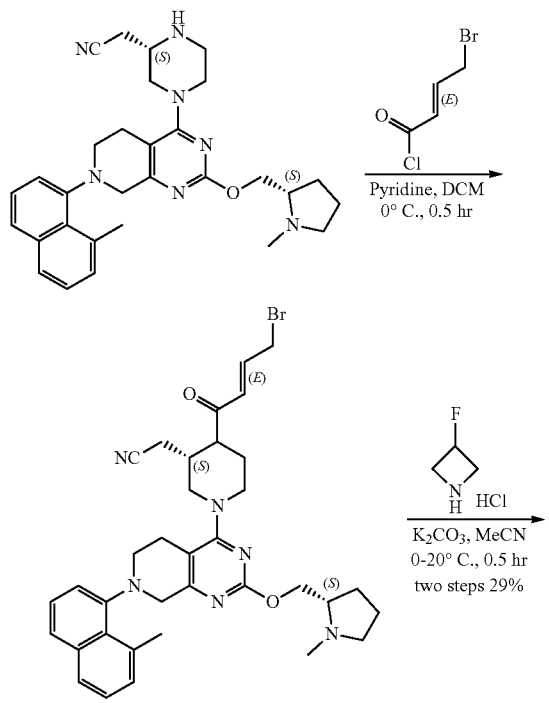

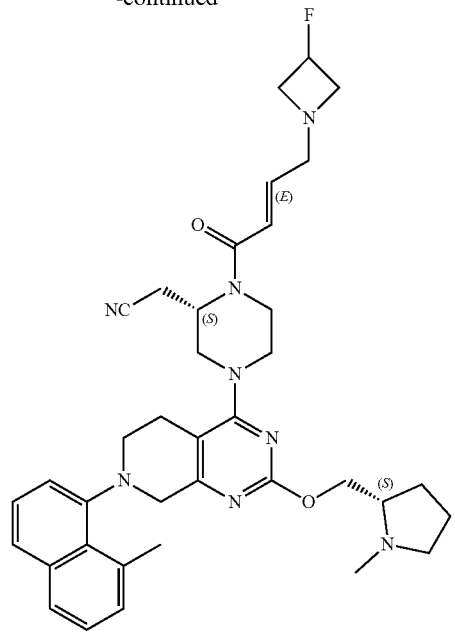

Step A: 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 293 umol, 1.0 eq) and pyridine (186 mg, 2.35 mmol, 189 µL, 8.0 eq) in dichloromethane (4.0 mL) was added (E)-4-bromobut-2-enoyl chloride (215 mg, 1.17 mmol, 4.0 eq). The mixture was stirred at 0° C. for 0.5 hour. After completion, the reaction mixture was concentrated to give the product 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (200 mg, crude) as yellow oil. The product was used for the next step without further purification. LCMS [ESI, M+1]: 658.

Step B: 2-[(2S)-1-[(E)-4-(3-fluoroazetidin-1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-1-[(E)-4-bromobut-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (150 mg, 228 umol, 1.0 eq) and $K_2CO_3$ (315 mg, 2.28 mmol, 10.0 eq) in acetonitrile (2.0 mL) was added 3-fluoroazetidine (152 mg, 1.37 mmol, 6.0 eq, HCl). The mixture was stirred at 0° C. for 0.5 hour. After completion, the reaction mixture was added water (5.0 mL) and extracted with ethyl acetate (5.0 mL×4). The organic layer was dried over $Na_2SO_4$, filtered and concentrated under vacuum. The residue was purified by prep-HPLC (column: Gemini 150*25 5 u; mobile phase: [water (0.05% ammonia hydroxide v/v)-ACN]; B %: 60%-90%,12 min) to give the title compound 2-[(2S)-1-[(E)-4-(3-fluoroazetidin- 1-yl)but-2-enoyl]-4-[7-(8-methyl-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (EXAMPLE 44, 45.0 mg, 66 umol, 29% yield, 96% purity) as white solid. LCMS [ESI, M+1]: 653.

$^1$H NMR (400 MHz, Chloroform-d) δ 7.70 (br d, J=8.0 Hz, 1H), 7.65 (t, J=8.4 Hz, 1H), 7.41 (dd, J=7.6, 15.2 Hz, 1H), 7.34 (t, J=7.6 Hz, 1H), 7.27-7.18 (m, 2H), 6.92-6.82 (m, 1H), 6.52-6.31 (m, 1H), 5.28-5.08 (m, 1H), 5.07-4.46 (m, 1H), 4.41-4.33 (m, 1H), 4.32-4.01 (m, 4H), 4.01-3.79 (m, 2H), 3.79-3.56 (m, 3H), 3.55-3.37 (m, 2H), 3.36-3.31 (m, 2H), 3.30-3.24 (m, 1H), 3.23-3.18 (m, 2H), 3.17-3.15 (m, 1H), 3.14-3.06 (m, 2H), 3.05-2.95 (m, 1H), 2.92 (s, 3H), 2.86-2.75 (m, 1H), 2.71-2.57 (m, 2H), 2.47 (d, J=4.0 Hz, 3H), 2.33-2.22 (m, 1H), 2.11-1.99 (m, 1H), 1.88-1.67 (m, 3H).

Example 45

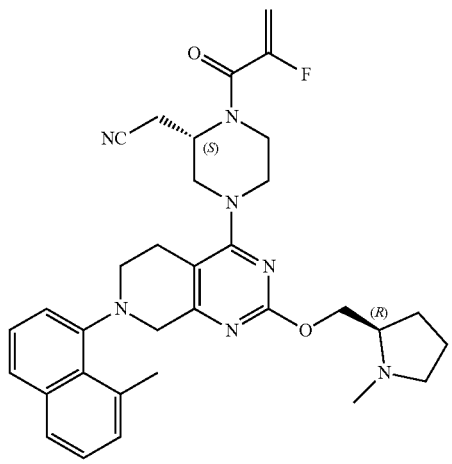

2-((S)-1-(2-fluoroacryloyl)-4-(7-(8-methylnaphthalen-1-yl)-2-(((R)-1-methylpyrrolidin-2-yl)methoxy)-5,6,7,8-tetrahydropyrido[3,4-d]pyrimidin-4-yl)piperazin-2-yl)acetonitrile

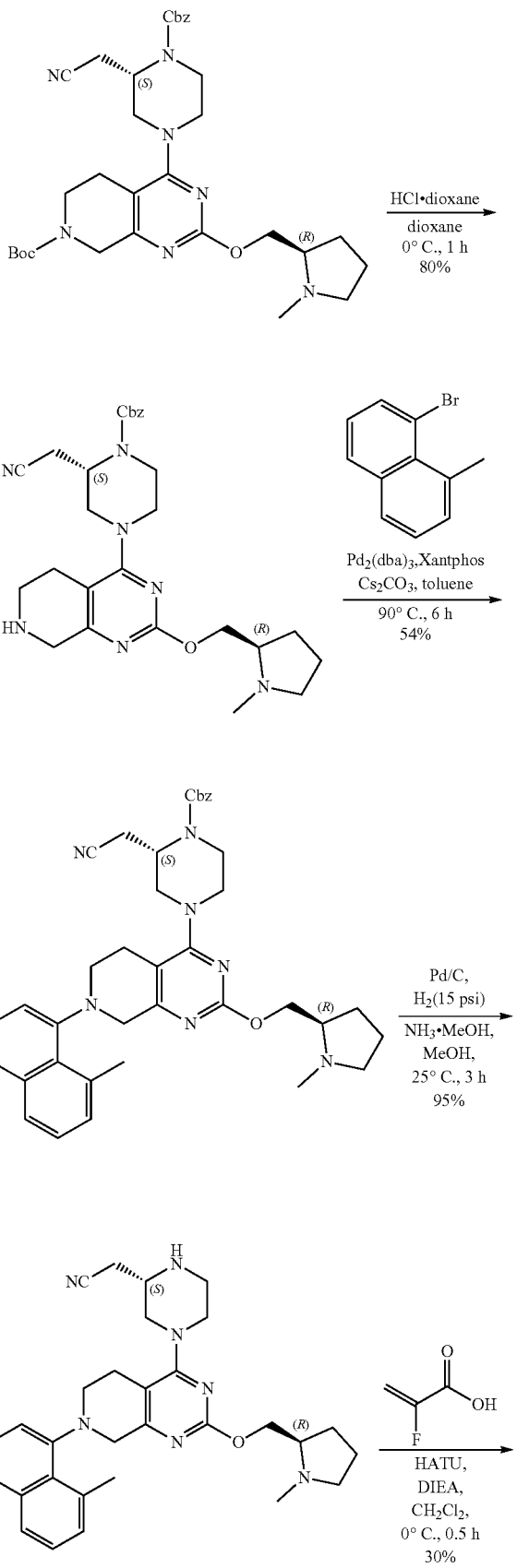

-continued

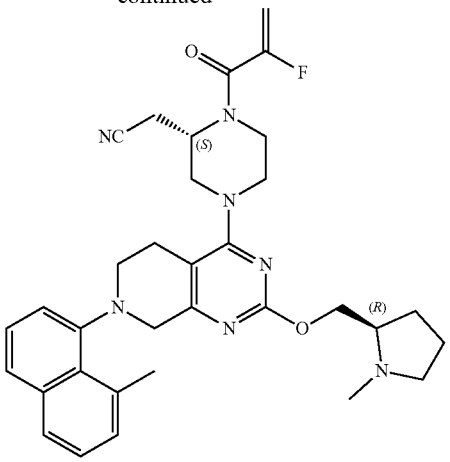

Step A: Tert-Butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate A mixture of tert-butyl 4-[(3S)-4-benzyloxycarbonyl-3-(cyanomethyl)piperazin-1-yl]-2-chloro-6,8-dihydro-5H-pyrido[3,4-d]pyrimidine-7-carboxylate (5.5 g, 10.4 mmol, 1 eq), [(2R)-1-methylpyrrolidin-2-yl]methanol (2.40 g, 20.9 mmol, 2.25 mL, 2 eq), Pd$_2$(dba)$_3$ (1.91 g, 2.09 mmol, 0.2 eq), RuPhos (1.95 g, 4.17 mmol, 0.4 eq) and Cs$_2$CO$_3$ (8.50 g, 26.1 mmol, 2.5 eq) in toluene (100 mL) was degassed and purged with N$_2$ for 3 times, and then the mixture was stirred at 90° C. for 5 hours under N$_2$ atmosphere. The reaction mixture was concentrated under reduced pressure to give a residue. The residue was diluted with ethyl acetate (100 mL) and water (50 mL). Then the mixture was acidified to PH~4 with 1 M HCl aqueous solution. The water phase was separated and basified to PH~8 with saturated Na$_2$CO$_3$ aqueous solution, then the mixture was extracted with ethyl acetate (50 mL×2). The combined organic layers were washed with brine (30 mL), dried over Na$_2$SO$_4$, filtered and concentrated under reduced pressure. tert-Butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (4 g, 5.55 mmol, 53% yield, 84% purity) was obtained as a yellow solid and used to next step without purification.

$^1$H NMR (400 MHz, chloroform-d) δ=7.46-7.31 (m, 5H), 5.23 (s, 2H), 4.74-4.49 (m, 2H), 4.43-4.27 (m, 2H), 4.21-3.70 (m, 5H), 3.42-3.17 (m, 3H), 3.09 (t, J=7.6 Hz, 1H), 2.98 (td, J=3.6, 12.4 Hz, 1H), 2.86-2.74 (m, 1H), 2.74-2.54 (m, 4H), 2.47 (s, 3H), 2.35-2.21 (m, 1H), 2.05-1.97 (m, 1H), 1.90-1.74 (m, 3H), 1.49 (s, 9H).

Step B: Benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate To a solution of tert-butyl 4-[(3S)-4-benzyloxycarbonyl-3-(cyanomethyl)piperazin-1-yl]-2-[[(2R)-1-methylpyrrolidin-2-yl]methoxy]-6,8-dihydro-5H-pyrido[3,4-d]pyrimidine-7-carboxylate (3.7 g, 6.11 mmol, 1 eq) in dioxane (20 mL) was added HCl/dioxane (4 M, 22.9 mL, 15 eq). The mixture was stirred at 0° C. for 1 hour. The liquid was decanted and the solid was collected. The solid residue was diluted with water (50 mL) and dichloromethane (100 mL), then the mixture was basified to pH~8 with saturated Na$_2$CO$_3$ aqueous solution and extracted with dichloromethane (100 mL×3). The combined organic layers were washed with brine (50 mL), dried over Na$_2$SO$_4$, filtered and concentrated under reduced pressure. Benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (2.6 g, 4.89 mmol, 80% yield, 95% purity) was obtained as a yellow solid and used next step without purification. LCMS [ESI, M+1]: 506.

Step C: Benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate A mixture of benzyl (2S)-2-(cyanomethyl)-4-[2-[[(2R)-1-methylpyrrolidin-2-yl]methoxy]-5,6,7,8-tetrahydropyrido[3,4-d]pyrimidin-4-yl]piperazine-1-carboxylate (2.3 g, 4.55 mmol, 1 eq), 1-bromo-8-methyl-naphthalene (Intermediate 69, 1.31 g, 5.91 mmol, 1.3 eq), Cs$_2$CO$_3$ (3.71 g, 11.4 mmol, 2.5 eq), Pd$_2$(dba)$_3$ (833 mg, 909 umol, 0.2 eq) and Xantphos (1.05 g, 1.82 mmol, 0.4 eq) in toluene (50 mL) was degassed and purged with N$_2$ for 3 times, and then the mixture was stirred at 90° C. for 6 hours under N$_2$ atmosphere. The reaction mixture was diluted with water (100 mL) and extracted with ethyl acetate (200 mL×3). The combined organic layers were washed with brine (100 mL), dried over Na$_2$SO$_4$, filtered and concentrated under reduced pressure to give a residue. The residue was purified by column chromatography (SiO$_2$, Ethyl acetate/Methanol=100/1 to 10/1). Benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (1.6 g, 2.48 mmol, 54% yield) was obtained as a yellow solid.

Step D: 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile A mixture of benzyl (2S)-2-(cyanomethyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazine-1-carboxylate (1.60 g, 2.48 mmol, 1.00 eq) in MeOH (20.0 mL) and NH$_3$ (20% w/w in MeOH, 7 mL) was hydrogenated with Pd/C (100 mg, 2.48 mmol, 10% purity, 1.00 eq) as a catalyst under H$_2$ (4.99 mg, 2.48 mmol, 1.00 eq, 15 psi) at 25° C. for 3 hours. The catalyst was filtered off through a pad of celite and the filtrate was concentrated under vacuum. The crude product was used to next step directly without further purification. 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (1.20 g, 2.35 mmol, 95% yield) was obtained as a light yellow solid. LCMS [ESI, M+1]: 512.

Step E: 2-[(2S)-1-(2-fluoroprop-2-enoyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a mixture of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (140 mg, 274 umol, 1.00 eq) and 2-fluoroprop-2-enoic acid (73.9 mg, 821 umol, 3.00 eq) in dichloromethane (3.00 mL) was added DIEA (212 mg, 1.64 mmol, 286 μL, 6.00 eq), HATU (312 mg, 821 umol, 3.00 eq) in one portion at 0° C. under N₂. After stirring at 0° C. for 30 min, the reaction mixture was diluted with water (10.0 mL) and extracted with dichloromethane (2×10.0 mL). The combined organic layers were washed with water (1×10.0 mL), dried over sodium sulfate, filtered and concentrated under reduced pressure to give a residue. The residue was purified by prep-HPLC (column: Phenomenex Gemini 150*25 mm*10 um; mobile phase: [water (0.04% NH₃H₂O+10 mM NH₄HCO₃)—ACN]; B %: 55%-85%, 10 min). Title compound 2-[(2S)-1-(2-fluoroprop-2-enoyl)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 45, 48.7 mg, 82.1 umol, 30% yield, 98.4% purity) was obtained as a white solid.

SFC condition: "Column: Chiralcel OJ-3 50×4.6 mm I.D., 3 um, Mobile phase: methanol (0.05% DEA) in CO₂ from 5% to 40%, Flow rate: 3 mL/min, Wavelength: 220 nm".

¹H NMR (400 MHz, chloroform-d) δ=7.73-7.62 (m, 2H), 7.45-7.31 (m, 2H), 7.27-7.17 (m, 2H), 5.53-5.34 (m, 1H), 5.26 (dd, J=3.6, 17.2 Hz, 1H), 4.88 (br s, 1H), 4.41-4.32 (m, 1H), 4.31-4.22 (m, 1H), 4.21-4.10 (m, 2H), 4.10-4.02 (m, 1H), 3.89 (br d, J=18.0 Hz, 1H), 3.78 (d, J=18.4 Hz, 1H), 3.59-3.40 (m, 2H), 3.27-3.15 (m, 2H), 3.14-3.04 (m, 2H), 3.03-2.90 (m, 4H), 2.90-2.73 (m, 2H), 2.72-2.56 (m, 2H), 2.47 (d, J=4.8 Hz, 3H), 2.33-2.23 (m, 1H), 2.11-1.98 (m, 1H), 1.90-1.74 (m, 3H).

Example 46

2-((S)-1-((E)-4-hydroxybut-2-enoyl)-4-(7-(8-methyl-naphthalen-1-yl)-2-(((R)-1-methylpyrrolidin-2-yl)methoxy)-5,6,7,8-tetrahydropyrido[3,4-d]pyrimidin-4-yl)piperazin-2-yl)acetonitrile

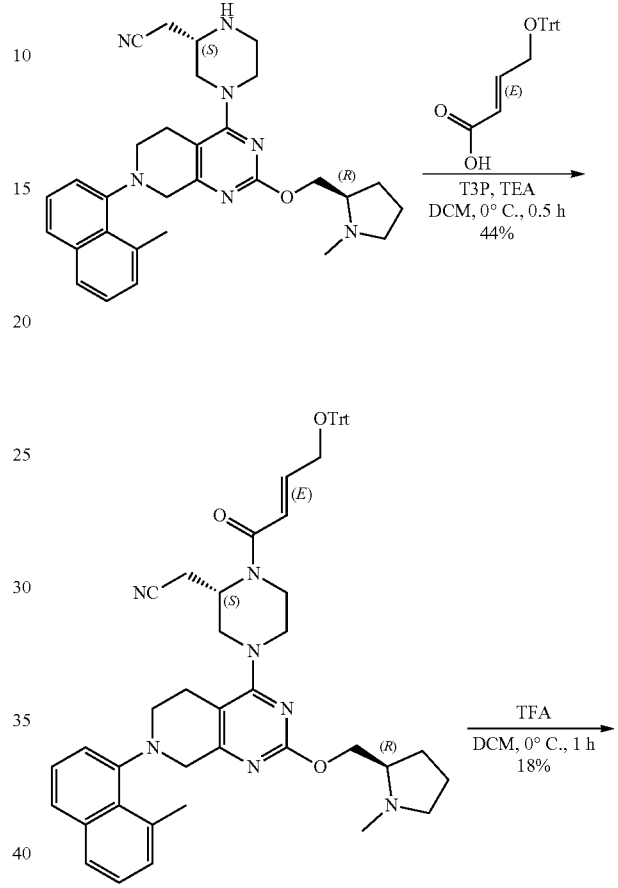

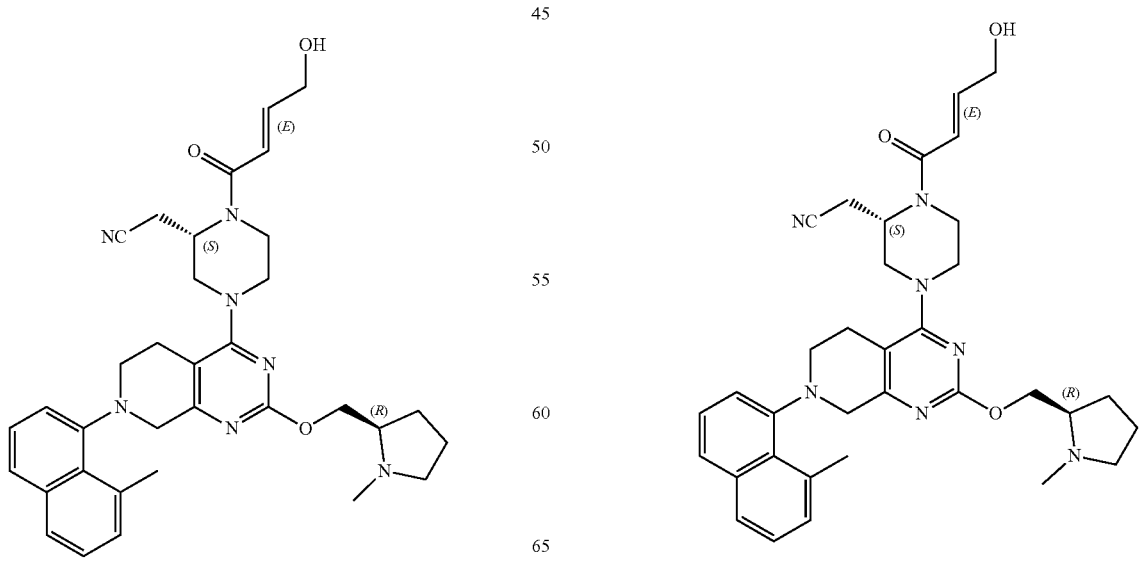

Step A: 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (120 mg, 234 umol, 1 eq), TEA (142 mg, 1.41 mmol, 195 μl, 6 eq) and (E)-4-trityloxybut-2-enoic acid (96.9 mg, 281 umol, 1.2 eq) in ethyl acetate (2 mL) was added T3P (448 mg, 703 umol, 418 μL, 50% purity in EtOAc, 3 eq) at 0° C. The mixture was stirred at 0° C. for 0.5 hour. The reaction mixture was diluted with water (5 mL) and extracted with ethyl acetate (10 mL×3). The combined organic layers were washed with brine (10 mL), dried over $Na_2SO_4$, filtered and concentrated under reduced pressure to give a residue. The residue was purified by column chromatography ($SiO_2$, Ethyl acetate/Methanol=200/1 to 10/1). 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (90 mg, 103 umol, 44% yield, 96% purity) was obtained as a yellow oil. LCMS [ESI, M+1]: 838.

Step B: 2-[(2S)-1-[(E)-4-hydroxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]-1-[(E)-4-trityloxybut-2-enoyl]piperazin-2-yl]acetonitrile (80 mg, 95.5 umol, 1 eq) in dichloromethane (200 uL) was added TFA (218 mg, 1.91 mmol, 141 μL, 20 eq). The mixture was stirred at 0° C. for 1 hour. The reaction mixture was diluted with water (5 mL) and basified to pH~8 with $NaHCO_3$ aqueous solution (2 mL). The mixture was extracted with dichloromethane (5 mL×3). The combined organic layers were washed with brine (3 mL), dried over $Na_2SO_4$, filtered and concentrated under reduced pressure to give a residue. The residue was purified by prep-HPLC (column: Gemini 150*25 5 u; mobile phase: [water (0.05% ammonia hydroxide v/v)—ACN]; B %: 50%-80%, 12 min). The mixture was collected and lyophlizated. Title compound 2-[(2S)-1-[(E)-4-hydroxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 46, 10.2 mg, 16.8 umol, 18% yield, 98.5% purity) was obtained as a off-white solid. LCMS [ESI, M+1]: 596.

SFC condition: Column: Chiralcel OD-3 50×4.6 mm I.D., 3 um, Mobile phase: 40% methanol (0.05% DEA) in $CO_2$, Flow rate: 3 mL/min, Wavelength: 220 nm.

$^1$H NMR (400 MHz, chloroform-d) δ=7.73-7.61 (m, 2H), 7.46-7.30 (m, 2H), 7.27-7.16 (m, 2H), 7.06 (d, J=14.8 Hz, 1H), 6.62 (br d, J=13.6 Hz, 1H), 5.25-4.53 (m, 1H), 4.48-4.32 (m, 3H), 4.30-3.95 (m, 4H), 3.93-3.82 (m, 1H), 3.81-3.61 (m, 1H), 3.59-3.39 (m, 2H), 3.30-2.96 (m, 5H), 2.92 (s, 3H), 2.87-2.53 (m, 4H), 2.47 (d, J=4.0 Hz, 3H), 2.34-2.21 (m, 1H), 2.13-1.99 (m, 1H), 1.98-1.82 (m, 3H).

Example 47

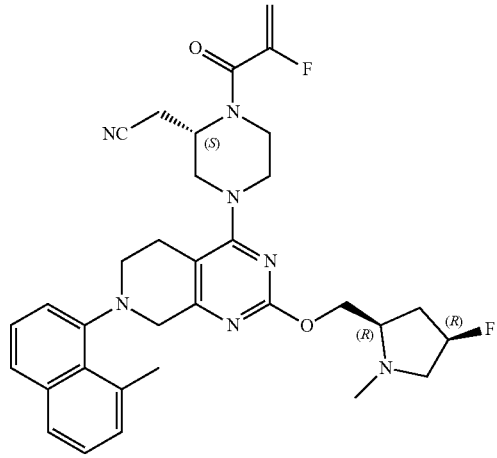

2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile

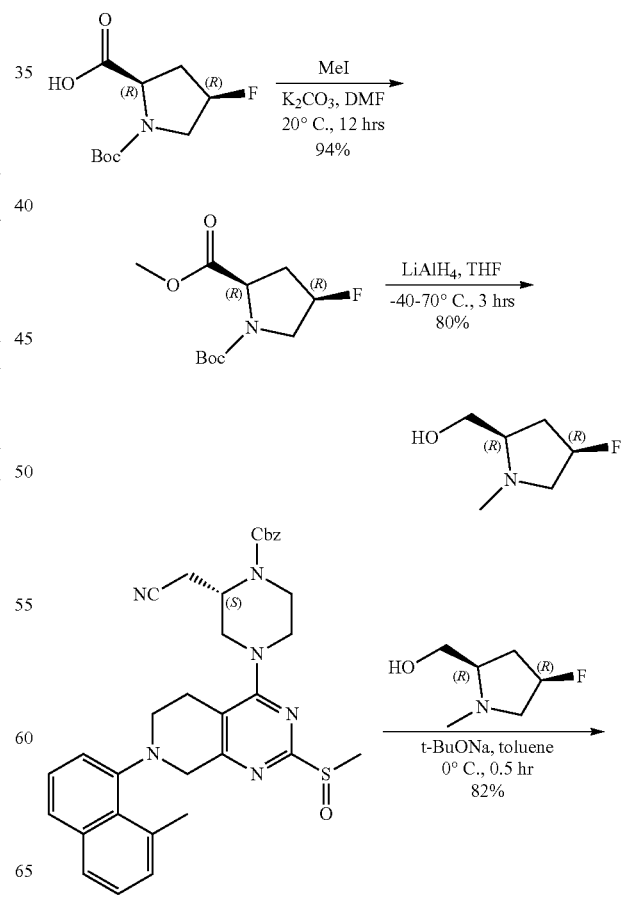

-continued

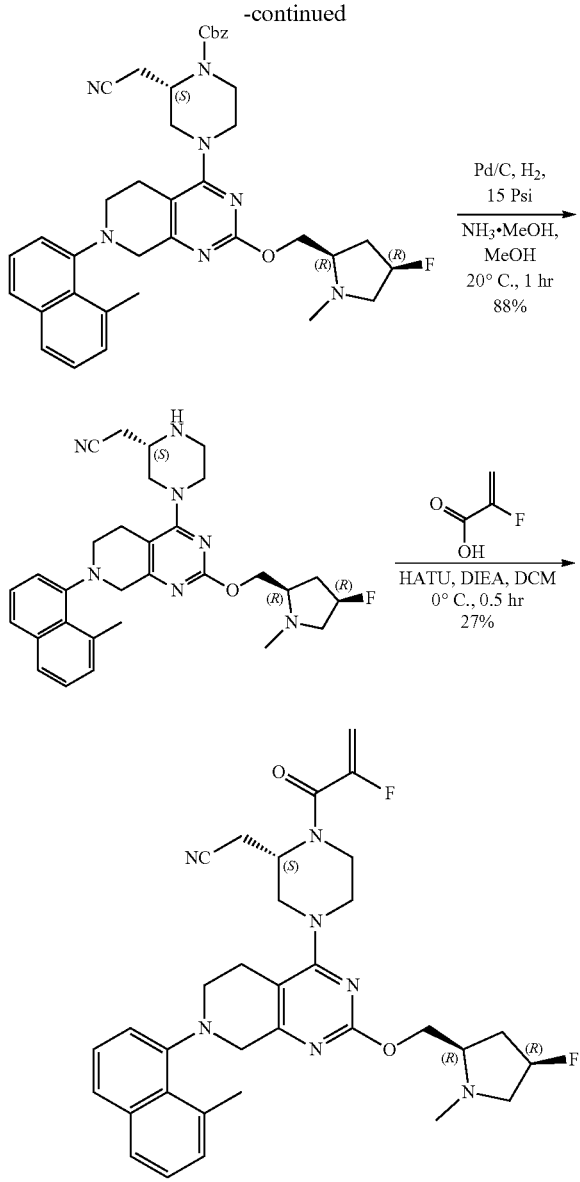

Step 1: O1-tert-butyl O2-methyl (2R,4R)-4-fluoropyrrolidine-1,2-dicarboxylate

To a solution of (2R,4R)-1-tert-butoxycarbonyl-4-fluoropyrrolidine-2-carboxylic acid (300 mg, 1.29 mmol, 1.0 eq) and K$_2$CO$_3$ (533 mg, 3.86 mmol, 3.0 eq) in DMF (2.0 mL) was added MeI (4.80 g, 33.8 mmol, 2.11 mL, 26.3 eq). The mixture was stirred at 20° C. for 12 hours. After completion, the reaction mixture was added water (5.0 mL) and extracted with ethyl acetate (10.0 ml×2). The organic layer was dried over Na$_2$SO$_4$, filtered and concentrated. The residue was purified by column chromatography (SiO$_2$, Petroleum ether: Ethyl acetate=10:1-1:1) to give the product O1-tert-butyl O2-methyl (2R,4R)-4-fluoropyrrolidine-1,2-dicarboxylate (300 mg, 1.21 mmol, 94% yield) as yellow oil.

$^1$H NMR (400 MHz, Chloroform-d) δ 5.30-5.10 (m, 1H), 4.58-4.37 (m, 1H), 3.94-3.76 (m, 1H), 3.75 (s, 3H), 3.72-3.55 (m, 1H), 2.54-2.23 (m, 2H), 1.52-1.40 (m, 9H).

Step 2: [(2R,4R)-4-fluoro-1-methyl-pyrrolidin-2-yl]methanol to a Solution of O1-tert-butyl O2-methyl (2R,4R)-4-fluoropyrrolidine-1,2-dicarboxylate (300 mg, 1.21 mmol, 1.0 eq) in THF (3.0 mL) was added LiAlH$_4$ (138 mg, 3.64 mmol, 3.0 eq) at −40° C. The mixture was stirred at this temperature for 1 hour, then heated to 70° C. and stirred at 70° C. for 2 hours. After completion, the reaction mixture was quenched with saturated Na$_2$SO$_4$ aqueous (0.30 mL), then filtered. The mother liquor was collected and concentrated under vacuum to give the product [(2R,4R)-4-fluoro-1-methyl-pyrrolidin-2-yl]methanol (130 mg, 976 umol, 80% yield) as yellow oil.

$^1$H NMR (400 MHz, Chloroform-d) δ 5.18-4.98 (m, 1H), 3.76-3.70 (m, 1H), 3.54-3.43 (m, 1H), 3.38-3.28 (m, 1H), 2.51-2.44 (m, 1H), 2.42-2.37 (m, 1H), 2.35 (s, 3H), 2.34-2.26 (m, 1H), 2.21-2.09 (m, 1H).

Step A: Benzyl(2S)-2-(cyanomethyl)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To a solution of [(2R,4R)-4-fluoro-1-methyl-pyrrolidin-2-yl] methanol (103 mg, 773 umol, 2.0 eq) and t-BuONa (55.8 mg, 580 umol, 1.50 eq) in toluene (2.0 mL) was added benzyl (2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (230 mg, 387 umol, 1.0 eq). The mixture was stirred at 0° C. for 0.5 hour. After completion, the reaction mixture was added water (10.0 mL) and extracted with ethyl acetate (10.0 ml×3). The organic layer was dried over Na$_2$SO$_4$, filtered and concentrated. The residue was purified by reversed phase flash HPLC (C18, 0.1% FA in water, 0-60% MeCN) to give the product benzyl(2S)-2-(cyanomethyl)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (210 mg, 316 umol, 82% yield) as yellow solid. LCMS [ESI, M+1]:664.

$^1$H NMR (400 MHz, Chloroform-d) δ 7.70 (br d, J=8.4 Hz, 1H), 7.65 (t, J=8.6 Hz, 1H), 7.45-7.32 (m, 7H), 7.26-7.17 (m, 2H), 5.24-5.02 (m, 3H), 4.73-4.61 (m, 1H), 4.53-4.42 (m, 1H), 4.30-4.18 (m, 2H), 4.11-3.96 (m, 2H), 3.94-3.81 (m, 1H), 3.81-3.67 (m, 1H), 3.58-3.47 (m, 1H), 3.46-3.29 (m, 2H), 3.24-3.06 (m, 3H), 3.05-2.96 (m, 1H), 2.92 (s, 3H), 2.82-2.71 (m, 2H), 2.70-2.51 (m, 2H), 2.50-2.47 (m, 4H), 2.45-2.35 (m, 1H), 2.12-2.05 (m, 1H).

Step B: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To a solution of benzyl (2S)-2-(cyanomethyl)-4-[2-[[(2R,4R)-4-fluoro-1-methyl-pyrrolidin-2-yl]methoxy]-7-(8-methyl-1-naphthyl)-6,8-dihydro-5H-pyrimidin-4-yl]piperazine-1-carboxylate (200 mg, 301 umol, 1.0 eq) and NH$_3$-MeOH (2.0 mL, 20% purity) in methanol (4.0 mL) was added Pd/C (80 mg, 10% purity). The mixture was purged by N$_2$ for 3 times, and then stirred under H$_2$ atmosphere (15 Psi) at 25° C. for 1 hour. After completion, the reaction mixture was filtered through Celite. The mother liquor was concentrated under vacuum to give the product 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (140 mg, 264 umol, 88% yield) as yellow oil. The product was used for the next step directly without further purification. LCMS [ESI, M+1]:664.

Step C: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (120 mg, 226 umol, 1.0 eq), 2-fluoroprop-2-enoic acid (61.2 mg, 680 umol, 3.0 eq) and DIEA (176 mg, 1.36 mmol, 238 μL, 6.0 eq) in DCM (3.0 mL) was added HATU (258.44 mg, 679.69 umol, 3 eq). The mixture was stirred at 0° C. for 0.5 hour. After completion, the reaction mixture was added water (5.0 mL) and extracted with ethyl acetate (5.0 mL×3). The organic layer was dried over $Na_2SO_4$, filtered and concentrated under vacuum. The residue was purified by prep-HPLC (column: Gemini 150*25 5 u; mobile phase: [water (0.05% ammonia hydroxide v/v)-ACN]; B %: 50%-80%,12 min) to give the title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-(2-fluoroprop-2-enoyl)piperazin-2-yl]acetonitrile (EXAMPLE 47, 37.9 mg, 60.1 umol, 27% yield, 96% purity) as white solid. LCMS [ESI, M+1]: 602.

$^1$H NMR (400 MHz, Chloroform-d) δ 7.70 (br d, J=8.0 Hz, 1H), 7.65 (t, J=8.2 Hz, 1H), 7.45-7.37 (m, 1H), 7.34 (t, J=7.6 Hz, 1H), 7.27-7.18 (m, 2H), 5.53-5.32 (m, 1H), 5.30-5.22 (m, 1H), 5.21-5.03 (m, 1H), 4.97-4.68 (m, 1H), 4.52-4.42 (m, 1H), 4.29-4.20 (m, 2H), 4.18-4.03 (m, 2H), 3.95-3.68 (m, 2H), 3.60-3.41 (m, 2H), 3.39-3.30 (m, 1H), 3.26-3.15 (m, 2H), 3.15-2.95 (m, 2H), 2.92 (s, 3H), 2.90-2.54 (m, 4H), 2.53-2.46 (m, 4H), 2.45-2.35 (m, 1H), 2.13-1.97 (m, 1H).

Example 48

2-[(2S)-1-(2-fluoroprop-2-enoyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

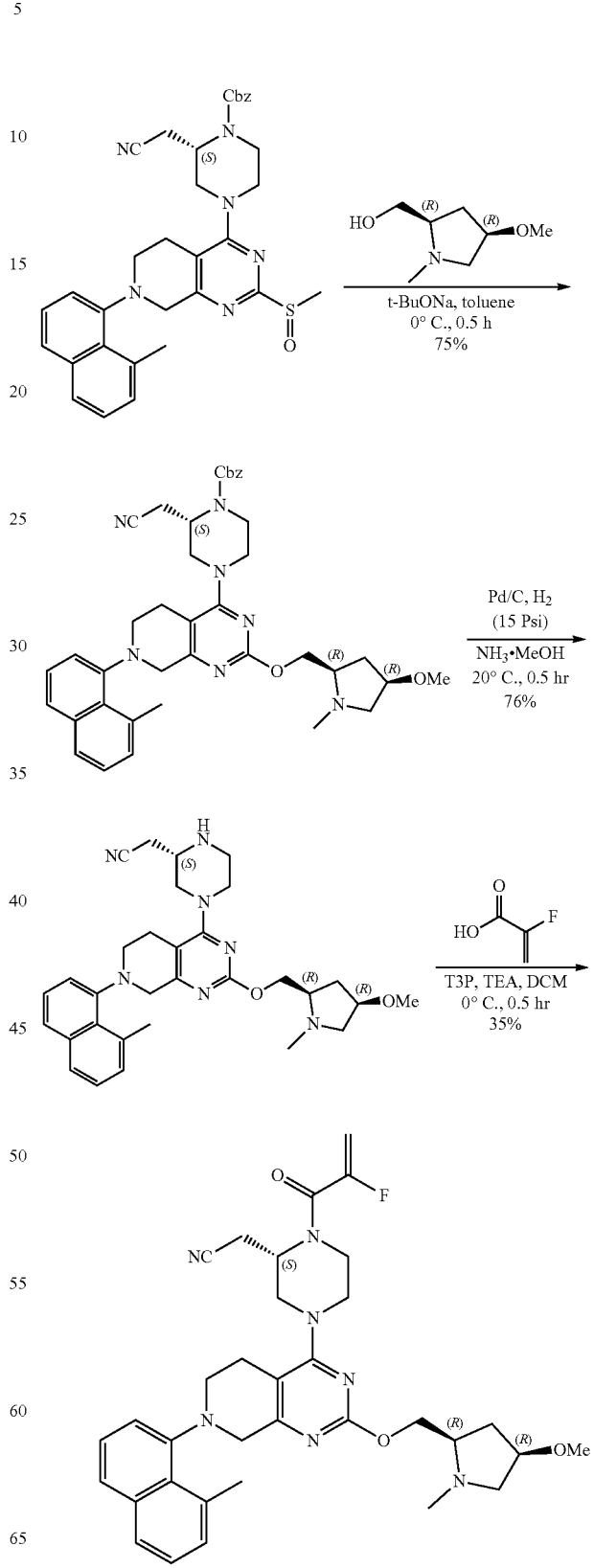

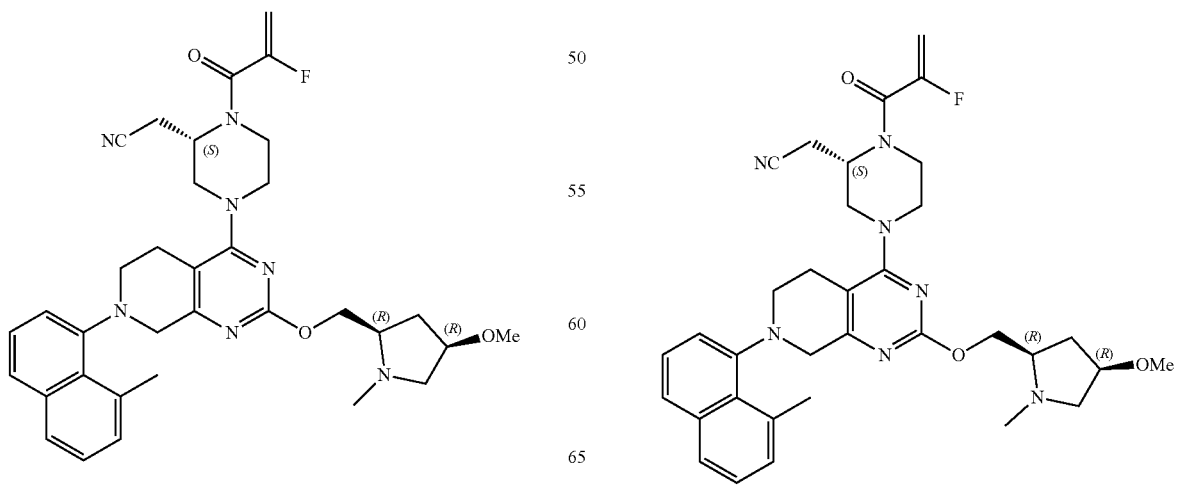

-continued

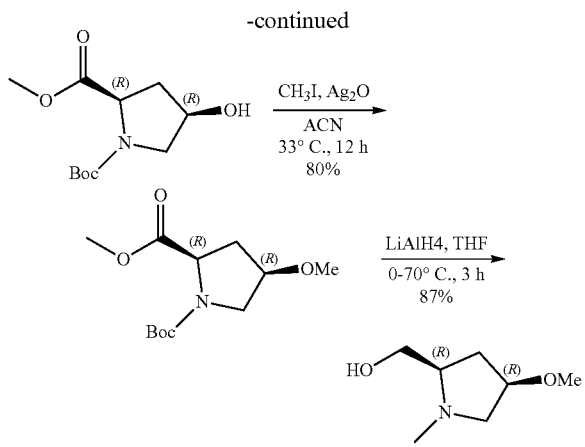

Step 1: O1-tert-butyl O2-methyl (2R,4R)-4-methoxypyrrolidine-1,2-dicarboxylate To a solution of O1-tert-butyl O2-methyl (2R,4R)-4-hydroxypyrrolidine-1,2-dicarboxylate (2.1 g, 8.56 mmol, 1 eq) in MeCN (42 mL) was added Ag$_2$O (5.95 g, 25.7 mmol, 3 eq) and CH$_3$I (7.75 g, 54.6 mmol, 3.40 mL, 6.38 eq). The reaction mixture was stirred at 33° C. for 12 hours. The reaction mixture was filtered and the filtrate was concentrated under vacuum. The residue was purified by column chromatography (SiO$_2$, Petroleum ether/Ethyl acetate=8/1 to 5/1) to give O1-tert-butyl O2-methyl (2R,4R)-4-methoxypyrrolidine-1,2-dicarboxylate (1.88 g, 6.89 mmol, 80% yield, 95.0% purity) as a colorless oil.

$^1$H NMR (400 MHz, chloroform-d) δ=4.45-4.26 (m, 1H), 3.96-3.89 (m, 1H), 3.72 (s, 3H), 3.68-3.55 (m, 1H), 3.54-3.43 (m, 1H), 3.27 (s, 3H), 2.38-2.17 (m, 2H), 1.51-1.37 (m, 9H).

Step 2: [(2R,4R)-4-methoxy-1-methyl-pyrrolidin-2-yl]methanol

To the solution of O1-tert-butyl O2-methyl (2R,4R)-4-methoxypyrrolidine-1,2-dicarboxylate (2.98 g, 11.5 mmol, 1 eq) in THF (60 mL) was added LiAlH$_4$ (872 mg, 23.0 mmol, 2 eq) at 0° C., the mixture was stirred at 0° C. for 1 hour. Then the reaction mixture was heated to 80° C. and stirred for 2 hours. The mixture was quenched with saturated Na$_2$SO$_4$ aqueous (3 mL), then filtered and the filter cake was washed with THF (3×20 mL). The filtrate was concentrated under vacuum to give [(2R,4R)-4-methoxy-1-methyl-pyrrolidin-2-yl]methanol (1.53 g, 10.0 mmol, 87% yield, 95.0% purity) as a brown oil which was used for next step without further purification.

$^1$H NMR (400 MHz, chloroform-d) δ=3.82-3.76 (m, 1H), 3.69 (dd, J=3.2, 11.2 Hz, 1H), 3.45 (dd, J=1.6, 10.8 Hz, 1H), 3.29 (s, 3H), 3.18 (d, J=10.4 Hz, 1H), 2.62 (br s, 1H), 2.42 (tdd, J=2.8, 6.4, 9.2 Hz, 1H), 2.38-2.33 (m, 1H), 2.32 (s, 3H), 2.16 (ddd, J=6.8, 8.8, 14.0 Hz, 1H), 1.92 (tdd, J=1.6, 6.8, 14.0 Hz, 1H).

Step A: (Benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate To the solution of [(2R,4R)-4-methoxy-1-methyl-pyrrolidin-2-yl]methanol (1.37 g, 9.42 mmol, 2.8 eq) in toluene (40 mL) was added t-BuONa (970 mg, 10.1 mmol, 3 eq) at 0° C., then benzyl (2S)-2-(cyanomethyl)-4-[7-(8-methyl-1-naphthyl)-2-methyl sulfinyl-6,8-dihydro-5H-pyrido[3,4-d]pyrimidin-4-yl]piperazine-1-carboxylate (2 g, 3.36 mmol, 1 eq) was added at 0° C., the reaction mixture was stirred at 0° C. for 0.5 hour. Water (20 mL) was added into the mixture. The mixture was diluted with EtOAc (10 mL) and extracted with EtOAc (2×20 mL). The combined organic layers were washed with brine (20 mL). The combined organic layers were dried over anhydrous Na$_2$SO$_4$, filtered and concentrated under vacuum. The residue was purified by reversed phase flash column (ACN/Water (0.1% FA)=57%) to give (benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (1.8 g, 2.53 mmol, 75% yield, 95.0% purity)) as a yellow solid. LCMS [ESI, M+1]: 676.

$^1$H NMR (400 MHz, chloroform-d) δ=7.73-7.60 (m, 2H), 7.47-7.31 (m, 7H), 7.27-7.16 (m, 2H), 5.21 (s, 2H), 4.67 (br s, 1H), 4.45 (br dd, J=4.4, 10.0 Hz, 1H), 4.24-4.16 (m, 2H), 4.10-3.96 (m, 2H), 3.96-3.65 (m, 3H), 3.59-3.40 (m, 2H), 3.29 (d, J=1.6 Hz, 3H), 3.25-3.06 (m, 4H), 3.00 (dt, J=3.6, 12.4 Hz, 1H), 2.91 (s, 3H), 2.81-2.55 (m, 4H), 2.45 (d, J=6.0 Hz, 3H), 2.42-2.29 (m, 2H), 1.88-1.68 (m, 2H).

Step B: 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of benzyl (2S)-2-(cyanomethyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (2 g, 2.96 mmol, 1 eq) and NH$_3$-MeOH (20 mL, 20% purity) in MeOH (40 mL) was added Pd/C (1 g, 10% purity) under N$_2$. The suspension was degassed under vacuum and purged with H$_2$ several times. The mixture was stirred under H$_2$ (15 psi) at 20° C. for 0.5 hour. The reaction mixture was filtered, the filtrate was concentrated under vacuum to give 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (1.29 g, 2.26 mmol, 76% yield, 95% purity) as a yellow solid which was used for next step without further purification. LCMS [ESI, M+1]: 542.

Step C: 2-[(2S)-1-(2-fluoroprop-2-enoyl)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 277 umol, 1 eq), 2-fluoroprop-2-enoic acid (74.8 mg, 831 umol, 3 eq) and TEA (336 mg, 1.66 mmol, 462 μL, 50% purity, 6 eq) in EtOAc (3 mL) was added T3P (264 mg, 831 umol, 247 μL, 3 eq) at 0° C., the mixture was stirred at 0° C. for 0.5 hour. Water (4 mL) was added into the mixture. The mixture was extracted with EtOAc (3×8 mL). The combined organic layers were dried over anhydrous Na$_2$SO$_4$, filtered and concentrated under vacuum. The residue was purified by reversed phase flash column (ACN/Water (0.1% FA)=32%). Then the residue was purified by prep-HPLC (column: Gemini 150*25 5 u; mobile phase: [water (0.05% ammonia hydroxide v/v)-ACN];B %: 55%-85%,12 min) to give title compound 2-[(2S)-1-(2-fluoroprop-2-enoyl)-4-[2-[[(2R,4R)-4- methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (EXAMPLE 48, 59.5 mg, 97.0 umol, 35% yield, 100% purity) as a white solid. LCMS [ESI, M+1]: 614.

$^1$H NMR (400 MHz, chloroform-d) δ=7.70 (br d, J=8.4 Hz, 1H), 7.65 (t, J=8.0 Hz, 1H), 7.45-7.38 (m, 1H), 7.34 (t, J=7.6 Hz, 1H), 7.27-7.17 (m, 2H), 5.53-5.33 (m, 1H), 5.26 (dd, J=3.6, 16.8 Hz, 1H), 4.88 (br s, 1H), 4.50-4.41 (m, 1H), 4.30-3.99 (m, 4H), 3.96-3.71 (m, 3H), 3.59-3.40 (m, 2H), 3.30 (s, 3H), 3.25-3.15 (m, 3H), 3.14-2.94 (m, 2H), 2.92 (s, 3H), 2.90-2.74 (m, 2H), 2.73-2.55 (m, 2H), 2.45 (d, J=5.6 Hz, 3H), 2.42-2.29 (m, 2H), 1.81 (br dd, J=7.2, 14.4 Hz, 1H).

Example 49

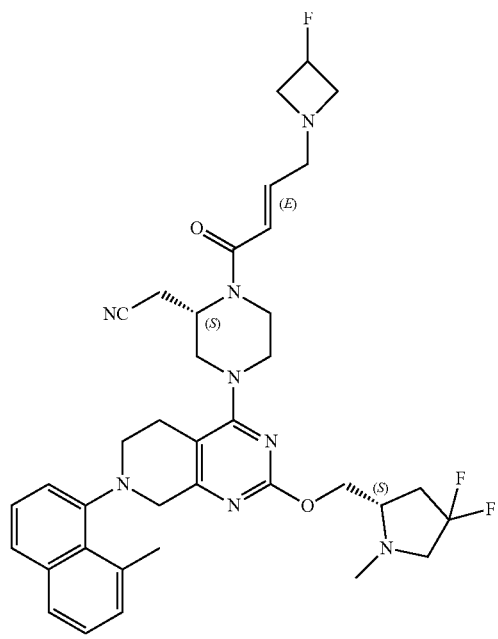

2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl]acetonitrile

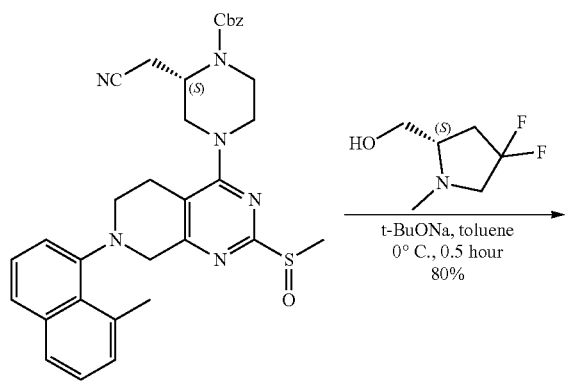

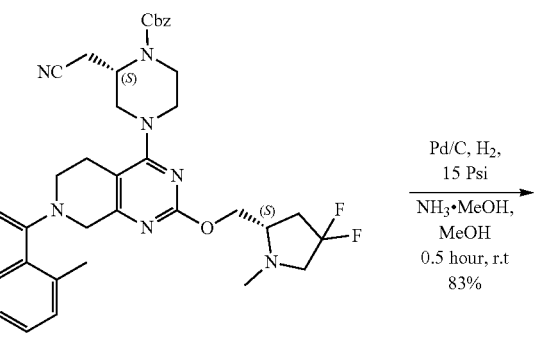

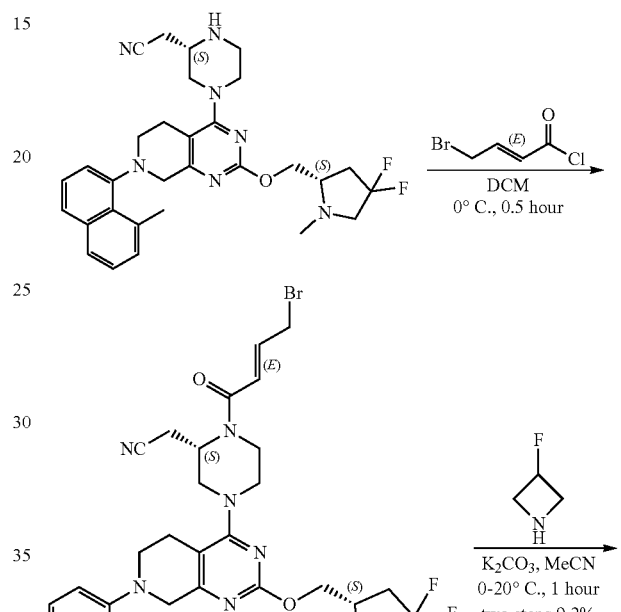

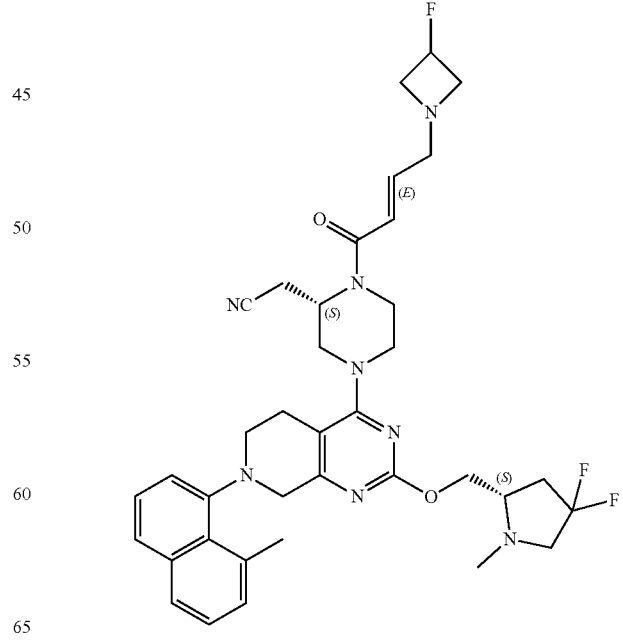

Step A: Benzyl(2S)-2-(cyanomethyl)-4-[2-[[(2S)-4, 4-difluoro-1-methyl-pyrrolidin-2-yl]methoxy]-7-(8-methyl-1-naphthyl)-6,8-dihydro-5H-pyrido[3,4-d] pyrimidin-4-yl]piperazine-1-carboxylate To a solution of [(2S)-4,4-difluoro-1-methyl-pyrrolidin-2-yl]methanol (609.98 mg, 4.04 mmol, 3.0 eq) and t-BuONa (388 mg, 4.04 mmol, 3.0 eq) in toluene (2.0 mL) was dropwise added a solution of benzyl(2S)-2-(cyanomethyl)-4-[7-(8-methyl-1-naphthyl)-2-methylsulfinyl-6,8-dihydro-5H-pyrido[3,4-d]pyrimidin-4-yl]piperazine-1-carboxylate (800 mg, 1.35 mmol, 1.0 eq) in toluene (4.0 mL) at 0° C. The reaction mixture was stirred at 0° C. for 0.5 hour. After completion, the reaction mixture was washed with water (15.0 mL) and extracted with ethyl acetate (3×20.0 mL). The Combine extracts were washed with brine (50.0 mL), dried with $Na_2SO_4$, filtrated and the solvent was removed under vacuum. The residue was purified by reversed phase flash HPLC [C18, 0.1% FA in water, 0-80% MeCN]. The obtained product was then concentrated, the aqueous was extracted with Ethyl acetate (3×50.0 mL), the combined organic layer was dried over $Na_2SO_4$, filtered and concentrated. Compound benzyl(2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl] piperazine-1-carboxylate (750 mg, 1.08 mmol, 80.1% yield, 98% purity) was obtained as yellow solid. LCMS [ESI, M+1]: 682.

Step B: 2-[(2S)-4-[2-[[(2S)-4,4-difluoro-1-methyl-pyrrolidin-2-yl]methoxy]-7-(8-methyl-1-naphthyl)-6, 8-dihydro-5H-pyrido[3,4-d]pyrimidin-4-yl]piperazin-2-yl]acetonitrile benzyl(2S)-2-(cyanomethyl)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazine-1-carboxylate (650 mg, 953 umol, 1.0 eq) and Pd/C (200 mg, 10% purity) was added in MeOH (8.0 mL) and $NH_3$.MeOH (8.0 mL, 20% purity) then the mixture was degassed and purged with $H_2$ for 3 times, and then the mixture was stirred at 20° C. for 0.5 hour under $H_2$ (15 psi) atmosphere. After completion, the crude mixture was filtered through a pad of celite. The cake was washed with MeOH (50.0 mL) and the filtrate dried under high vacuum. Compound 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (420 mg, 736 umol, 77.2% yield, 96% purity) was obtained as yellow solid. LCMS [ESI, M+1]: 548.

Step C: 2-[(2S)-1-[(E)-4-bromobut-2-enoyl]-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]piperazin-2-yl] acetonitrile To a solution of 2-[(2S)-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (420 mg, 822 umol, 1.0 eq) and pyridine (520 mg, 6.57 mmol, 531 μL, 8.0 eq) in DCM (6.0 mL) was added (E)-4-bromobut-2-enoyl chloride (603 mg, 3.29 mmol, 4.0 eq). The mixture was stirred at 0° C. for 0.5 hour. After completion, the mixture was concentrated under vacuum. The product 2-[(2S)-1-[(E)-4-bromobut-2-enoyl]-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (500 mg, crude) was obtained as yellow oil. The crude product was used directly to the next step without further purification. LCMS [ESI, M+1]: 695.

Step D: 2-[(2S)-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl] acetonitrile To a solution of 2-[(2S)-1-[(E)-4-bromobut-2-enoyl]-4-[2-[[(2S)-4,4-difluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (500 mg, 720 umol, 1.0 eq) and $K_2CO_3$ (995 mg, 7.20 mmol, 10.0 eq) in MeCN (12.0 mL) was added 3-fluoroazetidine (482 mg, 4.32 mmol, 6.0 eq, HCl) at 0° C. The mixture was stirred at 20° C. for 1 hour. After completion, the organic solvent was washed with water (10.0 mL). The aqueous phase was extracted with ethyl acetate (3×10 mL). Combine extracts were washed with brine (20.0 mL), dried with $Na_2SO_4$ the solvent was then removed under vacuum. The residue was purified by column chromatography (Base $Al_2O_3$, Petroleum ether: Ethyl acetate=3:1 to Ethyl acetate:Methanol=100:1), then the crude product was concentrated and purified by prep-HPLC (column: Waters Xbridge 150×25 5 u; mobile phase: [water (0.05% ammonia hydroxide v/v)-ACN];B %: 55%-79%,10 min];B %: 45%-75%,12 min) and lyophilization. Title compound 2-[(2S)-4-[2-[[(2S)-4,4-difluoro-1-methyl-pyrrolidin-2-yl] methoxy]-7-(8-methyl-1-naphthyl)-6,8-dihydro-5H-pyrido[3,4-d]pyrimidin-4-yl]-1-[(E)-4-(3-fluoroazetidin-1-yl)but-2-enoyl]piperazin-2-yl]acetonitrile (EXAMPLE 49, 45.8 mg, 66.5 umol, 9.24% yield, 100% purity) was obtained as yellow solid. LCMS [ESI, M+1]: 689.

$^1$H NMR (400 MHz, chloroform-d) δ=7.74-7.63 (m, 2H), 7.47-7.32 (m, 2H), 7.27-7.18 (m, 2H), 6.88 (br d, J=15.3 Hz, 1H), 6.42 (br d, J=15.4 Hz, 1H), 5.27-5.05 (m, 1H), 4.64 (br s, 1H), 4.48-4.41 (m, 1H), 4.31-4.18 (m, 2H), 4.16-3.95 (m, 2H), 3.94-3.84 (m, 1H), 3.82-3.66 (m, 3H), 3.54 (br d, J=7.6 Hz, 1H), 3.50-3.36 (m, 2H), 3.34 (br d, J=3.8 Hz, 2H), 3.30-3.24 (m, 1H), 3.24-3.08 (m, 4H), 3.07-2.95 (m, 2H), 2.92 (s, 3H), 2.86-2.76 (m, 1H), 2.76-2.57 (m, 3H), 2.57-2.47 (m, 1H), 2.46 (d, J=4.5 Hz, 3H), 2.34-2.17 (m, 1H).

Example 50

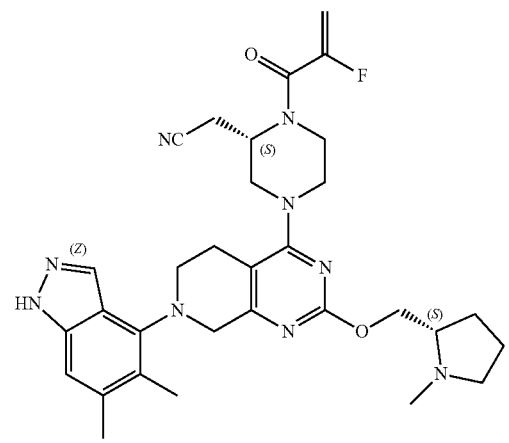

2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

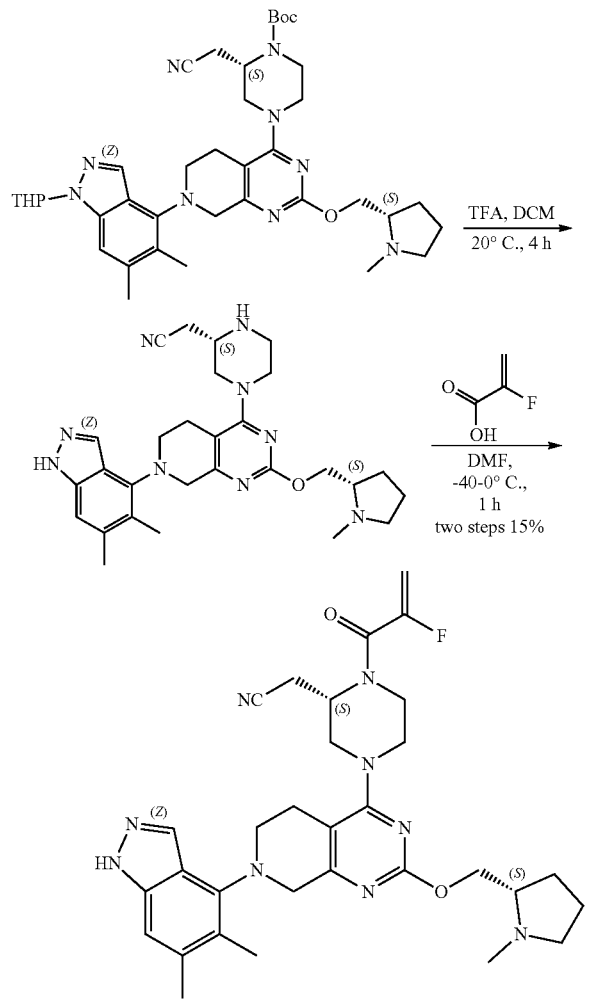

Step A: 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile To a solution of tert-butyl (2S)-2-(cyanomethyl)-4-[7-(5,6-dimethyl-1-tetrahydropyran-2-yl-indazol-4-yl)-2-[[(2S)-1-methylpyrrolidin-2-yl]methoxy]-6,8-dihydro-5H-pyrido[3,4-d]pyrimidin-4-yl]piperazine-1-carboxylate (720 mg, 1.03 mmol, 1 eq) in DCM (1 mL) was added TFA (4.62 g, 40.5 mmol, 3 mL, 39.4 eq). The mixture was stirred at 20° C. for 4 hours. Upon completion, the mixture was diluted with DCM (10 mL) and neutralized with saturated aqueous NaHCO₃. Then the aqueous phase was extracted with EtOAc (2×30 mL). The combined organic layers were dried over Na₂SO₄ and concentrated under vacuum to give 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (880 mg, crude) as a yellow solid which was used directly into the next step without further purification.

Step B: 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]piperazin-2-yl]acetonitrile (500 mg, crude), 2-fluoroprop-2-enoic acid (61.1 mg, 679 umol) and TEA (294 mg, 2.91 mmol, 405 uL) in DMF (10 mL) was added T3P (926 mg, 1.45 mmol, 865 µL, 50% purity in EtOAc) at −40° C. Then the mixture was stirred at −40° C. for 0.5 hour and 0° C. for another 0.5 hour. Upon completion, the mixture was diluted with water (20 mL) and extracted with EtOAc (2×40 mL). The organic layers were washed with brine (50 mL), dried over Na₂SO₄ and concentrated under vacuum. The residue was purified by reversed phase flash [water (0.1% FA)/acetonitrile]. The desired fractions were collected and neutralized with saturated aqueous NaHCO₃ and extracted with EtOAc (2×70 mL). The organic layers were dried over Na₂SO₄ and concentrated under vacuum. The residue was purified by prep-HPLC (column: Phenomenex Synergi C18 150*30 mm*4 um; mobile phase: [water (0.225% FA)-ACN]; B %: 10%-40%, 12 min). The desired fractions were collected and lyophilized to give title compound 2-[(2S)-4-[7-(5,6-dimethyl-1H-indazol-4-yl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 50, 52.5 mg, 79.8 umol, two steps 15% yield, 96.4% purity, FA) as a white solid. LCMS [ESI, M+1]:588.

SFC condition: Column: Chiralcel OJ-3 100×4.6 mm I.D., 3 um, Mobile phase: methanol (0.05% DEA) in CO₂ from 5% to 40%, Flow rate: 3 mL/min, Wavelength: 220 nm.

¹H NMR (400 MHz, chloroform-d) δ=8.03 (s, 1H), 7.15 (s, 1H), 5.53-5.34 (m, 1H), 5.25 (br dd, J=3.2, 16.8 Hz, 1H), 5.02-4.61 (m, 3H), 4.43 (dd, J=4.8, 11.6 Hz, 1H), 4.27 (s, 2H), 4.19 (br d, J=13.2 Hz, 1H), 4.01 (br d, J=12.4 Hz, 1H), 3.68-3.56 (m, 1H), 3.55-3.50 (m, 2H), 3.49-3.21 (m, 3H), 3.14 (br s, 1H), 2.98 (br s, 1H), 2.91-2.61 (m, 7H), 2.41 (s, 3H), 2.34 (s, 3H), 2.23 (qd, J=8.4, 12.4 Hz, 1H), 2.14-1.95 (m, 3H).

Example 51

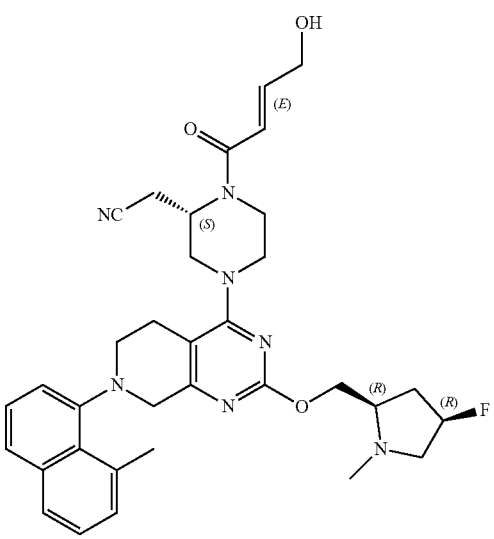

2-((S)-4-(2-(((2R,4R)-4-fluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-hydroxybut-2-enoyl)piperazin-2-yl)acetonitrile

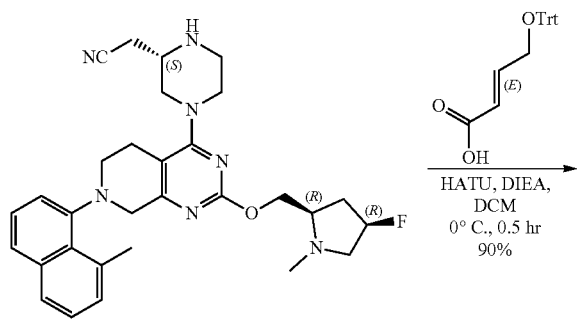

Step A: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityl oxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (200 mg, 378 umol, 1.0 eq), (E)-4-trityloxybut-2-enoic acid (169 mg, 491 umol, 1.3 eq) and DIEA (293 mg, 2.27 mmol, 395 μL, 6.0 eq) in DCM (3.0 mL) was added HATU (431 mg, 1.13 mmol, 3.0 eq). The mixture was stirred at 0° C. for 0.5 hour. After completion, the mixture was added water (10 mL) and extracted with ethyl acetate (2×10.0 mL). The organic layer was dried over Na$_2$SO$_4$, filtered and concentrated. The residue was purified by column chromatography (SiO$_2$, Petroleum ether/Ethyl acetate=3/1 to Ethyl acetate:Methanol=20:1). The product 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (290 mg, 339 umol, 90% yield) was obtained as yellow solid.

Step B: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-hydroxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (290 mg, 339 umol, 1.0 eq) in dichloromethane (1.5 mL) was added TFA (2.31 g, 20.3 mmol, 1.5 mL, 59.8 eq), the mixture was stirred at 20° C. for 0.5 hour. After completion, the reaction mixture was concentrated, then added dichloromethane (10.0 mL), the organic layer was washed with saturated NaHCO$_3$ aqueous (2×10.0 mL), the organic layer was dried over Na$_2$SO$_4$, filtered and concentrated. The residue was purified by column chromatography (Base Al$_2$O$_3$, Petroleum ether/Ethyl acetate=3/1 to Ethyl acetate:Methanol=20:1). The crude product was then repurified by prep-HPLC (column: Gemini 150*25 5 u; mobile phase: [water (0.05% ammonia hydroxide v/v)-ACN];B %: 45%-75%,12 min), the obtained product was concentrated and under lyophilization. Title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-hydroxybut-2-enoyl]piperazin-2-yl]acetonitrile (EXAMPLE 51, 61.3 mg, 99.9 umol, 29% yield, 99% purity) was obtained as white solid. LCMS [ESI, M+1]: 614.

$^1$H NMR (400 MHz, chloroform-d) δ 7.73-7.61 (m, 2H), 7.46-7.31 (m, 2H), 7.27-7.18 (m, 2H), 7.06 (br d, J=14.8 Hz, 1H), 6.62 (br d, J=14.8 Hz, 1H), 5.27-4.97 (m, 1H), 4.74-4.55 (m, 1H), 4.52-4.34 (m, 3H), 4.31-4.16 (m, 2H), 4.15-3.96 (m, 2H), 3.94-3.58 (m, 3H), 3.56-3.48 (m, 1H), 3.46-3.41 (m, 1H), 3.36-3.29 (m, 1H), 3.26-3.07 (m, 3H), 3.04-2.97 (m, 1H), 2.92 (s, 3H), 2.85-2.57 (m, 4H), 2.49 (d, J=4.8 Hz, 3H), 2.45-2.34 (m, 1H), 2.29-1.91 (m, 2H).

Example 52

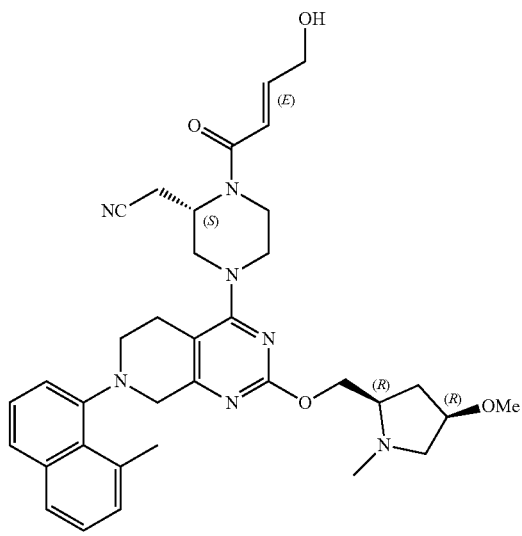

2-[(2S)-1-[(E)-4-hydroxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

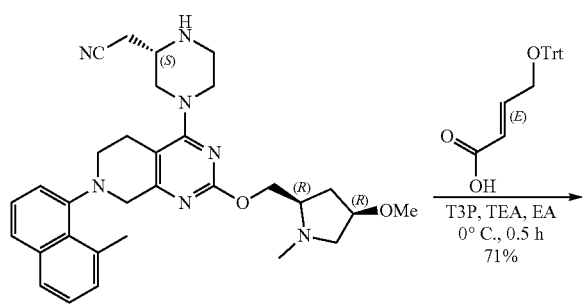

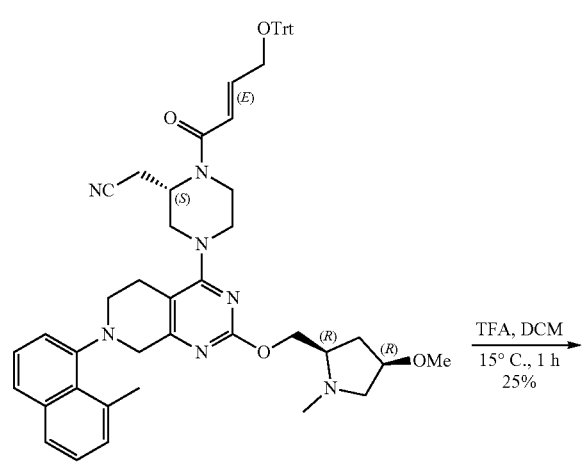

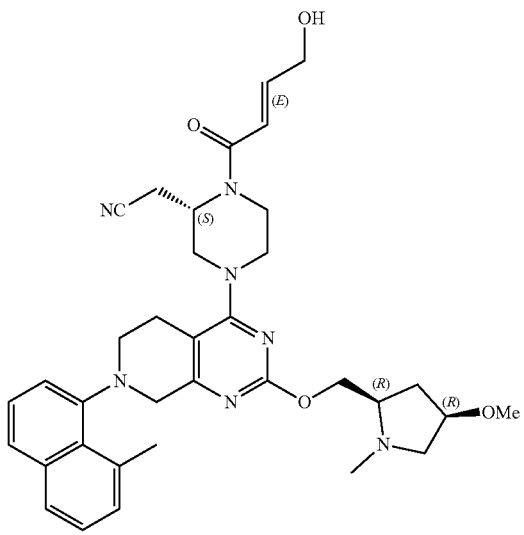

Step A: 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (200 mg, 369 umol, 1 eq), (E)-4-trityloxybut-2-enoic acid (254 mg, 738 umol, 2 eq) and TEA (374 mg, 3.69 mmol, 514 µL, 10 eq) in EtOAc (4 mL) was added T3P (705 mg, 1.11 mmol, 659 µL, 50% purity, 3 eq) at 0° C., the mixture was stirred at 0° C. for 0.5 hour. Water (10 mL) was added into the mixture. The mixture was diluted with EtOAc (5 mL) and extracted with EtOAc (15 mL). The organic layer was washed with brine (10 mL), dried over anhydrous $Na_2SO_4$, filtered and concentrated under vacuum. The residue was purified by reversed phase flash column (ACN/Water (0.1% FA)=70%) to give 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]-1-[(E)-4-trityloxybut-2-enoyl]piperazin-2-yl]acetonitrile (230 mg, 262 umol, 71% yield, 99% purity) as a yellow solid.

Step B: 2-[(2S)-1-[(E)-4-hydroxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile To the solution of 2-[(2S)-4-[2-[[(2R,4R)-4-methoxy-1-methyl-pyrrolidin-2-yl]methoxy]-7-(8-methyl-1-naphthyl)-

6,8-dihydro-5H-pyrido[3,4-d]pyrimidin-4-yl]-1-[(E)-4-trityloxybut-2-enoyl]piperazin-2-yl]acetonitrile (230 mg, 265 umol, 1 eq) in DCM (2.3 mL) was added TFA (3.54 g, 31.1 mmol, 2.3 mL, 117 eq), the mixture was stirred at 15° C. for 1 hour. The reaction mixture was basified with saturated NaHCO₃ (30 mL) to PH=7-8, then extracted with DCM (2×15 mL). The combined organic layers were dried over anhydrous Na₂SO₄, filtered and concentrated under vacuum. The residue was purified by reversed phase flash column (ACN/Water (0.1% FA)=32%). Then the residue was purified by prep-HPLC (column: Gemini 150*25 5 u; mobile phase: [water (0.05% ammonia hydroxide v/v)-ACN];B %: 37%-67%,12 min) to give title compound 2-[(2S)-1-[(E)-4-hydroxybut-2-enoyl]-4-[2-[[(2R,4R)-4-methoxy-1-methylpyrrolidin-2-yl]methoxy]-7-(8-methyl-1-naphthyl)-6,8-dihydro-5H-pyrido[3,4-d]pyrimidin-4-yl]piperazin-2-yl]acetonitrile (EXAMPLE 52, 41.7 mg, 66.6 umol, 25% yield, 100% purity) as a white solid. LCMS [ESI, M+1]: 626.

¹H NMR (400 MHz, chloroform-d) δ=7.70 (br d, J=8.4 Hz, 1H), 7.65 (t, J=8.0 Hz, 1H), 7.45-7.38 (m, 1H), 7.37-7.31 (m, 1H), 7.27-7.17 (m, 2H), 7.07 (br d, J=14.8 Hz, 1H), 6.62 (br d, J=14.0 Hz, 1H), 5.07 (br s, 1H), 4.85-4.55 (m, 1H), 4.51-4.37 (m, 3H), 4.30-3.97 (m, 4H), 3.94-3.65 (m, 2H), 3.58-3.40 (m, 2H), 3.29 (d, J=1.6 Hz, 3H), 3.25-2.96 (m, 5H), 2.92 (s, 3H), 2.86-2.54 (m, 4H), 2.45 (d, J=4.8 Hz, 3H), 2.42-2.28 (m, 2H), 1.81 (br dd, J=8.9, 13.6 Hz, 1H).

Example 53

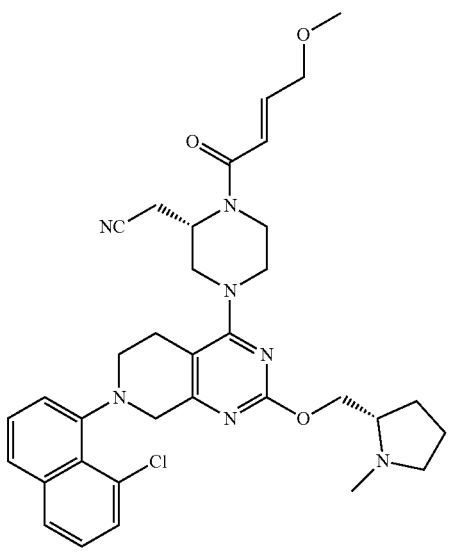

2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile

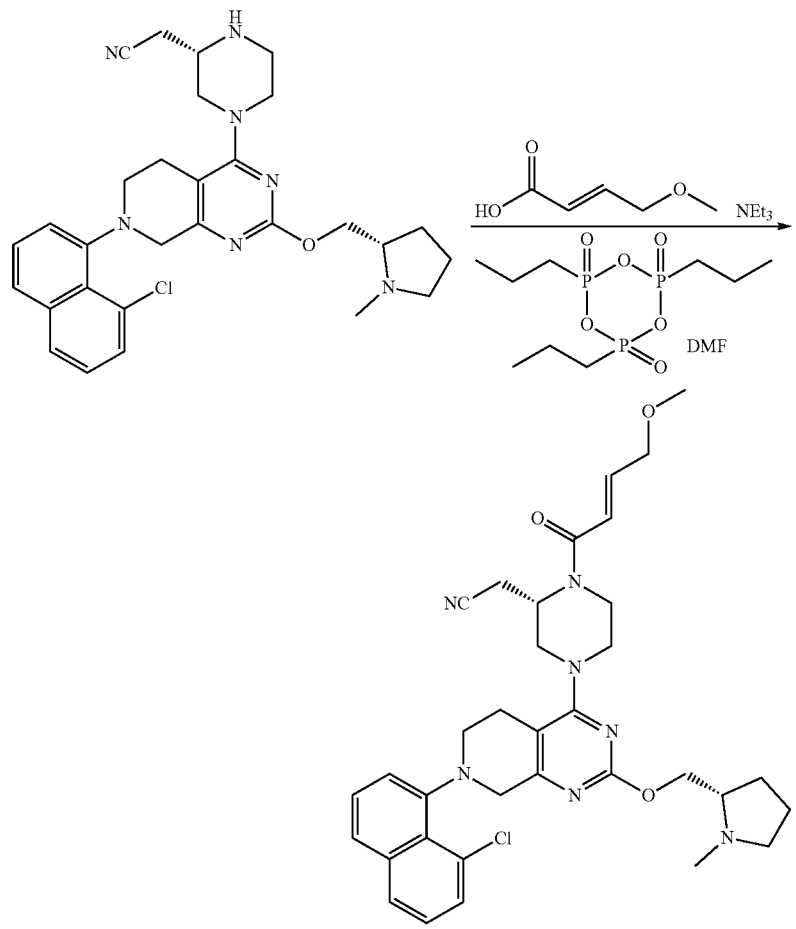

263

Step A: 2-((S)-4-(7-(8-chloronaphthalen-1-yl)-2-
(((S)-1-methylpyrrolidin-2-yl)methoxy)-5,6,7,8-
tetrahydropyrido[3,4-d]pyrimidin-4-yl)-1-((E)-4-
methoxybut-2-enoyl)piperazin-2-yl)acetonitrile A stirred mixture of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (100 mg, 0.1879 mmol), (E)-4-methoxybut-2-enoic acid (32.73 mg, 0.2819 mmol) and N,N-dimethylformamide (1 mL, 12.79 mmol) was cooled to 0° C. followed by addition of triethylamine (0.07859 mL, 0.5638 mmol) and 2,4,6-tripropyl-1,3,5,2,4,6-trioxatriphosphinane 2,4,6-trioxide, 50% in EtOAc (0.1678 mL, 0.2819 mmol). The reaction mixture was stirred for 2 hours while warming to room temperature. The mixture was partitioned between 0.5M Na$_2$CO$_3$ (5 mL) and EtOAc (15 mL) and the organics separated. The organics were next washed with water and brine (5 mL each), dried over Na$_2$SO$_4$ and evaporated in vacuo. The residue was next chromatographed on silica gel using 4% MeOH+0.4% NH$_4$OH/DCM as eluent to give impure material which was further purified by Gilson reverse prep HPLC eluting with 5 to 75% ACN+0.1% TFA/H$_2$O+0.1% TFA. Fractions containing pure product were combined and partitioned between DCM and a saturated solution of Na$_2$CO$_3$ and the layers separated. The organics were next washed with brine, dried over MgSO$_4$ and concentrated in vacuo to give pure title compound (EXAMPLE 53, 33 mg, 28%). ESI+APCI MS m/z 630.3 [M$^+$].

Example 54

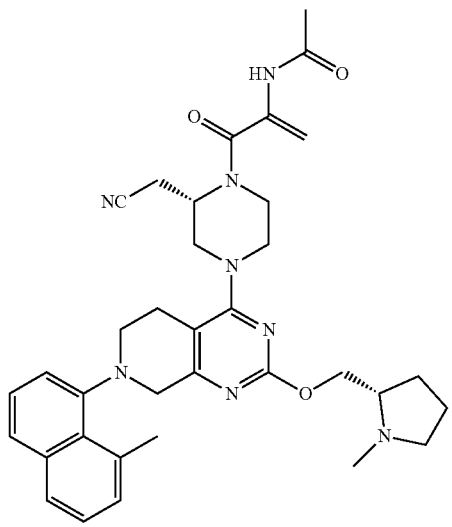 [SMILES: C=C(NC(C)=O)C(=O)N1CCN(c2nc(OC[C@@H]3CCCN3C)nc3c2CCN(c2cccc4cccc(C)c24)C3)C[C@@H]1CC#N]

264

N-(3-((S)-2-(cyanomethyl)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-1-yl)-3-oxoprop-1-en-2-yl)acetamide

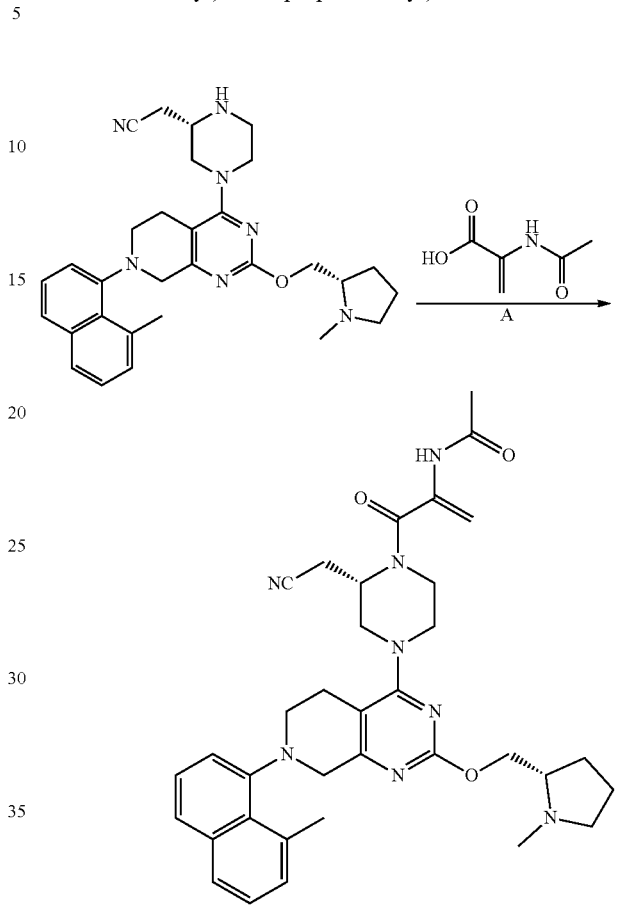

Step A: N-(3-((S)-2-(cyanomethyl)-4-(7-(8-methylnaphthalen-1-yl)-2-4(S)-1-methylpyrrolidin-2-yl)methoxy)-5,6,7,8-tetrahydropyrido[3,4-d]pyrimidin-4-yl)piperazin-1-yl)-3-oxoprop-1-en-2-yl)acetamide To a 25 mL round bottom flask containing dichloromethane (2932 μl, 0.2932 mmol) cooled to 0° C. was added 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (150 mg, 0.2932 mmol) and Hunig's base (307.2 μl, 1.759 mmol). The reaction mixture was vigorously stirred while 2-Acetamidoacrylic acid (227.1 mg, 1.759 mmol) was added in one portion. Next, 1-Propanephosphonic acid cyclic anhydride (1047 μl, 1.759 mmol) was added slowly to the stirring mixture. The reaction was stirred for 2 hours at 0° C. The reaction was treated with basic water and the aqueous layer extracted with EtOAc (3×). The combined organics were concentrated in vacuo and purified on the Gilson (prep HPLC) eluting with 5→95% ACN+0.1% TFA/water+0.1% TFA. Fractions containing product were combined and basified with 1M NaOH and the aqueous layer extracted with DCM (2×). The organics were dried over Na$_2$SO$_4$ and concentrated in vacuo to give title compound N-(3-((S)-2-(cyanomethyl)-4-(7-(8-methylnaphthalen-1-yl)-2-(((S)-1-methyl pyrrolidin-2-yl)methoxy)-5,6,7,8-tetrahydropyrido

[3,4-d]pyrimidin-4-yl)piperazin-1-yl)-3-oxoprop-1-en-2-yl)acetamide (EXAMPLE 54, 124.2 mg, 68.03% yield). ESI+ APCI MS m/z 623.3 [M+H]⁺.

Example 55

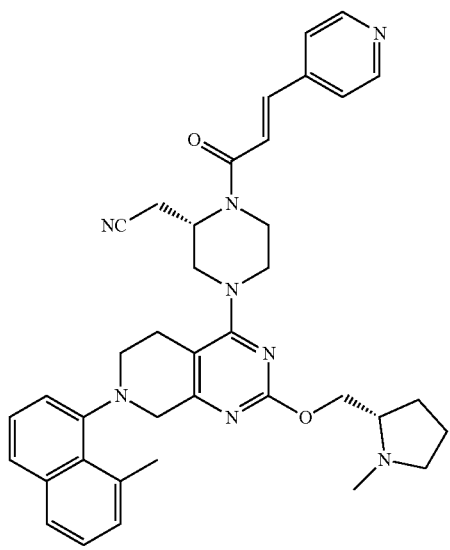

2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-4-yl)acryloyl)piperazin-2-yl)acetonitrile 2-((S)-4-(7-(8-methylnaphthalen-1-yl)-2-(((S)-1-methylpyrrolidin-2-yl)methoxy)-5,6,7,8-tetrahydropyrido[3,4-d]pyrimidin-4-yl)-1-((E)-3-(pyridin-4-yl)acryloyl)piperazin-2-yl)acetonitrile The title compound was prepared following Example 54 substituting Trans-3-(4-Pyridyl) Acrylic Acid for 2-Acetamidoacrylic acid in Step A. ESI+APCI MS m/z 643.3 [M+H]⁺.

Example 56

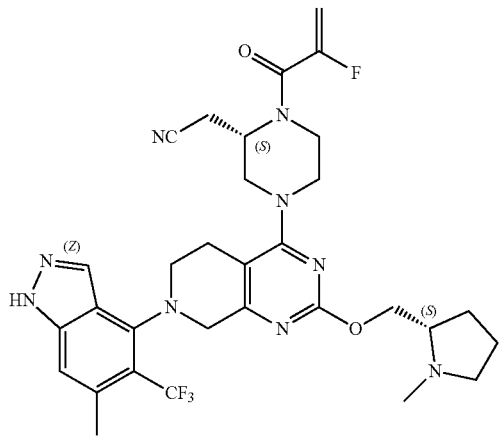

2-((S)-1-(2-fluoroacryloyl)-4-(7-(6-methyl-5-(trifluoromethyl)-1H-indazol-4-yl)-2-((((S)-1-methylpyrrolidin-2-yl)methoxy)-5,6,7,8-tetrahydropyrido[3,4-d]pyrimidin-4-yl)piperazin-2-yl)acetonitrile

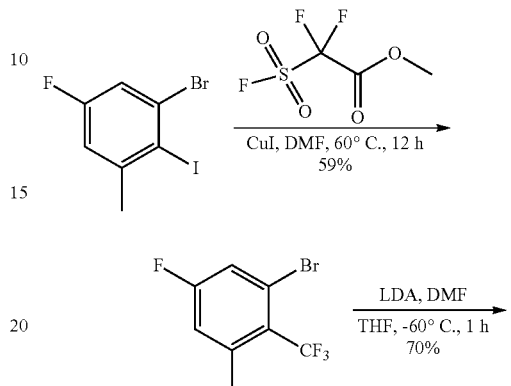

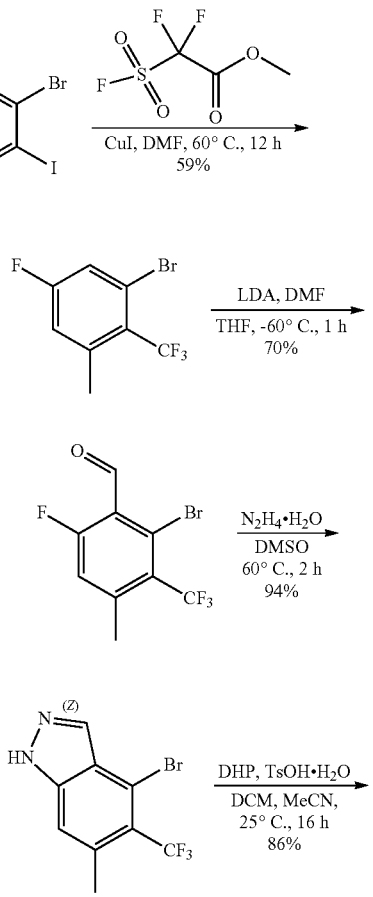

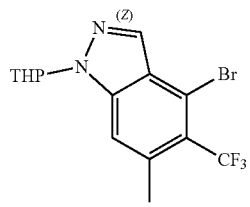

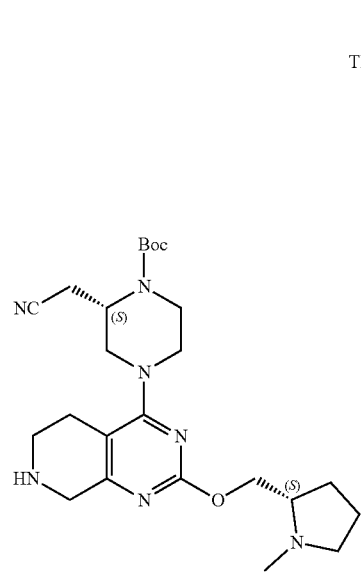

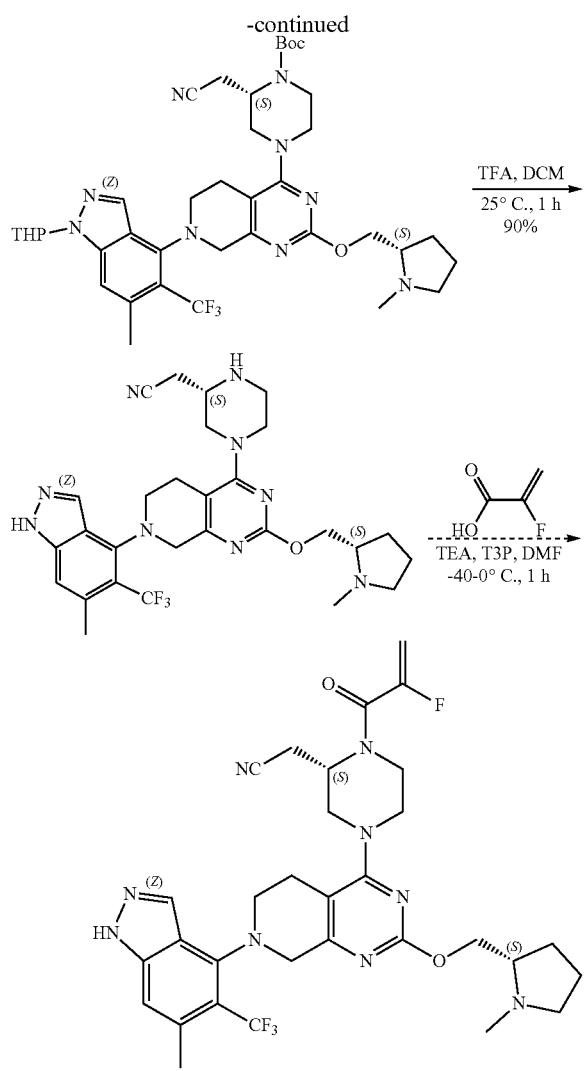

1-bromo-5-fluoro-3-methyl-2-(trifluoromethyl)benzene

To a solution of 1-bromo-5-fluoro-2-iodo-3-methyl-benzene (2 g, 6.35 mmol, 1 eq) in DMF (40 mL) was added CuI (7.26 g, 38.1 mmol, 6 eq) and methyl 2,2-difluoro-2-fluorosulfonyl-acetate (7.32 g, 38.1 mmol, 4.85 mL, 6 eq). The mixture was stirred at 60° C. for 12 hours. The reaction mixture was diluted with ethyl acetate (20 mL) and washed with water (20 mL×3). The organic layer was washed with brine (20 mL), dried over $Na_2SO_4$, filtered and concentrated under reduced pressure to give a residue. The residue was purified by column chromatography ($SiO_2$, Petroleum ether/ Ethyl acetate=I/O to 10/1). 1-bromo-5-fluoro-3-methyl-2-(trifluoromethyl)benzene (1.3 g, 3.74 mmol, 59% yield, 74% purity) was obtained as a yellow oil.

$^1$H NMR (400 MHz, chloroform-d) δ=7.33 (dd, J=2.4, 7.6 Hz, 1H), 6.95 (dd, J=2.0, 8.8 Hz, 1H), 2.54 (q, J=3.6 Hz, 3H).

2-bromo-6-fluoro-4-methyl-3-(trifluoromethyl)benzaldehyde

To a mixture of 1-bromo-5-fluoro-3-methyl-2-(trifluoromethyl)benzene (900 mg, 3.50 mmol, 1 eq) in THF (20 mL) was added LDA (2 M in THF, 3.50 mL, 2 eq) at −60° C. under nitrogen atmosphere. After stirring for 0.5 hour, to the mixture was added DMF (768 mg, 10.5 mmol, 808 μL, 3 eq). The mixture was stirred at −60° C. for 1 hour. The reaction was quenched with saturated $NH_4Cl$ aqueous solution (10 mL) and then extracted with ethyl acetate (50 mL×3). The combined organic phase was washed with brine (10 mL), dried over anhydrous $Na_2SO_4$, filtered and concentrated in vacuo. The residue was purified by column chromatography ($SiO_2$, Petroleum ether/Ethyl acetate=200/1 to 5/1). 2-bromo-6-fluoro-4-methyl-3-(trifluoromethyl)benzaldehyde (700 mg, 2.46 mmol, 70% yield) was obtained as a yellow oil.

$^1$H NMR (400 MHz, chloroform-d) δ=10.35 (s, 1H), 7.08 (d, J=10.4 Hz, 1H), 2.66-2.58 (m, 3H).

4-bromo-6-methyl-5-(trifluoromethyl)-1H-indazole

A solution of 2-bromo-6-fluoro-4-methyl-3-(trifluoromethyl)benzaldehyde (600 mg, 2.11 mmol, 1 eq) and hydrazine monohydrate (2.11 g, 42.1 mmol, 2.05 mL, 20 eq) in DMSO (8 mL) was stirred at 60° C. for 2 hours. The mixture was diluted with ethyl acetate (50 mL) and washed with water (3×50 mL) and brine (1×50 mL). The separated organic layer was dried over sodium sulfate, filtered and concentrated under vacuum. The residue was used to next step without further purification. 4-bromo-6-methyl-5-(trifluoromethyl)-1H-indazole (550 mg, 1.97 mmol, 94% yield) was obtained as a white solid.

4-bromo-6-methyl-1-tetrahydropyran-2-yl-5-(trifluoromethyl)indazole

To a solution of 4-bromo-6-methyl-5-(trifluoromethyl)-1H-indazole (500 mg, 1.79 mmol, 1 eq) in DCM (10 mL) was added 4-methylbenzenesulfonic acid hydrate (34.1 mg, 1791 umol, 0.1 eq) 1 followed by a solution of DHP (603 mg, 7.17 mmol, 655 μL, 4 eq) in $CH_3CN$ (2 mL). The mixture was stirred at 25° C. for 16 hours. The mixture was diluted with ethyl acetate (100 mL) and washed with water (2×100 mL) and brine (1×50 mL). The organic layer was dried over sodium sulfate, filtered and concentrated under vacuum. The residue was purified by column chromatography over silica gel (petroleum ether/ethyl acetate 20/1 to 3/1). The desired fractions were collected and concentrated under vacuum to give 4-bromo-6-methyl-1-tetrahydropyran-2-yl-5-(trifluoromethyl)indazole (600 mg, 1.54 mmol, 86% yield, 93% purity) as a light yellow gum. LCMS [MSI, M+1]: 363.

Step A: Tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl) indazol-4-yl]-6,8-dihydro-5H-pyrido[3,4-d] pyrimidin-4-yl]piperazine-1-carboxylate To a mixture of tert-butyl (2S)-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate (400 mg, 848 umol, 1 eq), 4-bromo-6-methyl-1-tetrahydropyran-2-yl-5-(trifluoromethyl)indazole (431 mg, 1.19 mmol, 1.4 eq) $Pd_2(dba)_3$ (155 mg, 170 umol, 0.2 eq), RuPhos (158 mg, 339 umol, 0.4 eq) and $Cs_2CO_3$ (691 mg, 2.12 mmol, 2.5 eq) in toluene (20 mL) was degassed and purged with $N_2$ for 3 times, and then the mixture was stirred at 100° C. for 16 hours under $N_2$ atmosphere. To the mixture was added $H_2O$ (20 mL×1) and Ethyl acetate (20 mL×1). The organic phase was separated, filtered and concentrated under reduced pressure to give a residue. The residue was purified by silica gel chromatography (Ethyl acetate/Methanol=50/1 to 2/1). tert-Butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (500 mg, 535 umol, 32% yield, 80.7% purity) was obtained as a yellow solid. LCMS [MSI, M+1]: 754.

Step B: 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile To a solution of tert-butyl (2S)-2-(cyanomethyl)-4-[2-[[(2S)-1-methylpyrrolidin-2-yl]methoxy]-7-[6-methyl-1-tetrahydropyran-2-yl-5-(trifluoromethyl)indazol-4-yl]-6,8-dihydro-5H-pyrido[3,4-d]pyrimidin-4-yl]piperazine-1-carboxylate (470 mg, 503 umol, 1 eq) in DCM (1 mL) was added TFA (2.29 g, 20.1 mmol, 1.49 mL, 40 eq). The mixture was stirred at 25° C. for 1 h. To the mixture was added dichloromethane (5 mL) and basified with saturated aqueous NaHCO₃ solution to pH=8~9. The organic phase was separated, dried over sodium sulfate, filtered and concentrated under reduced pressure to give 2-[(2S)-4-[2-[[(2S)-1-methylpyrrolidin-2-yl]methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (420 mg, 453 umol, 90% yield, 61.4% purity) was obtained as a yellow solid and used into next step without further purification. LCMS [MSI, M+1]: 570.

Step C: 2-((S)-1-(2-fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile To a solution of 2-[(2S)-4-[2-[[(2S)-1-methylpyrrolidin-2-yl] methoxy]-7-[6-methyl-5-(trifluoromethyl)-1H-indazol-4-yl]-6,8-dihydro-5H-pyrido[3,4-d]pyrimidin-4-yl]piperazin-2-yl]acetonitrile (380 mg, 410 umol, 1 eq), 2-fluoroprop-2-enoic acid (18.4 mg, 205 umol, 0.5 eq) and TEA (124 mg, 1.23 mmol, 171 μL, 3 eq) in DMF (8 mL) was added T3P (391 mg, 614 umol, 365 μL, 50% purity in DMF, 1.5 eq) at −40° C. Then the mixture was stirred at −40° C. for 0.5 hour and 0° C. for another 0.5 hour. 2-fluoroprop-2-enoic acid (11 mg) and T3P (100 uL) was added and the mixture was stirred at −40° C. for further 0.5 hour. The mixture was diluted with water (15 mL) and extracted with EtOAc (2×40 mL). The organic layers were washed with brine (50 mL), dried over Na₂SO₄ and concentrated under vacuum. The residue was purified by prep-HPLC (column: Luna C18 150*25 5 u; mobile phase: [water (0.225% FA)-ACN]; B %: 22%-42%, 7.8 min) and (column: Phenomenex Gemini 150*25 mm*10 um; mobile phase: [water (0.04% NH₃H₂O+10 mM NH₄HCO₃)—ACN]; B %: 50%-68%, 12 min). The desired fractions were collected and lyophilize to give title compound 2-((S)-1-(2-fluoroacryloyl)-4-(7-(6-methyl-5-(trifluoromethyl)-1H-indazol-4-yl)-2-(((S)-1-methylpyrrolidin-2-yl)methoxy)-5,6,7,8-tetrahydropyrido[3,4-d]pyrimidin-4-yl)piperazin-2-yl)acetonitrile (EXAMPLE 56) as white solid.

Example 57

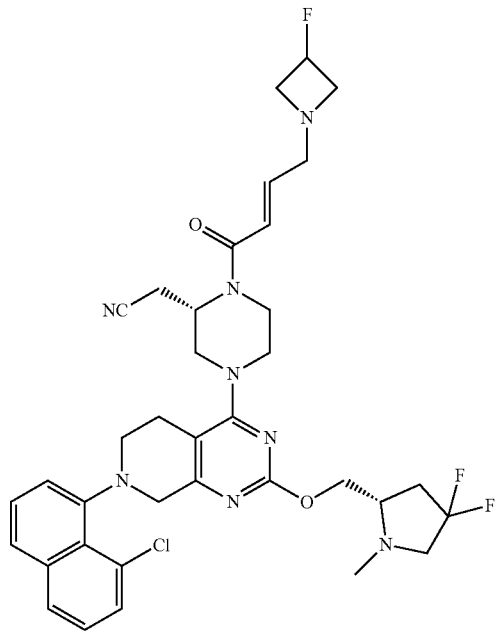 [SMILES: CN1CC(F)(F)C[C@H]1COc1nc2c(c(N3CCN(C(=O)/C=C/CN4CC(F)C4)[C@@H](CC#N)C3)n1)CCN(c1cccc3cccc(Cl)c13)C2]

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-(3-fluoroazetidin-1-yl)but-2-enoyl)piperazin-2-yl)acetonitrile The title compound is prepared following Example 49 by modifying Intermediate 66 by substituting (S)-(4,4-difluoro-1-methylpyrrolidin-2-yl)methanol for (1-methylpyrrolidin-2-yl)methanol in Intermediate 66, Step E, modified Intermediate 66 is deprotected using the conditions in Intermediate 71, Step A, then substituted for Intermediate 66 in Example 49, Step A.

Example 58

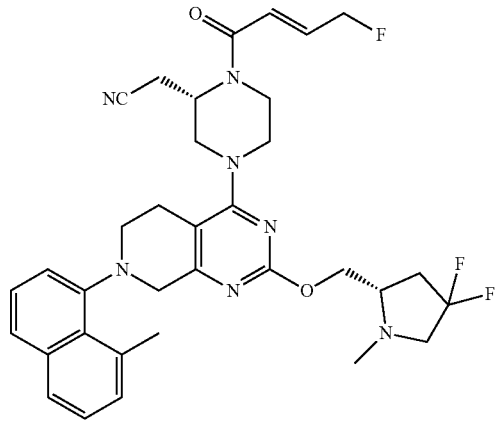 [SMILES: Cc1cccc2cccc(N3CCc4c(nc(OC[C@@H]5CC(F)(F)CN5C)nc4N4CCN(C(=O)/C=C/CF)[C@@H](CC#N)C4)C3)c12]

271

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound is prepared following Example 49 substituting (E)-4-fluorobut-2-enoic acid for 3-fluoroazetidine using the conditions of Example 49, Step D.

Example 59

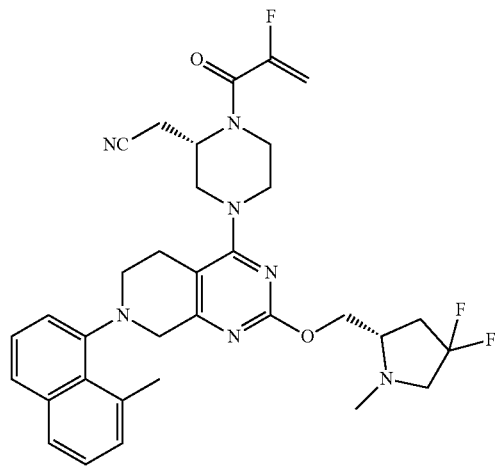 [SMILES: C=C(F)C(=O)N1CCN(c2nc(OC[C@@H]3CC(F)(F)CN3C)nc3c2CCN(c2cccc4cccc(C)c24)C3)C[C@@H]1CC#N]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile The title compound is prepared following Example 49 substituting 2-fluoroprop-2-enoyl chloride for 3-fluoroazetidine using the conditions of Example 49, Step D.

Example 60

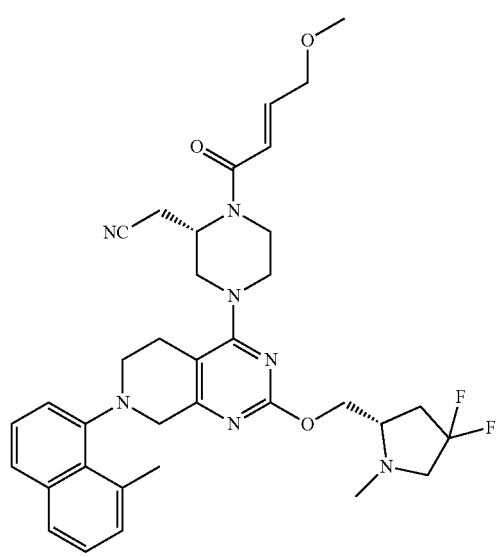 [SMILES: COC/C=C/C(=O)N1CCN(c2nc(OC[C@@H]3CC(F)(F)CN3C)nc3c2CCN(c2cccc4cccc(C)c24)C3)C[C@@H]1CC#N]

272

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-methoxybut-2-enoyl)piperazin-2-yl)acetonitrile The title compound is prepared following Example 49 substituting (methoxymethyl)prop-2-enoic acid for 3-fluoroazetidine using the conditions of Example 49, Step D.

Example 61

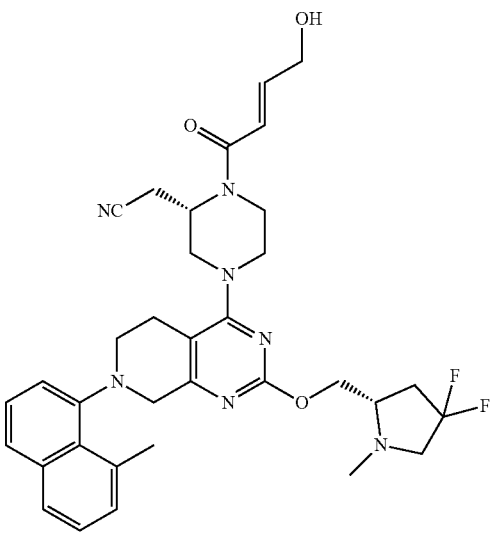 [SMILES: Cc1cccc2cccc(N3CCc4c(nc(OC[C@@H]5CC(F)(F)CN5C)nc4N4CCN(C(=O)/C=C/CO)[C@@H](CC#N)C4)C3)c12]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-hydroxybut-2-enoyl)piperazin-2-yl)acetonitrile The title compound is prepared following Example 49 substituting 4-[tert-butyl(dimethyl)silyl]oxybut-2-ynoic acid for 3-fluoroazetidine using the conditions of Example 49, Step D.

Example 62

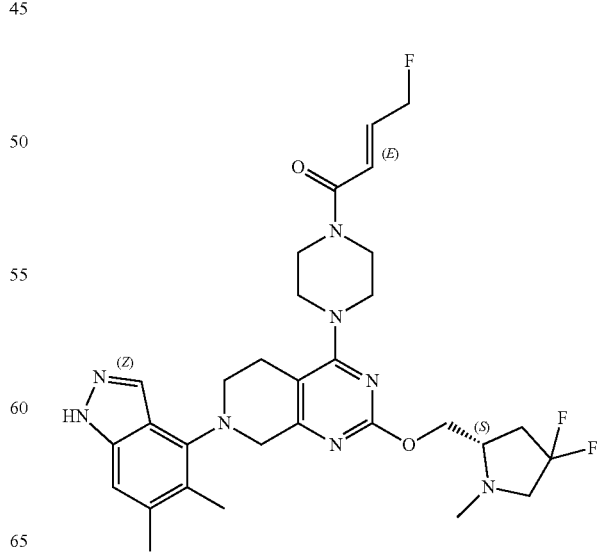

273

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-fluorobut-2-en-1-one The title compound is prepared following Example 50 substituting (E)-4-fluorobut-2-enoic acid for 2-fluoroprop-2-enoic acid in Example 50, Step B.

Example 62

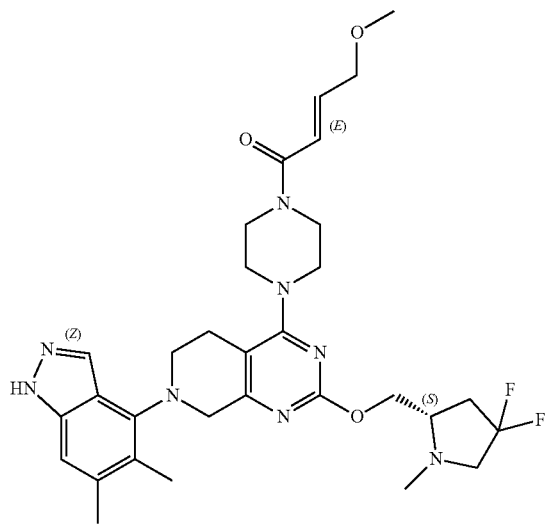

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-methoxybut-2-en-1-one The title compound is prepared following Example 50 substituting 2-(methoxymethyl)prop-2-enoic acid for 2-fluoroprop-2-enoic acid in Example 50, Step B.

Example 63

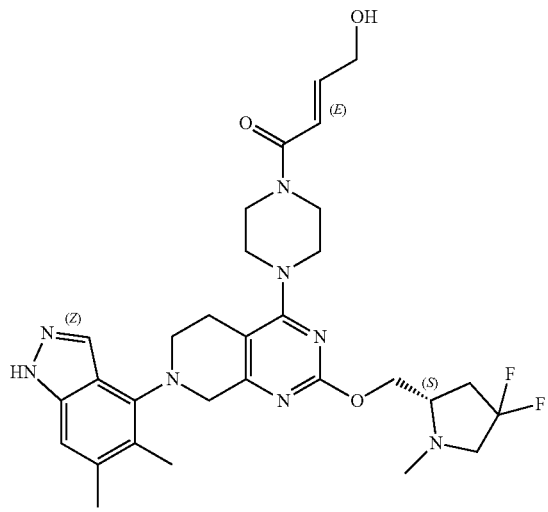

274

(S,E)-1-(4-(2-((4,4-difluoro-1-methylpyrrolidin-2-yl)methoxy)-7-(5,6-dimethyl-1H-indazol-4-yl)-5,6,7,8-tetrahydropyrido[3,4-d]pyrimidin-4-yl)piperazin-1-yl)-4-hydroxybut-2-en-1-one The title compound is prepared following Example 50 substituting 4-[tert-butyl(dimethyl)silyl]oxybut-2-ynoic acid for 2-fluoroprop-2-enoic acid in Example 50, Step B.

Example 64

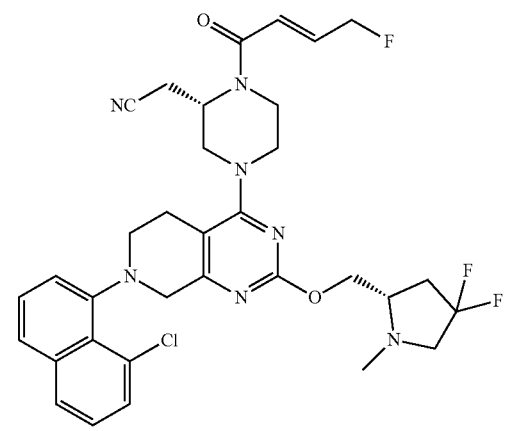 [SMILES: CN1CC(F)(F)C[C@H]1COc1nc2c(c(N3CCN(C(=O)/C=C/CF)[C@@H](CC#N)C3)n1)CCN(c1cccc3cccc(Cl)c13)C2]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound is prepared following Example 57 substituting 2-fluoroprop-2-enoyl chloride for 3-fluoroazetidine using the conditions of Example 49, Step A.

Example 65

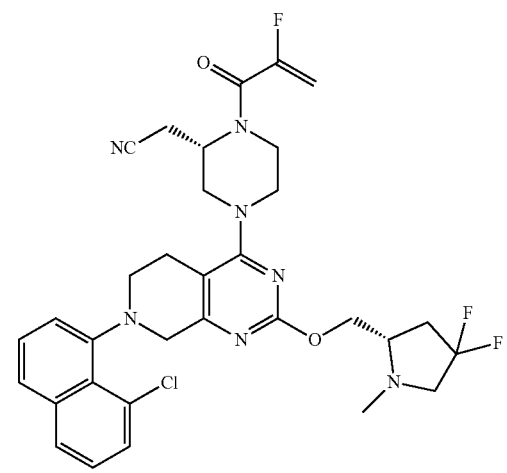 [SMILES: C=C(F)C(=O)N1CCN(c2nc(OC[C@@H]3CC(F)(F)CN3C)nc3c2CCN(c2cccc4cccc(Cl)c24)C3)C[C@@H]1CC#N]

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile The title compound is prepared following Example 57 substituting 2-fluoroprop-2-enoyl chloride for 3-fluoroazetidine using the conditions of Example 49, Step A.

Example 66

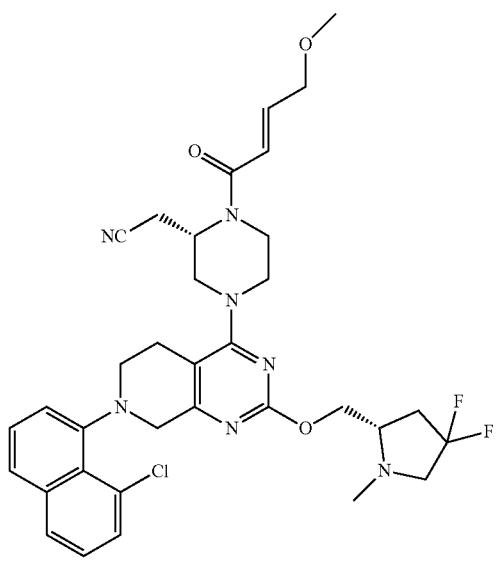 [SMILES: COC/C=C/C(=O)N1CCN(c2nc(OC[C@@H]3CC(F)(F)CN3C)nc3c2CCN(c2cccc4cccc(Cl)c24)C3)C[C@@H]1CC#N]

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile The title compound is prepared following Example 57 substituting (methoxymethyl)prop-2-enoic acid for 3-fluoroazetidine using the conditions of Example 49, Step A.

Example 67

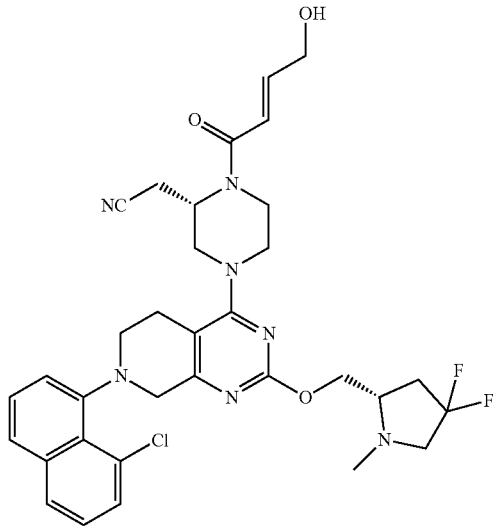 [SMILES: CN1CC(F)(F)C[C@H]1COc1nc2c(c(N3CCN(C(=O)/C=C/CO)[C@@H](CC#N)C3)n1)CCN(c1cccc3cccc(Cl)c13)C2]

2-((S)-4-(2-(((S)-4,4-difluoro-1-methylpyrrolidin-2-yl)methoxy)-7-(8-chloronaphthalen-1-yl)-5,6,7,8-tetrahydropyrido[3,4-d]pyrimidin-4-yl)-1-((E)-4-hydroxybut-2-enoyl)piperazin-2-yl)acetonitrile The title compound is prepared following Example 57 substituting 4-[tert-butyl(dimethyl)silyl]oxybut-2-ynoic acid for 3-fluoroazetidine using the conditions of Example 49, Step A.

Example 68

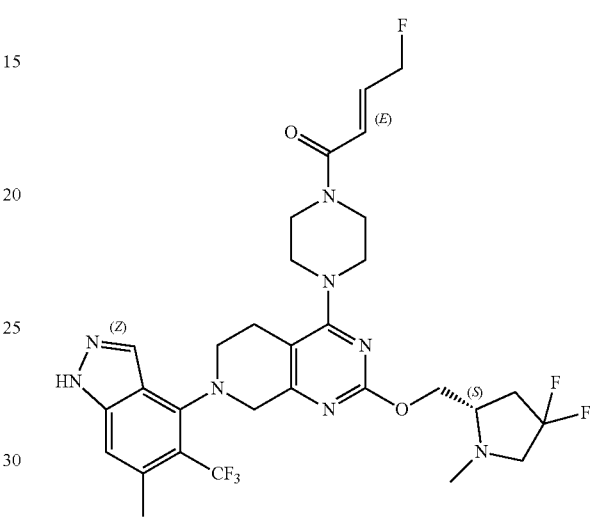

2-((S)-4-(2-(((S)-4,4-difluoro-1-methylpyrrolidin-2-yl)methoxy)-7-(8-methylnaphthalen-1-yl)-5,6,7,8-tetrahydropyrido[3,4-d]pyrimidin-4-yl)-1-((E)-4-fluorobut-2-enoyl)piperazin-2-yl)acetonitrile The title compound is prepared following Example 56 substituting 2-fluoroprop-2-enoyl chloride for 2-fluoroprop-2-enoyl chloride using the conditions of Example 56, Step C.

Example 69

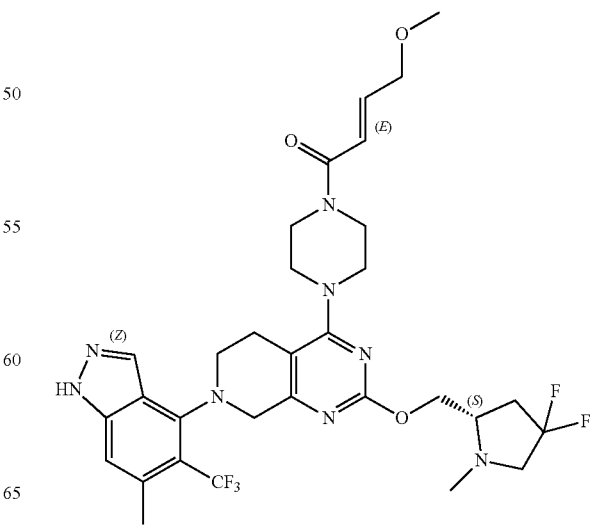

277

2-((S)-4-(7-(8-chloronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-((E)-4-methoxybut-2-enoyl)piperazin-2-yl)acetonitrile The title compound is prepared following Example 56 substituting (methoxymethyl)prop-2-enoic acid for 2-fluoroprop-2-enoyl chloride using the conditions of Example 56, Step C.

Example 70

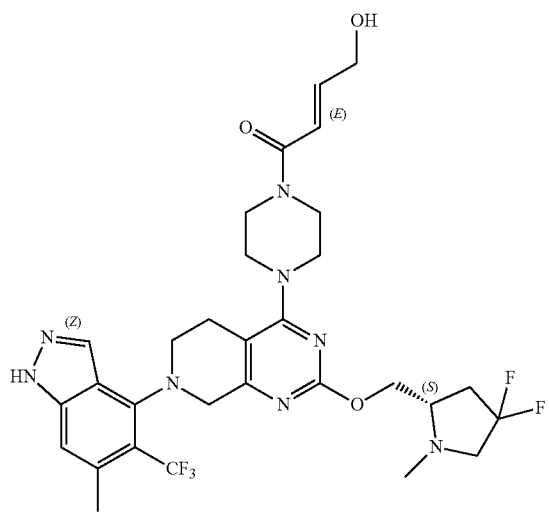

2-((S)-4-(2-(((S)-4,4-difluoro-1-methylpyrrolidin-2-yl)methoxy)-7-(8-chloronaphthalen-1-yl)-5,6,7,8-tetrahydropyrido[3,4-d]pyrimidin-4-yl)-1-((E)-4-hydroxybut-2-enoyl)piperazin-2-yl)acetonitrile The title compound is prepared following Example 56 substituting 4-[tert-butyl(dimethyl)silyl]oxybut-2-ynoic acid for 2-fluoroprop-2-enoyl chloride using the conditions of Example 56, Step C.

Example 71

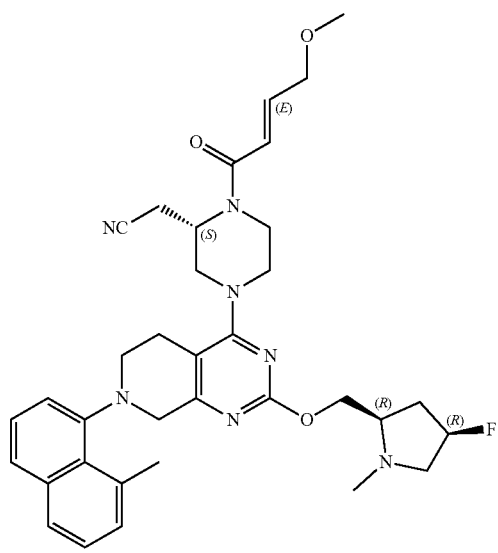

278

2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-methoxybut-2-enoyl]piperazin-2-yl]acetonitrile

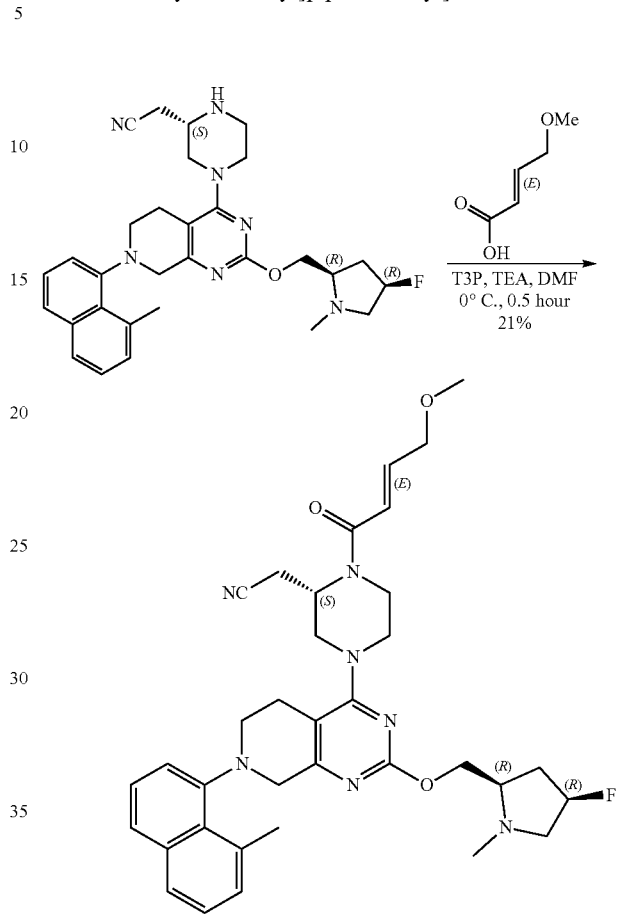

Step A: 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]-1-[(E)-4-methoxybut-2-enoyl]piperazin-2-yl]acetonitrile To a solution of 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (200 mg, 378 umol, 1.0 eq), (E)-4-methoxybut-2-enoic acid (110 mg, 944 umol, 2.5 eq) in DMF (3.0 mL) was added TEA (382 mg, 3.78 mmol, 526 μL, 10.0 eq) and T3P (721 mg, 1.13 mmol, 674 μL, 50% purity, 3.0 eq). The mixture was stirred at 0° C. for 0.5 hour. After completion, the organic solvent was washed with water (10.0 mL). The aqueous phase was extracted with ethyl acetate (3×10.0 mL). Combine extracts were washed with brine (20.0 mL), dried with Na₂SO₄ and filtrated. The solvent was then removed under vacuum. The residue was purified by column chromatography (Base Al₂O₃, Petroleum ether:Ethyl acetate=10:1 to 1:1), then the crude product was concentrated and repurified by prep-HPLC (column: Phenomenex Gemini 150×25 mm×10 um; mobile phase: [water (0.05% ammonia hydroxide v/v)-ACN]; B %: 48%-78%,9-10 min) and lyophilization to give title compound 2-[(2S)-4-[2-[[(2R,4R)-4-fluoro-1-methyl-pyrrolidin-2-yl]methoxy]-7-(8-methyl-1-naphthyl)-6,8-dihydro-5H-pyrido

[3,4-d]pyrimidin-4-yl]-1-[(E)-4-methoxybut-2-enoyl] piperazin-2-yl]acetonitrile (EXAMPLE 71, 50 mg, 79.6 umol, 21% yield, 99.9% purity) was obtained as yellow solid. LCMS [ESI, M+1]: 628.

$^1$H NMR (400 MHz, Chloroform-d) δ=7.73-7.62 (m, 2H), 7.45-7.31 (m, 2H), 7.27-7.18 (m, 2H), 7.05-6.94 (m, 1H), 6.55 (br d, J=15.0 Hz, 1H), 5.23-5.03 (m, 1H), 4.66 (br s, 1H), 4.52-4.42 (m, 1H), 4.30-4.18 (m, 2H), 4.18-3.94 (m, 4H), 3.93-3.84 (m, 1H), 3.83-3.65 (m, 1H), 3.54 (br d, J=6.7 Hz, 1H), 3.44 (s, 3H), 3.42-3.26 (m, 2H), 3.25-3.15 (m, 2H), 3.05 (br dd, J=8.5, 16.4 Hz, 2H), 2.92 (s, 3H), 2.88-2.58 (m, 4H), 2.57-2.35 (m, 5H), 2.14-1.96 (m, 1H).

Example 72

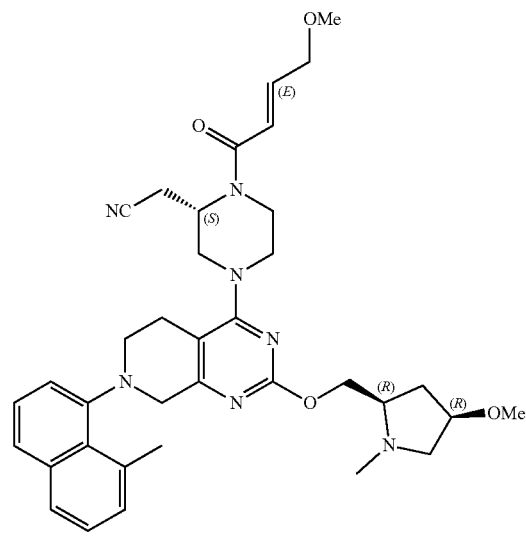

2-[(2S)-1-[(E)-4-methoxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile

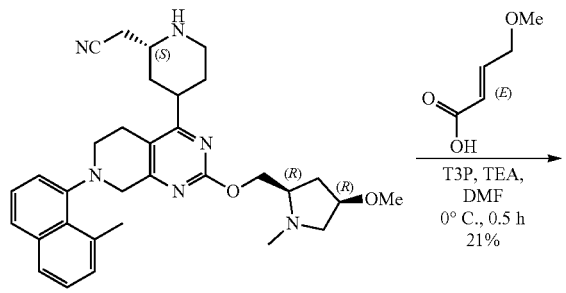

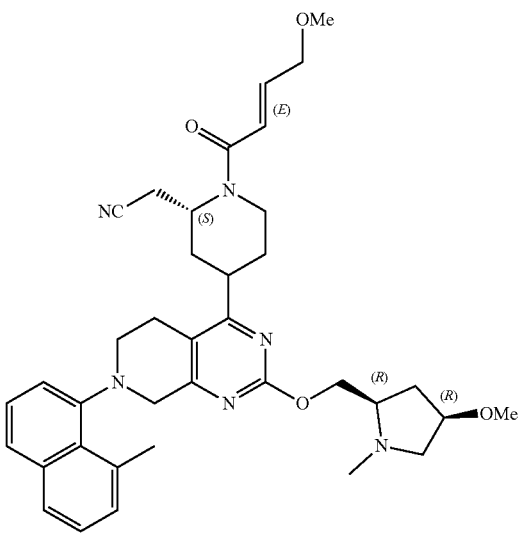

Step A: 2-[(2S)-1-[(E)-4-methoxybut-2-enoyl]-4-[2-[[(2R,4R)-4-methoxy-1-methyl-pyrrolidin-2-yl] methoxy]-7-(8-methyl-1-naphthyl)-6,8-dihydro-5H-pyrido[3,4-d]pyrimidin-4-yl]piperazin-2-yl] acetonitrile To the solution of 2-[(2S)-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl]piperazin-2-yl]acetonitrile (150 mg, 277 umol, 1 eq), (E)-4-methoxybut-2-enoic acid (64.3 mg, 554 umol, 2 eq) and TEA (280 mg, 2.77 mmol, 385 µL, 10 eq) in DMF (3 mL) was added T3P (529 mg, 831 umol, 494 µL, 50% purity, 3 eq) at 0° C., the mixture was stirred at 0° C. for 0.5 hour. Water (10 mL) was added into the mixture. The mixture was diluted with EtOAc (5 mL) and extracted with EtOAc (2×10 mL). The combined organic layers were washed with brine (10 mL), dried over anhydrous Na$_2$SO$_4$, filtered and concentrated under vacuum. The residue was purified by reversed phase flash column (ACN/Water (0.1% FA)=35%). Then the residue was purified by prep-HPLC (column: Waters Xbridge 150*25 5 u; mobile phase: [water (0.05% ammonia hydroxide v/v)—ACN]; B %: 50%-74%,10 min) to give title compound 2-[(2S)-1-[(E)-4-methoxybut-2-enoyl]-4-[2-[[(2R,4R)-4-methoxy-1-methyl-pyrrolidin-2-yl]methoxy]-7-(8-methyl-1-naphthyl)-6,8-dihydro-5H-pyrido[3,4-d]pyrimidin-4-yl] piperazin-2-yl]acetonitrile (EXAMPLE 72, 37.1 mg, 57.2 umol, 21% yield, 98.7% purity) as a white solid. LCMS [ESI, M+1]: 640.

$^1$H NMR (400 MHz, chloroform-d) δ=7.72-7.61 (m, 2H), 7.45-7.31 (m, 2H), 7.27-7.17 (m, 2H), 6.99 (br d, J=14.8 Hz, 1H), 6.55 (br d, J=15.2 Hz, 1H), 5.07 (br s, 1H), 4.51-4.40 (m, 1H), 4.31-4.04 (m, 5H), 3.95-3.68 (m, 3H), 3.63-3.47 (m, 2H), 3.44 (s, 3H), 3.42-3.35 (m, 1H), 3.30 (d, J=1.2 Hz, 3H), 3.24-2.96 (m, 5H), 2.92 (s, 3H), 2.76 (br dd, J=8.0, 16.8 Hz, 1H), 2.72-2.52 (m, 3H), 2.45 (d, J=5.2 Hz, 3H), 2.41-2.27 (m, 2H), 1.81 (br dd, J=7.2, 14.0 Hz, 1H).

Example 73

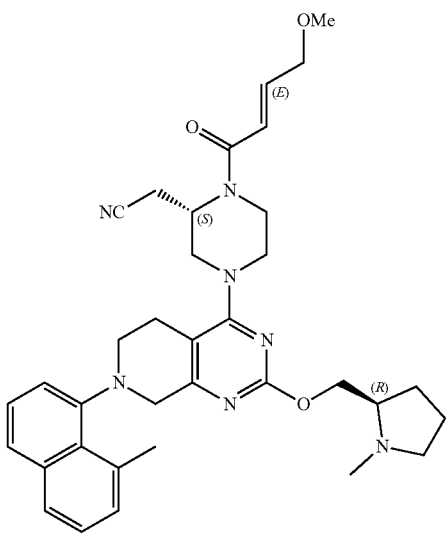

2-((S)-1-((E)-4-methoxybut-2-enoyl)-4-(7-(8-methylnaphthalen-1-yl)-2-(((R)-1-methylpyrrolidin-2-yl)methoxy)-5,6,7,8-tetrahydropyrido[3,4-d]pyrimidin-4-yl)piperazin-2-yl)acetonitrile

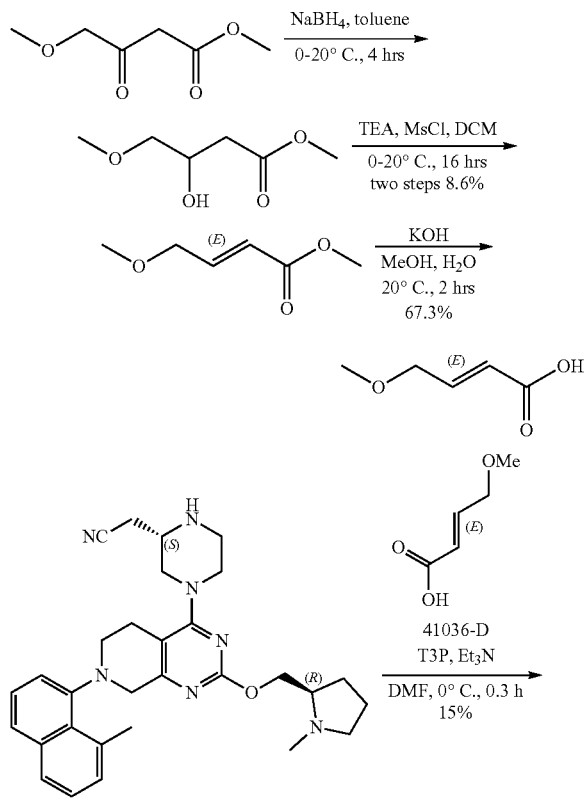

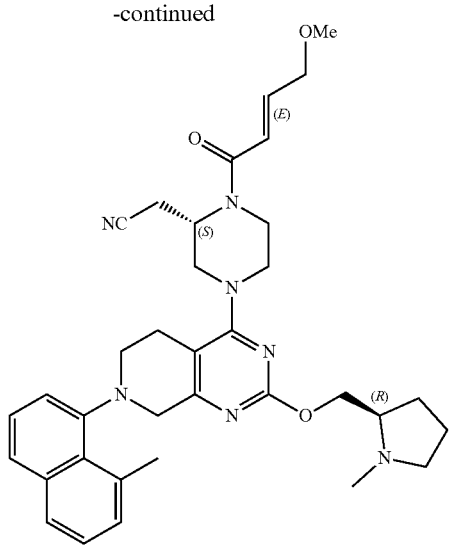

Step A: Methyl 3-hydroxy-4-methoxy-butanoate

To a solution of methyl 4-methoxy-3-oxo-butanoate (20 g, 137 mmol, 1.0 eq) in toluene (300 mL) was added NaBH₄ (5.44 g, 144 mmol, 1.05 eq) at 0° C. Then the mixture was stirred at 20° C. for 4 hours. After completion, the mixture was diluted with water (100 mL) at 0° C. and extracted with ethyl acetate (3×100 mL). The extracts were washed with brine (200 mL), dried over Na₂SO₄, filtered and concentrated under vacuum to give methyl 3-hydroxy-4-methoxy-butanoate (7.5 g, crude) as yellow oil and used into next step without further purification.

¹H NMR (400 MHz, chloroform-d) δ=4.23-4.15 (m, 1H), 3.70 (s, 3H), 3.44-3.38 (m, 2H), 3.37 (s, 3H), 3.04 (br s, 1H), 2.51 (d, J=6.4 Hz, 2H).

Step B: Methyl (E)-4-methoxybut-2-enoate

To a solution of methyl 3-hydroxy-4-methoxy-butanoate (7.5 g, crude) in DCM (50.0 mL) was added TEA (5.12 g, 50.6 mmol, 7.05 mL) and MSCl (8.70 g, 75.9 mmol, 5.88 mL) at 0° C. After stirred for 4 hours, to the mixture was added TEA (10.2 g, 101 mmol, 14.1 mL) 0° C. The mixture was warmed up to 20° C. and stirred for 12 hours. After completion, the mixture was diluted with water (50.0 mL), washed with HCl (1N, 15.0 mL) and brine (20.0 mL), dried over Na₂SO₄, filtered and concentrated under vacuum. The residue was purified by column chromatography (SiO₂, Petroleum ether/Ethyl acetate=I/O to 50:1) to give methyl (E)-4-methoxybut-2-enoate (1.7 g, 11.8 mmol, two steps 8.6% yield, 90% purity) as yellow oil.

¹H NMR (400 MHz, chloroform-d) δ=6.93 (td, J=4.3, 15.8 Hz, 1H), 6.04 (td, J=2.0, 15.8 Hz, 1H), 4.06 (dd, J=2.0, 4.3 Hz, 2H), 3.72 (s, 3H), 3.36 (s, 3H).

Step C: (E)-4-methoxybut-2-enoic Acid

A mixture of methyl (E)-4-methoxybut-2-enoate (300 mg, 2.31 mmol, 1.0 eq) and KOH (517 mg, 9.22 mmol, 4.0 eq) in MeOH (2.0 mL) and H₂O (2.0 mL) was stirred at 20° C. for 2 hours. After completion, the mixture was acidified with HCl (2N, 5.0 mL) to pH=1-3 and extracted with ethyl acetate (2×20 mL). The organic layers were dried over Na₂SO₄, filtered and concentrated under vacuum to give (E)-4-methoxybut-2-enoic acid (200 mg, 1.55 mmol, 67.3% yield, 90% purity) as yellow solid.

¹H NMR (400 MHz, chloroform-d) δ=11.13 (br s, 1H), 7.06 (td, J=4.1, 15.7 Hz, 1H), 6.08 (td, J=2.0, 15.7 Hz, 1H), 4.12 (dd, J=2.0, 4.1 Hz, 2H), 3.40 (s, 3H).

Step D: 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile To a solution of 2-[(2S)-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (200 mg, 391 umol, 1 eq), (E)-4-methoxybut-2-enoic acid (113 mg, 977 umol, 2.5 eq), TEA (395 mg, 3.91 mmol, 544 μL, 10 eq) in DMF (4 mL) was added T3P (746 mg, 1.17 mmol, 697 μL, 50% purity, 3 eq) at 0° C. The mixture was stirred at 0° C. for 0.3 hour. The reaction mixture was diluted with ethyl acetate (20 mL) and washed with water (10 mL×3). The organic layers were washed with brine (10 mL), dried over Na₂SO₄, filtered and concentrated under reduced pressure to give a residue. The residue was purified by column chromatography (SiO₂, Ethyl acetate/MeOH=100/1 to 10:1) and further purified by prep-HPLC (column: Boston pH—lex 150*25 10 um; mobile phase: [water (0.1% TFA)—ACN]; B %: 35%-59%, 8 min). The mixture was collected and lyophilized. Title compound 2-[(2S)-1-[(E)-4-methoxybut-2-enoyl]-4-[7-(8-methyl-1-naphthyl)-2-[[(2R)-1-methylpyrrolidin-2-yl]methoxy]-6,8-dihydro-5H-pyrido[3,4-d]pyrimidin-4-yl]piperazin-2-yl]acetonitrile (EXAMPLE 73, 37.5 mg, 60.4 umol, 15% yield, 98.2% purity) was obtained as a white solid. LCMS [ESI, M+1]: 610.

¹H NMR (400 MHz, chloroform-d) δ=7.77-7.57 (m, 2H), 7.46-7.37 (m, 1H), 7.34 (t, J=7.6 Hz, 1H), 7.27-7.17 (m, 2H), 6.99 (br d, J=14.4 Hz, 1H), 6.55 (br d, J=14.8 Hz, 1H), 5.24-4.49 (m, 1H), 4.46-4.32 (m, 1H), 4.32-3.74 (m, 7H), 3.73-3.25 (m, 6H), 3.25-2.94 (m, 5H), 2.92 (s, 3H), 2.86-2.54 (m, 4H), 2.49 (d, J=5.6 Hz, 3H), 2.38-2.23 (m, 1H), 2.11-2.00 (m, 1H), 1.93-1.65 (m, 3H).

Examples 74-129 are shown in Table 1:

| Example No. | Structure |
|---|---|
| 74 | *(structure)* |
| 75 | *(structure)* |
| 76 | *(structure)* |
| 77 | *(structure)* |

| Example No. | Structure |
|---|---|
| 78 | 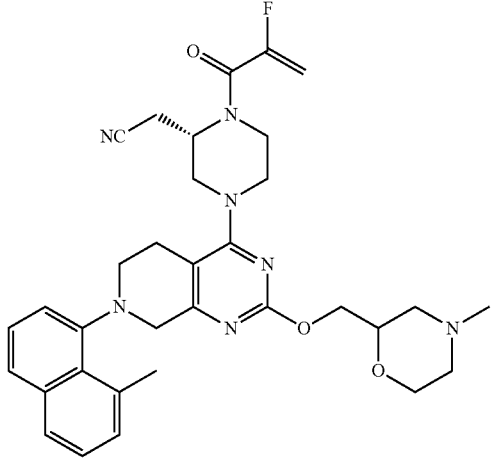 [SMILES: C=C(F)C(=O)N1CCN(c2nc(OCC3CN(C)CCO3)nc3c2CCN(c2cccc4cccc(C)c24)C3)C[C@@H]1CC#N] |
| 79 | 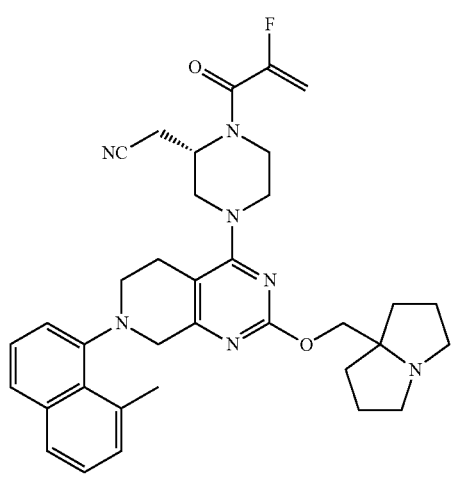 [SMILES: C=C(F)C(=O)N1CCN(c2nc(OCC34CCCN3CCC4)nc3c2CCN(c2cccc4cccc(C)c24)C3)C[C@@H]1CC#N] |
| 80 | 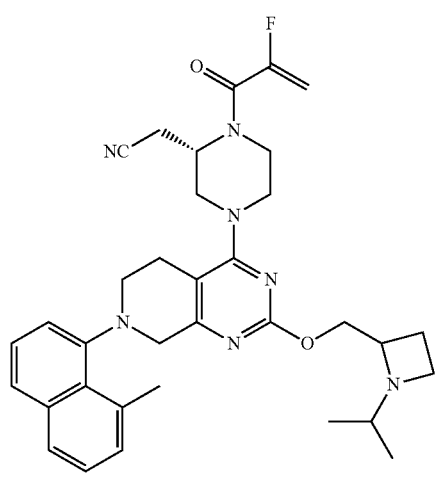 [SMILES: C=C(F)C(=O)N1CCN(c2nc(OCC3CCN3C(C)C)nc3c2CCN(c2cccc4cccc(C)c24)C3)C[C@@H]1CC#N] |
| 81 | 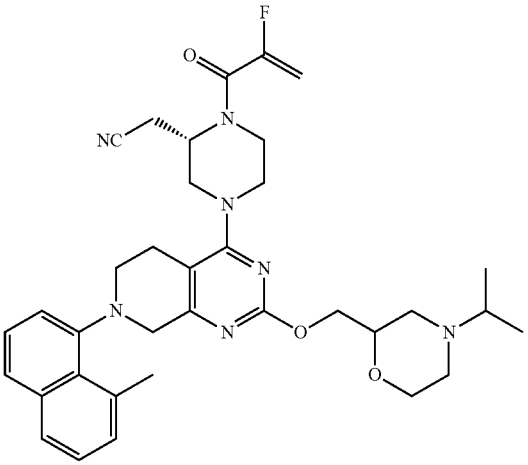 [SMILES: C=C(F)C(=O)N1CCN(c2nc(OCC3CN(C(C)C)CCO3)nc3c2CCN(c2cccc4cccc(C)c24)C3)C[C@@H]1CC#N] |
| 82 | 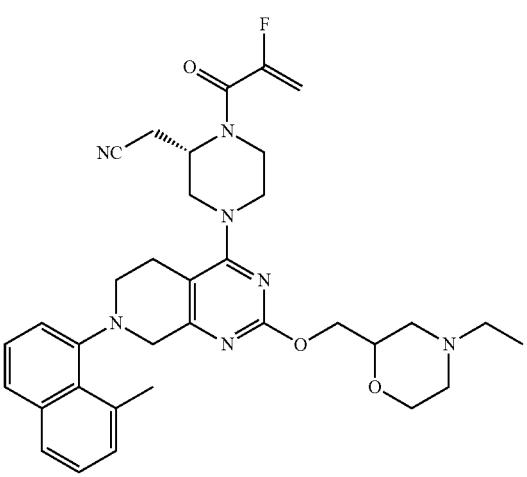 [SMILES: C=C(F)C(=O)N1CCN(c2nc(OCC3CN(CC)CCO3)nc3c2CCN(c2cccc4cccc(C)c24)C3)C[C@@H]1CC#N] |
| 83 | 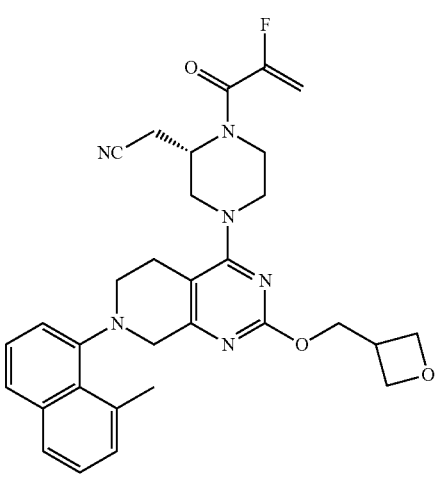 [SMILES: C=C(F)C(=O)N1CCN(c2nc(OCC3COC3)nc3c2CCN(c2cccc4cccc(C)c24)C3)C[C@@H]1CC#N] |

287
-continued
| Example No. | Structure |
|---|---|
| 84 | 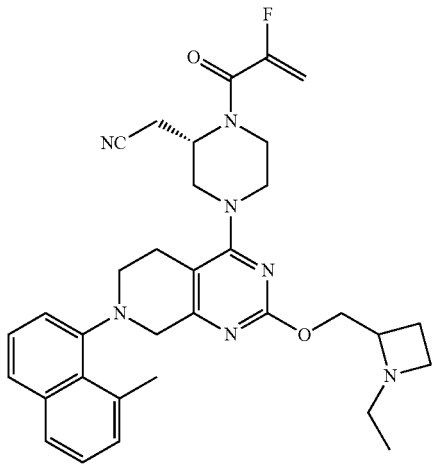 [SMILES: C=C(F)C(=O)N1CCN(c2nc(OCC3CCN3CC)nc3c2CCN(c2cccc4cccc(C)c24)C3)C[C@@H]1CC#N] |
| 85 | 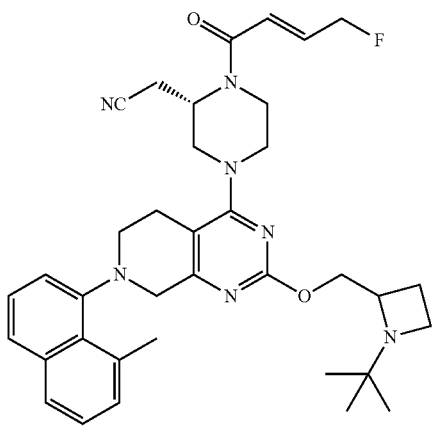 [SMILES: Cc1cccc2cccc(N3CCc4c(nc(OCC5CCN5C(C)(C)C)nc4N4CCN(C(=O)/C=C/CF)[C@@H](CC#N)C4)C3)c12] |
| 86 | 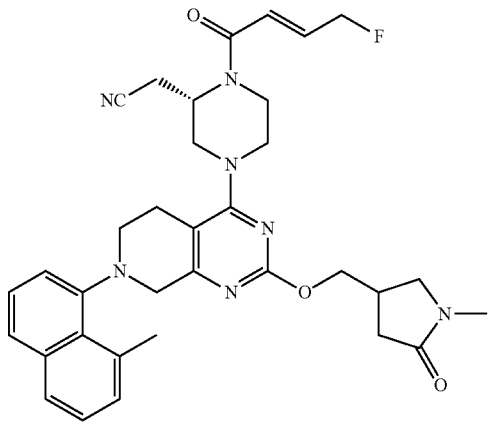 [SMILES: Cc1cccc2cccc(N3CCc4c(nc(OCC5CC(=O)N(C)C5)nc4N4CCN(C(=O)/C=C/CF)[C@@H](CC#N)C4)C3)c12] |
288
-continued
| Example No. | Structure |
|---|---|
| 87 | 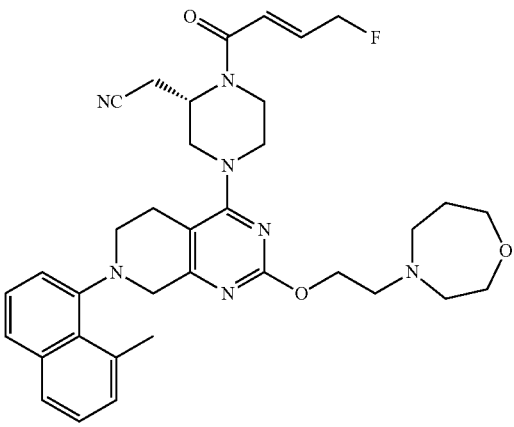 [SMILES: Cc1cccc2cccc(N3CCc4c(nc(OCCN5CCCOCC5)nc4N4CCN(C(=O)/C=C/CF)[C@@H](CC#N)C4)C3)c12] |
| 88 | 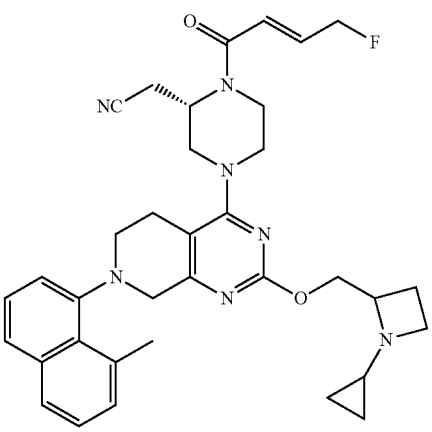 [SMILES: Cc1cccc2cccc(N3CCc4c(nc(OCC5CCN5C5CC5)nc4N4CCN(C(=O)/C=C/CF)[C@@H](CC#N)C4)C3)c12] |
| 89 | 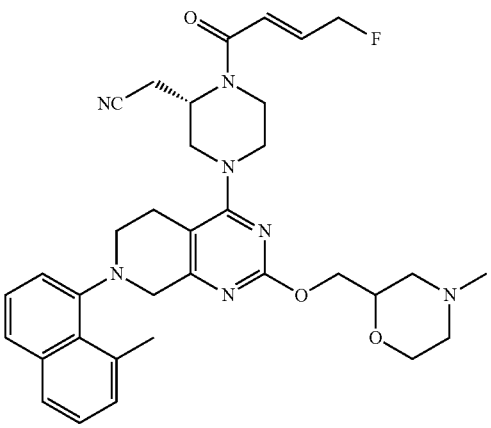 [SMILES: Cc1cccc2cccc(N3CCc4c(nc(OCC5CN(C)CCO5)nc4N4CCN(C(=O)/C=C/CF)[C@@H](CC#N)C4)C3)c12] |

-continued
| Example No. | Structure |
|---|---|
| 90 | 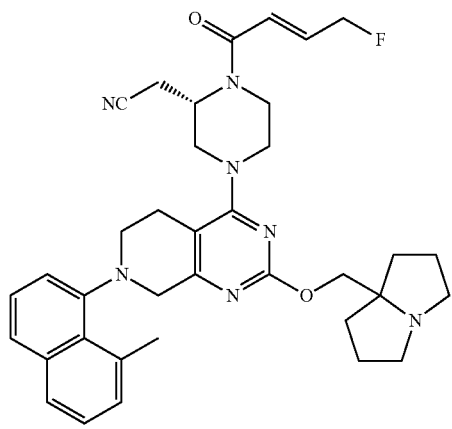 [SMILES: Cc1cccc2cccc(N3CCc4c(nc(OCC56CCCN5CCC6)nc4N4CCN(C(=O)/C=C/CF)[C@@H](CC#N)C4)C3)c12] |
| 91 | 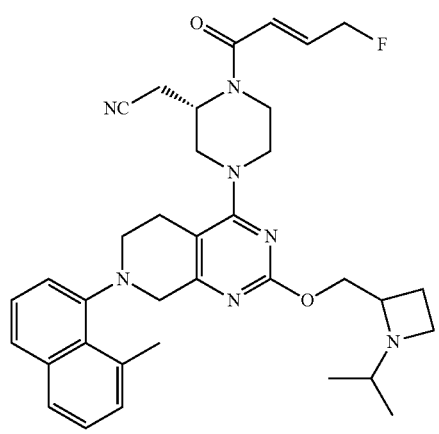 [SMILES: Cc1cccc2cccc(N3CCc4c(nc(OCC5CCN5C(C)C)nc4N4CCN(C(=O)/C=C/CF)[C@@H](CC#N)C4)C3)c12] |
| 92 | 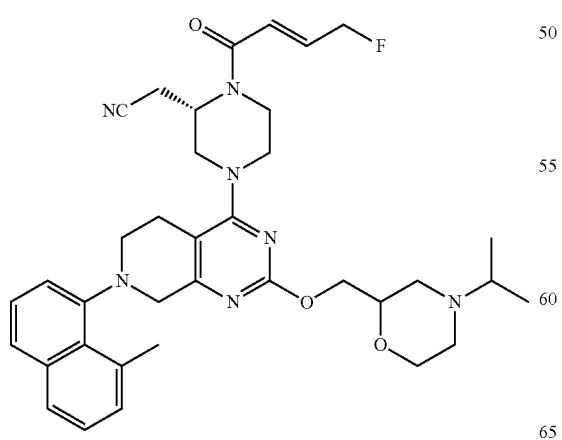 |
-continued
| Example No. | Structure |
|---|---|
| 93 | 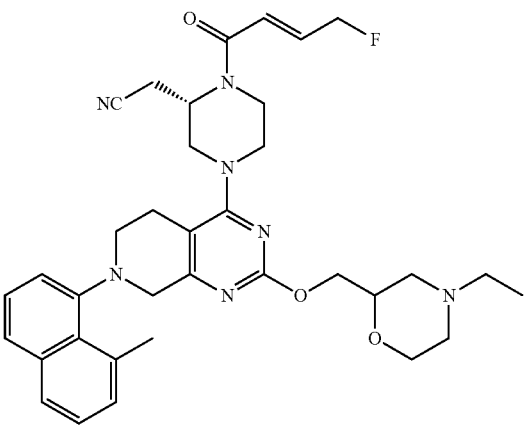 [SMILES: CCN1CCOC(COc2nc3c(c(N4CCN(C(=O)/C=C/CF)[C@@H](CC#N)C4)n2)CCN(c2cccc4cccc(C)c24)C3)C1] |
| 94 | 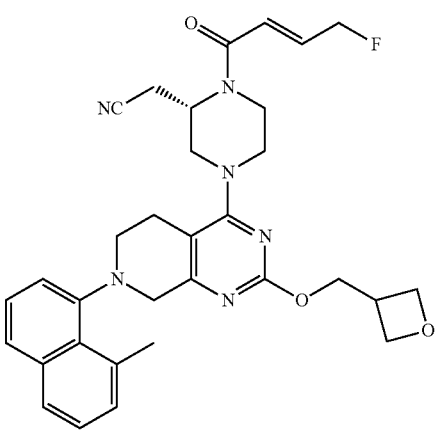 [SMILES: Cc1cccc2cccc(N3CCc4c(nc(OCC5COC5)nc4N4CCN(C(=O)/C=C/CF)[C@@H](CC#N)C4)C3)c12] |
| 95 | 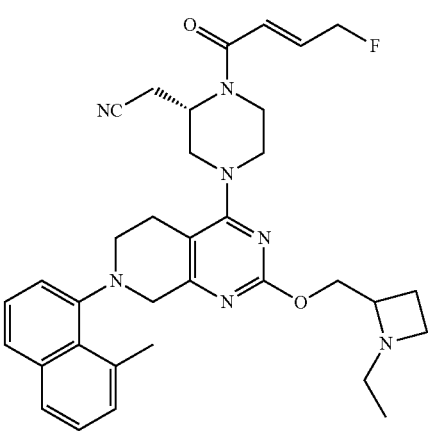 [SMILES: CCN1CCC1COc1nc2c(c(N3CCN(C(=O)/C=C/CF)[C@@H](CC#N)C3)n1)CCN(c1cccc3cccc(C)c13)C2] |

| Example No. | Structure |
|---|---|
| 96 | 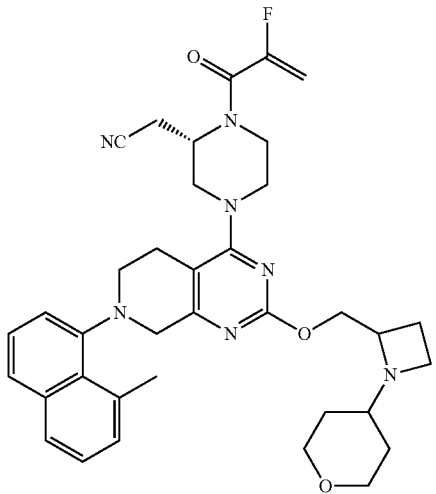 [SMILES: C=C(F)C(=O)N1CCN(c2nc(OCC3CCN3C3CCOCC3)nc3c2CCN(c2cccc4cccc(C)c24)C3)C[C@@H]1CC#N] |
| 97 | 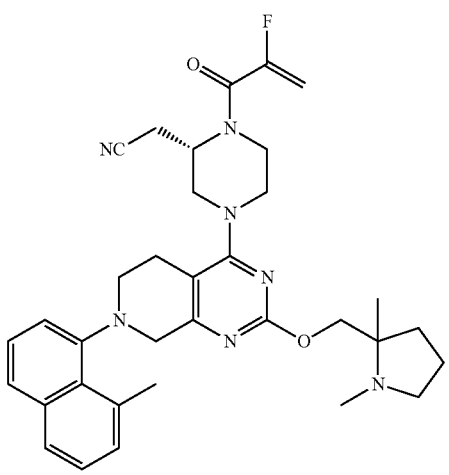 |
| 98 | 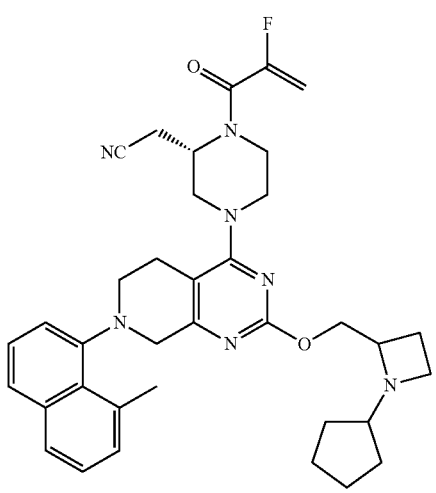 [SMILES: C=C(F)C(=O)N1CCN(c2nc(OCC3CCN3C3CCCC3)nc3c2CCN(c2cccc4cccc(C)c24)C3)C[C@@H]1CC#N] |
| 99 | 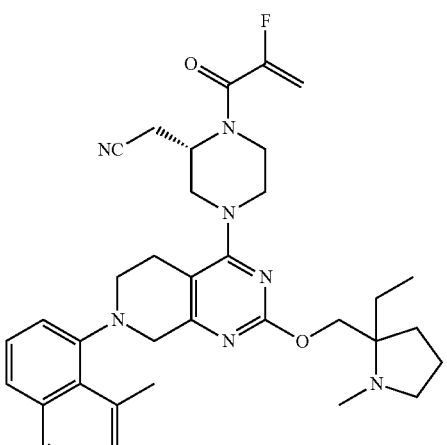 |
| 100 | 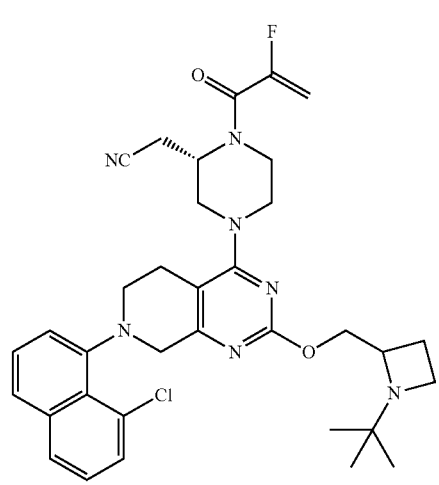 [SMILES: C=C(F)C(=O)N1CCN(c2nc(OCC3CCN3C(C)(C)C)nc3c2CCN(c2cccc4cccc(Cl)c24)C3)C[C@@H]1CC#N] |
| 101 | 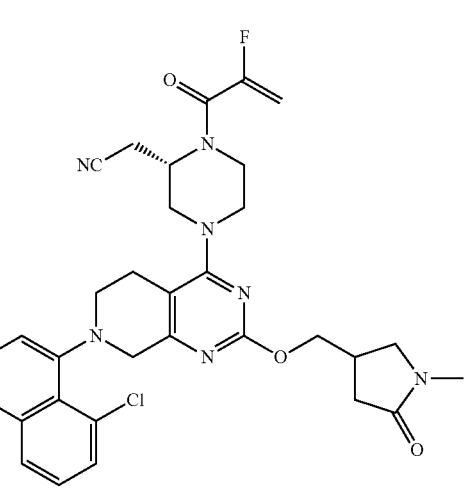 |

| Example No. | Structure |
|---|---|
| 102 | 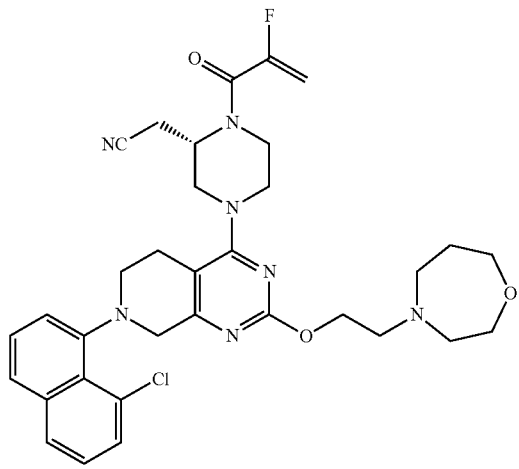 [SMILES: C=C(F)C(=O)N1CCN(c2nc(OCCN3CCCOCC3)nc3c2CCN(c2cccc4cccc(Cl)c24)C3)C[C@@H]1CC#N] |
| 103 | 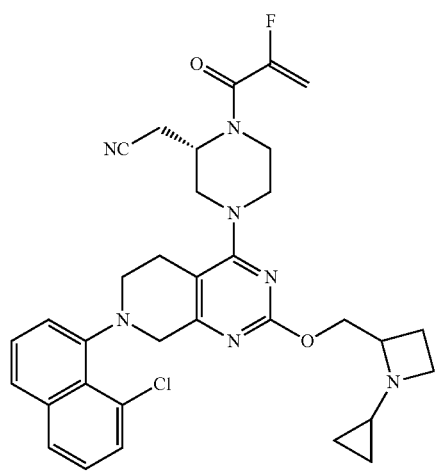 [SMILES: C=C(F)C(=O)N1CCN(c2nc(OCC3CCN3C3CC3)nc3c2CCN(c2cccc4cccc(Cl)c24)C3)C[C@@H]1CC#N] |
| 104 | 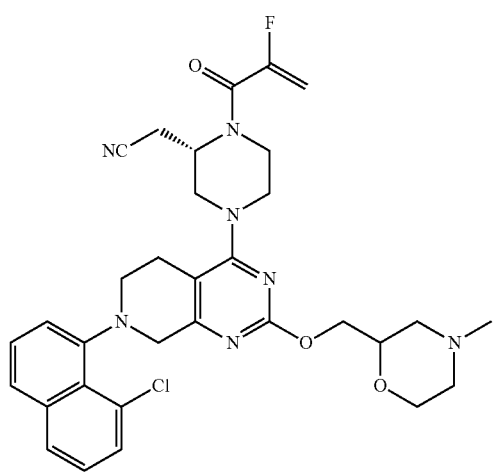 [SMILES: C=C(F)C(=O)N1CCN(c2nc(OCC3CN(C)CCO3)nc3c2CCN(c2cccc4cccc(Cl)c24)C3)C[C@@H]1CC#N] |
| 105 | 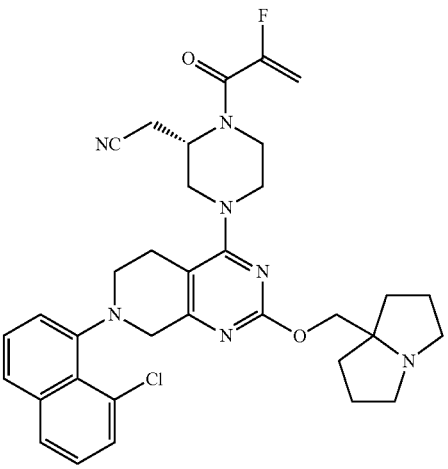 |
| 106 | 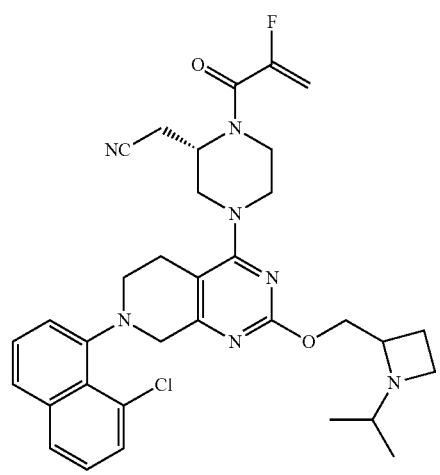 [SMILES: C=C(F)C(=O)N1CCN(c2nc(OCC3CCN3C(C)C)nc3c2CCN(c2cccc4cccc(Cl)c24)C3)C[C@@H]1CC#N] |
| 107 | 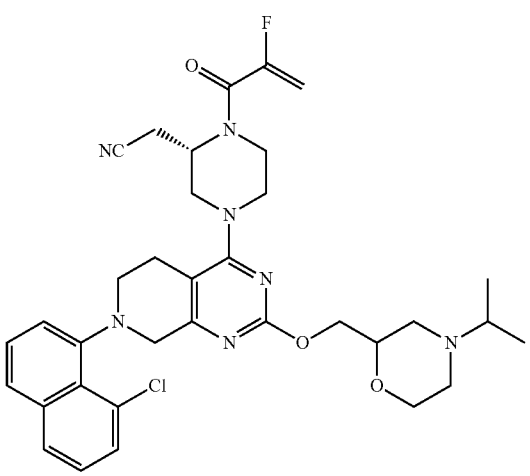 [SMILES: C=C(F)C(=O)N1CCN(c2nc(OCC3CN(C(C)C)CCO3)nc3c2CCN(c2cccc4cccc(Cl)c24)C3)C[C@@H]1CC#N] |

| Example No. | Structure |
|---|---|
| 108 | 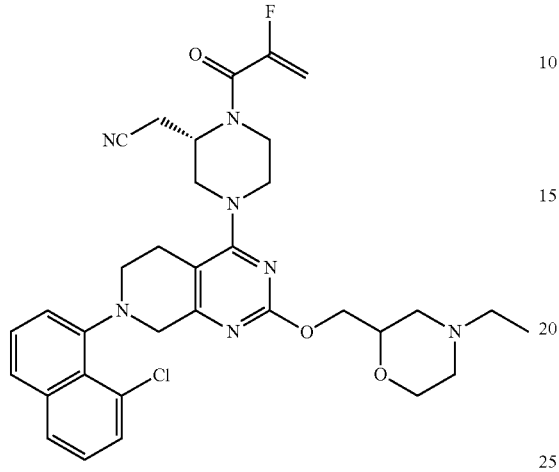 |
| 109 | 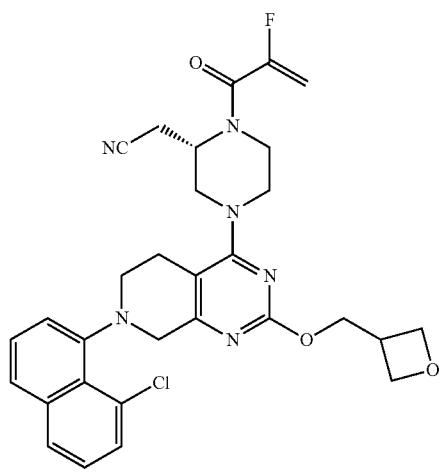 |
| 110 | 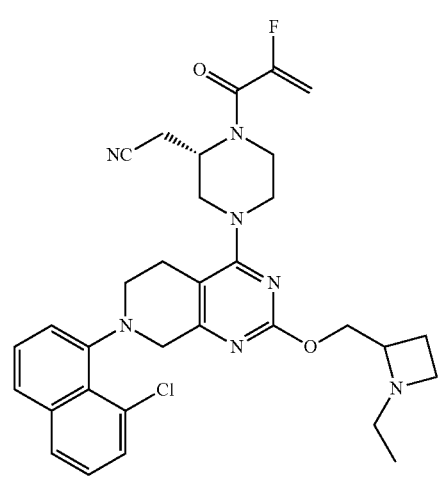 [SMILES: C=C(F)C(=O)N1CCN(c2nc(OCC3CCN3CC)nc3c2CCN(c2cccc4cccc(Cl)c24)C3)C[C@@H]1CC#N] |
| 111 | 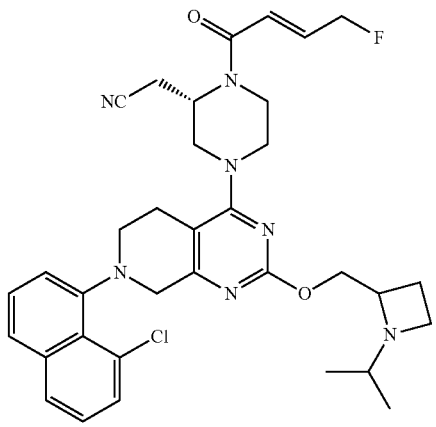 [SMILES: CC(C)N1CCC1COc1nc2c(c(N3CCN(C(=O)/C=C/CF)[C@@H](CC#N)C3)n1)CCN(c1cccc3cccc(Cl)c13)C2] |
| 112 | 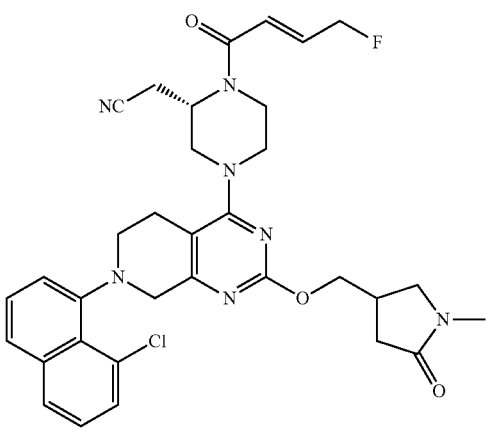 [SMILES: CN1CC(COc2nc3c(c(N4CCN(C(=O)/C=C/CF)[C@@H](CC#N)C4)n2)CCN(c2cccc4cccc(Cl)c24)C3)CC1=O] |
| 113 | 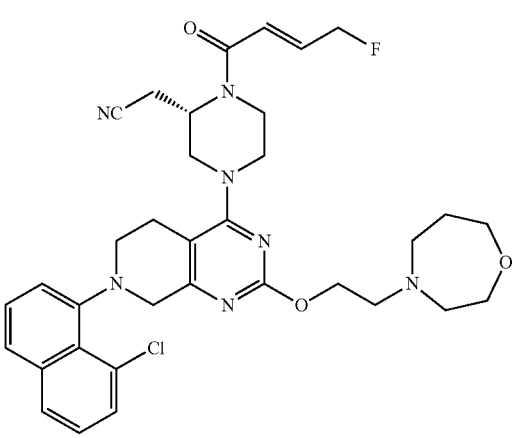 [SMILES: N#CC[C@H]1CN(c2nc(OCCN3CCCOCC3)nc3c2CCN(c2cccc4cccc(Cl)c24)C3)CCN1C(=O)/C=C/CF] |

| Example No. | Structure |
|---|---|
| 114 | 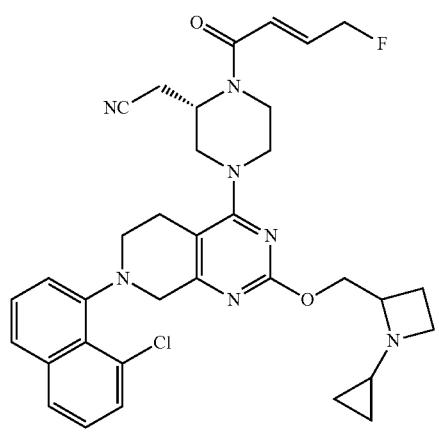 [SMILES: N#CC[C@H]1CN(c2nc(OCC3CCN3C3CC3)nc3c2CCN(c2cccc4cccc(Cl)c24)C3)CCN1C(=O)/C=C/CF] |
| 115 | 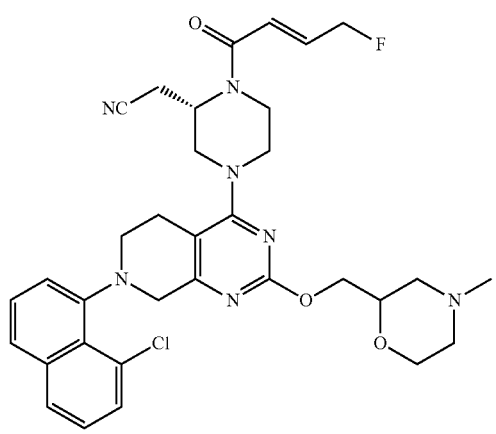 [SMILES: CN1CCOC(COc2nc3c(c(N4CCN(C(=O)/C=C/CF)[C@@H](CC#N)C4)n2)CCN(c2cccc4cccc(Cl)c24)C3)C1] |
| 116 | 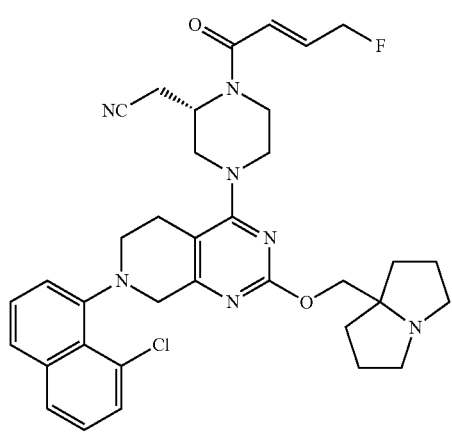 [SMILES: N#CC[C@H]1CN(c2nc(OCC34CCCN3CCC4)nc3c2CCN(c2cccc4cccc(Cl)c24)C3)CCN1C(=O)/C=C/CF] |
| Example No. | Structure |
|---|---|
| 117 | 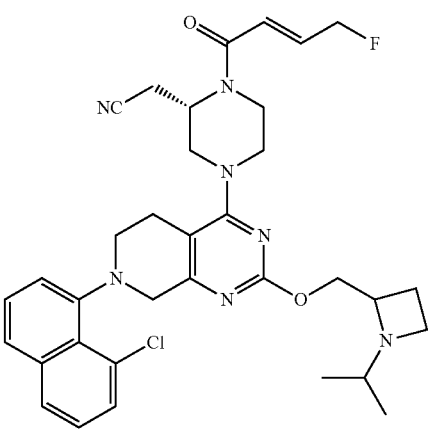 [SMILES: CC(C)N1CCC1COc1nc2c(c(N3CCN(C(=O)/C=C/CF)[C@@H](CC#N)C3)n1)CCN(c1cccc3cccc(Cl)c13)C2] |
| 118 | 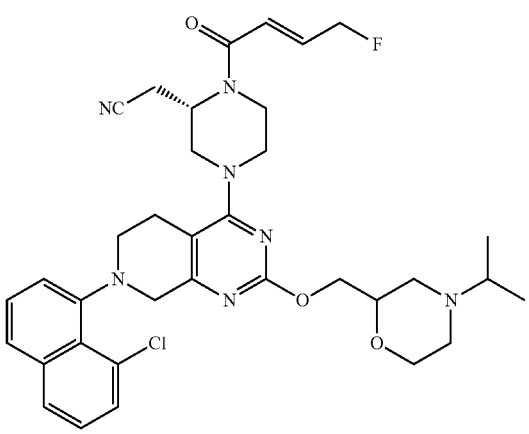 [SMILES: CC(C)N1CCOC(COc2nc3c(c(N4CCN(C(=O)/C=C/CF)[C@@H](CC#N)C4)n2)CCN(c2cccc4cccc(Cl)c24)C3)C1] |
| 119 | 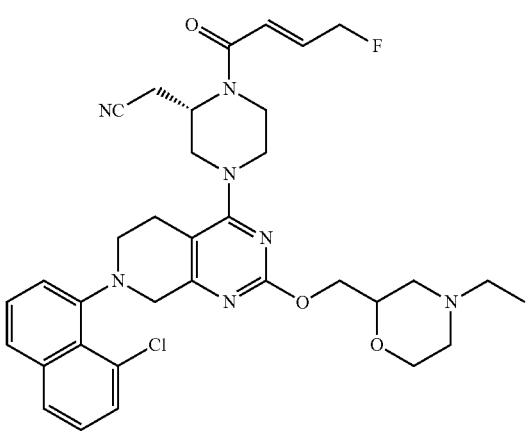 [SMILES: CCN1CCOC(COc2nc3c(c(N4CCN(C(=O)/C=C/CF)[C@@H](CC#N)C4)n2)CCN(c2cccc4cccc(Cl)c24)C3)C1] |

-continued
| Example No. | Structure |
|---|---|
| 120 | 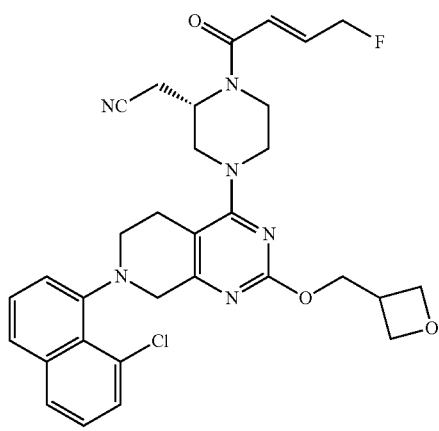 |
| 121 | 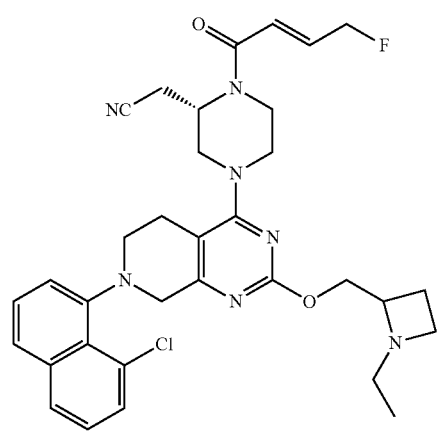 [SMILES: CCN1CCC1COc1nc2c(c(N3CCN(C(=O)/C=C/CF)[C@@H](CC#N)C3)n1)CCN(c1cccc3cccc(Cl)c13)C2] |
| 122 | 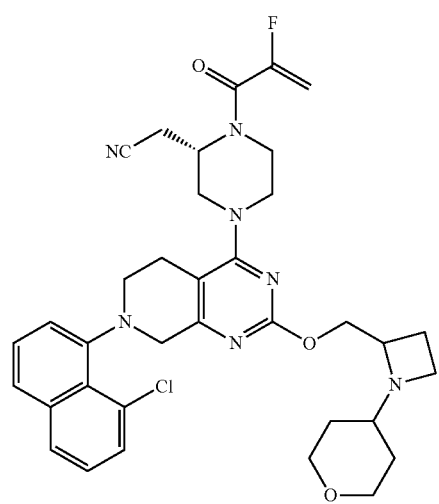 [SMILES: C=C(F)C(=O)N1CCN(c2nc(OCC3CCN3C3CCOCC3)nc3c2CCN(c2cccc4cccc(Cl)c24)C3)C[C@@H]1CC#N] |
-continued
| Example No. | Structure |
|---|---|
| 123 | 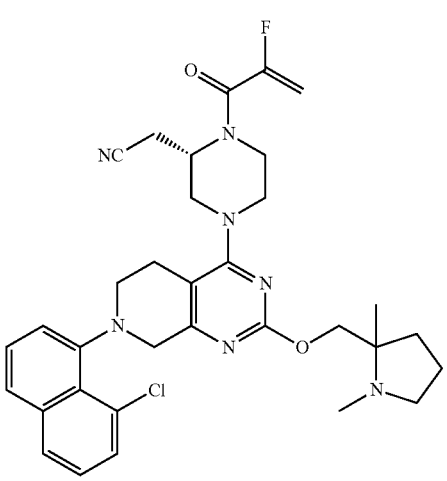 [SMILES: C=C(F)C(=O)N1CCN(c2nc(OCC3(C)CCCN3C)nc3c2CCN(c2cccc4cccc(Cl)c24)C3)C[C@@H]1CC#N] |
| 124 | 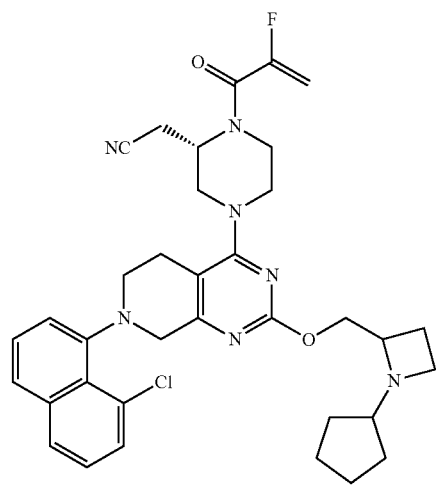 [SMILES: C=C(F)C(=O)N1CCN(c2nc(OCC3CCN3C3CCCC3)nc3c2CCN(c2cccc4cccc(Cl)c24)C3)C[C@@H]1CC#N] |
| 125 | 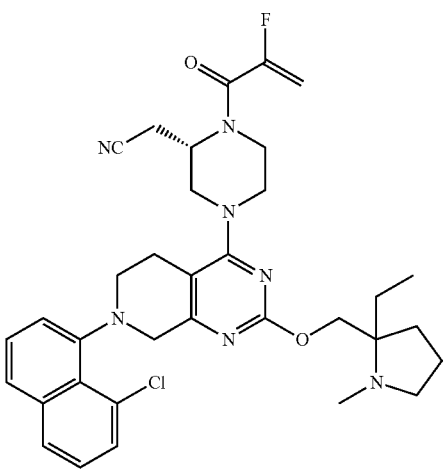 |

| Example No. | Structure |
|---|---|
| 126 | 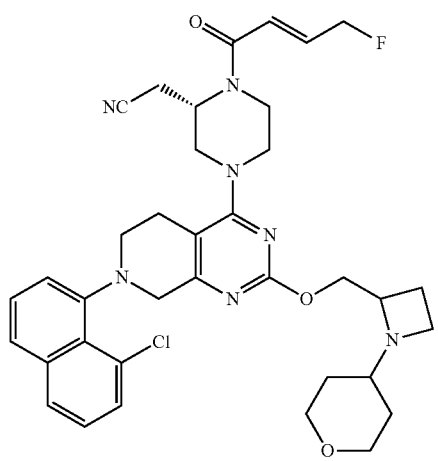 [SMILES: N#CC[C@H]1CN(c2nc(OCC3CCN3C3CCOCC3)nc3c2CCN(c2cccc4cccc(Cl)c24)C3)CCN1C(=O)/C=C/CF] |
| 127 | 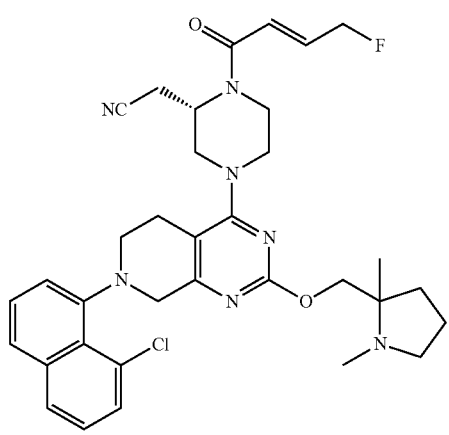 [SMILES: CN1CCCC1(C)COc1nc2c(c(N3CCN(C(=O)/C=C/CF)[C@@H](CC#N)C3)n1)CCN(c1cccc3cccc(Cl)c13)C2] |
| 128 | 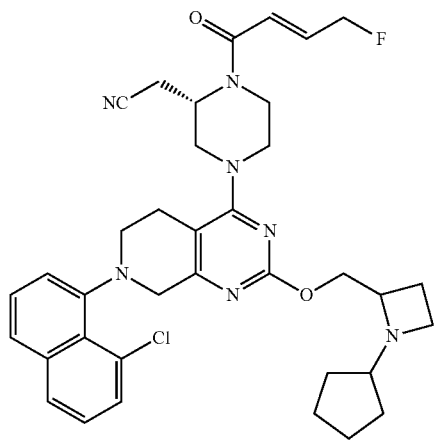 [SMILES: N#CC[C@H]1CN(c2nc(OCC3CCN3C3CCCC3)nc3c2CCN(c2cccc4cccc(Cl)c24)C3)CCN1C(=O)/C=C/CF] |
| 129 | |
Synthesis of Example 74
2-((2S)-4-(2-((1-(tert-butyl)azetidin-2-yl)methoxy)-7-(8-methylnaphthalen-1-yl)-5,6,7,8-tetrahydro-pyrido[3,4-d]pyrimidin-4-yl)-1-(2-fluoroacryloyl)piperazin-2-yl)acetonitrile
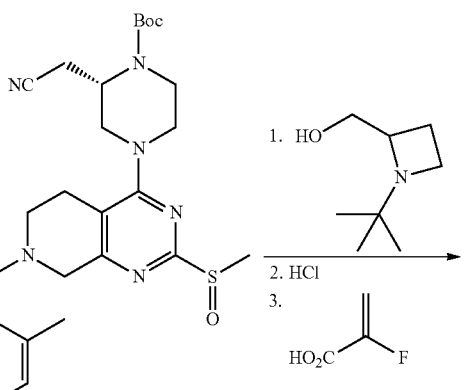

Step A

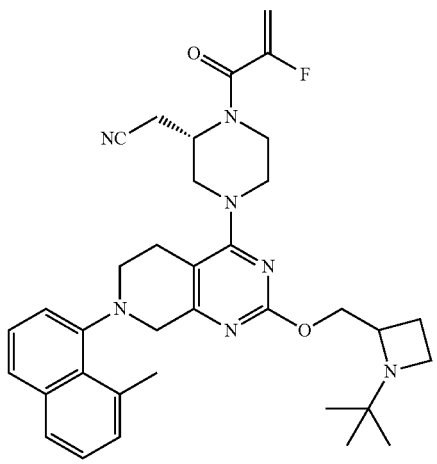

To a mixture of tert-butyl (2S)-2-(cyanomethyl)-4-(7-(8-methylnaphthalen-1-yl)-2-(methyl sulfinyl)-5,6,7,8-tetrahydropyrido[3,4-d]pyrimidin-4-yl)piperazine-1-carboxylate (200 mg, 357 µmol, 1.00 eq.) and (1-tert-butylazetidin-2-yl)methanol (102 mg, 713 µmol, 2.0 eq) in toluene (20.0 mL) was added t-BuONa (103 mg, 1.07 mmol, 3.0 eq) in portions at 0° C. under nitrogen. The mixture was stirred at 25° C. for 30 min. The reaction mixture was diluted with ethyl acetate (30.0 mL) and adjusted to pH 8-9 with 2 M aq HCl at 0° C. and then extracted with ethyl acetate (20.0 mL×2). The combined organic layer was washed with water (15.0 mL), dried over sodium sulfate, filtered and concentrated under reduced pressure. The residue was purified by reversed phase flash chromatography [water (0.1% formic acid)/acetonitrile]. The desired fractions were collected and neutralized with saturated NaHCO₃ solution (6.00 mL) and extracted with ethyl acetate (50.0 mL×2). The separated organic layer was dried over sodium sulfate, filtered and concentrated under vacuum to afford tert-butyl (2S)-4-(2-((1-(tert-butyl)azetidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (100 mg, 150 µmol, 42% yield, 96% purity) was obtained as a yellow solid. LCMS [M+1]: 640.

Step B

To a mixture of tert-butyl (2S)-4-(2-((1-(tert-butyl)azetidin-2-yl)methoxy)-7-(8-methylnaphthalen-1-yl)-5,6,7,8-tetrahydropyrido[3,4-d]pyrimidin-4-yl)-2-(cyanomethyl)piperazine-1-carboxylate (50.0 mg, 78.2 µmol, 1.00 eq) in MeCN (1.00 mL) was added HCl/dioxane (4 M, 1.50 mL, 76.8 eq.) and the mixture was stirred at 25° C. for 30 min. The reaction mixture was concentrated under reduced pressure to give a residue. The residue was diluted with ethyl acetate (5.00 mL) and saturated NaHCO₃ solution. The aqueous layer was separated and extracted with ethyl acetate (5.00 mL×3). The combined organic layer was washed with brine (3.00 mL), dried over sodium sulfate, filtered and concentrated under reduced pressure to provide the crude material. The residue was purified by prep-HPLC (column: Waters Xbridge 150×25 5 µm; mobile phase: [water (10 mM NH₄HCO₃)—ACN]; B %: 42%-72%, 10 min) to afford 2-((2S)-4-(2-((1-(tert-butyl)azetidin-2-yl)methoxy)-7-(8-methylnaphthalen-1-yl)-5,6,7,8-tetrahydropyrido[3,4-d]pyrimidin-4-yl)piperazin-2-yl)acetonitrile (10.4 mg, 19.0 µmol, 24% yield, 99.2% purity) as a white solid. LCMS [M+1]: 540.

SFC conditions: Column: Chiralpak IC-3 50×4.6 mm I.D., 3 um Mobile phase: Phase A for CO₂, and Phase B for IPA+CAN (0.05% DEA); Gradient elution: 50% IPA+ACN (0.05% DEA) in CO₂ Flow rate: 3 mL/min; Wavelength: 220 nm Column Temp: 35 C; Back Pressure: 100 Bar.

$^1$H NMR (400 MHz, CDCl₃): δ=7.72-7.68 (m, 1H), 7.67-7.62 (m, 1H), 7.44-7.37 (m, 1H), 7.37-7.31 (m, 1H), 7.27-7.19 (m, 2H), 4.50-4.39 (m, 1H), 4.30-4.16 (m, 2H), 4.04-3.72 (m, 4H), 3.52-3.45 (m, 1H), 3.37-3.28 (m, 1H), 3.25-3.07 (m, 6H), 3.06-2.96 (m, 2H), 2.95-2.92 (m, 3H), 2.61-2.49 (m, 3H), 2.15-1.94 (m, 2H), 1.06-0.96 (m, 9H).

Step C

To a mixture of 2-((2S)-4-(2-((1-(tert-butyl)azetidin-2-yl)methoxy)-7-(8-methylnaphthalen-1-yl)-5,6,7,8-tetrahydropyrido[3,4-d]pyrimidin-4-yl)piperazin-2-yl)acetonitrile (80.0 mg, 148 µmol, 1.0 eq.) and 2-fluoroprop-2-enoic acid (40.1 mg, 445 µmol, 3.0 eq) in ethyl acetate (3.00 mL) was added TEA (120 mg, 1.19 mmol, 165 µL, 8.0 eq) and T3P (283 mg, 445 µmol, 264 µL, 50% purity, 3.0 eq.) in portion at 0° C. under nitrogen. The mixture was stirred at 25° C. for 30 min. The reaction mixture was quenched by the addition of water (2.00 mL) at 0° C. and was subsequently extracted with ethyl acetate (5.00 mL×3). The combined organic layer was washed with brine (3.00 mL), dried over sodium sulfate, filtered and concentrated under reduced pressure to give a residue. The residue was purified by prep-HPLC (column: Waters Xbridge 150×25 5 µm; mobile phase: [water (10 mM NH₄HCO₃)-ACN]; B %: 45%-75%, 10 min) to afford 2-((2S)-4-(2-((1-(tert-butyl)azetidin-2-yl)methoxy)-7-(8-methylnaphthalen-1-yl)-5,6,7,8-tetrahydropyrido[3,4-d]pyrimidin-4-yl)-1-(2-fluoroacryloyl)piperazin-2-yl)acetonitrile (21.8 mg, 35.4 µmol, 24% yield, 99.2% purity) as a white solid. LCMS [M+1]: 612.

SFC conditions: Column: Chiralcel OJ-3 50×4.6 mm I.D., 3 µm Mobile phase: Phase A for CO₂, and Phase B for MeOH (0.05% DEA); Gradient elution: MeOH (0.05% DEA) in CO₂ from 5% to 40% Flow rate: 3 mL/min; Wavelength: 220 nm Column Temp: 20 C; Back Pressure: 100 Bar.

$^1$H NMR (400 MHz, CDCl₃): δ=7.73-7.67 (m, 1H), 7.67-7.62 (m, 1H), 7.46-7.38 (m, 1H), 7.38-7.32 (m, 1H), 7.27-7.17 (m, 2H), 5.53-5.33 (m, 1H), 5.31-5.16 (m, 1H), 5.03-4.64 (m, 1H), 4.53-4.37 (m, 1H), 4.33-4.21 (m, 2H), 4.20-3.99 (m, 3H), 3.94-3.73 (m, 3H), 3.60-3.40 (m, 2H), 3.27-3.03 (m, 6H), 2.95-2.89 (m, 3H), 2.86-2.76 (m, 1H), 2.68-2.54 (m, 1H), 2.19-1.91 (m, 2H), 1.06-0.92 (m, 9H).

Spectral data for Examples 100, 103 and 104 are provided in Table 2.

TABLE 2

| Ex. # | Structure | Spectral Data |
|---|---|---|
| 100 | 2-((2S)-4-(2-((1-(tert-butyl)azetidin-2-yl)methoxy)-7-(8-chloronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CD$_3$OD) δ = 7.83 (d, J = 8.0 Hz, 1H), 7.69 (br d, J = 8.4 Hz, 1H), 7.56-7.52 (m, 1H), 7.51-7.46 (dd, J = 1.2 Hz, J = 8.0 Hz, 1H), 7.38 (t, J = 8.0 Hz, 1H), 7.35-7.30 (m, 1H), 5.43-5.24 (m, 2H), 4.51-4.41 (m, 1H), 4.36-4.25 (m, 3H), 4.23-4.03 (m, 2H), 3.99-3.88 (m, 1H), 3.78-3.67 (m, 1H), 3.64-3.57 (m, 1H), 3.51-3.38 (m, 2H), 3.30-3.12 (m, 6H), 3.10-3.01 (m, 1H), 3.00-2.88 (m, 1H), 2.76-2.62 (m, 1H), 2.15-2.06 (m, 1H), 2.04-1.94 (m, 1H), 1.06 (s, 9H). LCMS [M + 1]: 632.4. |
| 103 | 2-((2S)-4-(7-(8-chloronaphthalen-1-yl)-2-((4-methylmorpholin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, MeOD) δ = 7.82 (dd, J = 0.8, 8.0 Hz, 1H), 7.67 (br d, J = 8.0 Hz, 1H), 7.52 (dd, J = 1.2, 7.6 Hz, 1H), 7.51-7.45 (m, 1H), 7.37 (t, J = 8.0 Hz, 1H), 7.34-7.29 (m, 1H), 5.40-5.23 (m, 2H), 4.44-4.25 (m, 4H), 4.20-4.04 (m, 2H), 3.93-3.85 (m, 2H), 3.77-3.53 (m, 4H), 3.50-3.39 (m, 1H), 3.28-3.06 (m, 5H), 2.95-2.85 (m, 2H), 2.75-2.61 (m, 2H), 12.31 (s, 3H), 2.22-2.12 (m, 1H), 2.09-2.04 (m, 1H). LCMS [M + 1]: 620.5. |

TABLE 2-continued

| Ex. # | Structure | Spectral Data |
|---|---|---|
| 104 | 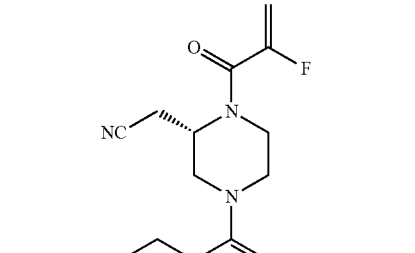
2-((2S)-4-(7-(8-chloronaphthalen-1-yl)-2-((1-cyclopropylazetidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, MeOD) δ = 7.82 (dd, J = 7.2 Hz, 1H), 7.68 (dd, J = 1.2, 8.0 Hz, 1H), 7.55-7.51 (m, 1H), 7.50-7.46 (m, 1H), 7.40-7.35 (m, 1H), 7.35-7.29 (m, 1H), 5.41-5.24 (m, 2H), 4.43-4.26 (m, 4H), 4.23-4.01 (m, 2H), 3.83-3.77 (m, 1H), 3.76-3.66 (m, 1H), 3.64-3.56 (m, 1H), 3.49-3.41 (m, 1H), 3.40-3.32 (m, 2H), 3.30-2.89 (m, 7H), 2.77-2.62 (m, 1H), 2.20-2.10 (m, 1H), 2.06-1.94 (m, 2H), 0.50-0.29 (m, 4H). LCMS [M + 1]: 616.5. |

Synthesis of Example 105

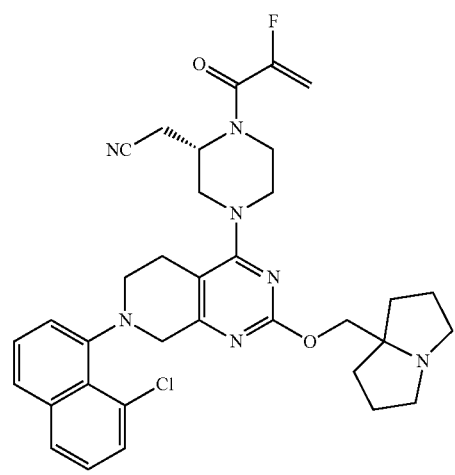 [SMILES: C=C(F)C(=O)N1CCN(c2nc(OCC34CCCN3CCC4)nc3c2CCN(c2cccc4cccc(Cl)c24)C3)C[C@@H]1CC#N]

(S)-2-(4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile

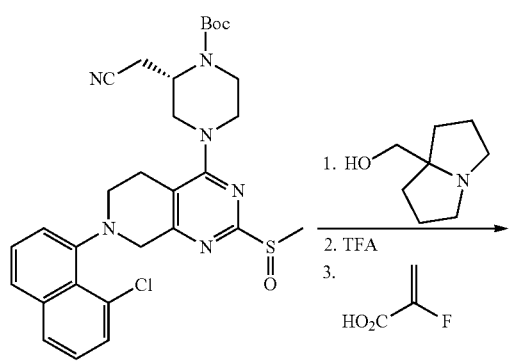

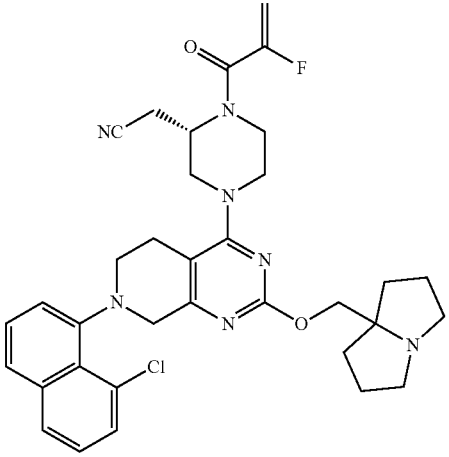

Step A

A solution of tert-butyl (2S)-4-(7-(8-chloronaphthalen-1-yl)-2-(methylsulfinyl)-5,6,7,8-tetrahydropyrido[3,4-d]pyrimidin-4-yl)-2-(cyanomethyl)piperazine-1-carboxylate (200 mg, 344 µmol, 1.00 eq.) and (tetrahydro-1H-pyrrolizin-7a(5H)-yl)methanol (97.2 mg, 688 µmol, 2.00 eq.) in toluene (2.00 mL) at 0° C. was stirred for 20 min prior to the addition of sodium tert-butoxide (99.2 mg, 1.03 mmol, 3.00 eq.). The mixture was stirred at 0° C. for 10 min and The reaction mixture was diluted with water (10.0 mL) and extracted with ethyl acetate (20.0 mL×3). The combined organic layer was washed with brine (50.0 mL×2), dried over anhydrous sodium sulfate, filtered and concentrated under reduced pressure to give a residue. The residue was purified by prep-TLC (SiO$_2$, dichloromethane:methanol=10:1) to afford tert-butyl (S)-4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-2-(cyanomethyl)

piperazine-1-carboxylate (120 mg, 182 µmol, 53.0% yield) as a red solid. LCMS [M+1]: 659.1. Step B. To a solution of tert-butyl (S)-4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-2-(cyanomethyl)piperazine-1-carboxylate (100 mg, 152 µmol, 1.00 eq.) in dichloromethane (2.00 mL) was added TFA (1.08 g, 9.45 mmol, 0.70 mL, 62.2 eq.). The mixture was stirred at 15° C. for 1 h. The reaction mixture was filtered and concentrated under reduced pressure to give a residue. The residue was purified by prep-HPLC (neutral conditions) to afford (S)-2-(4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (60.0 mg, 105 µmol, 69.3% yield, 97.9% purity) as an off-white solid. LCMS [M+1]: 558.2. $^1$H NMR (400 MHz, MeOD): δ=7.82 (d, J=7.8 Hz, 1H), 7.67 (d, J=8.0 Hz, 1H), 7.53 (dd, J=1.2, 7.2 Hz, 1H), 7.48 (dt, J=2.4, 7.6 Hz, 1H), 7.37 (t, J=8.0 Hz, 1H), 7.34-7.30 (m, 1H), 4.37-4.23 (m, 2H), 4.17-4.07 (m, 2H), 4.05-3.89 (m, 1H), 3.73-3.62 (m, 1H), 3.61-3.53 (m, 1H), 3.28-3.23 (m, 1H), 3.21-3.12 (m, 2H), 3.11-2.95 (m, 5H), 2.88-2.80 (m, 1H), 2.74-2.65 (m, 4H), 2.65-2.57 (m, 1H), 2.09-1.99 (m, 2H), 1.95-1.81 (m, 4H), 1.75-1.65 (m, 2H). Step C. To a solution of (S)-2-(4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (40.0 mg, 71.7 µmol, 1.00 eq.) and 2-fluoroprop-2-enoic acid (12.9 mg, 143 µmol, 2.00 eq.) in DMF (2.00 mL) was added DIEA (37.5 µL, 215 µmol, 3.00 eq.) and T3P (42.6 µL, 143 µmol, 2.00 eq.). The mixture was stirred at 15° C. for 1 h. The reaction mixture was diluted with water (10.0 mL) and extracted with ethyl acetate (20.0 mL×3). The combined organic layer was washed with brine (40.0 mL×2), dried over anhydrous sodium sulfate, filtered and concentrated under reduced pressure to give a residue. The residue was purified by prep-HPLC (neutral conditions) to afford (S)-2-(4-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile (11.6 mg, 17.3 µmol, 24.2% yield, 94.4% purity) as a white solid. LCMS [M+1]: 630.4. $^1$H NMR (400 MHz, MeOD) δ=7.82 (dd, J=0.8, 8.0 Hz, 1H), 7.67 (d, J=8.0 Hz, 1H), 7.53 (dd, J=1.2, 7.6 Hz, 1H), 7.51-7.46 (m, 1H), 7.37 (t, J=8.0 Hz, 1H), 7.34-7.29 (m, 1H), 5.41-5.23 (m, 2H), 4.35-4.29 (m, 1H), 4.21-4.08 (m, 4H), 3.75-3.65 (m, 1H), 3.63-3.57 (m, 1H), 3.50-3.38 (m, 1H), 3.29-3.27 (m, 1H), 3.26-2.88 (m, 8H), 2.75-2.62 (m, 3H), 2.09-1.80 (m, 7H), 1.75-1.65 (m, 2H).

Example 130

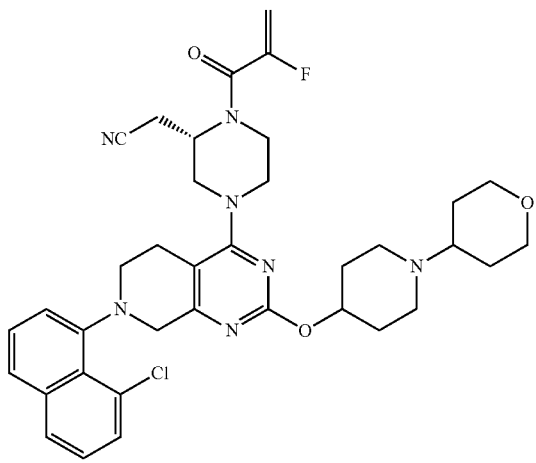 [SMILES: C=C(F)C(=O)N1CCN(c2nc(OC3CCN(C4CCOCC4)CC3)nc3c2CCN(c2cccc4cccc(Cl)c24)C3)C[C@@H]1CC#N]

(S)-2-(4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)-1-(2-fluoroacryloyl)piperazin-2-yl)acetonitrile

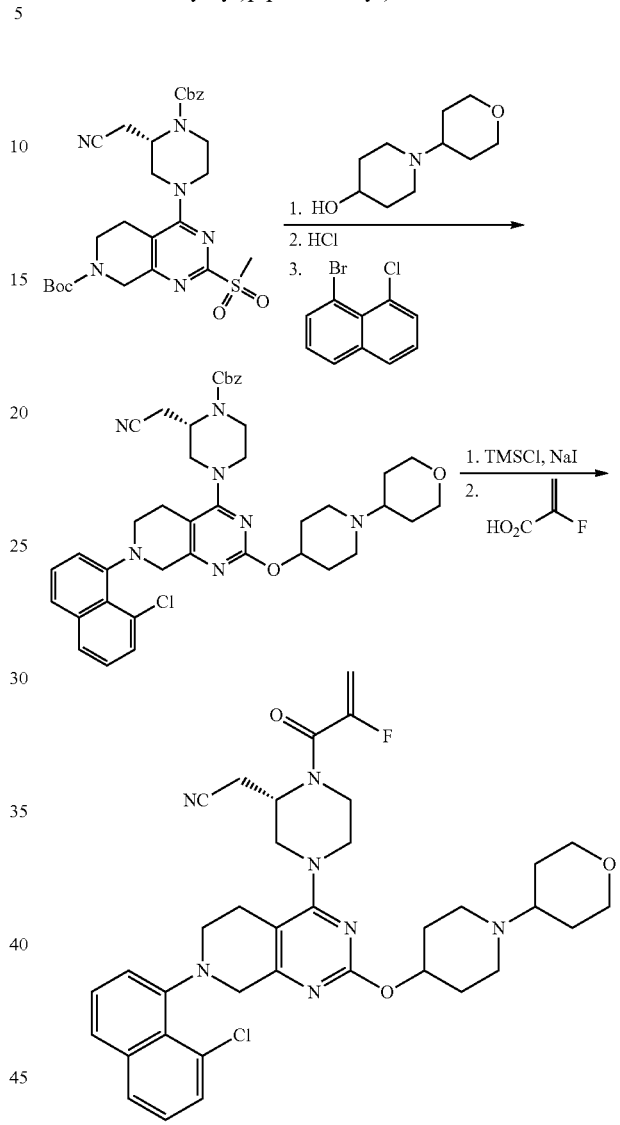

Step A

To a mixture of tert-butyl (S)-4-(4-((benzyloxy)carbonyl)-3-(cyanomethyl)piperazin-1-yl)-2-(methylsulfonyl)-5,8-dihydropyrido[3,4-d]pyrimidine-7(6H)-carboxylate (225 mg, 394 µmol, 1.0 eq.) and 1-tetrahydropyran-4-ylpiperidin-4-ol (110 mg, 591 µmol, 1.5 eq.) in toluene (4 mL) was added 4 Å molecular sieves (100 mg). After stirring at 0° C. for 0.5 h, t-BuONa (75.8 mg, 789 µmol, 2.0 eq.) was added and the mixture was stirred at 0° C. for 0.5 h. After completion, the reaction mixture was filtered and diluted with ethyl acetate (12 mL) and water (10 mL). The aqueous phase was separated and extracted with ethyl acetate (2×10 mL). The combined organic layer was washed with saturated brine (10 mL), dried over Na$_2$SO$_4$, filtered and concentrated under reduced pressure. The residue was purified by column chromatography (SiO$_2$, petroleum ether/ethyl acetate=1/1-0/1) to afford tert-butyl (S)-4-(4-((benzyloxy)carbonyl)-3-

(cyanomethyl)piperazin-1-yl)-2-((1-(tetrahydro-2H-pyran-4-yl)piperidin-4-yl)oxy)-5,8-dihydropyrido[3,4-d]pyrimidine-7(6H)-carboxylate (216 mg, 278 μmol, 70% yield, 86.8% purity) as a yellow solid. LCMS [M+1]: 676.

$^1$H NMR (400 MHz, CDCl$_3$) δ=7.41-7.36 (m, 5H), 5.19 (s, 2H), 4.95 (br d, J=3.2 Hz, 1H), 4.72-4.57 (m, 2H), 4.34 (br d, J=18.8 Hz, 1H), 4.04 (br dd, J=3.6, 11.2 Hz, 2H), 3.89-3.97 (br m, 1H), 3.84-3.71 (m, 1H), 3.34-3.26 (m, 5H), 2.97 (dt, J=3.2, 12.4 Hz, 1H), 2.91-2.78 (m, 3H), 2.75-2.62 (m, 3H), 2.61-2.42 (m, 4H), 2.09-2.06 (m, 1H), 2.05-2.01 (m, 1H), 1.92-1.83 (m, 2H), 1.77 (br d, J=10.8 Hz, 2H), 1.71-1.63 (m, 3H), 1.49 (s, 9H).

To a mixture of tert-butyl (S)-4-(4-((benzyloxy)carbonyl)-3-(cyanomethyl)piperazin-1-yl)-2-((1-(tetrahydro-2H-pyran-4-yl)piperidin-4-yl)oxy)-5,8-dihydropyrido[3,4-d]pyrimidine-7(6H)-carboxylate (380 mg, 562 μmol, 1.0 eq.) in acetonitrile (2 mL) was added HCl.dioxane (4.0 M, 4 mL, 29 eq.). The mixture was stirred at 0-15° C. for 1 h. After completion, the mixture was concentrated under reduced pressure and the mixture was diluted with satd aq NaHCO$_3$. The aqueous phase was extracted with dichloromethane/methanol=10/1 (3×2 mL) and the organic layer was dried over Na$_2$SO$_4$, filtered and concentrated under reduced pressure to afford benzyl (S)-2-(cyanomethyl)-4-(2-((1-(tetrahydro-2H-pyran-4-yl)piperidin-4-yl)oxy)-5,6,7,8-tetrahydropyrido[3,4-d]pyrimidin-4-yl)piperazine-1-carboxylate (307 mg) as a yellow solid that was used in the next step without purification. LCMS [M+1]: 576.

To a mixture of benzyl (S)-2-(cyanomethyl)-4-(2-((1-(tetrahydro-2H-pyran-4-yl)piperidin-4-yl)oxy)-5,6,7,8-tetrahydropyrido[3,4-d]pyrimidin-4-yl)piperazine-1-carboxylate (201 mg, 834 μmol), RuPhos (51.9 mg, 111 μmol), Cs$_2$CO$_3$ (543 mg, 1.67 mmol) in toluene (6 mL) was added Pd$_2$(dba)$_3$ (50.9 mg, 55.6 μmol) under an atmosphere of nitrogen. The mixture was heated at 100° C. for 3 h. The mixture was cooled to room temperature and was diluted with ethyl acetate (8 mL) and water (8 mL). The aqueous phase was extracted with ethyl acetate (2×7 mL) and the combined organic layer was washed with saturated brine (10 mL), dried over Na$_2$SO$_4$, filtered and concentrated under reduced pressure. The residue was purified by reversed phase flash [water (0.1% formic acid)/acetonitrile] to afford benzyl (S)-4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)-2-(cyanomethyl)piperazine-1-carboxylate (120 mg, 143 μmol, two steps 26% yield, 87.5% purity) as a brown solid. LCMS [M+1]: 736.

Step B

To a mixture of benzyl (S)-4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)-2-(cyanomethyl)piperazine-1-carboxylate (118 mg, 160 μmol, 1.0 eq.) and 4 Å molecular sieves (50 mg) in acetonitrile (2 mL) was added NaI (384 mg, 2.56 mmol, 16 eq.). The mixture was stirred at 0° C. for 0.5 h followed by the addition of TMSCl (261 mg, 2.40 mmol, 305 μL, 15 eq.) at 0° C. The mixture was stirred at 15° C. for 16 h and subsequently loaded directly on a alumina plug (Al$_2$O$_3$, ethyl acetate/methanol=10/1-0/1). This material was purified by reversed phase flash [water (0.1% formic acid)/acetonitrile] to afford (S)-2-(4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)piperazin-2-yl)acetonitrile (62.0 mg, 94.7 μmol, 59% yield, 91.9% purity) as a yellow solid. LCMS [M+1]: 602.

To a mixture of (S)-2-(4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)piperazin-2-yl)acetonitrile (47.0 mg, 78.1 μmol, 1.0 eq.), 2-fluoroprop-2-enoic acid (14.1 mg, 156 μmol, 2.0 eq.), 4 Å molecular sieves (20 mg) and DIEA (40.4 mg, 312 μmol, 54.4 μL, 4.0 eq.) in dichloromethane (2 mL) was added HATU (59.4 mg, 156.10 μmol, 2.0 eq.) at 0° C. The mixture was stirred at 0° C. for 30 min. The mixture was diluted with dichloromethane (4 mL) and water (3 mL). The aqueous phase was collected and extracted with dichloromethane (2×3 mL). The combined organic layer was washed with brine (5 mL), dried over Na$_2$SO$_4$, filtered and concentrated under reduced pressure to provide the crude residue. The residue was purified by column chromatography (Al$_2$O$_3$, ethyl acetate/methanol=10/1) followed by prep-HPLC (column: Waters Xbridge 150*50 10 μm; mobile phase: [water (0.05% ammonia hydroxide v/v)—ACN]; B %: 47%-77%, 10 min). Lyophilization afforded (S)-2-(4-(7-(8-chloronaphthalen-1-yl)-2-((1-(tetrahydro-2H-pyran-4-yl)piperidin-4-yl)oxy)-5,6,7,8-tetrahydropyrido[3,4-d]pyrimidin-4-yl)-1-(2-fluoroacryloyl)piperazin-2-yl)acetonitrile (11.6 mg, 17.2 μmol, 22% yield, 99% purity) as an off-white solid. LCMS [M+1]: 674.

SFC conditions: Chiralcel OD-3 50×4.6 mm I.D., 3 μm. Mobile phase: Phase A for CO$_2$, and Phase B for MeOH+ACN (0.05% DEA); Gradient elution: 40% MeOH+ACN (0.05% DEA) in CO$_2$. Flow rate: 3 mL/min; Wavelength: 220 nm. Column Temp: 35C; Back Pressure: 100 Bar.

$^1$H NMR (400 MHz, CDCl$_3$) δ=7.78-7.74 (m, 1H), 7.62 (t, J=7.6 Hz, 1H), 7.55-7.51 (d, J=7.6 Hz, 1H), 7.45 (dt, J=7.6, 14.0 Hz, 1H), 7.34 (t, J=7.6 Hz, 1H), 7.28-7.19 (m, 1H), 5.52-5.34 (m, 1H), 5.26 (dd, J=3.2, 16.4 Hz, 1H), 5.03-4.62 (m, 2H), 4.49-4.37 (m, 1H), 4.24-3.77 (m, 6H), 3.60 (br dd, J=3.2, 11.6 Hz, 1H), 3.48-3.32 (m, 3H), 3.30-2.67 (m, 8H), 2.63-2.38 (m, 4H), 2.13-2.01 (m, 2H), 1.89 (br d, J=8.6 Hz, 2H), 1.82-1.71 (m, 2H), 1.69-1.61 (m, 2H).

Example 131

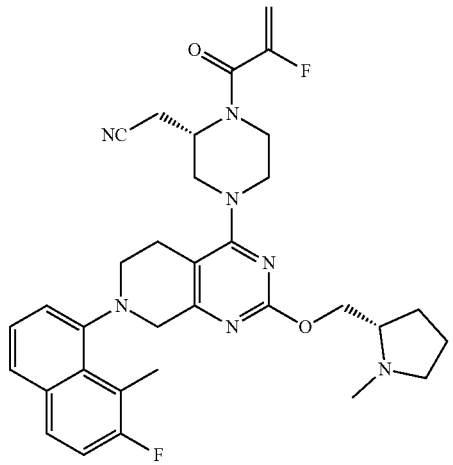 [SMILES: C=C(F)C(=O)N1CCN(c2nc(OC[C@@H]3CCCN3C)nc3c2CCN(c2cccc4ccc(F)c(C)c24)C3)C[C@@H]1CC#N]

313

2-((S)-4-(7-(7-fluoro-8-methylnaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile

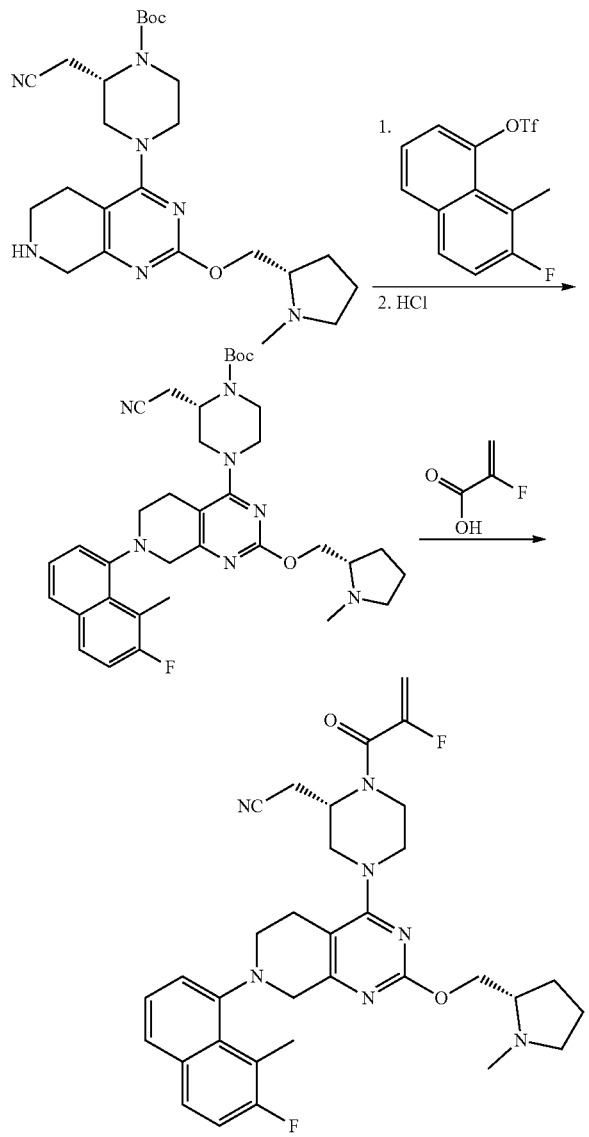

Step A

A mixture of tert-butyl (S)-2-(cyanomethyl)-4-(2-(((S)-1-methylpyrrolidin-2-yl)methoxy)-5,6,7,8-tetrahydropyrido[3,4-d]pyrimidin-4-yl)piperazine-1-carboxylate (335 mg, 1.09 mmol, 1.6 eq.), xantphos (78.5 mg, 136 μmol, 0.2 eq.), Xantphos Pd G3 (129 mg, 136 μmol, 0.2 eq.), 4 Å molecular sieves (200 mg) and Cs$_2$CO$_3$ (553 mg, 1.70 mmol, 2.5 eq.) in toluene (10.0 mL) was was stirred at 100° C. for 16 h under nitrogen. The mixture was subsequently purified by Al$_2$O$_3$ column chromatography (petroleum ether/ethyl acetate=1:1 to ethyl acetate/methanol=10:1) followed by reversed-phase flash chromatography [water (0.1% formic acid)/acetonitrile] to afford tert-butyl (S)-2-(cyanomethyl)-4-(7-(7-fluoro-8-methylnaphthalen-1-yl)-2-(((S)-1-methyl-

314 pyrrolidin-2-yl)methoxy)-5,6,7,8-tetrahydropyrido[3,4-d]pyrimidin-4-yl)piperazine-1-carboxylate (287 mg, 437 μmol, 64.5% yield, 96% purity) as a yellow solid. LCMS [M+1]: 630.

$^1$H NMR (400 MHz, CDCl$_3$) δ=7.67 (ddd, J=2.0, 6.0, 8.4 Hz, 1H), 7.60 (t, J=8.4 Hz, 1H), 7.41-7.31 (m, 1H), 7.27-7.18 (m, 2H), 4.68-4.55 (m, 1H), 4.44-4.33 (m, 1H), 4.31-4.15 (m, 2H), 4.09-3.73 (m, 4H), 3.60-3.48 (m, 1H), 3.40-3.29 (m, 1H), 3.22-2.90 (m, 5H), 2.84 (d, J=3.2 Hz, 3H), 2.80-2.56 (m, 4H), 2.48 (d, J=3.6 Hz, 3H), 2.34-2.24 (m, 1H), 2.05-1.99 (m, 1H), 1.86-1.70 (m, 3H), 1.52 (s, 9H).

To a solution of tert-butyl (S)-2-(cyanomethyl)-4-(7-(7-fluoro-8-methylnaphthalen-1-yl)-2-(((S)-1-methylpyrrolidin-2-yl)methoxy)-5,6,7,8-tetrahydropyrido[3,4-d]pyrimidin-4-yl)piperazine-1-carboxylate (50.0 mg, 79.4 μmol, 1.0 eq.) in acetonitrile (2.0 mL) was added HCl in dioxane (4 M, 2.0 mL, 101 eq.) at 0° C. The mixture was stirred at 0° C. for 0.5 h and then was concentrated under reduced pressure at 40° C. To the residue was added saturated aqueous Na$_2$CO$_3$ (10 mL) and the aqueous layer was extracted with ethyl acetate (5 mL×3). The combined organic layer was dried over anhydrous Na$_2$SO$_4$ and filtered. The filtrate was concentrated at reduced pressure at 40° C. The residue was purified by prep-HPLC (basic conditions; column: Waters Xbridge 150*50 10 μm; mobile phase: [water (0.05% ammonia hydroxide v/v)—ACN]; B %: 50%-77%, 10 min) and lyophilized to give 2-((S)-4-(7-(7-fluoro-8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (14 mg, 26.4 μmol, 33.3% yield, 99.9% purity) as a yellow solid. LCMS [M+1]: 530.

$^1$H NMR (400 MHz, CDCl$_3$) δ=7.67 (dd, J=6.0, 8.8 Hz, 1H), 7.63-7.58 (m, 1H), 7.36 (dt, J=4.4, 7.6 Hz, 1H), 7.23 (t, J=8.8 Hz, 2H), 4.39 (ddd, J=4.8, 10.8, 11.6 Hz, 1H), 4.23 (dd, J=6.4, 18.0 Hz, 1H), 4.14 (td, J=7.2, 10.4 Hz, 1H), 4.08-3.90 (m, 1H), 3.90-3.71 (m, 2H), 3.59-3.44 (m, 1H), 3.39-3.21 (m, 1H), 3.21-2.88 (m, 7H), 2.88-2.83 (m, 3H), 2.73-2.62 (m, 1H), 2.61-2.51 (m, 3H), 2.47 (d, J=2.8 Hz, 3H), 2.33-2.23 (m, 1H), 2.11-2.00 (m, 1H), 1.90-1.75 (m, 3H).

Step B

A mixture of 2-((S)-4-(7-(7-fluoro-8-methylnaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (80.0 mg, 151 μmol, 1.0 eq), 4 Å molecular sieves (50.0 mg) and 2-fluoroprop-2-enoic acid (40.8 mg, 453 μmol, 3.0 eq.) in ethyl acetate (3.0 mL) was stirred at 0° C. for 10 min. To this mixture was added TEA (61.1 mg, 604 μmol, 84.1 μL, 4.0 eq.) and T3P (384 mg, 604 μmol, 359 μL, 50% purity in EtOAc, 4.0 eq.) at 0° C. The mixture was stirred at 0° C. for 20 min and subsequently the mixture was quenched with saturated aqueous NH$_4$Cl aqueous solution (100 mL). The aqueous layer was extracted with ethyl acetate (60 mL×3) and the combined organic layer was dried over anhydrous Na$_2$SO$_4$, filtered and concentrated. The residue was purified by prep-HPLC (basic conditions; column: Xtimate C18 150*25 mm*5 μm; mobile phase: [water (0.05% ammonia hydroxide v/v)—ACN]; B %: 57%-87%, 10 min) and lyophilized to afford 2-((S)-4-(7-(7-fluoro-8-methylnaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (31 mg, 51.2 μmol, 33.9% yield, 99.4% purity) as an off-white solid. LCMS [M+1]: 602.

SFC conditions: Column: Chiralcel OJ-3 50×4.6 mm I.D., 3 μm; Mobile phase: methanol (0.05% DEA) in CO$_2$ from 5% to 40%; Flow rate: 3 mL/min; Wavelength: 220 nm.

$^1$H NMR (400 MHz, CDCl$_3$) δ=7.67 (dd, J=6.4, 8.8 Hz, 1H), 7.61 (t, J=8.0 Hz, 1H), 7.41-7.31 (m, 1H), 7.27-7.18 (m, 2H), 5.53-5.33 (m, 1H), 5.26 (dd, J=3.6, 16.8 Hz, 1H), 5.09-4.52 (m, 1H), 4.42-4.33 (m, 1H), 4.31-4.20 (m, 1H), 4.19-4.10 (m, 2H), 4.10-3.87 (m, 2H), 3.87-3.72 (m, 1H), 3.71-3.23 (m, 3H), 3.23-2.94 (m, 5H), 2.93-2.86 (m, 1H), 2.85-2.82 (m, 3H), 2.72-2.56 (m, 2H), 2.47 (d, J=3.2 Hz, 3H), 2.34-2.22 (m, 1H), 2.10-1.99 (m, 1H), 1.88-1.74 (m, 3H).

Following the teachings of the General Reaction Schemes, Examples 130 & 131 and the exemplary intermediates provided herein, Examples 132-137 were synthesized as shown in Table 3.

TABLE 3

Characterization of EXAMPLES 132-137

| Ex. # | Structure | Spectral Data |
|---|---|---|
| 132 | 2-((R)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonnitrile | $^1$H NMR (400 MHz, CDCl$_3$) δ = 7.76 (br d, J = 8.0 Hz, 1H), 7.62 (br. t, J = 7.6 Hz, 1H), 7.53 (br d, J = 7.6 Hz, 1H), 7.49-7.40 (m, 1H), 7.34 (t, J = 7.6 Hz, 1H), 7.26-7.19 (m, 1H), 5.34 (br d, J = 6.0 Hz, 1H), 5.25 (br dd, J = 3.2, 16.8 Hz, 1H), 4.87 (br s, 1H), 4.51-4.34 (m, 2H), 4.21-4.01 (m, 3H), 4.00-3.74 (m, 2H), 3.68-3.36 (m, 2H), 3.31-3.00 (m, 5H), 2.94-2.53 (m, 4H), 2.48 (d, J = 3.6 Hz, 3H), 2.28 (m, 1H), 2.12-2.00 (m, 1H), 1.91-1.69 (m, 3H). LCMS [M + 1]: 604. |
| 133 | 2-((S)-4-(7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.72-7.64 (m, 1H), 7.53 (t, J = 7.2 Hz, 1H), 7.35 (td, J = 7.8, 13.2 Hz, 1H), 7.28-7.20 (m, 2H), 5.44-5.26 (m, 1H), 5.18 (dd, J = 3.6, 16.8 Hz, 1H), 4.92-4.60 (m, 1H), 4.41-4.25 (m, 2H), 4.14-3.91 (m, 3H), 3.88-3.70 (m, 2H), 3.54-3.31 (m, 2H), 3.26-2.97 (m, 5H), 2.86-2.66 (m, 2H), 2.65-2.47 (m, 2H), 2.40 (d, J = 2.0 Hz, 3H), 2.28-2.14 (m, 1H), 2.06-1.93 (m, 1H), 1.82-1.66 (m, 3H). LCMS [M + 1]: 622. |

TABLE 3-continued

Characterization of EXAMPLES 132-137

| Ex. # | Structure | Spectral Data |
|---|---|---|
| 134 | 2-((S)-4-(7-(6,7-difluoroisoquinolin-4-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 8.95 (s, 1H), 8.28 (s, 1H), 7.88 (dd, J = 7.6, 11.1 Hz, 1H), 7.74 (dd, J = 8.0, 10.0 Hz, 1H), 5.53-5.34 (m, 1H), 5.27 (dd, J = 3.6, 16.8 Hz, 1H), 5.05-4.70 (m, 1H), 4.48-4.37 (m, 1H), 4.28 (s, 2H), 4.25-4.09 (m, 3H), 4.02 (br d, J = 13.6 Hz, 1H), 3.57-3.44 (m, 2H), 3.43-3.33 (m, 2H), 3.20-3.08 (m, 2H), 2.98 (br dd, J = 8.4, 16.8 Hz, 2H), 2.90-2.70 (m, 3H), 2.52 (s, 3H), 2.38-2.28 (m, 1H), 2.13-2.02 (m, 1H), 1.89-1.75 (m, 3H). LCMS [M + 1]: 607. |
| 135 | 2-((S)-4-(7-(2,3-dihydro-1H-inden-4-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.14 (t, J = 7.6 Hz, 1H), 6.97 (d, J = 7.2 Hz, 1H), 6.79 (d, J = 7.6 Hz, 1H), 5.55-5.33 (m, 1H), 5.26 (dd, J = 3.6, 17.2 Hz, 1H), 5.10-4.58 (m, 1H), 4.38 (dd, J = 5.2, 10.4 Hz, 1H), 4.34-3.99 (m, 5H), 3.95 (br d, J = 13.2 Hz, 1H), 3.70-3.15 (m, 4H), 3.14-3.01 (m, 2H), 3.01-2.87 (m, 5H), 2.86-2.73 (m, 3H), 2.70-2.59 (m, 1H), 2.49 (s, 3H), 2.29 (dt, J = 7.2, 9.6 Hz, 1H), 2.12-2.00 (m, 3H), 1.90-1.71 (m, 3H). LCMS [M + 1]: 560. |

TABLE 3-continued

Characterization of EXAMPLES 132-137

| Ex. # | Structure | Spectral Data |
|---|---|---|
| 136 | 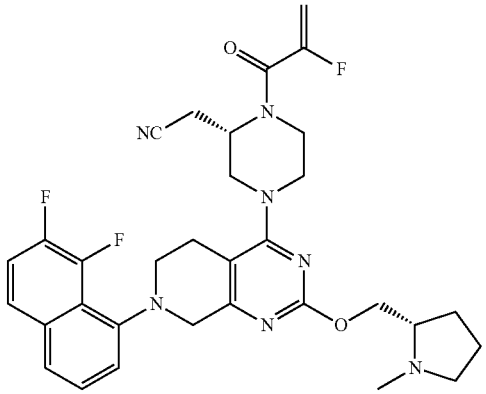<br>2-((S)-4-(7-(7,8-difluoronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.61 (br dd, J = 5.2, 7.6 Hz, 1H), 7.54 (d, J = 8.0 Hz, 1H), 7.44-7.32 (m, 2H), 7.18 (br s, 1H), 5.52-5.35 (m, 1H), 5.26 (dd, J = 3.6, 17.2 Hz, 1H), 4.88 (br s, 1H), 4.53-3.81 (m, 7H), 3.70 (br s, 1H), 3.49-2.80 (m, 8H), 2.75-2.56 (m, 2H), 2.50 (s, 3H), 2.35-2.27 (m, 1H), 2.13-2.02 (m, 1H), 1.82-1.72 (m, 3H). LCMS [M + 1]: 606.3. |
| 137 | 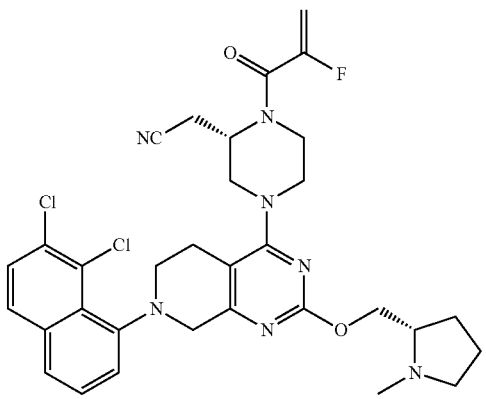<br>2-((S)-4-(7-(7,8-dichloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 8.17-8.07 (m, 1H), 7.57 (td, J = 8.0, 13.2 Hz, 1H), 7.45 (q, J = 8.0 Hz, 2H), 7.34-7.27 (m, 1H), 5.56-5.31 (m, 1H), 5.26 (dd, J = 3.6, 16.8 Hz, 1H), 4.86 (s, 1H), 4.47-4.32 (m, 2H), 4.24-3.99 (m, 3H), 3.95-3.34 (m, 4H), 3.33-2.98 (m, 5H), 2.95-2.37 (m, 7H), 2.29 (br d, J = 7.2 Hz, 1H), 2.11-1.99 (m, 1H), 1.91-1.66 (m, 3H). LCMS [M + 1]: 638.1. |

Example 138

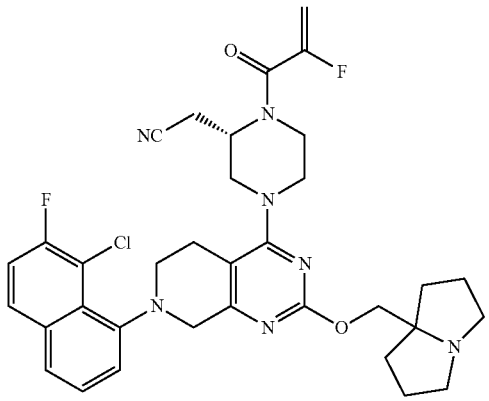 [SMILES: C=C(F)C(=O)N1CCN(c2nc(OCC34CCCN3CCC4)nc3c2CCN(c2cccc4ccc(F)c(Cl)c24)C3)C[C@@H]1CC#N]

(S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile

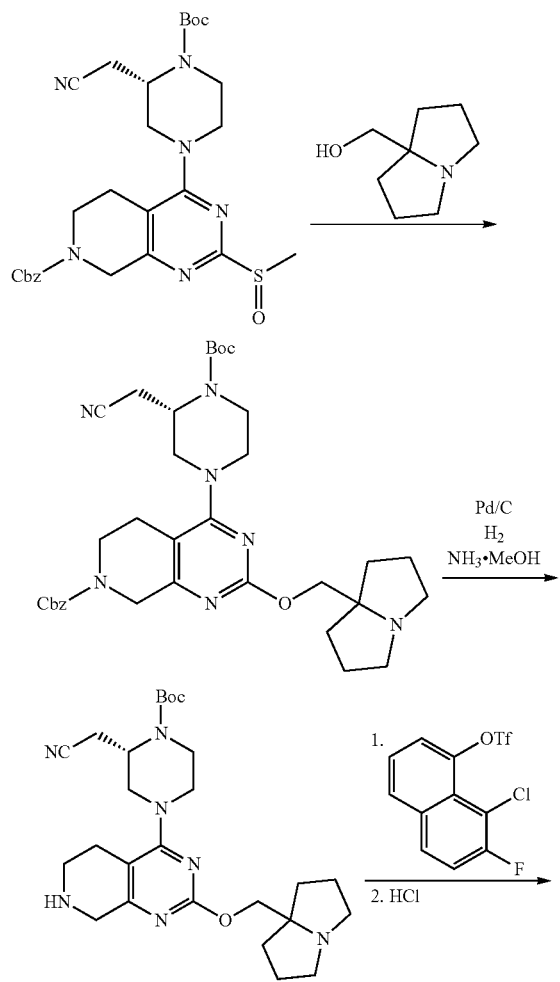

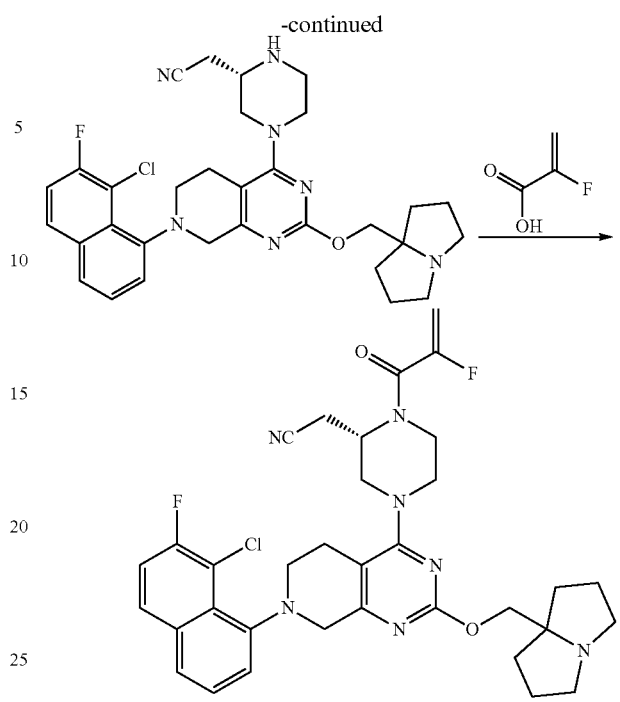

Step A

To a mixture of (tetrahydro-1H-pyrrolizin-7a(5H)-yl)methanol (1.34 g, 9.48 mmol) in THF (30 mL) was added NaH (474 mg, 11.9 mmol, 60% purity). After stirring at 15° C. for 0.5 hour, benzyl 4-((S)-4-(tert-butoxycarbonyl)-3-(cyanomethyl)piperazin-1-yl)-2-(methylsulfinyl)-5,8-dihydropyrido[3,4-d]pyrimidine-7(6H)-carboxylate (2.63 g, 4.74 mmol) in THF (20 mL) was added to the above mixture at 0° C. and the mixture was stirred at 0° C. for 1 hour. After completion, the mixture was quenched by $H_2O$ (65 mL) and separated. The aqueous phase was extracted with ethyl acetate (3×40 mL). Then the organic layer was washed with saturated brine (50 mL), dried over $Na_2SO_4$, filtered and concentrated under vacuum. The residue was purified by reversed phase flash [water (0.1% formic acid)/acetonitrile] to give benzyl (S)-4-(4-(tert-butoxycarbonyl)-3-(cyanomethyl)piperazin-1-yl)-2-((tetrahydro-1H-pyrrolizin-7a(5H)-yl)methoxy)-5,8-dihydropyrido[3,4-d]pyrimidine-7(6H)-carboxylate (1.9 g, 3.00 mmol, two steps 63% yield, >99.5% purity) as a brown solid. LCMS [M+1]: 632.
$^1$H NMR (400 MHz, $CDCl_3$) δ=7.43-7.30 (m, 5H), 5.18 (s, 2H), 4.69 (br d, J=19.2 Hz, 1H), 4.58 (br s, 1H), 4.45 (d, J=18.8 Hz, 1H), 4.09-3.74 (m, 6H), 3.49-3.36 (m, 1H), 3.31-3.04 (m, 4H), 3.03-2.90 (m, 1H), 2.81-2.55 (m, 6H), 2.07 (br s, 1H), 2.01 (br s, 1H), 1.90-1.81 (m, 4H), 1.69-1.62 (m, 2H), 1.51 (s, 9H), 1.27 (t, J=7.2 Hz, 1H).

Step B

To a mixture of benzyl (S)-4-(4-(tert-butoxycarbonyl)-3-(cyanomethyl)piperazin-1-yl)-2-((tetrahydro-1H-pyrrolizin-7a(5H)-yl)methoxy)-5,8-dihydropyrido[3,4-d]pyrimidine-7(6H)-carboxylate (1.90 g, 3.01 mmol, 1.0 eq) in MeOH (84 mL) was added Pd/C (190 mg, 10% purity) and $NH_3$-MeOH (12 mL, 40% purity in methanol). The mixture was stirred at 30° C. under 15 psi of $H_2$ for 2 hours. After completion, the reaction mixture was filtered through a pad of celite and concentrated in vacuum to give tert-butyl (S)-2-(cyanomethyl)-4-(2-((tetrahydro-1H-pyrrolizin-7a(5H)-yl)methoxy)-5,6,7,8-tetrahydropyrido[3,4-d]pyrimidin-4-yl)piperazine-1-carboxylate (1.42 g, 2.85 mmol, 95% yield, >99.5% purity) as a yellow solid and used into next step without further purification. LCMS [M+1]: 498.

Step C

To a mixture of tert-butyl (S)-2-(cyanomethyl)-4-(2-((tetrahydro-1H-pyrrolizin-7a(5H)-yl)methoxy)-5,6,7,8-tetrahydropyrido[3,4-d]pyrimidin-4-yl)piperazine-1-carboxylate (1.25 g, 2.51 mmol, 1.0 eq), 8-chloro-7-fluoronaphthalen-1-yl trifluoromethanesulfonate (1.24 g, 3.77 mmol, 1.5 eq), 4 Å molecular sieves (600 mg), RuPhos (234 mg, 502 μmol, 0.2 eq) and $Cs_2CO_3$ (2.46 g, 7.54 mmol, 3 eq) in toluene (25 mL) was added $Pd_2(dba)_3$ (230 mg, 251 μmol, 0.1 eq) under $N_2$. The mixture was de-gassed and then heated to 95° C. for 6 hours under $N_2$. After completion, the mixture was filtered. Then the mixture was diluted with ethyl acetate (10 mL) and water (25 mL) then separated. The aqueous phase was extracted with ethyl acetate (1×15 mL). Then the organic layer was washed with saturated brine (20 mL), dried over $Na_2SO_4$, filtered and concentrated under vacuum. The residue was purified by column chromatography ($SiO_2$, petroleum ether/ethyl acetate=1/1) and reversed phase flash [water (0.1% formic acid)/acetonitrile] to give tert-butyl (S)-4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-2-(cyanomethyl)piperazine-1-carboxylate (0.95 g, 1.40 mmol, 56% yield, 99.6% purity) as a brown solid. LCMS [M+1, M/2+1]: 676, 339.

$^1$H NMR (400 MHz, $CDCl_3$) δ=7.77-7.71 (m, 1H), 7.60 (t, J=8.0 Hz, 1H), 7.46-7.36 (m, 1H), 7.35-7.28 (m, 1H), 7.23 (d, J=7.6 Hz, 1H), 4.61 (br s, 1H), 4.46-4.33 (m, 1H), 4.03 (br s, 4H), 3.99-3.80 (m, 2H), 3.59-3.49 (m, 1H), 3.35 (br dd, J=3.6, 14.0 Hz, 1H), 3.27-2.50 (m, 11H), 2.16-2.06 (m, 2H), 1.88 (br d, J=5.2 Hz, 4H), 1.72-1.63 (m, 2H), 1.52 (s, 9H).

To a mixture of tert-butyl (S)-4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-2-(cyanomethyl)piperazine-1-carboxylate (50.0 mg, 73.9 μmol, 1.0 eq) in acetonitrile (0.5 mL) was added HCl (4 M in dioxane, 1.00 mL, 54 eq). The mixture was stirred at 15° C. for 0.5 hour. After completion, the mixture was concentrated under vacuum. Then the pH value was adjusted to 9 with saturated $Na_2CO_3$ solution (1 mL) and the mixture was washed with methanol (2×5 mL), filtered and concentrated under vacuum. The residue was purified by prep-HPLC (column: Waters Xbridge 150*25 mm*5 um; mobile phase: [water (10 mM $NH_4HCO_3$)—ACN]; B %: 30%-60%, 10 min) to give (S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (21.3 mg, 36.9 μmol, 49.96% yield, >99.5%) as an off-white solid. LCMS [M+1, M/2+1]: 576, 289.

$^1$H NMR (400 MHz, $CDCl_3$) δ=7.78-7.71 (m, 1H), 7.63-7.57 (m, 1H), 7.42 (q, J=6.8 Hz, 1H), 7.35-7.28 (m, 1H), 7.24 (br s, 1H), 4.39 (br dd, J=6.4, 17.8 Hz, 1H), 4.10-4.00 (m, 2H), 3.95-3.81 (m, 2H), 3.79-3.27 (m, 2H), 3.25-3.01 (m, 7H), 2.99-2.82 (m, 2H), 2.69-2.44 (m, 5H), 2.15-2.02 (m, 2H), 1.89-1.81 (m, 4H), 1.69-1.59 (m, 2H).

Step D

To a mixture of (S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (534 mg, 927 μmol, 1.0 eq), 2-fluoroprop-2-enoic acid (167 mg, 1.85 mmol, 2.0 eq), DIEA (4.80 g, 3.71 mmol, 646 μL, 4.0 eq) and 4 Å molecular sieves (250 mg) in dichloromethane (10 mL) was added HATU (705 mg, 1.85 mmol, 2.0 eq) at 0° C. The mixture was stirred at 0° C. for 0.5 hour. After completion, the mixture was filtered. Then the mixture was diluted with dichloromethane (5 mL) and water (10 mL) then separated. The aqueous phase was extracted with dichloromethane (2×10 mL). Then the organic layer was washed with saturated brine (15 mL), dried over $Na_2SO_4$, filtered and concentrated under vacuum. The residue was purified by prep-HPLC (column: WelchXtimate C18 100*25 mm*3 um; mobile phase: [water (0.04% $NH_3H_2O$)—ACN]; B %: 30%-60%, 11 min) to give (S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile (272 mg, 414.20 μmol, 45% yield, 98.7% purity) as a brown solid. LCMS [M+1, M/2+1]: 648, 325.

SFC conditions: Chiralcel OD-3 50×4.6 mm I.D., 3 um; Mobile phase: Phase A for $CO_2$, and Phase B for MeOH+ACN (0.05% DEA); Gradient elution: 50% MeOH+ACN (0.05% DEA) in $CO_2$; Flow rate: 3 mL/min; Wavelength: 220 nm; Column Temp: 35C; Back Pressure: 100 Bar.

$^1$H NMR (400 MHz, $CDCl_3$) δ=7.74-7.68 (m, 1H), 7.59-7.53 (m, 1H), 7.43-7.35 (m, 1H), 7.29 (s, 1H), 7.26-7.21 (m, 1H), 5.42-5.15 (m, 2H), 4.98-4.60 (m, 1H), 4.43-4.17 (m, 4H), 4.16-3.91 (m, 2H), 3.84 (br t, J=17.7 Hz, 1H), 3.53-3.35 (m, 4H), 3.26-3.00 (m, 4H), 2.97-2.75 (m, 4H), 2.63-2.49 (m, 1H), 2.25-2.10 (m, 2H), 1.99-1.96 (m, 4H), 1.86-1.74 (m, 2H).

Example 139

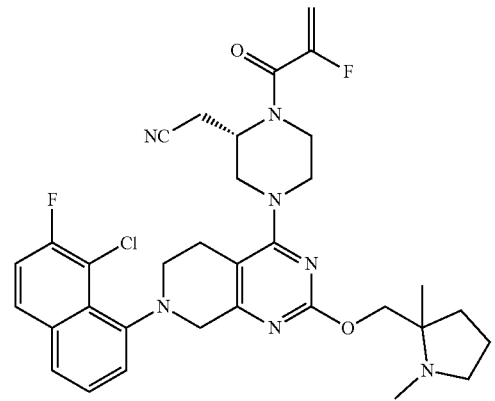 [SMILES: C=C(F)C(=O)N1CCN(c2nc(OCC3(C)CCCN3C)nc3c2CCN(c2cccc4ccc(F)c(Cl)c24)C3)C[C@@H]1CC#N]

325

2-((2S)-4-(7-(8-chloro-7-fluoronaphthalen-1-yl)-2-((1,2-dimethylpyrrolidin-2-yl)methoxy)-5,6,7,8-tetrahydropyrido[3,4-d]pyrimidin-4-yl)-1-(2-fluoroacryloyl)piperazin-2-yl)acetonitrile

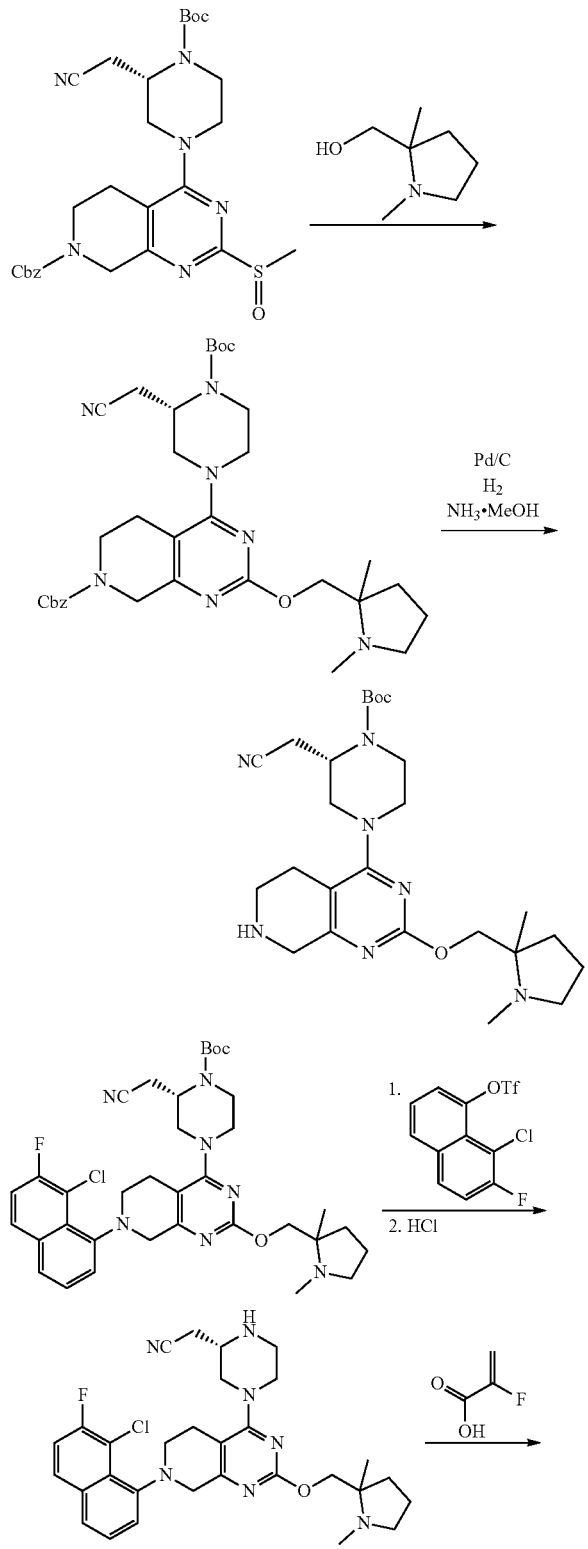

326

-continued

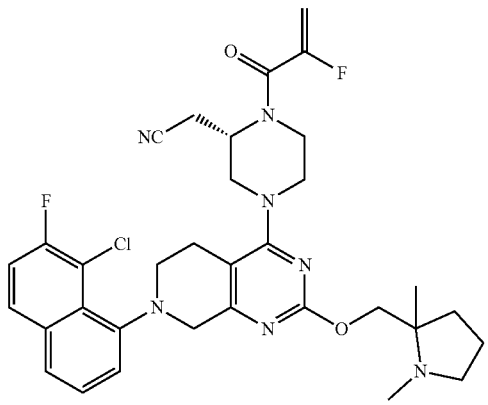 [SMILES: C=C(F)C(=O)N1CCN(c2nc(OCC3(C)CCCN3C)nc3c2CCN(c2cccc4ccc(F)c(Cl)c24)C3)C[C@@H]1CC#N]

Step A

To a mixture of (1,2-dimethylpyrrolidin-2-yl)methanol (512 mg, 3.97 mmol, 2.0 eq) in THF (20 mL) was added NaH (238 mg, 5.95 mmol, 60% purity, 3.0 eq). After stirring at 0° C. for 30 minutes, benzyl 4-((S)-4-(tert-butoxycarbonyl)-3-(cyanomethyl)piperazin-1-yl)-2-(methylsulfinyl)-5,8-dihydropyrido[3,4-d]pyrimidine-7(6H)-carboxylate (1.1 g, 1.98 mmol, 1 eq) in THF (10 mL) was added to the above mixture at 0° C. and the mixture was stirred at 0° C. for 1 hour. The reaction mixture was diluted with water (30 mL) and extracted with ethyl acetate (3×30 mL). The combined organic layers were washed with brine (30 mL), dried over Na$_2$SO$_4$, filtered and concentrated under reduced pressure. The residue was purified by column chromatography (SiO$_2$, petroleum ether/ethyl acetate=3/1 to 0/1) to give a residue which was further purified by reversed phase column chromatography [water (0.1% formic acid)/acetonitrile)] to give benzyl 4-((S)-4-(tert-butoxycarbonyl)-3-(cyanomethyl)piperazin-1-yl)-2-((1,2-dimethylpyrrolidin-2-yl)methoxy)-5,8-dihydropyrido[3,4-d]pyrimidine-7(6H)-carboxylate (410 mg, 33% yield, 99.2% purity) as a yellow solid.

Step B

To a solution of 4-((S)-4-(tert-butoxycarbonyl)-3-(cyanomethyl)piperazin-1-yl)-2-((1,2-dimethylpyrrolidin-2-yl)methoxy)-5,8-dihydropyrido[3,4-d]pyrimidine-7(6H)-carboxylate (390 mg, 629 μmol, 1.0 eq) in methanol (8.0 mL) was added dry Pd/C (50 mg, 10% purity) and NH$_3$-MeOH (4.0 mL, 20% purity) under N$_2$. The suspension was degassed under vacuum and purged with H$_2$ several times. The mixture was stirred under H$_2$ (15 psi) at 15° C. for 1 hour. The suspension was filtered through a pad of celite and the pad was washed with ethanol (3×15 mL). The combined filtrates were concentrated to give tert-butyl (2S)-2-(cyanomethyl)-4-(2-(1,2-dimethylpyrrolidin-2-yl)methoxy)-5,6,7,8-tetrahydropyrido[3,4-d]pyrimidin-4-yl)piperazine-1-carboxylate (220 mg, 70% yield, 96.7% purity) as a white solid. LCMS [M+1]: 486.

Step C

To a mixture of tert-butyl (2S)-2-(cyanomethyl)-4-(2-(1,2-dimethylpyrrolidin-2-yl)methoxy)-5,6,7,8-tetrahydropyrido[3,4-d]pyrimidin-4-yl)piperazine-1-carboxylate (200 mg, 412 μmol, 1.0 eq), (8-chloro-7-fluoro-1-naphthyl)trifluoromethanesulfonate (203 mg, 618 μmol, 1.5 eq), 4 Å molecular sieves (100 mg), RuPhos (38.4 mg, 82.4 μmol, 0.2 eq) and $Cs_2CO_3$ (402 mg, 1.24 mmol, 3.0 eq) in toluene (4.0 mL) was added $Pd_2(dba)_3$ (37.7 mg, 41.2 μmol, 0.1 eq) under $N_2$. The mixture was de-gassed and then heated to 95° C. for 6 hours under $N_2$. The reaction mixture was diluted with water (10 mL) and extracted with ethyl acetate (3×10 mL). The combined organic layers were washed with brine (20 mL), dried over $Na_2SO_4$, filtered and concentrated under reduced pressure. The residue was purified by column chromatography ($SiO_2$, petroleum ether/ethyl acetate=I/O to 20/1). The residue was purified by reversed phase flash column chromatography [water (0.1% formic acid)/acetonitrile)] to give tert-butyl (2S)-4-(7-(8-chloro-7-fluoronaphthalen-1-yl)-2-((1,2-dimethylpyrrolidin-2-yl)methoxy)-5,6,7,8-tetrahydropyrido[3,4-d]pyrimidin-4-yl)-2-(cyanomethyl)piperazine-1-carboxylate (120 mg, 36% yield, 81.8% purity) as a yellow solid. LCMS [M+1]: 664.

To a solution of tert-butyl (2S)-4-(7-(8-chloro-7-fluoronaphthalen-1-yl)-2-(1,2-dimethylpyrrolidin-2-yl)methoxy)-5,6,7,8-tetrahydropyrido[3,4-d]pyrimidin-4-yl)-2-(cyanomethyl)piperazine-1-carboxylate (60 mg, 90.3 μmol, 1.0 eq) in acetonitrile (1.0 mL) was added HCl (4M in dioxane, 2.0 mL) at 0° C., the mixture was stirred at 0° C. for 30 minutes. The reaction mixture was diluted with water (20 mL) and extracted with ethyl acetate (3×30 mL). The combined organic layers were washed with brine (30 mL), dried over $Na_2SO_4$, filtered and concentrated under reduced pressure. The residue was purified by prep-HPLC (column: Waters×bridge 150*25 mm*5 μm; mobile phase: [water (0.05% ammonia hydroxide v/v)—ACN]; B %: 48%-68%, 10 min). The desired fractions were collected and concentrated under vacuum to remove all volatiles. The mixture was lyophilized to give 2-((2S)-4-(7-(8-chloro-7-fluoronaphthalen-1-yl)-2-((1,2-dimethylpyrrolidin-2-yl)methoxy)-5,6,7,8-tetrahydropyrido[3,4-d]pyrimidin-4-yl)piperazin-2-yl)acetonitrile (9.88 mg, 19% yield) as a white solid. LCMS [M+1]: 564.

$^1$H NMR (400 MHz, $CDCl_3$) δ=7.75 (dd, J=5.6, 8.8 Hz, 1H), 7.60 (d, J=8.0 Hz, 1H), 7.42 (td, J=1.9, 7.8 Hz, 1H), 7.35-7.28 (m, 1H), 7.27-7.24 (m, 1H), 4.39 (br d, J=17.6 Hz, 1H), 4.31-4.00 (m, 2H), 3.97-3.80 (m, 2H), 3.80-3.69 (m, 1H), 3.58-3.46 (m, 1H), 3.40-2.84 (m, 8H), 2.79-2.64 (m, 1H), 2.61-2.48 (m, 3H), 2.44 (br s, 3H), 2.14-1.98 (m, 1H), 1.94-1.79 (m, 3H), 1.17 (s, 3H).

Step D

To a solution of 2-((2S)-4-(7-(8-chloro-7-fluoronaphthalen-1-yl)-2-((1,2-dimethylpyrrolidin-2-yl)methoxy)-5,6,7,8-tetrahydropyrido[3,4-d]pyrimidin-4-yl)piperazin-2-yl)acetonitrile (60 mg, 106 μmol, 1.0 eq) and 2-fluoroprop-2-enoic acid (28.7 mg, 319 μmol, 3.0 eq) in ethyl acetate (1.0 mL) was added 4 Å molecular sieves (50 mg), $Et_3N$ (86.1 mg, 851 μmol, 118 μL, 8.0 eq), T3P (203 mg, 319 μmol, 190 μL, 50% purity in ethyl acetate, 3.0 eq). The mixture was stirred at 0° C. for 30 minutes. The reaction mixture was diluted with water (10 mL) and extracted with ethyl acetate (3×10 mL). The combined organic layers were washed with brine (10 mL), dried over $Na_2SO_4$, filtered and concentrated under reduced pressure. The residue was purified by prep-HPLC (column: Waters×bridge 150*25 mm*5 um; mobile phase: [water (10 mM $NH_4HCO_3$)—ACN]; B %: 42%-72%, 10 min). The desired fractions were collected and concentrated under vacuum to remove all volatiles. The mixture was then lyophilized to give 2-((2S)-4-(7-(8-chloro-7-fluoronaphthalen-1-yl)-2-((1,2-dimethylpyrrolidin-2-yl)methoxy)-5,6,7,8-tetrahydropyrido[3,4-d]pyrimidin-4-yl)-1-(2-fluoroacryloyl)piperazin-2-yl)acetonitrile (33.6 mg, 47% yield) as a yellow solid. LCMS [M+1]: 636.

SFC conditions: Column: Chiralpak IC-3 50×4.6 mm I.D., 3 um. Mobile phase: Phase A for $CO_2$, and Phase B for MeOH+ACN (0.05% DEA); Gradient elution: 60% MeOH+ACN (0.05% DEA) in $CO_2$. Flow rate: 3 mL/min; Wavelength: 220 nm. Column Temp: 35° C.; Back Pressure: 100 Bar.

$^1$H NMR (400 MHz, $CDCl_3$) δ=7.75-7.73 (m, 1H), 7.61 (t, J=6.8 Hz, 1H), 7.48-7.38 (m, 1H), 7.36-7.28 (m, 1H), 7.26-7.23 (m, 1H), 5.53-5.32 (m, 1H), 5.31-5.19 (m, 1H), 5.10-4.57 (m, 1H), 4.48-4.34 (m, 1H), 4.23-3.80 (m, 6H), 3.64-3.36 (m, 2H), 3.31-2.74 (m, 7H), 2.72-2.52 (m, 2H), 2.43-2.34 (m, 3H), 2.10-1.98 (m, 1H), 1.87-1.65 (m, 3H), 1.19-1.11 (m, 3H).

Following the teachings of the General Reaction Schemes, Examples 138 & 139 and the exemplary intermediates provided herein, Examples 140-146 were synthesized as shown in Table 4.

TABLE 4

Characterization of EXAMPLES 140-146

| Ex. # | Structure | Spectral Data |
| --- | --- | --- |
| 140 | (S)-2-(4-(7-(3-fluoro-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ 7.51-7.44 (m, 1H), 7.05 (d, J = 8.0 Hz, 1H), 6.99-6.91 (m, 1H), 5.51-5.32 (m, 1H), 5.26 (dd, J = 3.6, 16.8 Hz, 1H), 5.06-4.57 (m, 1H), 4.29-3.89 (m, 6H), 3.63-3.23 (m, 3H), 3.20-3.02 (m, 4H), 2.99-2.90 (m, 1H), 2.89-2.68 (m, 3H), 2.63 (td, J = 6.8, 10.0 Hz, 2H), 2.14-2.01 (m, 2H), 1.92-1.80 (m, 4H), 1.71-1.60 (m, 2H). LCMS [M + 1]: 632. |
| 141 | (S)-2-(4-(7-(3-chloro-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$ ): δ 7.42-7.36 (m, 1H), 7.27-7.24 (m, 1H), 7.18 (d, J = 8.0 Hz, 1H), 5.52-5.30 (m, 1H), 5.23 (dd, J = 3.6, 16.8 Hz, 1H), 5.03-4.65 (m, 1H), 4.57-4.15 (m, 4H), 4.11 (s, 2H), 4.00 (br d, J = 12.4 Hz, 1H), 3.69-3.34 (m, 4H), 3.30-3.03 (m, 4H), 2.96-2.68 (m, 5H), 2.27 (td, J = 6.4, 12.8 Hz, 2H), 2.14-1.97 (m, 4H), 1.90-1.81 (m, 2H). LCMS [M + 1]: 648. |

TABLE 4-continued

Characterization of EXAMPLES 140-146

| Ex. # | Structure | Spectral Data |
|---|---|---|
| 142 | (S)-2-(4-(7-(2,3-dimethylphenyl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.15-7.07 (m, 1H), 6.99-6.89 (m, 2H), 5.54-5.32 (m, 1H), 5.26 (dd, J = 3.6, 16.8 Hz, 1H), 5.06-4.72 (m, 1H), 4.13-4.01 (m, 5H), 4.01-3.94 (m, 1H), 3.68-3.25 (m, 2H), 3.23-3.02 (m, 5H), 3.00-2.90 (m, 1H), 2.89-2.69 (m, 3H), 2.63 (td, J = 6.8, 10.0 Hz, 2H), 2.28 (d, J = 13.6 Hz, 6H), 2.12-2.00 (m, 2H), 1.91-1.83 (m, 3H), 1.73-1.57 (m, 2H). LCMS [M + 1]: 574. |
| 143 | (S)-2-(4-(7-(8-bromonaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.84-7.76 (m, 2H), 7.67-7.60 (m, 1H), 7.45 (td, J = 7.6, 15.2 Hz, 1H), 7.31-7.27 (m, 1H), 7.25-7.20 (m, 1H), 5.53-5.32 (m, 1H), 5.31-5.21 (m, 1H), 5.04-4.56 (m, 1H), 4.49-4.35 (m, 1H), 4.18-3.97 (m, 4H), 3.95-3.81 (m, 1H), 3.80-3.66 (m, 1H), 3.62-3.37 (m, 2H), 3.33-3.01 (m, 6H), 3.01-2.69 (m, 2H), 2.68-2.51 (m, 3H), 2.14-1.99 (m, 2H), 1.94-1.75 (m, 4H), 1.74-1.66 (m, 2H). LCMS [M + 1]: 676. |

TABLE 4-continued

Characterization of EXAMPLES 140-146

| Ex. # | Structure | Spectral Data |
|---|---|---|
| 144 | 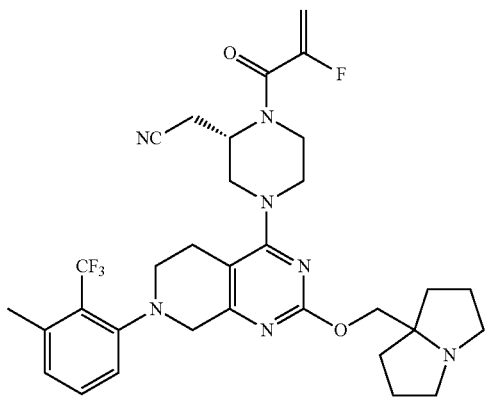<br><br>(S)-2-(1-(2-fluoroacryloyl)-4-(7-(3-methyl-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile | $^1$H NMR (400 MHz, CDCl$_3$): δ 7.38 (t, J = 7.6 Hz, 1H), 7.18 (d, J = 8.0 Hz, 1H), 7.07 (d, J = 7.6 Hz, 1H), 5.52-5.33 (m, 1H), 5.26 (br dd, J = 3.6, 16.8 Hz, 1H), 5.06-4.68 (m, 1H), 4.18-4.03 (m, 5H), 3.96 (br d, J = 12.4 Hz, 1H), 3.79-3.21 (m, 3H), 3.20-2.99 (m, 5H), 2.98-2.77 (m, 3H), 2.77-2.60 (m, 3H), 2.52 (q, J = 3.6 Hz, 3H), 2.16-2.04 (m, 2H), 1.94-1.81 (m, 4H), 1.74-1.62 (m, 2H). LCMS [M + 1]: 628. |
| 145 | 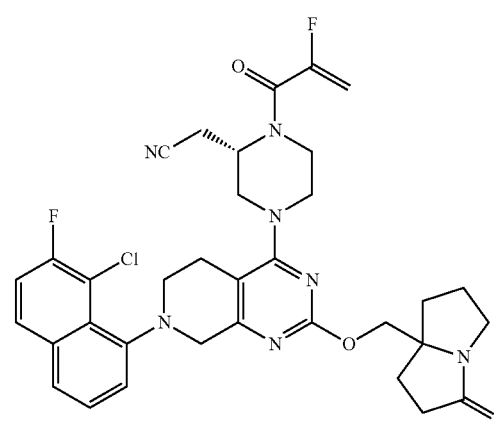<br><br>2-((2S)-4-(7-(8-chloro-7-fluoronaphthalen-1-yl)-2-((3-oxotetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ = 7.79-7.71 (m, 1H), 7.65-7.59 (m, 1H), 7.48-7.39 (m, 1H), 7.36-7.25 (m, 2H), 5.54-5.35 (m, 1H), 5.26 (dd, J = 3.6, 16.9 Hz, 1H), 4.85 (br s, 1H), 4.46-4.29 (m, 2H), 4.27-3.77 (m, 5H), 3.75-3.38 (m, 3H), 3.30-3.00 (m, 5H), 2.98-2.57 (m, 3H), 2.50-2.38 (m, 2H), 2.22-2.02 (m, 3H), 1.95 (q, J = 11.2 Hz, 1H), 1.70-1.59 (m, 2H). LCMS [M + 1]: 662. |

TABLE 4-continued

Characterization of EXAMPLES 140-146

| Ex. # | Structure | Spectral Data |
|---|---|---|
| 146 | (S)-2-(1-(2-fluoroacryloyl)-4-(7-(naphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile | $^1$H NMR (400 MHz, CDCl$_3$) δ 8.26-8.17 (m, 1H), 7.91-7.82 (m, 1H), 7.61 (d, J = 8.0 Hz, 1H), 7.54-7.47 (m, 2H), 7.43 (t, J = 8.0 Hz, 1H), 7.13 (d, J = 7.6 Hz, 1H), 5.56-5.33 (m, 1H), 5.27 (dd, J = 3.6, 16.8 Hz, 1H), 5.09-4.62 (m, 1H), 4.38-4.22 (m, 2H), 4.20-3.91 (m, 5H), 3.68-3.21 (m, 2H), 3.19-3.04 (m, 3H), 3.03-2.92 (m, 2H), 2.84 (br d, J = 11.2 Hz, 2H), 2.64 (td, J = 6.8, 10.0 Hz, 2H), 2.14-2.01 (m, 2H), 1.85 (qd, J = 6.4, 13.2 Hz, 4H), 1.68-1.61 (m, 2H). LCMS [M + 1]: 596. |

Example 147

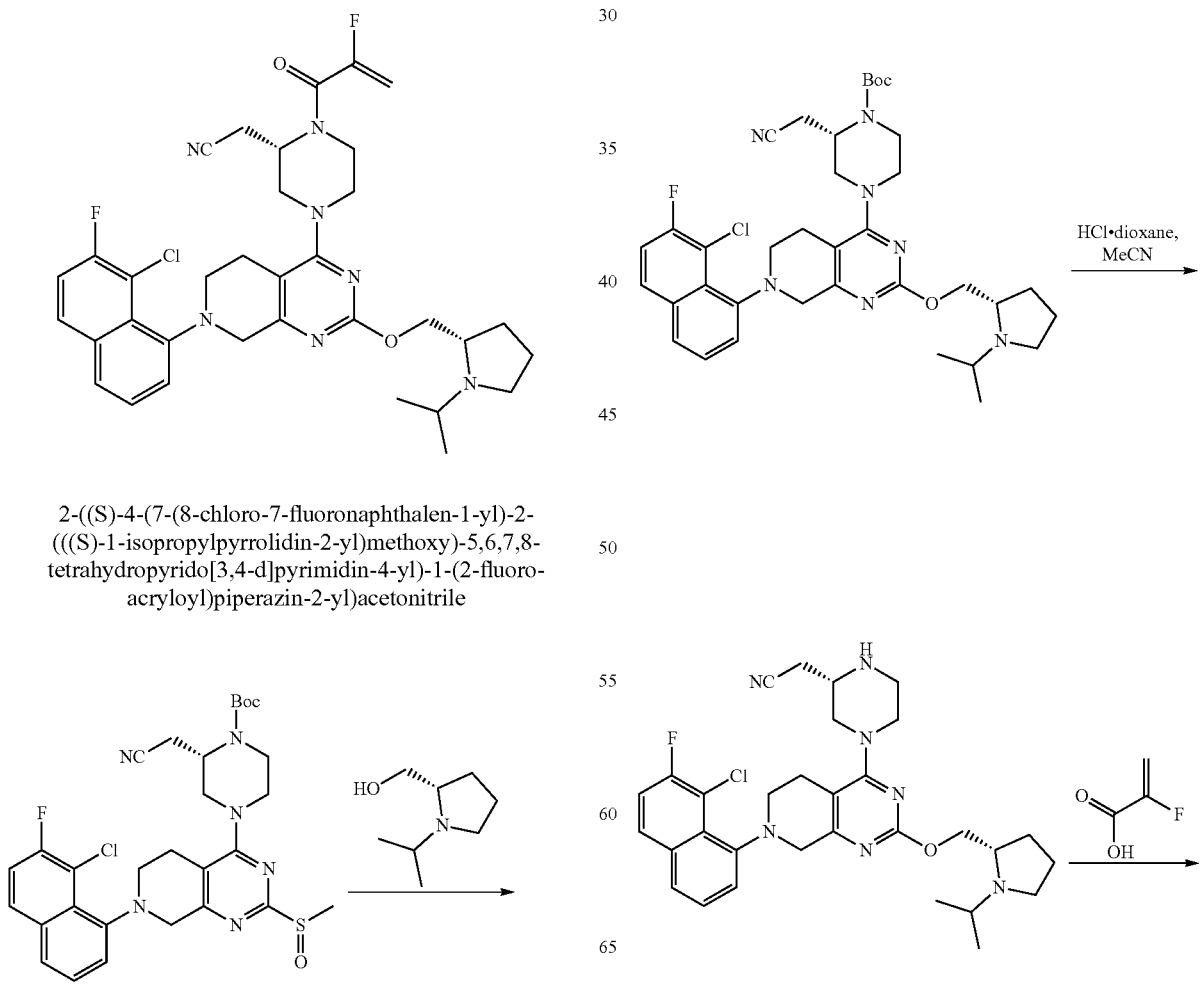

2-((S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)-1-(2-fluoroacryloyl)piperazin-2-yl)acetonitrile -continued

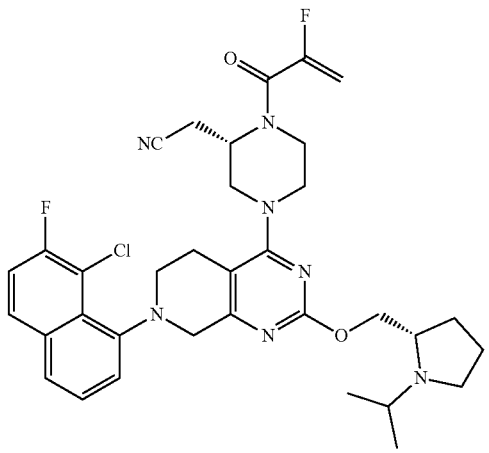 [SMILES: C=C(F)C(=O)N1CCN(c2nc(OC[C@@H]3CCCN3C(C)C)nc3c2CCN(c2cccc4ccc(F)c(Cl)c24)C3)C[C@@H]1CC#N]

Step A

To a solution of (S)-(1-isopropylpyrrolidin-2-yl)methanol, tBuONa (217 mg, 2.25 mmol, 3.0 eq) and 4 Å MS (500 mg) in toluene (10 mL) was added tert-butyl (2S)-4-(7-(8-chloro-7-fluoronaphthalen-1-yl)-2-(methyl sulfinyl)-5,6,7,8-tetrahydropyrido[3,4-d]pyrimidin-4-yl)-2-(cyanomethyl)piperazine-1-carboxylate (450 mg, 751 µmol, 1.0 eq) in toluene (3.0 mL) at 0° C. The reaction mixture was stirred at 0° C. for 10 min. Upon completion, the reaction mixture was diluted with ethyl acetate (20 mL) and water (8 mL). The mixture was separated. The organic layer was washed with brine (3×10 mL), dried over dried over anhydrous sodium sulfate, filtered and concentrated under vacuum, which was purified by reversed-phase flash [water (0.1% formic acid)/acetonitrile]. The fractions was concentrated under vacuum and basified by saturated NaHCO₃ (5 mL) and extracted with ethyl acetate (3×10 mL). The combined organic layers were dried over anhydrous sodium sulfate, filtered and concentrated under vacuum, to give tert-butyl (S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)-2-(cyanomethyl)piperazine-1-carboxylate (200 mg, 38% yield, 98% purity) as a yellow solid. LCMS [M+1]: 678.

$^1$H NMR (400 MHz, CDCl₃) δ 7.69-7.65 (m, 1H), 7.53 (t, J=8.8 Hz, 1H), 7.35 (td, J=7.6, 17.6 Hz, 1H), 7.28-7.20 (m, 2H), 4.61-4.48 (m, 1H), 4.38-4.25 (m, 1H), 4.23-4.15 (m, 1H), 4.02-3.70 (m, 5H), 3.54-3.42 (m, 1H), 3.34-2.78 (m, 9H), 2.70-2.58 (m, 1H), 2.54-2.36 (m, 2H), 1.85-1.65 (m, 4H), 1.45 (s, 9H), 1.07 (d, J=6.4 Hz, 3H), 0.99 (d, J=6.4 Hz, 3H).

Step B

To a solution of tert-butyl (S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)-2-(cyanomethyl)piperazine-1-carboxylate in MeCN (0.2 mL) was added HCl (4M in dioxane, 184 µL, 10 eq) at 25° C. The reaction mixture was stirred at 25° C. for 0.5 h. The reaction mixture was basified by saturated aq Na₂CO₃ to pH>8 and extracted with ethyl acetate (3×5 mL) and the combined organic layers were concentrated under vacuum, dried over anhydrous sodium sulfate, filtered and concentrated under vacuum to provide the crude material, which was purified by prep-HPLC (column: Waters Xbridge 150× 25 mm×5 µm; mobile phase: [water (10 mM NH₄HCO₃)-ACN]; B %: 40%-70%,10 min), followed by lyophilized, to give 2-((S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)piperazin-2-yl)acetonitrile (15.8 mg, 37% yield). White solid; LCMS [M+1]: 578.

$^1$H NMR (400 MHz, CDCl₃) δ 7.77-7.73 (m, 1H), 7.65-7.58 (m, 1H), 7.43 (dt, J=5.2, 7.6 Hz, 1H), 7.36-7.27 (m, 2H), 4.37 (dd, J=4.8, 17.6 Hz, 1H), 4.28 (ddd, J=4.0, 10.4, 16.4 Hz, 1H), 4.06-3.70 (m, 4H), 3.58-3.47 (m, 1H), 3.36-2.87 (m, 10H), 2.60-2.45 (m, 4H), 1.98-1.73 (m, 4H), 1.15 (dd, J=2.4, 6.4 Hz, 3H), 1.07 (d, J=6.4 Hz, 3H).

Step C

A reaction mixture of 2-((S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)piperazin-2-yl)acetonitrile (124 mg, 214 µmol, 1.0 eq), 4 Å MS (120 mg) and 2-fluoroprop-2-enoic acid (38.6 mg, 429 µmol, 2.0 eq) in ethyl acetate (4 mL) was stirred at 25° C. for 10 min. To the mixture was added TEA (407 mg, 4.03 mmol, 560 µL, 18.8 eq) and T3P (546 mg, 858 µmol, 510 µL, 50% purity, 4.0 eq) at 0° C. The reaction mixture was stirred at 25° C. for 0.5 hr. The reaction mixture was quenched by water (4 mL), and extracted with ethyl acetate (3×6 mL). The combined organic layers were dried over dried over anhydrous sodium sulfate, filtered and concentrated under vacuum to provide the crude material, which was purified by prep-HPLC (column: Waters Xbridge 150×25 mm×5 µm; mobile phase: [water (10 mM NH₄HCO₃)-ACN];B %: 47%-77%, 10 min), affording 2-((S)-4-(7-(8-chloro-7-fluoronaphthalen-1-yl)-2-(((S)-1-isopropylpyrrolidin-2-yl)methoxy)-5,6,7,8-tetrahydropyrido[3,4-d]pyrimidin-4-yl)-1-(2-fluoroacryloyl)piperazin-2-yl)acetonitrile (45.9 mg, 32% yield) as a yellow solid. LCMS [M+1]: 650.

$^1$H NMR (400 MHz, CDCl₃) δ 7.77-7.73 (m, 1H), 7.65-7.58 (m, 1H), 7.43 (dt, J=5.2, 7.6 Hz, 1H), 7.36-7.27 (m, 2H), 4.37 (dd, J=4.8, 17.6 Hz, 1H), 4.28 (ddd, J=4.0, 10.4, 16.4 Hz, 1H), 4.06-3.70 (m, 4H), 3.58-3.47 (m, 1H), 3.36-2.87 (m, 10H), 2.60-2.45 (m, 4H), 1.98-1.73 (m, 4H), 1.15 (dd, J=2.4, 6.4 Hz, 3H), 1.07 (d, J=6.4 Hz, 3H).

SFC conditions: Chiralcel OJ-3 50×4.6 mm I.D., 3 um, Mobile phase: Phase A for CO₂, and Phase B for MeOH (0.05% DEA); Gradient elution: MeOH (0.05% DEA) in CO₂ from 5% to 40%, Flow rate: 3 mL/min; Wavelength: 220 nm, Column Temp: 35C; Back Pressure: 100 Bar.

$^1$H NMR (400 MHz, CDCl₃) δ 7.77-7.73 (m, 1H), 7.65-7.58 (m, 1H), 7.46-7.38 (m, 1H), 7.35-7.27 (m, 2H), 5.53-5.33 (m, 1H), 5.26 (dd, J=3.6, 16.8 Hz, 1H), 5.03-4.71 (m, 1H), 4.46-4.33 (m, 1H), 4.32-4.24 (m, 1H), 4.15-3.81 (m, 5H), 3.63-3.50 (m, 1H), 3.48-3.37 (m, 1H), 3.31-2.75 (m, 9H), 2.65-2.47 (m, 2H), 1.94-1.73 (m, 4H), 1.14 (d, J=6.4 Hz, 3H), 1.07 (d, J=6.4 Hz, 3H).

Example 148

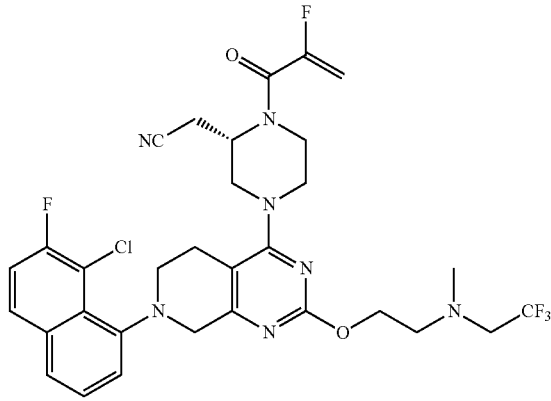 [SMILES: C=C(F)C(=O)N1CCN(c2nc(OCCN(C)CC(F)(F)F)nc3c2CCN(c2cccc4ccc(F)c(Cl)c24)C3)C[C@@H]1CC#N]

(S)-2-(4-(7-(8-chloro-7-fluoronaphthalen-1-yl)-2-(2-(methyl(2,2,2-trifluoroethyl)amino)ethoxy)-5,6,7,8-tetrahydropyrido[3,4-d]pyrimidin-4-yl)-1-(2-fluoro-acryloyl)piperazin-2-yl)acetonitrile

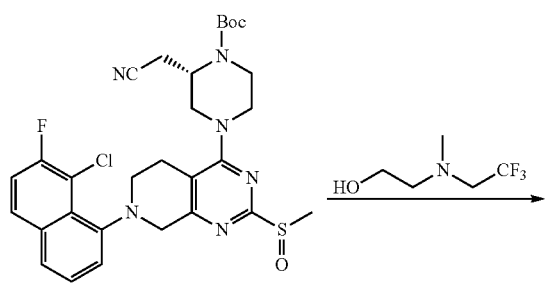

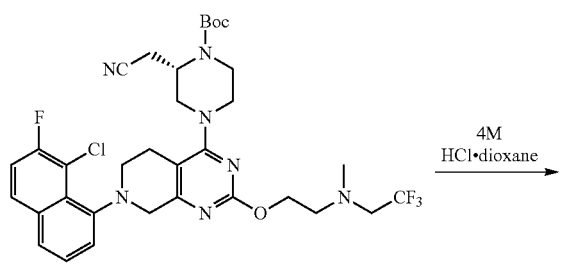

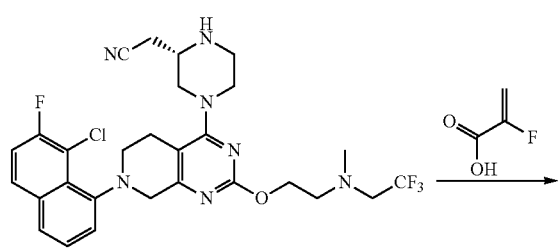

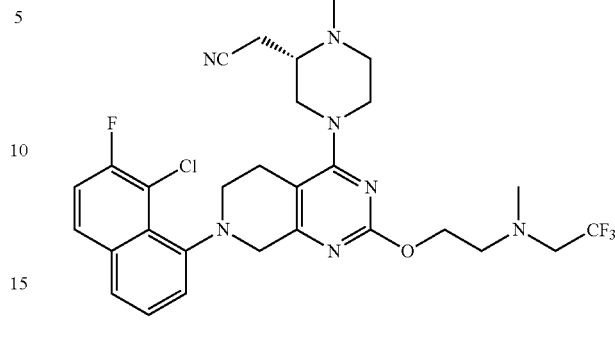

Step A

To a solution of 2-(methyl(2,2,2-trifluoroethyl)amino)ethan-1-ol (524 mg, 3.34 mmol, 4.0 eq) in toluene (10 mL) was added 4 Å molecular sieves (500 mg) at 15° C. The reaction mixture was stirred at 15° C. for 30 minutes. After this time, the reaction mixture was cooled to 0° C., and t-BuONa (481 mg, 5.01 mmol, 6.0 eq) was added followed by tert-butyl (2S)-4-(7-(8-chloro-7-fluoronaphthalen-1-yl)-2-(methyl sulfinyl)-5,6,7,8-tetrahydropyrido[3,4-d]pyrimidin-4-yl)-2-(cyanomethyl)piperazine-1-carboxylate (500 mg, 834 µmol, 1.0 eq) portionwise at 0° C. The reaction mixture was stirred at 0° C. for 1 hour. After completion, the reaction mixture was quenched with water (10 mL) at 0° C., diluted with ethyl acetate (20 mL) and separated. The aqueous layer was extracted with ethyl acetate (10 mL). The combined organic layers were dried over $Na_2SO_4$ and concentrated under reduced pressure. The residue was purified by reversed phased flash chromatography[water (0.1% formic acid)/acetonitrile] to give tert-butyl (S)-4-(7-(8-chloro-7-fluoronaphthalen-1-yl)-2-(2-(methyl (2,2,2-trifluoroethyl)amino)ethoxy)-5,6,7,8-tetrahydropyrido[3,4-d]pyrimidin-4-yl)-2-(cyanomethyl)piperazine-1-carboxylate (250 mg, 43% yield). Yellow solid; LCMS [M+1]: 692.

$^1$H NMR (400 MHz, $CDCl_3$) δ=7.79-7.72 (m, 1H), 7.61 (t, J=7.2 Hz, 1H), 7.43 (td, J=8.0, 14.0 Hz, 1H), 7.36-7.28 (m, 2H), 4.62 (br d, J=1.6 Hz, 1H), 4.45-4.33 (m, 3H), 4.11-3.77 (m, 4H), 3.56 (br dd, J=4.8, 11.2 Hz, 1H), 3.37 (br dd, J=3.6, 13.6 Hz, 1H), 3.30-2.87 (m, 9H), 2.82-2.67 (m, 2H), 2.56 (d, J=2.4 Hz, 3H), 1.52 (s, 9H).

Step B

To a solution of tert-butyl (S)-4-(7-(8-chloro-7-fluoronaphthalen-1-yl)-2-(2-(methyl (2,2,2-trifluoroethyl)amino)ethoxy)-5,6,7,8-tetrahydropyrido[3,4-d]pyrimidin-4-yl)-2-(cyanomethyl)piperazine-1-carboxylate (230 mg, 332 µmol, 1.0 eq) in MeCN (5 mL) was added HCl (4M in dioxane, 5 mL, 60 eq) at 15° C. The reaction mixture was stirred at 15° C. for 30 minutes, then concentrated under reduced pressure. The residue was diluted with ethyl acetate (15 mL), and aqueous $NaHCO_3$ (10 mL) then separated. The aqueous layer was extracted with ethyl acetate (15 mL), and the combined organic layers were dried over Na₂SO₄ and concentrated under reduced pressure. The residue was purified by prep-HPLC (column: Waters Xbridge 150*25 mm*5 μm; mobile phase: [water (0.05% ammonia hydroxide v/v)-ACN]; B %: 48%-75%, 10 min) then lyophilized to give (S)-2-(4-(7-(8-chloro-7-fluoronaphthalen-1-yl)-2-(2-(methyl(2,2,2-trifluoroethyl)amino)ethoxy)-5,6,7,8-tetrahydropyrido[3,4-d]pyrimidin-4-yl)piperazin-2-yl)acetonitrile (51.7 mg, 93% yield, 98.9% purity) as a white solid. LCMS [M+1]: 592.

¹H NMR (400 MHz, CDCl₃) δ=7.75 (dd, J=5.6, 8.8 Hz, 1H), 7.64-7.57 (m, 1H), 7.43 (dt, J=3.2, 8.0 Hz, 1H), 7.35-7.27 (m, 2H), 4.46-4.33 (m, 3H), 4.13-3.71 (m, 3H), 3.56-3.48 (m, 1H), 3.39-3.07 (m, 8H), 3.03 (t, J=6.0 Hz, 2H), 2.98-2.82 (m, 2H), 2.55 (s, 3H), 2.55-2.48 (m, 2H).

Step C

To a solution of (S)-2-(4-(7-(8-chloro-7-fluoronaphthalen-1-yl)-2-(2-(methyl (2,2,2-trifluoroethyl)amino)ethoxy)-5,6,7,8-tetrahydropyrido[3,4-d]pyrimidin-4-yl)piperazin-2-yl)acetonitrile (100 mg, 169 μmol, 1.0 eq) and 2-fluoroprop-2-enoic acid (45.6 mg, 507 μmol, 3.0 eq) in ethyl acetate (5 mL) was added 4 Å molecular sieves (100 mg) at 15° C. The reaction mixture was stirred at 15° C. for 0.5 hour. After this time the reaction was cooled to −40° C. and TEA (154 mg, 1.52 mmol, 211 μL, 9.0 eq) follow by T3P (430 mg, 676 μmol, 402 μL, 50% purity, 4.0 eq) were added to the mixture. The mixture was stirred at −40° C. for 30 minutes then quenched with water (3 mL) at 0° C., and extracted with ethyl acetate (5 mL×2). The combined organic layers were dried over Na₂SO₄ and concentrated under reduced pressure to dryness. The residue was purified by prep-HPLC (column: Waters Xbridge 150*25 mm*5 um; mobile phase: [water (0.05% ammonia hydroxide v/v)-ACN]; B %: 55%-80%, 10 min) then lyophilized to give (S)-2-(4-(7-(8-chloro-7-fluoronaphthalen-1-yl)-2-(2-(methyl(2,2,2-trifluoroethyl) amino)ethoxy)-5,6,7,8-tetrahydropyrido[3,4-d]pyrimidin-4-yl)-1-(2-fluoroacryloyl)piperazin-2-yl)acetonitrile (13.5 mg, 12% yield, 98.2% purity) as a white solid. LCMS [M+1]: 664.

SFC conditions: Cellucoat 50×4.6 mm I.D., 3 um, Mobile phase: Phase A for CO₂, and Phase B for MeOH (0.05% DEA); Gradient elution: 40% MeOH (0.05% DEA) in CO₂; Flow rate: 3 mL/min; Wavelength: 220 nm; Column Temp: 35° C.; Back Pressure: 100 Bar.

¹H NMR (400 MHz, CDCl₃) δ=7.75 (ddd, J=1.6, 5.6, 9.2 Hz, 1H), 7.61 (t, J=6.8 Hz, 1H), 7.43 (td, J=7.6, 12.0 Hz, 1H), 7.35-7.27 (m, 2H), 5.53-5.32 (m, 1H), 5.26 (dd, J=3.6, 16.8 Hz, 1H), 5.05-4.60 (m, 1H), 4.47-4.33 (m, 3H), 4.22-3.99 (m, 2H), 3.95-3.77 (m, 2H), 3.63-3.39 (m, 2H), 3.32-2.99 (m, 8H), 2.98-2.70 (m, 2H), 2.66-2.58 (m, 1H), 2.55 (s, 3H).

Following the teachings of the General Reaction Schemes, Examples 147 & 148 and the exemplary intermediates provided herein, Examples 149-205 were synthesized as shown in Table 5.

TABLE 5

Characterization of EXAMPLES 149-205.

| Ex. # | Structure | Spectral Data |
|---|---|---|
| 149 | (S)-2-(4-(7-(8-chloro-7-fluoronaphthalen-1-yl)-2-((2-methyl-2-azaspiro[3.3]heptan-6-yl)oxy)-5,6,7,8-tetrahydropyrido[3,4-d]pyrimidin-4-yl)-1-(2-fluoroacryloyl)piperazin-2-yl)acetonitrile | ¹H NMR (400 MHz, CDCl₃) δ = 7.77-7.71 (m, 1H), 7.63-7.57 (m, 1H), 7.47-7.38 (m, 1H), 7.35-7.24 (m, 2H), 5.52-5.33 (m, 1H), 5.25 (dd, J = 3.6, 16.8 Hz, 1H), 5.02 (td, J = 7.2, 9.6 Hz, 2H), 4.37 (dd, J = 14.4, 18.0 Hz, 1H), 4.16-3.97 (m, 2H), 3.92-3.75 (m, 2H), 3.60-3.36 (m, 2H), 3.28-3.14 (m, 6H), 3.13-2.99 (m, 2H), 2.93-2.75 (m, 2H), 2.71-2.50 (m, 3H), 2.37-2.23 (m, 5H). LCMS [M + 1]: 634. |

TABLE 5-continued

Characterization of EXAMPLES 149-205.

| Ex. # | Structure | Spectral Data |
|---|---|---|
| 150 | 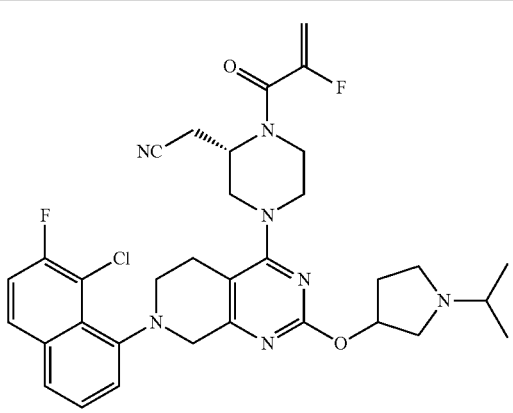<br>2-((2S)-4-(7-(8-chloro-7-fluoronaphthalen-1-yl)-2-((1-isopropylpyrrolidin-3-yl)oxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.61 (t, J = 7.6 Hz, 1H), 7.48-7.38 (m, 1H), 7.36-7.27 (m, 2H), 5.56-5.32 (m, 2H), 5.26 (dd, J = 3.6, 16.8 Hz, 1H), 5.11-4.56 (m, 1H), 4.45-4.33 (m, 1H), 4.15-3.98 (m, 2H), 3.95-3.37 (m, 4H), 3.30-3.00 (m ,5H), 2.94-2.53 (m, 6H), 2.49-2.25 (m, 2H), 2.11-1.97 (m, 1H), 1.11 (br d, J = 6.4 Hz, 6H). LCMS [M + 1]: 636. |
| 151 | 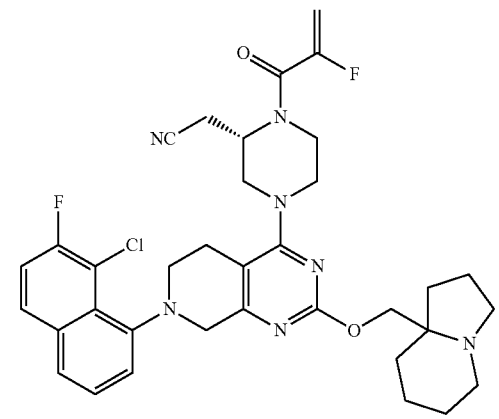<br>2-((2S)-4-(7-(8-chloro-7-fluoronaphthalen-1-yl)-2-((hexahydroindolizin-8a(1H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.73 (m, 1H), 7.64-7.58 (m, 1H), 7.47-7.38 (m, 1H), 7.36-7.22 (m, 2H), 5.54-5.32 (m, 1H), 5.31-5.19 (m, 1H), 5.08-4.61 (m, 1H), 4.59-4.48 (m, 1H), 4.47-4.36 (m, 1H), 4.20-3.99 (m, 3H), 3.96-3.61 (m, 2H), 3.56 (br d, J = 11.2 Hz, 1H), 3.52-3.32 (m, 1H), 3.30-3.02 (m, 5H), 3.02-2.73 (m, 5H), 2.64-2.51 (m, 1H), 2.10-1.95 (m, 1H), 1.94-1.78 (m, 3H), 1.67-1.54 (m, 4H), 1.49-1.33 (m, 2H). LCMS [M + H]: 662. |

TABLE 5-continued

Characterization of EXAMPLES 149-205.

| Ex. # | Structure | Spectral Data |
|---|---|---|
| 152 | 2-((2S)-4-(7-(8-chloro-7-fluoronaphthalen-1-yl)-2-((1-isopropylpiperidin-3-yl)oxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ = 7.75 (ddd, J = 2.4, 6.0, 8.8 Hz, 1H), 7.61 (t, J = 7.2 Hz, 1H), 7.47-7.38 (m, 1H), 7.37-7.28 (m, 2H), 7.25 (br d, J = 7.6 Hz, 1H), 5.53-5.32 (m, 1H), 5.25 (dd, J = 3.6, 16.8 Hz, 1H), 5.09-4.95 (m, 1H), 4.46-4.31 (m, 1H), 4.15-3.97 (m, 2H), 3.96-3.70 (m, 2H), 3.57 (br dd, J = 4.4, 11.6 Hz, 1H), 3.49-3.33 (m, 1H), 3.26-3.00 (m, 5H), 2.97-2.68 (m, 4H), 2.65-2.50 (m, 1H), 2.29-2.09 (m, 3H), 1.87-1.74 (m, 1H), 1.64 (br s, 1H), 1.57-1.29 (m, 2H), 1.11-0.99 (m, 6H). LCMS [M + 1]: 650. |
| 153 | 2-((S)-4-(7-(8-chloro-7-fluoronaphthalen-1-yl)-2-(((1S,2S)-2-(dimethylamino)cyclopentyl)oxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.81-7.70 (m, 1H), 7.67-7.56 (m, 1H), 7.49-7.39 (m, 1H), 7.37-7.23 (m, 2H), 5.53-5.34 (m, 1H), 5.34-5.20 (m, 2H), 5.12-4.53 (m, 1H), 4.45-4.30 (m, 1H), 4.17-3.97 (m, 2H), 3.96-3.61 (m, 2H), 3.60-3.53 (m, 1H), 3.51-3.33 (m, 1H), 3.33-2.67 (m, 7H), 2.64-2.53 (m, 1H), 2.39-2.24 (m, 6H), 2.18-2.07 (m, 1H), 2.06-1.94 (m, 1H), 1.85-1.74 (m, 3H), 1.60-1.47 (m, 1H); LCMS [M + 1]: 636. |

TABLE 5-continued

Characterization of EXAMPLES 149-205.

| Ex. # | Structure | Spectral Data |
|---|---|---|
| 154 | 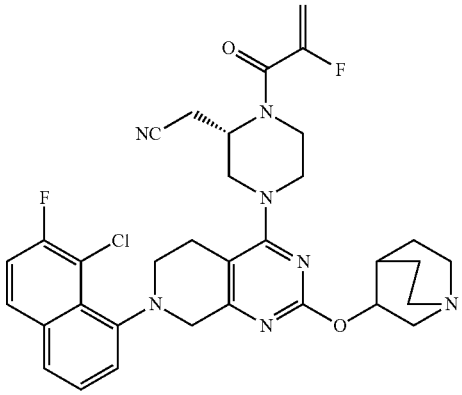<br>2-((2S)-4-(7-(8-chloro-7-fluoronaphthalen-1-yl)-2-(quinuclidin-3-yloxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.61 (t, J = 7.2 Hz, 1H), 7.48-7.38 (m, 1H), 7.35-7.30 (m, 1H), 7.27-7.23 (m, 1H), 5.52-5.33 (m, 1H), 5.26 (dd, J = 3.6, 16.8 Hz, 1H), 4.93 (dt, J = 4.0, 8.0 Hz, 1H), 4.47-4.33 (m, 1H), 4.20-3.97 (m, 2H), 3.96-3.79 (m, 2H), 3.57 (br dd, J = 4.4, 11.6 Hz, 1H), 3.50-3.40 (m, 1H), 3.34 (br dd, J = 8.4, 14.0 Hz, 1H), 3.25-2.97 (m, 5H), 2.92-2.76 (m, 5H), 2.65-2.55 (m, 1H), 2.24-2.17 (m, 1H), 2.10 (ddd, J = 2.8, 5.2, 10.4 Hz, 1H), 1.88-1.70 (m, 3H), 1.68-1.56 (m, 1H), 1.42 (br s, 1H). LCMS [M + 1]: 634. |
| 155 | 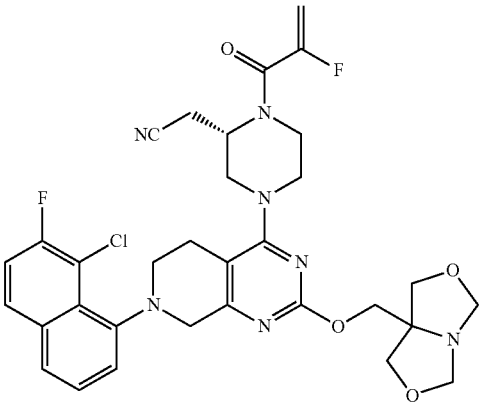<br>(S)-2-(4-(2-((1H,3H,5H-oxazolo[3,4-c]oxazol-7a(7H)-yl)methoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.76 (dd, J = 1.6, 5.6, 9.2 Hz, 1H), 7.62 (t, J = 6.8 Hz, 1H), 7.43 (td, J = 8.0, 12.4 Hz, 1H), 7.37-7.27 (m, 2H), 5.55-5.34 (m, 1H), 5.26 (dd, J = 3.6, 16.8 Hz, 1H), 5.05-4.71 (m, 1H), 4.54 (td, J = 2.8, 5.2 Hz, 2H), 4.49-4.43 (m, 2H), 4.43-4.32 (m, 3H), 4.30-4.14 (m, 1H), 4.14-3.97 (m, 2H), 3.97-3.80 (m, 5H), 3.69-3.38 (m, 2H), 3.32-3.01 (m, 4H), 2.99-2.70 (m, 2H), 2.68-2.55 (m, 1H); LCMS [M + 1]: 652. |

TABLE 5-continued

Characterization of EXAMPLES 149-205.

| Ex. # | Structure | Spectral Data |
|---|---|---|
| 156 | 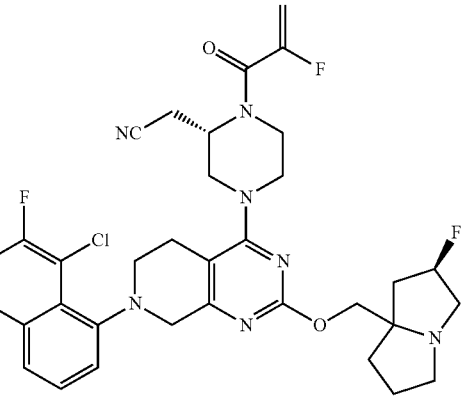<br>2-((2S)-4-(7-(8-chloro-7-fluoronaphthalen-1-yl)-2-((2R)-2-fluorotetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.64-7.57 (m, 1H), 7.47-7.38 (m, 1H), 7.36-7.24 (m, 2H), 5.52-5.17 (m, 3H), 5.07-4.70 (m, 1H), 4.45-4.24 (m, 2H), 4.20-4.01 (m, 3H), 3.98-3.62 (m, 2H), 3.60-3.37 (m, 3H), 3.28-3.00 (m, 8H), 2.69-2.53 (m, 3H), 2.19-2.08 (m, 1H), 1.98-1.79 (m, 4H). LCMS [M + 1]: 666. |
| 157 | 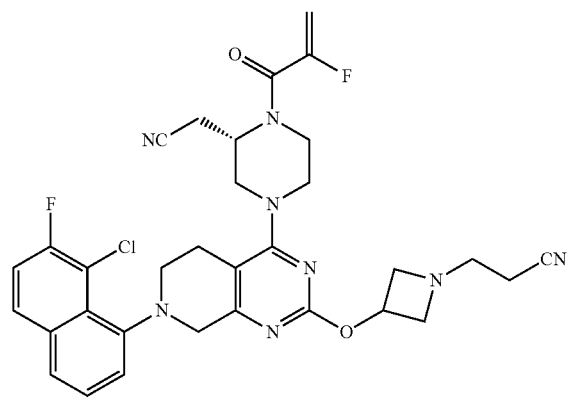<br>(S)-3-(3-((7-(8-chloro-7-fluoronaphthalen-1-yl)-4-(3-(cyanomethyl)-4-(2-fluoroacryloyl)piperazin-1-yl)-5,6,7,8-tetrahydropyrido[3,4-d]pyrimidin-2-yl)oxy)azetidin-1-yl)propanenitrile | $^1$H NMR (400 MHz, CDCl$_3$) δ 7.79-7.74 (m, 1H), 7.62 (t, J = 7.2 Hz, 1H), 7.48-7.39 (m, 1H), 7.36-7.27 (m, 2H), 5.53-5.34 (m, 1H), 5.30-5.18 (m, 2H), 5.05-4.66 (m, 1H), 7.38 (t, J = 17.2 Hz, 1H), 4.14-4.01 (m, 2H), 3.98-3.68 (m, 4H), 3.60-3.39 (m, 2H), 3.33-3.03 (m, 6H), 2.97-2.70 (m, 4H), 2.64-2.56 (m, 1H), 2.44-2.38 (m, 2H). LCMS [M + 1]: 633. |

TABLE 5-continued

Characterization of EXAMPLES 149-205.

| Ex. # | Structure | Spectral Data |
|---|---|---|
| 158 | 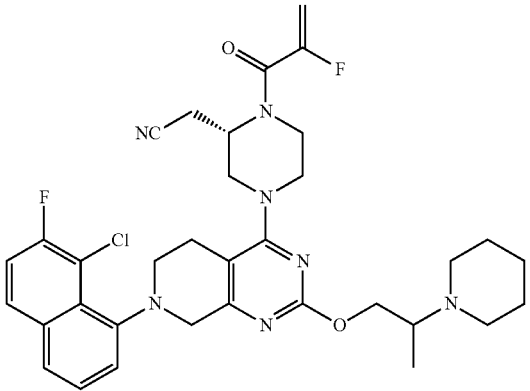<br>2-((2S)-4-(7-(8-chloro-7-fluoronaphthalen-1-yl)-2-(2-(piperidin-1-yl)propoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.72 (m, 1H), 7.64-7.58 (m, 1H), 7.47-7.39 (m, 1H), 7.36-7.27 (m, 2H), 5.51-5.33 (m, 1H), 5.31-5.22 (m, 1H), 5.08-4.67 (m, 1H), 4.51-4.42 (m, 1H), 4.42-4.34 (m, 1H), 4.09 (br s, 2H), 4.07-3.99 (m, 1H), 3.94-3.87 (m, 1H), 3.87-3.79 (m, 1H), 3.61-3.51 (m, 1H), 3.51-3.33 (m, 1H), 3.30-3.00 (m, 5H), 2.93-2.73 (m, 2H), 2.60 (br d, J = 3.6 Hz, 5H), 1.58 (br s, 4H), 1.49-1.38 (m, 2H), 1.16 (br d, J = 6.8 Hz, 3H); LCMS [M + 1]: 650. |
| 159 | 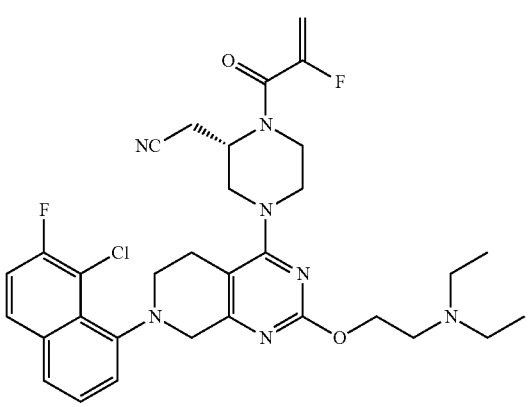<br>(S)-2-(4-(7-(8-chloro-7-fluoronaphthalen-1-yl)-2-(2-(diethylamino)ethoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ 7.75 (ddd, J = 2.0, 5.6, 8.8 Hz, 1H), 7.61 (t, J = 7.2 Hz, 1H), 7.43 (td, J = 7.6, 13.2 Hz, 1H), 7.37-7.27 (m, 2H), 5.57-5.33 (m, 1H), 5.26 (dd, J = 3.6, 16.8 Hz, 1H), 5.12-4.59 (m, 1H), 4.45-4.32 (m, 3H), 4.17-4.01 (m, 2H), 4.00-3.70 (m, 2H), 3.62-3.52 (m, 1H), 3.44 (br d, J = 12.0 Hz, 1H), 3.31-3.00 (m, 4H), 2.99-2.70 (m, 4H), 2.69-2.54 (m, 5H), 1.06 (dt, J = 2.0, 7.2 Hz, 6H). LCMS [M + 1]: 624. |

TABLE 5-continued

Characterization of EXAMPLES 149-205.

| Ex. # | Structure | Spectral Data |
|---|---|---|
| 160 | 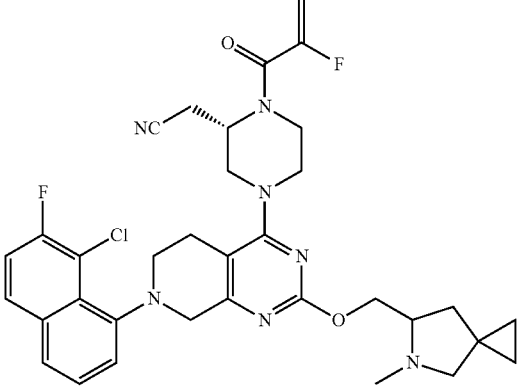<br>2-((2S)-4-(7-(8-chloro-7-fluoronaphthalen-1-yl)-2-((5-methyl-5-azaspiro[2.4]heptan-6-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.78-7.72 (m, 1H), 7.61 (d, J = 7.2 Hz, 1H), 7.47-7.38 (m, 1H), 7.36-7.27 (m, 2H), 5.53-5.32 (m, 1H), 5.26 (dd, J = 3.6, 16.8 Hz, 1H), 5.02-4.74 (m, 1H), 4.55-4.33 (m, 2H), 4.29-3.77 (m, 5H), 3.62-3.52 (m, 1H), 3.50-3.34 (m, 1H), 3.32-3.10 (m, 3H), 3.09-2.70 (m, 5H), 2.66-2.56 (m, 2H), 2.54-2.47 (m, 3H), 2.18-2.10 (m, 1H), 1.77-1.70 (m, 1H), 0.69-0.61 (m, 1H), 0.60-0.48 (m, 3H); LCMS [M + 1]: 648. |
| 161 | 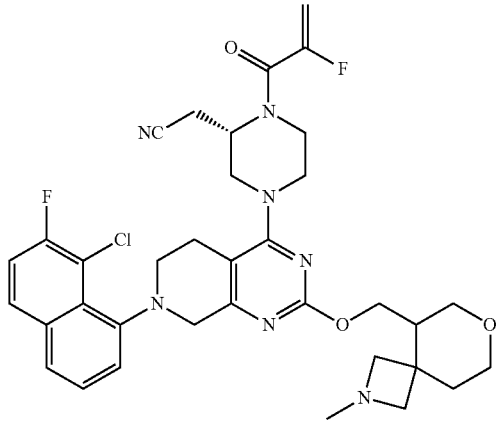<br>2-((2S)-4-(7-(8-chloro-7-fluoronaphthalen-1-yl)-2-((2-methyl-7-oxa-2-azaspiro[3.4]nonan-5-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ 7.76 (ddd, J = 1.6, 5.6, 9.2 Hz, 1H), 7.62 (t, J = 7.2 Hz, 1H), 7.43 (td, J = 7.6, 11.6 Hz, 1H), 7.36-7.27 (m, 2H), 5.51-5.33 (m, 1H), 5.26 (dd, J = 3.6, 16.8 Hz, 1H), 5.06-4.54 (m, 1H), 4.49-4.32 (m, 3H), 4.22-4.00 (m, 2H), 3.97-3.71 (m, 4H), 3.62-3.40 (m, 4H), 3.33-3.04 (m, 8H), 2.99-2.71 (m, 2H), 2.66-2.53 (m, 1H), 2.38-2.29 (m, 3H), 12.17-2.08 (m, 1H), 1.96-1.76 (m, 2H). LCMS [M + 1]: 678. |

TABLE 5-continued

Characterization of EXAMPLES 149-205.

| Ex. # | Structure | Spectral Data |
|---|---|---|
| 162 | 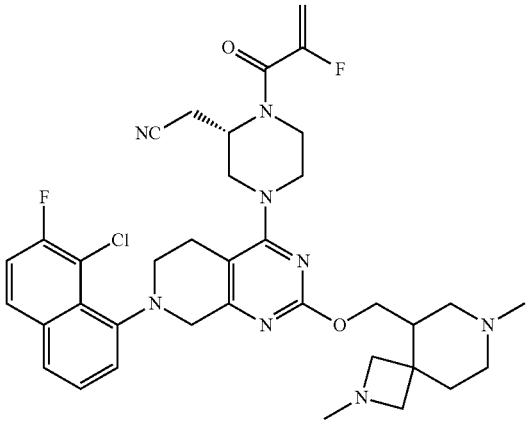<br><br>2-((2S)-4-(7-(8-chloro-7-fluoronaphthalen-1-yl)-2-((2,7-dimethyl-2,7-diazaspiro[3.5]nonan-5-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ 7.76 (ddd, J = 1.6, 5.6, 8.8 Hz, 1H), 7.62 (t, J = 6.8 Hz, 1H), 7.43 (td, J = 7.6, 11.2 Hz, 1H), 7.37-7.28 (m, 2H), 5.54-5.32 (m, 1H), 5.26 (dd, J = 3.6, 16.8 Hz, 1H), 5.06-4.66 (m, 1H), 4.60-4.46 (m, 1H), 4.45-4.34 (m, 2H), 4.22-4.00 (m, 2H), 3.97-3.72 (m, 2H), 3.57 (br d, J = 10.4 Hz, 1H), 3.50-3.29 (m, 3H), 3.28-2.98 (m, 6H), 2.96-2.75 (m, 2H), 2.66-2.51 (m, 2H), 2.42 (br d, J = 5.6 Hz, 4H), 2.21 (s, 5H), 1.90 (br s, 3H). LCMS [M + 1]: 691. |
| 163 | 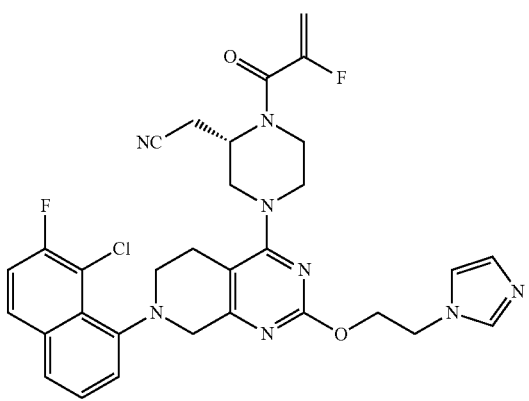<br><br>(S)-2-(4-(2-(2-(1H-imidazol-1-yl)ethoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.82-7.70 (m, 1H), 7.67-7.53 (m, 2H), 7.49-7.39 (m, 1H), 7.37-7.24 (m, 2H), 7.14-6.96 (m, 2H), 5.53-5.32 (m, 1H), 5.26 (dd, J = 3.6, 16.8 Hz, 1H), 5.07-4.71 (m, 1H), 4.66-4.52 (m, 2H), 4.43-4.31 (m, 3H), 4.29-3.70 (m, 4H), 3.67-3.39 (m, 2H), 3.37-2.70 (m, 6H), 2.66-2.51 (m, 1H); LCMS [M + 1]: 619. |

TABLE 5-continued

Characterization of EXAMPLES 149-205.

| Ex. # | Structure | Spectral Data |
|---|---|---|
| 164 | 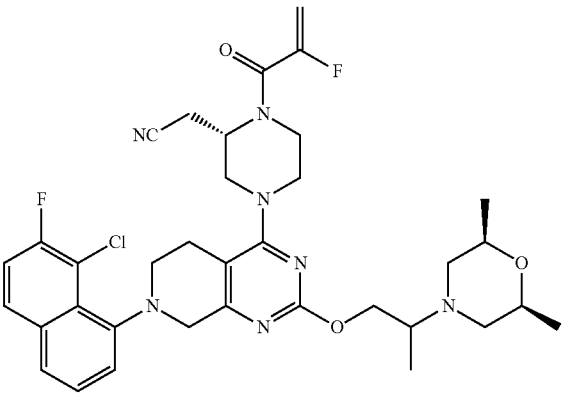<br>2-((2S)-4-(7-(8-chloro-7-fluoronaphthalen-1-yl)-2-(2-((2S,6R)-2,6-dimethylmorpholino)propoxy)-5,6,7,8-tetrahydropyrido[3,4-d]pyrimidin-4-yl)-1-(2-fluoroacryloyl)piperazin-1-yl)acetonitrile | $^1$H NMR (400 MHz, CDCl$_3$) δ 7.78-7.72 (m, 1H), 7.65-7.58 (m, 1H), 7.47-7.38 (m, 1H), 7.36-7.27 (m, 2H), 5.54-5.33 (m, 1H), 5.26 (dd, J = 3.2, 16.8 Hz, 1H), 5.10-4.60 (m, 1H), 4.48-4.35 (m, 2H), 4.19-3.99 (m, 3H), 3.96-3.53 (m, 5H), 3.52-3.33 (m, 1H), 3.29-2.97 (m, 5H), 2.95-2.53 (m, 5H), 2.15-2.06 (m, 2H), 1.19-1.13 (m, 9H). LCMS [M + 1]: 680. |
| 165 | 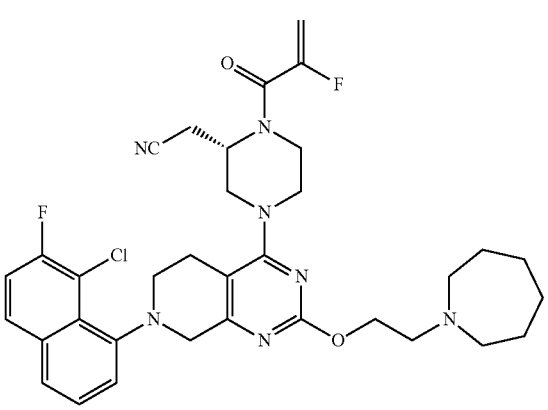<br>(S)-2-(4-(2-(2-(azepan-1-yl)ethoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.80-7.73 (m, 1H), 7.66-7.53 (m, 1H), 7.47-7.38 (m, 1H), 7.36-7.23 (m, 2H), 5.52-5.32 (m, 1H), 5.25 (dd, J = 3.6, 16.8 Hz, 1H), 5.09-4.60 (m, 1H), 4.46-4.34 (m, 3H), 4.20-3.98 (m, 2H), 3.96-3.33 (m, 4H), 3.32-2.67 (m, 12H), 2.66-2.53 (m, 1H), 1.68-1.55 (m, 8H). LCMS [M + 1]: 650. |

TABLE 5-continued

Characterization of EXAMPLES 149-205.

| Ex. # | Structure | Spectral Data |
|---|---|---|
| 166 | (S)-2-(4-(7-(8-chloro-7-fluoronaphthalen-1-yl)-2-((2-methyl-2-azabicyclo[2.2.2]octan-1-yl)methoxy)-5,6,7,8-tetrahydropyrido[3,4-d]pyrimidin-4-yl)-1-(2-fluoroacryloxy)piperazin-2-yl)acetonitrile | $^1$H NMR (400 MHz, CDCl$_3$) δ 7.79-7.70 (m, 1H), 7.64-7.56 (m, 1H), 7.46-7.36 (m, 1H), 7.35-7.22 (m, 2H), 5.54-5.31 (m, 1H), 5.25 (dd, J = 3.6, 16.8 Hz, 1H), 5.07-4.61 (m, 1H), 4.39 (dd, J = 14.0, 18.0 Hz, 1H), 4.21-3.99 (m, 4H), 3.96-3.77 (m, 2H), 3.61-3.38 (m, 2H), 3.30-2.99 (m, 4H), 2.96-2.71 (m, 4H), 2.64-2.51 (m, 1H), 2.33 (d, J = 2.8 Hz, 3H), 2.23-1.86 (m, 4H), 1.78-1.66 (m, 3H), 1.65-1.59 (m, 1H), 1.55-1.49 (m, 1H). LCMS [M + 1]: 662. |
| 167 | 2-((S)-4-(2-(((S)-4-benzylmorpholin-3-yl)methoxy)-7-(8-chloro-7-fluoronaphthalen-1-yl)-5,6,7,8-tetrahydropyrido[3,4-d]pyrimidin-4-yl)-1-(2-fluoroacryloyl)piperazin-1-yl)acetonitrile | $^1$H NMR (400 MHz, CDCl$_3$) δ 7.80-7.70 (m, 1H), 7.66-7.56 (m, 1H), 7.47-7.37 (m, 1H), 7.37-7.28 (m, 5H), 7.27-7.18 (m, 2H), 5.55-5.32 (m, 1H), 5.26 (dd, J = 3.6, 16.8 Hz, 1H), 5.06-4.70 (m, 1H), 4.61-4.48 (m, 1H), 4.46-4.31 (m, 2H), 4.15-3.93 (m, 4H), 3.92-3.53 (m, 6H), 3.52-3.32 (m, 2H), 3.31-2.64 (m, 8H), 2.63-2.52 (m, 1H), 2.39-2.27 (m, 1H). LCMS [M + 1]: 714. |

TABLE 5-continued

Characterization of EXAMPLES 149-205.

| Ex. # | Structure | Spectral Data |
|---|---|---|
| 168 | 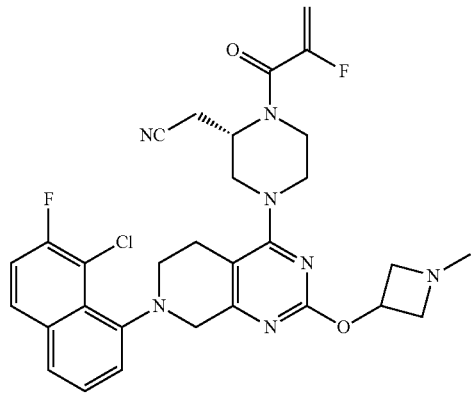<br>(S)-2-(4-(7-(8-chloro-7-fluoronaphthalen-1-yl)-2-((1-methylazetidin-3-yl)oxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.73 (m, 1H), 7.62 (t, J = 7.2 Hz, 1H), 7.43 (td, J = 7.6, 13.6 Hz, 1H), 7.37-7.27 (m, 2H), 5.55-5.34 (m, 1H), 5.26 (dd, J = 3.6, 16.8 Hz, 1H), 5.21-5.10 (m, 1H), 5.05-4.67 (m, 1H), 4.45-4.32 (m, 1H), 4.15-4.00 (m, 2H), 3.98-3.76 (m, 4H), 3.65-3.52 (m, 1H), 3.50-3.37 (m, 1H), 3.31-3.02 (m, 6H), 3.01-2.68 (m, 2H), 2.66-2.53 (m, 1H), 2.41 (d, J = 1.2 Hz, 3H). LCMS [M + 1]: 594. |
| 169 | 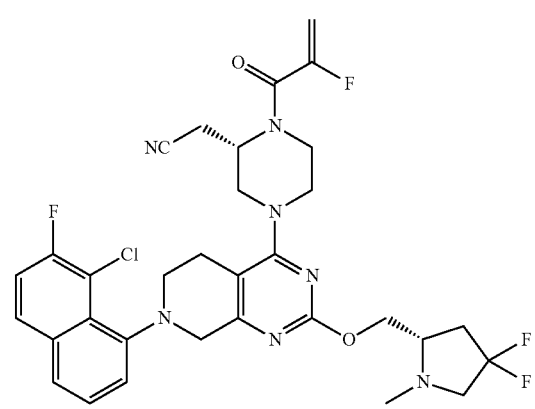<br>2-((S)-4-(7-(8-chloro-7-fluoronaphthalen-1-yl)-2-(((S)-4,4-difluoro-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.73 (m, 1H), 7.62 (t, J = 7.2 Hz, 1H), 7.48-7.39 (m, 1H), 7.37-7.27 (m, 2H), 5.55-5.33 (m, 1H), 5.26 (dd, J = 3.6, 16.8 Hz, 1H), 5.02-4.59 (m, 1H), 4.52-4.33 (m, 2H), 4.32-3.77 (m, 5H), 3.61-3.36 (m, 3H), 3.32-2.95 (m, 5H), 2.94-2.48 (m, 5H), 2.46 (s, 3H), 2.34-2.18 (m, 1H). LCMS [M + 1]: 658. |

TABLE 5-continued

Characterization of EXAMPLES 149-205.

| Ex. # | Structure | Spectral Data |
|---|---|---|
| 170 | 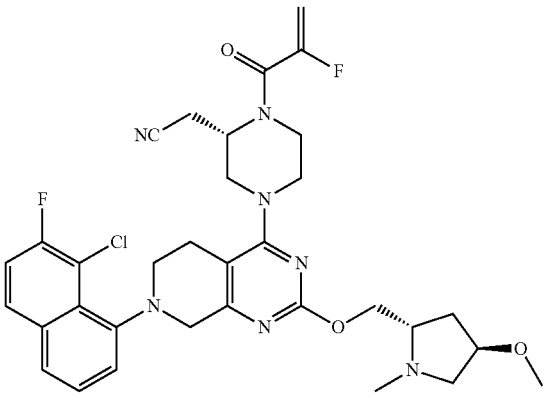<br>2-((S)-4-(7-(8-chloro-7-fluoronaphthalen-1-yl)-2-(((2S,4R)-4-methoxy-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.61 (t, J = 7.6 Hz, 1H), 7.47-7.38 (m, 1H), 7.36-7.27 (m, 2H), 5.54-5.33 (m, 1H), 5.26 (dd, J = 3.2, 16.8 Hz, 1H), 5.03-4.60 (m, 1H), 4.46-4.33 (m, 2H), 4.25-3.78 (m, 6H), 3.61-3.38 (m, 3H), 3.34-3.28 (m, 3H), 3.27-2.98 (m, 4H), 2.94-2.72 (m, 3H), 2.65-2.54 (m, 1H), 2.50-2.43 (m, 3H), 2.36-2.29 (m, 1H), 2.13-2.03 (m, 1H), 2.01-1.91 (m, 1H). LCMS [M + 1]: 652. |
| 171 | 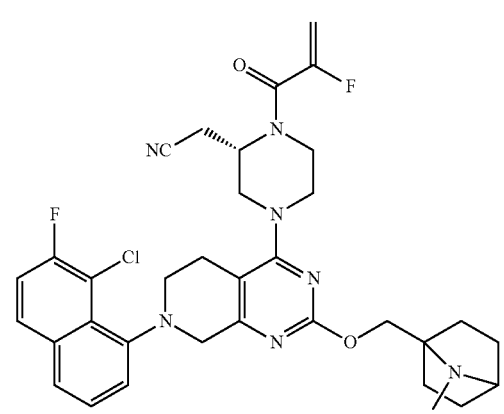<br>(s)-2-(4-(7-(8-chloro-7-fluoronaphthalen-1-yl)-2-((7-methyl-7-azabicyclo[2.2.1]heptan-1-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.80-7.73 (m, 1H), 7.62 (t, J = 7.2 Hz, 1H), 7.49-7.40 (m, 1H), 7.37-7.28 (m, 2H), 5.56-5.32 (m, 1H), 5.27 (dd, J = 3.6, 16.8 Hz, 1H), 5.03-4.72 (m, 1H), 4.59-4.48 (m, 2H), 4.47-4.37 (m, 1H), 4.24-3.80 (m, 4H), 3.65-3.41 (m, 2H), 3.32-3.03 (m, 5H), 2.96-2.84 (m, 1H), 2.67-2.54 (m, 1H), 2.35-2.24 (m, 3H), 1.99-1.74 (m, 5H), 1.58-1.48 (m, 2H), 1.46-1.36 (m, 2H). LCMS [M + 1]: 648. |

TABLE 5-continued

Characterization of EXAMPLES 149-205.

| Ex. # | Structure | Spectral Data |
|---|---|---|
| 172 | 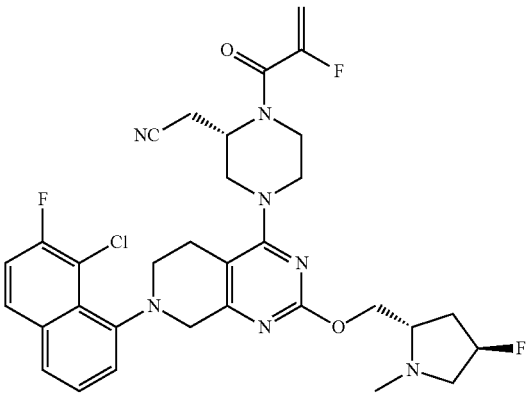<br>2-((S)-4-(7-(8-chloro-7-fluoronaphthalen-1-yl)-2-(((2S,4R)-4-fluoro-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.62 (t, J = 7.2 Hz, 1H), 7.48-7.39 (m, 1H), 7.36-7.27 (m, 2H), 5.56-5.33 (m, 1H), 5.31-5.06 (m, 2H), 5.00-4.65 (m, 1H), 4.48-4.33 (m, 2H), 4.29-3.78 (m, 5H), 3.62-3.38 (m, 3H), 3.31-2.99 (m, 5H), 2.97-2.71 (m, 2H), 2.69-2.54 (m, 2H), 2.53-2.48 (m, 3H), 2.39-2.24 (m, 1H), 2.08-1.86 (m, 1H). LCMS [M + 1]: 640. |
| 173 | 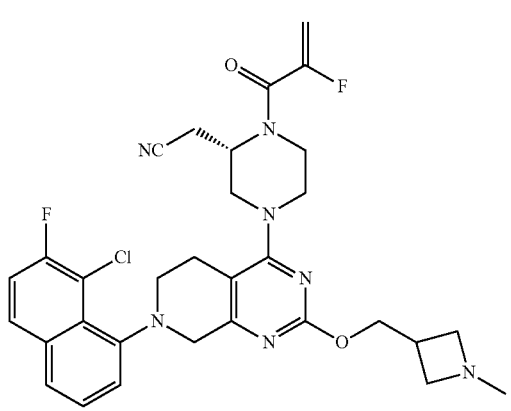<br>(S)-2-(4-(7-(8-chloro-7-fluoronaphthalen-1-yl)-2-((1-methylazetidin-3-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.75 (ddd, J = 1.6, 5.6, 8.8 Hz, 1H), 7.61 (t, J = 6.8 Hz, 1H), 7.43 (td, J = 7.6, 12.0 Hz, 1H), 7.35-7.24 (m, 2H), 5.52-5.32 (m, 1H), 5.26 (br dd, J = 3.6, 16.8 Hz, 1H), 5.03-4.72 (m, 1H), 4.50-4.32 (m, 3H), 4.22-3.79 (m, 4H), 3.64-3.51 (m, 1H), 3.48-3.33 (m, 3H), 3.30-2.98 (m, 6H), 2.96-2.73 (m, 3H), 2.66-2.52 (m, 1H), 2.32 (d, J = 1.6 Hz, 3H). LCMS [M + 1]: 608. |

TABLE 5-continued

Characterization of EXAMPLES 149-205.

| Ex. # | Structure | Spectral Data |
|---|---|---|
| 174 | 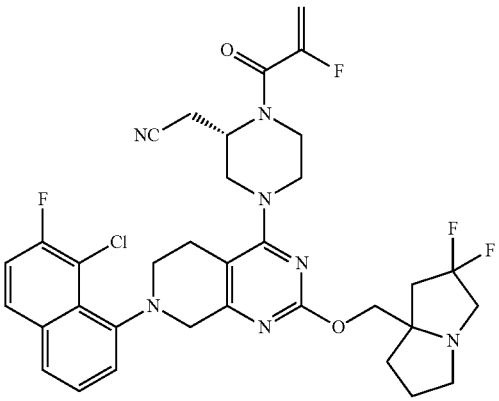<br>2-((2S)-4-(7-(8-chloro-7-fluoronaphthalen-1-yl)-2-((2,2-difluorotetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.61 (t, J = 7.6 Hz, 1H), 7.47-7.37 (m, 1H), 7.35-7.21 (m, 2H), 5.55-5.32 (m, 1H), 5.26 (br dd, J = 3.6, 16.8 Hz, 1H), 5.10-4.65 (m, 1H), 4.45-4.34 (m, 1H), 4.28-3.76 (m, 6H), 3.60-3.36 (m, 3H), 3.31-2.70 (m, 9H), 2.67-2.47 (m, 2H), 2.34-2.14 (m, 2H), 1.98-1.76 (m, 3H); LCMS [M + 1]: 684. |
| 175 | 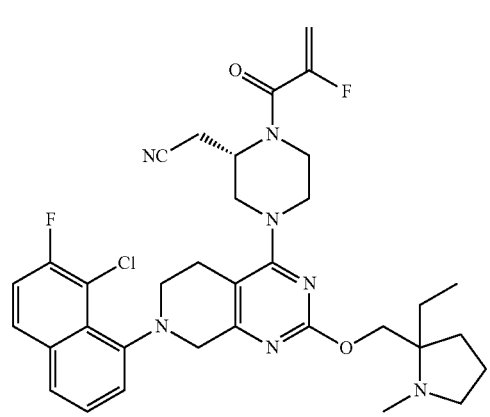<br>2-((2S)-4-(7-(8-chloro-7-fluoronaphthalen-1-yl)-2-((2-ethyl-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.76-7.73 (m, 1H), 7.64-7.57 (m, 1H), 7.47-7.37 (m, 1H), 7.35-7.326 (m, 2H), 5.54-5.32 (m, 1H), 5.31-5.21 (m, 1H), 5.10-4.65 (m, 1H), 4.46-4.36 (m, 1H), 4.26-3.70 (m, 6H), 3.63-3.38 (m, 2H), 3.29-2.74 (m, 8H), 2.63-2.53 (m, 1H), 2.46 (d, J = 2.4 Hz, 3H), 1.91-1.79 (m, 5H), 1.50-1.40 (m, 1H), 0.92 (t, J = 7.6 Hz, 3H); LCMS [M + 1]: 650. |

TABLE 5-continued

Characterization of EXAMPLES 149-205.

| Ex. # | Structure | Spectral Data |
|---|---|---|
| 176 | 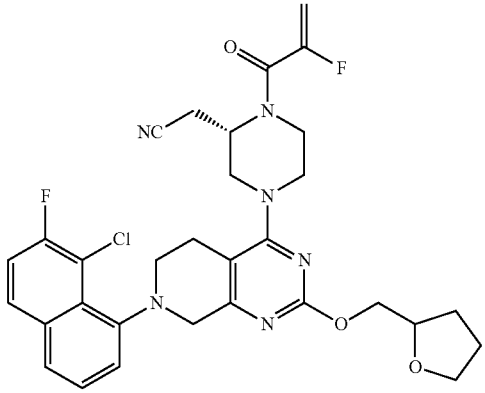<br>2-((2S)-4-(7-(8-chloro-7-fluoronaphthalen-1-yl)-2-((tetrahydrofuran-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl3) δ 7.83-7.72 (m, 1H), 7.68-7.58 (m, 1H), 7.49-7.38 (m, 1H), 7.37-7.24 (m, 2H), 5.53-5.33 (m, 1H), 5.26 (dd, J = 3.6, 16.8 Hz, 1H), 5.07-4.71 (m, 1H), 4.49-4.15 (m, 5H), 4.14-3.77 (m, 5H), 3.66-3.39 (m, 2H), 3.32-3.00 (m, 4H), 2.99-2.71 (m, 2H), 2.68-2.55 (m, 1H), 2.15-2.03 (m, 1H), 2.02-1.87 (m, 2H), 1.86-1.75 (m, 1H), LCMS [M + 1]: 609. |
| 177 | 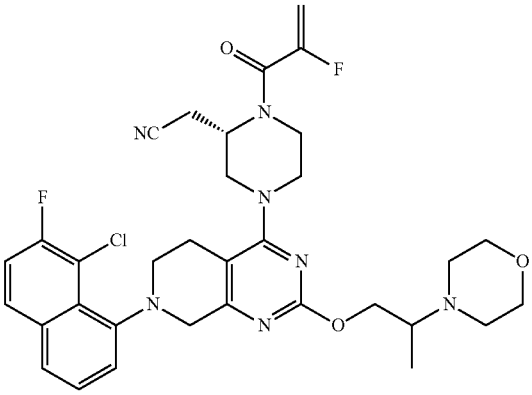<br>2-((2S)-4-(7-(8-chloro-7-fluoronaphthalen-1-yl)-2-(2-morpholinopropoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.73 (m, 1H), 7.62 (t, J = 7.2 Hz, 1H), 7.43 (td, J = 7.6, 12.4 Hz, 1H), 7.36-7.27 (m, 2H), 5.52-5.34 (m, 1H), 5.26 (dd, J = 3.2, 16.8 Hz, 1H), 5.01-4.70 (m, 1H), 4.52-4.34 (m, 2H), 4.23-3.98 (m, 3H), 3.95-3.78 (m, 2H), 3.70 (br d, J = 3.2 Hz, 4H), 3.62-3.40 (m, 2H), 3.26-2.76 (m, 7H), 2.71-2.52 (m, 5H), 1.18 (dd, J = 2.4, 6.8 Hz, 3H); LCMS [M + 1]: 652. |

TABLE 5-continued

Characterization of EXAMPLES 149-205.

| Ex. # | Structure | Spectral Data |
|---|---|---|
| 178 | 2-((2S)-4-(7-(8-chloro-7-fluoronaphthalen-1-yl)-2-((1-isopropylazetidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.61 (t, J = 7.2 Hz, 1H), 7.43 (td, J = 8.0, 13.6 Hz, 1H), 7.35-7.29 (m, 2H), 7.25 (d, J = 7.6 Hz, 1H), 5.52-5.33 (m, 1H), 5.26 (dd, J = 3.6, 17.2 Hz, 1H), 5.04-4.67 (m, 1H), 4.60-4.20 (m, 4H), 4.18-3.79 (m, 4H), 3.72-3.32 (m, 5H), 3.26-3.02 (m, 3H), 2.95-2.74 (m, 2H), 2.63-2.44 (m, 2H), 2.28-1.88 (m, 2H), 1.04 (dd, J = 3.2, 6.4 Hz, 3H), 0.95 (dd, J = 2.8, 6.4 Hz, 3H). LCMS [M + 1]: 636.4. |
| 179 | 2-((2S)-4-(7-(8-chloro-7-fluoronaphthalen-1-yl)-2-((1-ethylazetidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.61 (t, J = 7.2 Hz, 1H), 7.43 (td, J = 8.0, 12.6 Hz, 1H), 7.36-7.29 (m, 2H), 7.24 (s, 1H), 5.51-5.32 (m, 1H), 5.26 (dd, J = 3.6, 16.8 Hz, 1H), 4.87 (br s, 1H), 4.46-4.27 (m, 3H), 4.20-4.00 (m, 2H), 3.95-3.79 (m, 1H), 3.60-2.95 (m, 9H), 2.93-2.69 (m, 4H), 2.59 (br d, J = 13.2 Hz, 1H), 2.44 (br s, 1H), 2.17-2.05 (m, 2H), 1.01 (br t, J = 7.2 Hz, 3H). LCMS [M + 1]: 622.4. |

TABLE 5-continued

Characterization of EXAMPLES 149-205.

| Ex. # | Structure | Spectral Data |
|---|---|---|
| 180 | 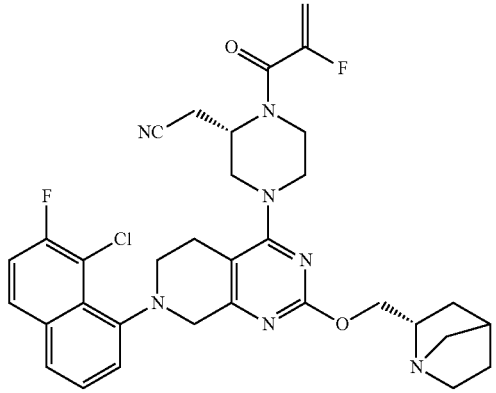<br>2-((2S)-4-(2-(((2S)-1-azabicyclo[2.2.1]heptan-2-yl)methoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.72 (m, 1H), 7.60 (t, J = 6.8 Hz, 1H), 7.42 (td, J = 7.6, 12.0 Hz, 1H), 7.36-7.28 (m, 2H), 5.51-5.33 (m, 1H), 5.25 (dd, J = 3.6, 16.8 Hz, 1H), 5.04-4.63 (m, 1H), 4.46-4.27 (m, 2H), 4.20-4.01 (m, 2H), 4.00-3.88 (m, 2H), 3.88-3.75 (m, 1H), 3.56 (br dd, J = 3.6, 11.6 Hz, 1H), 3.49-3.33 (m, 1H), 3.30-2.95 (m, 5H), 2.94-2.69 (m, 3H), 2.67-2.45 (m, 4H), 2.29 (br d, J = 9.6 Hz, 1H), 1.70-1.50 (m, 1H), 1.45-1.37 (m, 1H), 1.37-1.27 (m, 1H), 1.20-1.08 (m, 1H). LCMS [M + 1]: 634. |
| 181 | 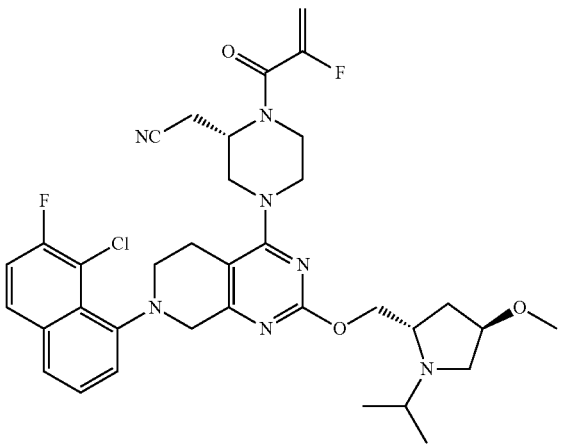<br>2-((S)-4-(7-(8-chloro-7-fluoronaphthalen-1-yl)-2-(((2S,4R)-1-isopropyl-4-methoxypyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$-d) δ 7.78-7.73 (m, 1H), 7.62 (t, J = 7.2 Hz, 1H), 7.47-7.39 (m, 1H), 7.36-7.23 (m, 2H), 5.50-5.34 (m, 1H), 5.26 (dd, J = 3.6, 16.8 Hz, 1H), 5.07-4.69 (m, 1H), 4.46-4.32 (m, 2H), 4.19-3.79 (m, 6H), 3.60-3.53 (m, 1H), 3.48-3.30 (m, 5H), 3.29-2.99 (m, 6H), 2.95-2.72 (m, 2H), 2.69-2.49 (m, 2H), 2.15-1.92 (m, 2H), 1.24-0.91 (m, 6H). LCMS [M + 1]: 680. |

TABLE 5-continued

Characterization of EXAMPLES 149-205.

| Ex. # | Structure | Spectral Data |
|---|---|---|
| 182 | 2-((S)-4-(7-(8-chloro-7-fluoronaphthalen-1-yl)-2-(((1R,2R)-2-(dimethylamino)cyclohexyl)oxy)-5,6,7,8-tetrahydropyrido[3,4-d]pyrimidin-4-yl)-1-(2-fluoroacryloyl)piperazin-2-yl)acetonitrile | $^1$H NMR (400 MHz, C$_2$D$_4$O$_2$) δ = 7.90-7.83 (m, 1H), 7.72 (d, J = 8.0 Hz, 1H), 7.52-7.46 (m, 1H), 7.44-7.37 (m, 2H), 5.59-5.23 (m, 3H), 5.13-4.76 (m, 1H), 4.64-4.04 (m, 4H), 3.99-3.70 (m, 2H), 3.66-3.50 (m, 3H), 3.43-3.31 (m, 1H), 3.29-3.13 (m, 2H), 3.09-2.86 (m, 7H), 2.84-2.69 (m, 1H), 2.65-2.47 (m, 1H), 2.30-2.17 (m, 1H), 1.98-1.76 (m, 3H), 1.74-1.38 (m, 4H). LCMS [M + 1]: 650. |
| 183 | 2-((S)-4-(7-(8-chloro-7-fluoronaphthalen-1-yl)-2-(((2S,4R)-4-fluoro-1-isopropylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.65-7.59 (m, 1H), 7.48-7.39 (m, 1H), 7.36-7.27 (m, 2H), 5.54-5.32 (m, 1H), 5.31-5.07 (m, 2H), 5.02-4.61 (m, 1H), 4.53-4.33 (m, 2H), 4.25-3.74 (m, 5H), 3.63-3.39 (m, 3H), 3.36-2.70 (m, 9H), 2.64-2.55 (m, 1H), 2.44-2.28 (m, 1H), 2.08-1.83 (m, 1H), 1.12 (br d, J = 6.4 Hz, 3H), 1.02 (br d, J = 6.0 Hz, 3H). LCMS [M + 1]: 668. |

TABLE 5-continued

Characterization of EXAMPLES 149-205.

| Ex. # | Structure | Spectral Data |
|---|---|---|
| 184 | 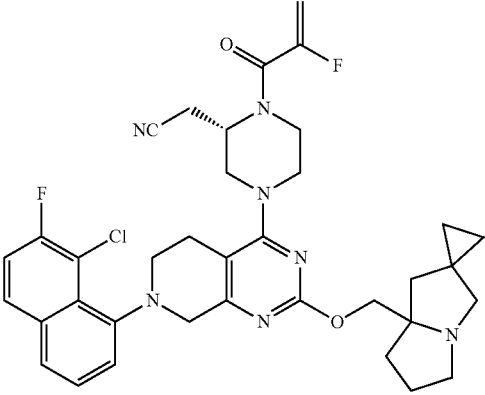<br>2-((2S)-4-(7-(8-chloro-7-fluoronaphthalen-1-yl)-2-(((dihydro-1'H,3'H-spiro[cyclopropan-1,2'-pyrrolizin]-7a'(5'H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.71 (m, 1H), 7.64-7.58 (m, 1H), 7.47-7.38 (m, 1H), 7.35-7.30 (m, 1H), 7.27-7.22 (m, 1H), 5.51-5.32 (m, 1H), 5.30-5.21 (m, 1H), 4.99-4.59 (m, 1H), 4.46-4.32 (m, 2H), 4.27-4.03 (m, 3H), 4.01-3.81 (m, 2H), 3.62-3.41 (m, 2H), 3.33-3.01 (m, 6H), 2.96-2.75 (m, 4H), 2.64-2.51 (m, 1H), 2.25-2.12 (m, 1H), 2.10-1.94 (m, 3H), 1.89-1.82 (m, 2H), 0.68-0.53 (m, 4H). LCMS [M + 1]: 674.2. |
| 185 | 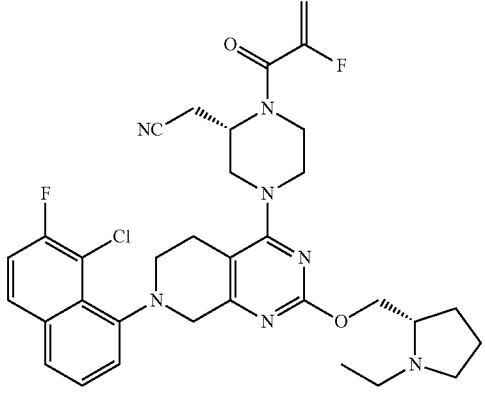<br>2-((S)-4-(7-(8-chloro-7-fluoronaphthalen-1-yl)-2-(((S)-1-ethylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.61 (t, J = 7.6 Hz, 1H), 7.47-7.38 (m, 1H), 7.36-7.27 (m, 2H), 5.54-5.32 (m, 1H), 5.26 (dd, J = 3.6, 16.8 Hz, 1H), 5.06-4.68 (m, 1H), 4.45-4.33 (m, 2H), 4.18-4.00 (m, 3H), 3.99-3.78 (m, 2H), 3.61-3.52 (m, 1H), 3.49-3.34 (m, 1H), 3.29-2.95 (m, 6H), 2.94-2.72 (m, 3H), 2.64-2.53 (m, 1H), 2.49-2.37 (m, 1H), 2.30-2.18 (m, 1H), 2.08-1.95 (m, 1H), 1.89-1.72 (m, 3H), 1.14 (t, J = 7.2 Hz, 3H). LCMS [M + 1]: 636. |

TABLE 5-continued

Characterization of EXAMPLES 149-205.

| Ex. # | Structure | Spectral Data |
|---|---|---|
| 186 | 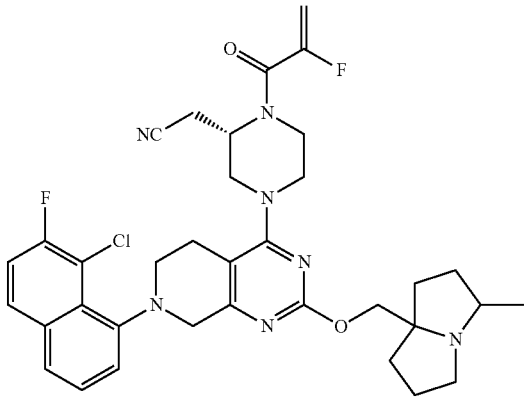<br><br>2-((2S)-4-(7-(8-chloro-7-fluoronaphthalen-1-yl)-2-((3-methyltetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, DMSO-d6) δ = 8.02 (dd, J = 6.0, 9.2 Hz, 1H), 7.79 (dd, J = 4.0, 7.6 Hz, 1H), 7.60 (t, J = 8.8 Hz, 1H), 7.53 (q, J = 7.6 Hz, 1H), 7.46-7.37 (m, 1H), 5.45-5.18 (m, 2H), 5.04-4.54 (m, 1H), 4.24-3.54 (m, 8H), 3.47 (br s, 1H), 3.29-2.67 (m, 9H), 2.04-1.37 (m, 9H), 1.23-0.80 (m, 3H). LCMS [M + 1]: 662.4. |
| 187 | 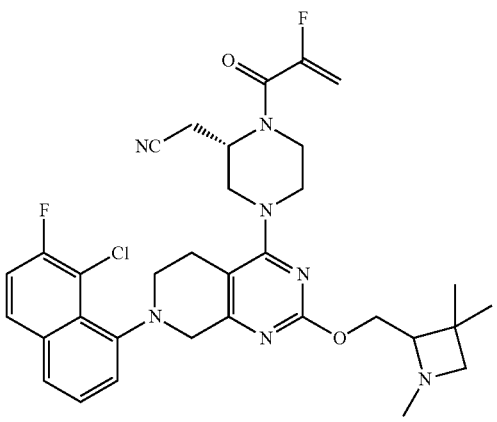<br><br>2-((2S)-4-(7-(8-chloro-7-fluoronaphthalen-1-yl)-2-((1,3,3-trimethylazetidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.61 (t, J = 7.2 Hz, 1H), 7.43 (td, J = 7.6, 12.8 Hz, 1H), 7.36-7.31 (m, 1H), 7.24 (s, 1H), 5.54-5.32 (m, 1H), 5.26 (dd, J = 3.6, 16.8 Hz, 1H), 4.46-4.39 (m, 1H), 4.37-4.31 (m, 2H), 4.20-4.00 (m, 2H), 3.96-3.80 (m, 1H), 3.61-3.40 (m, 2H), 3.29-3.02 (m, 6H), 2.93-2.77 (m, 1H), 2.68-2.54 (m, 2H), 2.42 (s, 3H), 1.70 (br s, 3H), 1.27 (s, 3H), 1.17 (d, J = 1.6 Hz, 3H). LCMS [M + 1]: 636.5. |

TABLE 5-continued

Characterization of EXAMPLES 149-205.

| Ex. # | Structure | Spectral Data |
|---|---|---|
| 188 | 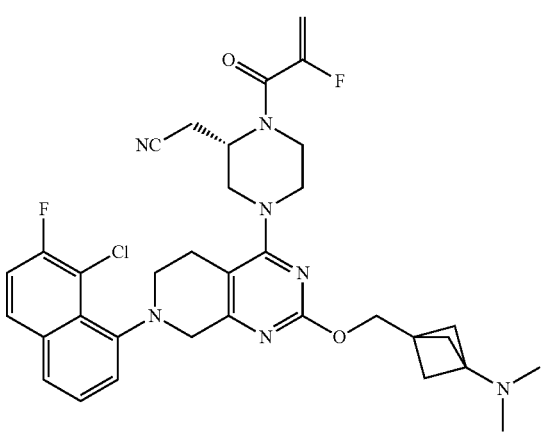<br><br>(S)-2-(4-(7-(8-chloro-7-fluoronaphthalen-1-yl)-2-((3-(dimethylamino)bicyclo[1.1.1]pentan-1-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.75 (ddd, J = 1.6, 5.6, 8.8 Hz, 1H), 7.61 (t, J = 7.2 Hz, 1H), 7.43 (td, J = 7.6, 13.2 Hz, 1H), 7.36-7.27 (m, 2H), 5.52-5.33 (m, 1H), 5.26 (dd, J = 3.6, 16.8 Hz, 1H), 5.07-4.67 (m, 1H), 4.51-4.33 (m, 3H), 4.22-3.78 (m, 4H), 3.65-3.36 (m, 2H), 3.28-2.97 (m, 4H), 2.97-2.74 (m, 2H), 2.67-2.53 (m, 1H), 2.23 (d, J = 1.2 Hz, 6H), 1.78 (d, J = 1.6 Hz, 6H). LCMS [M + 1]: 648. |
| 189 | 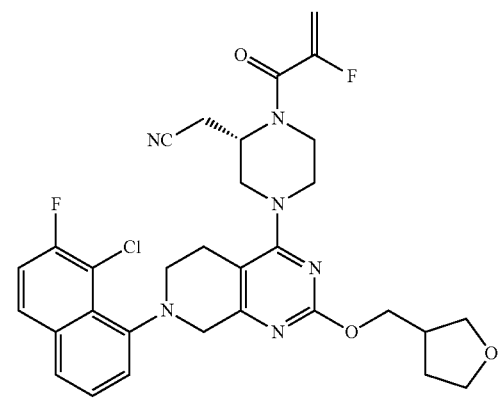<br><br>2-((2S)-4-(7-(8-chloro-7-fluoronaphthalen-1-yl)-2-((tetrahydrofuran-3-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.75 (m, 1H), 7.63 (t, J = 7.2 Hz, 1H), 7.45 (td, J = 8.0, 12.0 Hz, 1H), 7.37-7.29 (m, 2H), 5.60-5.34 (m, 1H), 5.27 (dd, J = 3.6, 16.8 Hz, 1H), 5.13-4.72 (m, 1H), 4.41 (br dd, J = 12.8, 17.6 Hz, 1H), 4.32-4.19 (m, 3H), 4.15-4.01 (m, 2H), 3.97-3.86 (m, 3H), 3.84-3.77 (m, 1H), 3.77-3.70 (m, 1H), 3.64-3.54 (m, 1H), 3.51-3.06 (m, 5H), 2.96-2.75 (m, 3H), 2.68-2.56 (m, 1H), 2.23-2.08 (m, 1H), 1.86-1.71 (m, 1H). LCMS [M + 1]: 609. |

TABLE 5-continued

Characterization of EXAMPLES 149-205.

| Ex. # | Structure | Spectral Data |
|---|---|---|
| 190 | 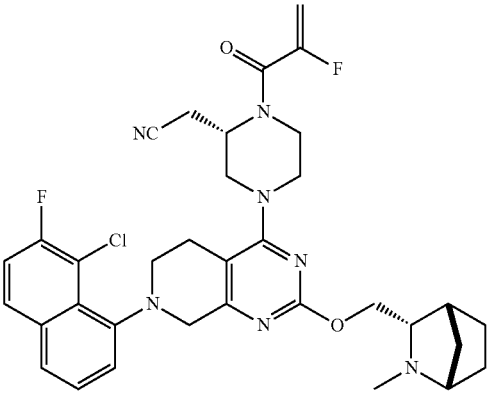<br>2-((S)-4-(7-(8-chloro-7-fluoronaphthalen-1-yl)-2-(((1S,3S,4R)-2-methyl-2-azabicyclo[2.2.1]heptan-3-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.75 (ddd, J = 2.4, 6.0, 8.8 Hz, 1H), 7.61 (t, J = 7.2 Hz, 1H), 7.48-7.38 (m, 1H), 7.36-7.28 (m, 2H), 5.51-5.33 (m, 1H), 5.26 (dd, J = 3.6, 16.8 Hz, 1H), 5.07-4.59 (m, 1H), 4.48-4.30 (m, 1H), 4.22-3.98 (m, 3H), 3.97-3.74 (m, 2H), 3.64-3.52 (m, 1H), 3.49-3.35 (m, 1H), 3.30-2.98 (m, 5H), 2.95-2.68 (m, 2H), 2.65-2.55 (m, 1H), 2.41 (s, 4H), 2.32-2.23 (m, 1H), 1.99-1.88 (m, 1H), 1.81-1.70 (m, 1H), 1.68-1.60 (m, 1H), 1.42-1.21 (m, 4H). LCMS [M + 1]: 648. |
| 191 | 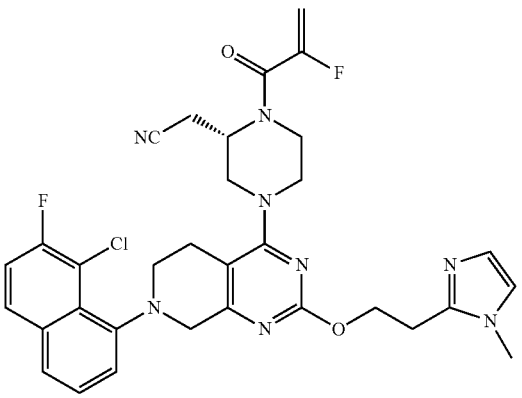<br>(S)-2-(4-(7-(8-chloro-7-fluoronaphthalen-1-yl)-2-(2-(1-methyl-1H-imidazol-2-yl)ethoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.73-7.64 (m, 1H), 7.54 (t, J = 6.8 Hz, 1H), 7.40-7.31 (m, 1H), 7.29-7.15 (m, 2H), 6.91-6.84 (m, 1H), 6.77-6.71 (m, 1H), 5.47-5.25 (m, 1H), 5.18 (dd, J = 3.6, 16.8 Hz, 1H), 4.96-4.70 (m, 1H), 4.67-4.55 (m, 2H), 4.30 (dd, J = 14.4, 17.6 Hz, 1H), 4.16-3.95 (m, 2H), 3.88-3.66 (m, 2H), 3.58 (d, J = 3.6 Hz, 3H), 3.53-3.31 (m, 2H), 3.26-2.92 (m, 6H), 2.87-2.64 (m, 2H), 2.59-2.41 (m, 1H). LCMS [M + 1]: 633. |

TABLE 5-continued

Characterization of EXAMPLES 149-205.

| Ex. # | Structure | Spectral Data |
|---|---|---|
| 192 | 2-((2S)-4-(7-(8-chloro-7-fluoronaphthalen-1-yl)-2-(3,3-difluoro-2-methylpropoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.73 (m, 1H), 7.64-7.58 (m, 1H), 7.47-7.37 (m, 1H), 7.36-7.24 (m, 2H), 6.17-5.81 (m, 1H)), 5.54-5.34 (m, 1H), 5.26 (dd, J =3.6, 17.2 Hz, 1H), 5.09-4.65 (m, 1H), 4.48-4.16 (m, 4H), 4.12-3.79 (m, 3H), 3.63-3.38 (m, 2H), 3.32-2.99 (m, 4H), 2.95-2.72 (m, 2H), 2.67-2.55 (m, 1H), 2.53-2.37 (m, 1H), 1.20-1.12 (m, 3H). LCMS [M + 1]: 617. |
| 193 | 2-((S)-4-(2-(2-((1S,4S)-2-oxa-5-azabicyclo[2.2.1]heptan-5-yl)ethoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.75 (ddd, J = 1.6, 5.6, 9.2 Hz, 1H), 7.61 (t, J = 6.8 Hz, 1H), 7.43 (td, J = 8.0, 12.0 Hz, 1H), 7.36-7.27 (m, 2H), 5.53-5.32 (m, 1H), 5.25 (dd, J = 3.6, 16.8 Hz, 1H), 5.04-4.63 (m, 1H), 4.45-4.33 (m, 4H), 4.21-3.99 (m, 3H), 3.95-3.77 (m, 2H), 3.64 (td, J = 1.6, 8.0 Hz, 1H), 3.61-3.52 (m, 2H), 3.45 (br d, J = 14.4 Hz, 1H), 3.30-2.93 (m, 7H), 2.92-2.74 (m, 2H), 2.67-2.55 (m, 2H), 1.88 (br d, J = 10.0 Hz, 1H), 1.76-1.73 (m, 1H). LCMS [M + 1]: 650. |

TABLE 5-continued

Characterization of EXAMPLES 149-205.

| Ex. # | Structure | Spectral Data |
|---|---|---|
| 194 | 2-((2S)-4-(7-(8-chloro-7-fluoronaphthalen-1-yl)-2-((tetrahydro-1H-pyrrolo[2,1-c][1,4]oxazin-8a(6H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$): δ 7.75 (ddd, J = 1.6, 4.5, 8.8 Hz, 1H), 7.61 (t, J = 6.8 Hz, 1H), 7.42 (td, J = 7.6, 12.4 Hz, 1H), 7.35-7.27 (m, 2H), 5.53-5.32 (m, 1H), 5.26 (dd, J = 3.5, 16.8 Hz, 1H), 5.13-4.74 (m, 1H), 4.73-4.60 (m, 1H), 4.46-4.35 (m, 1H), 4.22-4.02 (m, 3H), 4.02-3.79 (m, 3H), 3.79-3.69 (m, 1H), 3.63-3.53 (m, 2H), 3.51-3.34 (m, 2H), 3.29-2.99 (m, 7H), 2.99-2.69 (m, 3H), 2.64-2.53 (m, 1H), 2.04-1.93 (m, 1H), 1.93-1.82 (m, 2H), 1.61-1.53 (m, 1H). LCMS [M + 1]: 664. |
| 195 | 2-((S)-4-(7-(8-chloro-7-fluoronaphthalen-1-yl)-2-(((R)-4-methylmorpholin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.72 (m, 1H), 7.64-7.58 (m, 1H), 7.47-7.38 (m, 1H), 7.36-7.32 (m, 1H), 7.32-7.29 (m, 1H), 5.52-5.33 (m, 1H), 5.29-5.20 (m, 1H), 5.06-4.65 (m, 1H), 4.46-4.32 (m, 2H), 4.26 (s, 1H), 4.07 (br s, 2H), 4.00-3.89 (m, 3H), 3.88-3.78 (m, 1H), 3.76-3.67 (m, 1H), 3.63-3.40 (br d, J = 0.8 Hz, 2H), 3.30-2.98 (m, 4H), 2.94-2.73 (m, 3H), 2.70-2.52 (m, 2H), 2.34-2.29 (m, 3H), 2.24-2.14 (m, 1H), 2.06-1.97 (m, 1H). LCMS [M + 1]: 638. |

TABLE 5-continued

Characterization of EXAMPLES 149-205.

| Ex. # | Structure | Spectral Data |
|---|---|---|
| 196 | 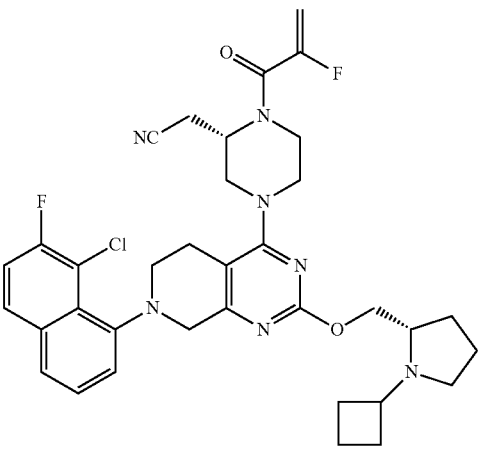<br>2-((S)-4-(7-(8-chloro-7-fluoronaphthalen-1-yl)-2-(((S)-1-cyclobutylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.80-7.71 (m, 1H), 7.61 (t, J = 7.6 Hz, 1H), 7.43 (td, J = 7.6, 13.2 Hz, 1H), 7.37-7.27 (m, 2H), 5.55-5.34 (m, 1H), 5.26 (dd, J = 3.6, 16.8 Hz, 1H), 4.47-4.32 (m, 2H), 4.26-4.00 (m, 4H), 3.97-3.78 (m, 2H), 3.62-2.97 (m, 10H), 2.95-2.76 (m, 2H), 2.64-2.56 (m, 1H), 2.53-2.35 (m, 1H), 2.20-1.97 (m, 5H), 1.94-1.74 (m, 4H). LCMS [M + 1]: 662. |
| 197 | 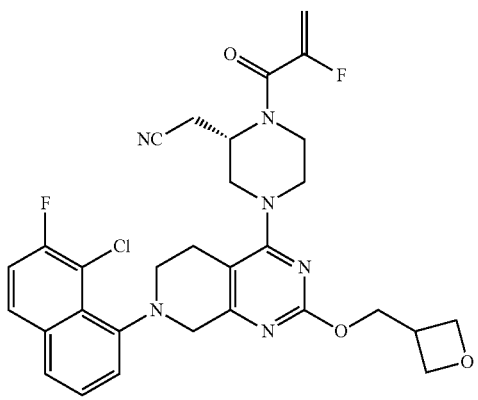<br>(S)-2-(4-(7-(8-chloro-7-fluoronaphthalen-1-yl)-2-(oxetan-3-ylmethoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.76 (ddd, J = 1.6, 5.6, 8.8 Hz, 1H), 7.62 (t, J = 6.8 Hz, 1H), 7.44 (td, J = 7.6, 12.0 Hz, 1H), 7.37-7.27 (m, 2H), 5.54-5.34 (m, 1H), 5.26 (dd, J = 3.6, 16.8 Hz, 1H), 4.87 (dt, J = 1.2, 7.2 Hz, 2H), 4.62-4.52 (m, 4H), 4.40 (dd, J = 12.4, 18.0 Hz, 1H), 4.29-4.01 (m, 2H), 3.99-3.76 (m, 2H), 3.76-3.53 (m, 2H), 3.53-3.40 (m, 2H), 3.32-3.00 (m, 4H), 3.00-2.70 (m, 2H), 2.66-2.56 (m, 1H). LCMS [M + 1]: 595. |

TABLE 5-continued

Characterization of EXAMPLES 149-205.

| Ex. # | Structure | Spectral Data |
|---|---|---|
| 198 | 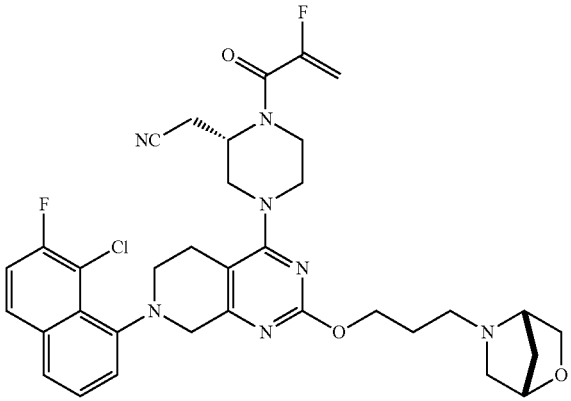<br>2-((S)-4-(2-(3-((1S,4S)-2-oxa-5-azabicyclo[3.3.2]heptan-5-yl)propoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.75 (ddd, J = 1.6, 5.6, 9.2 Hz, 1H), 7.61 (t, J = 6.8 Hz, 1H), 7.43 (td, J = 8.0, 12.4 Hz, 1H), 7.36-7.31 (m, 1H), 7.31-7.25 (m, 1H), 5.52-5.33 (m, 1H), 5.25 (dd, J = 3.6, 16.8 Hz, 1H), 5.08-4.64 (m, 1H), 4.44-4.32 (m, 4H), 4.20-3.99 (m, 3H), 3.95-3.78 (m, 2H), 3.64-3.53 (m, 2H), 3.51-3.39 (m, 2H), 3.29-2.99 (m, 4H), 2.96-2.67 (m, 5H), 2.64-2.51 (m, 2H), 1.94 (quin, J = 6.8 Hz, 2H), 1.86 (dd, J = 1.2, 9.6 Hz, 1H), 1.72 (br dd, J = 1.2, 9.6 Hz, 1H). LCMS [M + 1]: 664. |
| 199 | 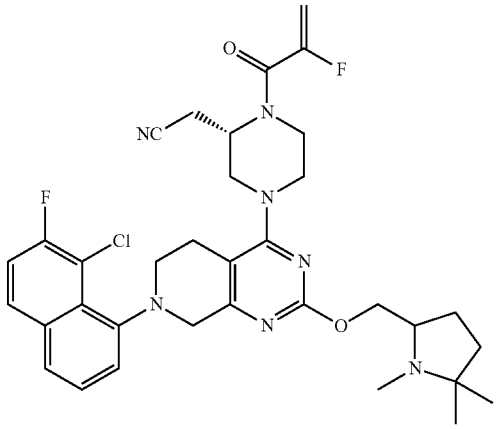<br>2-((2S)-4-(7-(8-chloro-7-fluoronaphthalen-1-yl)-2-((1,5,5-trimethylpyrrolidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.79-7.72 (m, 1H), 7.61 (t, J = 7.6 Hz, 1H), 7.48-7.38 (m, 1H), 7.37-7.27 (m, 2H), 5.55-5.34 (m, 1H), 5.26 (dd, J = 3.6, 17.2 Hz, 1H), 5.11-4.75 (m, 1H), 4.50-4.34 (m, 2H), 4.24-3.99 (m, 3H), 3.96-3.80 (m, 2H), 3.61-3.53 (m, 1H), 3.49-3.37 (m, 1H), 3.30-2.93 (m, 5H), 2.93-2.73 (m, 2H), 2.65-2.54 (m, 1H), 2.32 (br s, 3H), 2.14-2.00 (m, 1H), 1.77-1.62 (m, 3H), 1.14 (br s, 3H), 0.92 (br s, 3H); LCMS [M + 1]: 650. |

TABLE 5-continued

Characterization of EXAMPLES 149-205.

| Ex. # | Structure | Spectral Data |
|---|---|---|
| 200 | 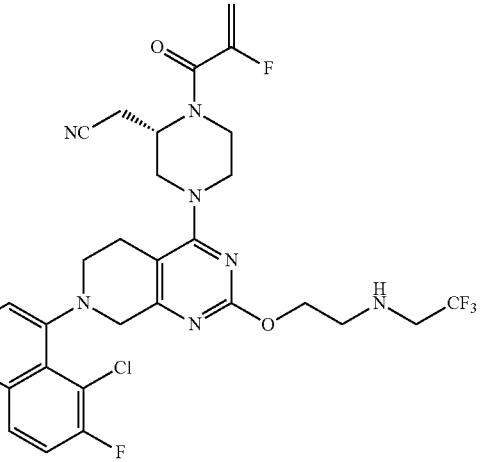<br>(S)-2-(4-(7-(8-chloro-7-fluoronaphthalen-1-yl)-2-(2-((2,2,2-trifluoroethyl)amino)ethoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.76 (m, 1H), 7.64-7.60 (m, 1H), 7.47-7.40 (m, 1H), 7.36-7.25 (m, 2H), 5.49-5.37 (m, 1H), 5.29-5.24 (m, 1H), 5.06-4.55 (m, 1H), 4.44-4.35 (m, 3H), 4.25-3.79 (m, 4H), 3.60-3.56 (m, 1H), 3.50-3.41 (m, 1H), 3.30-3.04 (m, 8H), 2.97-2.74 (m, 2H), 2.65-2.56 (m, 1H). LCMS [M + 1]: 650. |
| 201 | 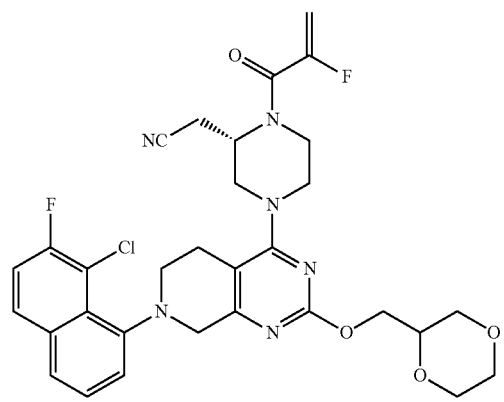<br>2-((2S)-4-(2-((1,4-dioxan-2-yl)methoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ 7.76 (ddd, J = 1.2, 5.6, 9.2 Hz, 1H), 7.61 (t, J = 6.8 Hz, 1H), 7.48-7.38 (m, 1H), 7.37-7.27 (m, 2H), 5.54-5.33 (m, 1H), 5.26 (dd, J = 3.6, 16.8 Hz, 1H), 4.45-4.19 (m, 4H), 4.18-3.97 (m, 3H), 3.96-3.62 (m, 7H), 3.61-3.40 (m, 3H), 3.32-2.72 (m, 6H), 2.67-2.51 (m, 1H). LCMS [M + 1]: 625. |

TABLE 5-continued

Characterization of EXAMPLES 149-205.

| Ex. # | Structure | Spectral Data |
|---|---|---|
| 202 | 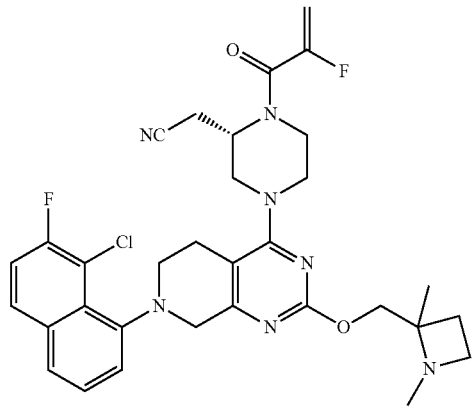<br>2-((2S)-4-(7-(8-chloro-7-fluoronaphthalen-1-yl)-2-((1,2-dimethylazetidin-2-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.78-7.72 (m, 2H), 7.61 (t, J = 7.2 Hz, 2H), 7.45-7.39 (m, 2H), 7.44 (br t, J = 7.8 Hz, 1H), 7.35-7.28 (m, 3H), 7.26-7.21 (m, 1H), 5.48 (br s, 1H), 5.36 (br s, 1H), 5.26 (dd, J = 3.6, 16.8 Hz, 2H), 4.92 (br s, 1H), 4.50-4.31 (m, 3H), 4.27-4.16 (m, 5H), 4.16-3.99 (m, 3H), 3.98-3.72 (m, 4H), 3.68-3.48 (m, 3H), 3.42 (br s, 4H), 3.28-3.02 (m, 10H), 3.01-2.75 (m, 4H), 2.72-2.46 (m, 2H), 2.37-2.22 (m, 8H), 1.93-1.73 (m, 5H), 1.36 (t, J = 3.6 Hz, 6H). LCMS [M + 1]: 622.3. |
| 203 | 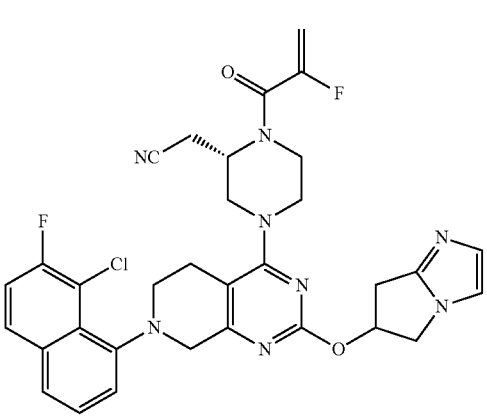<br>2-((2S)-4-(7-(8-chloro-7-fluoronaphthalen-1-yl)-2-((6,7-dihydro-5H-pyrrolo[1,2-a]imidazol-6-yl)oxy)-5,6,7,8-tetrahydropyrido[3,4-d]pyrimidin-4-yl)-1-(2-fluoroacryloyl)piperazin-1-yl)acetonitrile | $^1$H NMR (400 MHz, CDCl$_3$) δ = 7.81-7.72 (m, 1H), 7.63 (t, J = 7.2 Hz, 1H), 7.49-7.40 (m, 1H), 7.34 (t, J = 8.8 Hz, 2H), 7.07 (s, 1H), 6.90-6.86 (m, 1H), 6.00 (ddd, J = 3.2, 6.8, 10.0 Hz, 1H), 5.54-5.34 (m, 1H), 5.31-5.23 (m, 1H), 4.47-4.35 (m, 2H), 4.21-3.79 (m, 5H), 3.60 (br d, J = 10.0 Hz, 1H), 3.52-3.35 (m, 8H), 2.96-2.73 (m, 2H), 2.64 (br d, J = 14.8 Hz, 1H). LCMS [M + 1]: 631.4. |

TABLE 5-continued

Characterization of EXAMPLES 149-205.

| Ex. # | Structure | Spectral Data |
|---|---|---|
| 204 | 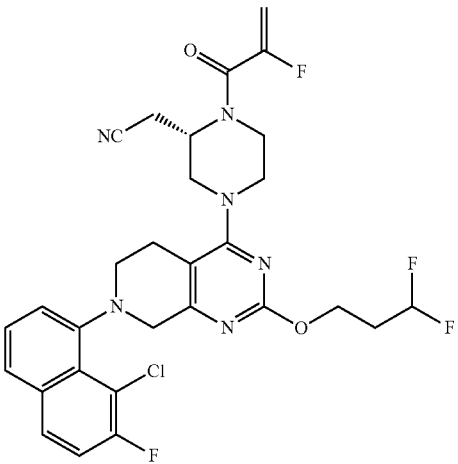<br>(S)-2-(4-(7-(8-chloro-7-fluoronaphthalen-1-yl)-2-(3,3-difluoropropoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.76 (ddd, J = 1.6, 5.6, 8.8 Hz, 1H), 7.62 (t, J = 6.8 Hz, 1H), 7.43 (td, J = 8.0, 12.0 Hz, 1H), 7.37-7.28 (m, 2H), 6.31-5.90 (m, 1H), 5.54-5.33 (m, 1H), 5.26 (dd, J = 3.6, 16.8 Hz, 1H), 5.10-4.66 (m, 1H), 4.47 (q, J = 6.0 Hz, 2H), 4.44-4.35 (m, 1H), 4.28-3.78 (m, 4H), 3.65-3.40 (m, 2H), 3.34-3.02 (m, 4H), 2.99-2.72 (m, 2H), 2.69-2.55 (m, 1H), 2.46-2.24 (m, 2H). LCMS [M + 1]: 603. |
| 205 | 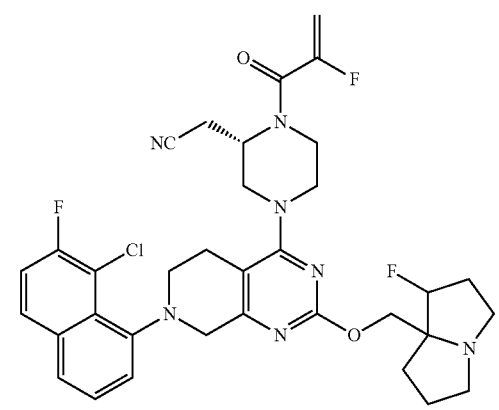<br>2-((2S)-4-(7-(8-chloro-7-fluoronaphthalen-1-yl)-2-((1-fluorotetrahydro-1H-pyrrolizin-7a(5H)-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.74-7.58 (m, 1H), 7.60 (t, J = 7.2 Hz, 1H), 7.46-7.37 (m, 1H), 7.35-7.27 (m, 2H), 5.52-5.32 (m, 1H), 5.30-4.98 (m, 2H), 4.96-4.70 (m, 1H), 4.50-4.34 (m, 2H), 4.20-4.00 (m, 3H), 3.98-3.79 (m, 2H), 3.62-3.34 (m, 2H), 3.31-2.98 (m, 6H), 2.95-2.72 (m, 3H), 2.64-2.48 (m, 2H), 2.38-2.26 (m, 1H), 2.16-1.94 (m, 2H), 1.89-1.77 (m, 2H), 1.41-1.19 (m, 1H). LCMS [M + 1]: 666. |

Example 206

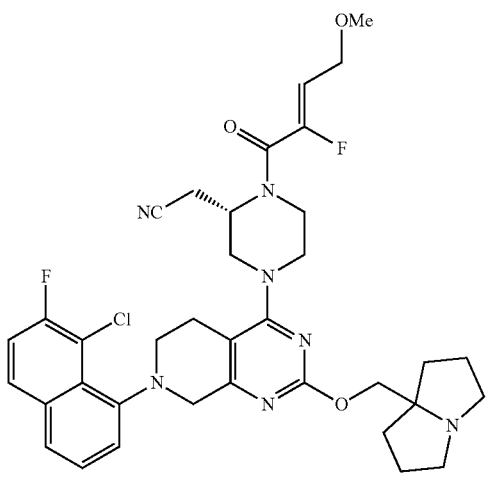 [SMILES: COC/C=C(\F)C(=O)N1CCN(c2nc(OCC34CCCN3CCC4)nc3c2CCN(c2cccc4ccc(F)c(Cl)c24)C3)C[C@@H]1CC#N]

(S, Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoro-4-methoxybut-2-enoyl)piperazin-2-yl)acetonitrile

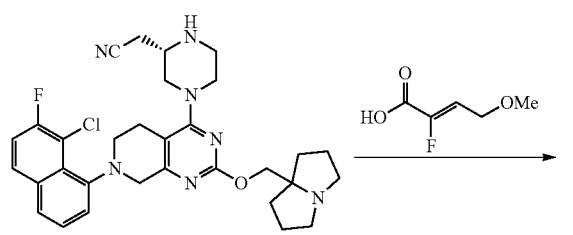

To a mixture of (S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (180 mg, 312 µmol, 1 eq), TEA (379 mg, 3.75 mmol, 522 µL, 12 eq), 4 Å molecular sieves (50 mg) and (Z)-2-fluoro-4-methoxybut-2-enoic acid (83.8 mg, 625 µmol, 2 eq) in ethyl acetate (5 mL) was added T3P (1.19 g, 1.87 mmol, 1.11 mL, 50% purity in ethyl acetate, 6 eq) at 0° C. The mixture was stirred at 0° C. for 30 minutes, then diluted with ethyl acetate (5.0 mL), washed with water (3.0 mL) and brine (3.0 mL), dried over $Na_2SO_4$, filtered and concentrated in vacuo. The residue was purified by prep-HPLC (column: Waters Xbridge 150*25 mm*5 µm; mobile phase: [water (10 mM $NH_4HCO_3$)-ACN]; B %: 38%-68%, 10 min) affording (S,Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoro-4-methoxybut-2-enoyl)piperazin-2-yl)acetonitrile (72 mg, 33% yield) as a yellow solid. LCMS [M+1]: 692.4.

SFC conditions: Column: Chiralpak IC-3 50×4.6 mm I.D., 3 µm. Mobile phase: Phase A for $CO_2$, and Phase B for MeOH+ACN (0.05% DEA); Gradient elution: 60% MeOH+ACN (0.05% DEA) in $CO_2$. Flow rate: 3 mL/min; Wavelength: 220 nm. Column Temp: 35C; Back Pressure: 100 Bar.

$^1$H NMR (400 MHz, $CDCl_3$) δ=7.79-7.71 (m, 1H), 7.60 (t, J=7.6 Hz, 1H), 7.47-7.37 (m, 1H), 7.35-7.28 (m, 2H), 7.23 (br d, J=7.2 Hz, 1H), 5.99-5.72 (m, 1H), 5.07-4.48 (m, 1H), 4.40 (br t, J=16.8 Hz, 1H), 4.28-3.76 (m, 8H), 3.71-3.29 (m, 5H), 3.27-2.77 (m, 8H), 2.69-2.51 (m, 3H), 2.06 (br dd, J=6.0, 12.4 Hz, 2H), 1.85 (br s, 4H), 1.72-1.56 (m, 2H).

Example 207

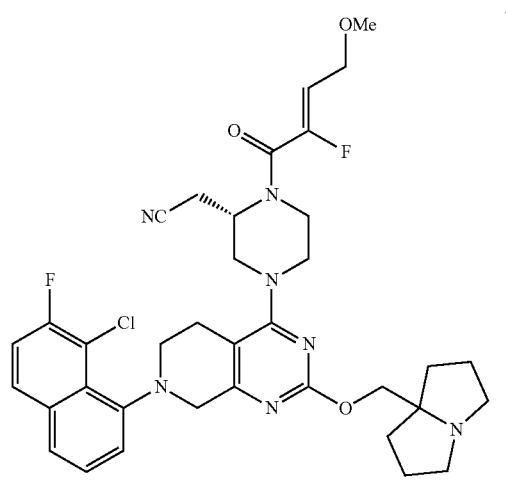

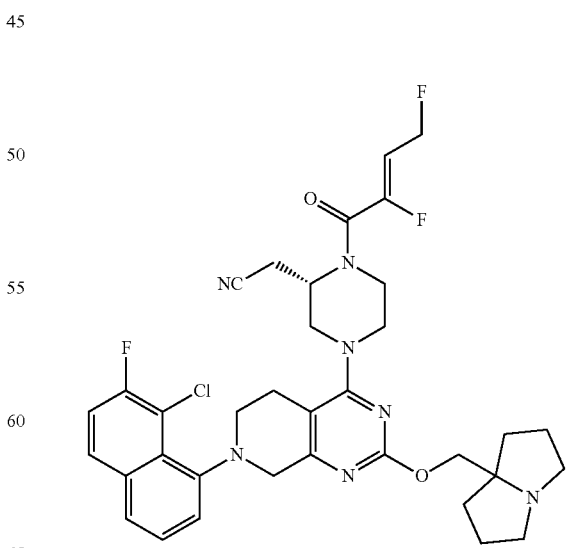

401

(S, Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2,4-difluorobut-2-enoyl)piperazin-2-yl)acetonitrile μmol, 495 μL, 50% purity, 4.0 eq) at 0° C., and the mixture was stirred at 0° C. for 30 minutes. After completion, the reaction mixture was quenched by addition of saturated NH₄Cl (aqueous solution, 5 mL) at 10° C., and then diluted

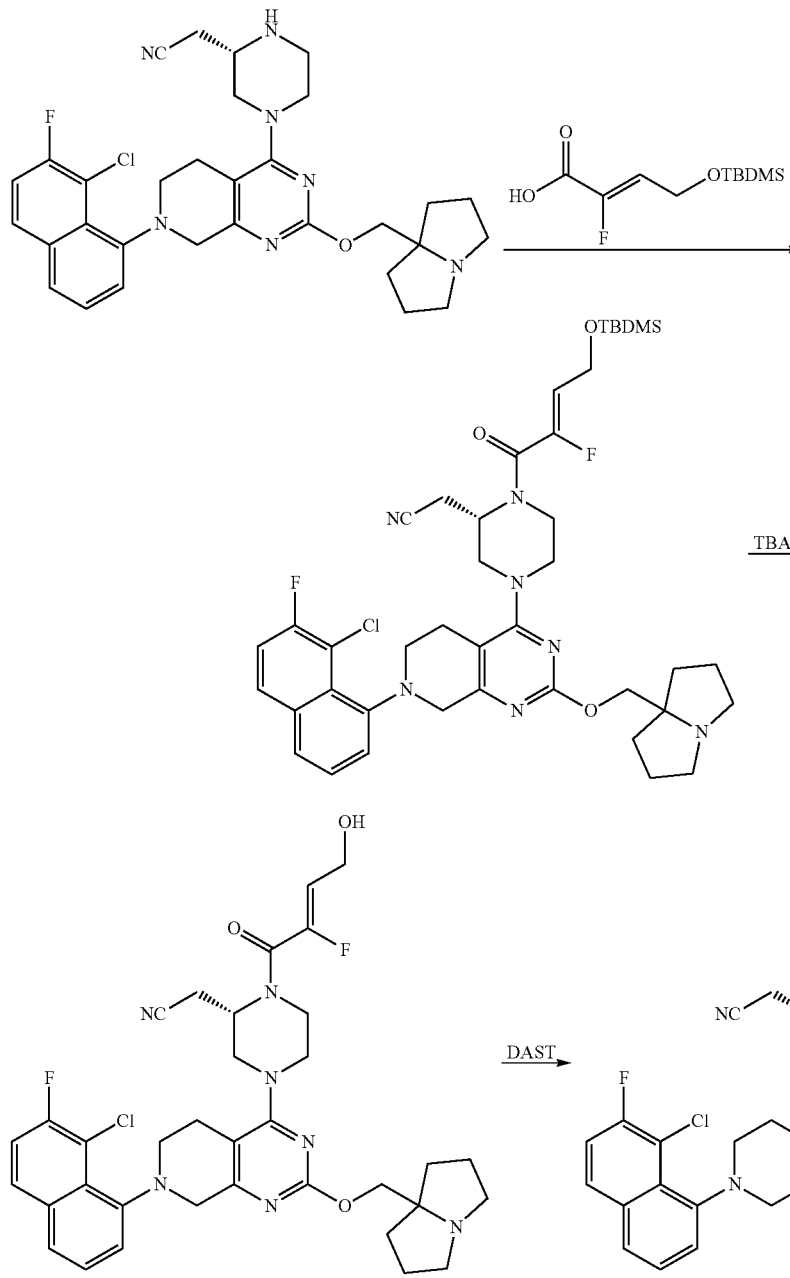

Step A

A mixture of (S)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (120 mg, 208 μmol, 1.0 eq) and (Z)-4-((tert-butyldimethylsilyl)oxy)-2-fluorobut-2-enoic acid (146 mg, 625 μmol, 3.0 eq) in ethyl acetate (2 mL) was added 4 Å molecular sieves (200 mg) and stirred at 0° C. for 30 minutes. Then to the reaction mixture was added TEA (316 mg, 3.12 mmol, 435 μL, 15.0 eq) and T3P (530 mg, 833 with water (10 mL), followed by extraction with ethyl acetate (3×15 mL). The combined organic layers were dried over anhydrous sodium sulfate and filtered. The filtrate was concentrated under reduced pressure to provide (S,Z)-2-(1-(4-((tert-butyldimethylsilyl)oxy)-2-fluorobut-2-enoyl)-4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (190 mg, crude) as a yellow solid. $R_f$=0.30 (dichloromethane/methanol=10/1). LCMS [M+1]: 792.

Step B

To a solution of (S,Z)-2-(1-(4-(((tert-butyldimethylsilyl)oxy)-2-fluorobut-2-enoyl)-4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)piperazin-2-yl)acetonitrile (190 mg, 240 μmol, 1.0 eq) in THF (2.0 mL) was added TBAF (1 M, 479 μL, 2.0 eq), the mixture was stirred at 25° C. for 30 minutes. The mixture was then filtered through a pad of $Al_2O_3$ with ethyl acetate/ethanol (3/1, 100 mL). The filtrate was then concentrated under reduced pressure and the crude product was purified by reversed-phase flash chromatography [water (0.1% formic acid)/acetonitrile] affording (S,Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoro-4-hydroxybut-2-enoyl)piperazin-2-yl)acetonitrile (80.0 mg, 49% yield) as a yellow solid. $R_f$=0.60 (dichloromethane/methanol=5/1). LCMS [M+1]: 678.

Step C

To a solution of (S,Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2-fluoro-4-hydroxybut-2-enoyl)piperazin-2-yl)acetonitrile (80.0 mg, 118 μmol, 1.0 eq) in dichloromethane (1 mL) was added DAST (57.0 mg, 354 μmol, 46.8 μL, 3.0 eq) at 0° C., the mixture was stirred at 0° C. for 30 minutes. After completion, the reaction mixture was quenched by addition of saturated $NaHCO_3$ (aqueous solution, 10 mL) at 0° C., and then diluted with water (5 mL), followed by extraction with ethyl acetate (3×15 mL). The combined organic layers were dried over anhydrous sodium sulfate and filtered. The filtrate was concentrated to dryness and the residue was purified by prep-TLC ($SiO_2$, dichloromethane/methanol=10/1). The desired fractions were concentrated under reduced pressure and the residue was further purified by prep-HPLC (column: Waters Xbridge 150*25 mm*5 μm; mobile phase: [water (10 mM $NH_4HCO_3$)—ACN]; B %: 35%-65%, 10 min) affording (S,Z)-2-(4-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-1-(2,4-difluorobut-2-enoyl)piperazin-2-yl)acetonitrile (3.48 mg, 4% yield, 92.7% purity) as a white solid. $R_f$=0.20 (dichloromethane/methanol=10/1). LCMS [M+1]: 680.7.

SFC conditions: Chiralpak IC-3 column (50×4.6 mm I.D., 3 um), 60% MeOH+ACN (0.05% DEA) in $CO_2$, 3 mL/min, 220 nm; $t_R$: 0.626 min (major), 0.816 min (minor).

$^1$H NMR (400 MHz, $CDCl_3$) δ 7.75 (ddd, J=1.6, 5.6, 8.8 Hz, 1H), 7.61 (t, J=7.2 Hz, 1H), 7.42 (td, J=7.6, 13.2 Hz, 1H), 7.35-7.28 (m, 2H), 6.17-5.72 (m, 1H), 5.29-5.02 (m, 2H), 4.48 (br s, 1H), 4.45-4.34 (m, 1H), 4.17-4.01 (m, 3H), 3.99-3.63 (m, 3H), 3.60-3.50 (m, 1H), 3.49-3.33 (m, 1H), 3.30-3.00 (m, 6H), 2.98-2.77 (m, 2H), 2.71-2.52 (m, 3H), 2.09 (br dd, J=6.0, 12.4 Hz, 2H), 1.87 (br d, J=5.6 Hz, 4H), 1.72-1.69 (m, 2H).

Example 208

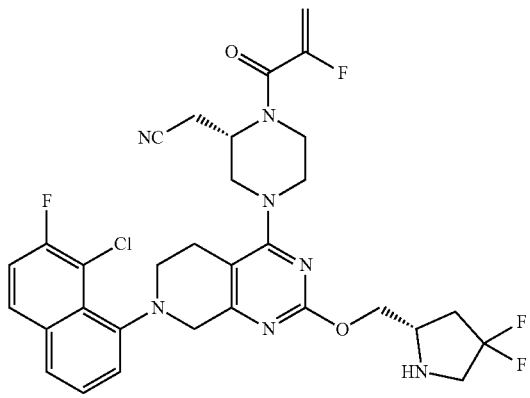 [SMILES: C=C(F)C(=O)N1CCN(c2nc(OC[C@@H]3CC(F)(F)CN3)nc3c2CCN(c2cccc4ccc(F)c(Cl)c24)C3)C[C@@H]1CC#N]

2-((S)-4-(7-(8-chloro-7-fluoronaphthalen-1-yl)-2-(((S)-4,4-difluoropyrrolidin-2-yl)methoxy)-5,6,7,8-tetrahydropyrido[3,4-d]pyrimidin-4-yl)-1-(2-fluoroacryloyl)piperazin-2-yl)acetonitrile

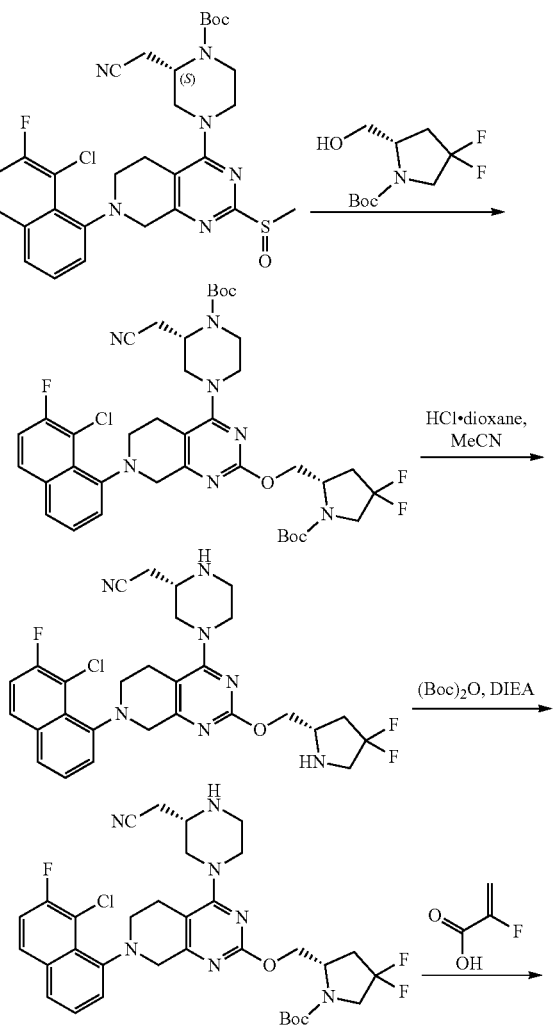

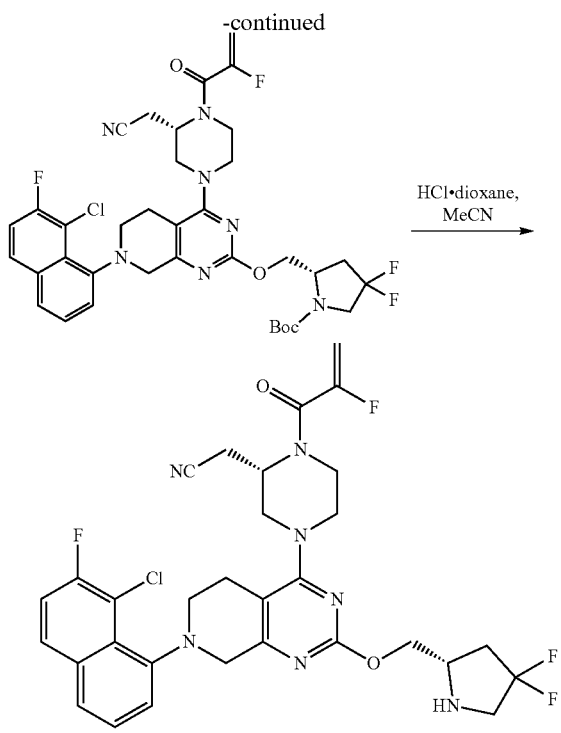

Step A

To a solution of tert-butyl (S)-4,4-difluoro-2-(hydroxymethyl)pyrrolidine-1-carboxylate (713 mg, 3.00 mmol, 3.0 eq) in toluene (6 mL) was added 4 Å molecular sieve (100 mg) and t-BuONa (193 mg, 2.00 mmol, 2.0 eq). After addition, the mixture was stirred at 0° C. for 30 minutes, and then tert-butyl (2S)-4-(7-(8-chloro-7-fluoronaphthalen-1-yl)-2-(methyl sulfinyl)-5,6,7,8-tetrahydropyrido[3,4-d]pyrimidin-4-yl)-2-(cyanomethyl)piperazine-1-carboxylate (600 mg, 1.00 mmol, 1.0 eq) was added to the above mixture at −10° C. The resulting mixture was stirred at −10° C. for 30 minutes. After completion, the reaction mixture was diluted with H$_2$O (15 mL) and extracted with ethyl acetate (3×20 mL). The combined organic layers were washed with saturated brine (80 mL), dried over Na$_2$SO$_4$, filtered and concentrated under reduced pressure to give a residue. The residue was purified by reversed phase flash column chromatography [C18 column, 0.1% formic acid in water, 0-100% MeCN] to provide tert-butyl (S)-4-(2-(((S)-1-(tert-butoxycarbonyl)-4,4-difluoropyrrolidin-2-yl)methoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (370 mg, 41% yield) as a yellow solid. LCMS [M+1]: 772.

Step B

To a solution of tert-butyl (S)-4-(2-(((S)-1-(tert-butoxycarbonyl)-4,4-difluoropyrrolidin-2-yl)methoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (60 mg, 66.0 μmol, 1.0 eq) in MeCN (1 mL) was added HCl.dioxane (4.0 M, 2 mL), the mixture was stirred at 0° C. for 30 minutes. After completion, the reaction mixture was diluted with saturated Na$_2$CO$_3$ aqueous (6 mL) and extracted with ethyl acetate (3×10 mL). The combined organic layers were washed with saturated brine (20 mL), dried over Na$_2$SO$_4$, filtered and concentrated under reduced pressure to give a residue. The residue was purified by reversed phased prep-HPLC (column: Waters Xbridge 150*25 mm*5 μm; mobile phase: [water (10 mM NH$_4$HCO$_3$)-ACN]; B %: 36%-66%, 10 min) and lyophilized to give 2-((S)-4-(7-(8-chloro-7-fluoronaphthalen-1-yl)-2-(((S)-4,4-difluoropyrrolidin-2-yl)methoxy)-5,6,7,8-tetrahydropyrido[3,4-d]pyrimidin-4-yl)piperazin-2-yl)acetonitrile (8.25 mg, 22% yield) as a white solid.
$^1$H NMR (400 MHz, CDCl$_3$) δ 7.76 (dd, J=5.6, 9.2 Hz, 1H), 7.61 (d, J=8.0 Hz, 1H), 7.46-7.40 (m, 1H), 7.36-7.27 (m, 2H), 4.42-4.29 (m, 3H), 4.15-3.72 (m, 4H), 3.59-3.49 (m, 1H), 3.41-3.06 (m, 7H), 3.05-2.82 (m, 2H), 2.59-2.48 (m, 3H), 2.47-2.34 (m, 1H), 2.24-2.04 (m, 1H). LCMS [M+1]: 572.

Step C

To a solution of 2-((S)-4-(7-(8-chloro-7-fluoronaphthalen-1-yl)-2-(((S)-4,4-difluoropyrrolidin-2-yl)methoxy)-5,6,7,8-tetrahydropyrido[3,4-d]pyrimidin-4-yl)piperazin-2-yl)acetonitrile (130 mg, 227 μmol, 1.0 eq) and DIEA (88.1 mg, 682 μmol, 119 μL, 3.0 eq) in DCM (2 mL) was added (Boc)$_2$O (44.6 mg, 204 μmol, 47.0, 0.9 eq). The mixture was stirred at 0° C. for 30 minutes. After completion, the mixture was added water (5 mL) and extracted with ethyl acetate (3×5 mL). The organic layer was dried over Na$_2$SO$_4$, filtered and concentrated. The residue was purified by reversed phase flash Column chromatography [C18, 0.1% formic acid in water 0-80% MeCN] affording tert-butyl (S)-2-(((7-(8-chloro-7-fluoronaphthalen-1-yl)-4-((S)-3-(cyanomethyl)piperazin-1-yl)-5,6,7,8-tetrahydropyrido[3,4-d]pyrimidin-2-yl)oxy)methyl)-4,4-difluoropyrrolidine-1-carboxylate (50 mg, 30% yield, 92.4% purity). Yellow solid; LCMS [M+1]: 672.

Step D

To a solution of tert-butyl (S)-2-(((7-(8-chloro-7-fluoronaphthalen-1-yl)-44(S)-3-(cyanomethyl)piperazin-1-yl)-5,6,7,8-tetrahydropyrido[3,4-d]pyrimidin-2-yl)oxy)methyl)-4,4-difluoropyrrolidine-1-carboxylate (50 mg, 74.4 μmol, 1.0 eq) in ethyl acetate (2 mL) was added TEA (45.2 mg, 446 μmol, 62.1 μL, 6.0 eq), 2-fluoroprop-2-enoic acid (13.4 mg, 149 μmol, 2.0 eq) and T3P (189 mg, 298 μmol, 177 μL, 50% purity, 4.0 eq) at 0° C. The resulting mixture was stirred at 0° C. for 30 minutes. After completion, the reaction mixture was diluted with H$_2$O (10 mL) and extracted with ethyl acetate (3×10 mL). The combined organic layers were washed with saturated brine (20 mL), dried over Na$_2$SO$_4$, filtered and concentrated under reduced pressure affording tert-butyl (S)-2-(((7-(8-chloro-7-fluoronaphthalen-1-yl)-4-((S)-3-(cyanomethyl)-4-(2-fluoroacryloyl)piperazin-1-yl)-5,6,7,8-tetrahydropyrido[3,4-d]pyrimidin-2-yl)oxy)methyl)-4,4-difluoropyrrolidine-1-carboxylate (50 mg, 78% yield, 86.6% purity) as a yellow solid. LCMS [M+1]: 744.

Step E

To a solution of (S)-2-(((7-(8-chloro-7-fluoronaphthalen-1-yl)-4-((S)-3-(cyanomethyl)-4-(2-fluoroacryloyl)piperazin-1-yl)-5,6,7,8-tetrahydropyrido[3,4-d]pyrimidin-2-yl)oxy)methyl)-4,4-difluoropyrrolidine-1-carboxylate (50 mg, 58.4 μmol, 1.0 eq) in MeCN (1 mL) was added HCl (4.0 M in dioxane, 2 mL). The mixture was stirred at 0° C. for 30 minutes. After completion, the reaction mixture was diluted with saturated aqueous Na₂CO₃ (3 mL) and extracted with ethyl acetate (3×5 mL). The combined organic layers were washed with saturated brine (15 mL), dried over Na₂SO₄, filtered and concentrated under reduced pressure to give a residue. The residue was purified by reversed phased prep-HPLC (column: Waters Xbridge 150*25 mm*5 μm; mobile phase: [water (10 mM NH₄HCO₃)-ACN]; B %: 46%-76%, 10 min) and lyophilized to give 2-((S)-4-(7-(8-chloro-7-fluoronaphthalen-1-yl)-2-(((S)-4,4-difluoropyrrolidin-2-yl)methoxy)-5,6,7,8-tetrahydropyrido[3,4-d]pyrimidin-4-yl)-1-(2-fluoroacryloyl)piperazin-2-yl)acetonitrile (14.4 mg, 38% yield) as a white solid. LCMS [M+1]: 644.

SFC conditions: Column: Chiralcel OD-3 50×4.6 mm I.D., 3 μm Mobile phase: Phase A for CO₂, and Phase B for MeOH (0.05% DEA); Gradient elution: 40% MeOH (0.05% DEA) in CO₂ Flow rate: 3 mL/min; Wavelength: 220 nm Column Temp: 35C; Back Pressure: 100 Bar.

¹H NMR (400 MHz, CDCl₃) δ 7.78-7.73 (m, 1H), 7.65-7.60 (m, 1H), 7.47-7.40 (m, 1H), 7.36-7.24 (m, 2H), 5.54-5.34 (m, 1H), 5.26 (dd, J=3.6, 16.8 Hz, 1H), 5.05-4.63 (m, 1H), 4.46-4.31 (m, 3H), 4.27-3.71 (m, 5H), 3.62-3.53 (m, 1H), 3.50-2.74 (m, 9H), 2.65-2.55 (m, 1H), 2.48-2.35 (m, 1H), 2.24-2.06 (m, 1H).

Following the teachings of the General Reaction Schemes, Example 208 and the exemplary intermediates provided herein, Examples 209-214 were synthesized as shown in Table 6.

TABLE 6

Characterization of EXAMPLES 209-214

| Ex. # | Structure | Spectral Data |
|---|---|---|
| 209 | 2-((S)-4-(7-(8-chloro-7-fluoronaphthalen-1-yl)-2-(((2S,4R)-4-fluoropyrrolidin-2-yl)methoxy)-5,6,7,8-tetrahydropyrido[3,4-d]pyrimidin-4-yl)-1-(2-fluoroacryloyl)piperazin-2-yl)acetonitrile | ¹H NMR (400 MHz, CDCl₃) δ = 7.79-7.72 (m, 1H), 7.65-7.59 (m, 1H), 7.47-7.38 (m, 1H), 7.36-7.24 (m, 2H), 5.54-5.14 (m, 3H), 5.07-4.65 (m, 1H), 4.45-4.17 (m, 4H), 4.14-3.78 (m, 4H), 3.62-3.40 (m, 2H), 3.32-2.97 (m, 6H), 2.94-2.72 (m, 2H), 2.67-2.52 (m, 1H), 2.34-2.18 (m, 1H), 1.94-1.87 (m, 1H). LCMS [M + 1]: 626. |
| 210 | 2-((S)-4-(7-(8-chloro-7-fluoronaphthalen-1-yl)-2-(((2S,4R)-4-methoxypyrrolidin-2-yl)methoxy)-5,6,7,8-tetrahydropyrido[3,4-d]pyrimidin-4-yl)-1-(2-fluoroacryloyl)piperazin-2-yl)acetonitrile | ¹H NMR (400 MHz, CDCl₃) δ = 7.75 (dd, J = 5.6, 8.8 Hz, 1H), 7.64-7.58 (m, 1H), 7.47-7.38 (m, 1H), 7.36-7.23 (m, 2H), 5.56-5.32 (m, 1H), 5.26 (dd, J = 3.6, 16.8 Hz, 1H), 5.07-4.67 (m, 1H), 4.39 (br dd, J = 12.8, 17.6 Hz, 1H), 4.30-4.15 (m, 3H), 4.12-3.92 (m, 3H), 3.89-3.78 (m, 1H), 3.76-3.67 (m, 1H), 3.60-3.52 (m, 1H), 3.49-3.37 (m, 1H), 3.30 (s, 3H), 3.27-2.98 (m, 6H), 2.93-2.74 (m, 2H), 2.64-2.53 (m, 1H), 2.10-2.00 (m, 1H), 1.71-1.64 (m, 1H); LCMS [M + 1]: 638. |

TABLE 6-continued

Characterization of EXAMPLES 209-214

| Ex. # | Structure | Spectral Data |
|---|---|---|
| 211 | (S)-2-(4-(7-(8-chloro-7-fluoronaphthalen-1-yl)-2-(2-((2,2-difluoroethyl)amino)ethoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.73 (m, 1H), 7.64-7.59 (m, 1H), 7.48-7.39 (m, 1H), 7.36-7.28 (m, 2H), 6.04-5.66 (m, 1H), 5.54-5.34 (m, 1H), 5.30-5.21 (m, 1H), 5.05-4.65 (m, 1H), 4.48-4.32 (m, 3H), 4.26-4.00 (m, 2H), 3.96-3.75 (m, 2H), 3.63-3.40 (m, 2H), 3.31-2.50 (m, 11H). LCMS [M + 1]: 632. |
| 212 | 2-((S)-4-(7-(8-chloro-7-fluoronaphthalen-1-yl)-2-(((R)-5,5-difluoropiperidin-3-yl)methoxy)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.76 (ddd, J = 1.6, 5.6, 8.8 Hz, 1H), 7.62 (t, J = 6.8 Hz, 1H), 7.43 (td, J = 7.6, 11.6 Hz, 1H), 7.36-7.28 (m, 2H), 5.55-5.34 (m, 1H), 5.26 (dd, J = 3.6, 16.8 Hz, 1H), 5.04-4.66 (m, 1H), 4.40 (br dd, J = 13.2, 17.6 Hz, 1H), 4.28-3.93 (m, 5H), 3.91-3.80 (m, 1H), 3.63-3.41 (m, 2H), 3.36-2.97 (m, 7H), 2.96-2.71 (m, 3H), 2.66-2.50 (m, 2H), 2.39-2.26 (m, 2H), 1.89-1.73 (m, 1H). LCMS [M + 1]: 658. |
| 213 | (S)-2-(4-(2-(azetidin-3-yloxy)-7-(8-chloro-7-fluoro-naphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.79-7.72 (m, 1H), 7.62 (t, J = 7.6 Hz, 1H), 7.43 (td, J = 7.6, 13.2 Hz, 1H), 7.36-7.32 (m, 1H), 7.31 (s, 1H), 5.50-5.35 (m, 2H), 5.26 (dd, J = 4.0, 17.2 Hz, 1H), 5.30-5.22 (m, 1H), 4.88 (br s, 1H), 4.45-4.29 (m, 1H), 4.16-4.04 (m, 1H), 4.03-3.95 (m, 2H), 3.94-3.85 (m, 3H), 3.80 (br d, J = 17.6 Hz, 1H), 3.61-3.41 (m, 2H), 3.38-2.96 (m, 5H), 2.92-2.72 (m, 2H), 2.60 (br d, J = 14.8 Hz, 1H). LCMS [M + 1]: 580.0. |

TABLE 6-continued

Characterization of EXAMPLES 209-214

| Ex. # | Structure | Spectral Data |
|---|---|---|
| 214 | (S)-2-(4-(2-((1-aminocyclobutyl)methoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile | $^1$H NMR (400 MHz, CDCl$_3$) δ = 7.81-7.71 (m, 1H), 7.66-7.58 (m, 1H), 7.48-7.39 (m, 1H), 7.37-7.29 (m, 2H), 5.48-5.33 (m, 1H), 5.26 (dd, J = 3.7, 16.9 Hz, 1H), 5.08-4.57 (m, 1H), 4.45-4.32 (m, 3H), 4.27-4.00 (m, 2H), 3.97-3.81 (m, 2H), 3.64-3.37 (m, 2H), 3.30-3.04 (m, 4H), 2.89-2.54 (m, 3H), 2.29-2.14 (m, 2H), 2.09-1.79 (m, 4H). LCMS [M + 1]: 608. |

Example 215

2-((2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile

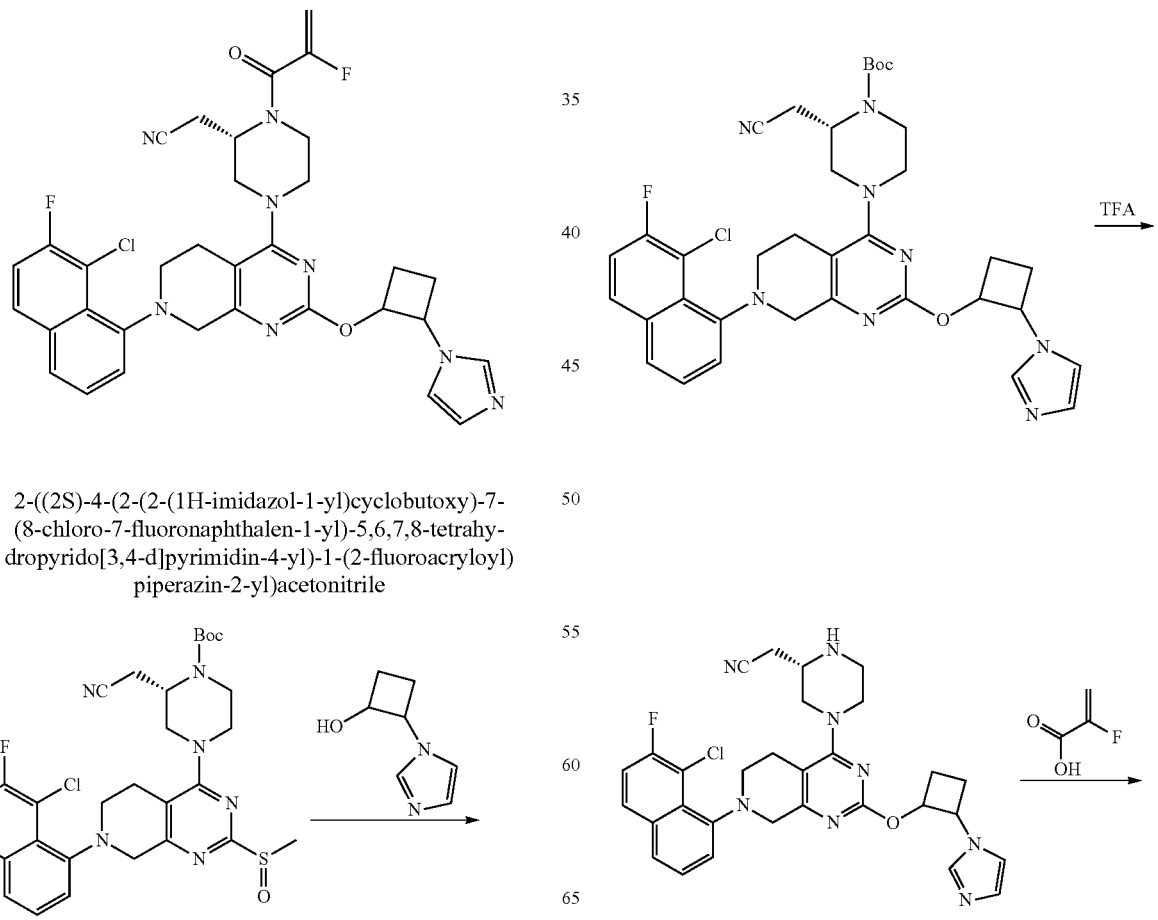

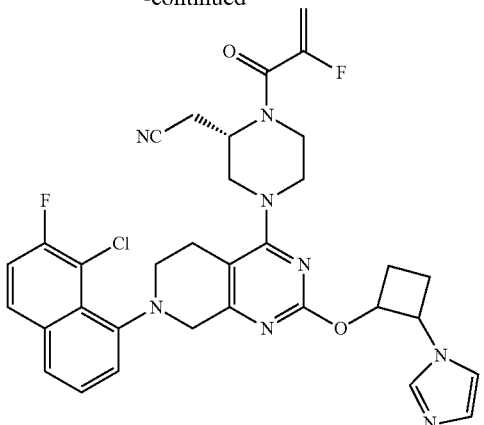

Step A

To a solution of 2-(1H-imidazol-1-yl)cyclobutan-1-ol (166 mg, 1.20 mmol, 3 eq) in DMF (6 mL) was added NaH (48.1 mg, 1.20 mmol, 60% purity, 3 eq) at 0° C. and stirred for 30 minutes. Then tert-butyl (2S)-4-(7-(8-chloro-7-fluoronaphthalen-1-yl)-2-(methylsulfinyl)-5,6,7,8-tetrahydropyrido[3,4-d]pyrimidin-4-yl)-2-(cyanomethyl)piperazine-1-carboxylate (300 mg, 401 μmol, 1 eq) was added, the mixture was stirred at 20° C. for 30 minutes. Upon completion, the reaction was quenched by addition saturated NaHCO₃ and extracted with ethyl acetate (3×50 mL). The combined organic layers were washed with saturated brine (50 mL), dried over Na₂SO₄, filtered, and concentrated under reduced pressure to give a residue. The residue was purified by prep-TLC (DCM:MeOH=10:1) to give tert-butyl (2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (300 mg, 356 μmol, 89% yield) as a yellow oil. LCMS [M+1]: 673.2.

Step B

To a solution of tert-butyl (2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (300 mg, 446 μmol, 1 eq) in DCM (3 mL) was added TFA (3 mL). The mixture was stirred at 20° C. for 30 minutes. Upon completion, the reaction was quenched by addition saturated NaHCO₃ to pH-8.0 and extracted with ethyl acetate (3×50 mL). The combined organic layers were washed with saturated brine (50 mL), dried over Na₂SO₄, filtered, and concentrated under reduced pressure to give a crude product (150 mg) as a white solid. 100 mg of the crude product was used to next step without purification. Another 50 mg of crude product was purified by prep-HPLC (column: Waters Xbridge BEH C18 100*25 mm*5 um; mobile phase: [water (10 mM NH₄HCO₃)-ACN]; B %: 35%-65%, 8 min) affording 2-((2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)piperazin-2-yl)acetonitrile (5.66 mg, 9.85 μmol, 6.6% yield) as a yellow solid.

¹H NMR (400 MHz, CDCl₃) δ 7.75 (dd, J=5.6, 9.2 Hz, 1H), 7.64-7.58 (m, 2H), 7.47-7.40 (m, 1H), 7.33 (dt, J=2.0, 8.8 Hz, 1H), 7.26 (br s, 1H), 7.09-6.99 (m, 2H), 5.52-5.37 (m, 1H), 4.73-4.63 (m, 1H), 4.34-4.22 (m, 1H), 4.05-3.56 (m, 3H), 3.55-3.44 (m, 1H), 3.24-2.98 (m, 5H), 2.96-2.67 (m, 2H), 2.66-2.39 (m, 5H), 2.12-1.94 (m, 2H). LCMS [M+1]: 573.

Step C

To a solution of 2-((2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)piperazin-2-yl)acetonitrile (100 mg, 174 μmol, 1 eq) and 2-fluoroprop-2-enoic acid (31.4 mg, 349 μmol, 2.0 eq) in ethyl acetate (2 mL) was added triethylamine (35.3 mg, 349 μmol, 48.6 μL, 2 eq), then cooled to 0° C., followed by T3P (222 mg, 349 μmol, 207 μL, 50% purity, 2 eq). The reaction was quenched by addition saturated NaHCO₃ and extracted with ethyl acetate (3×50 mL). The combined organic layers were washed with saturated brine (50 mL), dried over Na₂SO₄, filtered, and concentrated under reduced pressure to give a residue. The residue was purified by prep-HPLC (column: Waters Xbridge BEH C18 100*30 mm*10 μm; mobile phase: [water (10 mM NH₄HCO₃)-ACN]; B %: 45%-65%, 10 min) affording 2-((2S)-4-(2-(2-(1H-imidazol-1-yl)cyclobutoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile (23.0 mg, 35.0 μmol, 20% yield) as a white solid. LCMS [M+1]: 645.

SFC condition: Column: CD-PH 150×4.6 mm I.D., 5 μm, Mobile phase A: water with 0.375% TFA B: acetonitrile with 0.1875% A/B=65/35, Flow rate: 1.0 mL/min; Wavelength: 220 nm.

¹H NMR (400 MHz, CDCl₃) δ 7.80-7.71 (m, 1H), 7.66-7.52 (m, 2H), 7.48-7.39 (m, 1H), 7.36-7.29 (m, 1H), 7.27-7.21 (m, 1H), 7.10-6.84 (m, 2H), 5.62-5.32 (m, 2H), 5.30-5.20 (m, 1H), 5.06-4.58 (m, 2H), 4.38-4.19 (m, 1H), 4.14-3.86 (m, 2H), 3.85-3.67 (m, 1H), 3.65-3.46 (m, 2H), 3.44-2.94 (m, 5H), 2.92-2.74 (m, 2H), 2.66-2.42 (m, 3H), 2.23-1.95 (m, 2H).

Example 216

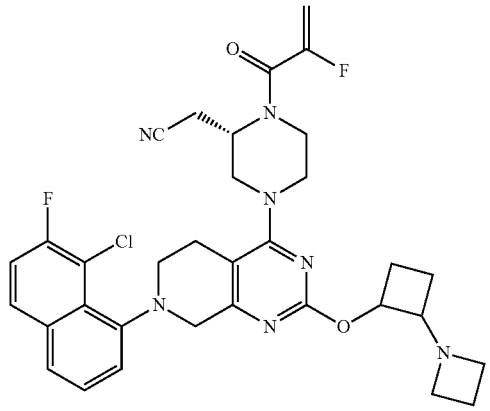 [SMILES: C=C(F)C(=O)N1CCN(c2nc(OC3CCC3N3CCC3)nc3c2CCN(c2cccc4ccc(F)c(Cl)c24)C3)C[C@@H]1CC#N]

2-((2S)-4-(2-(2-(azetidin-1-yl)cyclobutoxy)-7-(8-chloro-7-fluoronaphthalen-1-yl)-5,6,7,8-tetrahydro-pyrido[3,4-d]pyrimidin-4-yl)-1-(2-fluoroacryloyl)piperazin-2-yl)acetonitrile

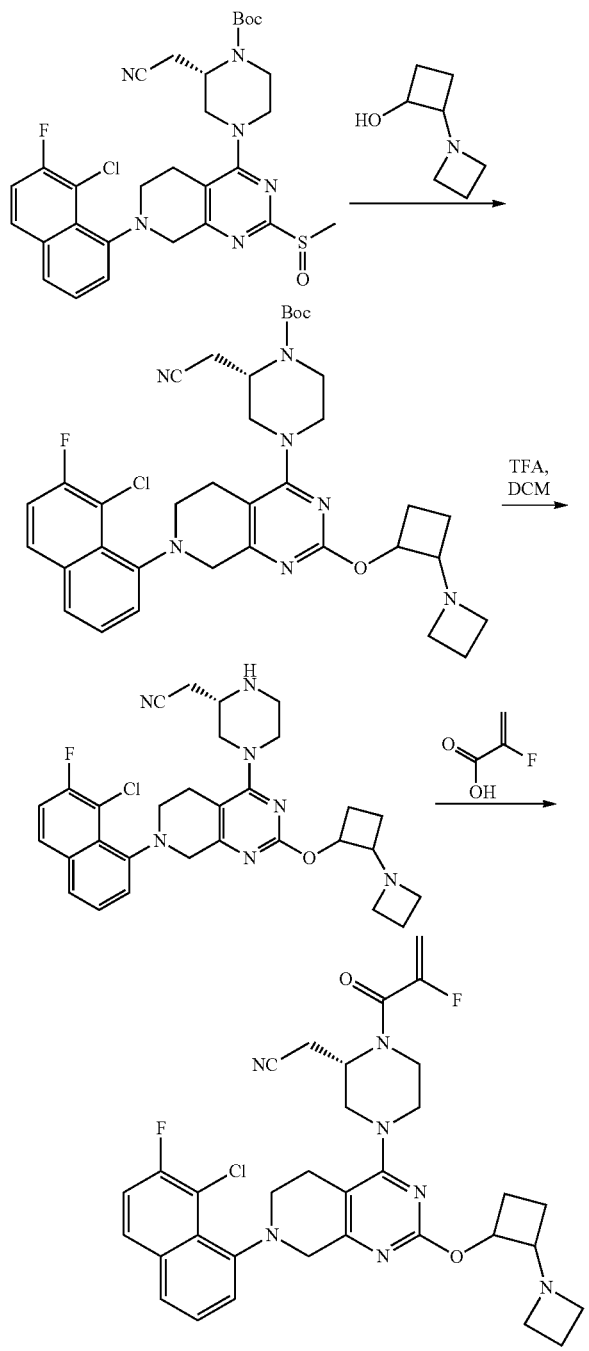

Step A

To a solution of tert-butyl (2S)-4-(7-(8-chloro-7-fluoronaphthalen-1-yl)-2-(methyl sulfinyl)-5,6,7,8-tetrahydropyrido[3,4-d]pyrimidin-4-yl)-2-(cyanomethyl)piperazine-1-carboxylate (200 mg, 334 μmol, 1 eq) and 2-(azetidin-1-yl)cyclobutan-1-ol (127 mg, 1.0 mmol, 3 eq) in toluene (6 mL) was added 4 Å molecular sieves (100 mg) and t-BuONa (48.1 mg, 500.7 μmol, 1.5 eq) at 0° C. and stirred for 1 hour. The reaction was quenched by addition $H_2O$ (50 mL) and extracted with ethyl acetate (3×10 mL). The combined organic layer was washed with sat. NaCl 10 mL, dried over $Na_2SO_4$, filtered, and concentrated under reduced pressure to give a residue. The residue was purified by prep-TLC (Dichloromethane:Methanol=10:1) to give the product tert-butyl (2S)-4-(2-(2-(azetidin-1-yl)cyclobutoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (200 mg, 302.0 μmol, 90% yield) as a yellow oil. LCMS [M+1]: 662.2.

Step B

To a solution of tert-butyl (2S)-4-(2-(2-(azetidin-1-yl)cyclobutoxy)-7-(8-chloro-7-fluoronaphthalen-1-yl)-5,6,7,8-tetrahydropyrido[3,4-d]pyrimidin-4-yl)-2-(cyanomethyl)piperazine-1-carboxylate (200 mg, 302 μmol, 1 eq) in DCM (1 mL) was added TFA (1 mL). The mixture was stirred at 20° C. for 1 hour. Upon completion, the reaction was quenched by addition of sat. $NaHCO_3$ and extracted with ethyl acetate (3×50 mL). The combined organic layers were washed with sat. NaCl (50 mL), dried over $Na_2SO_4$, filtered, and concentrated under reduced pressure to give a crude product (150 mg) as a yellow solid. 100 mg of the crude product was used to next step without purification. Another 50 mg of crude product was purified by prep-HPLC (column: Waters Xbridge BEH C18 100*25 mm*5 μm; mobile phase: [water (10 mM $NH_4HCO_3$)-ACN]; B %: 40%-65%, 8 min) to give 242S)-4-(2-(2-(azetidin-1-yl)cyclobutoxy)-7-(8-chloro-7-fluoronaphthalen-1-yl)-5,6,7,8-tetrahydropyrido[3,4-d]pyrimidin-4-yl)piperazin-2-yl)acetonitrile (7.6 mg, 13.5 μmol, 15% yield) as a yellow solid. LCMS [M+1]: 562.

$^1$H NMR (400 MHz, $CDCl_3$) δ=7.75 (dd, J=5.6, 9.2 Hz, 1H), 7.60 (d, J=8.0 Hz, 1H), 7.46-7.39 (m, 1H), 7.35-7.27 (m, 2H), 5.09-4.99 (m, 1H), 4.37 (br d, J=17.6 Hz, 1H), 4.13-3.89 (m, 1H), 3.89-3.69 (m, 2H), 3.58-3.47 (m, 1H), 3.41-2.78 (m, 12H), 2.58-2.44 (m, 4H), 2.37-2.26 (m, 1H), 2.10-1.98 (m, 2H), 1.72-1.53 (m, 2H).

Step C

To a solution of 2-((2S)-4-(2-(2-(azetidin-1-yl)cyclobutoxy)-7-(8-chloro-7-fluoronaphthalen-1-yl)-5,6,7,8-tetrahydropyrido[3,4-d]pyrimidin-4-yl)piperazin-2-yl)acetonitrile (100 mg, 178 μmol, 1 eq) and 2-fluoroprop-2-enoic acid (32.0 mg, 356 μmol, 2 eq) in ethyl acetate (2 mL) was added TEA (36.0 mg, 356 μmol, 49.5 μL, 2 eq) and cooled to −40° C., then T3P (226 mg, 356 μmol, 212 μL, 50% purity, 2 eq) was added at −40° C. and stirred for 1 hour. The reaction was quenched by addition saturated $NaHCO_3$ and extracted with ethyl acetate (3×50 mL). The combined organic layer was washed with saturated NaCl (50 mL), dried over $Na_2SO_4$, filtered, and concentrated under reduced pressure to give a crude product (150 mg). The crude product was purified by prep-HPLC (column: Waters Xbridge BEH C18 100*25 mm*5 μm; mobile phase: [water (10 mM $NH_4HCO_3$)-ACN]; B %: 45%-70%, 8 min) to give the product 2-((2S)-4-(2-(2-(azetidin-1-yl)cyclobutoxy)-7-(8-chloro-7-fluoronaphthalen-1-yl)-5,6,7,8-tetrahydropyrido[3,4-d]pyrimidin-4-yl)-1-(2-fluoroacryloyl)piperazin-2-yl)acetonitrile (19.4 mg, 17% yield) as a white solid. LCMS [M+1]: 634.

SFC condition: Column: CD-PH 150×4.6 mm I.D., 5 um, Mobile phase A: water with 0.375% TFA B: acetonitrile with 0.1875% A/B=65/35, Flow rate: 1.0 mL/min; Wavelength: 220 nm.

$^1$H NMR (400 MHz, CDCl$_3$) δ 7.80-7.72 (m, 1H), 7.61 (t, J=7.6 Hz, 1H), 7.43 (td, J=7.6, 12.0 Hz, 1H), 7.36-7.27 (m, 2H), 5.53-5.33 (m, 1H), 5.26 (br dd, J=3.2, 16.8 Hz, 1H), 5.11-4.74 (m, 2H), 4.45-4.34 (m, 1H), 4.20-4.00 (m, 2H), 3.95-3.76 (m, 2H), 3.63-3.52 (m, 1H), 3.49-3.38 (m, 1H), 3.34-3.04 (m, 9H), 2.95-2.73 (m, 2H), 2.65-2.44 (m, 2H), 2.38-2.27 (m, 1H), 2.11-1.98 (m, 2H), 1.67-1.57 (m, 2H).

Following the teachings of the General Reaction Schemes and the exemplary intermediates provided herein, Examples 217-228 shown in Table 7 may be synthesized:

TABLE 7

EXAMPLES 217-228

| Example | Structure |
|---|---|
| 217 | 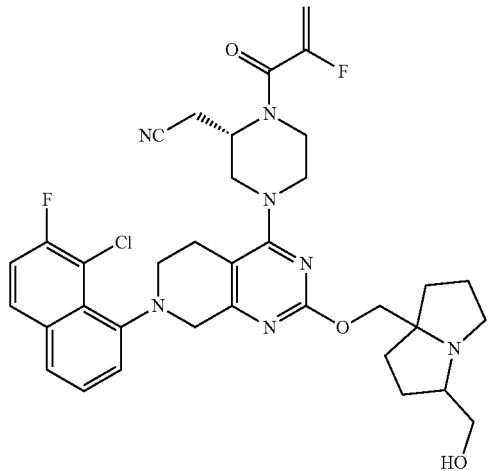 [SMILES: C=C(F)C(=O)N1CCN(c2nc(OCC34CCCN3C(CO)CC4)nc3c2CCN(c2cccc4ccc(F)c(Cl)c24)C3)C[C@@H]1CC#N] |
| 218 | 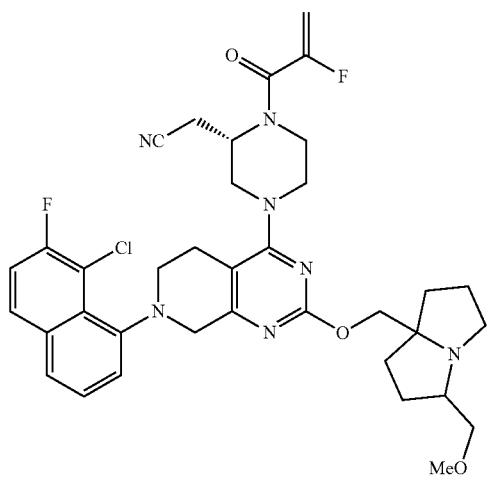 [SMILES: C=C(F)C(=O)N1CCN(c2nc(OCC34CCCN3C(COC)CC4)nc3c2CCN(c2cccc4ccc(F)c(Cl)c24)C3)C[C@@H]1CC#N] |

TABLE 7-continued

EXAMPLES 217-228

| Example | Structure |
|---|---|
| 219 | 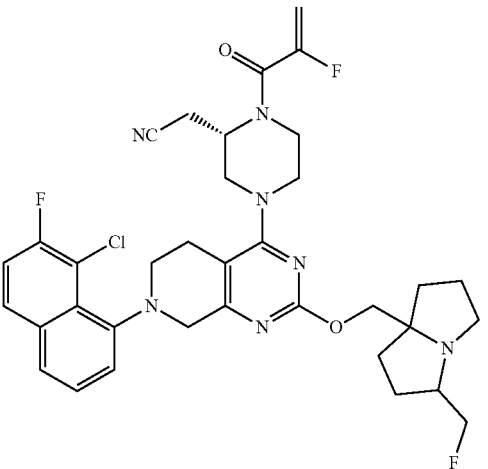 [SMILES: C=C(F)C(=O)N1CCN(c2nc(OCC34CCCN3C(CF)CC4)nc3c2CCN(c2cccc4ccc(F)c(Cl)c24)C3)C[C@@H]1CC#N] |
| 220 | 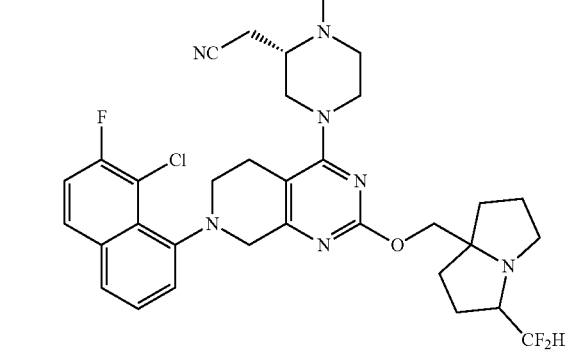 |
| 221 | 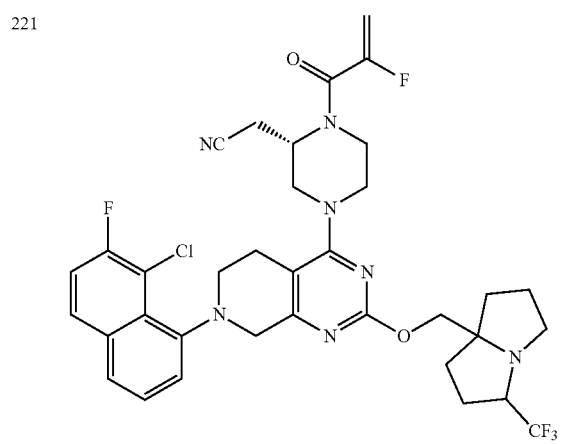 |

TABLE 7-continued
EXAMPLES 217-228
| Example | Structure |
|---|---|
| 222 | 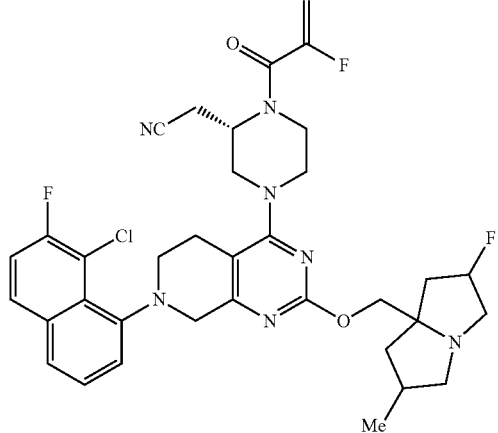 [SMILES: C=C(F)C(=O)N1CCN(c2nc(OCC34CC(C)CN3CC(F)C4)nc3c2CCN(c2cccc4ccc(F)c(Cl)c24)C3)C[C@@H]1CC#N] |
| 223 | 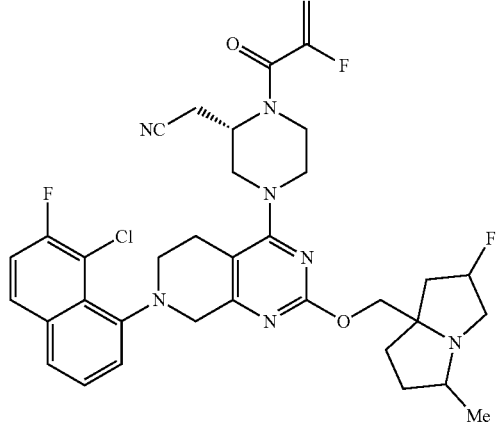 [SMILES: C=C(F)C(=O)N1CCN(c2nc(OCC34CCC(C)N3CC(F)C4)nc3c2CCN(c2cccc4ccc(F)c(Cl)c24)C3)C[C@@H]1CC#N] |
| 224 | 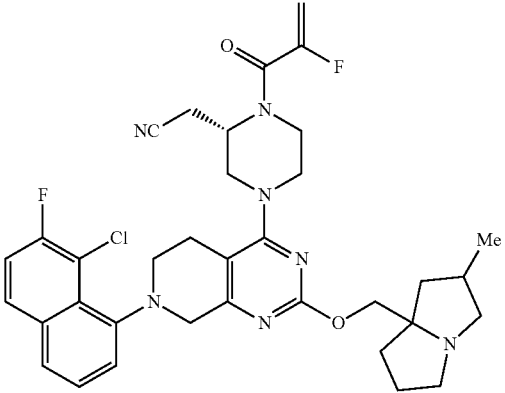 [SMILES: C=C(F)C(=O)N1CCN(c2nc(OCC34CCCN3CC(C)C4)nc3c2CCN(c2cccc4ccc(F)c(Cl)c24)C3)C[C@@H]1CC#N] |
| 225 | 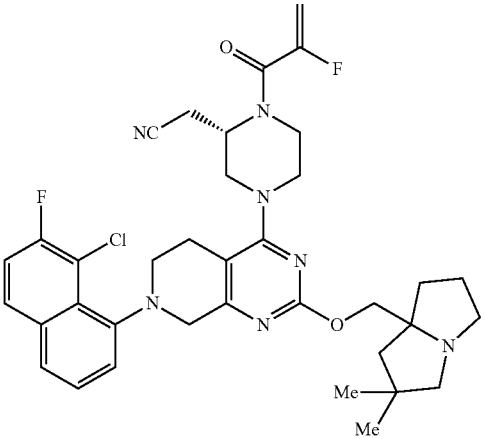 [SMILES: C=C(F)C(=O)N1CCN(c2nc(OCC34CCCN3CC(C)(C)C4)nc3c2CCN(c2cccc4ccc(F)c(Cl)c24)C3)C[C@@H]1CC#N] |
| 226 | 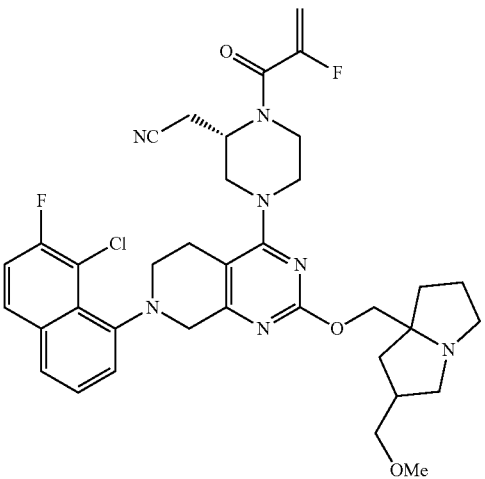 [SMILES: C=C(F)C(=O)N1CCN(c2nc(OCC34CCCN3CC(COC)C4)nc3c2CCN(c2cccc4ccc(F)c(Cl)c24)C3)C[C@@H]1CC#N] |
| 227 | 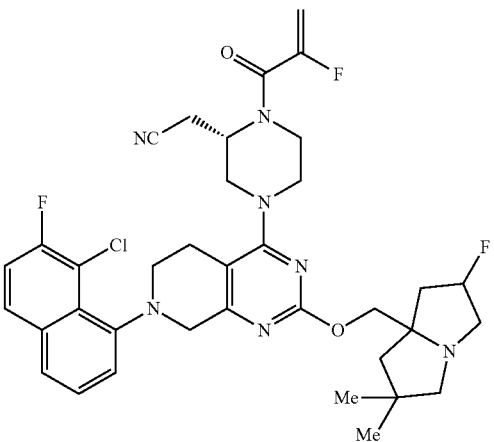 [SMILES: C=C(F)C(=O)N1CCN(c2nc(OCC34CC(F)CN3CC(C)(C)C4)nc3c2CCN(c2cccc4ccc(F)c(Cl)c24)C3)C[C@@H]1CC#N] |

TABLE 7-continued

EXAMPLES 217-228

| Example | Structure |
|---|---|
| 228 | 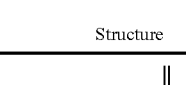 |

Example A

KRas G12C Modification Assay

This Example illustrates that exemplary compounds of the present invention covalently bind to KRas G12C using a LCMS assay to detect a covalent adduct of the exemplary compound and KRAS G12C.

The protein concentration of GDP-loaded K-Ras (1-169) G12C, C51S, C80 L, C118S and GTP-loaded K-Ras (1-169) G12C, C51S, C80 L, C118S, Q61H was adjusted to 2 µM in K-Ras Assay Buffer (25 mM HEPES, 150 mM NaCl, 5 mM $MgCl_2$, and 10 mM Octyl β-glucopyranoside at pH 7.5). A 10 µL aliquot of each protein solution was then transferred to a 384 well microtiter plate. Initial compound stocks were generated at fifty times their desired final assay concentration in DMSO.

Exemplary compounds of Formula (II) were diluted 25-fold into K-Ras Assay Buffer to a final of two times their final concentration. A 10 µL aliquot of each diluted compound solution was then added to each of the protein solutions in the microtiter plate to initiate reaction. Typical final compound concentrations were 3.0, 5.0 and 25.0 µM. At each time point, the reactions were quenched with 20 µL of a 25 mM acetic acid solution. Usual assay endpoints were 15, 180 and 1440 minutes. Once all reactions were quenched, the plates were heat sealed and the samples were injected into a LC/MS system for data acquisition.

Data collection took place on an Agilent 6520 Q-TOF Accurate Mass Spectrometer. Samples were injected in their liquid phase onto a C-3 reverse phase column to remove assay buffer and prepare the samples for mass spectrometer. The proteins were eluted from the column using an acetonitrile gradient and fed directly into the mass analyzer. Initial raw data analysis took place in Agilent MassHunter software immediately post data acquisition.

Raw data analysis of the intact protein was exclusively a deconvolution of the multiple charge states of each protein in solution using a maximum entropy deconvolution provided in Mass Hunter. To minimize complexity, only the data over limited mass ranges were considered for analysis, with a minimum of one Dalton mass step intervals. The heights of all masses identified during raw data analysis were exported to be further analyzed in Spotfire® data analysis software.

Final data analysis was a multistep process in the Spotfire® data analysis software package. Briefly, each protein mass was calculated as a percent of the total signal of that sample, that percentage was then normalized to the percentage of signal of the protein in the absence of reactive compounds. Those normalized signals were reported as normalized percent of control (POC). An increased POC value indicates a compound that displays a higher degree of modification at a given condition compared to other compounds under the same conditions. The results for exemplary compounds of Formula (II), Formula II-A and Formula II-B tested at 5 µM concentration for 3 hours are shown in Table 8. Key: "A"≤25% POC; "B"≥25% POC—≤50% POC; "C">50% POC and ND=not determined.

TABLE 8

Inhibition of KRas G12C Activity by Exemplary Compounds of Formula (II)

| Example No. | POC |
|---|---|
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | A |
| 15 | C |
| 16 | A |
| 17 | B |
| 18 | C |
| 19 | C |
| 20 | C |
| 21 | A |
| 22 | C |
| 23 | C |
| 24 | C |
| 25 | C |
| 26 | C |
| 27 | C |
| 28 | C |
| 29 | C |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | A |
| 42 | C |
| 43 | A |
| 53 | C |
| 54 | B |
| 55 | C |

Example B

Inhibition of KRas G12C-Dependent Cell Growth

This Example illustrates that exemplary compounds of the present invention inhibit the growth of tumor cell lines that express KRas G12C.

The cellular inhibition of KRAs G12C by exemplary compounds of the present invention was determined by measuring the amount of a downstream marker of KRas activity, phosphorylated ERK ("Phospho-ERK").

NCI-H358 cells (ATCC CRL-5807) express KRas G12C and were grown in RPMI medium supplemented with 10% fetal bovine serum, penicillin/streptomycin and 10 mM HEPES. Cells were plated in poly-D-Lysine coated 96-well plates at a concentration of 50,000 cells/well and allowed to attach for 8-12 hours. Diluted compounds were then added at a final concentration of 0.5% DMSO. After 3 hours, the medium was removed, 150 μL of 4% formaldehyde was added and the plates were incubated for 20 minutes. The plates were washed with PBS, and permeabilized using 150 μL of ice cold 100% methanol for 10 minutes. Non-specific antibody binding to the plates was blocked using 100 μL Licor Blocking Buffer (Li-Cor Biotechnology, Lincoln Nebr.) for 1 hour at room temperature. Positive control samples and samples lacking cells were parallel processed with test samples as standards.

The amount Phospho-ERK was determined using an antibody specific for the phosphorylated form of ERK and compared to the amount of GAPDH. Primary antibodies used for detection were added as follows: Phospho-ERK (Cell Signaling cs9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 in Licor Block+0.05% Tween 20 and incubated for 1 hour at room temperature. The plates were washed with PBS+0.05% Tween 20. A 100 μL aliquot of PBS was added to each well and the plates were read on a LICOR AERIUS plate reader.

The pERK(Thr202/Tyr204) signal was normalized with the GAPDH signal and percent of DMSO control values were calculated. $IC_{50}$ values were generated using a 4 parameter fit of the dose response curve. The results for exemplary compounds of Formula (II) are shown in Table 9. Key: "A"≥0.0001-≤1 μM; "B"≥1 μM-≤10 μm, and ND=not determined.

TABLE 9

Inhibition of KRas G12C-mediated Cell Proliferation by Exemplary Compounds

| Example No. | $IC_{50}$ |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | B |
| 18 | A |
| 19 | A |
| 20 | A |
| 21 | A |
| 22 | A |
| 23 | B |
| 24 | A |
| 25 | A |
| 26 | A |
| 27 | A |
| 28 | A |
| 29 | A |
| 30 | A |
| 31 | A |
| 32 | B |
| 33 | A |
| 34 | B |
| 35 | A |
| 36 | A |
| 37 | A |
| 38 | A |
| 39 | A |
| 40 | A |
| 41 | B |
| 42 | A |
| 43 | B |
| 44 | N.D. |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | B |
| 58 | A |
| 59 | A |
| 60 | A |
| 61 | N.D. |
| 74 | A |
| 103 | A |
| 104 | A |
| 105 | A |
| 130 | B |
| 131 | A |
| 132 | B |
| 133 | A |
| 134 | A |
| 135 | A |
| 136 | A |
| 137 | B |
| 138 | A |
| 139 | A |
| 140 | A |
| 141 | A |
| 142 | A |
| 143 | A |
| 144 | A |
| 145 | B |
| 146 | A |
| 147 | A |
| 148 | B |

TABLE 9-continued

Inhibition of KRas G12C-mediated Cell Proliferation by Exemplary Compounds

| Example No. | IC$_{50}$ |
|---|---|
| 149 | B |
| 150 | A |
| 151 | A |
| 152 | B |
| 153 | B |
| 154 | B |
| 155 | A |
| 156 | A |
| 157 | B |
| 158 | A |
| 159 | A |
| 160 | A |
| 161 | A |
| 162 | A |
| 163 | B |
| 164 | B |
| 165 | A |
| 166 | A |
| 167 | A |
| 168 | B |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | B |
| 183 | A |
| 184 | A |
| 185 | A |
| 186 | A |
| 187 | A |
| 188 | A |
| 189 | B |
| 190 | A |
| 191 | A |
| 192 | B |
| 193 | A |
| 194 | A |
| 195 | A |
| 196 | A |
| 197 | A |
| 198 | A |
| 199 | A |
| 200 | A |
| 201 | A |
| 206 | A |
| 207 | A |
| 208 | A |
| 209 | A |
| 210 | A |
| 211 | A |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound, wherein the compound is:

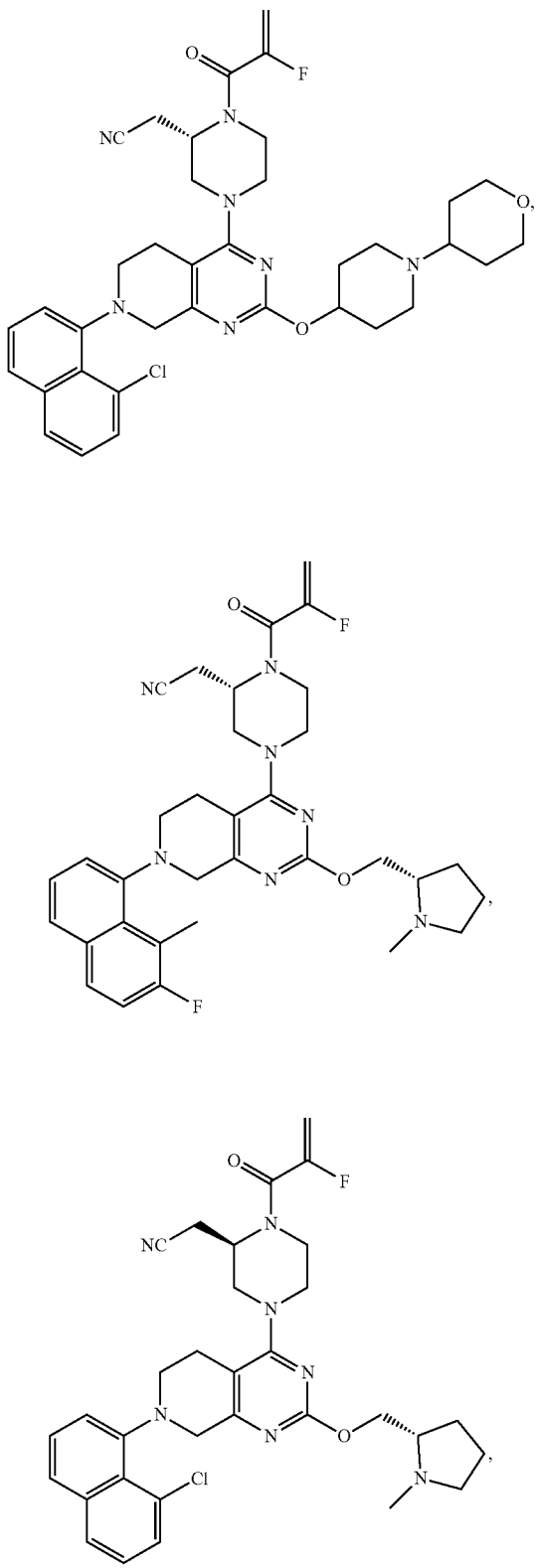

427
-continued
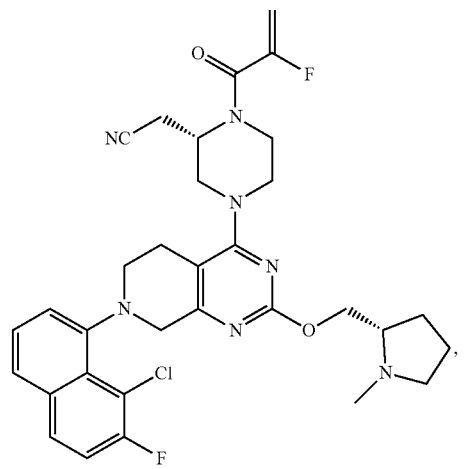
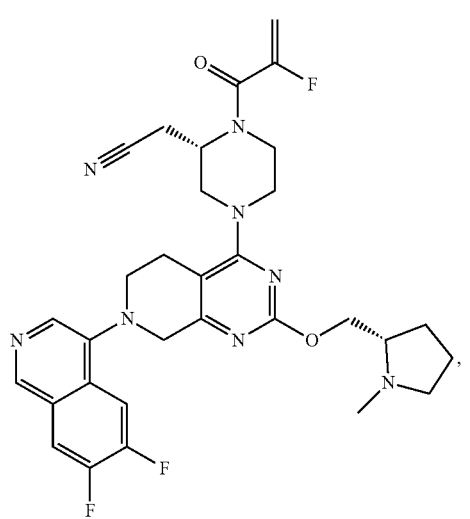
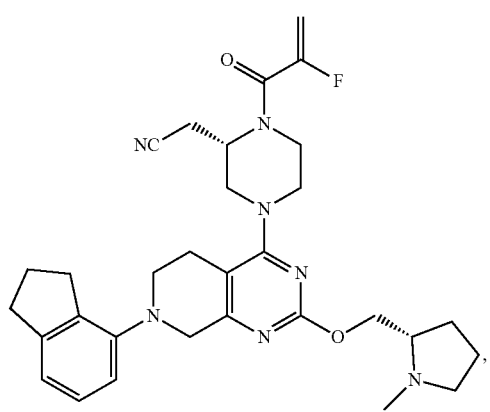
428
-continued
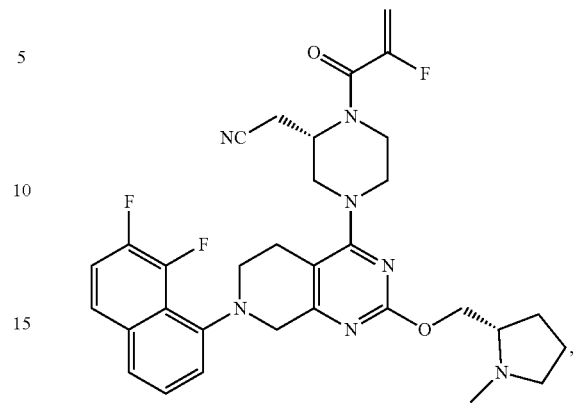
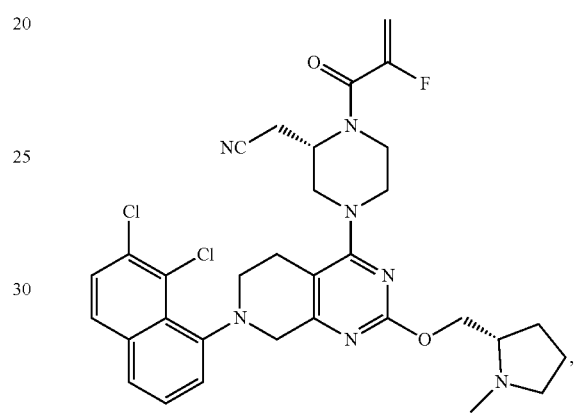
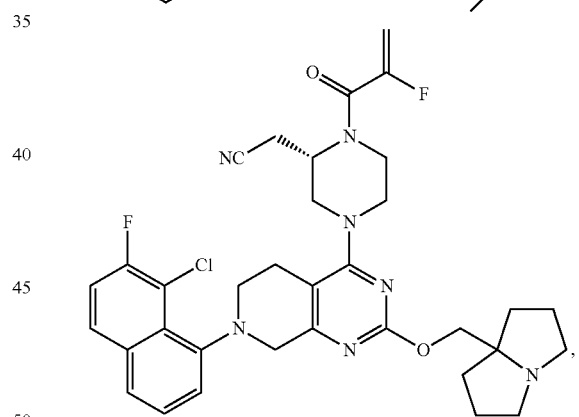
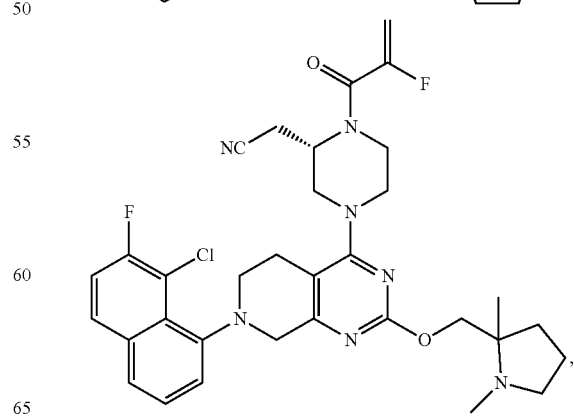

429
-continued
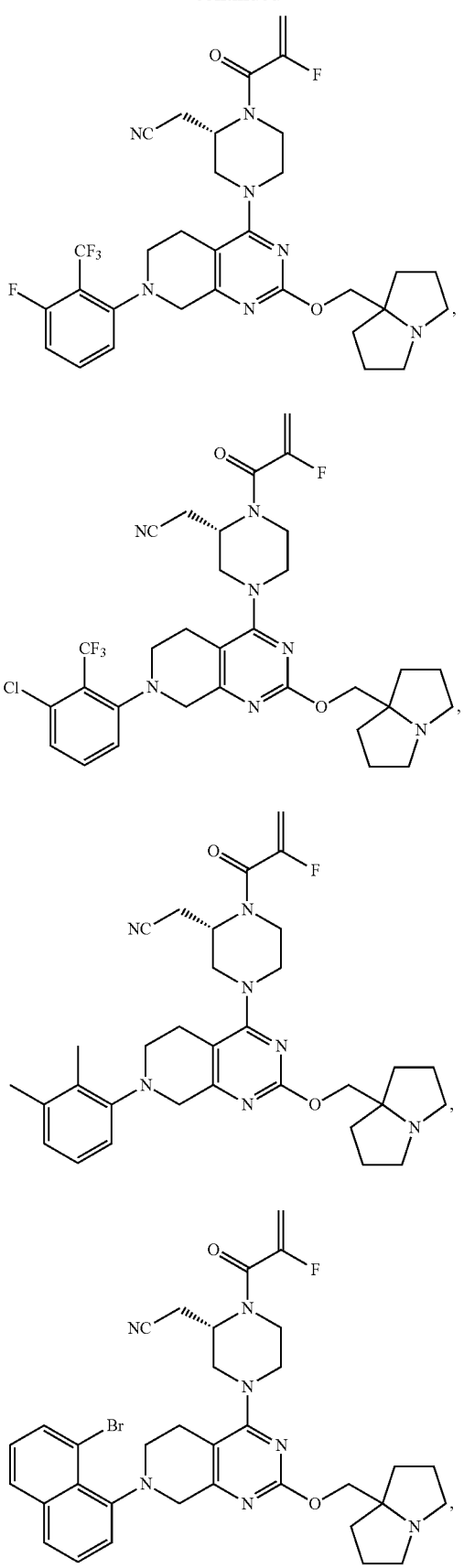 [SMILES: C=C(F)C(=O)N1CCN(c2nc(OCC34CCCN3CCC4)nc3c2CCN(c2cccc(F)c2C(F)(F)F)C3)C[C@@H]1CC#N ; C=C(F)C(=O)N1CCN(c2nc(OCC34CCCN3CCC4)nc3c2CCN(c2cccc(Cl)c2C(F)(F)F)C3)C[C@@H]1CC#N ; C=C(F)C(=O)N1CCN(c2nc(OCC34CCCN3CCC4)nc3c2CCN(c2cccc(C)c2C)C3)C[C@@H]1CC#N ; C=C(F)C(=O)N1CCN(c2nc(OCC34CCCN3CCC4)nc3c2CCN(c2cccc4cccc(Br)c24)C3)C[C@@H]1CC#N]
430
-continued
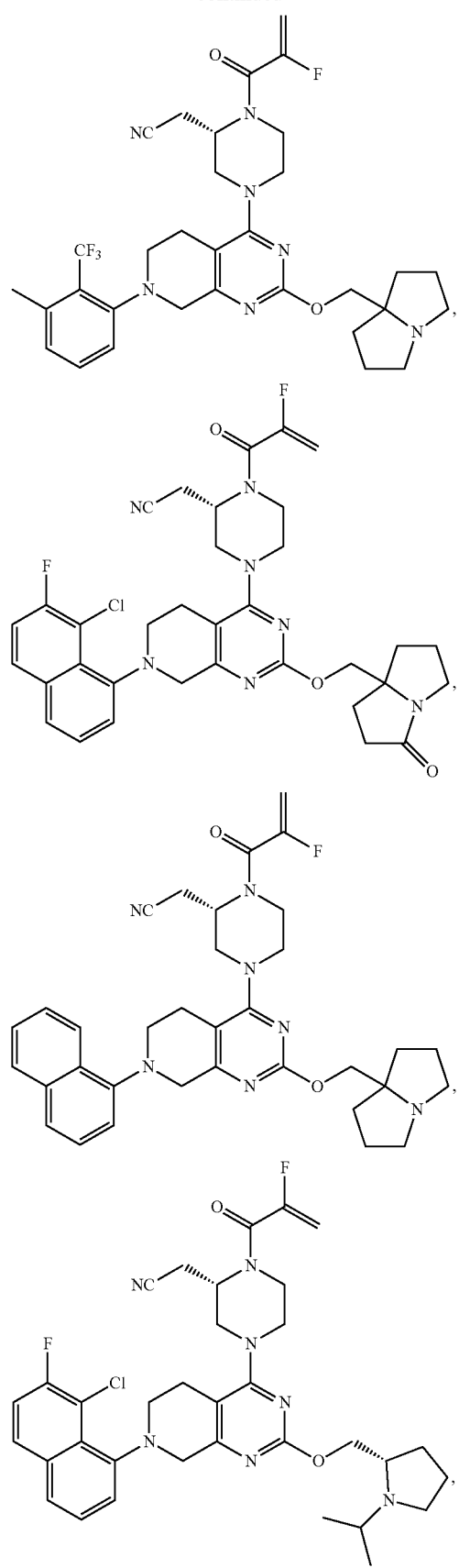 [SMILES: C=C(F)C(=O)N1CCN(c2nc(OCC34CCCN3CCC4)nc3c2CCN(c2cccc(C)c2C(F)(F)F)C3)C[C@@H]1CC#N ; C=C(F)C(=O)N1CCN(c2nc(OCC34CCCN3C(=O)CC4)nc3c2CCN(c2cccc4ccc(F)c(Cl)c24)C3)C[C@@H]1CC#N ; C=C(F)C(=O)N1CCN(c2nc(OCC34CCCN3CCC4)nc3c2CCN(c2cccc4ccccc24)C3)C[C@@H]1CC#N ; C=C(F)C(=O)N1CCN(c2nc(OC[C@@H]3CCCN3C(C)C)nc3c2CCN(c2cccc4ccc(F)c(Cl)c24)C3)C[C@@H]1CC#N]

431
-continued
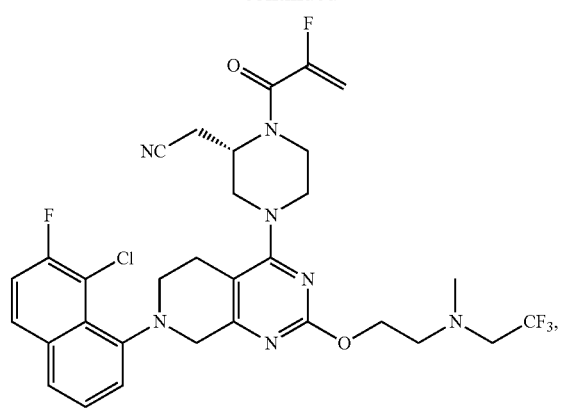
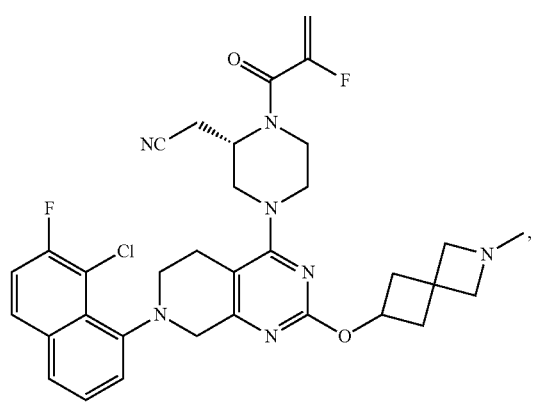
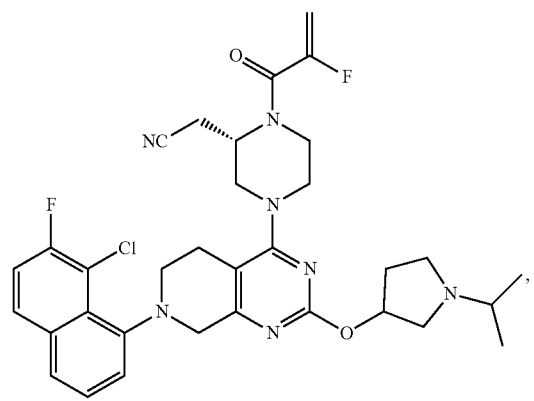
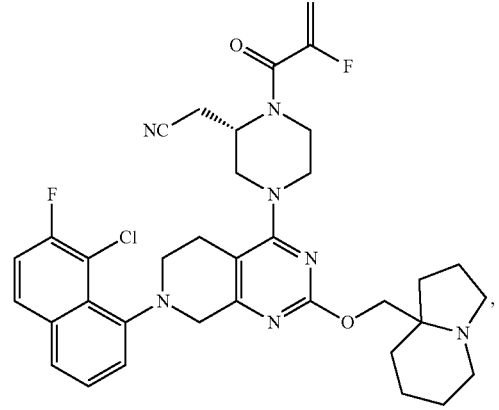
432
-continued
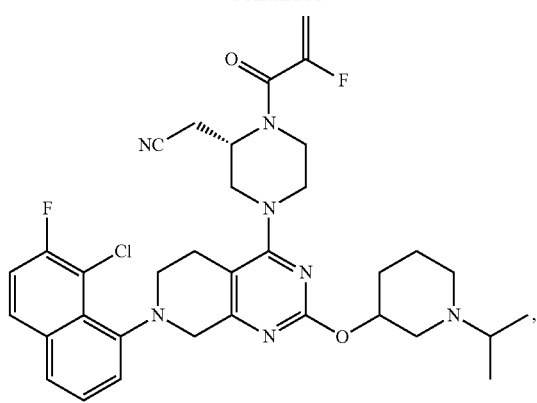
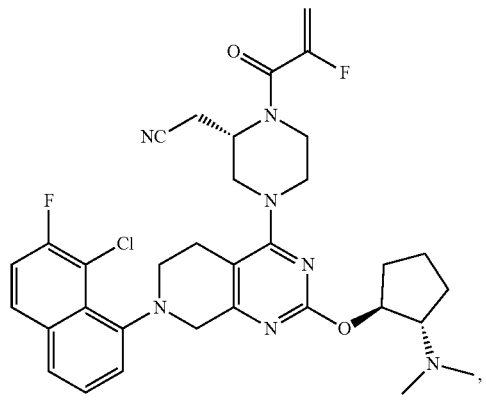
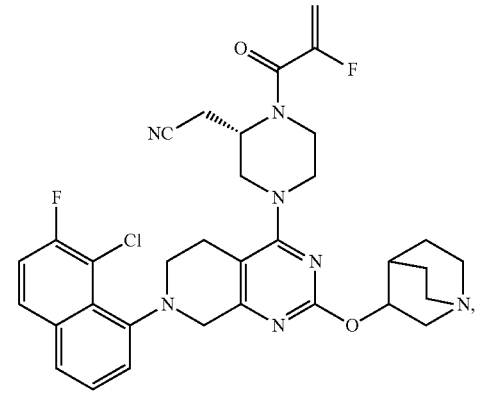
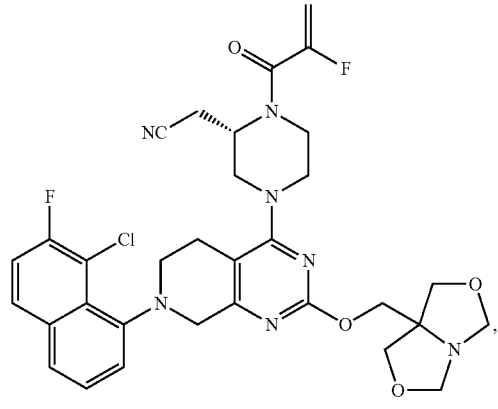

433
-continued
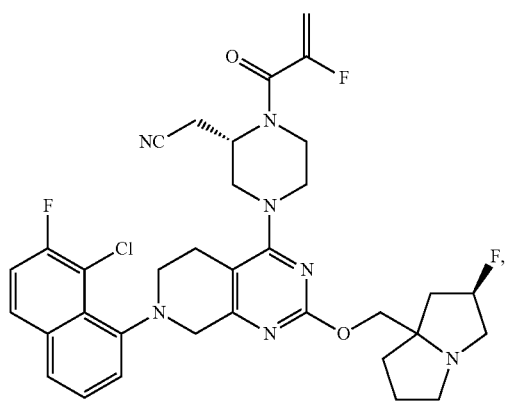
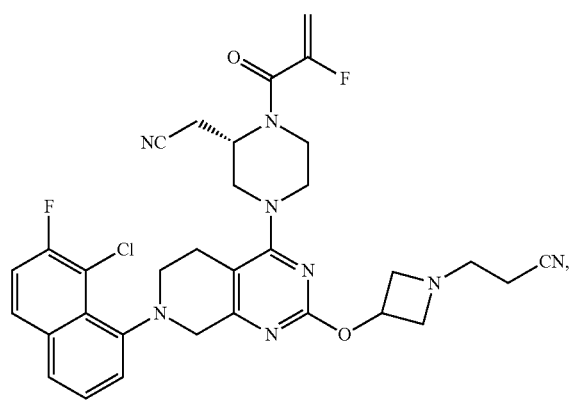
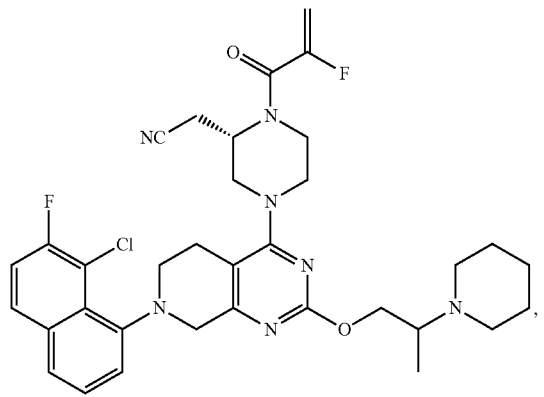
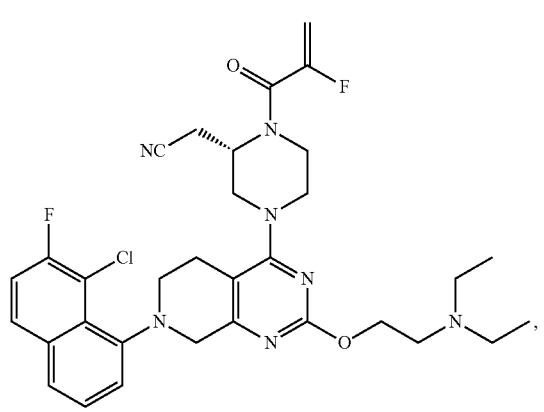
434
-continued
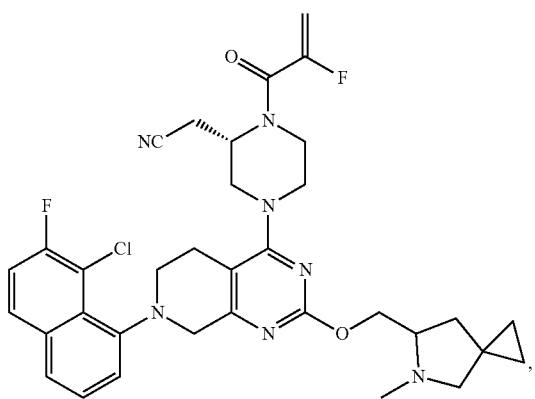
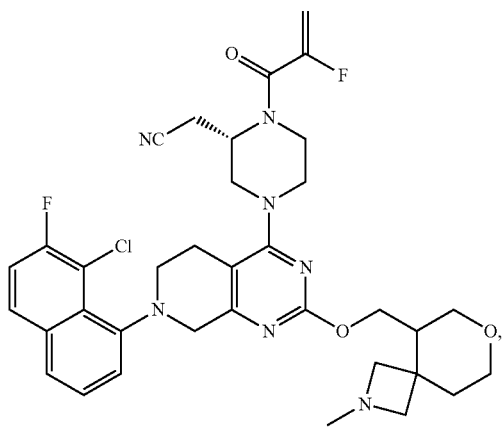
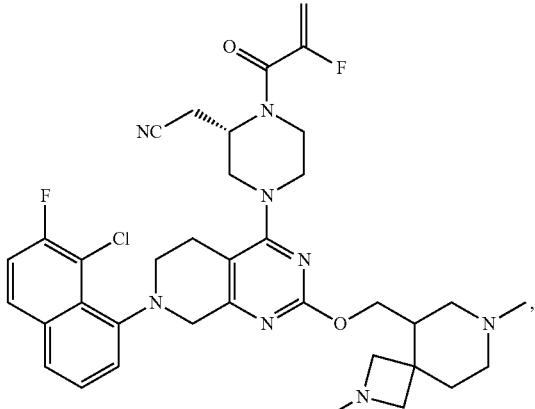
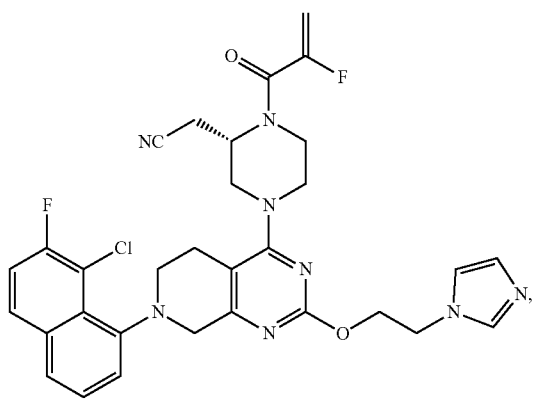

435
-continued
436
-continued
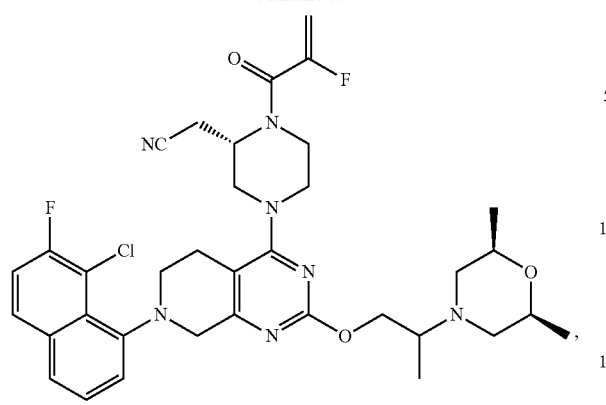
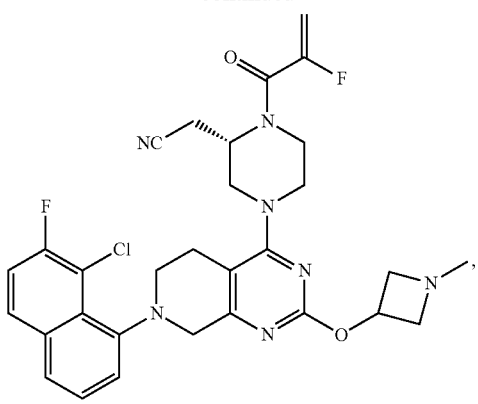

437
-continued
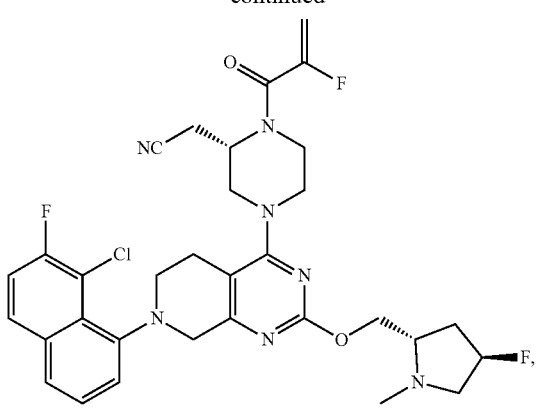
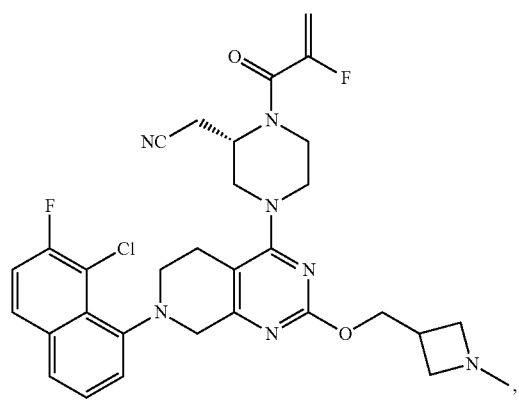
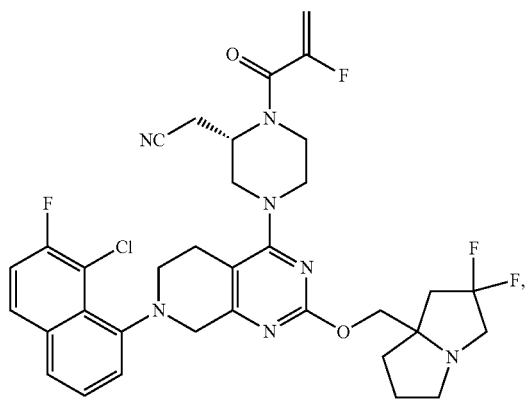
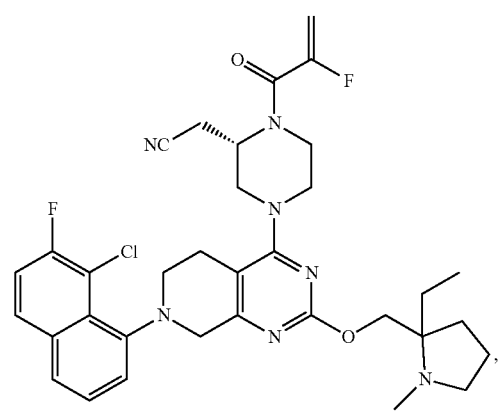
438
-continued
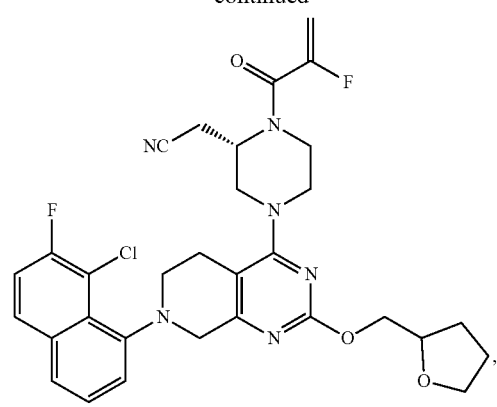
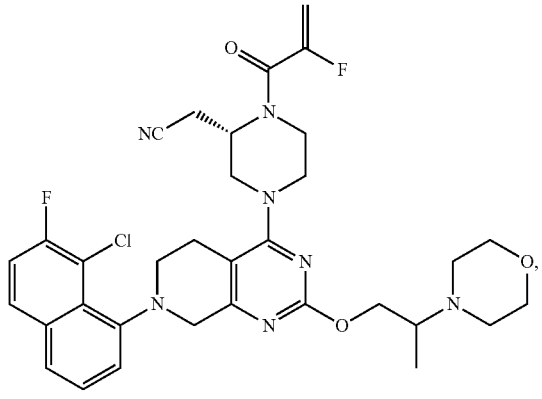
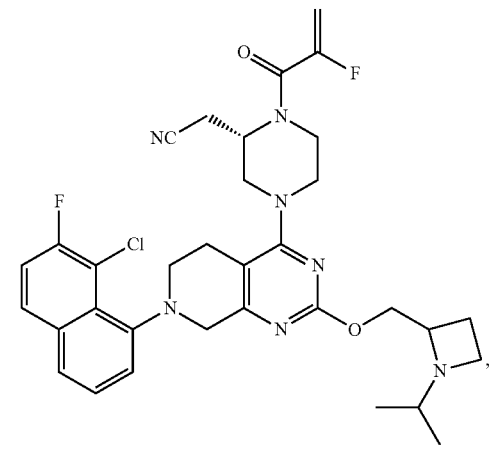
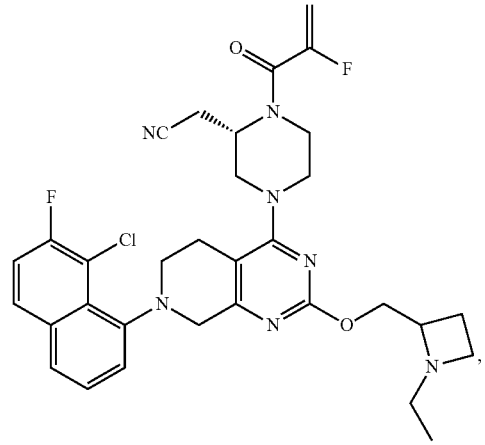

439
-continued
440
-continued
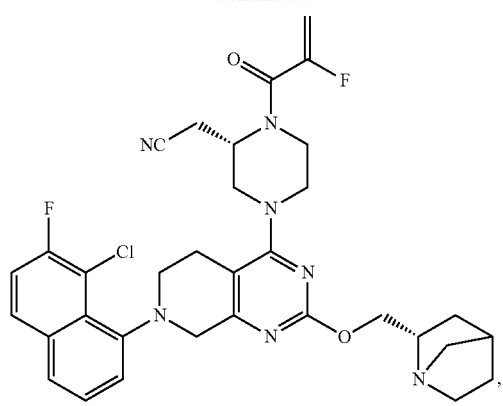
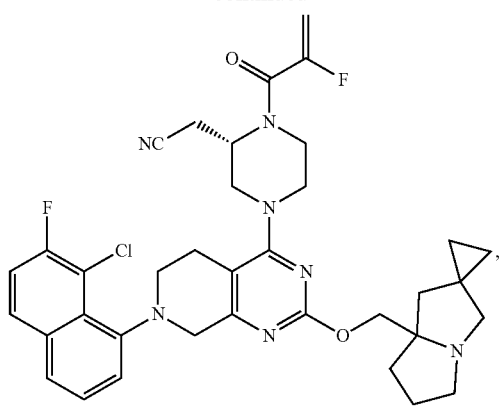

-continued
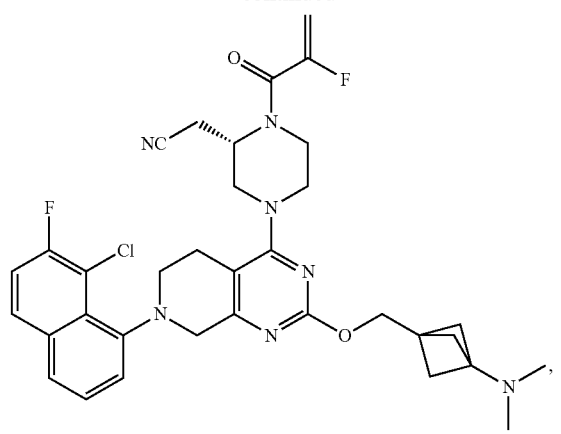
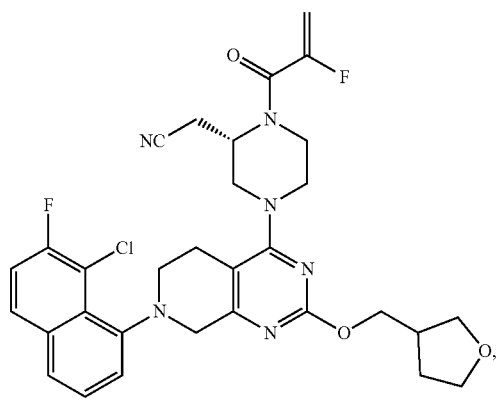
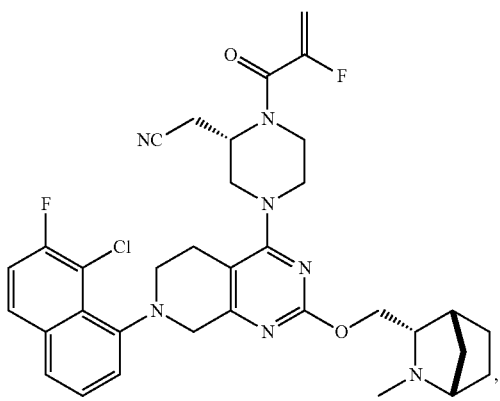
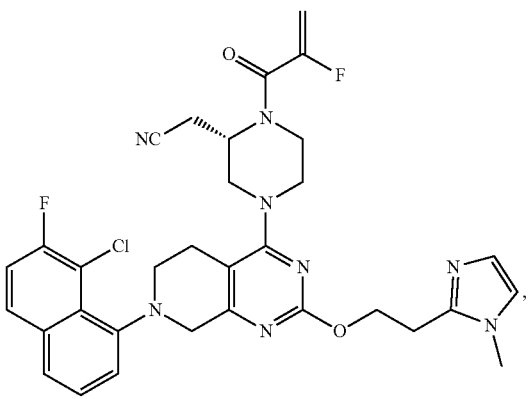
-continued
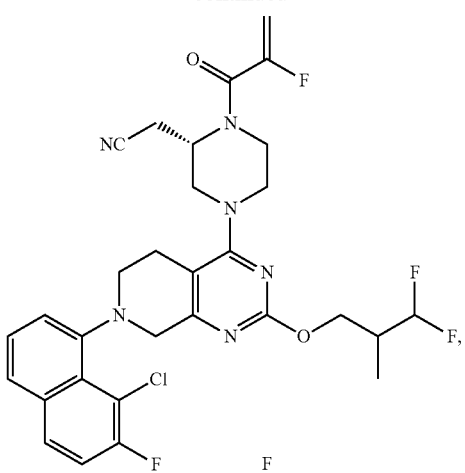
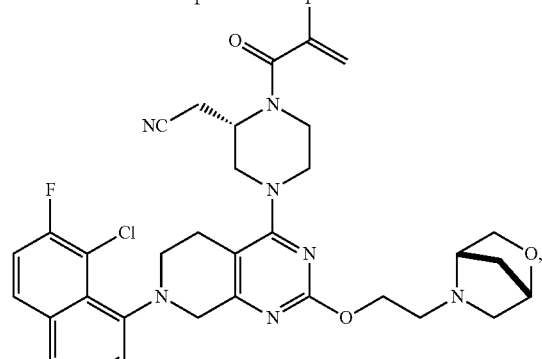
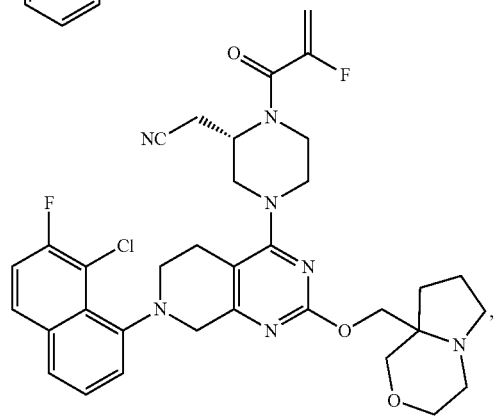
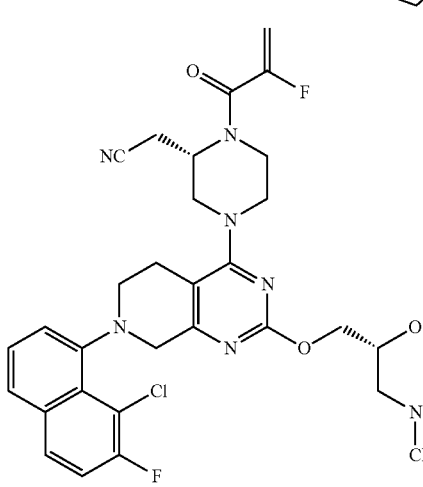

443
-continued
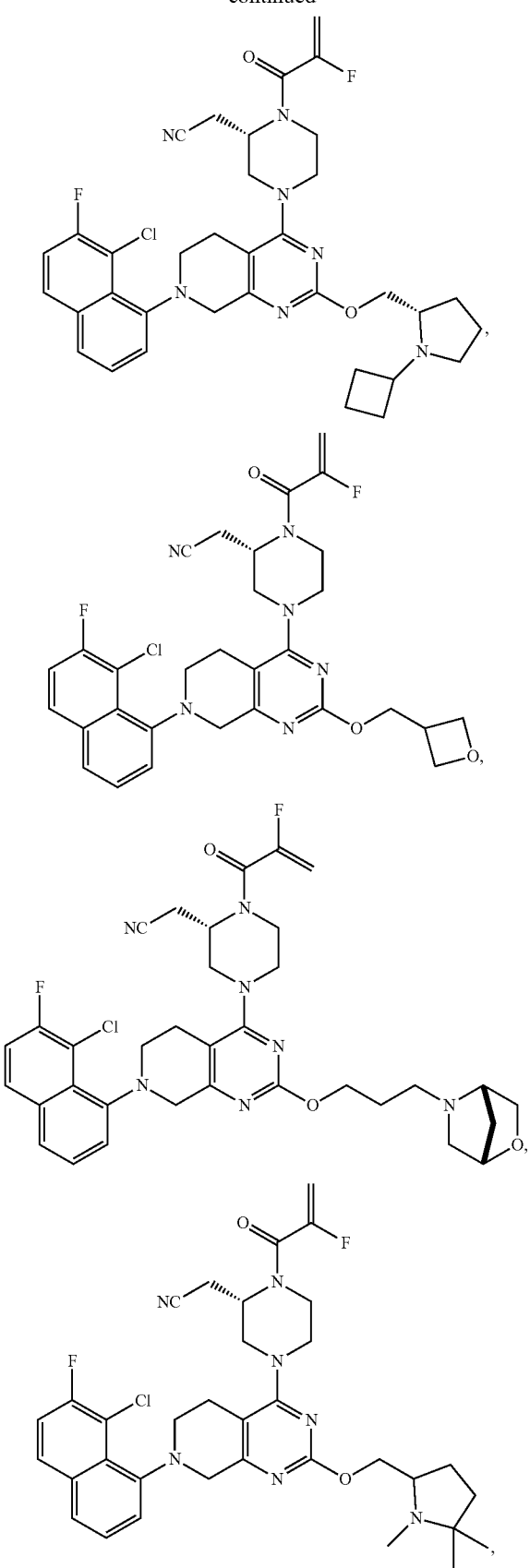
444
-continued
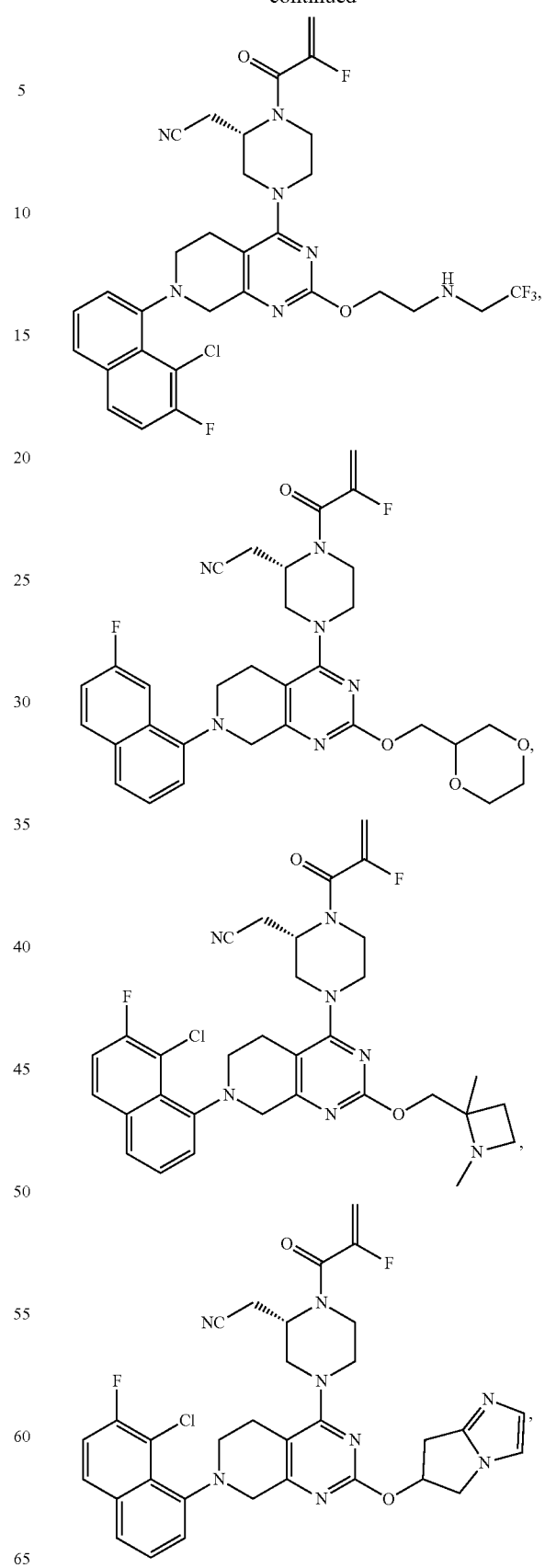

-continued
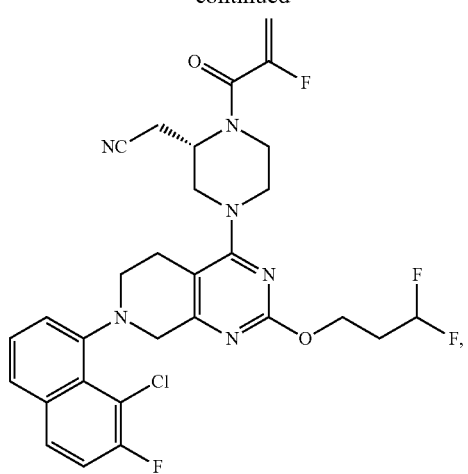
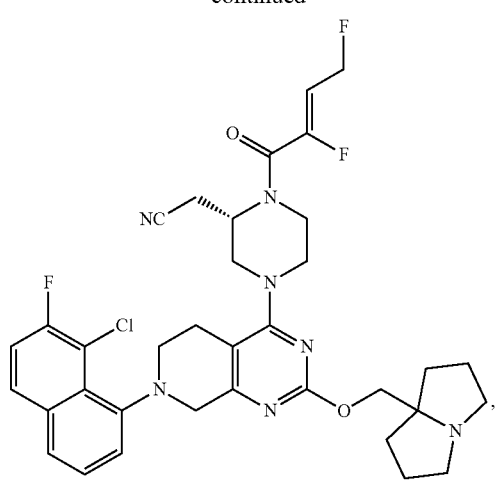
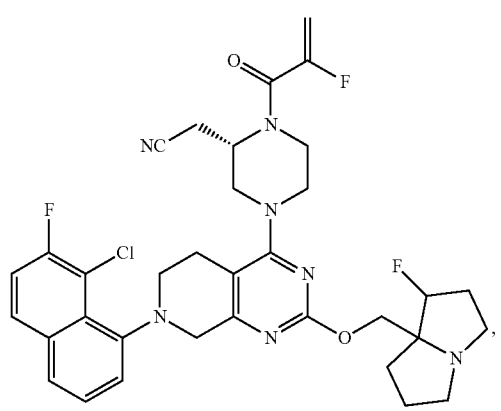
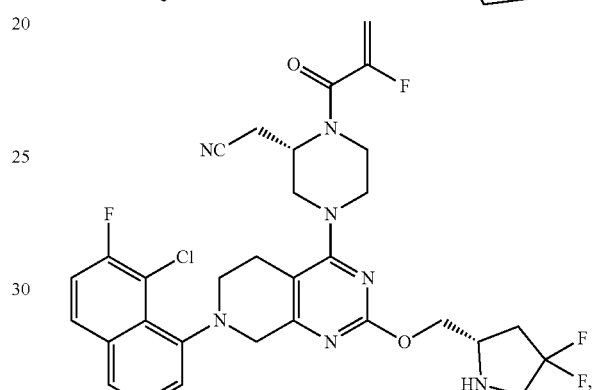
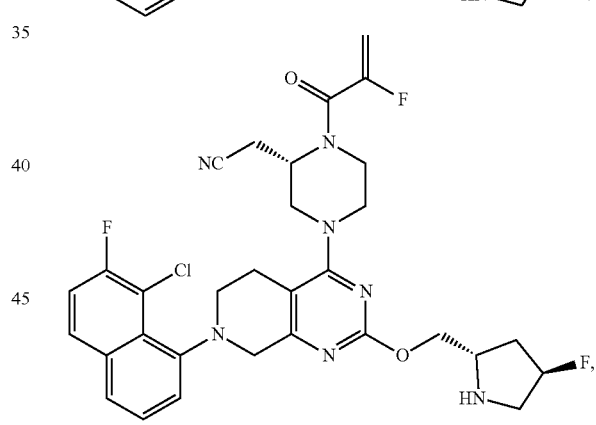
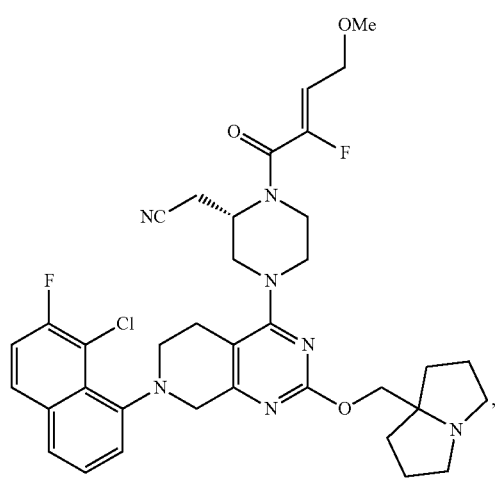
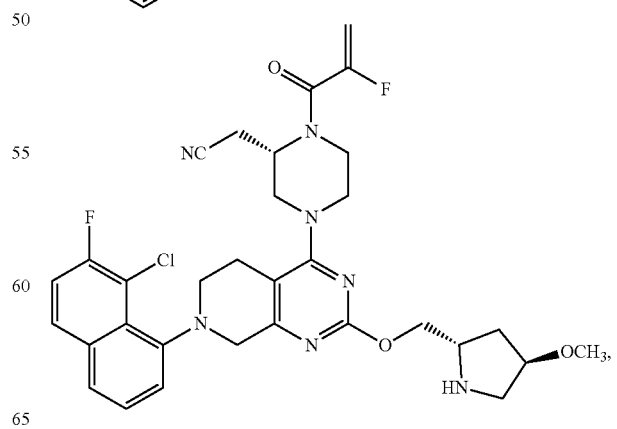

447
-continued
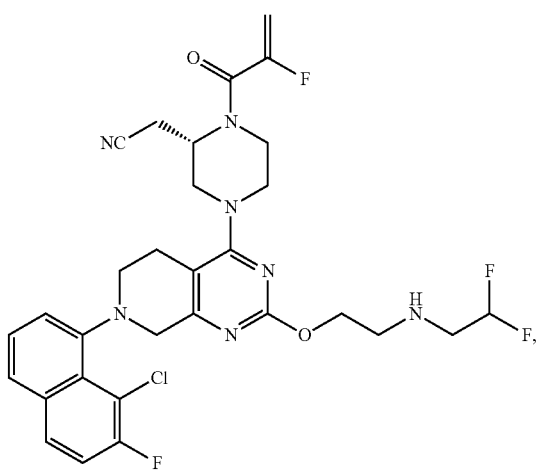
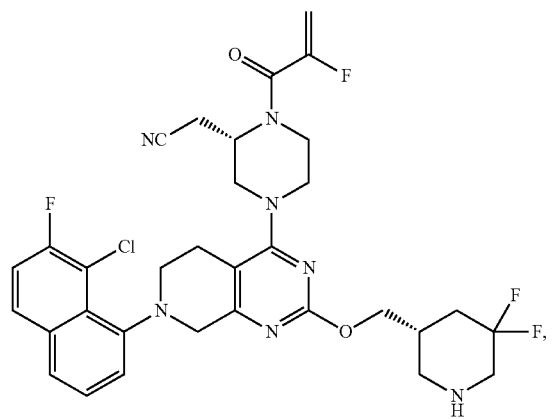
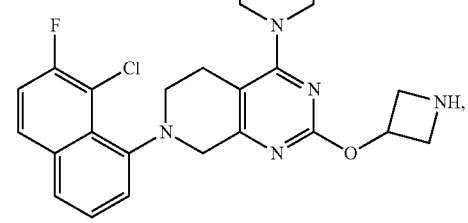
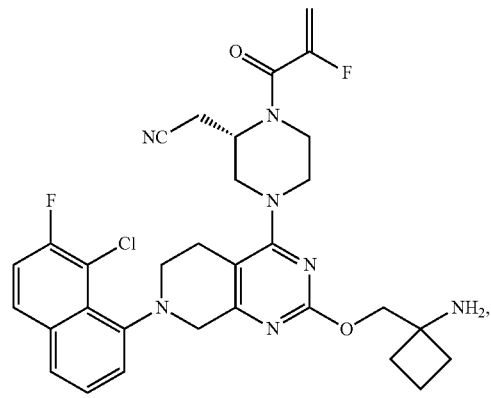
448
-continued
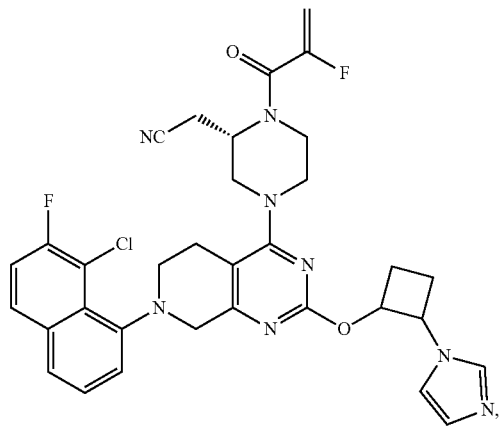
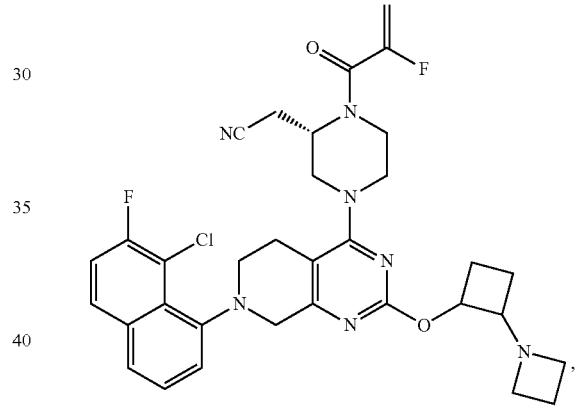
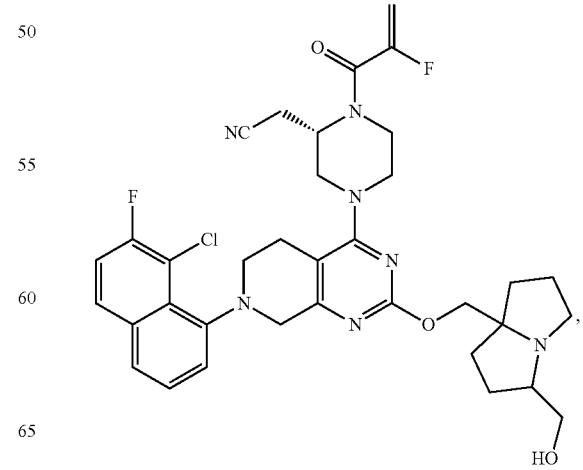

449
-continued
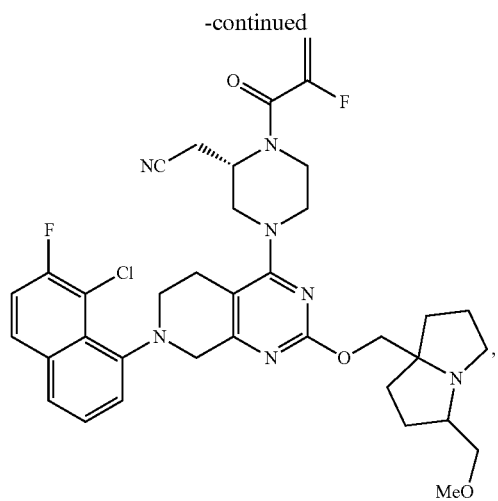
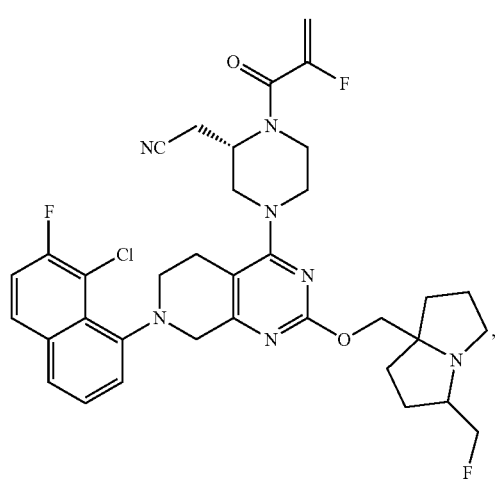
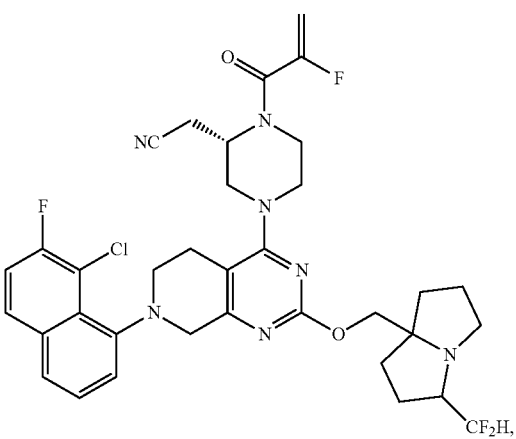
450
-continued
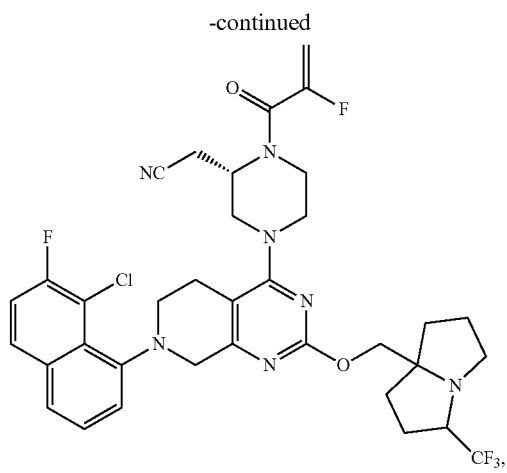
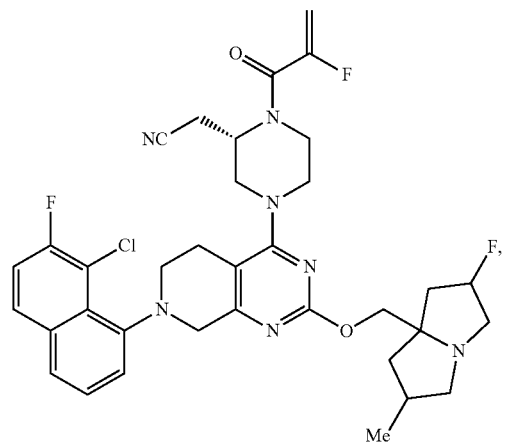
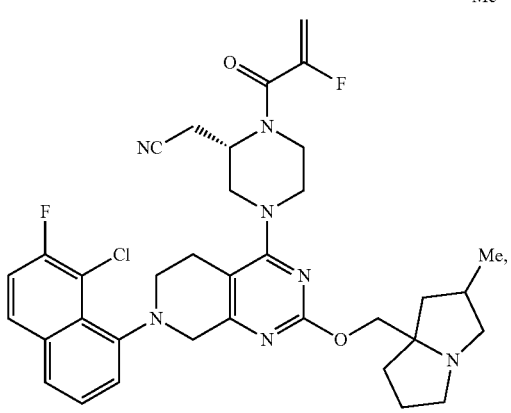

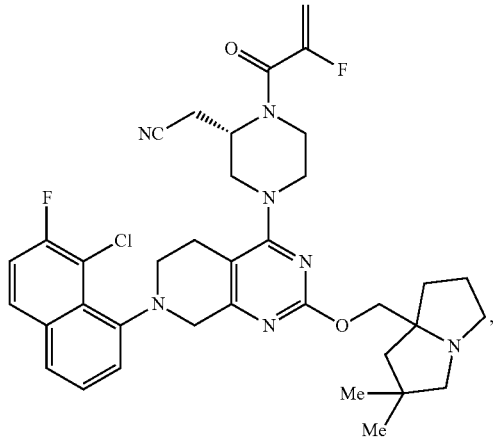

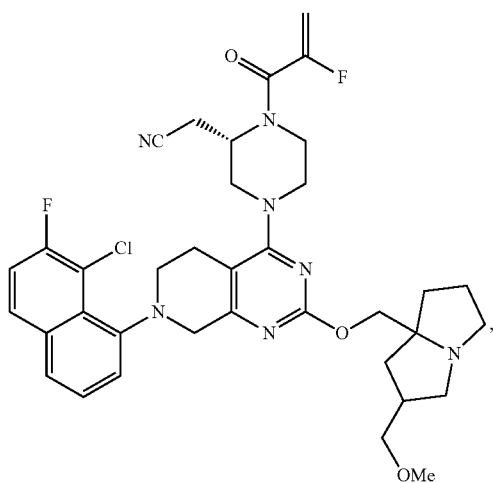

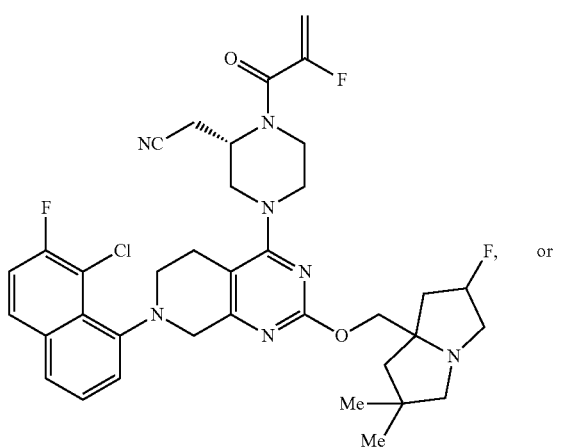

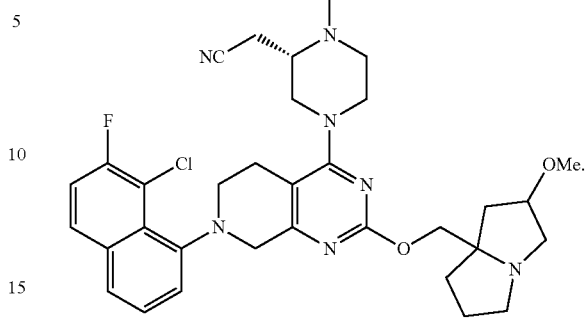

or a pharmaceutically acceptable salt thereof.

2. A pharmaceutical composition, comprising a therapeutically effective amount of a compound of claim 1, and a pharmaceutically acceptable excipient.

3. A method for inhibiting KRas G12C activity in a cell, comprising contacting the cell in which inhibition of KRas G12C activity is desired with an effective amount of a compound of claim 1 in vivo, wherein the cell is in a patient having a KRAS G12C-associated cancer.

4. A method for treating a KRAS G12C-associated cancer comprising administering to a patient having a KRAS G12C-associated cancer a therapeutically effective amount of a compound according to claim 1.

5. The method of claim 4, wherein the therapeutically effective amount of the compound is between about 0.01 to 100 mg/kg per day.

6. The method of claim 5, wherein the therapeutically effective amount of the compound is between about 0.1 to 50 mg/kg per day.

7. The method of claim 4, wherein the cancer is selected from the group consisting of Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial 'carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

8. The method of claim 4, wherein the cancer is non-small cell lung cancer.

9. A method for treating a cancer in a patient in need thereof, the method comprising (a) determining that the cancer is associated with a KRas G12C mutation; and (b) administering to the patient having a KRAS G12C-associated cancer a therapeutically effective amount of a compound according to claim 1.

\* \* \* \* \*